US010683302B2

(12) United States Patent
Cacatian et al.

(10) Patent No.: US 10,683,302 B2
(45) Date of Patent: Jun. 16, 2020

(54) INHIBITORS OF THE MENIN-MLL INTERACTION

(71) Applicant: VITAE PHARMACEUTICALS, LLC, Madison, NJ (US)

(72) Inventors: Salvacion Cacatian, Conshohocken, PA (US); David A. Claremon, Maple Glen, PA (US); Lawrence Wayne Dillard, Yardley, PA (US); Chengguo Dong, Staten Island, NY (US); Yi Fan, Doylestown, PA (US); Lanqi Jia, Horsham, PA (US); Stephen D. Lotesta, Burlington, NJ (US); Andrew Marcus, Media, PA (US); Angel Morales-Ramos, Blue Bell, PA (US); Suresh B. Singh, Kendall Park, NJ (US); Shankar Venkatraman, Lansdale, PA (US); Jing Yuan, Lansdale, PA (US); Yajun Zheng, Hockessin, DE (US); Linghang Zhuang, Chalfont, PA (US); Stephan D. Parent, West Lafayette, IN (US); Travis L. Houston, Lafayette, IN (US)

(73) Assignee: VITAE PHARMACEUTICALS, LLC, Madison, NJ (US)

( * ) Notice: Subject to any disclaimer, the term of this patent is extended or adjusted under 35 U.S.C. 154(b) by 0 days.

(21) Appl. No.: 16/308,739

(22) PCT Filed: Jun. 8, 2017

(86) PCT No.: PCT/US2017/036506
§ 371 (c)(1),
(2) Date: Dec. 10, 2018

(87) PCT Pub. No.: WO2017/214367
PCT Pub. Date: Dec. 14, 2017

(65) Prior Publication Data
US 2019/0144459 A1 May 16, 2019

Related U.S. Application Data

(60) Provisional application No. 62/348,496, filed on Jun. 10, 2016.

(51) Int. Cl.
| | | |
|---|---|---|
| C07D 405/14 | (2006.01) |
| C07D 403/04 | (2006.01) |
| C07D 403/14 | (2006.01) |
| C07D 471/10 | (2006.01) |
| C07D 487/10 | (2006.01) |
| C07D 491/10 | (2006.01) |
| A61P 35/02 | (2006.01) |
| C07D 491/107 | (2006.01) |
| C07F 9/6561 | (2006.01) |

(52) U.S. Cl.
CPC ............ *C07D 487/10* (2013.01); *A61P 35/02* (2018.01); *C07D 403/04* (2013.01); *C07D 403/14* (2013.01); *C07D 405/14* (2013.01); *C07D 471/10* (2013.01); *C07D 491/10* (2013.01); *C07D 491/107* (2013.01); *C07F 9/6561* (2013.01); *C07B 2200/13* (2013.01)

(58) Field of Classification Search
CPC .. C07D 405/14; C07D 403/04; C07D 403/14; C07D 471/10; C07D 487/10; C07D 491/10
See application file for complete search history.

(56) References Cited

FOREIGN PATENT DOCUMENTS

| WO | WO 2009/137733 | 11/2009 |
| WO | WO 2014/164543 A1 | 10/2014 |
| WO | WO 2015/191701 A1 | 12/2015 |

OTHER PUBLICATIONS

Borkin et al. "Pharmacologic Inhibition of the Menin-MLL Interaction Blocks Progression of MLL Leukemia In Vivo", Cancer Cell, vol. 27, p. 589-602 (2015).
Chamberlain et al. "Menin determines K-RAS proliferative outputs in endocrine cells", The Journal of Clinical Investigation, vol. 124, No. 9, p. 4093-4101 (2014).
Cierpicki T. et al. "Challenges and opportunities in targeting the menin-MLL interaction", Future Med. Chem. vol. 6, No. 4, p. 447-462 (2014).
Grembecka J. et al. "Menin-MLL inhibitors reverse oncogenic activity of MLL fusion proteins in leukemia", Nature Chemical Biology, vol. 8, p. 277-284 (2012).
Kress et al. "Chemistry of Pyrimidine. 2. Synthesis of Pyrimidine JV-Oxides and 4-Pyrimidinones by Reaction of 5-Substituted Pyrimidines with Peracids. Evidence for Covalent Hydrates as Reaction Intermediates", J. Org. Chem., vol. 50, p. 3073-3076 (1985).
Maiti D. et al. "Cu-Catalyzed Arylation of Phenols: Synthesis of Sterically Hindered and Heteroaryl Diaryl Ethers", J. Org. Chem. vol. 75, p. 1791-1794 (2010).
Malik R. et al. "Targeting the MLL complex in castration-resistant prostate cancer", Nature Medicine, vol. 21, No. 4, p. 344-354 (2015).

(Continued)

*Primary Examiner* — Bruck Kifle
(74) *Attorney, Agent, or Firm* — Cooley LLP; Heidi A. Erlacher; Eric A. Owens

(57) ABSTRACT

The present invention is directed to inhibitors of the interaction of menin with MLL and MLL fusion proteins, pharmaceutical compositions containing the same, and their use in the treatment of cancer and other diseases mediated by the menin-MLL interaction.

28 Claims, 12 Drawing Sheets

(56) References Cited

OTHER PUBLICATIONS

Salvi L. et al. "A New Biarylphosphine Ligand for the Pd-Catalyzed Synthesis of Diaryl Ethers under Mild Conditions", Organic Letters, vol. 14, No. 1, p. 170-173 (2012).
Shi A. et al. "Structural insights into inhibition of the bivalent menin-MLL interaction by small molecules in leukemia", Blood, vol. 120, No. 23, 2012, pp. 4461-4469.
Yang Y. et al. "Reversal of preexisting hyperglycemia in diabetic mice by acute deletion of the Men1 gene", PNAS, vol. 107, No. 47, p. 20358-20363 (2010).
Yokoyama A. et al. "The Menin Tumor Suppressor Protein Is an Essential Oncogenic Cofactor for MLL-Associated Leukemogenesis", Cell, vol. 123, p. 207-218, (2005).

INHIBITORS OF THE MENIN-MLL INTERACTION

CROSS-REFERENCE TO RELATED APPLICATIONS

This application is a national stage application, filed under 35 U.S.C. 371, of PCT Application No. PCT/US2017/036506 filed Jun. 8, 2017, which claims the benefit of U.S. Provisional Application No. 62/348,496 filed Jun. 10, 2016, which are incorporated by reference herein in their entireties.

TECHNICAL FIELD

The present invention is directed to inhibitors of the interaction of menin with MLL and MLL fusion proteins, pharmaceutical compositions containing the same, and their use in the treatment of cancer and other diseases mediated by the menin-MLL interaction.

BACKGROUND

The mixed-lineage leukemia (MLL) protein is a histone methyltransferase that is mutated in clinically and biologically distinctive subsets of acute leukemia. Rearranged mixed lineage leukemia (MLL-r) involves recurrent translocations of the 11q23 chromosome locus which lead to an aggressive form of acute leukemia with limited therapeutic options. These translocations target the MLL gene creating an oncogenic fusion protein comprising the amino-terminus of MLL fused in frame with more than 60 different fusion protein partners. Menin, a ubiquitously expressed, nuclear protein encoded by the multiple endocrine neoplasia type 1 (MEN1) tumor suppressor gene, has a high affinity binding interaction with MLL fusion proteins and is an essential co-factor of oncogenic MLL-r fusion proteins (Yokoyama et al., 2005, Cell, 123:207-18; Cierpicki & Grembecka, 2014, Future Med. Chem., 6:447-462). Disruption of this interaction leads to selective growth inhibition and apoptosis of MLL-r leukemia cells both in vitro (Grembecka et al., 2012, Nat. Chem. Biol., 8:277-284) and in vivo (Yokoyama et al., 2005, op. cit.; Borkin et al., 2015, Cancer Cell, 27:589-602).

The menin-MLL complex plays a role in castration-resistant/advanced prostate cancer, and a menin-MLL inhibitor has been shown to reduce tumor growth in vivo (Malik et al., 2015, Nat. Med., 21:344-352). Additionally, a menin-MLL inhibitor has been shown to enhance human β cell proliferation (Chamberlain et al., 2014, J. Clin. Invest., 124:4093-4101), supporting a role for inhibitors of the menin-MLL interaction in the treatment of diabetes (Yang et al., 2010, Proc Natl Acad Sci USA., 107:20358-20363). The interaction between menin and MLL or MLL fusion proteins is an attractive target for therapeutic intervention, and there is a need for novel agents that inhibit the menin-MLL interaction for the treatment of various diseases and conditions, including leukemia, other cancers and diabetes.

SUMMARY

The present invention provides inhibitors of the menin-MLL interaction, such as a compound of Formula I:

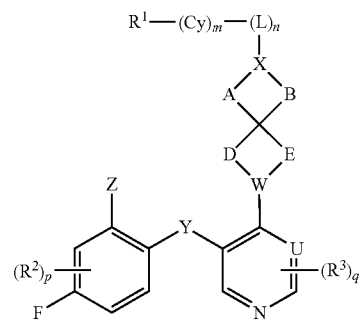

or a pharmaceutically acceptable salt thereof, wherein constituent variables are defined herein.

The present invention further provides a pharmaceutical composition comprising a compound of Formula I, or a pharmaceutically acceptable salt thereof, and at least one pharmaceutically acceptable carrier.

The present invention further provides pharmaceutically acceptable salt forms of the compounds of Formula I.

The present invention further provides crystalline forms of the compounds of Formula I.

The present invention further provides a method of inhibiting the interaction between menin and MLL comprising contacting the menin and MLL with a compound of Formula I, or a pharmaceutically acceptable salt thereof.

The present invention further provides a method of treating cancer in a patient comprising administering to the patient a therapeutically effective amount of a compound of Formula I, or a pharmaceutically acceptable salt thereof.

The present invention further provides a method of treating insulin resistance, pre-diabetes, diabetes, risk of diabetes, or hyperglycemia in a patient comprising administering to the patient a therapeutically effective amount of a compound of Formula I, or a pharmaceutically acceptable salt thereof.

DETAILED DESCRIPTION

Figure 1:
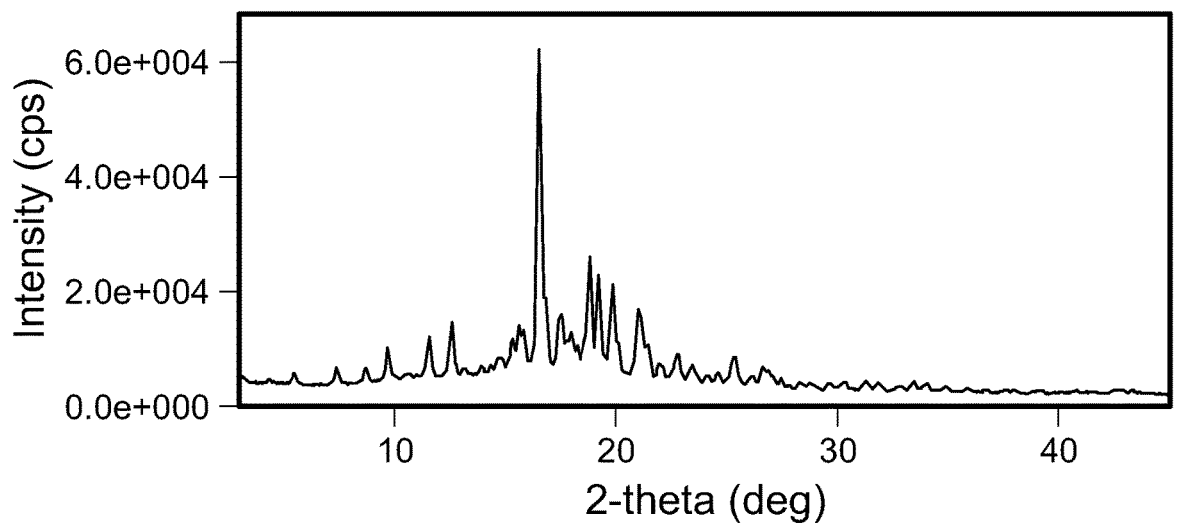
FIG. 1 shows an XRPD pattern characteristic of N-ethyl-2-((4-(7-(((1r,4r)-4-(ethylsulfonamido)cyclohexyl)methyl)-2,7-diazaspiro[3.5]nonan-2-yl)pyrimidin-5-yl)oxy)-5-fluoro-N-isopropylbenzamide.

The present invention provides inhibitors of the menin-MLL interaction, such as a compound of Formula I:

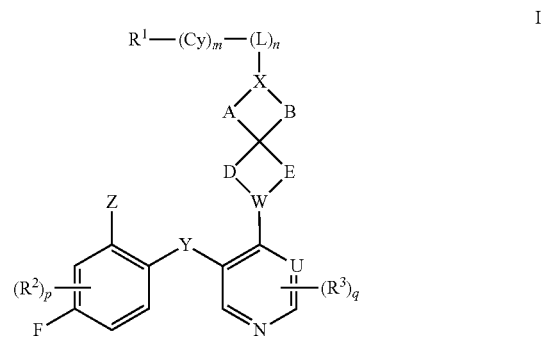

or a pharmaceutically acceptable salt thereof, wherein:

A, B, D, and E are each independently selected from —C($R^{A1}$)($R^{A2}$)—, —C($R^{A1}$)($R^{A2}$)—C($R^{A1}$)($R^{A2}$)—, —C($R^{A1}$)($R^{A2}$)—O—, —C($R^{A1}$)($R^{A2}$)—$NR^{S3}$—, —C(=O)—, —C($R^{A1}$)($R^{A2}$)—C(=O)—, and —N=C($NH_2$)— wherein no more than one of A, B, D, and E is —C($R^{A1}$)($R^{A2}$)—O—, —C($R^{A1}$)($R^{A2}$)—$NR^{A3}$—, —C($R^{A1}$)($R^{A2}$)—C(=O)—, —C(=O)—, or —N=C($NH_2$)—;

U is N or $CR^U$, wherein $R^U$ is H, halo, CN, OH, $C_{1-4}$ alkyl, $C_{1-4}$ alkoxy, amino, $C_{1-4}$ alkyl amino, or $C_{2-8}$ dialkylamino;

W is N or $CR^W$, wherein $R^W$ is H, halo, CN, OH, $C_{1-4}$ alkyl, $C_{1-4}$ alkoxy, amino, $C_{1-4}$ alkyl amino, or $C_{2-8}$ dialkylamino;

X is N or $CR^X$, wherein $R^X$ is H, halo, CN, OH, $C_{1-4}$ alkyl, $C_{1-4}$ alkoxy, amino, $C_{1-4}$ alkyl amino, or $C_{2-8}$ dialkylamino, wherein when X is N, the atom of L that is directly bonded with X is other than N, O, or S;

L is selected from —$C_{1-6}$ alkylene- and —($C_{1-4}$ alkylene)$_a$-Q-($C_{1-4}$ alkylene)$_b$-, wherein the $C_{1-6}$ alkylene group and any $C_{1-4}$ alkylene group of the —($C_{1-4}$ alkylene)$_a$-Q-($C_{1-4}$ alkylene)$_b$- group is optionally substituted with 1, 2, or 3 substituents independently selected from halo, CN, OH, $C_{1-3}$ alkyl, $C_{1-3}$ alkoxy, $C_{1-3}$ haloalkyl, $C_{1-3}$ haloalkoxy, amino, $C_{1-3}$ alkylamino, and di($C_{1-3}$ alkyl)amino;

Q is —O—, —S—, —S(=O)—, —S(=O)$_2$—, —C(=O)—, —C(=O)$NR^{q1}$—, —C(=O)O—, —OC(=O)$NR^{q1}$—, —$NR^{q1}$—, —$NR^{q1}$C(=O)O—, —$NR^{q1}$C(=O)$NR^{q1}$—, —S(=O)$_2NR^{q1}$—, —C(=$NR^{q2}$)—, or —C(=$NR^{q2}$)—$NR^{q1}$—, wherein each $R^{q1}$ is independently selected from H or $C_{1-6}$ alkyl, and wherein each $R^{q2}$ is independently selected from H, $C_{1-6}$ alkyl, and CN;

Cy is a linking $C_{6-14}$ aryl, $C_{3-18}$ cycloalkyl, 5-16 membered heteroaryl, or 4-18 membered heterocycloalkyl group, each of which is optionally substituted with 1, 2, 3, or 4 substituents independently selected from $R^{Cy}$;

each $R^{Cy}$ is independently selected from halo, $C_{1-6}$ alkyl, $C_{1-4}$ haloalkyl, $C_{1-4}$ cyanoalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycloalkyl are each optionally substituted by 1, 2, 3, or 4 substituents independently selected from CN, $NO_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$;

$R^1$ is H, $Cy^1$, halo, $C_{1-6}$ alkyl, $C_{1-4}$ haloalkyl, $C_{1-4}$ cyanoalkyl, $C_{2-6}$ alkenyl, $C_{2-6}$ alkynyl, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$. $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$ and $S(O)_2NR^{c2}R^{d2}$, wherein said $C_{1-6}$ alkyl, $C_{2-6}$ alkenyl, and $C_{2-6}$ alkynyl are each optionally substituted by 1, 2, 3, or 4 substituents independently selected from halo, CN, $NO_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

Y is O, S, $CR^{Y1}R^{Y2}$ or $NR^{Y3}$, wherein $R^{Y1}$, $R^{Y2}$, and $R^{Y3}$ are each independently selected from H and $C_{1-4}$ alkyl;

Z is $Cy^2$, halo, $C_{1-6}$ alkyl, $C_{1-4}$ haloalkyl, $C_{1-4}$ cyanoalkyl, $C_{2-6}$ alkenyl, $C_{2-6}$ alkynyl, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, $S(O)_2NR^{c3}R^{d3}$, and $P(O)R^{c3}R^{d3}$ wherein said $C_{1-6}$ alkyl, $C_{2-6}$ alkenyl, and $C_{2-6}$ alkynyl are each optionally substituted by 1, 2, 3, or 4 substituents independently selected from $Cy^2$, halo, CN, $NO_2$, CN, $NO_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;

each $R^2$ and $R^3$ is independently selected from H, halo, $C_{1-6}$ alkyl, $C_{1-4}$ haloalkyl, $C_{1-4}$ cyanoalkyl, $C_{2-6}$ alkenyl, $C_{2-6}$ alkynyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $C(=NR^{e4})NR^{c4}R^{d4}$, $NR^{c4}C(=NR^{e4})NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$, wherein said $C_{1-6}$ alkyl, $C_{2-6}$ alkenyl, and $C_{2-6}$ alkynyl are each optionally substituted by 1, 2, 3, or 4 substituents independently selected from halo, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $C(=NR^{e4})NR^{c4}R^{d4}$, $NR^{c4}C(=NR^{e4})NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, and $S(O)_2NR^{c4}R^{d4}$;

each $R^{A1}$ is independently selected from H, halo, $C_{1-4}$ alkyl, $C_{1-4}$ alkoxy, $C_{1-4}$ haloalkyl, $C_{1-4}$ haloalkoxy, amino, $C_{1-4}$ alkylamino, $C_{2-8}$ dialkylamino, CN, $NO_2$, and OH;

each $R^{A2}$ is independently selected from H, halo, $C_{1-4}$ alkyl, $C_{1-4}$ alkoxy, $C_{1-4}$ haloalkyl, $C_{1-4}$ haloalkoxy, amino, $C_{1-4}$ alkylamino, $C_{2-8}$ dialkylamino, CN, $NO_2$, and OH;

each $R^{A3}$ is independently selected from H, $C_{1-4}$ alkyl, $C_{1-4}$ alkoxy, $C_{1-4}$ haloalkyl, $C(O)R^z$, and $C(O)OR^z$, wherein said $C_{1-4}$ alkyl is optionally substituted by phenyl, $C_{1-4}$ alkoxy, $C_{1-4}$ haloalkoxy, CN, $NO_2$, or OH;

$R^z$ is H, $C_{1-4}$ alkyl, or phenyl;

each $Cy^1$ is independently selected from $C_{6-14}$ aryl, $C_{3-18}$ cycloalkyl, 5-16 membered heteroaryl, and 4-18 membered heterocycloalkyl, each of which is optionally substituted with 1, 2, 3, or 4 substituents independently selected from $R^{Cy1}$;

each $Cy^2$ is independently selected from $C_{6-14}$ aryl, $C_{3-18}$ cycloalkyl, 5-16 membered heteroaryl, and 4-18 membered heterocycloalkyl, each of which is optionally substituted with 1, 2, 3, or 4 substituents independently selected from $R^{Cy2}$;

each $R^{Cy1}$ and $R^{Cy2}$ is independently selected from halo, $C_{1-6}$ alkyl, $C_{1-4}$ haloalkyl, $C_{1-4}$ cyanoalkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $C(=NR^{e5})NR^{c5}R^{d5}$, $NR^{c5}C(=NR^{e5})NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$, wherein said $C_{1-6}$ alkyl, $C_{2-6}$ alkenyl, $C_{2-6}$ alkynyl, phenyl, $C_{3-7}$ cycloalkyl, 5-6 membered heteroaryl, and 4-7 membered heterocycloalkyl are each optionally substituted by 1, 2, 3, or 4 substituents independently selected from CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $C(=NR^{e5})NR^{c5}R^{d5}$, $NR^{c5}C(=NR^{e5})NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$;

each $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$, $R^{d3}$, $R^{a4}$, $R^{b4}$, $R^{c4}$, $R^{d4}$, $R^{a5}$, $R^{b5}$, $R^{c5}$, and $R^{d5}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl, $C_{3-10}$ cycloalkyl-$C_{1-6}$ alkyl, (5-10 membered heteroaryl)-$C_{1-6}$ alkyl, and (4-10 membered heterocycloalkyl)-$C_{1-6}$ alkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycloalkyl, $C_{6-10}$ aryl-$C_{1-6}$ alkyl, $C_{3-10}$ cycloalky-$C_{1-6}$ alkyl, (5-10 membered heteroaryl)-$C_{1-6}$ alkyl, and (4-10 membered heterocycloalkyl)-$C_{1-6}$ alkyl are each optionally substituted with 1, 2, 3, 4, or 5 substituents independently selected from $R^g$;

each $R^{e1}$, $R^{e2}$, $R^{e3}$, $R^{e4}$, and $R^{e5}$ is independently selected from H, $C_{1-4}$ alkyl, and CN;

each $R^g$ is independently selected from the group consisting of OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thiol, $C_{1-6}$ alkylthio, $C_{1-6}$ alkylsulfinyl, $C_{1-6}$ alkylsulfonyl, carboxy, aminocarbonyl, $C_{1-6}$ alkylcarbonyl, and $C_{1-6}$ alkoxycarbonyl;

n is 0 or 1;

m is 0 or 1;

p is 0, 1, 2, or 3;

q is 0, 1, or 2;

a is 0 or 1; and b is 0 or 1, wherein any cycloalkyl or heterocycloalkyl group is optionally further substituted by 1 or 2 oxo groups.

In some embodiments, Y is O.

In some embodiments, Y is $NR^{Y3}$. In some embodiments, Y is NH.

In some embodiments, U is $CR^U$. In some embodiments, U is CH.

In some embodiments, W is N.

In some embodiments, W is $CR^W$. In some embodiments, W is CH.

In some embodiments, X is N.

In some embodiments, X is $CR^X$. In some embodiments, X is selected from CH or $CNH_2$.

In some embodiments, A, B, D, and E are each independently selected from —C($R^{A1}$)($R^{A2}$)—, —C($R^{A1}$)($R^{A2}$)—C($R^{A1}$)($R^{A2}$)—, —C($R^{A1}$)($R^{A2}$)—O—, —C($R^{A1}$)($R^{A2}$)—C(=O)—, and —C(=O)—, wherein no more than one of A, B, D, and E is —C($R^{A1}$)($R^{A2}$)—O—, —C($R^{A1}$)($R^{A2}$)—C(=O)—, or —C(=O)—.

In some embodiments, A, B, D, and E are each independently selected from —C($R^{A1}$)($R^{A2}$)—, —C($R^{A1}$)($R^{A2}$)—C($R^{A1}$)($R^{A2}$)—, and —C($R^{A1}$)($R^{A2}$)—O—, wherein no more than one of A, B, D, and E is —C($R^{A1}$)($R^{A2}$)—O—.

In some embodiments, A, B, D, and E are each independently selected from —C($R^{A1}$)($R^{A2}$)— or —C($R^{A1}$)($R^{A2}$)—C($R^{A1}$)($R^{A2}$)—.

In some embodiments, each $R^{A1}$ and $R^{A2}$ are independently selected from H, OH, and $NH_2$.

In some embodiments, A, B, D, and E are each independently selected from —$CH_2$—, —$CH_2$—$CH_2$—, and —$CH_2O$—.

In some embodiments, A, B, D, and E are each independently selected from —$CH_2$— or —$CH_2$—$CH_2$—.

In some embodiments, the spiro moiety represented by the below formula:

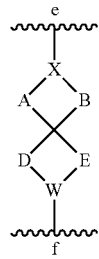

wherein e and f indicate points of attachment to the remainder of the molecule, is selected from:

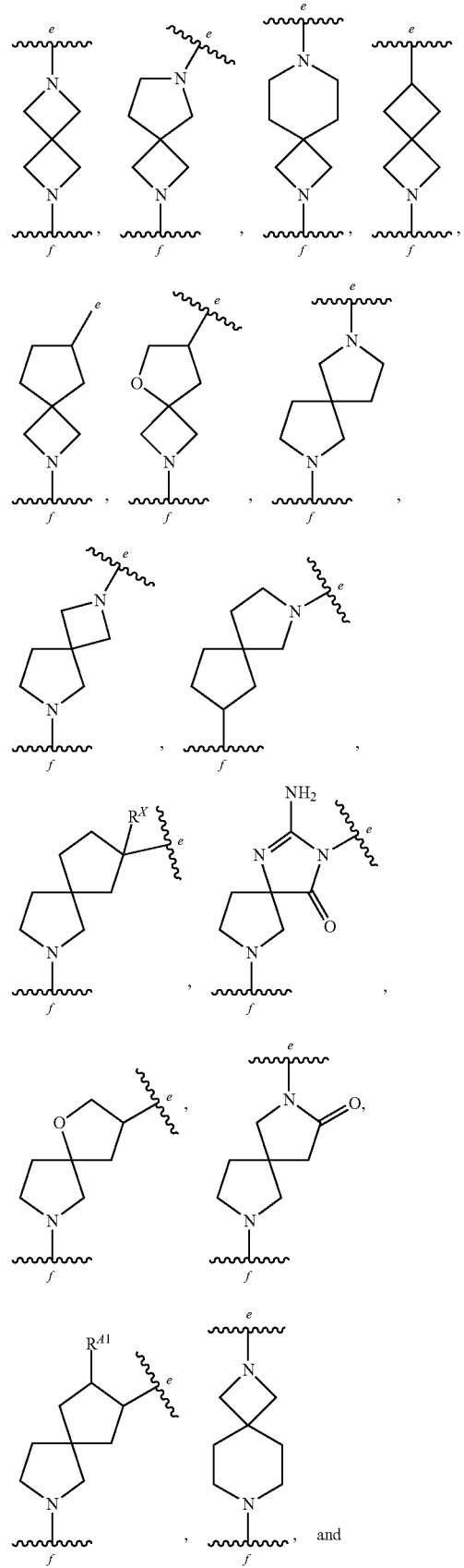

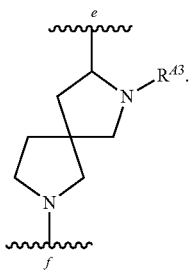

In some embodiments, the spiro moiety represented by the below formula:

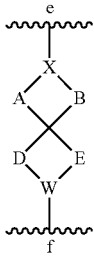

wherein e and f indicate points of attachment to the remainder of the molecule, is selected from:

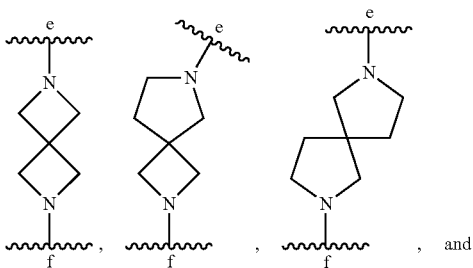

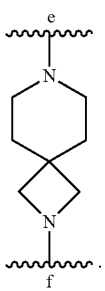

In some embodiments, the spiro moiety represented by the below formula:

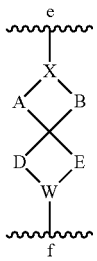

wherein e and f indicate points of attachment to the remainder of the molecule, is selected from:

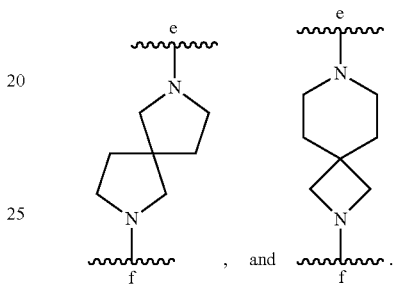

In some embodiments, L is selected from —$C_{1-6}$ alkylene- optionally substituted with 1, 2, or 3 substituents independently selected from halo, CN, OH, $C_{1-3}$ alkyl, $C_{1-3}$ alkoxy, $C_{1-3}$ haloalkyl, $C_{1-3}$ haloalkoxy, amino, $C_{1-3}$ alkylamino, and di($C_{1-3}$ alkyl)amino.

In some embodiments, L is selected from methylene, ethylene, and —CH$_2$—CH(OH)—.

In some embodiments, L is methylene.

In some embodiments, L is selected from —(C$_{1-4}$ alkylene)$_a$-Q-(C$_{1-4}$ alkylene)$_b$-, wherein any C$_{1-4}$ alkylene group of the —(C$_{1-4}$ alkylene)$_a$-Q-(C$_{1-4}$ alkylene)$_b$- group is optionally substituted with 1, 2, or 3 substituents independently selected from halo, CN, OH, $C_{1-3}$ alkyl, $C_{1-3}$ alkoxy, $C_{1-3}$ haloalkyl, $C_{1-3}$ haloalkoxy, amino, $C_{1-3}$ alkylamino, and di($C_{1-3}$ alkyl)amino.

In some embodiments, a is 1.
In some embodiments, a is 0.
In some embodiments, b is 1.
In some embodiments, b is 0.
In some embodiments, a and b are each 1.
In some embodiments, a and b are each 0.
In some embodiments, a is 1 and b is 0.
In some embodiments, a is 0 and b is 1.
In some embodiments, L is selected from —C(O)—CH$_2$—, —C(O)—CH$_2$—CH$_2$—, C(O), —NH—CH$_2$—, NH, —C(O)—CH(NH$_2$)—, —NH—CH(CH$_3$)—, —N(CH$_3$)—C(O)—, N(CH$_3$)—CH$_2$—, —CH$_2$—CH$_2$—O—, and —C(O)—NH—.

In some embodiments, Cy is a linking phenyl, C$_{3-18}$ cycloalkyl, 5-10 membered heteroaryl, or 4-9 membered heterocycloalkyl group, each of which is optionally substituted with 1, 2, 3, or 4 substituents independently selected from R$^{Cy}$.

In some embodiments, Cy is a linking phenyl, C$_{3-18}$ cycloalkyl, 5-10 membered heteroaryl, or 4-9 membered heterocycloalkyl group, each of which is optionally substituted with 1, 2, 3, or 4 substituents independently selected from R$^{Cy}$.

In some embodiments, Cy is a linking group having the formula:

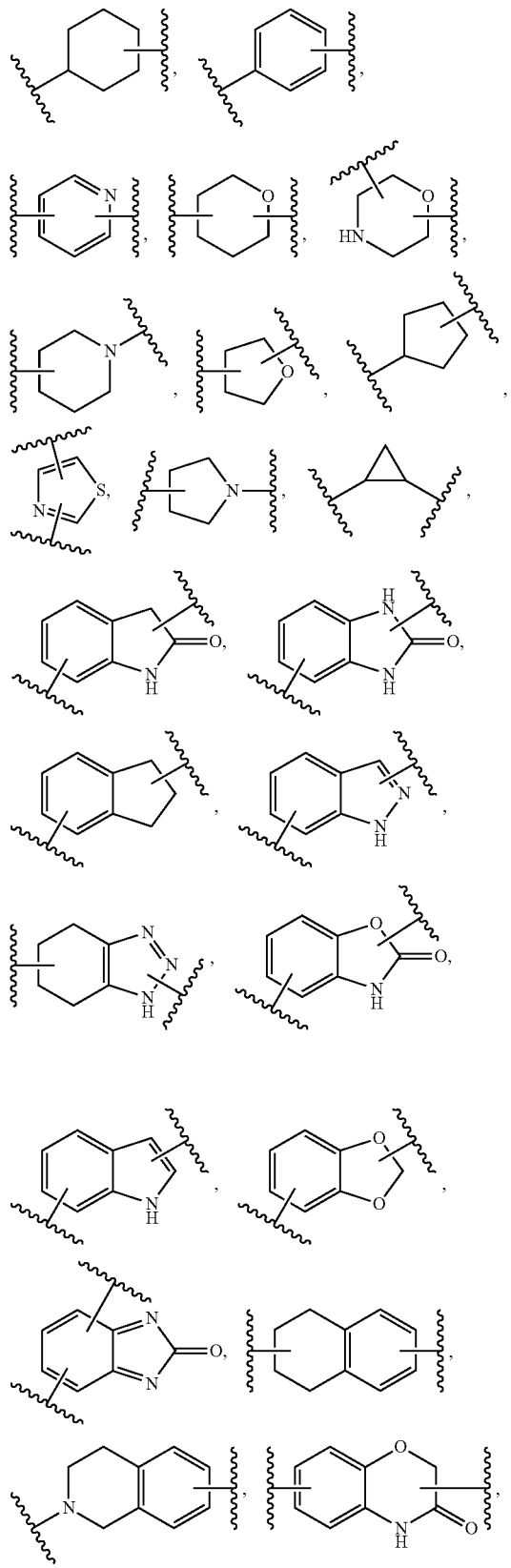

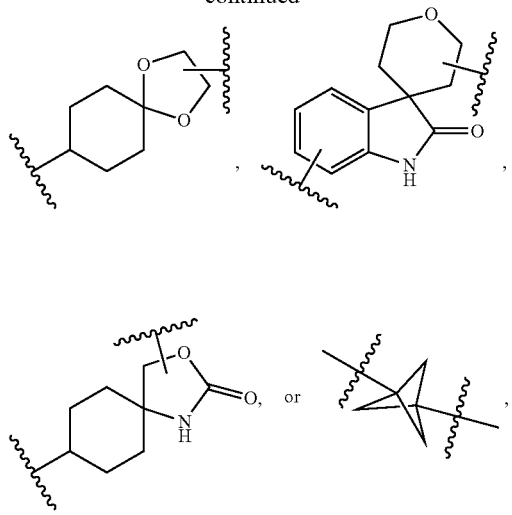

each of which is optionally substituted with 1, 2, 3, or 4 substituents independently selected from $R^{Cy}$.

In some embodiments, Cy is a linking group having the formula:

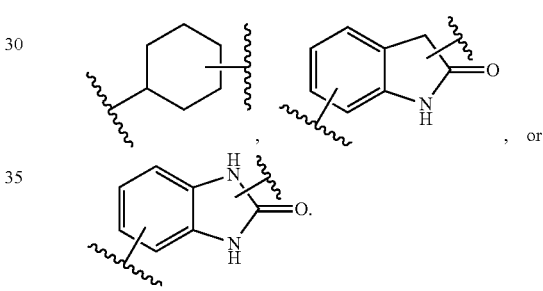

In some embodiments, Z is $Cy^2$ or $C(O)NR^{c3}R^{d3}$.

In some embodiments, each $Cy^2$ is independently selected from $C_{6-10}$ aryl, $C_{3-10}$ cycloalkyl, 5-10 membered heteroaryl, and 4-10 membered heterocycloalkyl, each of which is optionally substituted with 1, 2, 3, or 4 substituents independently selected from $R^{Cy2}$.

In some embodiments, each $Cy^2$ is independently selected from phenyl, $C_{3-10}$ cycloalkyl, 5-6 membered heteroaryl, and 4-6 membered heterocycloalkyl, each of which is optionally substituted with 1, 2, 3, or 4 substituents independently selected from $R^{Cy2}$.

In some embodiments, n is 0.

In some embodiments, n is 1.

In some embodiments, m is 0.

In some embodiments, m is 1.

In some embodiments, p is 0.

In some embodiments, p is 1.

In some embodiments, q is 0.

In some embodiments, q is 1.

In some embodiments, the compound of Formula I, or a pharmaceutically acceptable salt thereof, is a compound of Formula IIa, IIb, IIIa, or IIIb:

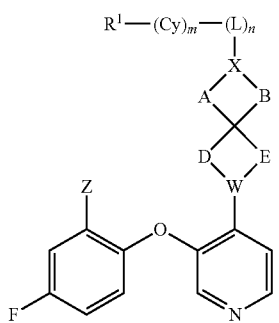
IIa
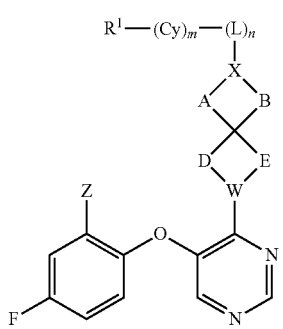
IIb
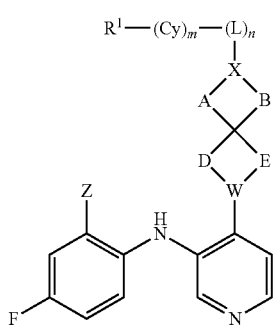
IIIa
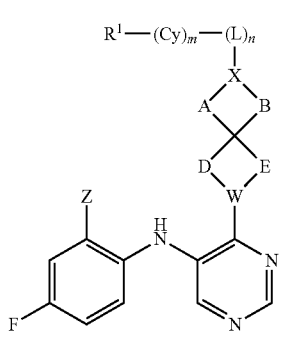
IIIb
or a pharmaceutically acceptable salt thereof.
In some embodiments, the compound of Formula I, or a pharmaceutically acceptable salt thereof, is a compound of Formula IVa, IVb, IVc, IVd, IVe, or IVf:
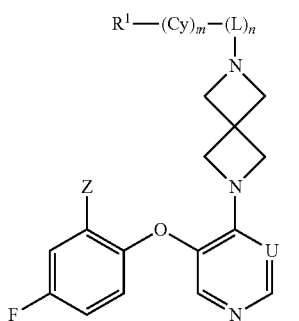
IVa
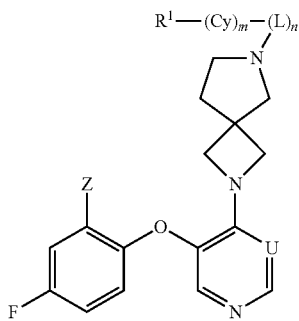
IVb
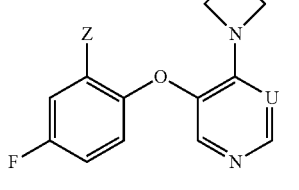
IVc
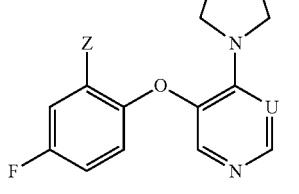
IVd
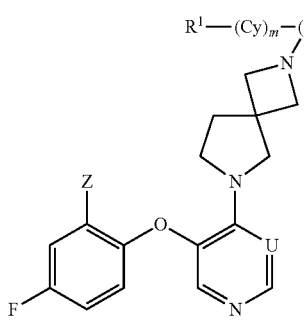
IVe -continued

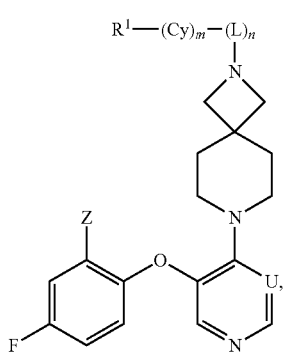

IVf or a pharmaceutically acceptable salt thereof.

In some embodiments, the compound or pharmaceutically acceptable salt of the compound of Formula I provided herein is crystalline. As used herein, "crystalline" or "crystalline form" is meant to refer to a certain lattice configuration of a crystalline substance. Different crystalline forms of the same substance typically have different crystalline lattices (e.g., unit cells) which are attributed to different physical properties that are characteristic of each of the crystalline forms. In some instances, different lattice configurations have different water or solvent content.

Different crystalline forms of the same compound or salt can have different bulk properties relating to, for example, hygroscopicity, solubility, stability, and the like. Forms with high melting points often have good thermodynamic stability which is advantageous in prolonging shelf-life drug formulations containing the solid form. Forms with lower melting points often are less thermodynamically stable, but are advantageous in that they have increased water solubility, translating to increased drug bioavailability. Forms that are weakly hygroscopic are desirable for their stability to heat and humidity and are resistant to degradation during long storage.

The different crystalline forms can be identified by solid state characterization methods such as by X-ray powder diffraction (XRPD). Other characterization methods such as differential scanning calorimetry (DSC), thermogravimetric analysis (TGA), dynamic vapor sorption (DVS), and the like further help identify the form as well as help determine stability and solvent/water content.

An XRPD pattern of reflections (peaks) is typically considered a fingerprint of a particular crystalline form. It is well known that the relative intensities of the XRPD peaks can widely vary depending on, inter alia, the sample preparation technique, crystal size distribution, various filters used, the sample mounting procedure, and the particular instrument employed. In some instances, new peaks may be observed or existing peaks may disappear, depending on the type of the instrument or the settings. As used herein, the term "peak" refers to a reflection having a relative height/intensity of at least about 5% of the maximum peak height/intensity. Moreover, instrument variation and other factors can affect the 2-theta values. Thus, peak assignments, such as those reported herein, can vary by plus or minus about 0.2° (2-theta), and the term "substantially" and "about" as used in the context of XRPD herein is meant to encompass the above-mentioned variations.

In the same way, temperature readings in connection with DSC, TGA, or other thermal experiments can vary about ±3° C. depending on the instrument, particular settings, sample preparation, etc. Accordingly, a crystalline form reported herein having a DSC thermogram "substantially" as shown in any of the Figures or the term "about" is understood to accommodate such variation.

The present invention provides crystalline forms of certain compounds, or salts thereof. In some embodiments, the compound of Formula I is 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide, or a pharmaceutically acceptable salt thereof.

Figure 5:
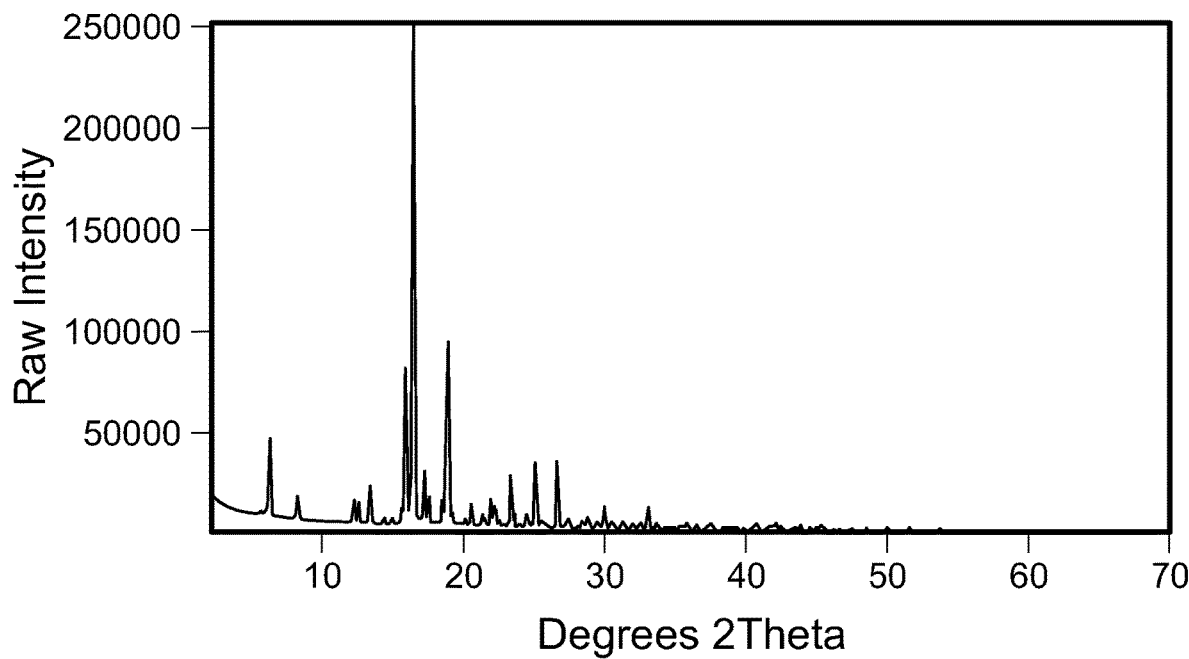
FIG. 5 shows an XRPD pattern characteristic of 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide.

In some embodiments, the present invention provides crystalline the 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide characterized, for example, by an XRPD profile substantially as shown in FIG. 5.

In some embodiments, crystalline 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide has at least one, at least two, at least three, or at least four XRPD peaks, in terms of 2-theta, selected from about 6.2°, about 8.3°, about 16.1°, about 16.6°, about 17.3°, about 19.0°, about 23.5°, about 25.3°, and about 26.9°.

In some embodiments, crystalline 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide has at least one, at least two, at least three, or at least four XRPD peaks, in terms of 2-theta, selected from about 6.2°, about 8.3°, about 16.1°, about 16.6°, and about 19.0°.

Figure 6:
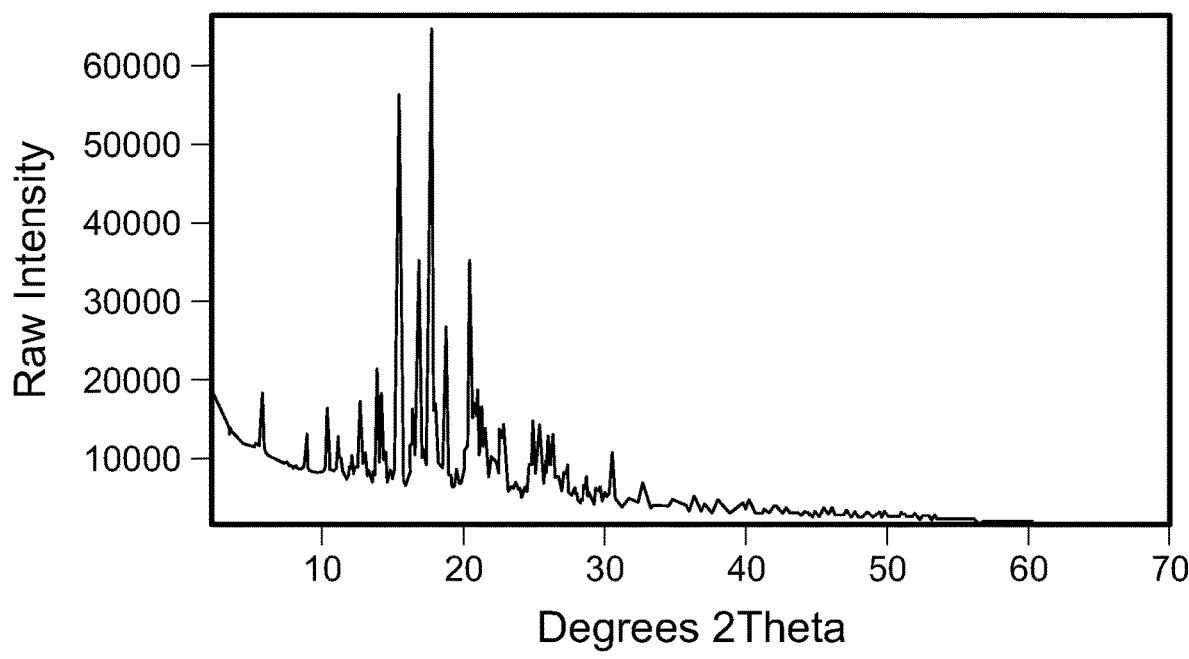
FIG. 6 shows an XRPD pattern characteristic of 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide bis-methanesulfonic acid salt.

In some embodiments, the 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide can be isolated as a bis-methanesulfonic acid salt which can be crystalline having an XRPD profile substantially as shown in FIG. 6.

In some embodiments, the crystalline form of the 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide bis-methanesulfonic acid salt has at least one, at least two, at least three, or at least four XRPD peaks, in terms of 2-theta, selected from about 5.6°, about 8.8°, about 10.2°, about 12.6°, about 13.8°, about 15.3°, about 16.2°, about 16.8°, about 17.6°, about 18.6°, about 20.3°, about 20.9°, about 21.2°, about 22.7°, and about 24.6°.

In some embodiments, the crystalline form of the 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide bis-methanesulfonic acid salt has at least one, at least two, at least three, or at least four XRPD peaks, in terms of 2-theta, selected from about 5.6°, about 8.8°, about 10.2°, about 12.6°, about 13.8°, about 15.3°, about 16.2°, about 16.8°, about 17.6°, about 18.6°, about 20.3°.

Figure 8:
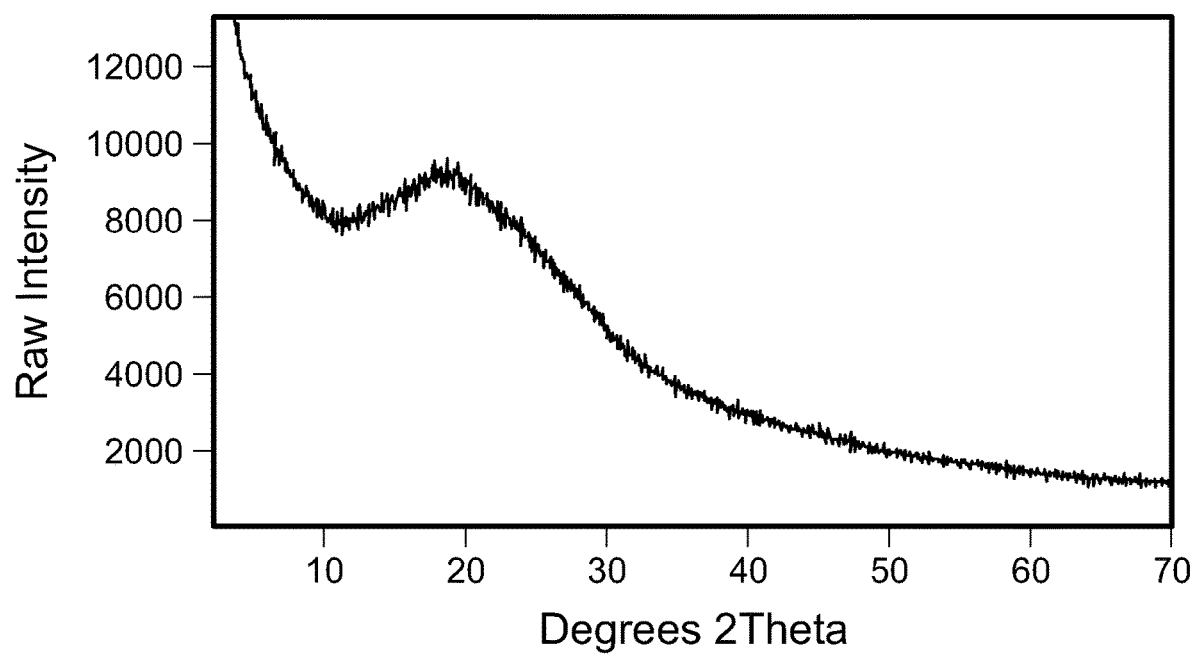
FIG. 8 shows an XRPD pattern characteristic of 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide bis-hydrochloric acid salt.

In some embodiments, the 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide can be isolated as a bis-hydrochloric acid salt which can be crystalline having an XRPD profile substantially as shown in FIG. 8.

In some embodiments, the 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide can be isolated as a fumaric acid salt, such as a sesquifumaric acid salt which can be crystalline. The crystalline sesquifumaric acid salt can be hydrated (e.g., a monohydrate), solvated (e.g., contains solvent other than water), or anhydrous and unsolvated. In some embodiments, the crystalline form of the sesquifumaric acid salt is substantially anhydrous or substantially unsolvated. In some embodiments, the crystalline form of the sesquifumaric acid salt is hydrated or solvated. In some embodiments, the crystalline form of the sesquifumaric acid salt is hydrated. In some embodiments, the crystalline form of the sesquifumaric acid salt is a monohydrate.

Figure 7:
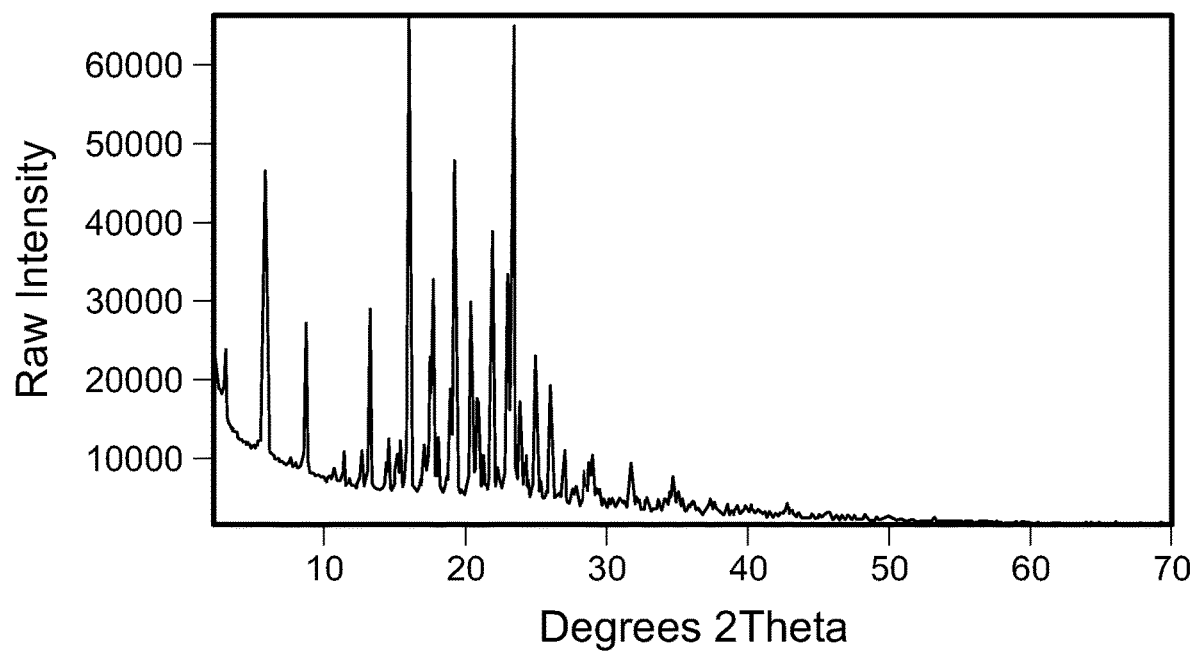
FIG. 7 shows an XRPD pattern characteristic of 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide sesquifumaric acid salt.

In some embodiments, the crystalline form of the 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide sesquifumaric acid salt has an XRPD profile substantially as shown in FIG. 7.

In some embodiments, the crystalline form of the 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide sesquifumaric acid salt has at least one, at least two, at least three, or at least four XRPD peaks, in terms of 2-theta, selected from about 2.9°, about 5.8°, about 8.7°, about 13.2°, about 16.0°, about 17.6°, about 19.1°, about 20.3°, about 20.4°, about 20.8°, about 21.8°, about 22.9°, about 23.0°, about 23.3°, about 24.9°, and about 26.0°.

In some embodiments, the crystalline form of the 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide sesquifumaric acid salt has at least one, at least two, at least three, or at least four XRPD peaks, in terms of 2-theta, selected from about 2.9°, about 5.8°, about 8.7°, about 13.2°, about 16.0°, about 17.6°, about 19.1°, about 20.3°, about 20.4°, about 20.8°, about 21.8°, about 23.0°, about 23.3°, about 24.9°, and about 26.0°.

In some embodiments, the crystalline form of the 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide sesquifumaric acid salt has at least one, at least two, at least three, or at least four XRPD peaks, in terms of 2-theta, selected from about 2.9°, about 5.8°, about 8.7°, about 13.2°, about 16.0°, about 19.1°, about 21.8°, about 24.9°, and about 26.0°.

In some embodiments, the crystalline form of the 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide sesquifumaric acid salt has at least one, at least two, at least three, or at least four XRPD peaks, in terms of 2-theta, selected from about 2.9°, about 5.8°, about 8.7°, about 13.2°, about 16.0°, about 19.1°, and about 21.8°.

In some embodiments, the crystalline form of the 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide sesquifumaric acid salt is selected from crystalline Form A, crystalline Form B, crystalline Form C, crystalline Form D, crystalline Form E, and crystalline Form F.

Figure 10:
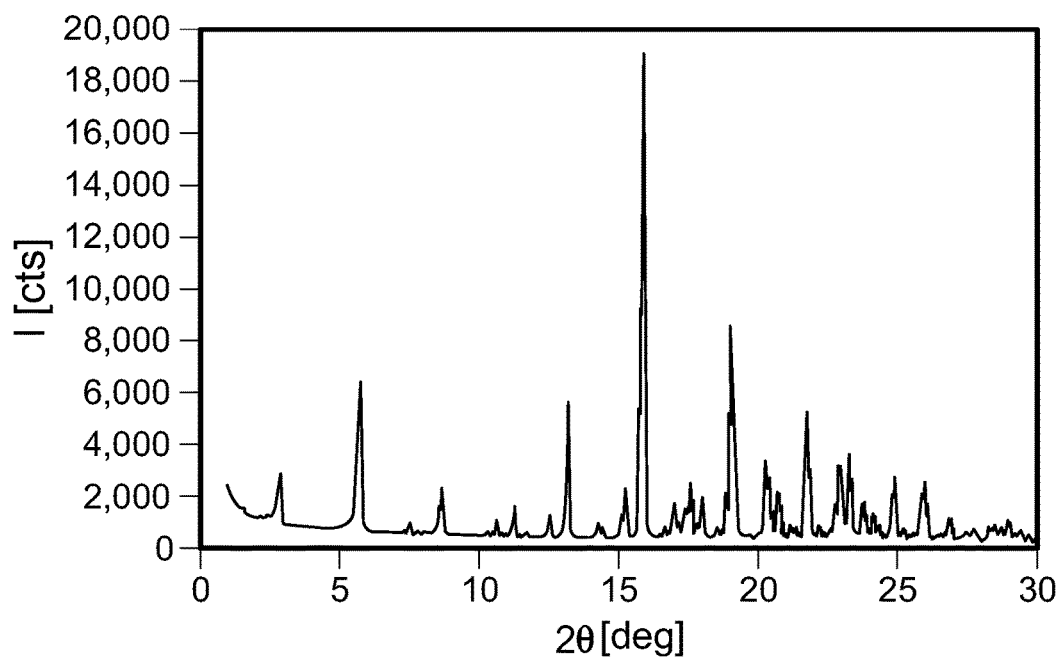
FIG. 10 shows an XRPD pattern characteristic of 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide sesquifumaric acid salt, crystalline Form A.

In some embodiments, crystalline Form A of the 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide sesquifumaric acid salt monohydrate has an XRPD profile substantially as shown in FIG. 10.

In some embodiments, crystalline Form A of the 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide sesquifumaric acid salt has at least one, at least two, at least three, or at least four XRPD peaks, in terms of 2-theta, selected from about 5.8°, about 13.2°, about 15.9°, about 19.2°, about 20.3°, about 21.8°, about 23.0°, and about 23.3°.

In some embodiments, crystalline Form A of the 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide sesquifumaric acid salt monohydrate is characterized by a DSC thermogram having an endothermic peak at about 183° C.

Figure 12:
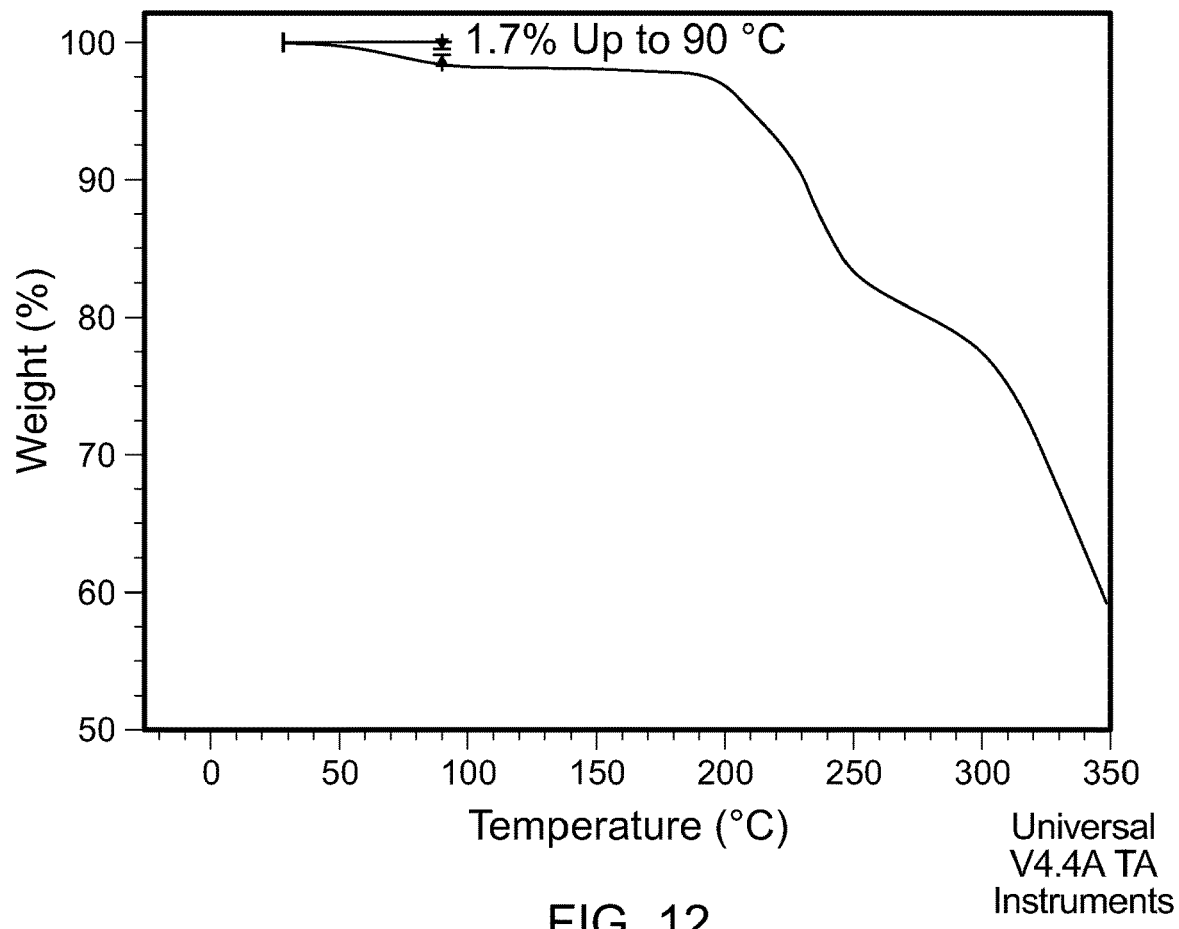
FIG. 12 shows a TGA thermogram characteristic of 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide sesquifumaric acid salt, crystalline Form A.

In some embodiments, crystalline Form A of the 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide sesquifumaric acid salt monohydrate is characterized by a thermographic analysis (TGA) substantially as shown in FIG. 12.

Figure 13:
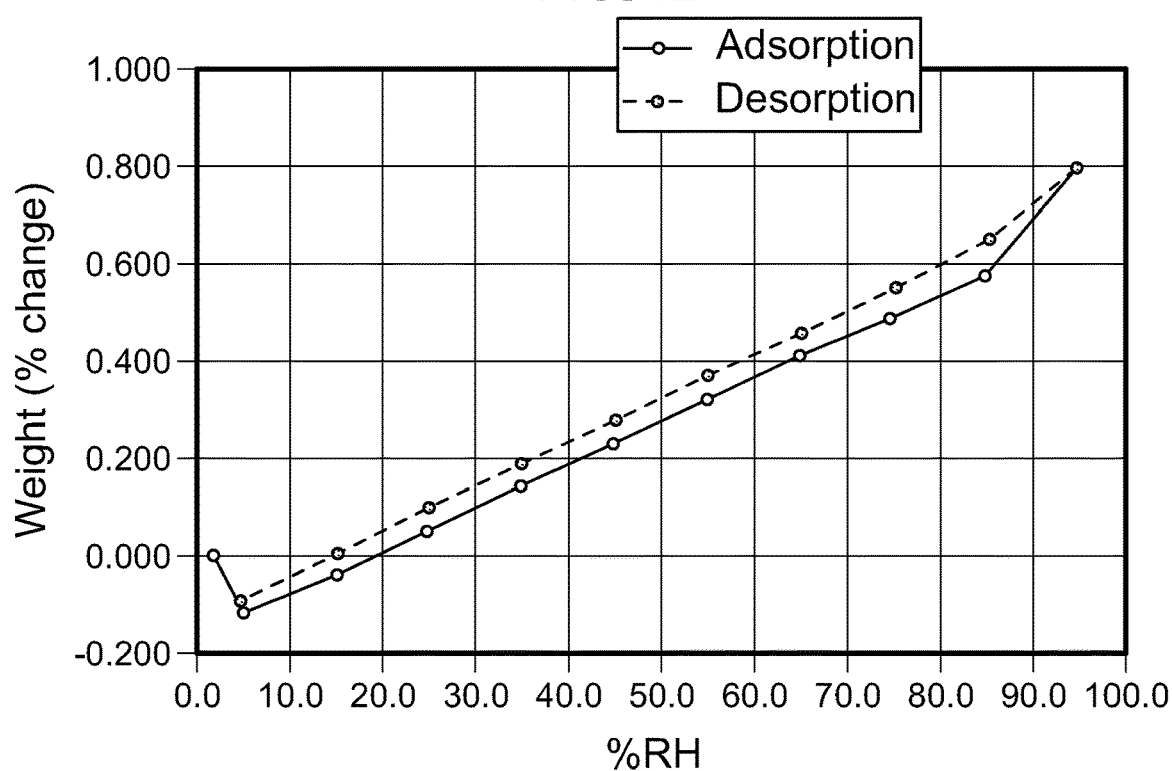
FIG. 13 shows a DVS pattern of 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide sesquifumaric acid salt, crystalline Form A.

In some embodiments, crystalline Form A of the 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide sesquifumaric acid salt monohydrate is characterized by a dynamic vapor sorption analysis substantially as shown in FIG. 13.

Figure 15:
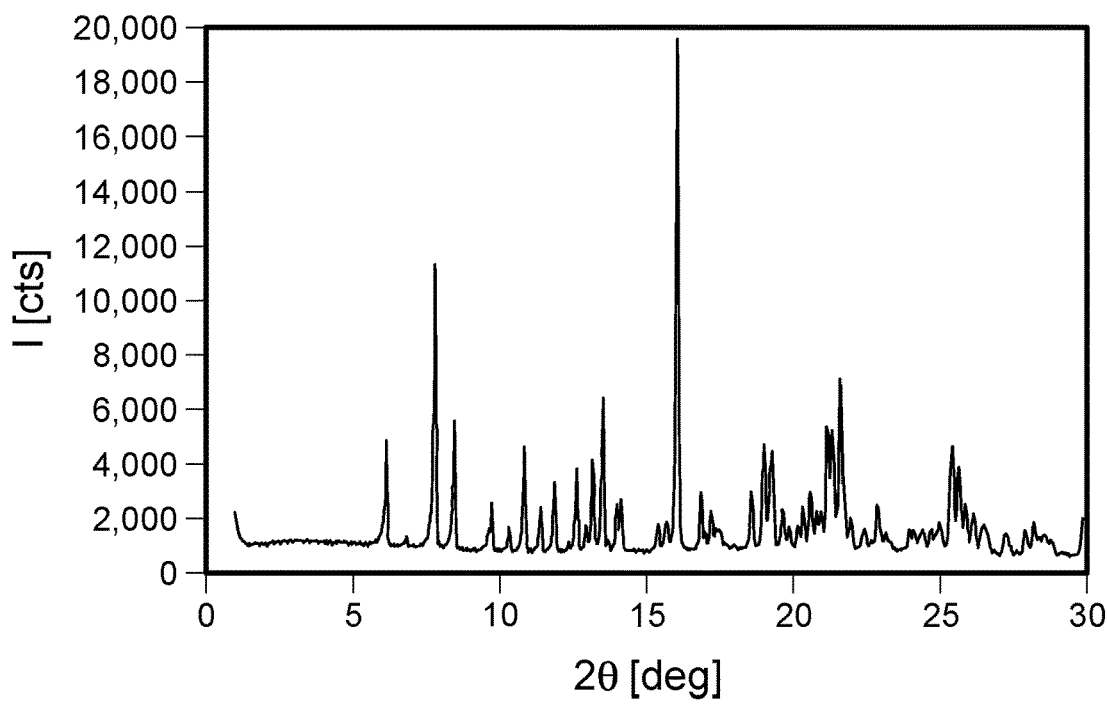
FIG. 15 shows an XRPD pattern characteristic of 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide sesquifumaric acid salt, crystalline Form B.

In some embodiments, crystalline Form B of the 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide sesquifumaric acid salt has an XRPD profile substantially as shown in FIG. 15.

In some embodiments, crystalline Form B of the 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide sesquifumaric acid salt has at least one, at least two, at least three, or at least four XRPD peaks, in terms of 2-theta, selected from about 6.2°, about 7.8°, about 8.5°, about 10.9°, about 12.6°, about 13.2°, about 13.5°, about 16.1°, about 19.0°, about 19.3°, about 21.2°, about 21.4°, and about 21.6°.

Figure 23:
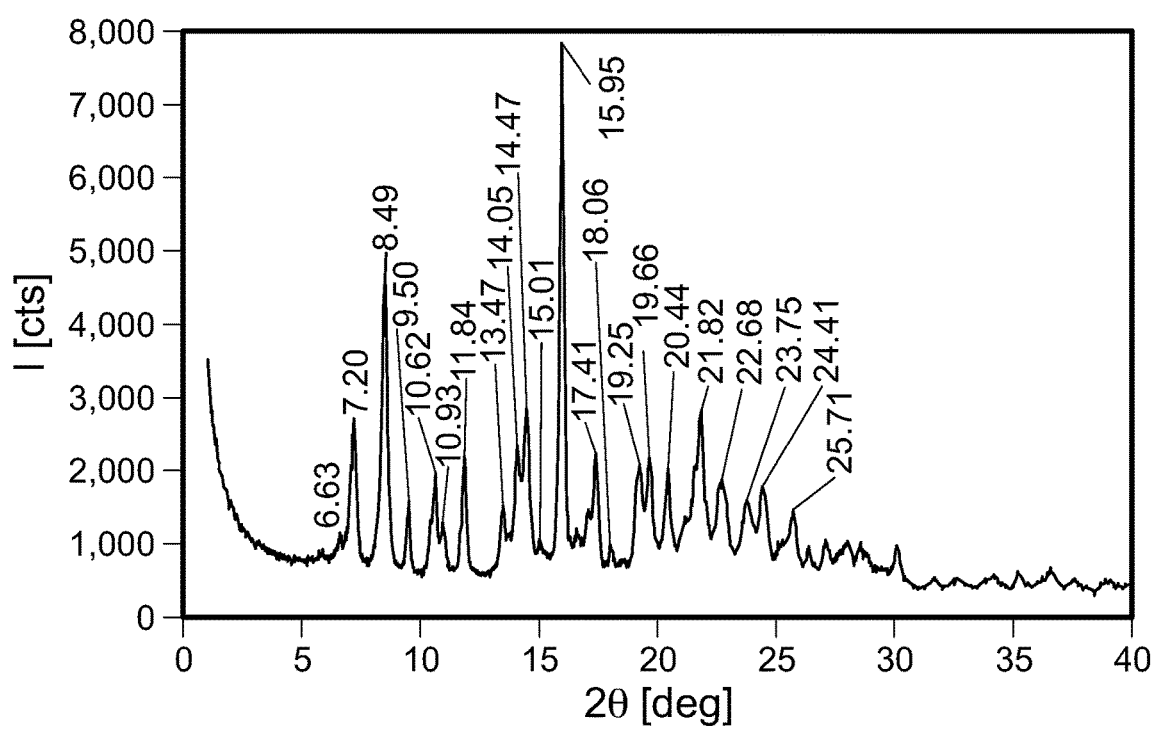
FIG. 23 shows an XRPD pattern characteristic of 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide sesquifumaric acid salt, crystalline Form D.

In some embodiments, crystalline Form D of the 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide sesquifumaric acid salt has an XRPD profile substantially as shown in FIG. 23.

In some embodiments, crystalline Form D of the 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide sesquifumaric acid salt has at least one, at least two, at least three, or at least four XRPD peaks, in terms of 2-theta, selected from about 7.2°, about 8.5°, about 11.8°, about 14.5°, about 16.0°, about 17.4°, about 19.3°, about 19.7°, and about 21.8°.

In some embodiments, crystalline Form D of the 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide sesquifumaric acid salt is characterized by a DSC thermogram having an endothermic peak at about 167° C.

Figure 18:
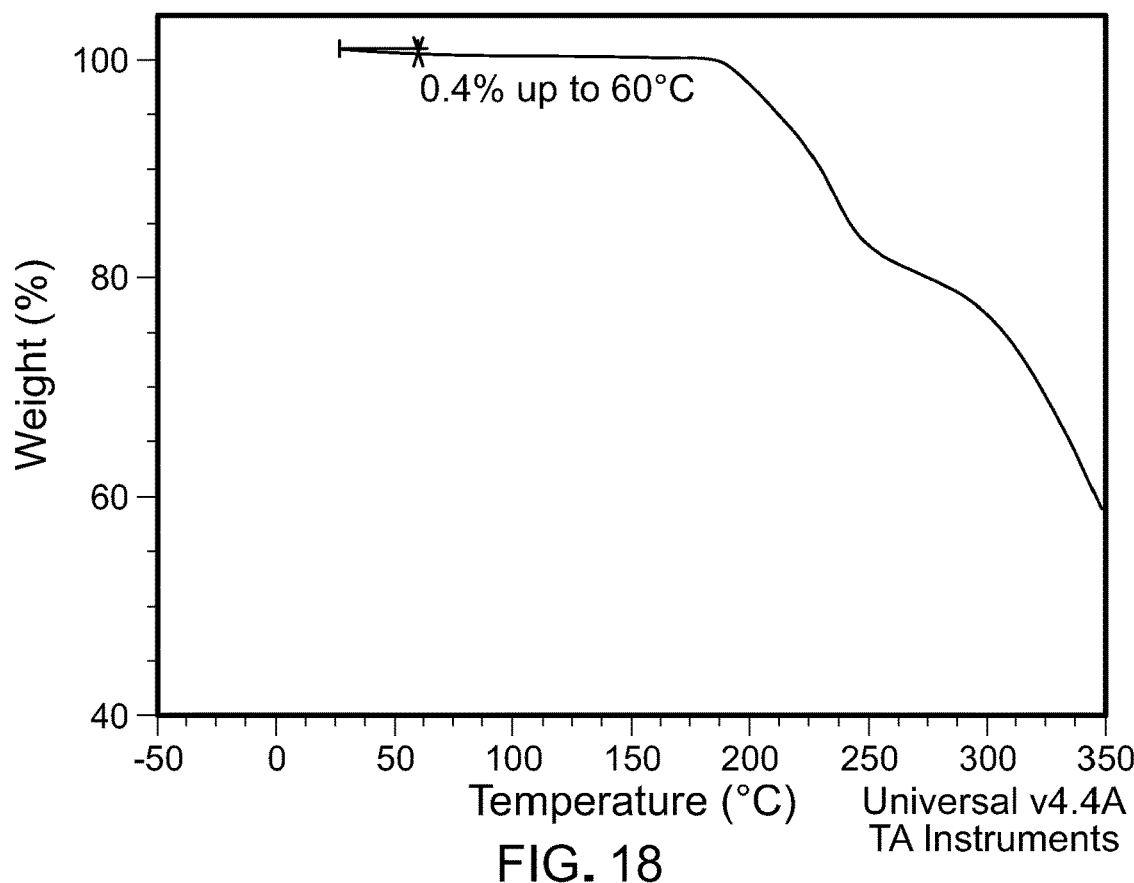
FIG. 18 shows a TGA thermogram characteristic of 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide sesquifumaric acid salt, crystalline Form D.

In some embodiments, crystalline Form D of the 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide sesquifumaric acid salt is characterized by a thermographic analysis (TGA) substantially as shown in FIG. 18.

Figure 9:
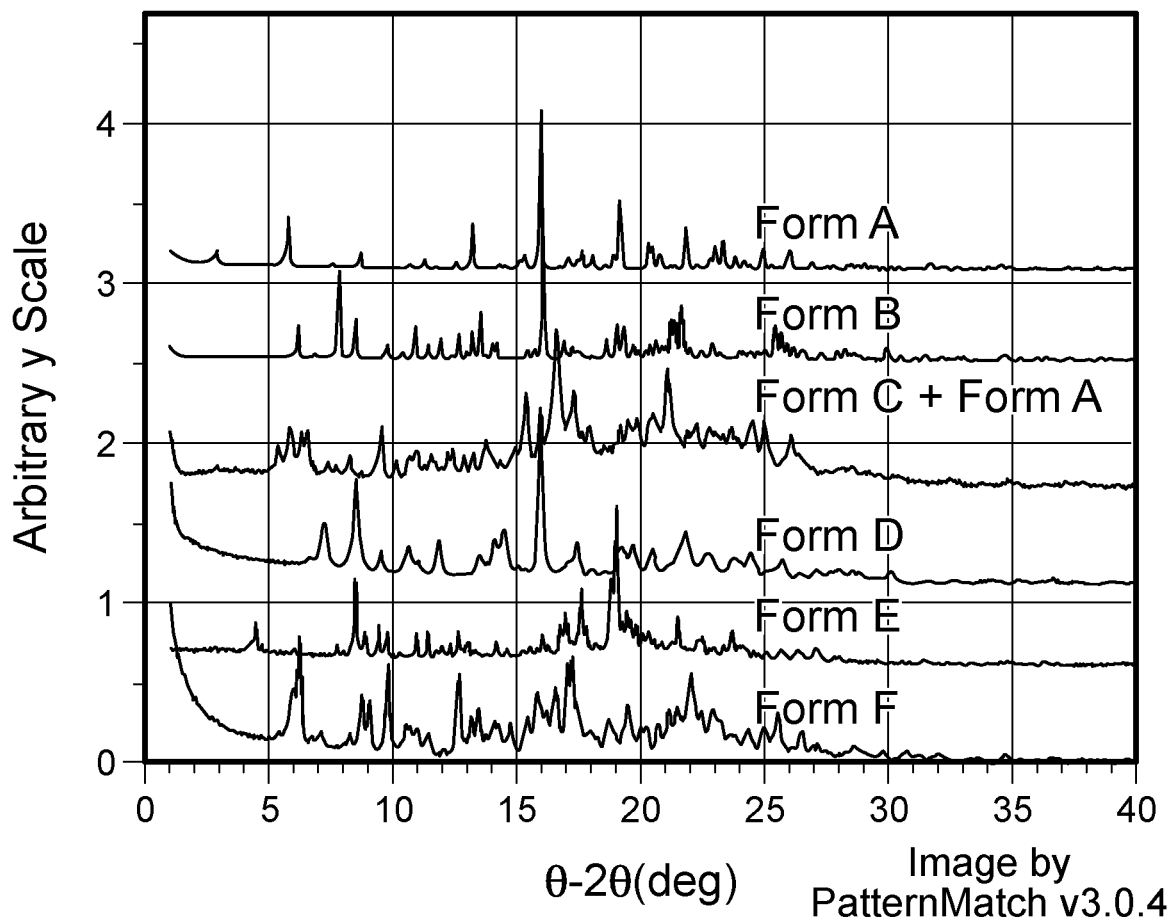
FIG. 9 shows XRPD pattern characteristics of 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide sesquifumaric acid salt, crystalline Form A, Form B, Form C+Form A, Form D, Form, E, and Form F.

In some embodiments, crystalline Form E of the 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide sesquifumaric acid salt has an XRPD profile substantially as shown in FIG. 9.

In some embodiments, the crystalline Form F of the 5-fluoro-N,N-diisopropyl-2-((4-(7-(((1r,4r)-4-(methylsulfonamido)cyclohexyl)methyl)-2,7-diazaspiro[3.5]nonan-2-yl) pyrimidin-5-yl)oxy)benzamide sesquifumaric acid salt has an XRPD profile substantially as shown in FIG. 9.

In some embodiments, the crystalline Form F of the 5-fluoro-N,N-diisopropyl-2-((4-(7-(((1r,4r)-4-(methylsulfonamido)cyclohexyl)methyl)-2,7-diazaspiro[3.5]nonan-2-yl) pyrimidin-5-yl)oxy)benzamide sesquifumaric acid salt is characterized by a thermographic analysis (TGA) substantially as shown in FIG. 18.

In some embodiments, the 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide is a benzenesulfonic acid salt (besylate) which can be crystalline.

In some embodiments, the 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide is a naphthalenedisulfonic acid (napadisylate) salt which can be crystalline. In some embodiments, the 5-fluoro-N,N-diisopropyl-2-((4-(7-(((1r,4r)-4-(methylsulfonamido)cyclohexyl)methyl)-2,7-diazaspiro[3.5]nonan-2-yl) pyrimidin-5-yl)oxy)benzamide is a naphthalene-1,5-disulfonic acid salt which can be crystalline.

In some embodiments, the 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide is a toluenesulfonic acid (tosylate) salt which can be crystalline.

The present invention further provides crystalline forms of the compound N-ethyl-2-((4-(7-(((r,4r)-4-(ethylsulfonamido)cyclohexyl)methyl)-2,7-diazaspiro[3.5]nonan-2-yl) pyrimidin-5-yl)oxy)-5-fluoro-N-isopropylbenzamide, or a pharmaceutically acceptable salt thereof.

In some embodiments, the present invention provides a crystalline form of N-ethyl-2-((4-(7-(((1r,4r)-4-(ethylsulfonamido)cyclohexyl)methyl)-2,7-diazaspiro[3.5]nonan-2-yl) pyrimidin-5-yl)oxy)-5-fluoro-N-isopropylbenzamide, having, for example, an XRPD profile substantially as shown in FIG. 1.

In some embodiments, the crystalline form of N-ethyl-2-((4-(7-(((1r,4r)-4-(ethylsulfonamido)cyclohexyl)methyl)-2,7-diazaspiro[3.5]nonan-2-yl)pyrimidin-5-yl)oxy)-5-fluoro-N-isopropylbenzamide has at least one, at least two, at least three, or at least four XRPD peaks, in terms of 2-theta, selected from about 9.7°, about 11.6°, about 12.6°, about 16.6°, about 17.5°, about 18.8°, about 19.2°, about 19.8°, about 21.0°, and about 25.3°.

In some embodiments, the N-ethyl-2-((4-(7-(((1r,4r)-4-(ethylsulfonamido)cyclohexyl)methyl)-2,7-diazaspiro[3.5]nonan-2-yl)pyrimidin-5-yl)oxy)-5-fluoro-N-isopropylbenzamide can be isolated as a fumaric acid salt, such as a sesquifumaric acid salt, which can be crystalline. In some embodiments, the crystalline form of the sesquifumaric acid salt is substantially anhydrous. In some embodiments, the crystalline form of the sesquifumaric acid salt is hydrated or solvated. In some embodiments, the crystalline form of the sesquifumaric acid salt is hydrated. In some embodiments, the crystalline form of the sesquifumaric acid salt is a monohydrate.

Figure 2:
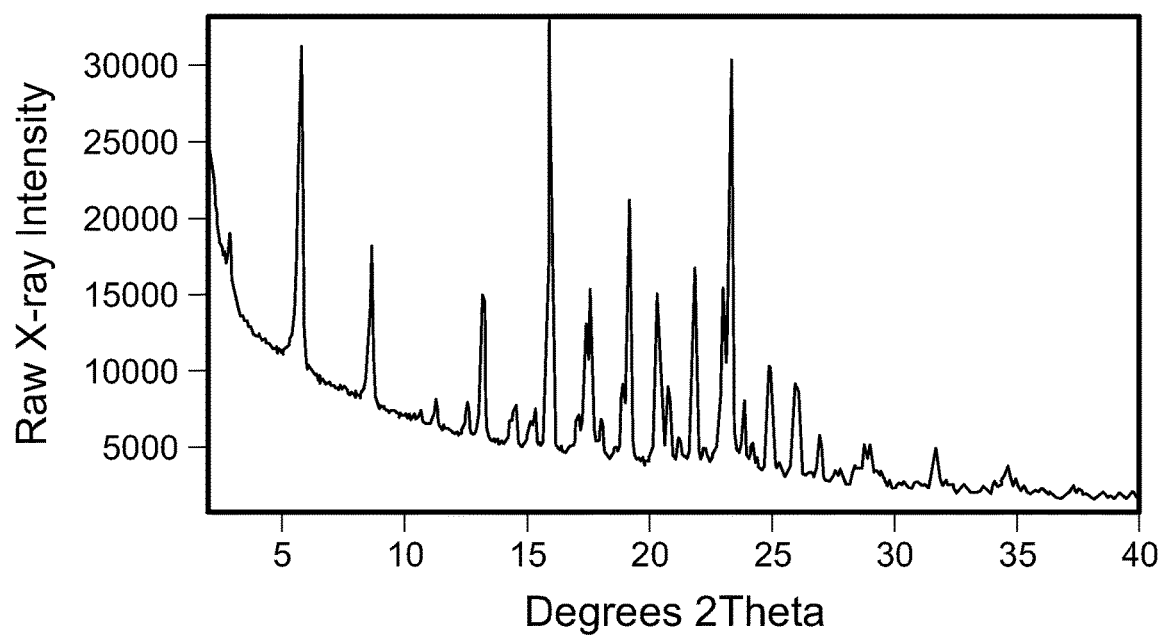
FIG. 2 shows an XRPD pattern characteristic of N-ethyl-2-((4-(7-(((1r,4r)-4-(ethyl sulfonamido)cyclohexyl)methyl)-2,7-diazaspiro[3.5]nonan-2-yl)pyrimidin-5-yl)oxy)-5-fluoro-N-isopropylbenzamide sesquifumaric acid salt.

In some embodiments, the crystalline form of the N-ethyl-2-((4-(7-(((1r,4r)-4-(ethylsulfonamido)cyclohexyl)methyl)-2,7-diazaspiro[3.5]nonan-2-yl)pyrimidin-5-yl)oxy)-5-fluoro-N-isopropylbenzamide sesquifumaric acid salt has an XRPD profile substantially as shown in FIG. 2.

In some embodiments, the crystalline form of the N-ethyl-2-((4-(7-(((1r,4r)-4-(ethylsulfonamido)cyclohexyl)methyl)-2,7-diazaspiro[3.5]nonan-2-yl)pyrimidin-5-yl)oxy)-5-fluoro-N-isopropylbenzamide sesquifumaric acid salt has at least one, at least two, at least three, or at least four XRPD peaks, in terms of 2-theta, selected from about 5.8°, about 8.7°, about 13.2°, about 16.0°, about 17.4°, about 17.6°, about 19.1°, about 20.3°, about 21.8°, about 23.0°, about 23.3°, about 24.9°, and about 26.0°.

In some embodiments, the crystalline form of the N-ethyl-2-((4-(7-(((1r,4r)-4-(ethylsulfonamido)cyclohexyl)methyl)-2,7-diazaspiro[3.5]nonan-2-yl)pyrimidin-5-yl)oxy)-5-fluoro-N-isopropylbenzamide sesquifumaric acid salt has at least one, at least two, at least three, or at least four XRPD peaks, in terms of 2-theta, selected from about 5.8°, about 8.7°, about 13.2°, about 16.0°, about 17.4°, about 17.6°, about 19.1°, about 20.3°, about 21.8°, and about 23.0θ.

In some embodiments, the crystalline form of the N-ethyl-2-((4-(7-(((1r,4r)-4-(ethylsulfonamido)cyclohexyl)methyl)-2,7-diazaspiro[3.5]nonan-2-yl)pyrimidin-5-yl)oxy)-5-fluoro-N-isopropylbenzamide sesquifumaric acid salt has at least one, at least two, at least three, or at least four XRPD peaks, in terms of 2-theta, selected from about 5.8°, about 8.7°, about 13.2°, about 16.0°, about 17.4°, about 17.6°, and about 19.1θ.

Figure 3:
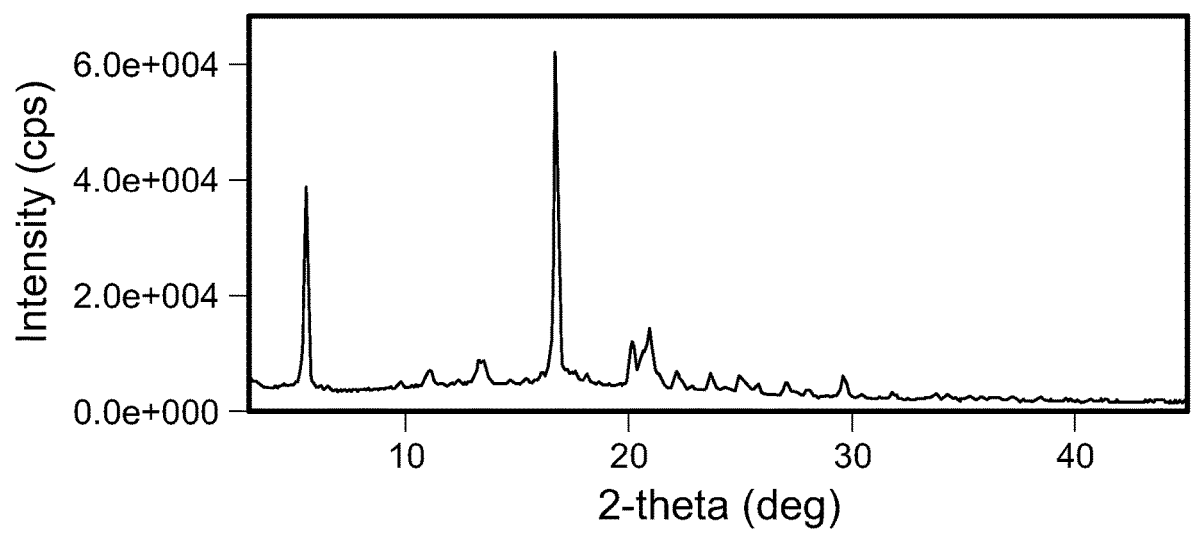
FIG. 3 shows an XRPD pattern characteristic of N-ethyl-2-((4-(7-(((1r,4r)-4-(ethylsulfonamido)cyclohexyl)methyl)-2,7-diazaspiro[3.5]nonan-2-yl)pyrimidin-5-yl)oxy)-5-fluoro-N-isopropylbenzamide bis-methanesulfonic acid salt.

In some embodiments, the N-ethyl-2-((4-(7-(((1r,4r)-4-(ethylsulfonamido)cyclohexyl)methyl)-2,7-diazaspiro[3.5]nonan-2-yl)pyrimidin-5-yl)oxy)-5-fluoro-N-isopropylbenzamide is a bis-methanesulfonic acid salt which can be crystalline, having, for example, an XRPD profile substantially as shown in FIG. 3.

In some embodiments, the crystalline form of the N-ethyl-2-((4-(7-(((1r,4r)-4-(ethylsulfonamido)cyclohexyl)methyl)-2,7-diazaspiro[3.5]nonan-2-yl)pyrimidin-5-yl)oxy)-5-fluoro-N-isopropylbenzamide bis-methanesulfonic acid salt has at least one, at least two, at least three, or at least four XRPD peaks, in terms of 2-theta, selected from about 5.6°, about 11.0°, about 13.3°, about 16.7°, about 20.1°, about 20.9°, about 22.1°, about 23.6°, about 24.9°, and about 29.6θ.

In some embodiments, the crystalline form of the N-ethyl-2-((4-(7-(((1r,4r)-4-(ethylsulfonamido)cyclohexyl)methyl)-2,7-diazaspiro[3.5]nonan-2-yl)pyrimidin-5-yl)oxy)-5-fluoro-N-isopropylbenzamide bis-methanesulfonic acid salt has at least one XRPD peak, in terms of 2-theta, selected from about 5.6° and about 16.7°.

Figure 4:
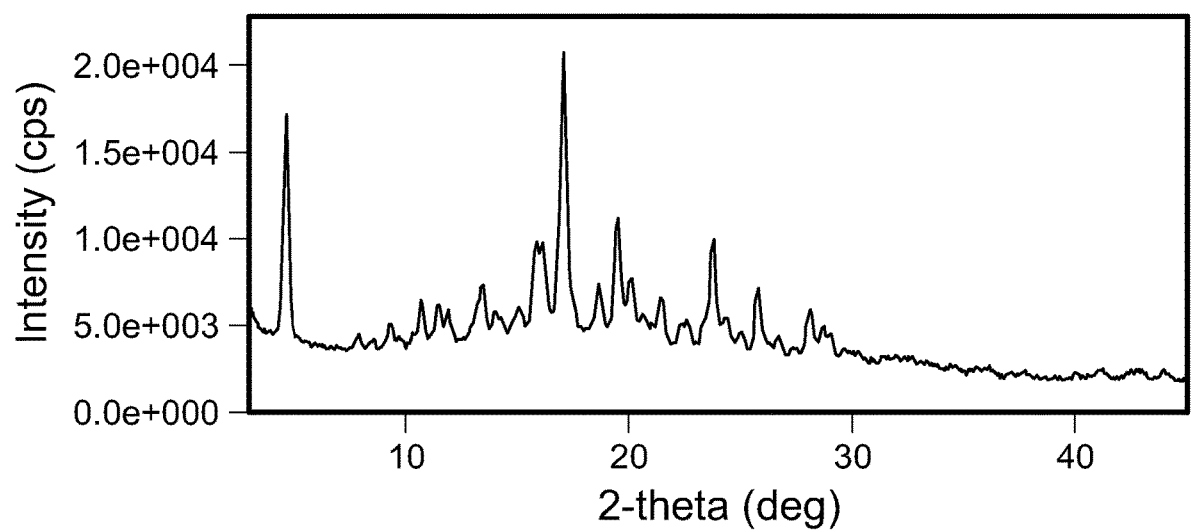
FIG. 4 shows an XRPD pattern characteristic of N-ethyl-2-((4-(7-(((1r,4r)-4-(ethylsulfonamido)cyclohexyl)methyl)-2,7-diazaspiro[3.5]nonan-2-yl)pyrimidin-5-yl)oxy)-5-fluoro-N-isopropylbenzamide bis-hydrochloric acid salt.

In some embodiments, the N-ethyl-2-((4-(7-(((1r,4r)-4-(ethylsulfonamido)cyclohexyl)methyl)-2,7-diazaspiro[3.5]nonan-2-yl)pyrimidin-5-yl)oxy)-5-fluoro-N-isopropylbenzamide is a bis-hydrochloric acid salt which can be crystalline, having, for example, an XRPD profile substantially as shown in FIG. 4.

In some embodiments, the crystalline form of the N-ethyl-2-((4-(7-(((1r,4r)-4-(ethylsulfonamido)cyclohexyl)methyl)-2,7-diazaspiro[3.5]nonan-2-yl)pyrimidin-5-yl)oxy)-5-fluoro-N-isopropylbenzamide bis-hydrochloric acid salt has at least one, at least two, at least three, or at least four XRPD peaks, in terms of 2-theta, selected from about 4.7°, about 10.7°, about 13.4°, about 15.9°, about 17.0°, about 19.5°, about 20.1°, about 23.8°, about 25.8°, and about 28.1°.

In some embodiments, the crystalline form of the N-ethyl-2-((4-(7-(((1r,4r)-4-(ethylsulfonamido)cyclohexyl)methyl)-2,7-diazaspiro[3.5]nonan-2-yl)pyrimidin-5-yl)oxy)-5-fluoro-N-isopropylbenzamide bis-hydrochloric acid salt has at least one or two XRPD peaks, in terms of 2-theta, selected from about 4.7°, about 17.0°, and about 19.5°.

It is appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

As used herein, the phrase "optionally substituted" means unsubstituted or substituted. As used herein, the term "substituted" means that a hydrogen atom is removed and replaced by a substituent. The term "substituted" may also mean that two hydrogen atoms are removed and replaced by a divalent substituent such as an oxo or sulfide group. It is to be understood that substitution at a given atom is limited by valency.

At various places in the present specification, substituents of compounds of the invention are disclosed in groups or in ranges. It is specifically intended that the invention include each and every individual subcombination of the members of such groups and ranges. For example, the term "$C_{1-6}$ alkyl" is specifically intended to individually disclose methyl, ethyl, $C_3$ alkyl, $C_4$ alkyl, $C_5$ alkyl, and $C_6$ alkyl.

The term "z-membered" (where z is an integer) typically describes the number of ring-forming atoms in a moiety where the number of ring-forming atoms is z. For example, piperidinyl is an example of a 6-membered heterocycloalkyl ring, pyrazolyl is an example of a 5-membered heteroaryl ring, pyridyl is an example of a 6-membered heteroaryl ring, and 1, 2, 3, 4-tetrahydro-naphthalene is an example of a 10-membered cycloalkyl group.

At various places in the present specification, linking substituents are described. It is specifically intended that each linking substituent include both the forward and backward forms of the linking substituent. For example, —NR(CR'R")$_n$— includes both —NR(CR'R")$_n$— and —(CR'R")$_n$NR—. Where the structure clearly requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

At various places in the present specification various aryl, heteroaryl, cycloalkyl, and heterocycloalkyl rings are described. Unless otherwise specified, these rings can be attached to the rest of the molecule at any ring member as permitted by valency. For example, the term "a pyridine ring" or "pyridinyl" may refer to a pyridin-2-yl, pyridin-3-yl, or pyridin-4-yl ring.

For compounds of the invention in which a variable appears more than once, each variable can be a different moiety independently selected from the group defining the variable. For example, where a structure is described having two R groups that are simultaneously present on the same compound, the two R groups can represent different moieties independently selected from the group defined for R.

As used herein, the term "$C_{i-j}$ alkyl," employed alone or in combination with other terms, refers to a saturated hydrocarbon group that may be straight-chain or branched, having i to j carbons. In some embodiments, the alkyl group contains from 1 to 6 carbon atoms, or from 1 to 4 carbon atoms, or from 1 to 3 carbon atoms. Examples of alkyl moieties include, but are not limited to, chemical groups such as methyl, ethyl, n-propyl, isopropyl, n-butyl, s-butyl, and t-butyl. In some embodiments, where an alkyl group is a linking group, it may be referred to as "$C_{i-j}$ alkylene."

As used herein, the term "$C_{i-j}$ alkoxy," employed alone or in combination with other terms, refers to a group of formula —O-alkyl, wherein the alkyl group has i to j carbons. Example alkoxy groups include methoxy, ethoxy, and propoxy (e.g., n-propoxy and isopropoxy). In some embodiments, the alkyl group has 1 to 3 carbon atoms.

As used herein, "$C_{i-j}$ alkenyl," employed alone or in combination with other terms, refers to an unsaturated hydrocarbon group having one or more double carbon-carbon bonds and having i to j carbons. In some embodiments, the alkenyl moiety contains 2 to 6 or 2 to 4 carbon atoms. Example alkenyl groups include, but are not limited to, ethenyl, n-propenyl, isopropenyl, n-butenyl, sec-butenyl, and the like.

As used herein, "$C_{i-j}$ alkynyl," employed alone or in combination with other terms, refers to an unsaturated hydrocarbon group having one or more triple carbon-carbon bonds and having i to j carbons. Example alkynyl groups include, but are not limited to, ethynyl, propyn-1-yl, propyn-2-yl, and the like. In some embodiments, the alkynyl moiety contains 2 to 6 or 2 to 4 carbon atoms.

As used herein, the term "$C_{i-j}$ alkylamino," employed alone or in combination with other terms, refers to a group of formula —NH(alkyl), wherein the alkyl group has i to j carbon atoms. In some embodiments, the alkyl group has 1 to 6 or 1 to 4 carbon atoms.

As used herein, the term "di-$C_{i-j}$-alkylamino," employed alone or in combination with other terms, refers to a group of formula —N(alkyl)$_2$, wherein each of the two alkyl groups has, independently, i to j carbon atoms. In some embodiments, each alkyl group independently has 1 to 6 or 1 to 4 carbon atoms. In some embodiments, the dialkylamino group is —N($C_{1-4}$ alkyl)$_2$ such as, for example, dimethylamino or diethylamino.

As used herein, the term "$C_{i-j}$ alkylthio," employed alone or in combination with other terms, refers to a group of formula —S-alkyl, wherein the alkyl group has i to j carbon atoms. In some embodiments, the alkyl group has 1 to 6 or 1 to 4 carbon atoms. In some embodiments, the alkylthio group is $C_{1-4}$ alkylthio such as, for example, methylthio or ethylthio.

As used herein, the term "thiol," employed alone or in combination with other terms, refers to —SH.

As used herein, the term "amino," employed alone or in combination with other terms, refers to a group of formula —NH$_2$.

As used herein, "$C_{i-j}$ haloalkoxy," employed alone or in combination with other terms, refers to a group of formula —O-haloalkyl having i to j carbon atoms. An example haloalkoxy group is OCF$_3$. An additional example haloalkoxy group is OCHF$_2$. In some embodiments, the haloalkoxy group is fluorinated only. In some embodiments, the alkyl group has 1 to 6 or 1 to 4 carbon atoms. In some embodiments, the haloalkoxy group is $C_{1-4}$ haloalkoxy.

As used herein, the term "halo," employed alone or in combination with other terms, refers to a halogen atom selected from F, Cl, I or Br. In some embodiments, "halo" refers to a halogen atom selected from F, Cl, or Br. In some embodiments, the halo substituent is F.

As used herein, the term "$C_{i-j}$ haloalkyl," employed alone or in combination with other terms, refers to an alkyl group having from one halogen atom to 2s+1 halogen atoms which may be the same or different, where "s" is the number of carbon atoms in the alkyl group, wherein the alkyl group has i to j carbon atoms. In some embodiments, the haloalkyl group is fluorinated only. In some embodiments, the haloalkyl group is fluoromethyl, difluoromethyl, or trifluoromethyl. In some embodiments, the haloalkyl group is trifluoromethyl. In some embodiments, the haloalkyl group is 2,2,2-trifluoroethyl. In some embodiments, the haloalkyl group is 2,2-difluoroethyl. In some embodiments, the haloalkyl group has 1 to 6 or 1 to 4 carbon atoms.

As used herein, "$C_{i-j}$ cyanoalkyl," employed alone or in combination with other terms, refers to a group of formula CN—($C_{i-j}$ alkyl)-.

As used herein, the term "aryl," employed alone or in combination with other terms, refers to a monocyclic or polycyclic (e.g., having 2, 3 or 4 fused rings) aromatic hydrocarbon, such as, but not limited to, phenyl, 1-naphthyl, 2-naphthyl, anthracenyl, phenanthrenyl, and the like. In some embodiments, aryl is $C_{6-10}$ aryl. In some embodiments, aryl is $C_{6-14}$ aryl. In some embodiments, the aryl group is a naphthalene ring or phenyl ring. In some embodiments, the aryl group is phenyl.

As used herein, the term "$C_{i-j}$ cycloalkyl," employed alone or in combination with other terms, refers to a non-aromatic cyclic hydrocarbon moiety having i to j ring-forming carbon atoms, which may optionally contain one or more alkenylene groups as part of the ring structure. Cycloalkyl groups can include mono- or polycyclic ring systems. Polycyclic ring systems can include fused ring systems and spirocycles. Also included in the definition of cycloalkyl are moieties that have one or more aromatic rings fused (i.e., having a bond in common with) to the cycloalkyl ring, for example, benzo or pyrido derivatives of cyclopentane, cyclopentene, cyclohexane, and the like. A heterocycloalkyl group that includes a fused aromatic (e.g., aryl or heteroaryl) moiety can be attached to the molecule through an atom from either the aromatic or non-aromatic portion. One or more ring-forming carbon atoms of a cycloalkyl group can be oxidized to form carbonyl linkages. In some embodiments, cycloalkyl is $C_{3-10}$ cycloalkyl, $C_{3-7}$ cycloalkyl, or $C_{5-6}$ cycloalkyl. Exemplary cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, and the like. Further exemplary cycloalkyl groups include cyclopropyl, cyclobutyl, cyclopentyl, and cyclohexyl. Additional example cycloalkyl groups, where the cycloalkyl group has a fused aryl or heteroaryl moiety, include tetrahydronaphthalen-2-yl, 2,3-dihydro-1H-inden-2-yl; 2,3,4,9-tetrahydro-1H-carbazol-7-yl; 2,6,7,8-tetrahydrobenzo[cd]indazol-4-yl; and 5,6,7,8,9,10-hexahydrocyclohepta[b]indol-3-yl.

As used herein, the term "heteroaryl," employed alone or in combination with other terms, refers to a monocyclic or polycyclic (e.g., having 2, 3 or 4 fused rings) aromatic heterocylic moiety, having one or more heteroatom ring members selected from nitrogen, sulfur and oxygen. In some embodiments, the heteroaryl group has 1, 2, 3, or 4 heteroatom ring members. In some embodiments, the heteroaryl group has 1, 2, or 3 heteroatom ring members. In some embodiments, the heteroaryl group has 1 or 2 heteroatom ring members. In some embodiments, the heteroaryl group has 1 heteroatom ring member. In some embodiments, the heteroaryl group is 5- to 10-membered or 5- to 6-membered. In some embodiments, the heteroaryl group is 5-membered. In some embodiments, the heteroaryl group is 6-membered. In some embodiments, the heteroaryl group is 9- or 10-membered bicyclic. In some embodiments, the heteroaryl is 9-member bicyclic. When the heteroaryl group contains more than one heteroatom ring member, the heteroatoms may be the same or different. The nitrogen atoms in the ring(s) of the heteroaryl group can be oxidized to form N-oxides. Example heteroaryl groups include, but are not limited to, pyridinyl, pyrimidinyl, pyrazinyl, pyridazinyl, pyrrolyl, pyrazolyl, azolyl, oxazolyl, isoxazolyl, thiazolyl, isothiazolyl, imidazolyl, furanyl, thiophenyl, triazolyl, tetrazolyl, thiadiazolyl, quinolinyl, isoquinolinyl, indolyl, benzothiopheneyl, benzofuranyl, benzisoxazolyl, benzoimidazolyl, imidazo[1, 2-b]thiazolyl, purinyl, triazinyl, and the like. In some embodiments, the heteroaryl group is 9H-carbazol-2-yl; 1H-benzo[d]imidazol-6-yl; 1H-indol-6-yl; 1H-indazol-6-yl; 2H-indazol-4-yl; 1H-benzo[d][1,2,3]triazol-6-yl; benzo[d]oxazol-2-yl; quinolin-6-yl; or benzo[d]thiazol-2-yl.

As used herein, the term "heterocycloalkyl," employed alone or in combination with other terms, refers to a non-aromatic heterocyclic ring system, which may optionally contain one or more unsaturations as part of the ring structure, and which has at least one heteroatom ring member independently selected from nitrogen, sulfur and oxygen. In some embodiments, the heterocycloalkyl group has 1, 2, 3, or 4 heteroatom ring members. In some embodiments, the heterocycloalkyl group has 1, 2, or 3 heteroatom ring members. In some embodiments, the heterocycloalkyl group has 1 or 2 heteroatom ring members. In some embodiments, the heterocycloalkyl group has 1 heteroatom ring member. When the heterocycloalkyl group contains more than one heteroatom in the ring, the heteroatoms may be the same or different. Example ring-forming members include CH, $CH_2$, C(O), N, NH, O, S, S(O), and $S(O)_2$. Heterocycloalkyl groups can include mono- or polycyclic (e.g., having 2, 3 or 4 fused rings) ring systems. Polycyclic rings can include both fused systems and spirocycles. Also included in the definition of heterocycloalkyl are moieties that have one or more aromatic rings fused (i.e., having a bond in common with) to the non-aromatic ring, for example, 1, 2, 3, 4-tetrahydro-quinoline, dihydrobenzofuran and the like. A heterocycloalkyl group that includes a fused aromatic moiety can be attached to the molecule through an atom from either the aromatic or non-aromatic portion. The carbon atoms or heteroatoms in the ring(s) of the heterocycloalkyl group can be oxidized to form a carbonyl, sulfinyl, or sulfonyl group (or other oxidized linkage) or a nitrogen atom can be quaternized. In some embodiments, heterocycloalkyl is 5- to 10-membered, 4- to 10-membered, 4- to 7-membered, 5-membered, or 6-membered. Examples of heterocycloalkyl groups include 1, 2, 3, 4-tetrahydro-quinolinyl, dihydrobenzofuranyl, azetidinyl, azepanyl, pyrrolidinyl, piperidinyl, piperazinyl, morpholinyl, thiomorpholinyl, and pyranyl. Examples of heterocycloalkyl groups that include one or more fused aromatic groups (e.g., aryl or heteroaryl) include N-(2'-oxospiro[cyclohexane-1,3'-indolin]-6'-yl; 1,2,3,4-tetrahydroisoquinolin-6-yl; 2,3-dihydro-1H-benzo[d]imidazol-5-yl; 1,3-dihydrospiro[indene-2,3'-indolin]-6'-yl; 2,3-dihydrobenzo[d]oxazol-5-yl; 1,2-dihydroquinolin-7-yl; indolin-6-yl; spiro[cyclopentane-1,3'-indolin]-6'-yl; spiro[cyclohexane-1,3'-indolin]-6'-yl; chroman-6-yl; 3,4-dihydro-2H-benzo[b][1,4]oxazin-6-yl; and benzo[d][1,3]dioxol-5-yl.

As used herein, the term "arylalkyl," employed alone or in combination with other terms, refers to an alkyl group substituted by an aryl group.

As used herein, the term "cycloalkylalkyl," employed alone or in combination with other terms, refers to an alkyl group substituted by a cycloalkyl group.

As used herein, the term "heteroarylalkyl," employed alone or in combination with other terms, refers to an alkyl group substituted by a heteroaryl group.

As used herein, the term "hetercycloalkylalkyl," employed alone or in combination with other terms, refers to an alkyl group substituted by a heterocycloalkyl group.

As used herein, the term "$C_{i-j}$ alkylsulfinyl," employed alone or in combination with other terms, refers to a group of formulat —S(=O)—($C_{i-j}$ alkyl).

As used herein, the term "$C_{i-j}$ alkylsulfinyl," employed alone or in combination with other terms, refers to a group of formulat —S(=O)$_2$—($C_{i-j}$ alkyl).

As used herein, the term "carboxy," employed alone or in combination with other terms, refers to a —C(=O)OH group.

As used herein, the term "$C_{i-j}$ alkylcarbonyl," employed alone or in combination with other terms, refers to a group of formula —C(=O)—($C_{i-j}$ alkyl).

As used herein, the term "$C_{i-j}$ alkoxycarbonyl," employed alone or in combination with other terms, refers to a group of formula —C(=O)O—($C_{i-j}$ alkyl).

As used herein, the term "aminocarbonyl," employed alone or in combination with other terms, refers to a group of formula —C(=O)NH$_2$.

The compounds described herein can be asymmetric (e.g., having one or more stereocenters). All stereoisomers, such as enantiomers and diastereoisomers, are intended unless otherwise indicated. Where a compound name or structure is silent with respect to the stereochemistry of a stereocenter, all possible configurations at the stereocenter are intended. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Geometric isomers of olefins, C=N double bonds, and the like can also be present in the compounds described herein, and all such stable isomers are contemplated in the present invention. Cis and trans geometric isomers of the compounds of the present invention are described and may be isolated as a mixture of isomers or as separated isomeric forms.

When the compounds of the invention contain a chiral center, the compounds can be any of the possible stereoisomers. In compounds with a single chiral center, the stereochemistry of the chiral center can be (R) or (S). In compounds with two chiral centers, the stereochemistry of the chiral centers can each be independently (R) or (S) so the configuration of the chiral centers can be (R) and (R), (R) and (S); (S) and (R), or (S) and (S). In compounds with three chiral centers, the stereochemistry each of the three chiral centers can each be independently (R) or (S) so the configuration of the chiral centers can be (R), (R) and (R); (R), (R) and (S); (R), (S) and (R); (R), (S) and (S); (S), (R) and (R); (S), (R) and (S); (S), (S) and (R); or (S), (S) and (S).

Resolution of racemic mixtures of compounds can be carried out by any of numerous methods known in the art. An example method includes fractional recrystallization using a chiral resolving acid which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereoisomerically pure forms), 2-phenylglycinol, norephedrine, ephedrine, N-methylephedrine, cyclohexylethylamine, 1, 2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

When a disclosed compound is named or depicted without indicating the stereochemistry of one or more stereocenters, each of the stereoisomers resulting from the possible stereochemistries at the undefined stereocenter(s) are intended to be encompassed. For example, if a stereocenter is not designated as R or S, then either or both are intended.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, amide-imidic acid pairs, enamine-imine pairs, and annular forms where a proton can occupy two or more positions of a heterocyclic system, for example, 1H- and 3H-imidazole, 1H-, 2H- and 4H-1, 2, 4-triazole, 1H- and 2H-isoindole, and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. Isotopes of constituent atoms of the compounds of the invention can be present in natural or non-natural abundance. Examples of isotopes of hydrogen include deuterium and tritium. In some embodiments, the compounds of the invention are deuterated, meaning at least one deuterium atom is present in the place of a hydrogen atom. In some embodiments, 1, 2, 3, 4, 5, 6, 7, or 8 hydrogens in a compound of the invention are replaced by deuterium. Methods for replacing hydrogen with deuterium in a molecule are known in the art.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified (e.g., in the case of purine rings, unless otherwise indicated, when the compound name or structure has the 9H tautomer, it is understood that the 7H tautomer is also encompassed).

All compounds, and pharmaceutically acceptable salts thereof, can be found together with other substances such as water and solvents (e.g., hydrates and solvates) or can be isolated.

In some embodiments, the compounds of the invention, or salts thereof, or crystalline forms of any of the aforementioned, are purified or substantially isolated. By "substantially isolated" is meant that the compound is at least partially or substantially separated from the environment in which it was formed or detected. Partial separation can include, for example, a composition enriched in a compound of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof. In some embodiments, the compounds of the invention, or salts thereof, or crystalline forms of any of the aforementioned, can be prepared with a purity of about 75% or more, 80% or more, 85% or more, 90% or more, 95% or more, 98% or more, or 99% or more.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions, "ambient temperature" and "room temperature," as used herein, are understood in the art, and refer generally to a temperature, e.g., a reaction temperature, that is about the temperature of the room in which the reaction is carried out, for example, a temperature from about 20° C. to about 30° C.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (MeCN) are preferred. Lists of suitable salts are found in *Remington's Pharmaceutical Sciences*, 17$^{th}$ Ed., (Mack Publishing Company, Easton, 1985), p. 1418, Berge et al., *J. Pharm. Sci.,* 1977, 66(1), 1-19, and in Stahl et al., *Handbook of Pharmaceutical Salts: Properties, Selection, and Use*, (Wiley, 2002).

As used herein the terms "subject" and "patient" may be used interchangeably, and means a mammal in need of treatment, e.g., companion animals (e.g., dogs, cats, and the like), farm animals (e.g., cows, pigs, horses, sheep, goats and the like) and laboratory animals (e.g., rats, mice, guinea pigs and the like). Typically, the subject or patient is a human in need of treatment.

Synthesis

Compounds of the invention, including salts thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups ("Pg"), can be readily determined by one skilled in the art. The chemistry of protecting groups ("Pg") can be found, for example, in P. G. M. Wuts and T. W. Greene, *Protective Groups in Organic Synthesis*, 4$^{th}$ Ed., Wiley & Sons, Inc., New York (2006), which is incorporated herein by reference in its entirety.

Compounds of the invention can be prepared employing conventional methods that utilize readily available reagents and starting materials. The reagents used in the preparation of the intermediates of this invention can be either commercially obtained or can be prepared by standard procedures described in the literature. Various technologies such as solid phase chemistry, microwave chemistry or flow chemistry etc., can also be utilized to synthesize intermediates or final compounds. Furthermore, other methods of preparing compounds of the invention will be readily apparent to person of ordinary skill in the art in light of the following reaction and schemes and examples. Unless otherwise indicated all the variables are defined below. Suitable method of synthesis are described in the following references: March, *Advanced Organic Chemistry*, 3$^{rd}$ edition, John Wiley & Sons, 1985; Greene and Wuts, *Protective Groups in Organic Chemistry*, 2$^{nd}$ edition, John Wiley & Sons 1991; and Larock, *Comprehensive Organic Transformations*, 4$^{th}$ edition, VCH publishers Inc., 1989. Furthermore, in any one synthesis, one or more of the reagents, intermediates or chemicals may be used in excess amount to ensure the completion of reaction. Suitable reaction temperatures generally range from about 0° C. to about the boiling point of the solvent. More typically, temperatures are sufficiently high to allow refluxing, for example, about 68° C. for tetrahydrofuran. In some cases, such as microwave conditions, the temperature of the reaction may exceed the boiling point of the solvent.

The compounds of the invention can be synthesized by the methods described in Schemes 1-3 below. Many of the synthetic steps are well described in as in F. A. Carey, R. J. Sundberg, *Advanced Organic Chemistry*, 2$^{nd}$ ed., Plenum publication in 1983. The synthesis of various hydroxyl-substituted heterocycles is well documented in the literature and can be synthesized by known literature methods. The general synthesis of useful heterocyclic rings are referenced in *The Handbook of Heterocyclic Chemistry*, Alan R. Katritzky; Pergamon Press, NY, USA, 1st ed. 1986. The depicted intermediates may also be available as commercial reagents from numerous vendors.

Scheme 1.

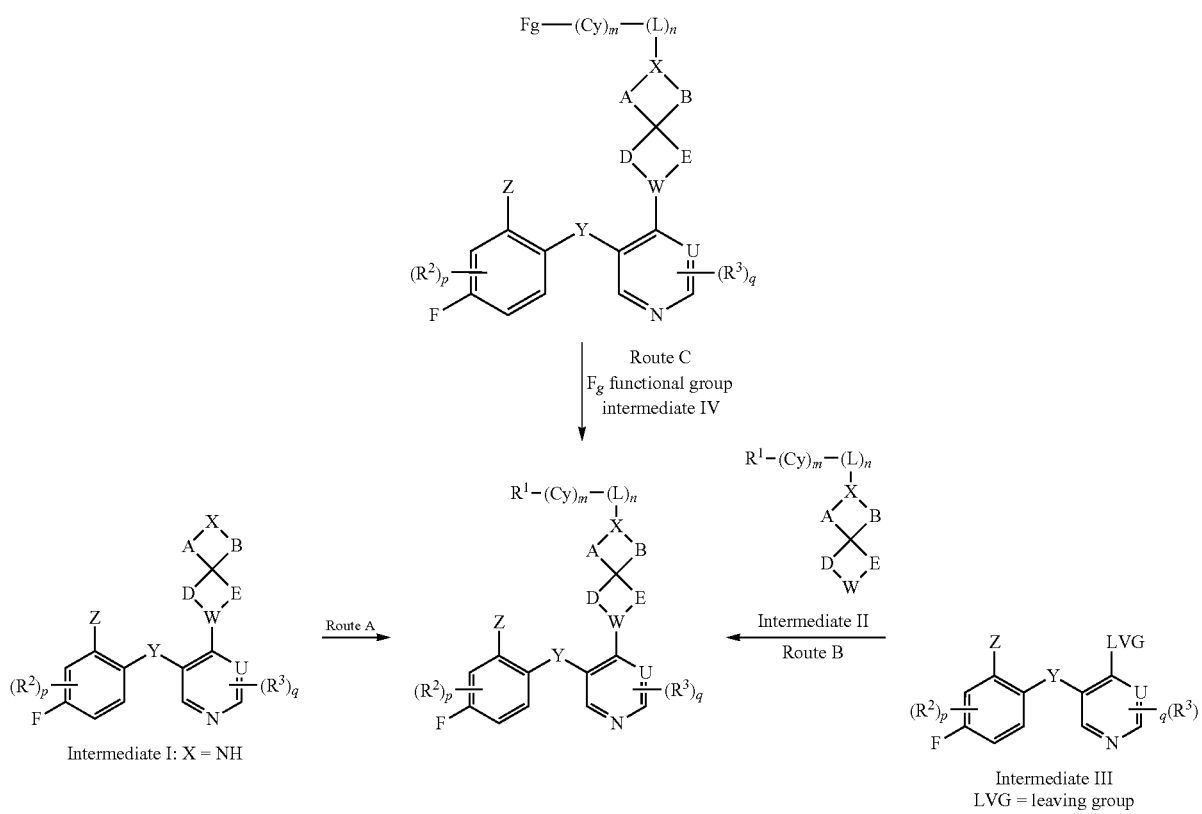

The compounds of the invention can be synthesized by numerous methods, based on retro synthetic analysis of final targets. Exemplary methods are shown in routes A, B & C.

Route A:

This method involves coupling of amine Intermediate I with various aldehydes, amines, acids, aryl halides, and the like. The aldehydes and ketones can be condensed with Intermediate I by reductive amination. This method involves reaction of aldehydes or ketones with amine in presence of a reducing agent (e.g., sodium cyanoborohydride or triacetoxy sodium cyanoborohydride). Various alternative methods for reaction of amines with aldehyde and ketones under reductive conditions are well known in the art. For example, these reactions can be performed in various protic and aprotic solvents and at temperatures from −78° C. to refluxing conditions. One method involves reaction of amines with aldehydes or ketones in solvents such as, for example, methanol, ethanol, tetrahydrofuran, dichloromethane or 1,2-dichloroethane or a combination thereof in presence of a reducing agent (e.g., triacetoxy sodium borohydride or sodium cyanoborohydride) between RT and refluxing conditions in the presence or absence of microwave reactor.

Route B:

This method involves the coupling of Intermediate II with Intermediate III. The Intermediate II (W=NH) can be synthesized, for example, from various spirocyclic amines using known synthetic procedures as described in literature and by methods known to a person skilled in the art. For example, Intermediate III can be synthesized by any of the various methods described below. The leaving group (LVG) can be any suitable group such as, for example, a halogen, mesylate, tosylate, or any other groups that can be suitable for nucleophilic substitution catalyzed by base or by metal catalyzed displacement (e.g., copper, palladium, and the like). These methods are well described in Handbook of Reagents for Organic Synthesis, Catalyst Components for Coupling Reactions; Gary Molander, 1st. edition, 2013; John Wiley & sons. One method involves reaction of halo derivatives of Intermediate III with amine under protic or aprotic solvents in the presence of organic or inorganic base at elevated temperature. An additional example involves treatment of chloro derivatives of Intermediate III with an amine in an aprotic solvent (e.g., DMF or DMSO) in the presence of organic base (e.g., triethylamine or pyridine) at elevated temperatures. For compounds of Intermediate II where W is carbon the reaction can be performed, for example, by a cross coupling reaction of vinyl boronates of spiroamines with Intermediate III, followed by hydrogenation to yield carbon analogs.

Route C:

The final compound can be synthesized from Intermediate IV by functional group modification. The functional group may be, for example, an acid, alcohol, amine, aryl halide, and the like. This reaction utilizes amines with various acylating agents (e.g., acyl chloride, sulfonyl chloride, isocyanates, and the like). Alternatively, functional groups such as acid can be converted to amides. Aryl halides can be converted to the desired product using conventional methods known for other functional groups and many of these functional group transformations are well known in literature and described in "Comprehensive Organic Transformations: A Guide to Functional Group Preparations" by Richard C. Larock, Edition 2, 1999, Wiley & Sons. One functional group transformation involves reaction of an amine with various acylating agents (e.g., acyl chloride or sulfonyl chloride) in the presence of an aprotic solvent and base. Another example involves reaction of an amine with sulfonyl chloride in dichloromethane in the presence of an organic base (e.g., pyridine, trimethylamine, and the like).

Wiley-Interscience; 6 edition 2007. An example reaction involves the cross coupling of an aryl halide (e.g., where Fg is a halogen) of Intermediate V with various boronates, tin reagents, and the like. These cross coupling reactions can be effected with various metal catalysts (e.g., copper, palladium, rhodium, and the like) in a variety of protic/aprotic solvents or combination thereof, in the presence of inorganic Scheme 2.

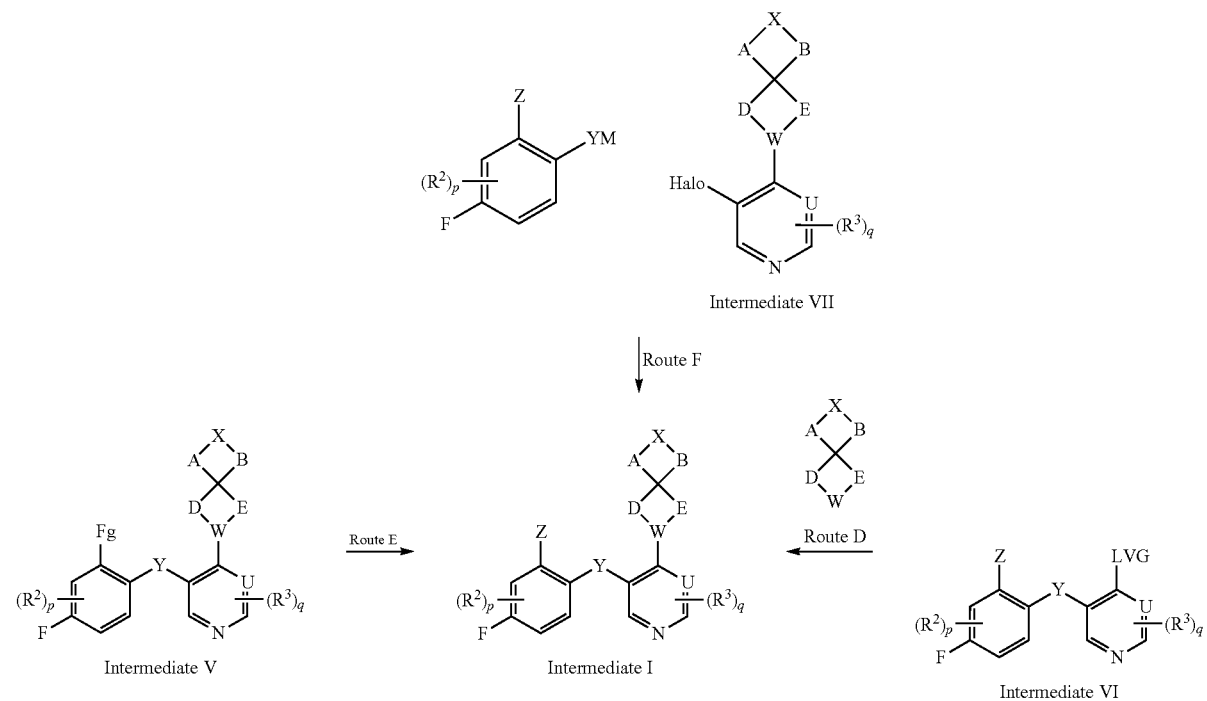

YM = OH, NH2, SH or CH2Metal

Intermediate I can be synthesized by numerous methods as depicted in Scheme 2. Exemplary methods are shown in routes D, E & F.

Route D:

The method employed in route D is analogous to the method employed in route B (Scheme 1). For spirodiamines, one of the amine functionalities may be selectively protected so as to perform the reaction in a regioselective manner. The protecting groups are chosen such that they can be compatible with other functional groups and their transformations, and can be removed selectively. Various amine protecting groups are well known in literature and are well documented in Greene's Protective Groups in Organic Synthesis by Peter G. M. Wuts & Theodora W. Greene; 4th Edition; 2006, Wiley-Interscience. Commonly used amine protecting group include, for example, tert-butoxycarbonyl which is cleaved under acidic condition in aprotic solvents. One example method comprises the use of trifluoroacetic acid or hydrochloride gas in aprotic solvents (e.g., 1,4-dioxane, dichloromethane, and the like) at RT.

Route E:

The functional group Fg of Intermediate V can undergo various functional group transformation to prepare Intermediate I. Such transformations are well documented in the literature, for example, as in Advanced Organic Chemistry: Reactions, Mechanisms, and Structure, by Jerry March, or organic bases at temperatures varying from RT to elevated temperatures. An optional microwave reactor may also be used. An example method involves reaction of a chloro- or bromo-derivative of Intermediate V with an aryl Suzuki reagent in the presence of a palladium catalyst in various solvents (e.g., DMF, toluene/water, and the like) at elevated temperature in presence of inorganic base (e.g., cesium carbonate or potassium phosphate). In certain cases further functionalization can be performed to arrive at the desired compound. For example, an Fg halo group in Intermediate V can be converted into an acid and further converted into an amide, alcohol, ether, and the like. Similarly, the Fg halo group of Intermediate V can be converted into a cyano group, which can be further converted into other functional groups as is well known in the art.

Route F:

This method involves reactions of phenols, thiols, anilines with 3-halopyridines or 5-halo pyrimidine using metal mediated reactions. The nucelophilic displacement of 3-halopyridines or 5-halo pyrimidine by phenols, anilines and aryl thiols are well known in literature as described, for example, in Copper-Mediated Cross-Coupling Reactions by Gwilherm Evano & Nicolas Blanchard by John Wiley & Sons, Edition 1, 2013. For example, Intermediate VII can be synthesized from a 3,4-di halopyridine or a 4,5-dihalo pyrimidine by reaction with a spiroamine using methods similar to that described in Route B. Additionally, the carbon analog can be synthesized, for example, by cross coupling reaction of Intermediate VII with various alkyl zinc halides in the presence of metal catalyst as described in "Applied Cross-Coupling Reactions" by Yasushi Nishihara Springer Science Edition 1, 2013. An example method involves reaction of benzyl zinc bromide with palladium catalyst in an aprotic solvent (e.g., diethylether or tetrahydrofuran) at elevated temperature in the presence or absence of a microwave reactor. Fluoro substituted phenols, anilines, and thiols are well known in literature and can be synthesized by various methods known to one skilled in the art.

Various methods are available for synthesis of Intermediate III containing a pyrimide-phenol ether. Some of the methods are illustrated in Scheme 3, Routes A and B

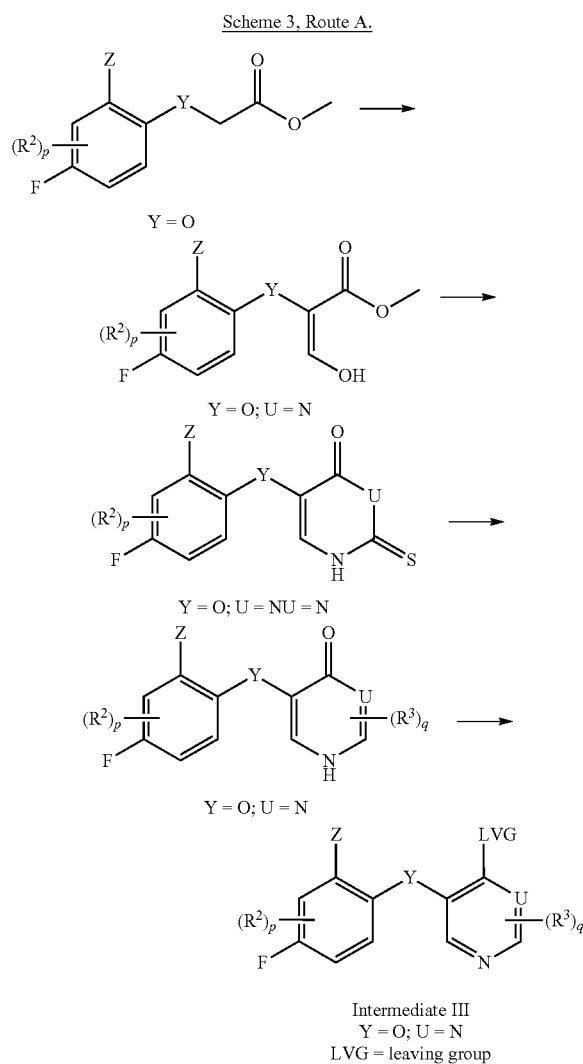

Scheme 3, Route A involves reaction of a phenol with a 2-halo acetate. This method is well known in literature and described, for example, in Journal of Medicinal Chemistry (1980), 23(9), 1026-31. This reaction is achieved by converting a phenol into the corresponding phenolate by reaction with a metal hydride in an aprotic solvent (e.g., DMF, THF, and the like). One example involves reaction of phenol with sodium hydride in an aprotic solvents (e.g., DMF), followed by addition of methylchloroacetate in the same pot at temperature varying from −78° C. to RT. The 2-phenoxyacetate intermediate is further condensed with formaldehyde in presence of a metal hydride (e.g., NaH) in an aprotic solvent as described in the first step. This intermediate is then reacted with thiourea in a protic solvent (e.g., alcohol) under elevated temperature to yield 2-thiopyrimidine intermediate. The thiopyrimidine can be reduced to pyrimidine or converted to 2-substituted pyrimidine by various synthetic routes known in the literature. An example method involves reduction of thiopyrimidine to pyrimidine under metal catalyzed hydrogenation conditions (e.g., nickel in a protic solvent such as ethanol, and the like). The 4-pyrimidone intermediate can then be converted to a 4-halopyrimidone by reaction with a chlorinating solvent (e.g., thionyl chloride, phosphorousoxy trichloride, and the like) either neat or in an aprotic solvent (e.g., toluene, THF, and the like) at elevated temperature. Alternatively the 4-pyrimidone can be reacted with a sulfonyl chloride (e.g., methane sulfonyl chloride or trifluoromethane sulfonyl chloride) to generate a sulfonate as a leaving group suitable for nucleophilic displacement, which can be further utilized in preparing the desired compounds as described herein in Schemes 1 and 2.

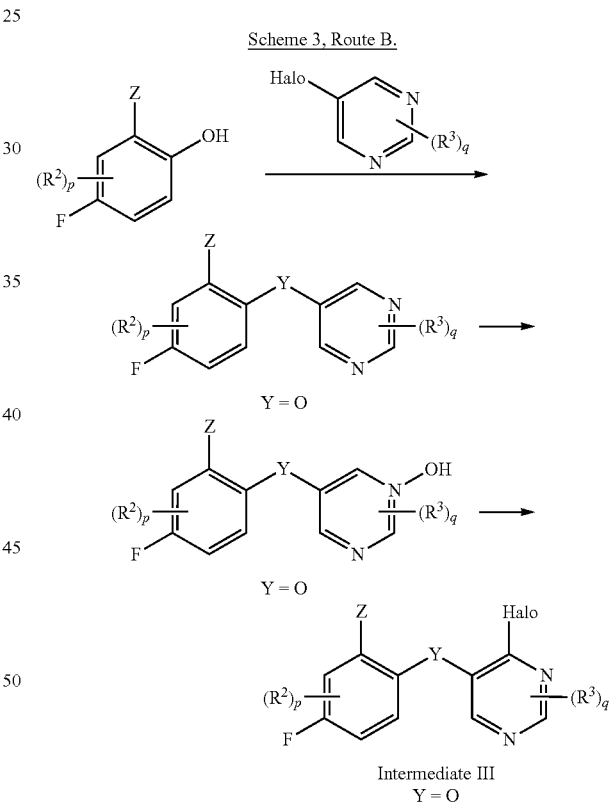

The first step in Scheme 3, Route B, involves the coupling of phenol with 5-halopyrimidine as described, for example, in *Organic Letters*, 14(1), 170-173; 2012, or in *Journal of Organic Chemistry*, 75(5), 1791-1794; 2010. The resulting pyrimidine can then be oxidized with a peracid in an aprotic solvent at RT to yield a pyrimidine N-oxide. An example method involves reaction of pyrimdine ether with metaperchloro perbenzoic acid in a halogenated solvent (e.g., dichloromethane, 1,2-dichloroethane, and the like) as described in *J. Org. Chem.*, 1985, 50 (17), pp 3073-3076. The crude intermediate can be further treated with phosphorousoxytrichloride or phosphorous pentachloride to yield Intermediate III as described in Int. Patent Appl. No., WO 2009/137733.

Methods of Use

The compounds of the invention are inhibitors of the interaction of menin with MLL and MLL fusion proteins. In some embodiments, the present invention is directed to a method of inhibiting the interaction between menin and MLL or an MLL fusion protein by contacting menin and MLL or the MLL fusion protein with a compound of the invention. The contacting can be carried out in vitro or in vivo. In some embodiments, the compounds of the invention can bind to menin, thereby interfering with the binding of MLL to menin. In some embodiments, the present invention provides a method of inhibiting the activity of menin by contacting menin with a compound of the invention in the presence of MLL or an MLL fusion protein. In further embodiments, the present invention provides a method of inhibiting the binding of MLL or an MLL fusion protein to menin, comprising contacting menin with a compound of the invention in the presence of the MLL or MLL fusion protein.

The compounds of the invention are also useful in treating diseases associated with the menin-MLL interaction or menin-MLL fusion protein interaction. For example, diseases and conditions treatable according to the methods of the invention include cancer, such as leukemia, and other diseases or disorders mediated by the menin-MLL interaction or menin-MLL fusion protein interaction such as diabetes.

Accordingly, the compounds of the invention are believed to be effective against a broad range of cancers, including, but not limited to, hematological cancer (e.g., leukemia and lymphoma), bladder cancer, brain cancer (e.g., glioma, diffuse intrinsic pontine glioma (DIPG)), breast cancer (e.g., triple-negative breast cancer, estrogen-receptor-positive breast cancer (i.e., ER+ breast cancer)), colorectal cancer, cervical cancer, gastrointestinal cancer (e.g., colorectal carcinoma, gastric cancer), genitourinary cancer, head and neck cancer, liver cancer, lung cancer, melanoma, ovarian cancer, pancreatic cancer, prostate cancer (e.g., castration resistant prostate cancer), renal cancer (e.g., renal cell carcinoma), skin cancer, thyroid cancer (e.g., papillary thyroid carcinoma), testicular cancer, sarcoma (e.g., Ewing's sarcoma), and AIDS-related cancers. In some embodiments, the cancer is associated with a rearranged MLL gene. In some embodiments, the pathophysiology of the cancer is dependent on the MLL gene. In some embodiments, the cancer is associated with mutant p53 gain-of-function.

In some embodiments, the specific cancers that may be treated by the compounds, compositions and methods described herein include cardiac cancers, such as for example, sarcoma (e.g., angiosarcoma, fibrosarcoma, rhabdomyosarcoma, and liposarcoma), myxoma, rhabdomyoma, fibroma, lipoma and teratoma; lung cancers, including, for example, bronchogenic carcinoma (e.g., squamous cell, undifferentiated small cell, undifferentiated large cell, and adenocarcinoma), alveolar and bronchiolar carcinoma, bronchial adenoma, sarcoma, lymphoma, chondromatous hamartoma, mesothelioma, non-small cell lung cancer, small cell lung cancer, bronchial adenomas/carcinoids, and pleuropulmonary blastoma; gastrointestinal cancer, including, for example, cancers of the esophagus (e.g., squamous cell carcinoma, adenocarcinoma, leiomyosarcoma, and lymphoma), cancers of the stomach (e.g., carcinoma, lymphoma, and leiomyosarcoma), cancers of the pancreas (e.g., ductal adenocarcinoma, insulinoma, glucagonoma, gastrinoma, carcinoid tumors, and vipoma), cancers of the small bowel (e.g., adenocarcinoma, lymphoma, carcinoid tumors, Kaposi's sarcoma, leiomyoma, hemangioma, lipoma, neurofibroma, and fibroma), cancers of the large bowel or colon, (e.g., adenocarcinoma, tubular adenoma, villous adenoma, hamartoma, and leiomyoma), and other cancers of the digestive tract (e.g., anal cancer, anorectal cancer, appendix cancer, cancer of the anal canal, cancer of the tongue, gallbladder cancer, gastrointestinal stromal tumor (GIST), colon cancer, colorectal cancer, extrahepatic bile duct cancer, intrahepatic bile duct cancer, rectal cancer, and small intestine cancer); genitourinary tract cancers, including, for example, cancers of the kidney (e.g., adenocarcinoma, Wilm's tumor (nephroblastoma), lymphoma, and leukemia), cancers of the bladder and urethra (e.g., squamous cell carcinoma, transitional cell carcinoma, and adenocarcinoma), cancers of the prostate (e.g., adenocarcinoma and sarcoma), cancers of the testis, (e.g., seminoma, teratoma, embryonal carcinoma, teratocarcinoma, choriocarcinoma, sarcoma, interstitial cell carcinoma, fibroma, fibroadenoma, adenomatoid tumors, and lipoma), as well as transitional cell cancer, transitional cell cancer of the renal pelvis and ureter and other urinary organs, urethral cancer, and urinary bladder cancer; liver cancers, including, for example, hepatoma (e.g., hepatocellular carcinoma), cholangiocarcinoma, hepatoblastoma, angiosarcoma, hepatocellular adenoma, and hemangioma; bone cancers, including, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochrondroma (osteocartilaginous exostoses), benign chondroma, chondroblastoma, chondromyxofibroma, osteoid osteoma and giant cell tumors; nervous system cancers, including, for example, cancers of the skull (e.g., osteoma, hemangioma, granuloma, xanthoma, and osteitis deformans); cancers of the meninges (e.g., meningioma, meningiosarcoma, and gliomatosis); cancers of the brain (e.g., astrocytoma, medulloblastoma, glioma, ependymoma, germinoma (pinealoma), glioblastoma multiforme, oligodendroglioma, schwannoma, retinoblastoma, and congenital tumors); cancers of the spinal cord (e.g., neurofibroma, meningioma, glioma, and sarcoma), and other nervous system cancers (e.g., brain stem glioma, diffuse intrinsic pontine glioma (DIPG), brain tumor, central nervous system cancer, cerebellar astrocytoma, cerebral astrocytoma/malignant glioma, childhood cerebellar astrocytoma, childhood cerebral astrocytoma, primary central nervous system lymphoma, visual pathway and hypothalamic glioma, nervous system lymphoma, supratentorial primitive neuroectodeimal tumors, pineoblastoma and supratentorial primitive neuroectodermal tumors); gynecological cancers, including, for example, cancers of the uterus (e.g., endometrial carcinoma), cancers of the cervix (e.g., cervical carcinoma, and pre tumor cervical dysplasia), cancers of the ovaries (e.g., ovarian carcinoma, including serous cystadenocarcinoma, mucinous cystadenocarcinoma, unclassified carcinoma, granulosa thecal cell tumors, Sertoli Leydig cell tumors, dysgerminoma, and malignant teratoma), cancers of the vulva (e.g., squamous cell carcinoma, intraepithelial carcinoma, adenocarcinoma, fibrosarcoma, and melanoma), cancers of the vagina (e.g., clear cell carcinoma, squamous cell carcinoma, botryoid sarcoma, and embryonal rhabdomyosarcoma), and cancers of the fallopian tubes (e.g., carcinoma); other reproductive tract cancers, including, for example, endometrial cancer, endometrial uterine cancer, germ cell tumor, gestational trophoblastic tumor, gestational trophoblastic tumor glioma, ovarian epithelial cancer, ovarian germ cell tumor, ovarian low malignant potential tumor, penile cancer, vaginal cancer, vulvar cancer, extracranial germ cell tumor, extragonadal germ cell tumor, uterine cancer, uterine corpus cancer, uterine sarcoma; lymphatic and hematologic cancers, including, for example, cancers of the blood (e.g., acute myeloid leukemia (AML), chronic myeloid leukemia (CML), acute lymphoblastic leukemia (ALL), chronic lymphoblastic leukemia, chronic lymphocytic leukemia, myeloproliferative diseases, multiple myeloma, and myelodysplastic syndrome, Hodgkin's lymphoma, non Hodgkin's lymphoma (malignant lymphoma) and Waldenstrom's macroglobulinemia), and other lymphatic or hematologic cancers including, for example, childhood leukemia, myeloproliferative disorders (e.g., primary myelofibrosis), plasma cell neoplasm/multiple myeloma, myelodysplasia, myelodysplastic syndrome, cutaneous T-cell lymphoma, lymphoid neoplasm, AIDS-related lymphoma, thymoma, thymoma and thymic carcinoma, mycosis fungoides, and Sezary Syndrome; skin cancers, including, for example, malignant melanoma, basal cell carcinoma, squamous cell carcinoma, Kaposi's sarcoma, moles dysplastic nevi, lipoma, angioma, dermatofibroma, keloids, psoriasis, merkel cell carcinoma, merkel cell skin carcinoma, melanoma, and carcinoid tumor; adrenal gland cancers, including, for example, neuroblastoma; other cancers associated with the endocrine system including, for example, adrenocortical carcinoma, multiple endocrine neoplasia (e.g., multiple endocrine neoplasia type I), multiple endocrine neoplasia syndrome, parathyroid cancer, pituitary tumor, pheochromocytoma, islet cell pancreatic cancer, and islet cell tumors); connective tissue cancer (e.g., bone cancer, bone and joint cancer, osteosarcoma and malignant fibrous histiocytoma); cancer associated with the head, neck, and mouth (e.g., head and neck cancer, paranasal sinus and nasal cavity cancer, metastatic squamous neck cancer, mouth cancer, throat cancer, esophageal cancer, laryngeal cancer, pharyngeal cancer, hypopharyngeal cancer, lip and oral cavity cancer, nasopharyngeal cancer, oral cancer, oropharyngeal cancer, and salivary gland cancer); and cancer associated with the eye (e.g., ocular cancer, intraocular melanoma). In some embodiments, the cancer is Ewing's sarcoma.

In some embodiments, the cancer is a hematological cancer such as leukemia or lymphoma. Example leukemia and lymphomas treatable by the compounds of the invention include mixed lineage leukemia (MLL), MLL-related leukemia, MLL-associated leukemia, MLL-positive leukemia, MLL-induced leukemia, rearranged mixed lineage leukemia (MLL-r), leukemia associated with a MLL rearrangement or a rearrangement of the MLL gene, acute leukemia, chronic leukemia, indolent leukemia, lymphoblastic leukemia, lymphocytic leukemia, myeloid leukemia, myelogenous leukemia, childhood leukemia, acute lymphocytic leukemia (ALL) (also referred to as acute lymphoblastic leukemia or acute lymphoid leukemia), acute myeloid leukemia (AML) (also referred to as acute myelogenous leukemia or acute myeloblastic leukemia), acute granulocytic leukemia, acute nonlymphocytic leukemia, chronic lymphocytic leukemia (CLL) (also referred to as chronic lymphoblastic leukemia), chronic myelogenous leukemia (CML) (also referred to as chronic myeloid leukemia), therapy related leukemia, myelodysplastic syndrome (MDS), myeloproliferative disease (MPD) (such as primary myelofibrosis (PMF)), myeloproliferative neoplasia (MPN), plasma cell neoplasm, multiple myeloma, myelodysplasia, cutaneous T-cell lymphoma, lymphoid neoplasm, AIDS-related lymphoma, thymoma, thymic carcinoma, mycosis fungoides, Alibert-Bazin syndrome, granuloma fungoides, Sezary Syndrome, hairy cell leukemia, T-cell prolymphocytic leukemia (T-PLL), large granular lymphocytic leukemia, meningeal leukemia, leukemic leptomeningitis, leukemic meningitis, multiple myeloma, Hodgkin's lymphoma, non Hodgkin's lymphoma (malignant lymphoma), and Waldenstrom's macroglobulinemia. In some embodiments, the acute myeloid leukemia (AML) is abstract nucleophosmin (NPM1)-mutated acute myeloid leukemia (i.e., NPM1$^{mut}$ acute myloid leukemia).

In particular embodiments, compounds of the invention are used to treat leukemia associated with a MLL rearrangement, acute lymphocytic leukemia associated with a MLL rearrangement, acute lymphoblastic leukemia associated with a MLL rearrangement, acute lymphoid leukemia associated with a MLL rearrangement, acute myeloid leukemia associated with a MLL rearrangement, acute myelogenous leukemia associated with a MLL rearrangement, or acute myeloblastic leukemia associated with a MLL rearrangement. As used herein, "MLL rearrangement" means a rearrangement of the MLL gene.

In some embodiments, diseases and conditions treatable with compounds of the invention include insulin resistance, pre-diabetes, diabetes (e.g., Type 2 diabetes or Type 1 diabetes), and risk of diabetes. In some embodiments, diseases and conditions treatable with compounds of the invention include hyperglycemia. In some embodiments, the hyperglycemia is associated with diabetes, such as Type 2 diabetes. In some embodiments, compounds of the invention are used to treat loss of response to other anti-diabetic agents and/or reduced beta cell function in a patient or subject. In some embodiments, compounds of the invention are used to restore response to other anti-diabetic agents and/or to restore beta cell function and/or to reduce the need for insulin in a patient or subject. In some embodiments, compounds of the invention are used to reduce insulin resistance, reduce the risk of diabetes, or reduce increases in blood glucose caused by a statin in a subject taking a statin. In some embodiments, compounds of the invention are used to treat diabetes in a subject taking a statin or to prevent diabetes in a subject taking a statin. Methods of the invention include decreasing, reducing, inhibiting, suppressing, limiting or controlling in the patient elevated blood glucose levels. In further aspects, methods of the invention include increasing, stimulating, enhancing, promoting, inducing or activating in the subject insulin sensitivity. Statins include, but are not limited to atorvastatin, cerivastatin, fluvastatin, lovastatin, mevastatin, pitavastatin, pravastatin, rousuvastatin and simvastatin.

In some embodiments, a patient is treated with (e.g., administered) a compound of the present invention in an amount sufficient to treat or ameliorate one or more of the diseases and conditions recited above (e.g., a therapeutically effective amount). The compounds of the invention may also be useful in the prevention of one or more of the diseases recited therein.

Combination Therapy

The invention further relates to a combination therapy for treating a disease or a disorder described herein. In some embodiments, the combination therapy comprises administering at least one compound of the present invention in combination with one or more other pharmaceutically active agents for treating cancer or other disorders mediated by menin/MLL. In some embodiments, the combination therapy comprises administering at least one compound of the present invention in combination with one or more other pharmaceutically active agents, such as for the treatment of cancer. The pharmaceutically active agents can be combined with a compound of the invention in a single dosage form, or the therapeutics can be administered simultaneously or sequentially as separate dosage forms.

The compounds according to the invention may also be used in combination with immunotherapies, including but not limited to cell-based therapies, antibody therapies and cytokine therapies, for the treatment of a disease or disorder disclosed herein.

In certain embodiments, compounds according to the invention are used in combination with one or more passive immunotherapies, including but not limited to naked monoclonal antibody drugs and conjugated monoclonal antibody drugs. Examples of naked monoclonal antibody drugs that can be used include, but are not limited to rituximab (Rituxan®), an antibody against the CD20 antigen; trastuzumab (Herceptin®), an antibody against the HER2 protein; alemtuzumab (Lemtrada®, Campath®), an antibody against the CD52 antigen; cetuximab (Erbitux®), an antibody against the EGFR protein; and bevacizumab (Avastin®) which is an anti-angiogenesis inhibitor of VEGF protein.

Examples of conjugated monoclonal antibodies that can be used include, but are not limited to, radiolabeled antibody ibritumomab tiuxetan (Zevalin®); radiolabeled antibody tositumomab (Bexxar®); and immunotoxin gemtuzumab ozogamicin (Mylotarg®) which contains calicheamicin; BL22, an anti-CD22 monoclonal antibody-immunotoxin conjugate; radiolabeled antibodies such as OncoScint® and ProstaScint®; brentuximab vedotin (Adcetris®); ado-trastuzumab emtansine (Kadcyla®, also called TDM-1).

Further examples of therapeutic antibodies that can be used include, but are not limited to, REOPRO® (abciximab), an antibody against the glycoprotein IIb/IIIa receptor on platelets; ZENAPAX® (daclizumab) an immunosuppressive, humanized anti-CD25 monoclonal antibody; PANOREX™, a murine anti-17-IA cell surface antigen IgG2a antibody; BEC2, a murine anti-idiotype (GD3 epitope) IgG antibody; IMC-C225, a chimeric anti-EGFR IgG antibody; VITAXIN™ a humanized anti-αVβ3 integrin antibody; Campath 1H/LDP-03, a humanized anti CD52 IgG1 antibody; Smart M195, a humanized anti-CD33 IgG antibody; LYMPHOCIDE™, a humanized anti-CD22 IgG antibody; LYMPHOCIDE™ Y-90; Lymphoscan; Nuvion® (against CD3; CM3, a humanized anti-ICAM3 antibody; IDEC-114 a primatized anti-CD80 antibody; IDEC-131 a humanized anti-CD40L antibody; IDEC-151 a primatized anti-CD4 antibody; IDEC-152 a primatized anti-CD23 antibody; SMART anti-CD3, a humanized anti-CD3 IgG; 5G1.1, a humanized anti-complement factor 5 (C5) antibody; D2E7, a humanized anti-TNF-α antibody; CDP870, a humanized anti-TNF-α Fab fragment; IDEC-151, a primatized anti-CD4 IgG1 antibody; MDX-CD4, a human anti-CD4 IgG antibody; CD20-streptdavidin (+biotin-yttrium 90); CDP571, a humanized anti-TNF-α IgG4 antibody; LDP-02, a humanized anti-α4β7 antibody; OrthoClone OKT4A, a humanized anti-CD4 IgG antibody; ANTOVA™, a humanized anti-CD40L IgG antibody; ANTEGREN™, a humanized anti-VLA-4 IgG antibody; and CAT-152, a human anti-TGF-β$_2$ antibody.

In certain embodiments, compounds according to the invention are used in combination with one or more targeted immunotherapies containing toxins but not an antibody, including but not limited to denileukin diftitox (Ontak®), IL-2 linked to diphtheria toxin.

The compounds according to the invention may also be used in combination with adjuvant immunotherapies for the treatment of a disease or disorder disclosed herein. Such adjuvant immunotherapies include, but are not limited to, cytokines, such as granulocyte-macrophage colony-stimulating factor (GM-CSF), granulocyte-colony stimulating factor (G-CSF), macrophage inflammatory protein (MIP)-1-alpha, interleukins (including IL-1, IL-2, IL-4, IL-6, IL-7, IL-12, IL-15, IL-18, IL-21, and IL-27), tumor necrosis factors (including TNF-alpha), and interferons (including IFN-alpha, IFN-beta, and IFN-gamma); aluminum hydroxide (alum); Bacille Calmette-Guerin (BCG); Keyhole limpet hemocyanin (KLH); Incomplete Freund's adjuvant (IFA); QS-21; DETOX; Levamisole; and Dinitrophenyl (DNP), and combinations thereof, such as, for example, combinations of interleukins, for example IL-2, with other cytokines, such as IFN-alpha.

In certain embodiments, compounds according to the invention are used in combination with vaccine therapy, including but not limited to autologous and allogeneic tumor cell vaccines, antigen vaccines (including polyvalent antigen vaccines), dendritic cell vaccines, and viral vaccines.

In another embodiment, the present disclosure comprises administering to a subject with cancer an effective amount of a compound of the invention and one or more additional anti-cancer therapies selected from: surgery, anti-cancer agents/drugs, biological therapy, radiation therapy, anti-angiogenesis therapy, immunotherapy, adoptive transfer of effector cells, gene therapy or hormonal therapy. Examples of anti-cancer agents/drugs are described below.

In some embodiments, the anti-cancer agents/drug is, for example, adriamycin, aactinomycin, bleomycin, vinblastine, cisplatin, acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cladribine; crisnatol mesylate; cyclophosphamide; cytarabine; dacarbazine; daunorubicin hydrochloride; decitabine; dexormaplatin; dezaguanine; dezaguanine mesylate; diaziquone; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; pegaspargase; peliomycin; pentamustine; peplomycin sulfate; perfosfamide; pipobroman; piposulfan; piroxantrone hydrochloride; plicamycin; plomestane; porfimer sodium; porfiromycin;

prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride; palbociclib; Yervoy® (ipilimumab); Mekinist™ (trametinib); peginterferon alfa-2b, recombinant interferon alfa-2b; Sylatron™ (peginterferon alfa-2b); Tafinlar® (dabrafenib); Zelboraf® (vemurafenib); or nivolumab.

The compounds according to the present invention can be administered in combination with existing methods of treating cancers, for example by chemotherapy, irradiation, or surgery. Thus, there is further provided a method of treating cancer comprising administering an effective amount of a compound of the invention, or a pharmaceutically acceptable salt form thereof, to a subject in need of such treatment, wherein an effective amount of at least one additional cancer chemotherapeutic agent is administered to the subject. Examples of suitable cancer chemotherapeutic agents include any of: abarelix, ado-trastuzumab emtansine, aldesleukin, alemtuzumab, alitretinoin, allopurinol, altretamine, anastrozole, arsenic trioxide, asparaginase, azacitidine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, emtansine, epirubicin, eribulin, erlotinib, estramustine, etoposide phosphate, etoposide, everolimus, exemestane, fentanyl citrate, filgrastim, floxuridine, fludarabine, fluorouracil, fruquintinib, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, ixabepilone, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, paclitaxel albumin-stabilized nanoparticle formulation, pamidronate, panitumumab, pegaspargase, pegfilgrastim, pemetrexed disodium, pentostatin, pertuzuma, pipobroman, plicamycin, procarbazine, quinacrine, rasburicase, rituximab, sorafenib, streptozocin, sulfatinib, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, volitinib, vorinostat, and zoledronate.

In particular embodiments, compounds according to the invention are used in combination with one or more anti-cancer agent selected from methotrexate, paclitaxel albumin-stabilized nanoparticle formulation, ado-trastuzumab emtansine, eribulin, doxorubicin, fluorouracil, everolimus, anastrozole, pamidronate disodium, exemestane, capecitabine, cyclophosphamide, docetaxel, epirubicin, toremifene, fulvestrant, letrozole, gemcitabine, gemcitabine hydrochloride, goserelin acetate, trastuzumab, ixabepilone, lapatinib ditosylate, megestrol acetate, tamoxifen citrate, pamidronate disodium, palbociclib, and pertuzumab for the treatment of breast cancer.

Other anti-cancer agents/drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; andrographolide; angiogenesis inhibitors; antagonist D; antagonist G; antarelix; anti-dorsalizing morphogenetic protein-1; antiandrogen; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors; castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclin-dependent kinase inhibitors; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; 9-dioxamycin; diphenyl spiromustine; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitors; microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen-binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; zanoterone; zilascorb; zinostatin stimalamer; 5-fluorouracil; and leucovorin.

In some embodiments, the anti-cancer agent/drug is an agent that stabilizes microtubules. As used herein, a "microtubulin stabilizer" means an anti-cancer agent/drug which acts by arresting cells in the G2-M phases due to stabilization of microtubules. Examples of microtubulin stabilizers include ACLITAXEL® and Taxol® analogues. Additional examples of microtubulin stabilizers include without limitation the following marketed drugs and drugs in development: Discodermolide (also known as NVP-XX-A-296); Epothilones (such as Epothilone A, Epothilone B, Epothilone C (also known as desoxyepothilone A or dEpoA); Epothilone D (also referred to as KOS-862, dEpoB, and desoxyepothilone B); Epothilone E; Epothilone F; Epothilone B N-oxide; Epothilone A N-oxide; 16-aza-epothilone B; 21-aminoepothilone B (also known as BMS-310705); 21-hydroxyepothilone D (also known as Desoxyepothilone F and dEpoF), 26-fluoroepothilone); FR-182877 (Fujisawa, also known as WS-9885B), BSF-223651 (BASF, also known as ILX-651 and LU-223651); AC-7739 (Ajinomoto, also known as AVE-8063A and CS-39.HCl); AC-7700 (Ajinomoto, also known as AVE-8062, AVE-8062A, CS-39-L-Ser.HCl, and RPR-258062A); Fijianolide B; Laulimalide; Caribaeoside; Caribaeolin; Taccalonolide; Eleutherobin; Sarcodictyin; Laulimalide; Dictyostatin-1; Jatrophane esters; and analogs and derivatives thereof.

In another embodiment, the anti-cancer agent/drug is an agent that inhibits microtubules. As used herein, a "microtubulin inhibitor" means an anti-cancer agent which acts by inhibiting tubulin polymerization or microtubule assembly. Examples of microtubulin inhibitors include without limitation the following marketed drugs and drugs in development: Erbulozole (also known as R-55104); Dolastatin 10 (also known as DLS-10 and NSC-376128); Mivobulin isethionate (also known as CI-980); Vincristine; NSC-639829; ABT-751 (Abbott, also known as E-7010); Altorhyrtins (such as Altorhyrtin A and Altorhyrtin C); Spongistatins (such as Spongistatin 1, Spongistatin 2, Spongistatin 3, Spongistatin 4, Spongistatin 5, Spongistatin 6, Spongistatin 7, Spongistatin 8, and Spongistatin 9); Cemadotin hydrochloride (also known as LU-103793 and NSC-D-669356); Auristatin PE (also known as NSC-654663); Soblidotin (also known as TZT-1027), LS-4559-P (Pharmacia, also known as LS-4577); LS-4578 (Pharmacia, also known as LS-477-P); LS-4477 (Pharmacia), LS-4559 (Pharmacia); RPR-112378 (Aventis); Vincristine sulfate; DZ-3358 (Daiichi); GS-164 (Takeda); GS-198 (Takeda); KAR-2 (Hungarian Academy of Sciences); SAH-49960 (Lilly/Novartis); SDZ-268970 (Lilly/Novartis); AM-97 (Armad/Kyowa Hakko); AM-132 (Armad); AM-138 (Armad/Kyowa Hakko); IDN-5005 (Indena); Cryptophycin 52 (also known as LY-355703); Vitilevuamide; Tubulysin A; Canadensol; Centaureidin (also known as NSC-106969); T-138067 (Tularik, also known as T-67, TL-138067 and TI-138067); COBRA-1 (Parker Hughes Institute, also known as DDE-261 and WHI-261); H10 (Kansas State University); H16 (Kansas State University); Oncocidin A1 (also known as BTO—956 and DIME); DDE-313 (Parker Hughes Institute); SPA-2 (Parker Hughes Institute); SPA-1 (Parker Hughes Institute, also known as SPIKET-P); 3-IAABU (Cytoskeleton/Mt. Sinai School of Medicine, also known as MF-569); Narcosine (also known as NSC-5366); Nascapine, D-24851 (Asta Medica), A-105972 (Abbott); Hemiasterlin; 3-BAABU (Cytoskeleton/Mt. Sinai School of Medicine, also known as MF-191); TMPN (Arizona State University); Vanadocene acetylacetonate; T-138026 (Tularik); Monsatrol; Inanocine (also known as NSC-698666); 3-IAABE (Cytoskeleton/Mt. Sinai School of Medicine); A-204197 (Abbott); T-607 (Tularik, also known as T-900607); RPR-115781 (Aventis); Eleutherobins (such as Desmethyleleutherobin, Desaetyleleutherobin, Isoeleutherobin A, and Z-Eleutherobin); Halichondrin B; D-64131 (Asta Medica); D-68144 (Asta Medica); Diazonamide A; A-293620 (Abbott); NPI-2350 (Nereus); TUB-245 (Aventis); A-259754 (Abbott); Diozostatin; (−)-Phenylahistin (also known as NSCL-96F037); D-68838 (Asta Medica); D-68836 (Asta Medica); Myoseverin B; D-43411 (Zentaris, also known as D-81862); A-289099 (Abbott); A-318315 (Abbott); HTI-286 (also known as SPA-110, trifluoroacetate salt) (Wyeth); D-82317 (Zentaris); D-82318 (Zentaris); SC-12983 (NCI); Resverastatin phosphate sodium; BPR-0Y-007 (National Health Research Institutes); SSR-250411 (Sanofi); Combretastatin A4; eribulin (Halaven®); and analogs and derivatives thereof.

In further embodiments, compounds according to the invention are used in combination with one or more alkylating agents, antimetabolites, natural products, or hormones.

Examples of alkylating agents useful in the methods of the invention include but are not limited to, nitrogen mustards (e.g., mechloroethamine, cyclophosphamide, chlorambucil, melphalan, etc.), ethylenimine and methylmelamines (e.g., hexamethylmelamine, thiotepa), alkyl sulfonates (e.g., busulfan), nitrosoureas (e.g., carmustine, lomusitne, semustine, streptozocin, etc.), or triazenes (decarbazine, etc.).

Examples of antimetabolites useful in the methods of the invention include but are not limited to folic acid analog (e.g., methotrexate), or pyrimidine analogs (e.g., fluorouracil, floxouridine, cytarabine), and purine analogs (e.g., mercaptopurine, thioguanine, pentostatin). Examples of natural products useful in the methods of the invention include but are not limited to vinca alkaloids (e.g., vinblastin, vincristine), epipodophyllotoxins (e.g., etoposide, teniposide), antibiotics (e.g., actinomycin D, daunorubicin, doxorubicin, bleomycin, plicamycin, mitomycin) or enzymes (e.g., L-asparaginase).

Examples of hormones and antagonists useful for the treatment of cancer include but are not limited to adrenocorticosteroids (e.g., prednisone), progestins (e.g., hydroxyprogesterone caproate, megestrol acetate, medroxyprogesterone acetate), estrogens (e.g., diethlystilbestrol, ethinyl estradiol), antiestrogen (e.g., tamoxifen), androgens (e.g., testosterone propionate, fluoxymesterone), antiandrogen (e.g., flutamide), and gonadotropin releasing hormone analog (e.g., leuprolide).

Other agents that can be used in combination with the compounds of the invention for the treatment of cancer include platinum coordination complexes (e.g., cisplatin, carboblatin), anthracenedione (e.g., mitoxantrone), substituted urea (e.g., hydroxyurea), methyl hydrazine derivative (e.g., procarbazine), and adrenocortical suppressant (e.g., mitotane, aminoglutethimide). Other anti-cancer agents/drugs that can be used in combination with the compounds of the invention include, but are not limited to, liver X receptor (LXR) modulators, including LXR agonists and LXR beta-selective agonists; aryl hydrocarbon receptor (AhR) inhibitors; inhibitors of the enzyme poly ADP ribose polymerase (PARP), including olaparib, iniparib, rucaparib, veliparib; inhibitors of vascular endothelial growth factor (VEGF) receptor tyrosine kinases, including cediranib; programmed cell death protein 1 (PD-1) inhibitors, including nivolumab (Bristol-Myers Squibb Co.) and pembrolizumab (Merck & Co., Inc.; MK-3475); MEK inhibitors, including cobimetinib; B-Raf enzyme inhibitors, including vemurafenib; cytotoxic T lymphocyte antigen (CTLA-4) inhibitors, including tremelimumab; programmed death-ligand 1 (PD-L1) inhibitors, including MEDI4736 (AstraZeneca); inhibitors of the Wnt pathway; inhibitors of epidermal growth factor receptor (EGFR) including AZD9291 (AstraZeneca), erlotinib, gefitinib, panitumumab, and cetuximab; adenosine A2A receptor inhibitors; adenosine A2B receptor inhibitors; colony-stimulating factor-1 receptor (CSF1R) inhibitors, including PLX3397 (Plexxikon), and inhibitors of CD73.

The compounds of the invention can be used in combination with one or more therapeutic strategies including immune checkpoint inhibitors, including inhibitors of PD-1, PD-L1, and CTLA-4.

The compounds of the invention can be used in combination with one or more anti-cancer agents selected from MCL-1 inhibitors, e.g., homoharringtonin (HHT) and omacetaxine; BCL-2 inhibitors, e.g., venetoclax (ABT-199), navitoclax (ABT-263), ABT-737, gossypol (AT-101), apogossypolone (ApoG2) and obatoclax; selective inhibitors of nuclear export (SINEs), e.g., selinexor (KPT-330).

In particular embodiments, the compounds of the invention are used in combination with one or more anti-cancer agents selected from methotrexate (Abitrexate®; Folex®; Folex PFS®; Mexate®; Mexate-AQ®); nelarabine (Arranon®); blinatumomab (Blincyto®); rubidomycin hydrochloride or daunorubicin hydrochloride (Cerubidine®); cyclophosphamide (Clafen®; Cytoxan®; Neosar®); clofarabine (Clofarex®; Clolar®); cytarabine (Cytosar-U®; Tarabine PFS®); dasatinib (Sprycel®); doxorubicin hydrochloride; asparaginase *Erwinia chrysanthemi* (Erwinaze); imatinib mesylate (Gleevec®); ponatinib hydrochloride (Iclusig®); mercaptopurine (Purinethol; Purixan); pegaspargase (Oncaspar®); prednisone; vincristine sulfate (Oncovin®, Vincasar PFS®, Vincrex®); vincristine sulfate liposome (Marqibo®); hyper-CVAD (fractionated cyclophosphamide, vincristine, adriamycin, and dexamethasone); arsenic trioxide (Trisenox®); idarubicin hydrochloride (Idamycin®); mitoxantrone hydrochloride; thioguanine (Tabloid®); ADE (cytarabine, daunorubicin, and etoposide); alemtuzumab (Lemtrada®, Campath®); chlorambucil (Ambochlorin®, Amboclorin®, Leukeran®, Linfolizin®); ofatumumab (Arzerra®); bendamustine hydrochloride (Treanda®); fludarabine phosphate (Fludara®); obinutuzumab (Gazyva®); ibrutinib (Imbruvica®); idelalisib (Zydelig®); mechlorethamine hydrochloride (Mustargen®); rituximab (Rituxan®); chlorambucil-prednisone; CVP (cyclophosphamide, vincristine, and prednisone); bosutinib (Bosulif®); busulfan (Busulfex®; Myleran®); omacetaxine mepesuccinate (Synribo®); nilotinib (Tasigna®); Intron® A (recombinant interferon Alfa-2b); DOT1L inhibitors, including EPZ-5676 (Epizyme, Inc.); and inhibitors of bromodomain and extra-terminal motif (BET) proteins (BET inhibitors), including MS417, JQ1, I-BET 762, and I-BET 151 for the treatment of leukemia.

Compounds of the invention can be used in combination with one or more other agents or therapies for the treatment of insulin resistance, pre-diabetes, diabetes (e.g., Type 2 diabetes or Type 1 diabetes), and risk of diabetes, including but not limited to insulins and insulin analogues, such as Humulin® (Eli Lilly), Lantus® (Sanofi Aventis), Novolin® (Novo Nordisk), and Exubera® (Pfizer); Avandamet® (metformin HCl and rosiglitazone maleate, GSK); Avandaryl® (glimepiride and rosiglitazone maleate, GSK); Metaglip® (glipizide and metformin HCl, Bristol Myers Squibb); Glucovance® (glyburide and metformin HCl, Bristol Myers Squibb); PPAR gamma agonists, such as Avandia® (rosiglitizone maleate, GSK) and Actos® (pioglitazone hydrochloride, Takeda/Eli Lilly); sulfonylureas, such as Amaryl® (glimepiride, Sanofi Aventis), Diabeta® (glyburide, Sanofi Aventis), Micronase®/Glynase® (glyburide, Pfizer), and Glucotrol®/Glucotrol XL® (glipizide, Pfizer); meglitinides, such as Prandin®/NovoNorm® (repaglinide, Novo Nordisk), Starlix® (nateglinide, Novartis), and Glufast® (mitiglinide, Takeda); biguanides, such as Glucophase®/Glucophase XR® (metformin HCl, Bristol Myers Squibb) and Glumetza® (metformin HCl, Depomed); thiazolidinediones; amylin analogs; GLP-1 analogs; DPP-IV inhibitors such as Januvia® (sitagliptin, Merck) and Galvus® (vildagliptin, Novartis); PTB-1 B inhibitors; protein kinase inhibitors (including AMP-activated protein kinase inhibitors); glucagon antagonists, glycogen synthase kinase-3 beta inhibitors; glucose-6-phoshatase inhibitors; glycogen phosphorylase inhibitors; sodium glucose co-transporter inhibitors; and alpha-glucosidase inhibitors, such as Glycet® (miglitol, Pfizer); statins, fibrates, and Zetia® (ezetimibe); alpha-blockers; beta-blockers; calcium channel blockers; diuretics; angiotensin converting enzyme (ACE) inhibitors; dual ACE and neutral endopeptidase (NEP) inhibitors; angiotensin-receptor blockers (ARBs); aldosterone synthase inhibitors; aldosterone-receptor antagonists; endothelin receptor antagonists; orlistat; phentermine; sibutramine; Acomplia® (rimonabant); thiazolidinediones (e.g., rosiglitazone, pioglitazone); SGLT 2 inhibitors (e.g., dapagliflozin, remogliflozin etabonate, sergliflozin, canagliflozin, and 1-chloro-4-(β-D-glucopyranos-1-yl)-2-[4-(('S)-tetrahydrofuran-3-yloxy)-benzyl]-benzene); PPAR-gamma-agonists (e.g., Gl 262570) and antagonists; PPAR-gamma/alpha modulators (e.g., KRP 297); alpha-glucosidase inhibitors (e.g., acarbose, voglibose); DPPIV inhibitors (e.g., Januvia® (sitagliptin), Galvus®/Zomelis® (vildagliptin), Onglyza® (saxagliptin), Nesina®/Vipidia® (alogliptin), and Tradjenta®/Trajenta® (linagliptin)); alpha2-antagonists; glucagon-like protein-1 (GLP-1) receptor agonists and analogues (e.g., exendin-4); amylin; inhibitors of protein tyrosinephosphatase 1; substances that affect deregulated glucose production in the liver, e.g., inhibitors of glucose-6-phosphatase, or fructose-1,6-bisphosphatase, glycogen phosphorylase; glucagon receptor antagonists; inhibitors of phosphoenol pyruvate carboxykinase; glycogen synthase kinase and glucokinase activators; lipid lowering agents such as HMG-CoA-reductase inhibitors (e.g., simvastatin, atorvastatin); fibrates (e.g., bezafibrate, fenofibrate), nicotinic acid and the derivatives thereof, PPAR-alpha agonists, PPAR-delta agonists; ACAT inhibitors (e.g., avasimibe); cholesterol absorption inhibitors such as ezetimibe; bile acid-binding substances such as cholestyramine; inhibitors of ileac bile acid transport; HDL-raising compounds such as CETP inhibitors and ABC1 regulators; active substances for treating obesity such as sibutramine and tetrahydrolipostatin; SDRIs; axokine; leptin; leptin mimetics; antagonists of the cannabinoid 1 receptor; and MCH-1 receptor antagonists; MC4 receptor agonists; NPY5 and NPY2 antagonists; beta3 adrenergic agonists such as SB-418790 and AD-9677; agonists of the 5HT2c receptor; GABA-receptor antagonists; Na-channel blockers; topiramate; protein-kinase C inhibitors; advanced glycation end product inhibitors; and aldose reductase inhibitors.

Pharmaceutical Formulations, Administration, and Dosage Forms

When employed as pharmaceuticals, the compounds of the invention can be administered in the form of a pharmaceutical composition which refers to a combination of a compound of the invention, or its pharmaceutically acceptable salt, and at least one pharmaceutically acceptable carrier. These compositions can be prepared in a manner well known in the pharmaceutical art, and can be administered by a variety of routes, depending upon whether local or systemic treatment is desired and upon the area to be treated. Administration may be topical (including ophthalmic and to mucous membranes including intranasal, vaginal and rectal delivery), pulmonary (e.g., by inhalation or insufflation of powders or aerosols, including by nebulizer; intratracheal, intranasal, epidermal and transdermal), ocular, oral or parenteral. Methods for ocular delivery can include topical administration (eye drops), subconjunctival, periocular or intravitreal injection or introduction by balloon catheter or ophthalmic inserts surgically placed in the conjunctival sac. Parenteral administration includes intravenous, intraarterial, subcutaneous, intraperitoneal, or intramuscular injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, one or more of the compounds of the invention above in combination with one or more pharmaceutically acceptable carriers. In making the compositions of the invention, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

Compounds or compositions described herein may be administered to a patient using any amount and any route of administration effective for treating or lessening the severity of one or more of the diseases and conditions described herein. The exact amount required will vary from subject to subject, depending on the species, age, and general condition of the subject, the severity of the infection, disease or disorder, the particular agent, its mode of administration, and the like. Provided compounds are preferably formulated in a particular unit dosage form for ease of administration and uniformity of dosage. The expression "unit dosage form" as used herein refers to a physically discrete unit of agent appropriate for the patient to be treated.

The therapeutic dosage of the compounds of the present invention can vary according to, for example, the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 µg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

EXAMPLES

As depicted in the Examples below, compounds of the invention were prepared and isolated according to the following general procedures. It will be appreciated that, although the general methods may depict the synthesis of certain compounds of the present invention, the following general methods, and other methods known to one of ordinary skill in the art, can be applied to all compounds and subclasses and species of each of these compounds, as described herein.

Microwave reactions were performed in a CEM reactor using discovery SP system. Where NMR data are presented, spectra were obtained in a Varian-400 (400 MHz). Spectra are reported as ppm downfield from tetramethylsilane with the number of proton, multiplicities and, in certain instances, coupling constants indicated parenthetically along with reference to deuterated solvent. Compounds were also purified by ISCO flash chromatography system utilizing standard methods described in the manual.

Compounds were purified by acidic, basic, or neutral preparative HPLC method as described below in HPLC Methods A to G.

Preparative RP-HPLC Method A:

RP-HPLC (C-18, Boston Green ODS 150*30 mm*5 µm; eluent-gradient: water+0.1% TFA/acetonitrile=81:19 to 51:49)

Mobile phase A: water+0.1% TFA; Mobile phase B: CH$_3$CN; Flow rate: 30 mL/min; Detection: UV 220 nm/254 nm; Column: Boston Green ODS 150*30 mm*5 µm; Column temperature: 30° C.

| Time in min | % A | % B |
| --- | --- | --- |
| 0.00 | 81 | 19 |
| 8.00 | 51 | 49 |
| 8.20 | 0 | 100 |
| 10.00 | 0 | 100 |

Preparative RP-HPLC Method B:

RP-HPLC (C-18, Phenomenex Synergi C18 250*21.2 mm*4 µm; eluent-gradient: water+0.1% TFA/acetonitrile=75:25 to 45:55).

Mobile phase A: water+0.1% TFA; Mobile phase B: CH$_3$CN; Flow rate: 25 mL/min; Detection: UV 220 nm/254 nm; Column: Phenomenex Synergi C18 250*21.2 mm*4 µm; Column temperature: 30° C.

| Time in min | % A | % B |
| --- | --- | --- |
| 0.00 | 75 | 25 |
| 10.00 | 45 | 55 |
| 10.20 | 0 | 100 |
| 12.00 | 0 | 100 |

Preparative RP-HPLC Method C:

RP-HPLC (C-18, Phenomenex Synergi C18 250*21.2 mm*4 µm; eluent-gradient: water+0.05% HCl/acetonitrile=82:18 to 52:48).

Mobile phase A: water with 0.05% HCl; Mobile phase B: CH$_3$CN; Flow rate: 30 mL/min; Detection: UV 220 nm/254 nm; Column: Phenomenex Gemini 150*30 mm*4 µm; Column temperature: 30° C.

| Time in min | % A | % B |
| --- | --- | --- |
| 0.00 | 82 | 18 |
| 8.00 | 52 | 48 |
| 8.20 | 0 | 100 |
| 10.00 | 0 | 100 |

Preparative RP-HPLC Method D:

RP-HPLC (C-18, Phenomenex Gemini 150*25 mm*10 µm; eluent-gradient: water+0.05% ammonia hydroxide/acetonitrile=30:70 to 0:100).

Mobile phase A: water with 0.05% ammonia hydroxide; Mobile phase B: CH$_3$CN; Flow rate: 25 mL/min; Detection: UV 220 nm/254 nm; Column: Phenomenex Gemini 150*25 mm*10 µm; Column temperature: 30° C.

| Time in min | % A | % B |
| --- | --- | --- |
| 0.00 | 30 | 70 |
| 8.00 | 0 | 100 |
| 8.20 | 0 | 100 |
| 10.00 | 0 | 100 |

Preparative RP-HPLC Method E:

Mobile phase A: water with 0.1% TFA; Mobile phase B: acetonitrile with 0.1% TFA; Flow rate: 25 mL/min; Detection: UV 220 nm/254 nm; Column: C-18 Synergi Max-RP 150*30 mm*4 µm; Column temperature: 30° C.

| Time in min | % A | % B |
| --- | --- | --- |
| 0.00 | 90 | 10 |
| 12.00 | 60 | 40 |
| 12.20 | 10 | 90 |
| 13.5 | 90 | 10 |

Neutral Preparative HPLC Method F:

Mobile phase A: water

Mobile phase B: CH$_3$CN

Flow rate: 120 mL/min

Detection: UV 220 nm/254 nm

Column: Phenomenex Synergi Max-RP 250*50 mm*10 um

Column temperature: 30° C.

| Time in min | % A | % B |
|---|---|---|
| 0.00 | 80 | 20 |
| 23.00 | 35 | 65 |
| 23.20 | 0 | 100 |
| 26.00 | 0 | 100 |

Preparative HPLC Method G:
Mobile phase A: water (10 mM $NH_4HCO_3$)
Mobile phase B: $CH_3CN$
Flow rate: 25 mL/min
Detection: UV 220 nm/254 nm
Column: Xtimate C18 150*25 mm*5 um
Column temperature: 30° C.

| Time in min | % A | % B |
|---|---|---|
| 0.00 | 72 | 28 |
| 10.00 | 52 | 48 |
| 10.20 | 0 | 100 |
| 13.00 | 0 | 100 |

LCMS data were obtained by utilizing the following chromatographic conditions:
LCMS Method A:
HPLC System: Waters ACQUITY; Column: Waters ACQUITY CSH™ C18 1.7 μM. Guard column: Waters Assy. Frit, 0.2 M, 2.1 mm; Column temperature: 40° C.
Mobile Phase: A: TFA: Water (1:1000, v:v); Mobile phase B: TFA: ACN (1:1000, v:v); Flow Rate: 0.65 mL/min; Injection Volume: 2 μL; Acquisition time: approximately 1.5 min.
Gradient Program:

| Time (min) | B % |
|---|---|
| 0.00 | 10 |
| 1.0 | 90 |
| 1.20 | 10 |

Mass Spectrometer: Waters SQD; Ionization: Positive Electrospray Ionization (ESI); Mode Scan (100-1400 m/z in every 0.2 second); ES Capillary Voltage: 3.5 kV; ES Cone Voltage: 25 V.
Source Temperature: 120° C.; Desolvation Temperature: 500° C.; Desolvation Gas Flow: Nitrogen Setting 650 (L/h); Cone Gas Flow: Nitrogen Setting 50 (L/h).
LCMS Method B:
HPLC System: Waters ACQUITY; Column: Waters ACQUITY CSH™ C18 1.7 μM. Guard column: Waters Assy. Frit, 0.2 μM, 2.1 mm; Column tem: 40° C.
Mobile Phase: A: TFA: Water (1:1000, v:v); Mobile phase B: TFA: ACN (1:1000, v:v); Flow Rate: 0.65 mL/min; Injection Volume: 2 μL; Acquisition time: approximately 1.5 min.

| Time (min) | B % |
|---|---|
| 0.00 | 10 |
| 2 | 90 |
| 2.20 | 90 |

Mass Spectrometer: Waters SQD; Ionization: Positive Electrospray Ionization (ESI); Mode Scan (100-1400 m/z in every 0.2 second); ES Capillary Voltage: 3.5 kV; ES Cone Voltage: 25 v.
Source Temperature: 120° C.; Desolvation Temperature: 500° C.; Desolvation Gas Flow: Nitrogen Setting 650 (L/h); Cone Gas Flow: Nitrogen Setting 50 (L/h).
LCMS Method C:

| Column | MERCK, RP-18e 25-2 mm |
|---|---|
| Mobile Phase | A: water(4 L) + TFA(1.5 mL) |
| | B: acetonitrile(4 L) + TFA(0.75 mL) |

| TIME (min) | B % |
|---|---|
| 0 | 5 |
| 0.7 | 95 |
| 1.1 | 95 |
| 1.11 | 5 |
| 1.5 | 5 |

| Flow Rate | 1.5 mL/min |
|---|---|
| wavelength | UV 220, 224 nm |
| Oven Temp | 50° C. |
| MS ionization | ESI |

LCMS Method D:

| Column | Xbrige Shield RP-18, 5 μm, 2.1*50 mm |
|---|---|
| Mobile Phase | A: water(1 L) + $NH_3H_2O$(0.5 mL) |
| | B: acetonitrile |

| TIME(min) | B % |
|---|---|
| 0 | 10 |
| 2 | 80 |
| 2.48 | 80 |
| 2.49 | 10 |
| 3 | 10 |

| Flow Rate | 1.0 mL/min |
|---|---|
| wavelength | UV 220 nm |
| Oven Temp | 30° C. |
| MS ionization | ESI |

LCMS Method E:

| Column | Xtimate C18 2.1*30 mm, 3 μm |
|---|---|
| Mobile Phase | A: water(4 L) + TFA(1.5 mL) |
| | B: acetonitrile(4 L) + TFA(0.75 mL) |

| TIME(min) | B % |
|---|---|
| 0 | 10 |
| 0.9 | 80 |
| 1.5 | 80 |
| 1.51 | 10 |
| 2 | 10 |

| Flow Rate | 1.2 mL/min |
|---|---|
| wavelength | UV 220 nm |
| Oven Temp | 50° C. |
| MS ionization | ESI |

LCMS Method F:

| Column | Xtimate C18 2.1*30 mm, 3 μm |
|---|---|
| Mobile Phase | A: water(4 L) + TFA(1.5 mL) |
| | B: acetonitrile(4 L) + TFA(0.75 mL) |

| TIME(min) | B % |
|---|---|
| 0 | 0 |
| 0.9 | 60 |
| 1.5 | 60 |
| 1.51 | 0 |

-continued

| | | |
|---|---|---|
| | 2 | 0 |
| Flow Rate | 1.2 mL/min | |
| wavelength | UV 220 nm | |
| Oven Temp | 50° C. | |
| MS ionization | ESI | |

LCMS Method G:

HPLC System: Waters ACQUITY; Column: Waters ACQUITY CSH™ C18 1.7 μM. Guard column: Waters Assy. Frit, 0.2 μM, 2.1 mm; Column tem: 40° C.

Mobile Phase: A: TFA: Water (1:1000, v:v); Mobile phase B: TFA: ACN (1:1000, v:v); Flow Rate: 1 mL/min; Injection Volume: 2 μL; Acquisition time: approximately 115 min.

| Time in min | B % |
|---|---|
| 0.1 | 10 |
| 2.0 | 10 |
| 14 | 90 |
| 15 | 90 |
| 16 | 10 |

Mass Spectrometer: Waters SQD; Ionization: Positive Electrospray Ionization (ESI); Mode Scan (100-1400 m/z in every 0.2 second); ES Capillary Voltage: 3.5 kV; ES Cone Voltage: 25 v.

Source Temperature: 120° C.; Desolvation Temperature: 500° C.; Desolvation Gas Flow: Nitrogen Setting 650 (L/h); Cone Gas Flow: Nitrogen Setting 50 (L/h).

The following are Supercritical Fluid Chromatography (SFC) separation methods for racemic compounds.
Method A Instrument: Thar SFC 80; Column: AD 250 mm*30 mm, 5 μm; Mobile phase: A: Supercritical $CO_2$, B: IPA (0.05% DEA), A:B=80:20 at 60 mL/min; Column Temp: 38° C.; Nozzle Pressure: 100 Bar; Nozzle Temp: 60° C.; Evaporator Temp: 20° C.; Trimmer Temp: 25° C.; Wavelength: 220 nm.
Method B Instrument: SFC MG2; Column: OJ 250 mm*30 mm, 5 μm; Mobile phase: A: Supercritical $CO_2$, B: MeOH (0.05% DEA), A:B=90:10 at 70 mL/min; Column Temp: 38° C.; Nozzle Pressure: 100 Bar Nozzle Temp: 60° C.; Evaporator Temp: 20° C.; Trimmer Temp: 25° C.; Wavelength: 220 nm.

The following are SFC analytical (anal.) methods utilized to characterize final compounds.

SFC Anal. Method A: Instrument: Thar SFC 80; Column: AD_H 4 mm*40 mm, 5 μm; Mobile phase: A: Supercritical $CO_2$, B: IPA (0.05% DEA), A:B=80:20 at 4 mL/min; 3 min run, Column Temp: 38° C.; Nozzle Pressure: 100 Bar; Nozzle Temp: 60° C.; Evaporator Temp: 20° C.; Trimmer Temp: 25° C.; Wavelength: 220 nm.

SFC Anal. Method B: Instrument: Thar SFC 80; Column: AD_H 4 mm*40 mm, 5 μm; Mobile phase: A: Supercritical $CO_2$, B: IPA (0.05% DEA), A:B=80:20 at 2.4 mL/min; 10 min run, Column Temp: 38° C.; Nozzle Pressure: 100 Bar; Nozzle Temp: 60° C.; Evaporator Temp: 20° C.; Trimmer Temp: 25° C.; Wavelength: 220 nm.

SFC Anal. Method C: Instrument: Thar SFC 80; Column: AD_H 4 mm*40 mm, 5 μm; Mobile phase: A: Supercritical $CO_2$, B: IPA (0.05% DEA), A:B=80:20 at 2.8 mL/min; 13 min run, Column Temp: 38° C.; Nozzle Pressure: 100 Bar; Nozzle Temp: 60° C.; Evaporator Temp: 20° C.; Trimmer Temp: 25° C.; Wavelength: 220 nm.

SFC Anal. Method D: Instrument: Thar SFC 80; Column: AD-3, 5 mm*40 mm, 5 m; Mobile phase: A: Supercritical $CO_2$, B: IPA (0.05% DEA), A:B=80:20 at 25 mL/min; 5 min run, Column Temp: 38° C.; Nozzle Pressure: 100 Bar; Nozzle Temp: 60° C.; Evaporator Temp: 20° C.; Trimmer Temp: 25° C.; Wavelength: 220 nm.

X-Ray Powder Diffraction (XRPD) Method A

Rigaku MiniFlex 600 X-ray diffractometer with a high speed D/teX detector was used under the following conditions: 40 kV, 15 mA, Cu K-alpha radiation (wavelength=1.54 Å). The 2-theta scanning range was 3-45° and the scanning rate was 10°/min.

X-Ray Powder Diffraction (XRPD) Method B

| Parameter | Value |
|---|---|
| Instrument | Rigaku SmartLab System |
| Geometry | Reflection BB |
| X-ray Tube | copper |
| Monochromatization | beta filter |
| Detector | D'teX PSD |
| Voltage (kV) | 40.00 |
| Current (mA) | 44.00 |
| Start Angle (2θ) | 2.00 |
| End Angle (2θ) | 70.00 |
| Step Size (2θ) | 0.04 |
| Scan Speed (2θ) | 3.00 |
| Slits (S0 deg, S1 deg, S3 mm) | ⅓, 4, 13 |
| Measurement Type | symmetric θ:2θ |
| Sample Holder | Si low-background |
| Sample Rotation (RPM) | 75 |

X-Ray Powder Diffraction (XRPD) Method C
Transmission Geometry

XRPD patterns were collected with a PANalytical X'Pert PRO MPD diffractometer using an incident beam of Cu radiation produced using an Optix long, fine-focus source. An elliptically graded multilayer mirror was used to focus Cu Kα X-rays through the specimen and onto the detector. Prior to the analysis, a silicon specimen (NIST SRM 640e) was analyzed to verify the observed position of the Si-111 peak was consistent with the NIST-certified position. A specimen of the sample was placed between 3-μm-thick films and analyzed in transmission geometry. A beam-stop, short antiscatter extension, and antiscatter knife edge were used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v.2.2b.

Reflection Geometry

XRPD patterns were collected with a PANalytical X'Pert PRO MPD diffractometer using an incident beam of Cu Kα radiation produced using a long, fine-focus source and a nickel filter. The diffractometer was configured using the symmetric Bragg-Brentano geometry. Prior to the analysis, a silicon specimen (NIST SRM 640e) was analyzed to verify the observed position of the Si-111 peak was consistent with the NIST-certified position. A specimen of the sample was prepared as a thin, circular layer centered on a silicon zero-background substrate. Antiscatter slits (SS) were used to minimize the background generated by air. Soller slits for the incident and diffracted beams were used to minimize broadening from axial divergence. Diffraction patterns were collected using a scanning position-sensitive detector (X'Celerator) located 240 mm from the sample and Data Collector software v.2.2b.

Differential Scanning Calorimetry (DSC)

DSC measurements were performed using a TA Instruments 2920 differential scanning calorimeter. Temperature calibration was performed using NIST-traceable indium metal.

Dynamic Vapor Sorption/Desorpotion (DVS)

Moisture sorption/desorption data were collected on a VTI SGA-100 Vapor Sorption Analyzer. NaCl and PVP were used as calibration standards. Samples were not dried prior to analysis. Sorption and desorption data were collected over a range from 5% to 95% RH at 10% RH increments under a nitrogen purge. The equilibrium criterion used for analysis was less than 0.0100% weight change in 5 minutes with a maximum equilibration time of 3 hours. Data were not corrected for the initial moisture content of the samples.

Thermal Gravimetric Analysis (TGA)

TG analyses were performed using a TA Instruments Q5000 IR thermogravimetric analyzer. Temperature calibration was performed using nickel and ALUMEL™. Each sample was prepared in a platinum pan and the furnace was heated under nitrogen.

The invention is illustrated by the following examples, in which the following abbreviations may be employed:

| Abbreviation | Meaning |
| --- | --- |
| ACN | acetonitrile |
| BOP | (benzotriazol-1-yloxy)tris(dimethylamino)phosphonium hexafluorophosphate |
| BTC | bis(trichloromethyl) carbonate |
| DCE | 1,2-dichloroethane |
| DCM | methylene chloride |
| DIEA | diisopropylethyl amine |
| DMA | dimethyl acetamide |
| DMF | dimethyl formamide |
| dppf | 1,1-bis(diphenylphosphino)ferrocene |
| DSC | differential scanning calorimetry |
| DVS | dynamic vapor sorption/desorption |
| EDX | energy-dispersive X-ray spectroscopy |
| EtN | triethylamine |
| EtOAc | ethyl acetate |
| EtOH | ethanol |
| h | hour(s) |
| HATU | 1-[bis(dimethylamino)methylene]-1H-1,2,3-triazolo[4,5-b]pyridinium 3-oxid hexafluorophosphate. |
| HBTU | 2-(1H-benzotriazole-1-yl)-1,1,3,3-tetramethyluronium hexafluorophosphate |
| HCl | hydrochloric acid |
| HPLC | high performance liquid chromatography |
| Im | imidazaole |
| KI | potassium iodide |
| K3PO4 | Potassium phosphate |
| LCMS | liquid chromatography-mass spectorphotmetry |
| min | minute(s) |
| Me | methyl |
| mL | milliliters |
| mmol | millimoles |
| mg | milligram |
| NaBH$_3$CN | sodium cyanoborohydride |
| PLM | polarized light microscopy |
| RP | reverse phase |
| RT | room temperature |
| SFC | supercritical fluid chromatography |
| SPhos Gen 2 | Chloro(2-dicyclohexylphosphino-2',6'-dimethoxy-1,1'-biphenyl)[2-(2'-amino-1,1'-biphenyl)]palladium(II), |
| $t_R$, $t_r$, $R_r$, | retention time |
| TBAF | tetra butyl ammonium fluoride |
| TBDMS | tert butyl dimethyl silyl |
| TEA | triethylamine |
| TFA | trifluoroacetic acid |
| THF | tetrahydrofuran |
| TGA | thermogravimetric analysis |

| Abbreviation | Meaning |
| --- | --- |
| TLC | thin layer chromatography |
| XPhos | dicyclohexyphosphino-2',4',6' triiso-propyl-1,1'-biphenyl |
| XRPD | X-ray powder diffraction |

Intermediate 1

5-(2-bromo-4-fluorophenoxy)-4-chloropyrimidine

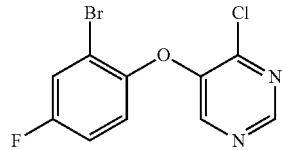

Step 1: Ethyl 2-(2-bromo-4-fluorophenoxy)acetate

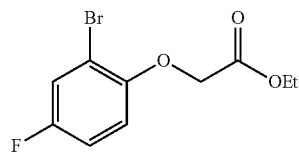 [SMILES: CCOC(=O)COc1ccc(F)cc1Br]

To solution of 2-bromo-4-fluorophenol (250 g, 1.31 mol) in CH$_3$CN (2 L) was added K$_2$CO$_3$ (270 g, 1.97 mol) and ethyl 2-bromoacetate (219 g, 1.31 mol). The suspension was heated at 90° C. for 1.5 h. The mixture was filtered and the filtrate was concentrated to give crude ethyl 2-(2-bromo-4-fluorophenoxy)acetate as a brown oil, which was used directly in next step. Yield: 312 g; $^1$H NMR (CDCl$_3$): δ 7.32 (dd, J=7.6, 3.2 Hz, 1H), 6.95-6.97 (m, 1H), 6.82 (dd, J=8.8, 4.4 Hz, 1H), 4.66 (s, 2H), 4.27 (q, J=7.2 Hz, 2H), 1.31 (t, J=7.2 Hz, 3H). $^1$F NMR (CDCl$_3$): δ −120.06 (s, 1F).

Step 2. 5-(2-bromo-4-fluorophenoxy)-2-thioxo-2,3-dihydropyrimidin-4(1H)-one

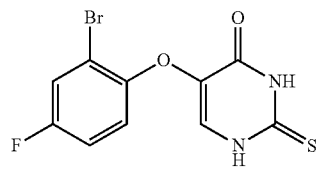 [SMILES: O=c1[nH]c(=S)[nH]cc1Oc1ccc(F)cc1Br]

To a solution of ethyl 2-(2-bromo-4-fluorophenoxy)acetate (100 g) in anhydrous THF (2 L) was added ethyl formate (108 g) and NaH (20 g) at 0° C. The mixture was stirred at 35-45° C. for 18 h. The solvent was removed under vacuum and anhydrous EtOH (2 L) and thiourea (25 g, 324.8 mmol) were added and stirred at 90° C. for 16 h. The mixture was concentrated and diluted with water (2 L) and extracted with petroleum ether:ethyl acetate (10:1; 500 mL×3). The aqueous layer was acidified to pH=4 by aq. HCl (1N, 200 mL) and white solid was precipitated. The mixture was filtered and the resulting filter cake was dried to give crude 5-(2-bromo-4-fluorophenoxy)-2-thioxo-2,3-dihydropyrimidin-4(1H)-one (62 g) as a with solid, which was used directly in next step without purification. Yield: 62 g; LCMS method C: $R_t$=0.638 min; (M+H)$^+$=316.9, 318.9 (chlorine isotopes).

Step 3: 5-(2-bromo-4-fluorophenoxy)pyrimidin-4-ol

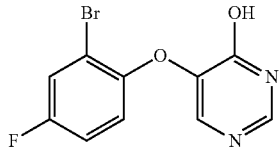 [SMILES: Oc1ncncc1Oc1ccc(F)cc1Br]

To a solution of 5-(2-bromo-4-fluorophenoxy)-2-thioxo-2,3-dihydropyrimidin-4(1H)-one (62 g) in anhydrous EtOH (1.5 L) was added Raney Ni (62 g) and the mixture was heated at reflux for 6 h. The solvent was removed under vacuum and anhydrous EtOH (2 L) was added. The mixture was filtered and filtrate stock was concentrated to give crude 5-(2-bromo-4-fluorophenoxy)pyrimidin-4-ol as a grey solid. Yield: 55 g. LCMS method C: $R_t$=0.619 min, (M+H)$^+$= 284.9 287.0 (chlorine isotopes).

Step 4: 5-(2-bromo-4-fluorophenoxy)-4-chloropyrimidine

To a solution of 5-(2-bromo-4-fluorophenoxy)pyrimidin-4-ol (55 g) in SOCl$_2$ (500 mL) was added anhydrous DMF (5 mL). The mixture was heated at 70° C. for 4 h. The mixture was concentrated, dissolved with DCM (500 mL), then poured into saturated NaHCO$_3$ (aq) (500 mL) and stirred at RT for 2 h. The organic layer was separated, dried over Na$_2$SO$_4$, filtered, and concentrated. The residue was then purified by ISCO column on silica gel (from 100% petroleum ether to EtOAc:petroleum ether=9:1) to give 5-(2-bromo-4-fluorophenoxy)-4-chloropyrimidine as a light yellow solid. Yield: 32 g. LCMS method C: $R_t$=0.858 min, (M+H)$^+$=302.9, 304.9 (chlorine & bromine isotopes); $^1$H NMR (CDCl$_3$): δ 8.77 (s, 1H), 8.07 (s, 1H), 7.45 (dd, J=7.6 3.2 Hz, 1H), 7.06-7.12 (m, 2H). $^{19}$F NMR (CDCl$_3$): δ −113.64 (s, 1F).

Intermediates 2-10a

The following intermediates were prepared according to the procedure described for Intermediate 1.

TABLE 1

Intermediates 2-10a.

| Int. No. | Name | Structural formula | Yield | Mass peak(s) (M + H)$^+$ | $R_f$ value or $R_t$ |
|---|---|---|---|---|---|
| 2 | 4-chloro-5-(2,6-dichloro-4-fluorophenoxy)pyrimidine | | 87% | 294.9, 296.9 | $R_t$ = 0.828 LCMS method C |

$^1$H NMR (CDCl$_3$): δ 8.75 (s, 1H), 7.88 (s, 1H), 7.26 (s, 1H), 7.24 (s, 1H). $^{19}$F NMR: (CDCl$_3$): δ −110.54 (s, 1F).

| 3 | 4-chloro-5-(2-chloro-3,4-difluorophenoxy)pyrimidine | | 42% | 277.0, 279.0 | 0.994 min LCMS method C |

$^1$H NMR (CDCl$_3$): δ 8.81 (s, 1H), 8.17 (s, 1H), 7.10-7.20 (m, 1H), 6.80-6.85 (m, 1H). $^{19}$F NMR: (CDCl$_3$): δ −132.37, −136.57.

| 4 | 4-chloro-5-(4-fluoro-2-(trifluoromethyl)phenoxy)pyrimidine | | 32% | 292.9 | 0.886 min in LCMS method C |

$^1$H NMR (CDCl$_3$): δ 8.80 (s, 1H), 8.26 (s, 1H), 7.46 (d, J = 8.0 Hz, 1H), 7.15-7.25 (m, 1H), 6.81-6.95 (m, 1H). $^{19}$F NMR: (CDCl$_3$): δ −62.00~−62.29, −114.92~−114.95.

| 5 | ethyl 2-(2-chloro-4-(trifluoromethyl)phenoxy)acetate | | 15% | 308.8, 310.8 | 0.854 min in LCMS method C |

TABLE 1-continued

Intermediates 2-10a.

| Int. No. | Name | Structural formula | Yield | Mass peak(s) (M + H)+ | $R_f$ value or $R_t$ |
|---|---|---|---|---|---|
| 6 | 4-chloro-5-(4-fluoro-2-(trifluoromethyl)phenoxy)pyrimidine | | 36% | 276.8, 278.8 | 0.834 min in LCMS method C |

<sup>1</sup>H NMR (CDCl<sub>3</sub>): δ 8.79 (s, 1H), 8.15 (s, 1H), 7.55 (d, J = 2.0 Hz, 1H), 7.30 (dd, J = 8.8 2.4 Hz, 1H), 6.99 (d, J = 8.8 Hz, 1H).

| | | | | | |
|---|---|---|---|---|---|
| 7 | 4-chloro-5-(4-fluoro-2-(trifluoromethyl)phenoxy)pyrimidine | | 14% | 320.8, 322.8 | 0.878 min in LCMS method C |
| 8 | 4-chloro-5-(2-bromo-3,4-difluorophenoxy)pyrimidine | | 31% | 321.0, 323.1 | 1.645 min in LCMS method C |
| 9 | 5-(2-bormo-4,5difluorophenoxy)-4chloropyrimidine | | 31% | 320.8, 322.8 | 1.025 min in LCMS method C |
| 10 | 4-chloro-5-(2-chloro-3-(trifluoromethyl)phenoxy)pyrimidine | | 25% | 309.1, 310.9 | 0.841 min in LCMS method C |

¹H NMR (CD₃OD): δ 8.82 (s, 1 H), 8.40 (s, 1 H), 7.70 (d, J = 8.0 Hz, 1 H), 7.54 (t, J = 8.0 Hz, 1 H) 7.39 (d, J = 8.0 Hz, 1 H). ¹⁹F NMR (CD₃OD): δ −63.82 (m, 3 F).

| | | | | | |
|---|---|---|---|---|---|
| 10a | 4-chloro-5-(2-chloro-4-fluorophenoxy)pyrimidine | | 45% | 258.1, 260.1 | 0.829 min in LCMS method C |

Intermediate 11 tert-Butyl 7-(5-(2-bromo-4-fluorophenoxy)pyrimidin-4-yl)-2,7-diazaspiro[4.4]nonane-2-carboxylate

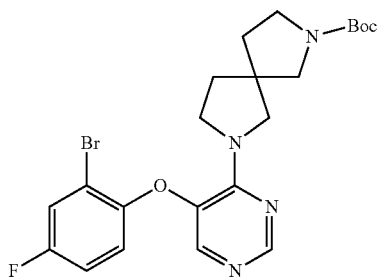 [SMILES: CC(C)(C)OC(=O)N1CCC2(CCN(c3ncncc3Oc3ccc(F)cc3Br)C2)C1]

A solution of 5-(2-bromo-4-fluorophenoxy)-4-chloropyrimidine (Intermediate 1, 4 g, 13.18 mmol), tert-butyl 2,7-diazaspiro[4.4]nonane-2-carboxylate (3.0 g, 13.18 mmol) and $K_2CO_3$ (7.3 g, 52.72 mmol) in $CH_3CN$ (100 mL) was stirred at 95° C. for 8 h. The solid was filtered off and the filtrate was concentrated under reduced pressure. The residue was purified by column chromatography on silica gel (eluting with petroleum ether:ethyl acetate=10:1 to 3:2) to afford tert-butyl 7-(5-(2-bromo-4-fluorophenoxy)pyrimidin-4-yl)-2,7-diazaspiro[4.4]nonane-2-carboxylate (Intermediate 11) as a yellow oil. Yield: 9.5 g; HPLC method C: $R_t$=0.749 min; $(M+H)^+$=493.0 495.1 (bromine isotopes); $^1H$ NMR ($CD_3OD$): δ 8.29 (s, 1H), 7.66 (s, 1H), 7.54 (d, J=2.8 Hz, 1H), 7-16 (d, J=6.0 Hz, 1H), 6.96 (d, J=4.8 Hz, 1H), 3.67-3.81 (t, 4H), 3.37 (s, 2H), 3.23-3.27 (m, 2H), 1.87-1.96 (t, 4H), 1.44 (s, 9H). $^{19}F$ NMR ($CD_3OD$): δ −119.01.

Intermediates 12-19

The following intermediates were prepared according to the procedure described for Intermediate 11.

TABLE 2

Intermediates 12-19

| Int. No. | Name | Structural formula | Yield | Mass peak(s) $(M + H)^+$ | $R_f$-value or $R_t$ |
|---|---|---|---|---|---|
| 12 | 7-(5-(2,6-dichloro-4-fluorophenoxy) pyrimidin-4-yl)-2,7-diazaspiro[4.4] nonane-2-carboxylate | | 80% | 483.0, 485.0 | 0.775 in LCMS method C |
| 13 | tert-butyl-6-(5-(2-chloro-4-fluorophenoxy) pyrimidin-4-yl)-2,6-diazaspiro[3.4] octane-2-carboxylate | | 86% | 467.3, 469.3 | 1.023 min in LCMS method C |

$^1H$ NMR ($CDCl_3$): δ 8.44 (s, 1H), 7.83 (s, 1H), 7.00-7.10 (m, 1H), 6.45-6.55 (m, 1H), 3.55-3.90 (m, 4H), 3.20-3.50 (m, 4H), 1.80-2.00 (m, 4H), 1.45 (s, 9H). $^{19}F$ NMR: ($CDCl_3$ 400 MHz): δ −133.24∼−133.47, −140.23∼−140.44.

| 14 | tert-butyl 7-(5-(4-fluoro-2-(trifluoromethyl)phenoxy)pyrimidin-4-yl)-2,7-diazaspiro[4.4] nonane-2-carboxylate | | 85% | 483.1 | 0.821 min in LCMS method C |

TABLE 2-continued

Intermediates 12-19

| Int. No. | Name | Structural formula | Yield | Mass peak(s) (M + H)+ | R_f value or R_t |
|---|---|---|---|---|---|

¹H NMR (CD₃OD): δ 8.30-8.40 (m, 1H), 7.80 (s, 1H), 7.55 (dd, J = 8.0 2.8 Hz, 1H), 7.36-7.40 (m, 1H), 6.91-7.00 (m, 1H), 3.70-3.88 (m, 2H), 3.55-3.69 (m, 2H), 3.32-3.50 (m, 2H), 3.15-3.29 (m, 2H), 1.84-2.00 (m, 4H), 1.45 (d, J = 3.6 Hz, 9H). ¹⁹F NMR: (CD₃OD): δ −63.9∼−63.53, −120.02∼−120.32.

| 15 | tert-butyl 7-(5-(2-chloro-4-(trifluoromethyl)phenoxy)pyrimidin-4-yl)-2,7-diazaspiro[4.4]nonane-2-carboxylate | | 70% | 499.3, 502.3 (chlorine isotopes) | 0.819 min in LCMS method E |

¹H NMR (CDCl₃): δ 8.49 (s, 1 H), 7.94 (s, 1 H), 7.76 (s, 1 H), 7.47 (d, J = 8.4 Hz, 1 H), 6.80-6.82 (m, 1 H), 3.65-3.76 (m, 2 H), 3.57-3.60 (m, 2 H), 3.41-3.47 (m, 2 H), 3.23-3.32 (m, 2 H), 1.85-1.92 (m, 4 H), 1.46 (s, 9 H). ¹⁹F NMR: (CDCl₃): δ −62.09.

| 16 | tert-butyl 7-(5-(2,4-dichlorophenoxy)pyrimidin-4-yl)-2,7-diazaspiro[4.4]nonane-2-carboxylate | | 94% | (M + H)+ = 464.9, 466.9 (chlorine isotopes) | 0.788 min in LCMS method C |

¹H NMR (CDCl₃): δ 8.44 (s, 1H), 7.84 (s, 1H), 7.48 (s, 1H), 7.19 (d, J = 8.4 2.4 Hz, 1H), 6.72 (d, J = 8.0 Hz, 1H), 3.60-3.80 (m, 4H), 3.25-3.46 (m, 4H), 1.87-1.93 (m, 4H), 1.46 (s, 9H).

| 17 | tert-butyl 7-(5-(2-bromo-4,6-difluorophenoxy)pyrimidin-4-yl)-2,7-diazaspiro[4.4]nonane-2-carboxylate | | 90% | (M + H)+ = 513.1, 515.1 (bromine isotopes) | 0.762 min in LCMS method C |

TABLE 2-continued

Intermediates 12-19

| Int. No. | Name | Structural formula | Yield | Mass peak(s) (M + H)+ | $R_f$-value or $R_t$ |
|---|---|---|---|---|---|
| 18 | tert-butyl 7-(5-(2-bromo-4,5-difluorophenoxy)pyrimidin-4-yl)-2,7-diazaspiro[4.4]nonane-2-carboxylate | | 90% | (M + H)+ = 510.9, 512.9, (bromine isotopes) | 0.823 min in LCMS method C |
| 19 | tert-butyl 7-(5-(2-chloro-3-(trifluoromethyl)phenoxy)pyrimidin-4-yl)-2,7-diazaspiro[4.4]nonane-2-carboxylate | | 74% | (M + H)+ = 499.3, 501.3 (chlorine isotopes) | 1.060 min in LCMS method D |

$^1$H NMR (CD$_3$OD): δ 8.38 (s, 1 H), 7.86 (s, 1 H), 7.47-7.60 (m, 2 H), 7.18 (s, 1 H), 3.80-3.84 (m, 2 H), 3.61-3.67 (m, 2 H), 3.44-3.52 (m, 2 H), 3.24-3.27 (m, 2 H), 1.89-1.99 (m, 4H), 1.46-1.48 (m, 9 H). $^{19}$F NMR (CD$_3$OD): δ −63.71 (m, 3 F).

Intermediate 20 tert-butyl 6-(5-(2-bromo-4-fluorophenoxy)pyrimidin-4-yl)-2,6-diazaspiro[3.3]heptane-2-carboxylate

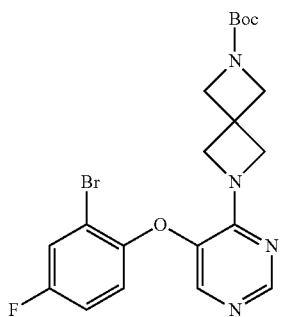 [SMILES: CC(C)(C)OC(=O)N1CC2(C1)CN(c1ncncc1Oc1ccc(F)cc1Br)C2]

To a solution of 5-(2-bromo-4-fluorophenoxy)-4-chloropyrimidine (Intermediate 1, 5.55 g, 18.4 mmol) in CH$_3$CN (80 mL) was added tert-butyl 2,6-diazaspiro[3.3]heptane-2-carboxylate (3.62 g, 18.4 mmol) and Na$_2$CO$_3$ (3.89 g, 36.74 mmol). The mixture was stirred at 90-95° C. for 16 h. The mixture was filtered and the filtrate was concentrated. The residue was purified by silica gel column chromatography (petroleum ether:ethyl acetate=0:1) to give tert-butyl 6-(5-(2-bromo-4-fluorophenoxy)pyrimidin-4-yl)-2,6-diazaspiro[3.3]heptane-2-carboxylate as a yellow solid. Yield: 6.5 g; HPLC method C: R$_t$=0.742 min, (M+H)$^+$=465.0, 467.0 (bromine isotopes).

Intermediates 20a-25

The following intermediates were prepared according to the procedure described for Intermediate 20.

TABLE 3

| | | Intermediates 20a-25 | | | |
|---|---|---|---|---|---|
| Int. No. | Name | Structure | Yield | Mass peak(s) (M + H)+ | R$_f$ value or R$_t$ |
| 20a | tert-butyl 6-(5-(2-chloro-4-fluorophenoxy)pyrimidin-4-yl)-2,6-diazaspiro[3.3]heptane-2-carboxylate | | 70% | 421.1, 423.1 | 0.701 min in LCMS method C |
| 21 | tert-butyl(2-(5-(2-bromo-4-fluorophenoxy)pyrimidin-4-yl)-2-azaspiro[3.3]heptan-6-yl)carbamate | | 76% | 478.9, 480.9 | 0.696 min in LCMS method C |
| 22 | 2-(5-(2-bromo-4-fluorophenoxy)pyrimidin-4-yl)-2-azaspiro[3.3]heptan-6-one | | 55 | 378.1, 380.1 | 0.721 min in LCMS method C |
| 23 | tert-butyl 2-(5-(2-bromo-4-fluorophenoxy)pyrimidin-4-yl)-2,7-diazaspiro[3.5]nonane-7-carboxylate | | 82% | 493.0, 495.0 | 0.696 min in LCMS method C |

TABLE 3-continued

Intermediates 20a-25

| Int. No. | Name | Structure | Yield | Mass peak(s) (M + H)+ | R$_f$ value or R$_t$ |
|---|---|---|---|---|---|
| 24 | tert-butyl 2-(5-(2-bromo-4-fluorophenoxy)pyrimidin-4-yl)-2,6-diazaspiro[3.4]octane-6-carboxylate | 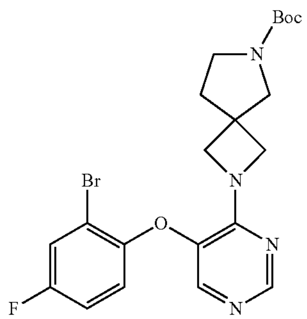 [SMILES: CC(C)(C)OC(=O)N1CCC2(C1)CN(c1ncncc1Oc1ccc(F)cc1Br)C2] | 90% | 478.9, 480.9 | 0.725 min in LCMS method C |
| 24A | tert-butyl 2-(5-(2-bromo-4-fluorophenoxy)pyrimidin-4-yl)-2,6-diazaspiro[3.4]octane-6-carboxylate | 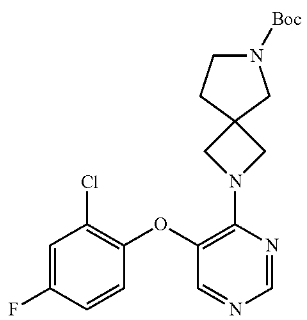 [SMILES: CC(C)(C)OC(=O)N1CCC2(C1)CN(c1ncncc1Oc1ccc(F)cc1Cl)C2] | 90% | 435.1 437.1 | 0.713 min in LCMS method C |
| 25 | tert-butyl 6-(5-(2-bromo-4-fluorophenoxy)pyrimidin-4-yl)-2,6-diazaspiro[3.4]octane-2-carboxylate | 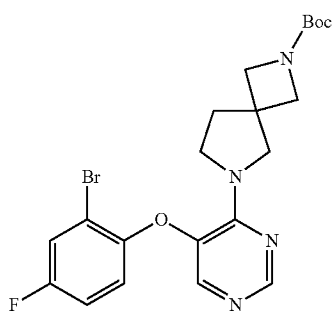 [SMILES: CC(C)(C)OC(=O)N1CC2(CCN(c3ncncc3Oc3ccc(F)cc3Br)C2)C1] | 78% | 479.0, 481.0 | 0.716 min in LCMS method C |

Intermediate 26

2-(5-(4-fluoro-2-(4-isopropylpyrimidin-5-yl)phenoxy)pyrimidin-4-yl)-2,7-diazaspiro[4.4]nonane

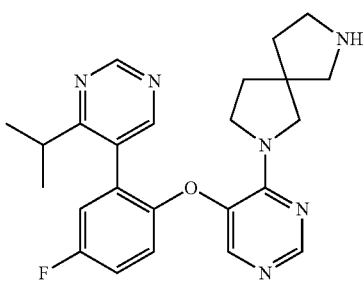 [SMILES: CC(C)c1ncncc1-c1cc(F)ccc1Oc1cncnc1N1CCC2(CCNC2)C1]

Step 1: tert-butyl 7-(5-(4-fluoro-2-(4-isopropylpyrimidin-5-yl)phenoxy)pyrimidin-4-yl)-2,7-diazaspiro[4.4]nonane-2-carboxylate

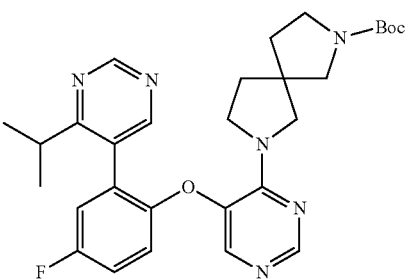 [SMILES: CC(C)c1ncncc1-c1cc(F)ccc1Oc1cncnc1N1CCC2(CCN(C(=O)OC(C)(C)C)C2)C1]

To a suspension of tert-butyl 7-(5-(2-bromo-4-fluorophenoxy)pyrimidin-4-yl)-2,7-diazaspiro[4.4]nonane-2-carboxylate (Intermediate 11, 200 mg, 0.40 mmol), (4-isopropylpyrimidin-5-yl)boronic acid (130 mg, 0.80 mmol) and K$_3$PO$_4$ (170 mg, 0.80 mmol) in dioxane (6 mL) and H$_2$O (2 mL) was added Sphos palladacycle (14.4 mg, 0.02 mmol) under N$_2$ atmosphere and the mixture was stirred at 90° C. for 16 h. The reaction mixture was washed with water (80 mL) and extracted with EtOAc (3×50 mL), the organic layers were dried over anhydrous Na$_2$SO$_4$, filtered, and concentrated under reduced pressure. The residue was purified by preparative TLC on silica gel (petroleum ether: EtOAc=1:1, R$_f$=0.25) to give tert-butyl 7-(5-(4-fluoro-2-(4-isopropylpyrimidin-5-yl)phenoxy)pyrimidin-4-yl)-2,7-diazaspiro[4.4] nonane-2-carboxylate as a white solid. Yield: 110 mg; HPLC method C: R$_t$=0.759 min; (M+H)$^+$=535.2.

Step 2: 2-(5-(4-fluoro-2-(4-isopropylpyrimidin-5-yl) phenoxy) pyrimidin-4-yl)-2,7-diazaspiro[4.4]nonane To a solution of tert-butyl 7-(5-(4-fluoro-2-(4-isopropylpyrimidin-5-yl)phenoxy)pyrimidin-4-yl)-2,7-diazaspiro [4.4]nonane-2-carboxylate (100 mg, 1.87 mmol) in CH$_2$Cl$_2$ (3 mL) was added TFA (1 mL). The mixture was stirred at 20-25° C. for 2 h. Then the reaction mixture was neutralized with NH$_3$—H$_2$O (pH=8) and washed with water (80 mL) and extracted with CH$_2$Cl$_2$ (3×50 mL). The organic layers were dried over anhydrous Na$_2$SO$_4$, filtered, and concentrated in vacuo to give crude 2-(5-(4-fluoro-2-(4-isopropylpyrimidin-5-yl)phenoxy)pyrimidin-4-yl)-2,7-diazaspiro [4.4]nonane as a yellow solid which was used in the next step without further purification. Yield: 90 mg; HPLC method C: R$_t$=0.575 min; (M+H)$^+$=435.2.

Intermediates 27-32

The following intermediates were prepared according to the procedure described for Intermediate 26.

TABLE 4

Intermediates 27-32

| Int No. | Name | Structure | Yield | Mass peak(s) (M + H)$^+$ | R$_f$ value or R$_t$ |
|---|---|---|---|---|---|
| 27 | 2-(5-(4-fluoro-2-(4-isopropylpyrimidin-5-yl)phenoxy)pyrimidin-4-yl)-2,6-diazaspiro[3.3]heptane | 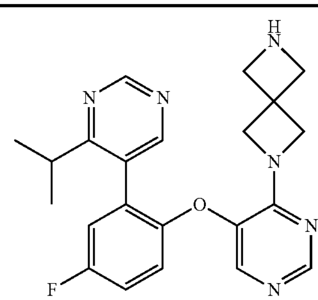 | 59% | 407.0 | 0.566 min in LCMS method C |
| 28 | (6-(5-(4-fluoro-2-(4-isopropylpyrimidin-5-yl)phenoxy)pyrimidin-4-yl)-2,6-diazaspiro[3.4]octane | 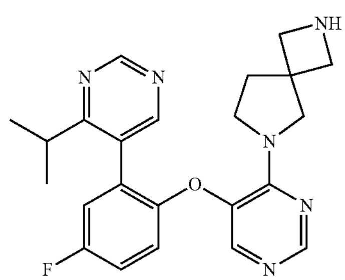 [SMILES: CC(C)c1ncncc1-c1cc(F)ccc1Oc1cncnc1N1CCC2(CNC2)C1] | 90% | 421.2 | 1.941 min in LCMS method D |
| 29 | 2-(5-(4-fluoro-2-(4-isopropylpyrimidin-5-yl)phenoxy)pyrimidin-4-yl)-2-azaspiro[3.3]heptan-6-amine | 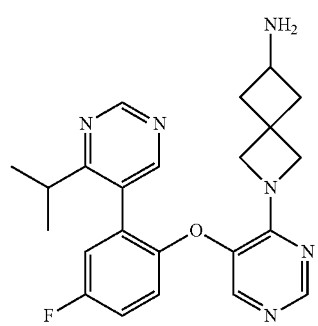 [SMILES: CC(C)c1ncncc1-c1cc(F)ccc1Oc1cncnc1N1CC2(CC(N)C2)C1] | 74% | 421.0 | 0.565 min in LCMS method C |

$^1$H NMR (MeOD): δ 9.12 (s, 1 H), 8.63-8.65 (m, 1 H), 8.26 (s, 1 H), 7.77 (s, 1 H), 7.25-7.30 (m, 2 H), 7.02-7.05 (m, 1 H) 3.58-3.74 (m, 8 H), 3.09-3.14 (m, 1 H), 2.05-2.16 (m, 2 H), 1.24 (d, J = 6.8 Hz, 6 H). $^{19}$F NMR (MeOD): δ −120.40.

TABLE 4-continued

Intermediates 27-32

| Int No. | Name | Structure | Yield | Mass peak(s) (M + H)+ | R$_f$ value or R$_t$ |
|---|---|---|---|---|---|
| 30 | 2-(5-((5-fluoro-2'-isopropyl-[1,1'-biphenyl]-2-yl)oxy)pyrimidin-4-yl)-2,6-diazaspiro[3.3]heptane | 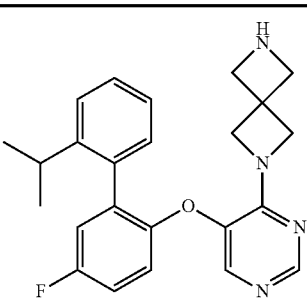 | 78% | 405.1 | 0.617 min in LCMS method C |
| 31 | 2'-((4-(2,7-diazaspiro[4.4]nonan-2-yl)pyrimidin-5-yl)oxy)-2-cyclopropyl-5'-fluoro-[1,1'-biphenyl]-4-carbonitrile | 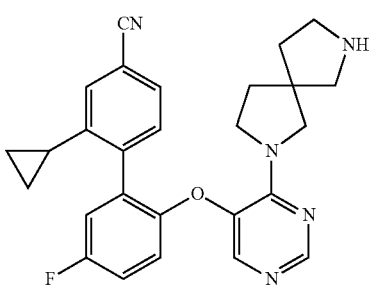 [SMILES: N#Cc1ccc(-c2cc(F)ccc2Oc2cncnc2N2CCC3(CCNC3)C2)c(C2CC2)c1] | 77% | 456.2 | 0.639 min in LCMS method C |
| 31a | 2-(5-(4-fluoro-2-(1-isopropyl-1H-pyrazol-5-yl)phenoxy)pyrimidin-4-yl)-2,7-diazaspiro[4.4]nonane | 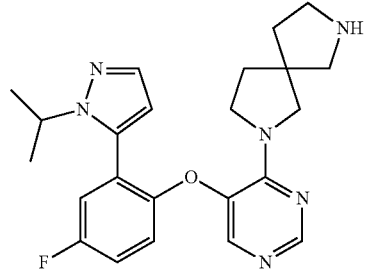 [SMILES: CC(C)n1nccc1-c1cc(F)ccc1Oc1cncnc1N1CCC2(CCNC2)C1] | 70% | 423.2 | 0.539 min in LCMS method C |
| 31b | 2-(5-(4-fluoro-2-(4-isopropylpyrimidin-5-yl)phenoxy)pyrimidin-4-yl)-2,7-diazaspiro[3.5]nonane | 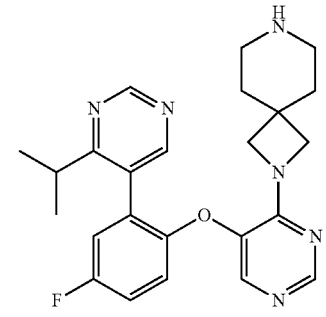 [SMILES: CC(C)c1ncncc1-c1cc(F)ccc1Oc1cncnc1N1CC2(CCNCC2)C1] | 58 | 435.2 | 0.551 min in LCMS method C |
| 31c | 2-(5-(2-(2-cyclopropylpyridin-3-yl)-4-fluorophenoxy)pyrimidin-4-yl)-2,6-diazaspiro[3.3]heptane | 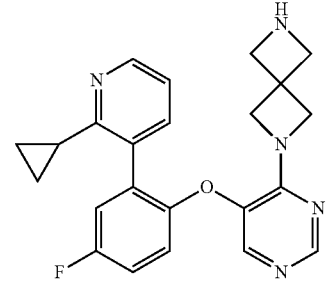 [SMILES: Fc1ccc(Oc2cncnc2N2CC3(CNC3)C2)c(-c2cccnc2C2CC2)c1] | 50% | 404.2 | 0.532 min in LCMS method C |

TABLE 4-continued

Intermediates 27-32

| Int No. | Name | Structure | Yield | Mass peak(s) (M + H)+ | R$_f$-value or R$_t$ |
|---|---|---|---|---|---|
| 32 | 2'-((4-(2,6-diaza-spiro[3.3]heptan-2-yl)pyrimidin-5-yl)oxy)-2-cyclopropyl-5'-fluoro-[1,1'-biphenyl]-4-carbonitrile | 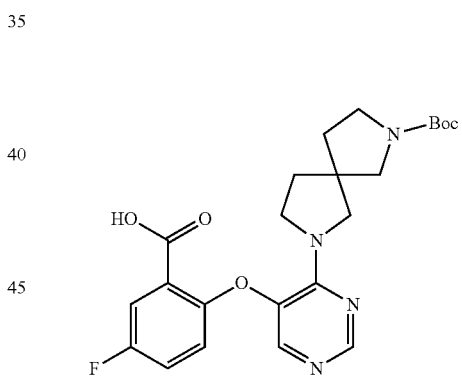 | 49% | 428.0 | 0.615 min in in LCMS method C |

Intermediate 33

2-((4-(2,7-diazaspiro[4.4]nonan-2-yl)pyrimidin-5-yl)oxy)-5-fluoro-N-isopropyl-N-methylbenzamide

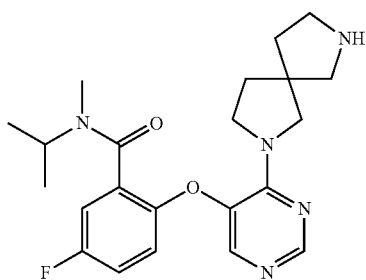 [SMILES: CC(C)N(C)C(=O)c1cc(F)ccc1Oc1cncnc1N1CCC2(CCNC2)C1]

Step 1. tert-butyl 7-(5-(4-fluoro-2-(methoxycarbonyl)phenoxy)pyrimidin-4-yl)-2,7-diazaspiro[4.4]nonane-2-carboxylate

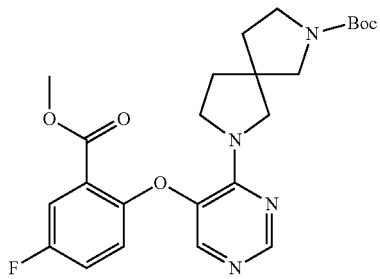 [SMILES: COC(=O)c1cc(F)ccc1Oc1cncnc1N1CCC2(CCN(C(=O)OC(C)(C)C)C2)C1]

To a solution of tert-butyl 7-(5-(2-bromo-4-fluorophenoxy)pyrimidin-4-yl)-2,7-diazaspiro[4.4]nonane-2-carboxylate (Intermediate 11, 9.5 g, 19.31 mmol) and Pd(dppf)Cl$_2$ (7.1 g, 9.66 mmol) was added in Et$_3$N (13.4 mL) and MeOH (100 mL). Then the reaction mixture was stirred at 65° C. under CO (50 Psi) for about 16 h. The reaction was filtered through Celite and concentrated under reduced pressure to afford the residue which was purified by column chromatography on silica gel (eluting with DCM:MeOH=1:0~10:1) to afford tert-butyl 7-(5-(4-fluoro-2-(methoxycarbonyl)phenoxy)pyrimidin-4-yl)-2,7-diazaspiro[4.4]nonane-2-carboxylate as brown oil. Yield: 9.0 g; LC-MS method E: R$_t$=0.914 min; (M+H)+=473.2.

Step 2. 2-((4-(7-(tert-butoxycarbonyl)-2,7-diazaspiro[4.4]nonan-2-yl)pyrimidin-5-yl)oxy)-5-fluorobenzoic Acid To a solution of tert-butyl 7-(5-(4-fluoro-2-(methoxycarbonyl)phenoxy)pyrimidin-4-yl)-2,7-diazaspiro[4.4]nonane-2-carboxylate (3.3 g, 6.99 mmol) in MeOH (30 mL), THF (30 mL) and H$_2$O (10 mL) was added KOH (0.78 g, 13.98 mmol). The mixture was stirred at 13-23° C. for 16 h. The mixture was concentrated, and adjusted to pH=3-4 with aqueous HCl (3 mol/L). The mixture was extracted with EtOAc (3×50 mL), and the combined organic layers were washed with brine (50 mL), directed over Na$_2$SO$_4$, filtered and concentrated to give crude 2-((4-(7-(tert-butoxycarbonyl)-2,7-diazaspiro[4.4]nonan-2-yl)pyrimidin-5-yl)oxy)-5-fluorobenzoic acid as a brown solid, which was used directly without further purification. Yield: 3.2 g; LCMS Method C: R$_t$=0.702 min, (M+H)+=459.0. $^1$H NMR (DMSO-d$_6$): δ 8.30 (s, 1H), 7.39-7.69 (m, 3H), 6.95-7.05 (m, 1H), 3.60-3.72 (m, 5H), 3.17 (s, 3H), 1.77-1.88 (m, 4H), 1.38 (s, 9H). $^{19}$F NMR (DMSO-d$_6$): δ −119.13.

Step 3. tert-butyl 7-(5-(4-fluoro-2-isopropyl(methyl) carbamoyl)phenoxy)pyrimidin-4-yl)-2,7-diazaspiro[4.4]nonane-2-carboxylate

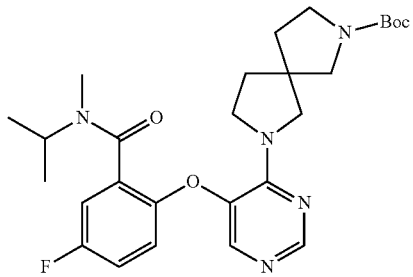 [SMILES: CC(C)N(C)C(=O)c1cc(F)ccc1Oc1cncnc1N1CCC2(CCN(C(=O)OC(C)(C)C)C2)C1]

To a solution of 2-((4-(7-(tert-butoxycarbonyl)-2,7-diazaspiro[4.4]nonan-2-yl)pyrimidin-5-yl)oxy)-5-fluorobenzoic acid (2.9 g, 5.45 mmol) and N-methylpropan-2-amine (0.6 g, 8.18 mmol) in DCM (100 mL) was added HATU (3.1 g, 8.18 mmol) and DIPEA (2.1 g, 16.3 mmol). The mixture was stirred at 13-21° C. for 16 h. The mixture was concentrated, and the residue was purified by neutral preparative HPLC to give tert-butyl 7-(5-(4-fluoro-2-isopropyl(methyl)carbamoyl)phenoxy)pyrimidin-4-yl)-2,7-diazaspiro[4.4]nonane-2-carboxylate. Yield: 2.1 g; LCMS method E: $R_t$=0.731 min (M+H)$^+$=514.1. $^1$H NMR (DMSO-d$_6$): δ 8.30-8.33 (m, 1H), 7.77-7.82 (m, 1H), 7.19-7.29 (m, 2H), 6.87-6.97 (m, 1H), 4.67 (s, 1H), 3.56-3.78 (m, 6H), 3.15-3.17 (m, 2H), 2.67-2.83 (m, 3H), 1.79-1.84 (m, 4H), 1.38 (s, 9H), 1.06-1.11 (m, 6H). $^{19}$F NMR (DMSO-d$_6$): δ −111.36.

Step 4. 2-((4-(2,7-diazaspiro[4.4]nonan-2-yl)pyrimidin-5-yl)oxy)-5-fluoro-N-isopropyl-N-methylbenzamide To a solution of tert-butyl 7-(5-(4-fluoro-2-(isopropyl(methyl)carbamoyl)phenoxy)pyrimidin-4-yl)-2,7-diazaspiro[4.4]nonane-2-carboxylate (1 g, 1.95 mmol) in anhydrous DCM (10 mL) was added HCl-MeOH (2 mL, 4 mol/L in MeOH) slowly at 0° C. under N$_2$. The reaction was stirred at 17-23° C. for 16 h. The mixture was adjusted to pH=11~12 with aq. NaOH (1 mol/L) then was extracted with EtOAc (50 mL×3). The combined organic layers were washed with brine (50 mL), dried over Na$_2$SO$_4$, filtered, and concentrated under reduced pressure to give crude 2-((4-(2,7-diazaspiro[4.4]nonan-2-yl)pyrimidin-5-yl)oxy)-5-fluoro-N-isopropyl-N-methylbenzamide as a brown solid. Yield: 0.8 g (95% crude); LCMS method C: $R_t$=0.508 min, (M+H)$^+$= 414.0.

Intermediates 35-39

The following intermediates were prepared according to the procedure provided for Intermediate 33.

TABLE 5

Intermediates 35-39

| Int. No. | Name | Structure | Yield | Mass peak(s) (M + H)$^+$ | $R_f$ value or $R_t$ |
|---|---|---|---|---|---|
| 35 | 2-((4-(2,6-diazaspiro[3.5]octan-2-yl)pyrimidin-5-yl)oxy)-5-fluoro-N-isopropyl-N-methylbenzamide | 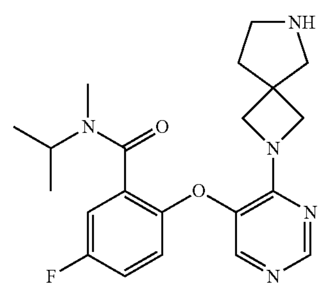 [SMILES: CC(C)N(C)C(=O)c1cc(F)ccc1Oc1cncnc1N1CC2(CCNC2)C1] | 77% | 400.0 | 0.420 min in LCMS method C |
| 36 | 2-((4-(2,7-diazaspiro[3.5]nonan-2-yl)pyrimidin-5-yl)oxy)-5-fluoro-N-isopropyl-N-methylbenzamide | 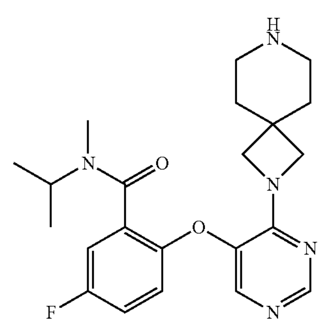 [SMILES: CC(C)N(C)C(=O)c1cc(F)ccc1Oc1cncnc1N1CC2(CCNCC2)C1] | 81% | 414.3 | 0.827 min in LCMS method F |

$^1$H NMR (CD$_3$OD): δ 8.22-8.27 (m, 1H), 7.70-7.80 (m, 1H), 6.94-7.22 (m, 3H), 4.77-4.79 (m, 1H), 3.90-4.01 (m, 4H), 2.77-3.31 (m, 7H), 1.84-1.86 (m, 4H), 1.15-1.28 (m, 6H). $^{19}$F NMR (CD$_3$OD): δ −115.01.

TABLE 5-continued

Intermediates 35-39

| Int. No. | Name | Structure | Yield | Mass peak(s) (M + H)+ | $R_f$-value or $R_t$ |
|---|---|---|---|---|---|
| 37 | 2-((4-(2,6-diazaspiro[3.4]octan-6-yl)pyrimidin-5-yl)oxy)-5-fluoro-N-isopropyl-N-methylbenzamide | | 54% | 400.2 | 1.850 min in LCMS Method D |

$^1$H NMR (CD$_3$OD): δ 8.25-8.35 (m, 1 H), 7.75-7.91 (m, 1 H), 7.15-7.25 (m, 2 H), 6.85-7.00 (m, 1 H), 3.60-4.05 (m, 9 H), 2.80-3.00 (m, 3 H), 2.15-2.25 (m, 2 H), 1.00-1.30 (m, 6 H). $^{19}$F NMR (CD$_3$OD): δ −120.13~−120.73.

| Int. No. | Name | Structure | Yield | Mass peak(s) (M + H)+ | $R_f$-value or $R_t$ |
|---|---|---|---|---|---|
| 38 | 2-((4-(6-amino-2-azaspiro[3.3]heptan-2-yl)pyrimidin-5-yl)oxy)-5-fluoro-N-isopropyl-N-methylbenzamide | 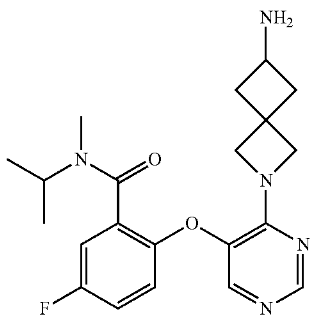 [SMILES: CC(C)N(C)C(=O)c1cc(F)ccc1Oc1cncnc1N1CC2(CC(N)C2)C1] | 37% | 399.8 | 1.45 min in LCMS Method D |
| 39 | ((4-(2,6-diazaspiro[3.3]heptan-2-yl)pyrimidin-5-yl)oxy)-5-fluoro-N-isopropyl-N-methylbenzamide | 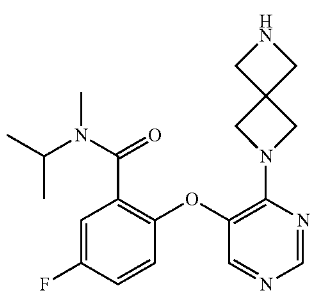 [SMILES: CC(C)N(C)C(=O)c1cc(F)ccc1Oc1cncnc1N1CC2(CNC2)C1] | 35% | 386.1 | 1.42 min in LCMS Method D |

Intermediate 40

2-oxo-2,3-dihydro-1H-benzo[d]imidazole-5-carbaldehyde

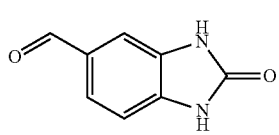 [SMILES: O=Cc1ccc2[nH]c(=O)[nH]c2c1]

To a suspension of 2-oxo-2,3-dihydro-1H-benzo[d]imidazole-5-carbonitrile (10 g, 57.75 mmol) in HCO$_2$H (187 mL) and H$_2$O (63 mL) was added Ni—Al alloy (6.19 g, 144.38 mmol) in portions. Then the mixture was stirred at 90° C. for 16 h. The reaction mixture was filtered and the filtrate was washed with EtOH and concentrated under reduced pressure. The residue was washed with water (150 mL) and filtered. The filter cake was dried under reduced pressure to give 2-oxo-2,3-dihydro-1H-benzo[d]imidazole-5-carbaldehyde as a grey white solid. Yield: 9.1 g (97.2%); LCMS method D: R$_t$=1.404 min, (M+H)$^+$=163.0. $^1$H NMR (CD$_3$OD): δ 9.87 (s, 1H), 7.65 (dd, J=8.4, 1.2 Hz, 1H), 7.55 (s, 1H), 7.19 (d, J=8.0 Hz, 1H).

Intermediate 41

2-((4-chloropyrimidin-5-yl)oxy)-5-fluoro-N,N-diisopropylbenzamide

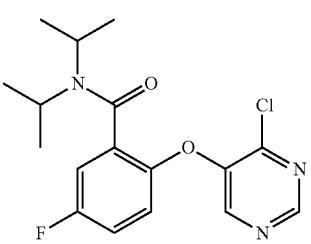 [SMILES: CC(C)N(C(=O)c1cc(F)ccc1Oc1cncnc1Cl)C(C)C]

Step 1. Methyl 5-fluoro-2-methoxybenzoate

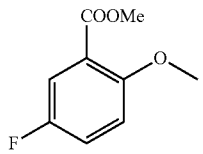

To a solution of 5-fluoro-2-hydroxybenzoic acid (100 g, 641 mmol) in acetone (1000 mL) was added K$_2$CO$_3$ (190 g, 1380 mmol) and MeI (268.3 g, 1890 mmol). The mixture was stirred at 50° C. for 16 h. The mixture was filtered and concentrated under reduced pressure. The residue was mixed with EtOAc (500 mL) and washed with H$_2$O (3×300 mL). The organic layer was then dried over anhydrous Na$_2$SO$_4$, filtered, and concentrated under reduced pressure. The residue was purified by column chromatography on silica gel eluting with petroleum ether:ethyl acetate=20:1 to afford methyl 5-fluoro-2-methoxybenzoate. Yield: 78 g (66%). $^1$H NMR (CDCl$_3$): δ 7.50 (dd, J=3.6 Hz, 8.8 Hz, 1H), 7.17-7.18 (m, 1H), 6.92 (dd, J=4.0 Hz, 8.8 Hz 1H), 3.89 (s, 3H), 3.88 (s, 3H).

Step 2. 5-fluoro-2-methoxybenzoic Acid

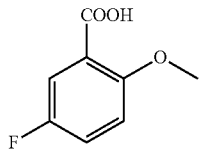

To a solution of methyl 5-fluoro-2-methoxybenzoate (25 g, 135.9 mmol) in MeOH (250 mL) and H$_2$O (50 mL) was added KOH (25 g, 446.4 mmol). The mixture was stirred at 60° C. for 3 h. The mixture was then adjusted to pH 3-4 by 2N HCl solution and concentrated to remove MeOH under reduced pressure. The residue was mixed with EtOAc (200 mL) and washed with H$_2$O (2×200 mL). The organic layer was dried over anhydrous Na$_2$SO$_4$, filtered, and concentrated under reduced pressure to afford crude 5-fluoro-2-methoxybenzoic acid as a white solid, which was used for next step without further purification. Yield: 23 g.

Step 3. 5-fluoro-N,N-diisopropyl-2-methoxybenzamide

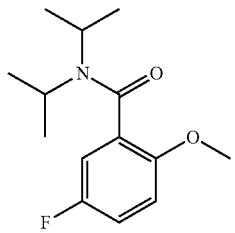 [SMILES: COc1ccc(F)cc1C(=O)N(C(C)C)C(C)C]

To a solution of 5-fluoro-2-methoxybenzoic acid (20 g, 117.6 mmol) and diisopropylamine (23.8 g, 235.6 mmol) in anhydrous CH$_2$Cl$_2$ (300 mL) was added DIEA (22.8 g, 176.7 mmol) and HATU (53.6 g, 141.4 mmol) at 0° C. The mixture was stirred at 25° C. for 16 h. The mixture was then washed with H$_2$O (3×200 mL). The organic layer was dried over anhydrous Na$_2$SO$_4$, filtered, and concentrated under reduced pressure. The residue was purified by column chromatography on silica gel eluting with petroleum ether:ethyl acetate=5:1 to afford 5-fluoro-N,N-diisopropyl-2-methoxybenzamide as a white solid. Yield: 22 g. LCMS method C: R$_t$ value: 0.785 min, (M+H)$^+$=254.0.

Step 4. 5-fluoro-2-hydroxy-N,N-diisopropylbenzamide

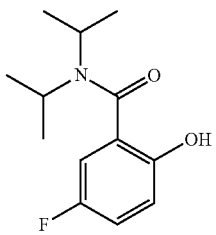 [SMILES: CC(C)N(C(=O)c1cc(F)ccc1O)C(C)C]

To a solution of 5-fluoro-N,N-diisopropyl-2-methoxybenzamide (15 g, 59.3 mmol) in anhydrous CH$_2$Cl$_2$ (250 mL) was added with BBr$_3$ (11 mL, 116.6 mmol) dropwise at −70° C. The mixture was stirred at 5° C. for 16 h. The reaction mixture was quenched with MeOH (30 mL) slowly at −78° C. and adjusted to pH 7-8 with sat. NaHCO$_3$ solution. The mixture was extracted with EtOAc (2×300 mL). The combined organic layers were dried over anhydrous Na$_2$SO$_4$, filtered, and concentrated under reduced pressure. The residue was purified by column chromatography on silica gel eluting with petroleum ether:ethyl acetate=4:1 to afford 5-fluoro-2-hydroxy-N,N-diisopropylbenzamide as a white solid. Yield: 11 g. LCMS method C: R$_t$=0.744 min; (M+H)$^+$= 240.0.

Step 5. 5-fluoro-N,N-diisopropyl-2-pyrimidin-5-yloxy)benzamide

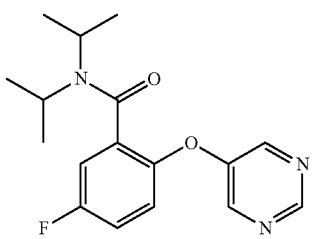 [SMILES: CC(C)N(C(=O)c1cc(F)ccc1Oc1cncnc1)C(C)C]

To a solution of 5-fluoro-2-hydroxy-N,N-diisopropylbenzamide (11.0 g, 46.0 mmol) and 5-bromopyrimidine (21.8 g, 138.0 mmol) in anhydrous DMF (300 mL) was added Cs$_2$CO$_3$ (45.0 g, 138.0 mmol). The mixture was stirred at 130° C. for 16 h. The mixture was added to EtOAc (500 mL) and washed with H$_2$O (3×300 mL). The organic layer was dried over anhydrous Na$_2$SO$_4$, filtered, and concentrated under reduced pressure. The residue was purified by column chromatography on silica gel eluting with petroleum ether: ethyl acetate=3:1 to afford 5-fluoro-N,N-diisopropyl-2-(pyrimidin-5-yloxy)benzamide as a white solid. Yield: 14 g (97%) LCMS method C: R$_t$=0.731 min; (M+H)$^+$=317.9.

Step 6. 5-(2-(diisopropylcarbamoyl)-4-fluorophenoxy)pyrimidine-1-oxide

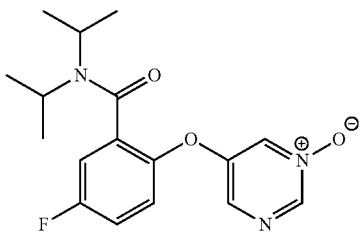 [SMILES: CC(C)N(C(=O)c1cc(F)ccc1Oc1cnc[n+]([O-])c1)C(C)C]

To a solution of 5-fluoro-N,N-diisopropyl-2-(pyrimidin-5-yloxy)benzamide (14 g, 44.2 mmol) in anhydrous $CH_2Cl_2$ (400 mL) was added m-CPBA (27 g, 132.7 mmol). The mixture was stirred at 10° C. for 16 h. The reaction mixture was quenched with sat. $Na_2SO_3$ solution (200 mL) and washed with $NaHCO_3$ (2×200 mL). The organic layer was dried over anhydrous $Na_2CO_3$, filtered, and concentrated under reduced pressure to afford crude 5-(2-(diisopropylcarbamoyl)-4-fluorophenoxy)pyrimidine 1-oxide as a pale yellow solid, which was used for next step without further purification. Yield: 16 g (109%). LCMS method C: $R_t$=0.705 min, $(M+H)^+$=333.9.

Step 7. 2-((4-chloropyrimidin-5-yl)oxy)-5-fluoro-N,N-diisopropylbenzamide

To a solution of $Et_3N$ (7.3 g, 72.3 mmol) in $CHCl_3$ (30 mL) was added $POCl_3$ (12.5 g, 81.7 mmol) at 0° C. Then the mixture was added to a solution of 5-(2-(diisopropylcarbamoyl)-4-fluorophenoxy)pyrimidine-1-oxide (16.0 g, 48.0 mmol) in $CHCl_3$ (270 mL) slowly at 0° C. The mixture was stirred at 65° C. for 16 h. The mixture was then slowly added to a sat. $NaHCO_3$ solution (500 mL) and the pH was adjusted to 7-8 by sat. $NaHCO_3$ solution. The mixture was extracted with ethyl acetate (2×300 mL). The combined organic layers were dried over anhydrous $Na_2SO_4$, filtered, and concentrated under reduced pressure. The residue was purified by column chromatography on silica gel eluting with petroleum ether:ethyl acetate=5:1 to afford 2-((4-chloropyrimidin-5-yl)oxy)-5-fluoro-N,N-diisopropylbenzamide (6 g) as a yellow solid. HPLC method C: $R_t$=0.735 min, $(M+H)^+$=351.9. $^1H$ NMR ($CDCl_3$): δ 8.71 (s, 1H), 8.21 (s, 1H), 7.02-7.12 (m, 3H), 3.73-3.80 (m, 1H), 3.46-3.53 (m, 1H), 1.49 (d, J=6.8 Hz, 3H), 1.34 (d, J=6.8 Hz, 3H), 1.26 (d, J=6.4 Hz, 3H), 1.14 (d, J=6.8 Hz, 3H). $^{19}F$ NMR ($CDCl_3$): δ −114.5.

Intermediate 41a 2-((4-(2,6-diazaspiro[3.3]heptan-2-yl)pyrimidin-5-yl)oxy)-5-fluoro-N,N-diisopropylbenzamide

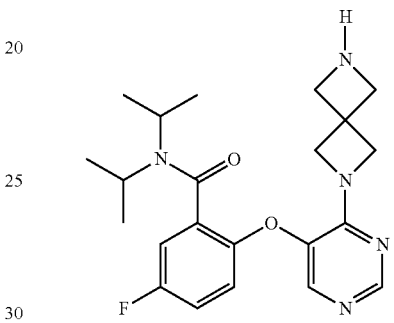

The title compound was synthesized from Intermediate 41 and tert-butyl 2,6-diazaspiro[3.3]heptane-2-carboxylate by method described for preparing Intermediate 20. LCMS—Method C: 0.620 min, $(M+H)^+$=413.2.

Intermediates 41b-41f

The following intermediates were prepared according to the procedure described for Intermediates 41 and 41a.

TABLE 6

Intermediates 42b-42f

| Int. No. | Name | Structure | Yield | Mass peak(s) | $R_f$ value or $R_t$ |
|---|---|---|---|---|---|
| 41b | 2-((4-(2,6-diazaspiro[3.4]octan-2-yl)pyrimidin-5-yl)oxy)-5-fluoro-N,N-diisopropylbenzamide | 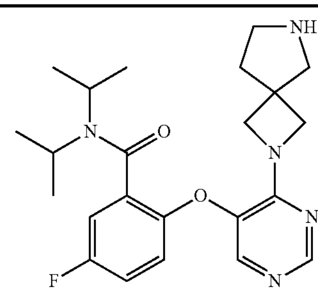 | 77% | $(M + H)^+$ = 428.0 | 0.520 min in LCMS method C |
| 41c | 2-((4-(2,6-diazaspiro[3.4]octan-6-yl)pyrimidin-5-yl)oxy)-5-fluoro-N,N-diisopropylbenzamide | 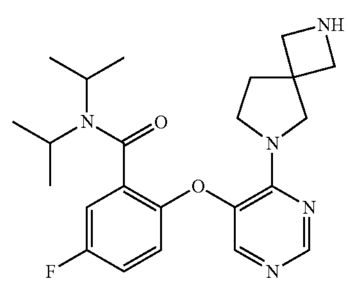 [SMILES: CC(C)N(C(=O)c1cc(F)ccc1Oc1cncnc1N1CCC2(CNC2)C1)C(C)C] | 54% | $(M + H)^+$ = 428.2 | 1.45 min in LCMS Method D |

TABLE 6-continued

Intermediates 42b-42f

| Int. No. | Name | Structure | Yield | Mass peak(s) | $R_f$ value or $R_t$ |
|---|---|---|---|---|---|
| 41d | 2-((4-(6-amino-2azaspiro[3.3]heptan-2-yl)pyrimidin-5-yl)oxy)-5-fluoro-N,N-diisopropyl-benzamide | 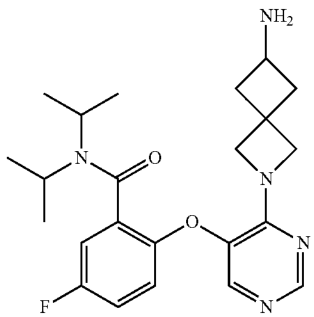 [SMILES: CC(C)N(C(=O)c1cc(F)ccc1Oc1cncnc1N1CC2(CC(N)C2)C1)C(C)C] | 37% | $(M + H)^+$ = 428.2 | 1.42 min in LCMS Method D |
| 41e | 2-((4-(2,6-diazaspiro[3.4]octan-2-yl)pyrimidin-5-yl)oxy)-N-ethyl-5-fluoro-N-isopropyl-benzamide | 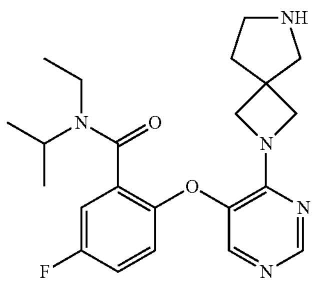 [SMILES: CCN(C(=O)c1cc(F)ccc1Oc1cncnc1N1CC2(CCNC2)C1)C(C)C] | 70% | $(M + H)^+$ = 414.1 | 0.512 min in LCMS method C |
| 41f | 2-((4-(2,7-diazaspiro[3.5]nonan-2-yl)pyrimidin-5-yl)oxy)-N-ethyl-5-fluoro-N-isopropyl-benzamide | 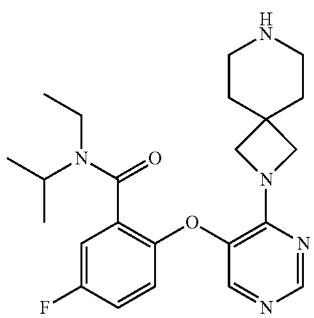 [SMILES: CCN(C(=O)c1cc(F)ccc1Oc1cncnc1N1CC2(CCNCC2)C1)C(C)C] | 54% | $(M + H)^+$ = 428.2 | 1.36 min in LCMS Method D |

Intermediates 42 and 42c. 1-(2-hydroxyethyl)-2-oxo-2,3-dihydro-1H-benzo[d]imidazole-5-carbaldehyde and 2-(5-formyl-2-oxo-2,3-dihydro-1H-benzo[d]imidazol-1-yl)ethyl formate

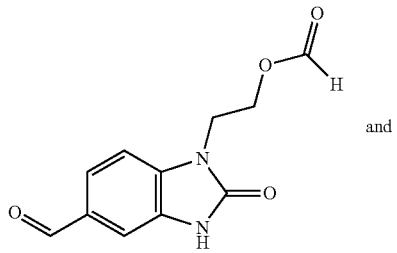

and

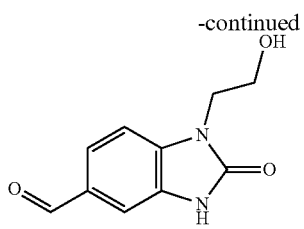

Step 1.
4-((2-hydroxyethyl)amino)-3-nitrobenzonitrile

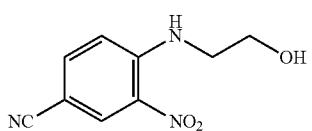 [SMILES: N#Cc1ccc(NCCO)c([N+](=O)[O-])c1]

To a solution of 4-fluoro-3-nitrobenzonitrile (15 g, 90.4 mmol) and 2-aminoethanol (11.0 g, 180.7 mmol) in anhydrous DMF (600 mL) was added K$_2$CO$_3$ (37.4 g, 271.2 mmol) under N$_2$, then the reaction mixture was stirred at 25° C. for 2 h. The reaction mixture was filtered and the filtrate was concentrated under reduced pressure. The residue was washed with H$_2$O (100 mL) and the mixture was extracted with EtOAc (3×500 mL). The organic layers were washed with brine (20 mL), dried over anhydrous Na$_2$SO$_4$, filtered, and concentrated to afford 4-((2-hydroxyethyl)amino)-3-nitrobenzonitrile. The residue was used for the next step without further purification as a yellow solid. Yield: 17.3 g. LCMS method E: R$_t$=1.016 min; (M+H)$^+$=207.9.

Step 2.
3-amino-4-((2-hydroxyethyl)amino)benzonitrile

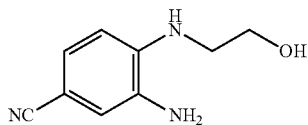 [SMILES: N#Cc1ccc(NCCO)c(N)c1]

To a solution of 4-((2-hydroxyethyl)amino)-3-nitrobenzonitrile (17.3 g, 83.6 mmol) in EtOH (800 mL) and H$_2$O (400 mL) were added Fe (23.4 g, 418.0 mmol) and NH$_4$Cl (44.8 g, 836.0 mmol) under N$_2$. The reaction mixture was stirred at 80° C. for 2 h. The reaction mixture was filtered and the filtrate was concentrated under reduced pressure. The residue was dissolved in EtOAc (500 mL), washed with H$_2$O (2×100 mL), brine (20 mL), dried over anhydrous Na$_2$SO$_4$, filtered, and concentrated to afford 3-amino-4-((2-hydroxyethyl)amino)benzonitrile. The residue was used for the next step without further purification as a brown red solid. Yield: 11.6 g. LCMS Method D: R$_t$=0.941 min; (M+H)$^+$=178.2.

Step 3. 3-amino-4-((2-((tert-butyldimethylsilyl)oxy)ethyl)amino)benzonitrile

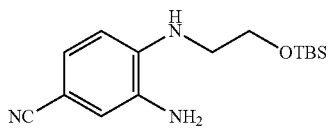 [SMILES: CC(C)(C)[Si](C)(C)OCCNc1ccc(C#N)cc1N]

To a solution of 3-amino-4-((2-hydroxyethyl)amino)benzonitrile (11.6 g, 65.46 mmol) and tert-butylchlorodimethylsilane (11.84 g, 78.55 mmol) in anhydrous DMF (300 mL) was added imidazole (11.14 g, 163.65 mmol), then the reaction was stirred at 35° C. for 16 h. The reaction mixture was filtered and the filtrate was concentrated under reduced pressure. The reaction mixture was added to water (1000 mL) and extracted with EtOAc (3×500 mL). The organic layer was washed with brine (100 mL), dried over anhydrous Na$_2$SO$_4$, filtered, and concentrated under reduced pressure to afford 3-amino-4-((2-((tert-butyldimethylsilyl)oxy)ethyl)amino)benzonitrile as a black oil, which was used for the next step without further purification. Yield: 25 g. LCMS method C: R$_t$=0.878 min; (M+H)$^+$=292.1.

Step 4. 1-(2-((tert-butyldimethylsilyl)oxy)ethyl)-2-oxo-2,3-dihydro-1H-benzo[d]imidazole-5-carbonitrile

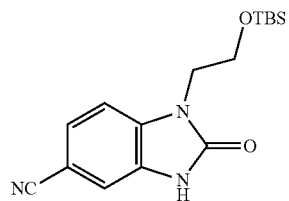 [SMILES: CC(C)(C)[Si](C)(C)OCCn1c(=O)[nH]c2cc(C#N)ccc21]

To a solution of 3-amino-4-((2-((tert-butyldimethylsilyl)oxy)ethyl)amino)benzonitrile (14 g, 48.1 mmol) in anhydrous THF (400 mL) was added a solution of BTC (28.5 g, 96.2 mmol) at 0° C. Then Et$_3$N (33 mL) was added dropwise to the mixture under at 0° C. After addition, the reaction was stirred at 25° C. for 2 h. The reaction was poured into sat. aq. NaHCO$_3$ (500 mL), extracted with EtOAc (3×300 mL). The organic layer was washed with brine, dried over anhydrous Na$_2$SO$_4$, filtered, and concentrated. The residue was purified by column chromatograph on silica gel (eluting with petroleum ether:EtOAc=5:1 to 1:1) to afford 1-(2-((tert-butyldimethyl silyl)oxy)ethyl)-2-oxo-2,3-dihydro-1H-benzo[d]imidazole-5-carbonitrile. Yield: 4.8 g (31%). LCMS method F: R$_t$=1.378 min, (M+H)$^+$=318.3 $^1$H NMR (CDCl$_3$): δ 10.06 (brs, 1H), 7.31 (d, J=8.4 Hz, 1H), 7.16 (s, 1H), 7.11 (d, J=8.0 Hz, 1H), 3.94-3.96 (m, 2H), 3.83-3.85 (m, 2H), 0.67 (s, 9H), −0.198 (s, 6H).

Step 5. 1-(2-hydroxyethyl)-2-oxo-2,3-dihydro-1H-benzo[d]imidazole-5-carbaldehyde and 2-(5-formyl-2-oxo-2,3-dihydro-1H-benzo[d]imidazol-1-yl)ethyl-formate

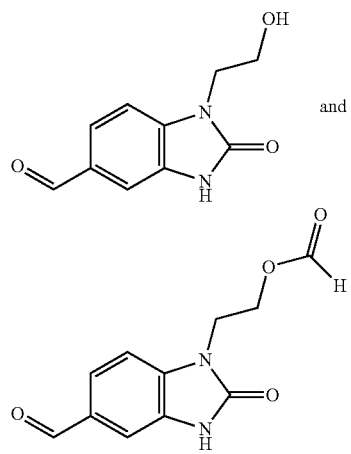

To a solution of 1-(2-((tert-butyldimethylsilyl)oxy)ethyl)-2-oxo-2,3-dihydro-1H-benzo[d]imidazole-5-carbonitrile (6.1 g, 19.2 mmol) in HCOOH (120 mL) and H$_2$O (40 mL) was added Ni—Al (8.27 g, 96.2 mmol) under N$_2$, then the reaction mixture was stirred at 90° C. for 16 h. The reaction mixture was then filtered and the filtrate was concentrated under reduced pressure. The residue was purified by column chromatograph on silica gel (eluting with DCM:MeOH=10:1) to afford 1-(2-hydroxyethyl)-2-oxo-2,3-dihydro-1H- benzo[d]imidazole-5-carbaldehyde as a white solid and 2-(5-formyl-2-oxo-2,3-dihydro-1H-benzo[d]imidazol-1-yl)ethyl formate as a yellow solid.

Intermediate 42.

2-(5-formyl-2-oxo-2,3-dihydro-1H-benzo[d]imidazol-1-yl)ethyl formate: Yield: 1.7 g (27%). LCMS method F: $R_t$=0.858 min; $(M+H)^+$=235.2 $^1$H NMR (DMSO-$d_6$): δ 11.27 (brs, 1H), 9.87 (s, 1H), 8.12 (s, 1H), 7.63 (dd, J=8.0, 1.2 Hz, 1H), 7.42 (s, 1H), 7.37 (d, J=8.0 Hz, 1H), 4.35-4.38 (m, 2H), 4.12-4.14 (m, 2H).

Intermediate 42c.

1-(2-hydroxyethyl)-2-oxo-2,3-dihydro-1H-benzo[d]imidazole-5-carbaldehyde: Yield: 1.5 g (27%). LCMS method F: $R_t$=0.788 min; $(M+H)^+$=207.2 $^1$H NMR (DMSO-$d_6$): δ 11.20 (brs, 1H), 9.86 (s, 1H), 7.60 (d, J=8.0 Hz, 1H), 7.40 (s, 1H), 7.31 (d, J=8.0 Hz, 1H), 4.86 (s, 1H), 3.85-3.86 (m, 2H), 3.63-3.65 (m, 2H).

Intermediate 42a 1-(2-methoxyethyl)-2-oxo-2,3-dihydro-1H-benzo[d]imidazole-5-carbaldehyde

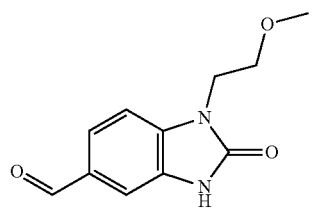 [SMILES: COCCn1c(=O)[nH]c2cc(C=O)ccc21]

The title product was prepared according to the procedure provided for Intermediate 41 starting with 2-methoxyethan-1-amine. LCMS method F: $R_t$=0.828 min; $(M+H)^+$=221.2.

Intermediate 42b 1-ethyl-2-oxo-2,3-dihydro-1H-benzo[d]imidazole-5-carbaldehyde

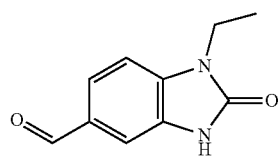

The title product was prepared according to the procedure provided for Intermediate 41, starting with ethylamine LCMS method F: $R_t$=0.868 min; $(M+H)^+$=191.2.

Intermediate 43

2-((4-chloropyrimidin-5-yl)oxy)-5-fluoro-N-isopropyl-N-methylbenzamide

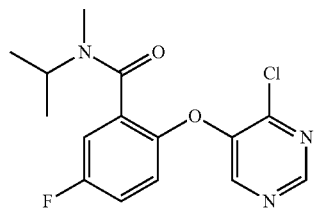 [SMILES: CC(C)N(C)C(=O)c1cc(F)ccc1Oc1cncnc1Cl]

Step 1. 5-(2-bromo-4-fluorophenoxy)pyrimidine

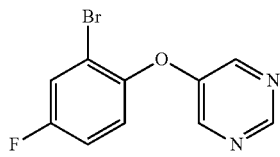 [SMILES: Fc1ccc(Oc2cncnc2)c(Br)c1]

To a solution of 2-bromo-4-fluorophenol (6 g, 31.41 mmol) and 5-bromopyrimidine (5.7 g, 36.12 mmol) in anhydrous DMF (60 mL) was added $Cs_2CO_3$ (30.7 g, 94.23 mmol) under $N_2$. The reaction mixture was stirred at 130° C. for 16 h. The reaction mixture was then filtered through a Celite and diluted with $H_2O$ (60 mL). The mixture was extracted with EtOAc (3×100 mL). The combined organic layers were washed with brine (3×100 mL), dried over anhydrous $Na_2SO_4$, filtered, and concentrated under reduced pressure to give 5-(2-bromo-4-fluorophenoxy)pyrimidine as brown oil which was used for next step directly. Yield: 6.5 g. LCMS method F: $R_t$=0.969 min, $(M+H)^+$=269.1.

Step 2. 5-fluoro-N-isopropyl-N-methyl-2-(pyrimidin-5-yloxy)benzamide

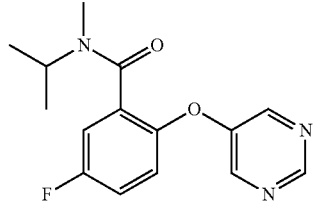 [SMILES: CC(C)N(C)C(=O)c1cc(F)ccc1Oc1cncnc1]

To a solution of 5-(2-bromo-4-fluorophenoxy)pyrimidine (5.5 g, crude, 20.45 mmol) and N-methylpropan-2-amine (12 g, 163.60 mmol) in anhydrous DMF (60 mL) was added Pd(dppf)Cl$_2$ (3 g, 4.09 mmol) and Et$_3$N (14 mL, 102.25 mmol, d=0.726 g/mL) under CO atmosphere. The reaction was stirred at 80° C. for 20 h with 50 psi. The reaction was concentrated under reduced pressure to afford the residue which was purified by column chromatography on silica gel (eluting with petroleum ether:EtOAc=10:1 to 1:1) to give 5-fluoro-N-isopropyl-N-methyl-2-(pyrimidin-5-yloxy)benzamide as a brown oil. Yield: 3.5 g. LCMS method E: $R_t$=0.700 min; $(M+H)^+$=290.1.

Step 3. 5-(4-fluoro-2-(isopropyl(methyl)carbamoyl)phenoxy)pyrimidine-1-oxide

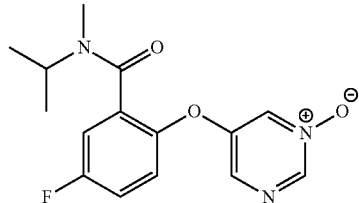 [SMILES: CC(C)N(C)C(=O)c1cc(F)ccc1Oc1cnc[n+]([O-])c1]

To a solution of 5-fluoro-N-isopropyl-N-methyl-2-(pyrimidin-5-yloxy)benzamide (1.8 g, 6.22 mmol) in anhydrous CH₂Cl₂ (80 mL) was added m-CPBA (2.6 g, 15.55 mmol) under N₂. The reaction was stirred at 11-20° C. for 30 h. The reaction was quenched with sat. NaHSO₃ solution (100 mL), extracted with CH₂Cl₂ (3×100 mL). The combined organic layers were washed with sat. NaHCO₃ solution (3×100 mL), brine (3×100 mL), dried over anhydrous Na₂SO₄, filtered, and concentrated under reduced pressure to give 5-(4-fluoro-2 (isopropyl(methyl)carbamoyl)-phenoxy)pyrimidine-1-oxide as a yellow solid which was used for next step directly. Yield: 1.6 g; LCMS method F: R$_t$=0.886 min; (M+H)⁺= 306.1.

Step 4. 2-((4-chloropyrimidin-5-yl)oxy)-5-fluoro-N-isopropyl-N-methylbenzamide

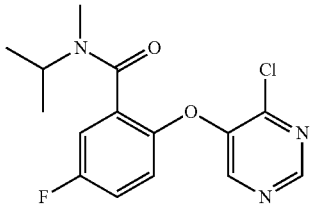 [SMILES: CC(C)N(C)C(=O)c1cc(F)ccc1Oc1cncnc1Cl]

To a solution of Et₃N (1.1 mL, 7.86 mmol, d=0.726 g/mL) and POCl₃ (1.2 g, 7.86 mmol) in CHCl₃ (5 mL) was added 5-(4-fluoro-2-(isopropyl(methyl)carbamoyl)phenoxy)pyrimidine-1-oxide (1.6 g, 5.24 mmol) in CHCl₃ (15 mL) slowly under N₂. The mixture reaction was stirred at 65° C. for 16 h. The reaction mixture was then quenched with sat. NaHCO₃ solution (100 mL) and extracted with CH₂Cl₂ (3×80 mL). The combined organic layers were washed with brine (3×80 mL), dried over anhydrous Na₂SO₄, filtered, and concentrated under reduced pressure to afford a residue which was purified by column chromatography on silica gel (eluting with petroleum ether:EtOAc=20:1 to 3:1) to give 2-((4-chloropyrimidin-5-yl)oxy)-5-fluoro-N-isopropyl-N-methylbenzamide as a yellow solid. Yield: 470 mg. LCMS method E: R$_t$=0.982 min; (M+H)⁺=324.2.

Intermediate 43a 5-(2-(benzyloxy)-4-fluorophenoxy)-4-chloropyrimidine

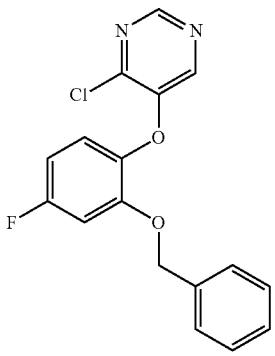 [SMILES: Fc1ccc(Oc2cncnc2Cl)c(OCc2ccccc2)c1]

The title product was synthesized according to the procedure described for Intermediate 43, starting from 2-(benzyloxy)-4-fluorophenol. LCMS method B: R$_t$=2.13 min; (M+H)⁺=313.3 ¹H NMR (CDCl₃, 400 MHz): δ 8.66 (s, 1H), 8.03 (s, 1H), 7.32-7.27 (m, 3H), 7.19-7.15 (m, 3H), 6.84-6.81 (m, 1H), 6.76-6.71 (m, 1H), 5.02 (s, 2H).

Intermediate 43b tert-Butyl 7-(5-(4-fluoro-2-hydroxyphenoxy)pyrimidin-4-yl)-2,7-diazaspiro[4.4]nonane-2-carboxylate

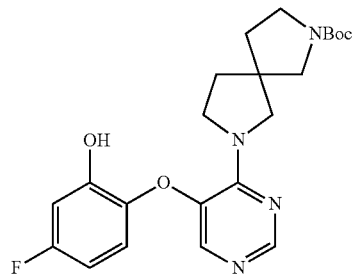 [SMILES: CC(C)(C)OC(=O)N1CCC2(CCN(c3ncncc3Oc3ccc(F)cc3O)C2)C1]

Step 1. tert-butyl 7-(5-(2-(benzyloxy)-4-fluorophenoxy)pyrimidin-4-yl)-2,7-diazaspiro[4.4]nonane-2-carboxylate

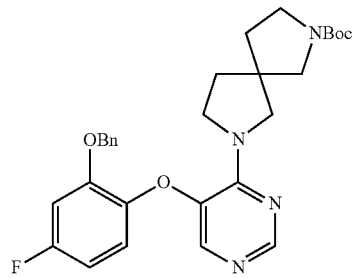 [SMILES: CC(C)(C)OC(=O)N1CCC2(CCN(c3ncncc3Oc3ccc(F)cc3OCc3ccccc3)C2)C1]

A solution of 5-(2-(benzyloxy)-4-fluorophenoxy)-4-chloropyrimidine (0.80 mmol) and tert-butyl 2,7-diazaspiro[4.4]nonane-2-carboxylate (218 mg, 0.96 mmol) in ⁱPrOH (2 mL) was added Hunig's base (285 μL, 1.60 mmol). The reaction mixture was heated in the microwave reactor at 120° C. for 90 min. After cooling to RT, the mixture was diluted with H₂O (10 mL) and extracted with EtOAc (3×15 mL). The organic layer was washed with brine, dried over Na₂SO₄, and concentrated under vacuum. The crude product was purified by flash chromatography over silica gel eluting with 3% MeOH/DCM to afford 170 mg tert-butyl 7-(5-(2-(benzyloxy)-4-fluorophenoxy)pyrimidin-4-yl)-2,7-diazaspiro[4.4]nonane-2-carboxylate as an orange oil. LCMS method B: R$_t$=1.71 min; (M+H)⁺=521.7.

Step 2. tert-butyl 7-(5-(4-fluoro-2-hydroxyphenoxy) pyrimidin-4-yl)-2,7-diazaspiro[4.4]nonane-2-carboxylate To a solution of tert-butyl 7-(5-(2-(benzyloxy)-4-fluorophenoxy)pyrimidin-4-yl)-2,7-diazaspiro[4.4]nonane-2-carboxylate (160 mg, 0.3 mmol) in MeOH (5 mL) was added palladium on carbon (5% dry basis, 33 mg, 30 μmol). The mixture was stirred at RT under the atmosphere of a hydrogen balloon for 3 h and filtered through a celite pad. The filtrate was then concentrated under reduced pressure. The crude product was used directly for the next step reaction without further purification. LCMS method B: R$_t$=1.56 min; (M+H)⁺=431.

Intermediate 44

N-(2-(5-formyl-2-oxo-2,3-dihydro-1H-benzo[d]imidazol-1-yl)ethyl)acetamide

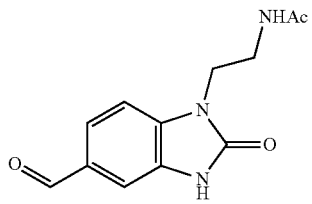 [SMILES: CC(=O)NCCn1c(=O)[nH]c2cc(C=O)ccc21]

Step 1. N-(2-((4-cyano-2-nitrophenyl)amino)ethyl)acetamide

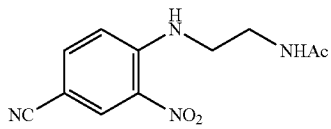

To a solution of 4-fluoro-3-nitrobenzonitrile (200 mg, 1.2 mmol) and N-(2-aminoethyl)acetamide (245 mg, 2.4 mmol) in anhydrous DMF (10 mL) was added $K_2CO_3$ (496 mg, 3.6 mmol) under $N_2$, then the reaction mixture was stirred at 14-20° C. for 4 h. The reaction mixture was filtered and the filtrate was concentrated under reduced pressure. The residue was then extracted with $H_2O$ (10 mL) and EtOAc (3×20 mL). The organic layers were washed with brine (20 mL), dried over anhydrous $Na_2SO_4$, filtered, and concentrated to afford N-(2-((4-cyano-2-nitrophenyl)amino)ethyl)acetamide. The residue was used for the next step without further purification as a yellow solid. Yield: 250 mg. LCMS method D: $R_t$=1.256 min, $(M+H)^+$=249.1.

Step 2. N-(2-((2-amino-4-cyanophenyl)amino)ethyl)acetamide

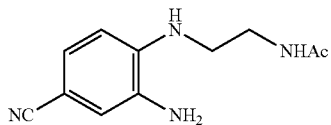 [SMILES: CC(=O)NCCNc1ccc(C#N)cc1N]

To a solution of N-(2-((4-cyano-2-nitrophenyl)amino)ethyl)acetamide (250 mg, 1.0 mmol) in EtOH (10 mL) and $H_2O$ (5 mL) was added Fe (280 mg, 5.0 mmol) and $NH_4Cl$ (530 mg, 10 mmol) under $N_2$. The reaction mixture was stirred at 80° C. for 2 h. The reaction mixture was then filtered and the filtrate was concentrated under reduced pressure. The residue was extracted with $H_2O$ (10 mL) and EtOAc (20 mL). The organic layer was washed with brine (20 mL), dried over anhydrous $Na_2SO_4$, filtered, and concentrated to afford N-(2-((2-amino-4-cyanophenyl)amino)ethyl)acetamide. The residue was used for the next step without further purification as a brown solid. Yield: 200 mg. LCMS method F: $R_t$=0.992 min, $(M+H)^+$=219.1.

Step 3. N-(2-(5-cyano-2-oxo-2,3-dihydro-1H-benzo[d]imidazol-1-yl)ethyl)acetamide

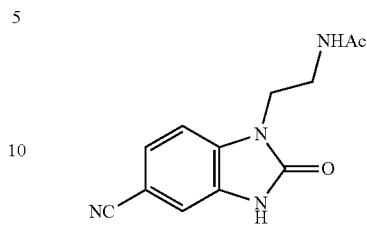

To a solution of N-(2-((2-amino-4-cyanophenyl)amino)ethyl)acetamide (10 mg, 0.046 mmol) in anhydrous THF (4 mL) was added $Et_3N$ (0.5 mL), then a solution of BTC (27 mg, 0.092 mmol) in anhydrous THF (2 mL) was added dropwise to the mixture at 0° C. After addition, the reaction mixture was stirred at 3-14° C. for 12 h. The reaction mixture was extracted with $H_2O$ (5 mL) and EtOAc (20 mL×3). The organic layers were washed with brine (20 mL), dried over anhydrous $Na_2SO_4$, filtered, and concentrated. The residue was purified by column chromatography on silica gel (eluting with $CH_2Cl_2$: MeOH=1:0 to 10:1) to afford N-(2-(5-cyano-2-oxo-2,3-dihydro-1H-benzo[d]imidazol-1-yl)ethyl)acetamide as a brown oil. Yield: 20 mg. LCMS method F: $R_t$=1.175 min; $(M+H)^+$=245.2.

Step 4. N-(2-(5-formyl-2-oxo-2,3-dihydro-1H-benzo[d]imidazol-1-yl)ethyl)acetamide To a solution of N-(2-(5-cyano-2-oxo-2,3-dihydro-1H-benzo[d]imidazol-1-yl)ethyl)acetamide (20 mg, 0.082 mmol) in HCOOH (3 mL) and $H_2O$ (1 mL) was added Ni—Al (35 mg, 0.41 mmol), then the reaction was stirred at 90° C. for 12 h. The reaction was filtered and the filtrate was concentrated under reduced pressure to afford N-(2-(5-formyl-2-oxo-2,3-dihydro-1H-benzo[d]imidazol-1-yl)ethyl)acetamide (15 mg, 92% purity, 75%). The residue was used for the next step without further purification as a brown solid. Yield: 15 mg. LCMS method F: $R_f$=$R_t$ value: 0.773 min; $(M+H)^+$=248.1.

Intermediate 44a 1-(2-(dimethylamino)ethyl)-2-oxo-2,3-dihydro-1H-benzo[d]imidazole-5-carbaldehyde

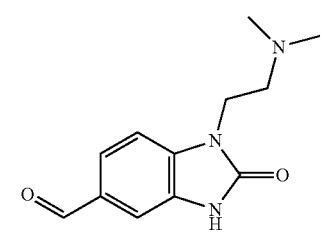 [SMILES: CN(C)CCn1c(=O)[nH]c2cc(C=O)ccc21]

The title product was synthesized according to the procedure described for Intermediate 44 starting with N1,N1-dimethylethane-1,2-diamine and 4-fluoro-3-nitrobenzonitrile. LCMS method F: $R_t$=0.773 min; $(M+H)^+$=233.1.

Intermediate 45

3,3-dimethyl-2-oxoindoline-6-carbaldehyde

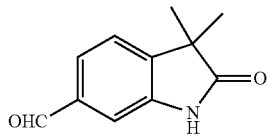

To a solution of 6-bromo-3,3-dimethylindolin-2-one (502 mg, 2.09 mmol) in DMF (10 mL) under $N_2$ atmosphere was added $Pd(OAc)_2$ (14 mg, 0.063 mmol), N-formyl saccharin (662 mg, 3.14 mmol), dppb (39 mg, 0.094 mmol), $Na_2CO_3$ (315 mg, 3.16 mmol) and $Et_3SiH$ (316 mg, 2.72 mmol). The resulting mixture was heated to 80° C. for 16 h. The reaction mixture was diluted with EtOAc, washed with $H_2O$, brine, dried over anhydrous $Na_2SO_4$, and filtered. The filtrate was then concentrated to dryness. The residue was purified by flash chromatography to afford 70 mg of 3,3-dimethyl-2-oxoindoline-6-carbaldehyde. LCMS method B: $R_t$=1.63 min; $(M+H)^+$=190.

Intermediate 46

6-formyl-3-methyl-2-oxoindoline-3-carbonitrile

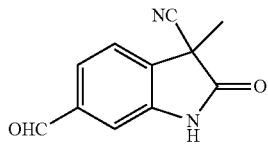

Step 1. Methyl 4-(2-cyano-1-ethoxy-1-oxopropan-2-yl)-3-nitrobenzoate

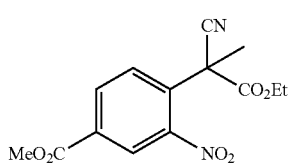 [SMILES: CCOC(=O)C(C)(C#N)c1ccc(C(=O)OC)cc1[N+](=O)[O-]]

To a 60% suspension of sodium hydride (2.0 g, 50 mmol) in dry DMF (50 mL) at 0° C. was added ethyl 2-cyanoacetate (5.33 mL, 50 mmol) dropwise and the reaction mixture was stirred for an additional 30 min at 0° C. To the resulting gray suspension was added methyl 4-fluoro-3-nitrobenzoate (7.97 g, 40 mmol) at 0° C. The resulting deep red mixture was stirred at 0° C. for 30 min and warmed to RT over 2 h. The reaction mixture was cooled to 0° C., and MeI (7.8 mL) was added, followed by KOtBu (8.4 g, 75 mmol). After the addition, the mixture was stirred for 2 days at RT and subsequently quenched with aqueous $NH_4Cl$ solution. The resulting mixture was then extracted with EtOAc twice. The organic layers were combined and washed with $H_2O$ and brine successively, and dried over anhydrous sodium sulfate, filtered, and concentrated. The residue was purified by flash-chromatography to afford methyl 4-(2-cyano-1-ethoxy-1-oxopropan-2-yl)-3-nitrobenzoate. Yield 6.04 g. LCMS method B: $R_t$=1.63 min.

Step 2. Methyl 3-cyano-3-methyl-2-oxoindoline-6-carboxylate

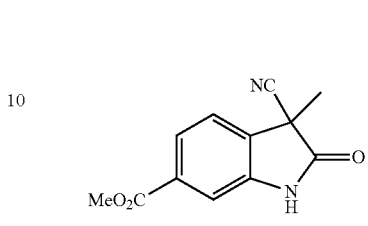

To a solution of methyl 4-(2-cyano-1-ethoxy-1-oxopropan-2-yl)-3-nitrobenzoate (6.039 g, 19.72 mmol) in EtOH (60 mL) was added saturated aqueous $NH_4Cl$ solution (15 mL) and iron powder (5.803 g, 98.61 mmol). The mixture was heated to reflux overnight. The mixture was then cooled to RT and filtered through a short pad of Celite and subsequently washed with EtOAc. The filtrate was washed with $H_2O$, brine, dried over anhydrous sodium sulfate, filtered, and concentrated. The residue was purified by flash-chromatography to afford methyl 3-cyano-3-methyl-2-oxoindoline-6-carboxylate. Yield 4.404 g. LCMS method B: $R_t$=1.07 min; $(M+H)^+$=231.

Step 3. 6-(Hydroxymethyl)-3-methyl-2-oxoindoline-3-carbonitrile

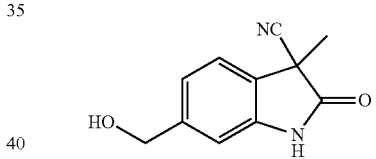

To a solution of methyl 3-cyano-3-methyl-2-oxoindoline-6-carboxylate (2.101 g, 9.12 mmol) in dry THF (40 mL) under $N_2$ atmosphere was added a solution of $LiBH_4$ (9.1 mL, 18.2 mmol), followed by MeOH (0.2 mL). The mixture was heated to reflux for 2 h and subsequently quenched with aqueous $NH_4Cl$ solution. The mixture was then extracted twice with EtOAc. The organic layers were combined and washed with $H_2O$ and brine successively, dried over anhydrous sodium sulfate, filtered, and concentrated. The residue was purified by flash-chromatography to afford 6-(hydroxymethyl)-3-methyl-2-oxoindoline-3-carbonitrile. Yield 1.42 g. LCMS method B: $R_t$=0.79 min; $(M+H)^+$=203.1.

Step 4. 6-formyl-3-methyl-2-oxoindoline-3-carbonitrile

To a solution of 6-(hydroxymethyl)-3-methyl-2-oxoindoline-3-carbonitrile (0.597 g, 2.95 mmol) in DCM was added active $MnO_2$ (2.57 g, 29.56 mmol). The mixture was stirred at RT overnight and then filtered through a short pad of Celite. The filtrate was concentrated to remove solvent. The residue was purified by flash-chromatography to afford 6-formyl-3-methyl-2-oxoindoline-3-carbonitrile. Yield 0.347 g. LCMS method B: $R_t$=1.25 min, $(M+H)^+$=201.1.

Intermediate 47

N-((1r,4r)-4-formylcyclohexyl)methanesulfonamide

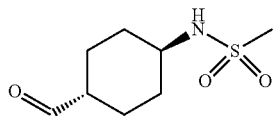

Step 1. Methyl (1r,4r)-4-(methylsulfonamido)cyclohexane-1-carboxylate

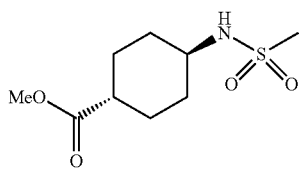

A mixture of methyl (1r,4r)-4-aminocyclohexane-1-carboxylate hydrochloride (50 g, 0.259 mol) and Et₃N (130.8 g, 1.295 mol) in anhydrous CH₂Cl₂ (2000 mL) was stirred RT for 20 min. MsCl (29.8 g, 0.259 mol) was added dropwise at 0° C. under N₂ and the mixture was stirred at 0° C. for 2 h. The DCM reaction mixture was washed with H₂O (3×800 mL) and brine (800 mL), dried over anhydrous Na₂SO₄, filtered and concentrated under reduced pressure. The mixture was purified by column chromatography on silica gel eluting with petroleum ether:EtOAc=2:1 to 1:1 (adding 25 mL of CH₂Cl₂ in 1 L of petroleum ether/ethyl acetate for the eluent) to afford methyl (1r,4r)-4-(methylsulfonamido)cyclohexane-1-carboxylate (58 g, 89.5%) as a white solid. $^1$H NMR (CDCl₃): δ 4.45 (d, J=7.6 Hz, 1H), 3.69 (s, 3H), 3.29-3.23 (m, 1H), 2.98 (s, 3H), 2.24-2.13 (m, 1H), 2.11-2.09 (m, 2H), 2.05-2.02 (m, 2H), 1.55-1.51 (m, 2H), 1.29-1.26 (m, 2H).

Step 2. N-((1r,4r)-4-formylcyclohexyl)methanesulfonamide

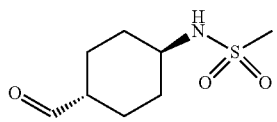

Methyl (1r,4r)-4-(methylsulfonamido)cyclohexane-1-carboxylate (20 g, 85.11 mmol) in anhydrous toluene (500 mL) was stirred at 40° C. for 30 min under N₂. The resulting solution was cooled to −70° C. (internal temperature). A solution of DIBAL-H (1 M in toluene, 180 mL, 180 mmol) was added dropwise within 110 min under N₂ (keeping the internal temperature below −70° C.). After addition, the mixture was stirred vigorously at −70° C. for 4 h. MeOH (30 mL) was then carefully added dropwise over a 30 min period (keeping the internal temperature below −70° C.). After being stirred for 10 min, sat. Rochelle salt solution (600 mL) was added at −70° C. and the mixture was warmed to RT. EtOAc (300 mL) was added and the mixture stirred at RT for 16 h. The mixture was separated and the aqueous layer was extracted with EtOAc (3×400 mL). The combined organic layers were washed with brine (3×500 mL), dried over anhydrous Na₂SO₄, filtered and concentrated under reduced pressure to afford crude N-((1r,4r)-4-formylcyclohexyl)methanesulfonamide (19 grams) which was used for next step without further purification. $^1$H NMR (CDCl₃): δ 9.65 (s, 0.035H), 9.62 (s, 1H), 4.40-4.39 (m, 1H), 3.28-3.25 (m, 1H), 2.98 (s, 3H), 2.18-2.03 (m, 5H), 1.38-1.28 (m, 4H).

Step 3. Sodium (R)-hydroxy((1r,4R)-4-(methylsulfonamido)cyclohexyl)methanesulfonate

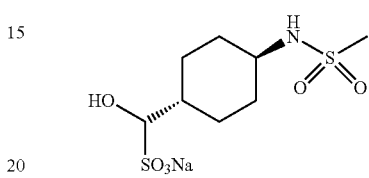

To a solution of crude N-((1r,4r)-4-formylcyclohexyl)methanesulfonamide (19 grams) in THF (200 mL) was added aq. NaHSO₃ solution (4 M, 110 mL) over a 10 min period at 45° C. After being stirred at 45° C. for 30 min, the mixture was cooled to RT and stirred for another 1 h. The resulting white precipitate was filtered and the filter cake was washed with THF (3×50 mL) and dried under high vacuum to afford sodium (R)-hydroxy((1r,4R)-4-(methylsulfonamido)cyclohexyl)methanesulfonate (16.5 g, 55% over Step 2-3) as a white solid, which was used for next step without further purification. $^1$H NMR (DMSO-d₆): δ 9.90 (s, 0.17H), 6.91 (d, J=7.2 Hz, 1H), 4.98 (d, J=5.2 Hz, 1H), 3.65 (t, J=4.4 Hz, 1H), 2.97-2.95 (m, 1H), 2.89 (d, J=6.8 Hz, 3H), 2.06-2.03 (m, 1H), 1.86-1.81 (m, 3H), 1.61 (brs, 1H), 1.23-1.06 (m, 4H).

Step 4. N-((1r,4r)-4-formylcyclohexyl)methanesulfonamide

To a mixture of sodium (R)-hydroxy((1r,4R)-4-(methylsulfonamido)cyclohexyl)methanesulfonate (16.5 g, 53.4 mmol) in CH₂Cl₂ (160 mL) was added aq. Na₂CO₃ solution (1M, 160 mL). The mixture was stirred at RT for 30 min. The mixture was separated and the aqueous layer was extracted with CH₂Cl₂ (3×80 mL). The combined organic layers were washed with brine (300 mL), dried over anhydrous Na₂SO₄, filtered and concentrated under reduced pressure to afford crude N-((1r,4r)-4-formylcyclohexyl)methanesulfonamide (7.5 g, 69%) as a white solid, which was used for next step without further purification. $^1$H NMR (CDCl₃): δ 9.66 (s, 0.021H), 9.62 (s, 1H), 4.38 (brs, 1H), 3.30-3.25 (m, 1H), 2.98 (s, 3H), 2.18-2.14 (m, 3H), 2.05-2.01 (m, 2H), 1.42-1.30 (m, 4H).

Intermediate 48

Methyl 2-((4-chloropyrimidin-5-yl)oxy)-5-fluorobenzoate

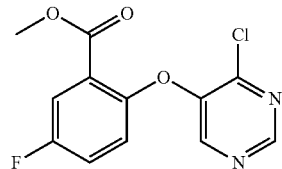 [SMILES: COC(=O)c1cc(F)ccc1Oc1cncnc1Cl]

Step 1: Ethyl 2-(2-bromo-4-fluorophenoxy)acetate

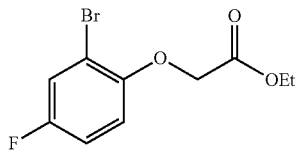

To solution of 2-bromo-4-fluorophenol (250 g, 1.31 mol) in MeCN (2 L) was added $K_2CO_3$ (270 g, 1.97 mol) and ethyl 2-bromoacetate (219 g, 1.31 mol). The suspension was heated at 90° C. for 1.5 h. The mixture was filtered and the filtrate was concentrated to give crude ethyl 2-(2-bromo-4-fluorophenoxy)acetate as a brown oil, which was used directly in next step (312 g); $^1$H NMR (CDCl$_3$): δ 7.32 (dd, J=7.6, 3.2 Hz, 1H), 6.95-6.97 (m, 1H), 6.82 (dd, J=8.8, 4.4 Hz, 1H), 4.66 (s, 2H), 4.27 (q, J=7.2 Hz, 2H), 1.31 (t, J=7.2 Hz, 3H); $^1$F NMR (CDCl$_3$): δ −120.06 (s, 1F).

Step 2: 5-(2-Bromo-4-fluorophenoxy)-2-thioxo-2,3-dihydropyrimidin-4(1H)-one

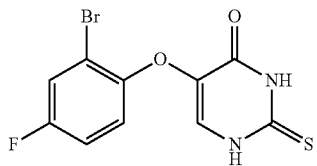

To a solution of ethyl 2-(2-bromo-4-fluorophenoxy)acetate (100 g) in anhydrous THF (2 L) was added ethyl formate (108 g) and NaH (20 g) at 0° C. The mixture was stirred at 35-45° C. for 18 h. The solvent was removed under vacuum and anhydrous EtOH (2 L) and thiourea (25 g, 324.8 mmol) were added and the mixture was stirred at 90° C. for 16 h. The mixture was concentrated and diluted with water (2 L) and extracted with petroleum ether:ethyl acetate (10:1; 500 mL×3). The aqueous layer was acidified to pH=4 by aq. HCl (1N, 200 mL) and a white solid was precipitated. The mixture was filtered and the resulting filter cake was dried to give crude 5-(2-bromo-4-fluorophenoxy)-2-thioxo-2,3-dihydropyrimidin-4(1H)-one (62 g) as a white solid, which was used directly in the next step without purification; LCMS method C: $R_t$=0.638 min; (M+H)$^+$=316.9, 318.9 (chlorine isotopes).

Step 3: 5-(2-Bromo-4-fluorophenoxy)pyrimidin-4-ol

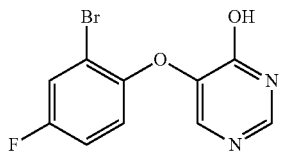 [SMILES: Oc1ncncc1Oc1ccc(F)cc1Br]

To a solution of 5-(2-bromo-4-fluorophenoxy)-2-thioxo-2,3-dihydropyrimidin-4(1H)-one (62 g) in anhydrous EtOH (1.5 L) was added Raney Ni (62 g), and the mixture was heated at reflux for 6 h. The solvent was removed under vacuum and anhydrous EtOH (2 L) was added. The mixture was filtered and the filtrate was concentrated to give crude 5-(2-bromo-4-fluorophenoxy)pyrimidin-4-ol as a grey solid (55 g); LCMS method C: $R_t$=0.62 min, (M+H)$^+$=284.9, 287.0 (bromine isotopes).

Step 4: Methyl 5-fluoro-2-((4-hydroxypyrimidin-5-yl)oxy)benzoate

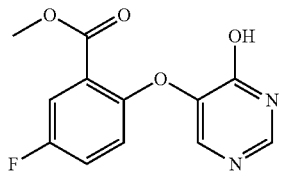 [SMILES: COC(=O)c1cc(F)ccc1Oc1cncnc1O]

To a solution of 5-(2-bromo-4-fluorophenoxy)pyrimidin-4-ol (60 g, 0.17 mol) in DMF (100 mL) and MeOH (150 mL) was added TEA (25.5 g, 0.252 mol) and Pd(dppf)Cl$_2$ (12.4 g, 0.017 mol). The resulting reaction mixture was stirred under 50 PSI of CO at 80° C. for 24 h. The mixture was then concentrated, diluted with H$_2$O (300 mL), and extracted with DCM/MeOH (10:1) (200 mL×3). The combined organic layers were dried over Na$_2$SO$_4$, filtered, and concentrated to give the crude product, which was washed with ethyl acetate (100 mL). The filter cake was dried to afford crude methyl 5-fluoro-2-((4-hydroxypyrimidin-5-yl)oxy)benzoate as a brown solid (20 g, 45%); LCMS method C: $R_t$=0.56 min; (M+H)$^+$=264.9.

Step 5: Methyl 2-((4-chloropyrimidin-5-yl)oxy)-5-fluorobenzoate

To a solution of crude methyl 5-fluoro-2-((4-hydroxypyrimidin-5-yl)oxy)benzoate (11 g, 42 mmol) in SOCl$_2$ (5 mL) was added DMF (0.5 mL). The resulting mixture was heated at 70° C. for 2 h. The mixture was concentrated to give the residue which was dissolved into DCM (100 mL) and H$_2$O (100 mL). The mixture was neutralized with saturated NaHCO$_3$ (50 mL). The separated organic layer was dried over Na$_2$SO$_4$, filtered, and concentrated, and the residue was purified by chromatography column (petroleum ether:ethyl acetate=5:1-1:1) to afford methyl 2-((4-chloropyrimidin-5-yl)oxy)-5-fluorobenzoate as a brown solid (8.3 g, 57%); LCMS method C: $R_t$=0.74 min; (M+H)$^+$=283.5.

Intermediate 49

5-Fluoro-2-(pyrimidin-5-yloxy)benzoic Acid

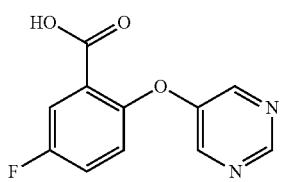 [SMILES: O=C(O)c1cc(F)ccc1Oc1cncnc1]

Step 1: 5-(2-Bromo-4-fluorophenoxy)pyrimidine

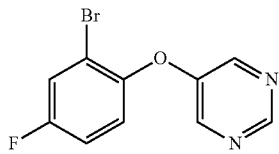

A 100-L jacketed reactor was charged with 2-bromo-4-fluorophenol (11.00 kg, 57.59 moles), 5-bromopyrimidine (9.43 kg, 59.32 moles), cesium carbonate (24.39 kg, 74.87 moles), and DMA (66.00 L), and the mixture was heated to 115-125° C. over 2.5 h. The batch was then stirred at 120° C. over 4 days. The internal temperature of the batch was then adjusted to 20-30° C. Once the batch was cooled it was partitioned between deionized water (132.00 L) and MTBE (44.00 L) in a 250 L Schott reactor. The reactor contents were agitated at RT for 30 min. After this time, the agitation was stopped and the layer separation was allowed to occur. The top organic layer was removed and placed in a separate container. A total of four MTBE extractions were performed. The MTBE extracts were combined and washed with 2 N sodium hydroxide (22.00 L), then by 0.5 M citric acid solution (11.00 L), and finally by 5 wt % sodium bicarbonate solution (11.00 L). The MTBE solution was concentrated using a rotary evaporator (25 in. Hg vacuum, 40° C. water bath). The residue was passed through a wiped film evaporator (WFE) system to remove volatiles (MTBE) and a portion of remaining 5-bromopyrimidine. The conditions for WFE distillation were as follows: the first pass—vacuum 10-15 in. Hg, wiper speed 600 rpm, jacket temperature 150-160° C., addition rate 4 mL/min; the second pass—vacuum 0.7 Torr, wiper speed 600 rpm, jacket temperature 160-170° C., addition rate 4 mL/min. The product 5-(2-bromo-4-fluorophenoxy)-pyrimidine was isolated in 45% yield (7.15 kg) with HPLC purity 95.3% (AUC).

Step 2: Methyl 5-fluoro-2-(pyrimidin-5-yloxy)benzoate

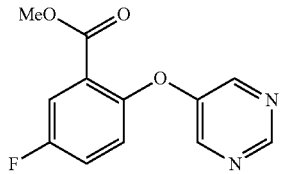 [SMILES: COC(=O)c1cc(F)ccc1Oc1cncnc1]

A 80-L jacketed stainless steel reactor was charged with palladium catalyst (Pd(dppf)Cl₂ DCM complex) (1.00 kg, 1.22 moles), 5-(2-bromo-4-fluorophenoxy)pyrimidine (8.54 kg, 31.59 moles), TEA (6.38 kg, 63.18 moles), and methanol (42.50 L). The reactor was purged with nitrogen (3 times up to 50 psig of nitrogen pressure) and then with carbon monoxide gas (3 times up to 50 psig of carbon monoxide). The reactor internal temperature was adjusted to 65-75° C. over 75 min. Once at temperature, the vessel internal pressure was adjusted to 50 psig with carbon monoxide gas. The reactor contents were stirred at the specified temperature and pressure for at least 34 h. After this time, the reaction mixture was cooled to 15-25° C. and was purged with nitrogen three times with 50 psig pressure to afford a methanolic solution containing methyl 5-fluoro-2-(pyrimidin-5-yloxy)benzoate. The batch was filtered over a Celite™ pad to remove the palladium catalyst.

Step 3: 5-Fluoro-2-(pyrimidin-5-yloxy)benzoic Acid

The methanolic solution containing compound methyl 5-fluoro-2-(pyrimidin-5-yloxy)benzoate from Step 2 was placed in a 100-L jacketed glass reactor and was diluted with water (17.00 L). After this, 50 wt % sodium hydroxide aqueous solution (10.11 kg, 126.36 moles) was added, keeping the batch internal temperature at 35-45° C. Once the addition was complete, the temperature was adjusted to 35-45° C., and the batch was stirred for at least 14 h. The reaction volume was decreased by vacuum distillation from 87 to 33 liters (27 in. Hg vacuum was achieved; at the end the batch temperature was 32.4° C.). The batch was then diluted with water (42.5 L), cooled to 20-30° C., and was filtered through a Celite™ pad to remove the catalyst. The aqueous layer was extracted two times with MTBE (17 L). The batch was adjusted to pH=2 using 6 M hydrochloric acid (about 17 L), keeping the internal batch temperature at 10-20° C. Once the acid addition was complete, the batch was cooled to 0-10° C. and filtered over a polypropylene cloth using a filter/dryer. The filter cake was washed with water (17.00 L) and dried under stream of nitrogen at 40-45° C. over several days until the water level was 0.3 wt % by KF analysis. The product was isolated in 102% yield (7.57 kg) with a HPLC purity of 97.5% (AUC) and 94 wt % purity by NMR analysis.

Intermediate 50

((1r,4r)-4-(Ethylsulfonamido)cyclohexyl)methyl 4-methylbenzenesulfonate

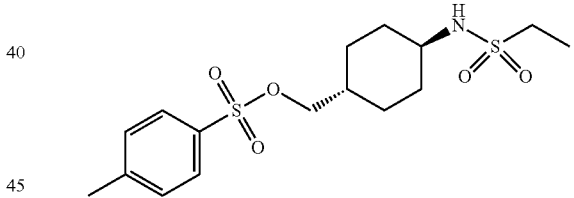

Step 1: Methyl (1r,4r)-4-(ethylsulfonamido)cyclohexane-1-carboxylate

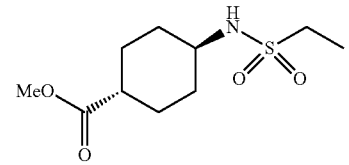 [SMILES: CCS(=O)(=O)N[C@H]1CC[C@H](C(=O)OC)CC1]

A solution of methyl (1r,4r)-4-aminocyclohexane-1-carboxylate hydrochloride (120 g, 0.62 mol) and Et₃N (346 mL, 2.48 mol) in anhydrous DCM (2.5 L) was stirred at RT for 30 min. Ethanesulfonyl chloride (80.6 g, 0.63 mol) was added dropwise over 30 min to the reaction mixture at 0-5° C. After addition, the mixture was stirred at 0° C. for 3 h. The mixture was quenched with water (250 mL) at 0° C.

After partition, the organic layer was washed with H₂O (600 mL, 5 volumes) and 1 N HCl (2×600 mL, 2×5 volumes), H₂O (600 mL, 5 volumes) and brine (600 mL, 5 volumes), dried over anhydrous Na₂SO₄, filtered, and concentrated under reduced pressure to afford crude methyl (1r,4r)-4-(ethylsulfonamido)cyclohexane-1-carboxylate (117.6 g, 76%) as a light yellow solid, which was used for the next step without further purification. ¹H NMR (CDCl₃ 400 MHz): δ 4.36 (d, J=8.0 Hz, 1H), 3.67 (s, 3H), 3.29-3.22 (m, 1H), 3.04 (q, J=7.6 Hz, 2H), 2.25-2.21 (m, 1H), 2.15-2.09 (m, 2H), 2.08-2.01 (m, 2H), 1.58-1.51 (m, 2H), 1.39-1.25 (m, 5H).

Step 2. N-((1r,4r)-4-(hydroxymethyl)cyclohexyl)ethanesulfonamide

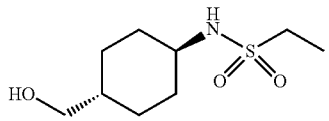

To a solution of crude methyl (1r,4r)-4-(ethylsulfonamido)cyclohexane-1-carboxylate (100 g, 402 mmol) in anhydrous THF (1 L) was added LiAlH₄ (403 mL, 403 mmol, 1 M in THF) dropwise at 0-5° C. under N₂ over about 1 h. The mixture was then stirred at 0° C. for 2 h under N₂. Additional LiAlH₄ (40 mL, 40 mmol, 1 Min THF) was then added to the reaction mixture. The mixture was stirred at 0° C. for 1 h under N₂. The mixture was quenched with 20% NaCl solution (20 mL) slowly at 0° C. and diluted with THF (500 mL, 5 volumes). The mixture was warmed to 15° C. and stirred for 15 min. The mixture was filtered and rinsed with THF (2×200 mL). The filter cake was suspended within THF (1 L, 10 volumes) for 30 min. The suspension was filtered and rinsed with THF (2×200 mL). The filter cake suspension and filtration was repeated twice in THF (1 L, 10 volumes), and was then rinsed with THF (2×200 mL). The combined filtrate was dried over anhydrous Na₂SO₄, concentrated under reduced pressure to afford crude N-((1r,4r)-4-(hydroxymethyl)cyclohexyl)ethanesulfonamide (72 g, 81%) as a white solid, which was used for the next step without further purification; ¹H NMR (CDCl₃ 400 MHz): δ 4.23 (d, J=8.0 Hz, 1H), 3.46 (t, J=6.4 Hz, 2H), 3.25-3.18 (m, 1 H), 3.04 (q, J=7.6 Hz, 2H), 2.11-2.07 (m, 2H), 1.88-1.84 (m, 2H), 1.46-1.35 (m, 4H), 1.29-1.24 (m, 2H), 1.09-1.00 (m, 2H).

Step 3: ((1r,4r)-4-(Ethylsulfonamido)cyclohexyl)methyl 4-methylbenzenesulfonate

To a solution of crude N-((1r,4r)-4-(hydroxymethyl)cyclohexyl)ethanesulfonamide (30 g, 136 mmol) in anhydrous DCM (300 mL) was added TsCl (25.84 g, 136 mmol), DMAP (1.66 g, 13.6 mmol) and Et₃N (41.2 g, 408 mmol). The mixture was stirred at 10° C. for 6 h under N₂. The mixture was then quenched with H₂O (200 mL). After partition, the organic layer was washed with H₂O (2×150 mL) and brine (150 mL), dried over anhydrous Na₂SO₄, and concentrated under reduced pressure. The residue was purified by column chromatography on silica gel eluting with petroleum ether/ethyl acetate=1/0~2/1 to give ((1r,4r)-4-(ethylsulfonamido)cyclohexyl)methyl 4-methylbenzenesulfonate (37 g, 73%) as a white solid; ¹H NMR (CDCl₃ 400 MHz): δ 7.78 (d, J=8.4 Hz, 2H), 7.35 (d, J=8.8 Hz, 2H), 4.23 (d, J=7.6 Hz, 1H), 3.81 (d, J=6.4 Hz, 2H), 3.19-3.14 (m, 1H), 3.01 (q, J=7.6 Hz, 2H), 2.46 (s, 3H), 2.09-2.03 (m, 2H), 1.79-1.74 (m, 2H), 1.66-1.56 (m, 1H), 1.35 (t, J=7.6 Hz, 3H), 1.28-1.18 (m, 2H), 1.09-1.01 (m, 2H).

Example 1

5-fluoro-N,N-diisopropyl-2-((4-(7-((2-oxo-2,3-dihydro-1H-benzo[d]imidazol-5-yl)methyl)-2,7-diazaspiro[4.4]nonan-2-yl)pyrimidin-5-yl)oxy)benzamide (Racemic Mixture)

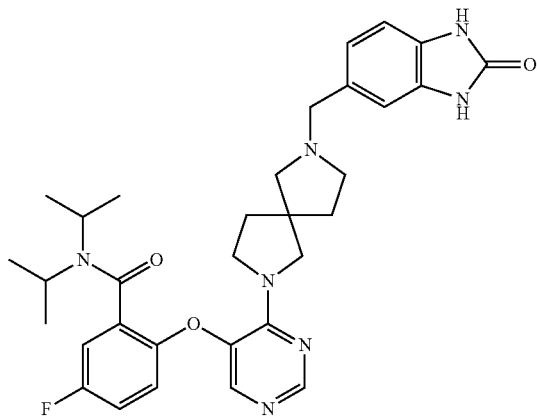 [SMILES: CC(C)N(C(=O)c1cc(F)ccc1Oc1cncnc1N1CCC2(CCN(Cc3ccc4[nH]c(=O)[nH]c4c3)C2)C1)C(C)C]

Step 1. tert-butyl 7-(5-(4-fluoro-2-(methoxycarbonyl)phenoxy)pyrimidin-4-yl)-2,7-diazaspiro[4.4]nonane-2-carboxylate

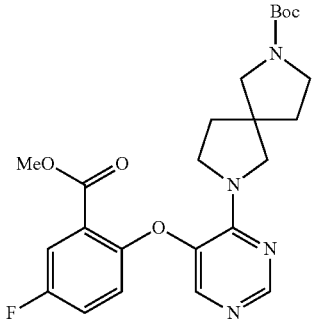 [SMILES: COC(=O)c1cc(F)ccc1Oc1cncnc1N1CCC2(CCN(C(=O)OC(C)(C)C)C2)C1]

To a solution of tert-butyl 7-(5-(2-bromo-4-fluorophenoxy)pyrimidin-4-yl)-2,7-diazaspiro[4.4]nonane-2-carboxylate (Intermediate 11, 900 mg, 1.82 mmol) and Pd(dppf)Cl₂ (134 mg, 0.18 mmol) were added in Et₃N (3 mL) and MeOH (20 mL). Then the reaction mixture was stirred at 65° C. under CO (50 psi) for about 16 h. The reaction mixture was filtered through a Celite pad, and concentrated under reduced pressure to afford the residue which was purified by column chromatography on silica gel (eluting with dichloromethane:methanol=1:0~0:1) to afford tert-butyl 7-(5-(4-fluoro-2-(methoxycarbonyl)phenoxy)pyrimidin-4-yl)-2,7-diazaspiro[4.4]nonane-2-carboxylate as a light yellow oil. Yield: 850 mg. LCMS method C: R$_f$=0.739 min; (M+H)⁺= 473.2.

Step 2. 2-((4-(7-(tert-butoxycarbonyl)-2,7-diazaspiro[4.4]nonan-2-yl)pyrimidin-5-yl)oxy)-5-fluorobenzoic Acid

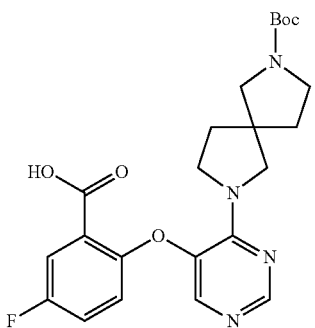 [SMILES: CC(C)(C)OC(=O)N1CCC2(CCN(c3ncncc3Oc3ccc(F)cc3C(=O)O)C2)C1]

To a mixture of tert-butyl 7-(5-(4-fluoro-2-(methoxycarbonyl)phenoxy)pyrimidin-4-yl)-2,7-diazaspiro[4.4]nonane-2-carboxylate (850 mg, 1.79 mmol) and NaOH (143 mg, 3.58 mmol) was added MeOH (10 mL) and H$_2$O (2 mL) under N$_2$. The reaction mixture was stirred at 21-27° C. for 12 h. The solvent was removed under reduced pressure to afford the residue. Then, 1N HCl was added to adjust the solution to pH 5-6 and EtOAc (10 mL) was added. The organic layer was concentrated under reduced pressure to afford 2-((4-(7-(tert-butoxycarbonyl)-2,7-diazaspiro[4.4]nonan-2-yl)pyrimidin-5-yl)oxy)-5-fluorobenzoic acid. Yield: 700 mg (85%). LCMS method C: R$_t$=0.705 min (M+H)$^+$=459.2.

Step 3. tert-butyl 7-(5-(2-(diisopropylcarbamoyl)-4-fluorophenoxy)pyrimidin-4-yl)-2,7-diazaspiro[4.4]nonane-2-carboxylate

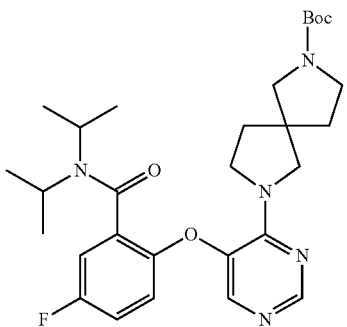 [SMILES: CC(C)N(C(=O)c1cc(F)ccc1Oc1cncnc1N1CCC2(CCN(C(=O)OC(C)(C)C)C2)C1)C(C)C]

To a solution of 2-((4-(7-(tert-butoxycarbonyl)-2,7-diazaspiro[4.4]nonan-2-yl)pyrimidin-5-yl)oxy)-5-fluorobenzoic acid (800 mg, 1.746 mmol) in anhydrous CH$_2$Cl$_2$ (15 mL) were added HATU (553 mg, 1.455 mmol) and DIEA (677 mg, 5.238 mmol) under N$_2$, and the reaction mixture was stirred at 9-20° C. for 30 min. Then diisopropylamine (265 mg, 2.619 mmol) was added to the solution and the reaction mixture was stirred at 9-20° C. for 12 h. The solvent was then removed under reduced pressure. The resulting residue was purified by column chromatography on silica gel (eluting with CH$_2$Cl$_2$:MeOH=1:0~10:1) to afford tert-butyl 7-(5-(2-(diisopropylcarbamoyl)-4-fluorophenoxy)pyrimidin-4-yl)-2,7-diazaspiro[4.4]nonane-2-carboxylate as brown oil. Yield: 900 mg. LCMS method F: R$_t$=1.238 min; (M+H)$^+$=542.4.

Step 4. 2-((4-(2,7-diazaspiro[4.4]nonan-2-yl)pyrimidin-5-yl)oxy)-5-fluoro-N,N-diisopropylbenzamide

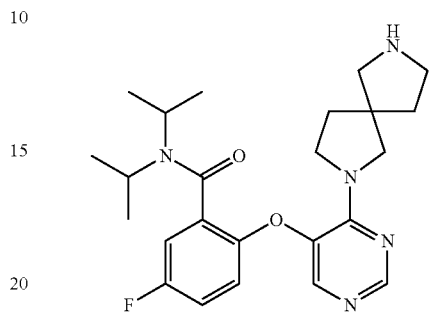

To a solution of tert-butyl 7-(5-(2-(diisopropylcarbamoyl)-4-fluorophenoxy)pyrimidin-4-yl)-2,7-diazaspiro[4.4]nonane-2-carboxylate (900 mg, 1.67 mmol) in anhydrous CH$_2$Cl$_2$ (25 mL) was added TFA (5 mL) under N$_2$. The reaction mixture was stirred at 10-22° C. for 2 h. The solvent was then removed under reduced pressure. The resulting residue was adjusted to pH to 9-10 using 10% NaOH. Then the mixture was extracted with CH$_2$Cl$_2$ (20 mL×3). The organic layers were washed with brine (20 mL), dried over anhydrous Na$_2$SO$_4$, filtered and concentrated under reduced pressure to afford 2-((4-(2,7-diazaspiro[4.4]nonan-2-yl)pyrimidin-5-yl)oxy)-5-fluoro-N,N-diisopropylbenzamide. The residue was used for the next step without further purification, as a brown oil. Yield: 730 mg. LCMS method F: R$_t$=0.888 min; (M+H)$^+$=442.4.

Step 5. 5-fluoro-N,N-diisopropyl-2-((4-(7-((2-oxo-2,3-dihydro-1H-benzo[d]imidazol-5-yl)methyl)-2,7-diazaspiro[4.4]nonan-2-yl)pyrimidin-5-yl)oxy)benzamide To a mixture of 2-((4-(2,7-diazaspiro[4.4]nonan-2-yl)pyrimidin-5-yl)oxy)-5-fluoro-N,N-diisopropylbenzamide (730 mg, 1.654 mmol), 2-oxo-2,3-dihydro-1H-benzo[d]imidazole-5-carbaldehyde (Intermediate 40, 536 mg, 3.308 mmol) and 4 Å-molecular sieves (100 mg) was added anhydrous MeOH (20 mL), then the reaction was stirred at 60° C. for 30 min under N$_2$. Then NaBH$_3$CN (513 mg, 8.270 mmol) was added to the solution and the reaction mixture was stirred at 60° C. for 4 h. The reaction mixture was then filtered and concentrated under reduced pressure. The resulting residue was diluted with MeOH (15 mL) and the mixture was purified by preparative RP-HPLC method C (HCl) to afford compound 5-fluoro-N,N-diisopropyl-2-((4-(7-((2-oxo-2,3-dihydro-1H-benzo[d]imidazol-5-yl)methyl)-2,7-diazaspiro[4.4]nonan-2-yl)pyrimidin-5-yl)oxy)benzamide as a white solid. Yield: 540 mg (55%). LCMS method C: R$_t$=0.931; (M+H)$^+$=588.5. $^1$H NMR (CD$_3$OD): δ 8.30-8.38 (m, 1H), 7.62-7.84 (m, 1H), 6.86-7.15 (m, 6H), 4.22-4.30 (m, 3H), 3.20-4.03 (m, 9H), 1.87-2.04 (m, 5H), 0.81-1.30 (m, 11H). $^{19}$F NMR (CD$_3$OD): δ −117.14.

Examples 1A and 1B 5-fluoro-N,N-diisopropyl-2-((4-(7-((2-oxo-2,3-dihydro-1H-benzo[d]imidazol-5-yl)methyl)-2,7-diazaspiro[4.4]nonan-2-yl)pyrimidin-5-yl)oxy)benzamide (Isomers 1 and 2)

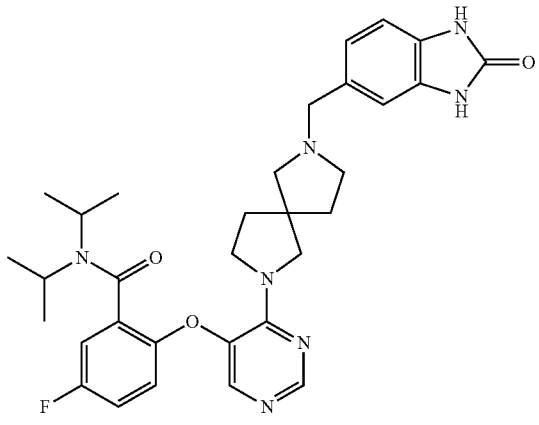 [SMILES: CC(C)N(C(=O)c1cc(F)ccc1Oc1cncnc1N1CCC2(CCN(Cc3ccc4[nH]c(=O)[nH]c4c3)C2)C1)C(C)C]

The racemic compound of Example 1 was separated by SFC method A to afford two isomers.

Isomer 1 (Example 1A): LCMS method C: $R_t$=0.931; (M+H)$^+$=588.5. $^1$H NMR (CD$_3$OD): δ 8.54-8.61 (m, 1H), 7.86-8.09 (m, 1H), 7.20-7.31 (m, 5H), 7.15 (d, J=36.4 Hz, 1H), 4.41-4.51 (m, 3H), 3.40-4.02 (m, 9H), 2.15-2.25 (m, 4H), 1.06-1.48 (m, 12H). $^{19}$F NMR (CD$_3$OD): δ −117.11. SFC Anal. Method A: $t_R$=0.569 min, ee=100%.

Isomer 2 (Example 1B): LCMS method C: $R_t$=0.930; (M+H)$^+$=588.5. $^1$H NMR (CD$_3$OD): δ 8.58-8.65 (m, 1H), 7.90-8.14 (m, 1H), 7.25-7.35 (m, 5H), 7.18 (d, J=44.8 Hz, 1H), 4.45-4.54 (m, 3H), 3.43-4.06 (m, 9H), 2.18-2.30 (m, 4H), 1.10-1.52 (m, 12H). $^{19}$F NMR (CD$_3$OD 400 MHz): δ −117.10. SFC Anal. Method A: $t_R$=0.809 min, ee=98.87%.

Example 2

N-ethyl-5-fluoro-N-isopropyl-2-((4-(7-((2-oxo-2,3-dihydro-1H-benzo[d]imidazol-5-yl)methyl)-2,7-diazaspiro[4.4]nonan-2-yl)pyrimidin-5-yl)oxy)benzamide (Racemic Mixture)

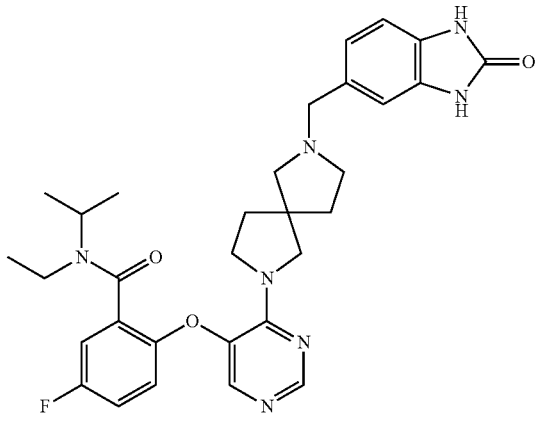 [SMILES: CCN(C(=O)c1cc(F)ccc1Oc1cncnc1N1CCC2(CCN(Cc3ccc4[nH]c(=O)[nH]c4c3)C2)C1)C(C)C]

The title product was synthesized by the method described in Example 1. In step 3, N-isopropyl-N-ethyl amine was utilized. LCMS method B: $R_t$=1.164; (M+H)$^+$=574.1.

Examples 2A and 2B

N-ethyl-5-fluoro-N-isopropyl-2-((4-(7-((2-oxo-2,3-dihydro-1H-benzo[d]imidazol-5-yl)methyl)-2,7-diazaspiro[4.4]nonan-2-yl)pyrimidin-5-yl)oxy)benzamide (Isomers 1-2)

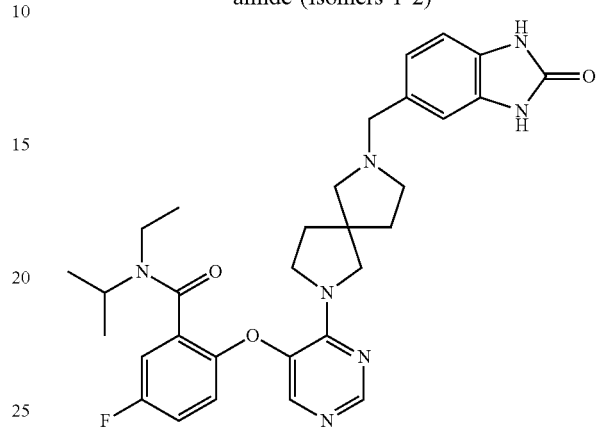

The racemic compound of Example 2 was separated by SFC method A to afford two isomers.

Isomer 1 (Example 2A): Yield: 92.5 mg. LCMS method E: $R_t$=1.132 min; (M+H)$^+$=574.3 $^1$H NMR (CD$_3$OD): δ8.20-8.29 (m, 1H), 7.72-7.80 (m, 1H), 6.85-7.16 (m, 6H), 4.35-4.41 (m, 1H), 3.45-3.89 (m, 8H), 3.12-3.23 (m, 1H), 2.50-2.71 (m, 4H), 1.76-1.96 (m, 4H), 1.05-1.27 (m, 8H). $^{19}$F NMR (CD$_3$OD): δ−120.380. SFC Anal. Method A: $t_R$=0.722 min, ee=100%.

Isomer 2 (Example 2B): Yield: 115.8 mg. LCMS method E: $R_t$=1.121 min; (M+H)$^+$=574.3. $^1$H NMR (CD$_3$OD): δ8.21-8.29 (m, 1H), 7.71-7.80 (m, 1H), 6.85-7.16 (m, 6H), 4.35-4.42 (m, 1H), 3.45-3.90 (m, 8H), 3.15-3.23 (m, 1H), 2.48-2.71 (m, 4H), 1.76-1.96 (m, 4H), 1.05-1.27 (m, 8H). $^{19}$F NMR (CD$_3$OD): δ−120.390. SFC Anal. Method A: $t_R$=1.455 min, ee=99.65%.

Examples 3A and 3B 5-fluoro-2-((4-(7-((1-(2-hydroxyethyl)-2-oxo-2,3-dihydro-1H-benzo[d]imidazol-5-yl)methyl)-2,7-diazaspiro[4.4]nonan-2-yl)pyrimidin-5-yl)oxy)-N,N-diisopropylbenzamide (Isomers 1-2)

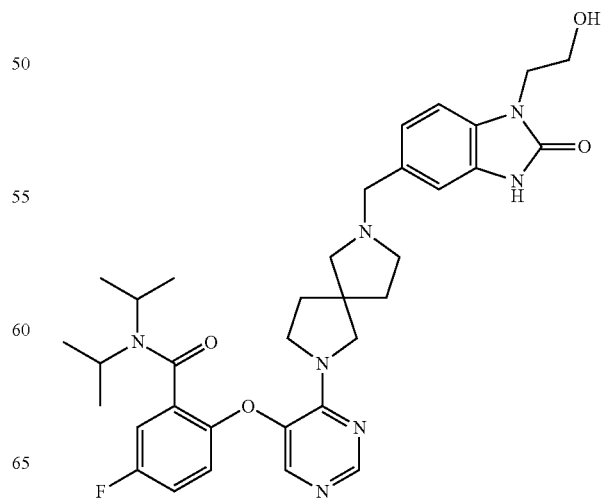

To a solution of 2-((4-(2,7-diazaspiro[4.4]nonan-2-yl)pyrimidin-5-yl)oxy)-5-fluoro-N,N-diisopropylbenzamide (70 mg, 0.16 mmol) and 1-(2-hydroxyethyl)-2-oxo-2,3-dihydro-1H-benzo[d]imidazole-5-carbaldehyde (Intermediate 42c, 33 mg, 0.16 mmol) in anhydrous MeOH (3 mL) was added NaBH$_3$CN (50 mg, 0.80 mmol) under N$_2$. The reaction was stirred at 55° C. for 16 h. The reaction was concentrated under reduced pressure to afford the residue which was purified by silica gel chromatography (CH$_2$Cl$_2$: MeOH=10:1), and further purified by preparative SFC method B and RP-HPLC method E to give the compound as two isomers.

Isomer 1 (Example 3A): White solid. LCMS method E: R$_t$=0.736 min (M+H)$^+$=632.4. $^1$H NMR (CD$_3$OD): δ 8.28 (s, 1H), 7.80 (d, J=2.4 Hz, 1H), 6.89-7.15 (m, 5H), 6.89-6.90 (m, 1H), 3.99 (t, J=5.6 Hz, 2H), 3.55-3.85 (m, 10H), 2.52-2.72 (m, 4H), 1.84-1.96 (m, 4H), 1.54 (dd, J=2.4, 6.8 Hz, 3H), 1.43 (t, J=4.8 Hz, 3H), 1.19 (d, J=3.2 Hz, 3H), 1.32 (t, J=4.8 Hz, 3H). $^{19}$F NMR (CD$_3$OD): δ −120.25-120.33. SFC Anal. Method B: t$_R$=7.26 min, ee=100%.

Isomer 2 (Example 3B): White solid. LCMS method E: R$_t$=0.738 min. (M+H)$^+$=632.4. $^1$H NMR (CD$_3$OD): δ 8.28 (s, 1H), 7.80 (d, J=2.4 Hz, 1H), 6.89-7.15 (m, 5H), 6.89-6.90 (m, 1H), 3.99 (t, J=5.6 Hz, 2H), 3.55-3.85 (m, 10H), 2.52-2.72 (m, 4H), 1.84-1.96 (m, 4H), 1.54 (dd, J=2.4, 6.8 Hz, 3H), 1.43 (t, J=4.8 Hz, 3H), 1.19 (d, J=3.2 Hz, 3H), 1.32 (t, J=4.8 Hz, 3H). $^{19}$F NMR (CD$_3$OD): δ −120.27-120.35. SFC Anal. Method B: t$_R$=7.92 min, ee=97.04%.

Example 4

N-ethyl-5-fluoro-2-((4-(7-((1-(2-hydroxyethyl)-2-oxo-2,3-dihydro-1H-benzo[d]imidazol-5-yl)methyl)-2,7-diazaspiro[4.4]nonan-2-yl)pyrimidin-5-yl)oxy)-N-isopropylbenzamide

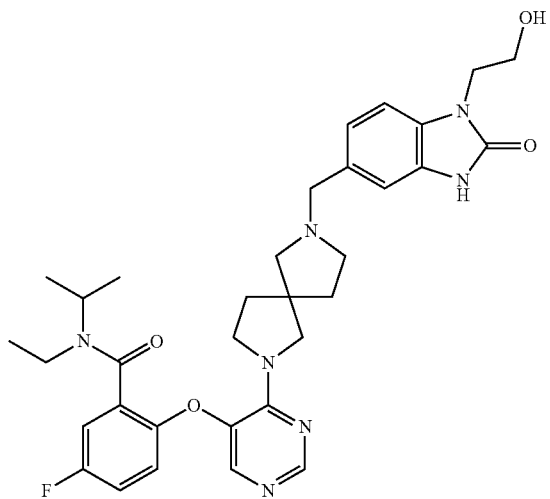 [SMILES: CCN(C(=O)c1cc(F)ccc1Oc1cncnc1N1CCC2(CCN(Cc3ccc4c(c3)[nH]c(=O)n4CCO)C2)C1)C(C)C]

To a solution of 2-((4-(2,7-diazaspiro[4.4]nonan-2-yl)pyrimidin-5-yl)oxy)-N-ethyl-5-fluoro-N-isopropylbenzamide (prepared as an intermediate during the synthesis of Example 2, 100 mg, 0.23 mmol) in anhydrous MeOH (10 mL) was added 1-(2-hydroxyethyl)-2-oxo-2,3-dihydro-1H-benzo[d]imidazole-5-carbaldehyde (Intermediate 42c, 72 mg, 0.35 mmol), and was stirred for 5 min under N$_2$. Then NaBH$_3$CN (71 mg, 1.15 mmol) was added and the mixture was stirred at 65° C. for 2 h. The reaction mixture, with an additional 20 mg of 2-((4-(2,7-diazaspiro[4.4]nonan-2-yl)pyrimidin-5-yl)oxy)-N-ethyl-5-fluoro-N-isopropylbenzamide, was concentrated under reduced pressure to afford the residue which was purified by column chromatograph on silica gel (eluting with dichloromethane:methanol=20:1 to 10:1) to give N-ethyl-5-fluoro-2-((4-(7-((1-(2-hydroxyethyl)-2-oxo-2,3-dihydro-1H-benzo[d]imidazol-5-yl)methyl)-2,7-diazaspiro[4.4]nonan-2-yl)pyrimidin-5-yl)oxy)-N-isopropylbenzamide as a yellow oil. Yield: 70 mg. LCMS method C: R$_t$=0.583 min; (M+H)$^+$=618.1.

Examples 4A and 4B

N-ethyl-5-fluoro-2-((4-(7-((1-(2-hydroxyethyl)-2-oxo-2,3-dihydro-1H-benzo[d]imidazol-5-yl)methyl)-2,7-diazaspiro[4.4]nonan-2-yl)pyrimidin-5-yl)oxy)-N-isopropylbenzamide (Isomers 1-2)

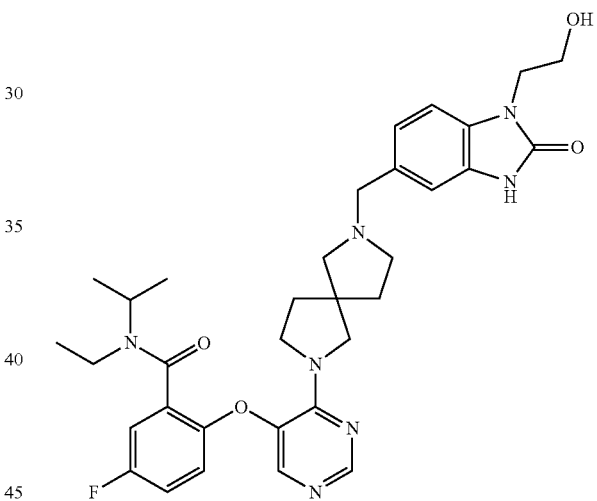

An amount of 70 mg of N-ethyl-5-fluoro-2-((4-(7-((1-(2-hydroxyethyl)-2-oxo-2,3-dihydro-1H-benzo[d]imidazol-5-yl)methyl)-2,7-diazaspiro[4.4]nonan-2-yl)pyrimidin-5-yl)oxy)-N-isopropylbenzamide (Example 4) was separated with SFC method A to give Isomers 1 and 2 as white solids.

Isomer 1 (Example 4A):

Yield: 8.70 mg. R$_t$=1.14 min; (M+H)$^+$=618.3. $^1$H NMR (CD$_3$OD): δ8.27-8.29 (m, 1H), 7.78-7.82 (m, 1H), 6.89-7.18 (m, 6H), 3.33-4.01 (m, 13H), 2.48-2.75 (m, 4H), 1.75-1.96 (m, 4H), 1.05-1.26 (m, 9H). $^{19}$F NMR (CD$_3$OD): δ−120.390. SFC Anal. Method C: t$_R$=1.870 min, ee=98.60%.

Isomer 2 (Example 4B):

Yield: 9.2 mg. LCMS method E: R$_t$=R$_t$ value: 1.140 min; (M+H)$^+$=618.3. $^1$H NMR (CD$_3$OD): δ8.25-8.31 (m, 1H), 7.76-7.25 (m, 1H), 6.85-7.20 (m, 6H), 3.48-4.00 (m, 13H), 2.48-2.75 (m, 4H), 1.75-1.96 (m, 4H), 1.05-1.33 (m, 9H). $^{19}$F NMR (CD$_3$OD): δ−120.398. SFC Anal. Method C: t$_R$=2.922 min, ee=99.43%.

Example 5

5-fluoro-N-(2-hydroxyethyl)-N-isopropyl-2-((4-(7-((2-oxo-2,3-dihydro-1H-benzo[d]imidazol-5-yl)methyl)-2,7-diazaspiro[4.4]nonan-2-yl)pyrimidin-5-yl)oxy)benzamide

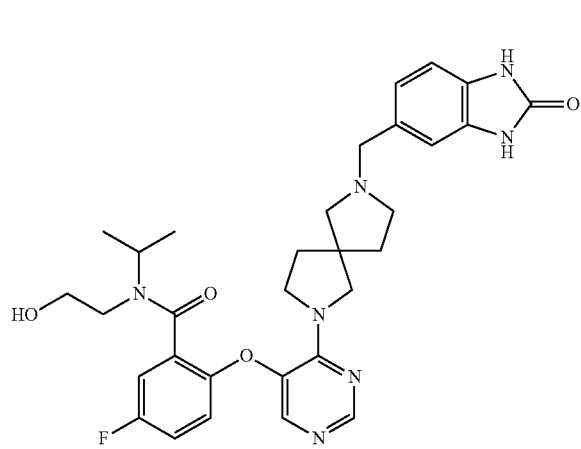 [SMILES: CC(C)N(CCO)C(=O)c1cc(F)ccc1Oc1cncnc1N1CCC2(CCN(Cc3ccc4[nH]c(=O)[nH]c4c3)C2)C1]

Step 1. tert-butyl 7-(5-(2-((2-(((tert-butyldimethylsilyl)oxy)ethyl)(isopropyl)carbamoyl)-4-fluorophenoxy)pyrimidin-4-yl)-2,7-diazaspiro[4.4]nonane-2-carboxylate

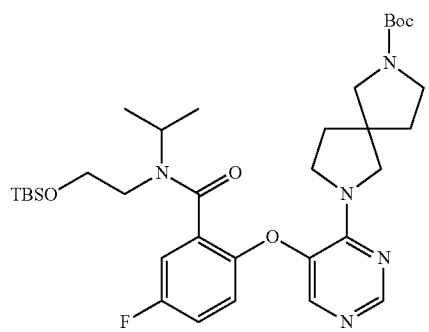 [SMILES: CC(C)N(CCO[Si](C)(C)C(C)(C)C)C(=O)c1cc(F)ccc1Oc1cncnc1N1CCC2(CCN(C(=O)OC(C)(C)C)C2)C1]

To a solution of 2-((4-(7-(tert-butoxycarbonyl)-2,7-diazaspiro[4.4]nonan-2-yl)pyrimidin-5-yl)oxy)-5-fluorobenzoic acid (Intermediate 33, Step 2, 50 mg, 0.1092 mmol) in anhydrous DMF (3 mL) was added N-(2-(((tert-butyldimethylsilyl)oxy)ethyl)propan-2-amine (36 mg, 0.1637 mmol), HATU (83 mg, 0.2183 mmol) and DIEA (28 mg, 0.2183 mmol) and the mixture was stirred at 16° C. for 6 h under $N_2$. The mixture was then diluted with EtOAc (20 mL) and washed with brine (3×20 mL). The organic layer was dried over anhydrous $Na_2SO_4$, filtered and concentrated under reduced pressure. The residue was purified by preparative TLC with EtOAc to afford tert-butyl 7-(5-(2-((2-(((tert-butyldimethylsilyl)oxy)ethyl)(isopropyl)carbamoyl)-4-fluorophenoxy)pyrimidin-4-yl)-2,7-diazaspiro[4.4]nonane-2-carboxylate as a yellow oil. Yield: 50 mg. LCMS method C: $R_t$=0.851 min, $(M+H)^+$=658.1.

Step 2. 2-((4-(2,7-diazaspiro[4.4]nonan-2-yl)pyrimidin-5-yl)oxy)-5-fluoro-N-(2-hydroxyethyl)-N-isopropylbenzamide

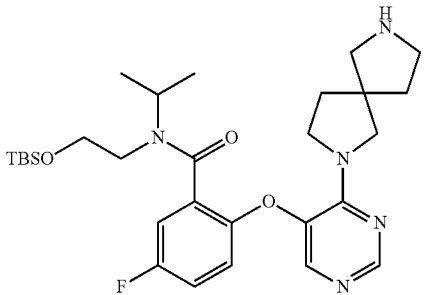 [SMILES: CC(C)N(CCO[Si](C)(C)C(C)(C)C)C(=O)c1cc(F)ccc1Oc1cncnc1N1CCC2(CCNC2)C1]

To a solution of tert-butyl 7-(5-(2-((2-((tert-butyldimethylsilyl)oxy)ethyl)(isopropyl)carbamoyl)-4-fluorophenoxy)pyrimidin-4-yl)-2,7-diazaspiro[4.4]nonane-2-carboxylate (50 mg, 0.0761 mmol) in $CH_2Cl_2$ (4 mL) was added TFA (1 mL) and the mixture was stirred at 16° C. for 3 h. The mixture was then concentrated under reduced pressure. The residue was adjusted to pH=8-9 with sat. $NaHCO_3$ solution and diluted with water (15 mL). The aqueous layer was extracted with $CH_2Cl$:$^i$PrOH (3:1, 3×20 mL). The combined organic layers were dried over anhydrous $Na_2SO_4$, filtered and concentrated under reduced pressure to give crude 2-((4-(2,7-diazaspiro[4.4]nonan-2-yl)pyrimidin-5-yl)oxy)-5-fluoro-N-(2-hydroxyethyl)-N-isopropylbenzamide as a yellow oil, which was used for the next step directly without further purification. Yield: 34 mg.

Step 3. 5-fluoro-N-(2-hydroxyethyl)-N-isopropyl-2-((4-(7-((2-oxo-2,3-dihydro-1H-benzo[d]imidazol-5-yl)methyl)-2,7-diazaspiro[4.4]nonan-2-yl)pyrimidin-5-yl)oxy)benzamide To a solution of 2-((4-(2,7-diazaspiro[4.4]nonan-2-yl)pyrimidin-5-yl)oxy)-5-fluoro-N-(2-hydroxyethyl)-N-isopropylbenzamide (34 mg, 0.0761 mmol) in anhydrous MeOH (3 mL) was added 2-oxo-2,3-dihydro-1H-benzo[d]imidazole-5-carbaldehyde (Intermediate 40, 25 mg, 0.1522 mmol) and $NaBH_3CN$ (24 mg, 0.3805 mmol). The mixture was stirred at 60° C. for 16 h under $N_2$. LCMS showed that the reaction was completed. The mixture was concentrated under reduced pressure and purified directly by RP-HPLC method D to give 5-fluoro-N-(2-hydroxyethyl)-N-isopropyl-2-((4-(7-((2-oxo-2,3-dihydro-1H-benzo[d]imidazol-5-yl)methyl)-2,7-diazaspiro[4.4]nonan-2-yl)pyrimidin-5-yl)oxy)benzamide as a pale yellow solid. Yield: 10.00 mg. LCMS method C: $R_t$=0.560 min, $(M+H)^+$=590.2 $^1$H NMR (CDCl$_3$): δ 10.35-10.15 (m, 0.5H), 9.75-9.60 (m, 0.5H), 9.01-8.77 (m, 1H), 8.36 (s, 1H), 7.81-7.70 (m, 1H), 7.35-7.25 (m, 0.5H), 7.18-7.08 (m, 0.5H), 7.05-6.90 (m, 2H), 6.89-6.75 (m, 2H), 6.65-6.50 (m, 1H), 4.05-3.25 (m, 12H), 2.97-2.25 (m, 4H), 2.12-1.85 (m, 4H), 1.30-1.07 (m, 6H). $^{19}$F NMR (CDCl$_3$): δ −119.3.

Example 6A 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide

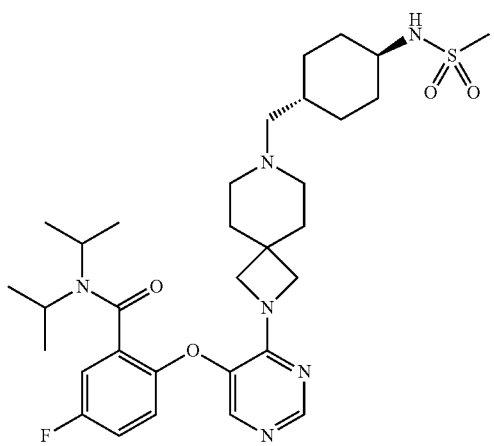 [SMILES: CC(C)N(C(=O)c1cc(F)ccc1Oc1cncnc1N1CC2(CCN(C[C@H]3CC[C@H](NS(C)(=O)=O)CC3)CC2)C1)C(C)C]

Step 1. tert-butyl 2-(5-(2-(diisopropylcarbamoyl)-4-fluorophenoxy)pyrimidin-4-yl)-2,7-diazaspiro[3.5]nonane-7-carboxylate

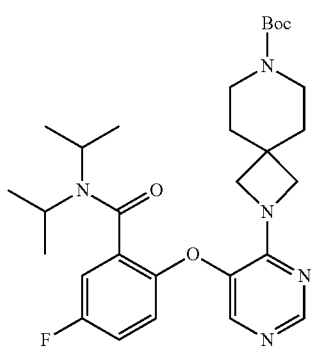

A mixture of 2-((4-chloropyrimidin-5-yl)oxy)-5-fluoro-N,N-diisopropylbenzamide (Intermediate 41, 1.8 g, 5.13 mmol), tert-butyl 2,7-diazaspiro[3.5]nonane-7-carboxylate (1.35 g, 5.13 mmol) and DIEA (1.32 g, 10.26 mmol) in $^i$PrOH (20 mL) was stirred at 70° C. for 16 h. After concentration, the mixture was purified directly by column chromatography on silica gel eluting with petroleum ether: ethyl acetate=3:7 to afford tert-butyl 2-(5-(2-(diisopropylcarbamoyl)-4-fluorophenoxy)pyrimidin-4-yl)-2,7-diazaspiro[3.5]nonane-7-carboxylate as a yellow oil. Yield: 2.9 g. LCMS method E: $R_t$=0.767 min; (M+H)$^+$=542.2

Step 2: 2-((4-(2,7-diazaspiro[3.5]nonan-2-yl)pyrimidin-5-yl)oxy)-5-fluoro-N,N-diisopropylbenzamide

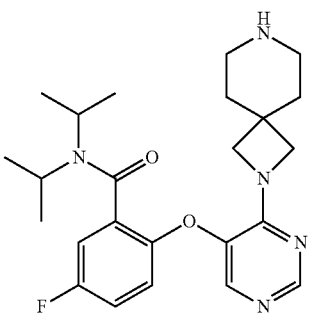 [SMILES: CC(C)N(C(=O)c1cc(F)ccc1Oc1cncnc1N1CC2(CCNCC2)C1)C(C)C]

The solution of tert-butyl 2-(5-(2-(diisopropylcarbamoyl)-4-fluorophenoxy)pyrimidin-4-yl)-2,7-diazaspiro[3.5]nonane-7-carboxylate (2.9 g, 5.35 mmol) in anhydrous CH$_2$Cl$_2$ (30 mL) was added TFA (10 mL) and the mixture was stirred at 25° C. for 2 h. The mixture was then concentrated under reduced pressure and to the residue was added 30% aqueous NaOH solution to a pH=11-12. The aqueous layer was then extracted with CH$_2$Cl$_2$/$^i$PrOH (4/1, 3×30 mL). The combined organic layers were dried over anhydrous Na$_2$SO$_4$, filtered and concentrated under reduced pressure to afford crude 2-((4-(2,7-diazaspiro[3.5]nonan-2-yl)pyrimidin-5-yl)oxy)-5-fluoro-N,N-diisopropylbenzamide as a yellow solid, which was used for next step without further purification. Yield: 2.3 g. LCMS method C: $R_t$=0.584 min, (M+H)$^+$=442.1.

Step 3: tert-butyl ((1r,4r)-4-((2-(5-(2-(diisopropylcarbamoyl)-4-fluorophenoxy)pyrimidin-4-yl)-2,7-diazaspiro[3.5]nonan-7-yl)methyl)cyclohexyl)carbamate (Example 99A)

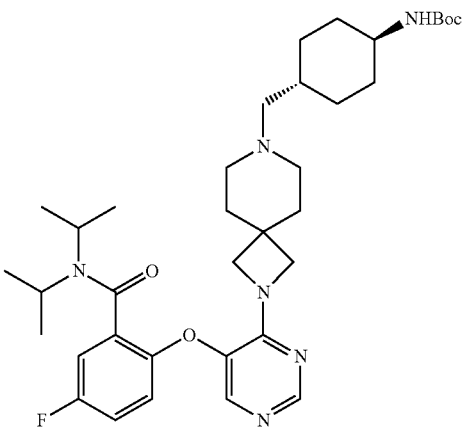 [SMILES: CC(C)N(C(=O)c1cc(F)ccc1Oc1cncnc1N1CC2(CCN(C[C@H]3CC[C@H](NC(=O)OC(C)(C)C)CC3)CC2)C1)C(C)C]

To a solution of 2-((4-(2,7-diazaspiro[3.5]nonan-2-yl)pyrimidin-5-yl)oxy)-5-fluoro-N,N-diisopropylbenzamide (2.3 g, 5.20 mmol) in anhydrous MeOH (50 mL) was adjusted to pH 6-7 by AcOH. Then tert-butyl ((1r,4r)-4-formylcyclohexyl)carbamate (1.3 g, 5.72 mmol) was added. After being stirred at 25° C. for 5 min, NaBH$_3$CN (656 mg, 10.41 mmol) was added and the mixture was stirred at 70° C. for 1 h. The mixture was then concentrated under reduced pressure. The residue was dissolved with EtOAc (50 mL) and washed with H₂O (2×30 mL). The organic layer was dried over anhydrous Na₂SO₄, filtered and concentrated under reduced pressure. The residue was purified by column chromatography on silica gel eluting with petroleum ether:ethyl acetate=3:7 to afford tert-butyl ((1r,4r)-4-((2-(5-(2-(diisopropylcarbamoyl)-4 fluorophenoxy)pyrimidin-4-yl)-2,7-diazaspiro[3.5]nonan-7-yl)methyl)cyclohexyl)carbamate as a white solid. Yield: 3.0 g. LCMS method C: $R_t$=0.929 min; (M+H)⁺=653.3.

Step 4: 2-((4-(7-(((1r,4r)-4-aminocyclohexyl) methyl)-2,7-diazaspiro[3.5]nonan-2-yl)pyrimidin-5-yl)oxy)-5-fluoro-N,N-diisopropylbenzamide

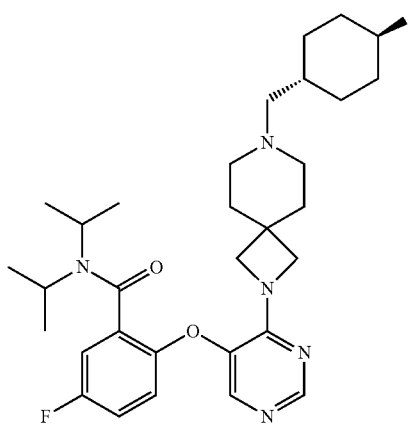

To a solution of tert-butyl ((1r,4r)-4-((2-(5-(2-(diisopropylcarbamoyl)-4-fluorophenoxy)pyrimidin-4-yl)-2,7-diazaspiro[3.5]nonan-7-yl)methyl)cyclohexyl)carbamate (3 g, 4.60 mmol) in anhydrous ethyl CH₂Cl₂ (30 mL) was added with TFA (10 mL) and the mixture was stirred at 25° C. for 2 h. The mixture was then concentrated under reduced pressure to afford crude 2-((4-(7-(((1r,4r)-4-aminocyclohexyl)methyl)-2,7-diazaspiro[3.5]nonan-2-yl)pyrimidin-5-yl)oxy)-5-fluoro-N,N-diisopropylbenzamide as a pale yellow oil, which was used for next step without further purification. Yield: 4.0 g. LCMS method C: $R_t$=0.513 min; (M+H)⁺=553.2.

Step 5: (5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide)

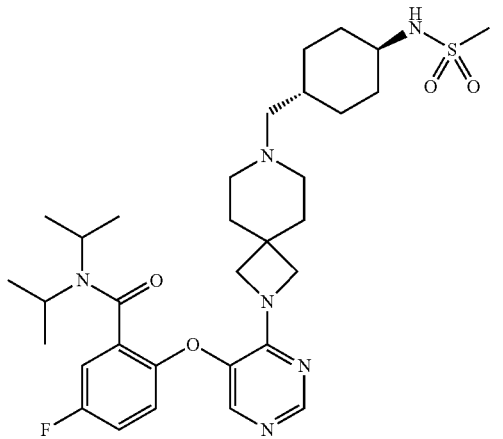

To a solution of 2-((4-(7-(((1r,4r)-4-aminocyclohexyl)methyl)-2,7-diazaspiro[3.5]nonan-2-yl)pyrimidin-5-yl)oxy)-5-fluoro-N,N-diisopropylbenzamide (3.6 g, crude, about 4.14 mmol) and Et₃N (2.47 g, 24.0 mmol) in anhydrous CH₂Cl₂ (50 mL) was added MsCl (844 mg, 7.34 mmol) dropwise at 0° C. under N₂ and the mixture was stirred at 0° C. for 2 h. The mixture was then washed with H₂O (3×50 mL) and brine (50 mL). The organic layer was dried over anhydrous Na₂SO₄, filtered and concentrated under reduced pressure. The residue was purified by column chromatography on silica gel eluting with CH₂Cl₂:CH₃OH=19:1 to afford 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide as a white solid, which was purified by RP-HPLC method D to afford 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide as a white solid. Yield: 1.59 g. LCMS method C: $R_t$=0.565 min; (M+H)⁺=631.1. ¹H NMR (CDCl₃): δ 8.27 (s, 1H), 8.78 (s, 1H), 7.17-7.15 (m, 2H), 7.03-6.99 (m, 1H), 4.06-4.03 (m, 2H), 3.96-3.89 (m, 2H), 3.87-3.84 (m, 1H), 3.66-3.63 (m, 1H), 3.34-3.32 (m, 1H), 3.20-3.15 (m, 1H), 2.95 (s, 3H), 2.55-2.51 (m, 3H), 2.33-2.30 (m, 2H), 2.06-2.04 (m, 2H), 1.89-1.87 (m, 6H), 1.56 (d, J=6.8 Hz, 4H), 1.48 (d, J=6.8 Hz, 3H), 1.33-1.30 (m, 2H), 1.20 (d, J=6.8 Hz, 3H), 1.13 (d, J=6.4 Hz, 3H), 1.08-1.07 (m, 2H). ¹⁹F NMR (CDCl₃): δ -119.7.

Examples 6A-6B

Alternative Synthesis of 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide (Example 6A) and 5-fluoro-N,N-diisopropyl-2-((4-(7-(((1s,4s)-4-(methylsulfonamido)cyclohexyl)methyl)-2,7-diazaspiro[3.5]nonan-2-yl)pyrimidin-5-yl)oxy) benzamide (Example 6B)

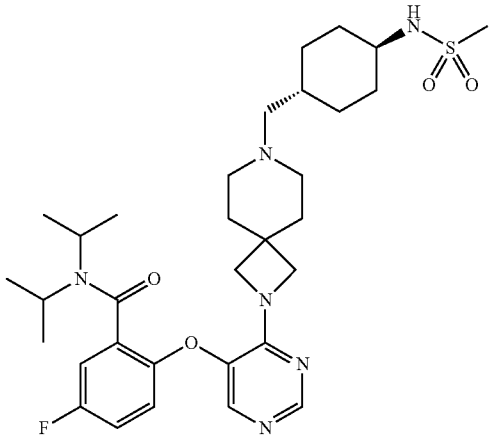 [SMILES: CC(C)N(C(=O)c1cc(F)ccc1Oc1cncnc1N1CC2(CCN(C[C@H]3CC[C@H](NS(C)(=O)=O)CC3)CC2)C1)C(C)C]

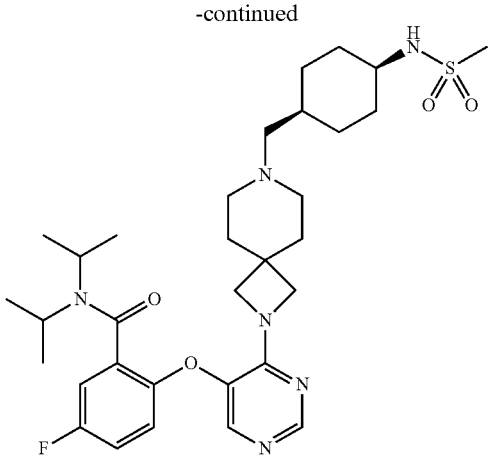

To a solution of 2-((4-(2,7-diazaspiro[3.5]nonan-2-yl)pyrimidin-5-yl)oxy)-5-fluoro-N,N-diisopropylbenzamide (Example 6A, Step 2, 11 g, 24.9 mmol) in anhydrous $CH_2Cl_2$ (170 mL) was added Intermediate 47 (7.5 g, 36.6 mmol). The mixture was stirred at RT for 15 min and $NaBH(OAc)_3$ (7.2 g, 33.9 mmol) was added in portions over 5 min. The mixture was stirred at RT for another 2 h. The mixture was washed with $H_2O$ (3×100 mL) and brine (100 mL), dried over anhydrous $Na_2SO_4$, filtered and concentrated under reduced pressure. The residue was purified by column chromatography on silica gel eluting with $CH_2Cl_2$/$CH_3OH$=24/1 to 10/1 to afford the title compound as the free base with a trans:cis ratio of 97:3. LC-MS Method D $t_R$=0.555 min, MS (m/z 631.3 [M+H]$^+$ The trans and cis isomers were separated by SFC method A.

Trans-isomer (Example 6A):

LC-MS Method E $t_R$=3.881 min, m/z 631.3 [M+H]$^+$. Isomer SFC $t_R$=4.430 min in 10 min chromatography (Column: OD-3; Method Name: OD-3_EtOH/diethylamine_5_40_25 mL, trans=100%). $^1$H NMR (CD$_3$OD): δ 8.22 (s, 1H), 7.73 (s, 1H), 7.23-7.10 (m, 2H), 7.01-6.95 (m, 1H), 4.08-3.80 (m, 5H), 3.68-3.56 (m, 1H), 3.20-3.07 (m, 1H), 2.92 (s, 3H), 2.48-2.25 (m, 4H), 2.13 (d, J=6.4 Hz, 2H), 2.06-1.96 (m, 2H), 1.91-1.76 (m, 6H), 1.53 (d, J=6.8 Hz, 3H), 1.51-1.45 (m, 1H), 1.45 (d, J=6.8 Hz, 3H), 1.35-1.24 (m, 2H), 1.17 (d, J=6.8 Hz, 3H), 1.09 (d, J=6.4 Hz, 3H), 1.06-0.98 (m, 2H). $^{19}$F NMR (CDCl$_3$): δ −119.711.

Cis-isomer (Example 6B):

LC-MS method D: $t_R$=0.582 minm/z 631.1 [M+H]$^+$. Isomer SFC $t_R$=4.461 min in 10 min chromatography (Column: OD-3; Method Name: OD-3_EtOH/diethylamine_5_40_25 mL, trans/cis=2.1%/97.9%). $^1$H NMR (CDCl$_3$): δ 8.36 (s, 1H), 7.75 (s, 1H), 7.05-6.96 (m, 2H), 6.80-6.71 (m, 1H), 4.40-4.30 (m, 1H), 4.05-3.75 (m, 5H), 3.70-3.60 (m, 1H), 3.55-3.45 (m, 1H), 2.96 (s, 3H), 2.45-2.09 (m, 6H), 1.85-1.65 (m, 10H), 1.60-1.45 (m, 7H), 1.44-1.19 (m, 2H), 1.13 (d, J=6.8 Hz, 3H), 1.09 (d, J=6.8 Hz, 3H). $^{19}$F NMR (CDCl$_3$): δ −118.583.

Example 7

5-((7-(5-(2-(amino(cyclopentyl)methyl)-4-fluorophenoxy)pyrimidin-4-yl)-2,7-diazaspiro[4.4]nonan-2-yl)methyl)-1,3-dihydro-2H-benzo[d]imidazol-2-one

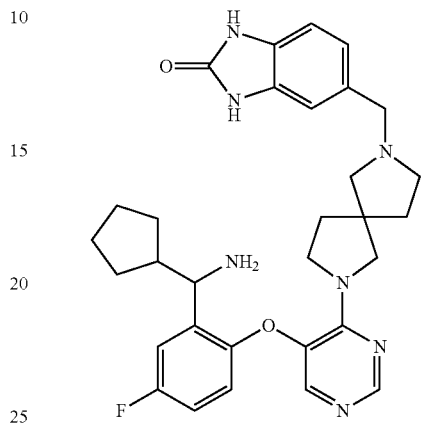

Step 1: tert-Butyl 7-(5-(2-(1-((tert-butylsulfinyl)amino)ethyl)-4-fluorophenoxy)pyrimidin-4-yl)-2,7-diazaspiro[4.4]nonane-2-carboxylate

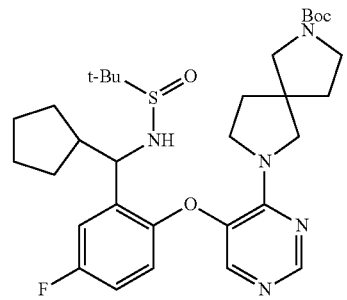 [SMILES: CC(C)(C)OC(=O)N1CCC2(CCN(c3ncncc3Oc3ccc(F)cc3C(NS(=O)C(C)(C)C)C3CCCC3)C2)C1]

To a solution of tert-butyl 7-(5-(2-bromo-4-fluorophenoxy)pyrimidin-4-yl)-2,7-diazaspiro[4.4]nonane-2-carboxylate (Intermediate 11, 407 mg, 0.83 mmol) and (E)-N-(cyclopentylmethylene)-2-methylpropane-2-sulfinamide (249 mg, 1.24 mmol) in anhydrous THF (6 mL) was added 1.6 M BuLi solution in hexane (0.78 mL, 1.24 mmol) dropwise under N$_2$ atmosphere at −78° C. After the addition, the mixture was stirred for another 30 min before quenching with aq. NH$_4$Cl solution. The reaction mixture was extracted twice with EtOAc and the combined organic phase was washed with H$_2$O, dried over anhydrous Na$_2$SO$_4$, filtered and evaporated under reduced pressure. The residue was purified by flash chromatography using DCM/MeOH as eluent to yield 461 mg of the desired product tert-butyl 7-(5-(2-(1-((tert-butylsulfinyl)amino)ethyl)-4-fluorophenoxy)pyrimidin-4-yl)-2,7-diazaspiro[4.4]nonane-2-carboxylate. LCMS method B: R$_t$=1.32 min, (M+H)$^+$=616.3.

Step 2: N-((2-((4-(2,7-diazaspiro[4.4]nonan-2-yl)pyrimidin-5-yl)oxy)-5-fluorophenyl)(cyclopentyl)methyl)-2-methylpropane-2-sulfinamide

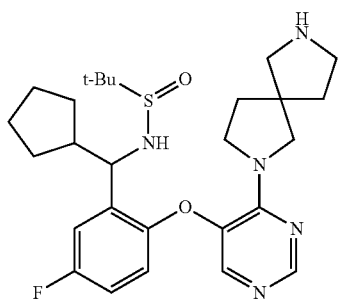 [SMILES: CC(C)(C)S(=O)NC(c1cc(F)ccc1Oc1cncnc1N1CCC2(CCNC2)C1)C1CCCC1]

To a solution of tert-butyl 7-(5-(2-(1-((tert-butylsulfinyl)amino)ethyl)-4-fluorophenoxy)pyrimidin-4-yl)-2,7-diazaspiro[4.4]nonane-2-carboxylate (61 mg, 0.099 mmol) in DCM (6 mL) was added TFA (0.3 mL). The mixture was stirred 16 h at RT. The reaction mixture was diluted with EtOAc, washed with aqueous NaHCO$_3$ solution and brine successively, dried over anhydrous Na$_2$SO$_4$, filtered and evaporated under reduced pressure to afford 37 mg of crude product, which was used in the next step without further purification.

Step 3: N-(cyclopentyl(5-fluoro-2-((4-(7-((2-oxo-2,3-dihydro-1H-benzo[d]imidazol-5-yl)methyl)-2,7-diazaspiro[4.4]nonan-2-yl)pyrimidin-5-yl)oxy)phenyl)methyl)-2-methylpropane-2-sulfinamide

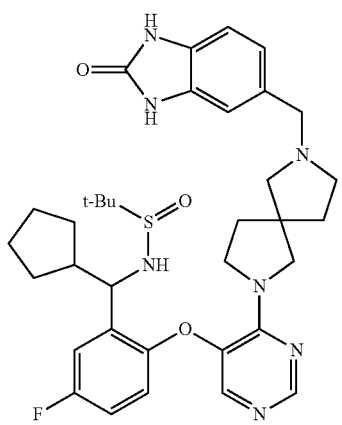 [SMILES: CC(C)(C)S(=O)NC(c1cc(F)ccc1Oc1cncnc1N1CCC2(CCN(Cc3ccc4[nH]c(=O)[nH]c4c3)C2)C1)C1CCCC1]

To a solution of N-((2-((4-(2,7-diazaspiro[4.4]nonan-2-yl)pyrimidin-5-yl)oxy)-5-fluorophenyl)(cyclopentyl)methyl)-2-methylpropane-2-sulfinamide (37 mg, 0.072 mmol) in MeOH (2 mL) was added 2-oxo-2,3-dihydro-1H-benzo[d]imidazole-5-carbaldehyde (Intermediate 40, 14 mg, 0.086 mmol) and NaBH$_3$CN (9 mg, 0.14 mmol). The suspension was stirred at RT for 24 h. Solvent was removed under reduced pressure. The residue was used for next step without further purification.

Step 4: 5-((7-(5-(2-(amino(cyclopentyl)methyl)-4-fluorophenoxy)pyrimidin-4-yl)-2,7-diazaspiro[4.4]nonan-2-yl)methyl)-1,3-dihydro-2H-benzo[d]imidazol-2-one Above crude product was dissolved in MeOH (1 mL) and 4 M HCl/dioxane (3 ml). The solution was stirred at RT for 30 min before solvents was removed under reduced pressure. The residue was purified by RP-HPLC method A to afford 5-((7-(5-(2-(amino(cyclopentyl)methyl)-4-fluorophenoxy)pyrimidin-4-yl)-2,7-diazaspiro[4.4]nonan-2-yl)methyl)-1,3-dihydro-2H-benzo[d]imidazol-2-one. LCMS method A: R$_t$=0.15 min, (M+H)$^+$=558.3. $^1$H NMR (CD$_3$OD) δ: 8.57 (s, 1H), 7.83 (m, 1H), 7.41 (m, 1H), 7.26-7.17 (m, 4H), 7.09 (d, J=7.6 Hz, 1H), 4.42 (m, 2H), 4.07 (m, 4H), 3.64-3.34 (m, 4H), 2.48 (m, 1H), 2.22-2.03 (m, 5H), 1.78-1.48 (m, 6H), 1.39 (d, J=6.4 Hz, 1H).

Example 8

5-((7-(5-(2-(cyclopentyl(dimethylamino)methyl)-4-fluorophenoxy)pyrimidin-4-yl)-2,7-diazaspiro[4.4]nonan-2-yl)methyl)-1,3-dihydro-2H-benzo[d]imidazol-2-one

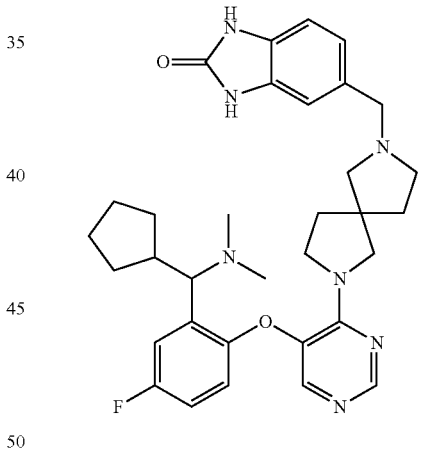

To a solution of 5-((7-(5-(2-(amino(cyclopentyl)methyl)-4-fluorophenoxy)pyrimidin-4-yl)-2,7-diazaspiro[4.4]nonan-2-yl)methyl)-1,3-dihydro-2H-benzo[d]imidazol-2-one tri-TFA salt (Example 7, 8.7 mg, 0.01 mmol) in DCM (2 mL) was added TEA (1 drop), paraformadehyde (4 mg), followed by NaBH$_3$(OAc)$_3$ (9 mg, 0.04 mmol). The mixture was stirred overnight at RT before the solvent was removed under reduced pressure. The residue was purified by RP-HPLC method A to afford the titled compound. LCMS method A: R$_t$=0.53 min, (M+H)$^+$=586.3. $^1$H NMR (CD$_3$OD) δ: δ: 8.57 (s, 1H), 7.83 (m, 1H), 7.61 (m, 1H), 7.36 (m, 1H), 7.26 (m, 1H), 7.21 (s, 1H), 7.18 (d, J=8.0 Hz, 1H), 7.09 (d, J=8.0 Hz, 1H), 4.43 (m, 2H), 4.14 (m, 2H), 3.62-3.45 (m, 3H), 2.84 (s, 6H), 2.20-2.06 (m, 5H), 1.76 (m, 2H), 1.62-1.47 (m, 4H), 0.99 (m, 1H).

Example 9

N-(cyclopentyl(5-fluoro-2-((4-(7-((2-oxo-2,3-di-hydro-1H-benzo[d]imidazol-5-yl)methyl)-2,7-diaz-aspiro[4.4]nonan-2-yl)pyrimidin-5-yl)oxy)phenyl)methyl)acetamide

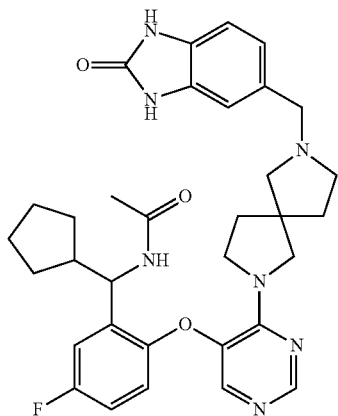 [SMILES: CC(=O)NC(c1cc(F)ccc1Oc1cncnc1N1CCC2(CCN(Cc3ccc4[nH]c(=O)[nH]c4c3)C2)C1)C1CCCC1]

The title product was synthesized by acylating the compound of Example 7 with acetic anhydride in pyridine. The final product was purified by RP-HPLC method A. LCMS method A: $R_t$=0.53 min, (M+H)$^+$=600.3.

Example 10

6-((7-(5-(4-fluoro-2-(1-hydroxy-2-methylpropyl)phenoxy)pyrimidin-4-yl)-2,7-diazaspiro[4.4]nonan-2-yl)methyl)-3,3-dimethylindolin-2-one

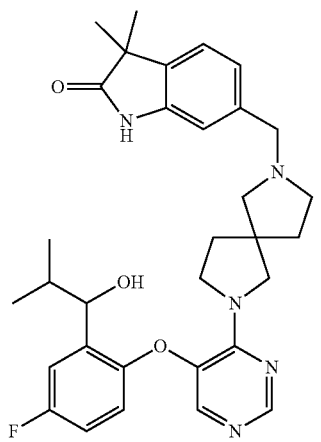 [SMILES: CC(C)C(O)c1cc(F)ccc1Oc1cncnc1N1CCC2(CCN(Cc3ccc4c(c3)NC(=O)C4(C)C)C2)C1]

Step 1: 1-(2-((4-(2,7-diazaspiro[4.4]nonan-2-yl)pyrimidin-5-yl)oxy)-5-fluorophenyl)-2-methylpropan-1-ol

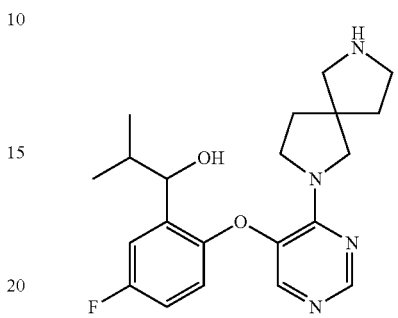

To a solution of tert-butyl 7-(5-(2-bromo-4-fluorophenoxy)pyrimidin-4-yl)-2,7-diazaspiro[4.4]nonane-2-carboxylate (Intermediate 11, 526 mg, 1.065 mmol) and N-methoxy-N-methylisobutyramide (268 mg, 2.04 mmol) in dry THF (6 mL) under $N_2$ atmosphere at −78° C. was added 1.6 M BuLi (0.7 mL, 1.067 mmol) dropwise. After the addition, the reaction mixture was stirred for another 10 min before quenched with aqueous $NH_4Cl$ solution. The resulting mixture was extracted with EtOAc, washed with $H_2O$, brine, dried over anhydrous $Na_2SO_4$ and filtered. The filtrate was concentrated to dryness. The residue was purified by flash chromatography to afford 249 mg of tert-butyl 7-(5-(4-fluoro-2-isobutyrylphenoxy)pyrimidin-4-yl)-2,7-diazaspiro[4.4]nonane-2-carboxylate (Intermediate 41b). LCMS Method B: $t_R$: 1.76 min, (M+H)$^+$=485.3

To a cold solution of Intermediate 41b (83 mg, 0.17 mmol) in THF/MeOH (2/0.5 mL) at 0° C. was added $NaBH_4$ (20 mg, 0.53 mmol). The mixture was stirred for another 20 min and quenched with acetone. The solvent was removed to give the crude product. The crude product was then dissolved in MeOH (1 mL) 4 M HCl/dioxane (0.5 mL) was added and the mixture was stirred for 30 min. The solvents were removed under reduced pressure to afford crude product as the bis-HCl salt.

Step 2: 6-((7-(5-(4-fluoro-2-(1-hydroxy-2-methylpropyl)phenoxy)pyrimidin-4-yl)-2,7-diazaspiro[4.4]nonan-2-yl)methyl)-3,3-dimethylindolin-2-one The crude product from Step 1 was dissolved in DCM (1 mL) containing TEA (0.1 mL). Solvent was then removed under reduced procedure. The resulting residue was dissolved in DCM (2 mL). To this solution was added Intermediate 45 (32 mg, 0.17 mmol) and NaBH(OAc)$_3$ (72 mg, 0.34 mmol) and the mixture was stirred for 30 min. The solvents were removed and the residue was purified by preparative HPLC method A to afford the titled compound as a TFA salt. LCMS method A: $R_t$=075 min, (M+H)$^+$=560.3.
$^1$H NMR (CD$_3$OD) δ: 8.53 (s, 1H), 7.58 (s, 1H), 7.36-7.10 (m, 6H), 4.53-3.78 (m, 11H), 2.22 (m, 4H), 1.96 (m, 1H), 1.34 (s, 6H), 1.00 (d, J=6.8 Hz, 3H), 0.84 (d, J=6.8 Hz, 3H).

Example 11

6-((7-(5-(4-fluoro-2-isobutyrylphenoxy)pyrimidin-4-yl)-2,7-diazaspiro[4.4]nonan-2-yl)methyl)-3-methyl-2-oxoindoline-3-carbonitrile

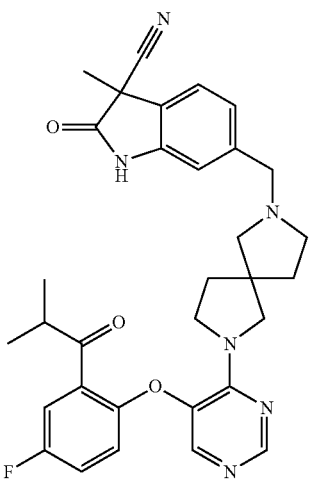 [SMILES: CC(C)C(=O)c1cc(F)ccc1Oc1cncnc1N1CCC2(CCN(Cc3ccc4c(c3)NC(=O)C4(C)C#N)C2)C1]

The title compound was synthesized from tert-butyl 7-(5-(4-fluoro-2-isobutyrylphenoxy)pyrimidin-4-yl)-2,7-diazaspiro[4.4]nonane-2-carboxylate (Intermediate 41b), by the method described for step 2 and 3 in the synthesis of Example 10. In step 3, 6-formyl-3-methyl-2-oxoindoline-3-carbonitrile was utilized. LCMS method A: $R_t$=0.57 min, $(M+H)^+$=569.3.

Example 12

5-fluoro-2-((4-(6-(3-(4-fluorophenyl)propanoyl)-2,6-diazaspiro[3.4]octan-2-yl)pyrimidin-5-yl)oxy)-N,N-diisopropylbenzamide

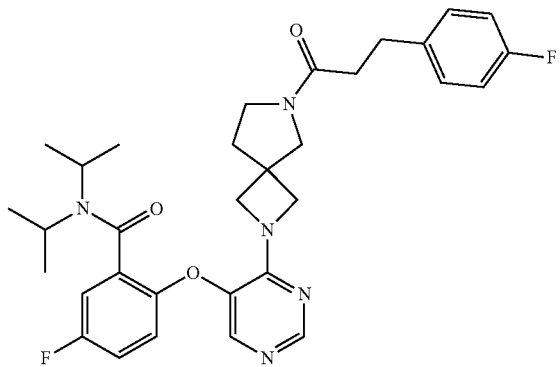 [SMILES: CC(C)N(C(=O)c1cc(F)ccc1Oc1cncnc1N1CC2(CCN(C(=O)CCc3ccc(F)cc3)C2)C1)C(C)C]

To a solution of Intermediate 41b (10 mg, 0.02 mmol), 3-(4-fluorophenyl)propanoic acid (10 mg, 0.06 mmol) and iPr₂NEt (0.02 mL, 0.11 mmol) in DMF (2 mL) was added HATU (12 mg, 0.03 mmol) at RT and the reaction mixture was stirred for 1 h at RT. EtOAc (5 mL) and H₂O (2 mL) were added for the workup. The EtOAc layer was dried using Na₂SO₄ and evaporated. The crude residue was purified by ISCO flash column chromatography (eluting with 10% MeOH in DCM) to afford 5-fluoro-2-((4-(6-(3-(4-fluorophenyl)propanoyl)-2,6-diazaspiro[3.4]octan-2-yl)pyrimidin-5-yl)oxy)-N,N-diisopropylbenzamide as the free base. LCMS Method G: $t_R$=6.728 min, MS (ESI) m/z 578.56 $[M+H]^+$. ¹H NMR (CD₃OD): δ 8.45 (s, 1H), 7.72 (s, 1H), 7.25-7.17 (m, 5H), 6.93 (t, J=8.4 Hz, 2H), 4.65-4.20 (m, 4H), 3.77-3.72 (m, 1H), 3.60-3.56 (m, 3H), 3.44-3.40 (m, 2H), 2.85 (t, J=7.6 Hz, 2H), 2.55 (t, J=7.6 Hz, 2H), 2.16-2.10 (m, 2H), 1.46 (d, J=6.4 Hz, 3H), 1.37)d, J=6.4 Hz, 3H), 1.15 (d, J=6.4 Hz, 3H), 1.03 (d, J=6.4 Hz, 3H).

Example 13

5-((7-(5-(4-fluoro-2-(1-isopropyl-1H-pyrazol-5-yl)phenoxy)pyrimidin-4-yl)-3-oxo-2,7-diazaspiro[4.4]nonan-2-yl)methyl)-1H-benzo[d]imidazol-2(3H)-one

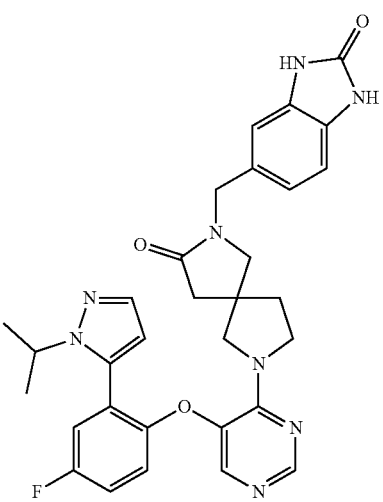 [SMILES: CC(C)n1nccc1-c1cc(F)ccc1Oc1cncnc1N1CCC2(CC(=O)N(Cc3ccc4[nH]c(=O)[nH]c4c3)C2)C1]

Step 1: 2, 7-diazaspiro[4.4]nonan-3-one

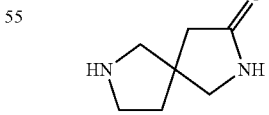

To solution of tert-butyl 8-oxo-2,7-diazaspiro[4.4]nonane-2-carboxylate (1 g, 4.2 mmol) in anhydrous CH₂Cl₂ (5 mL) was added HCl-dioxane (5 mL) and stirred at 16-34° C. for 1 h. The mixture was concentrated to afford 2,7-diazaspiro[4.4]nonan-3-one (HCl salt, crude) as white solid, which was used in next step directly. Yield: 900 mg (HCl salt).

Step 2: 7-(5-(2-bromo-4-fluorophenoxy)pyrimidin-4-yl)-2,7-diazaspiro[4.4]nonan-3-one

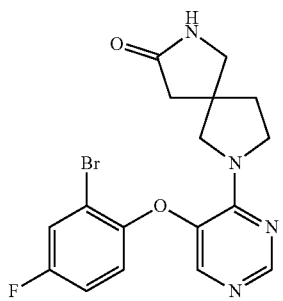 [SMILES: O=C1CC2(CCN(c3ncncc3Oc3ccc(F)cc3Br)C2)CN1]

To solution of 2,7-diazaspiro[4.4]nonan-3-one (900 mg, 4.1 mmol, HCl salt, crude) in $CH_3CN$ (20 mL) was added 5-(2-bromo-4-fluorophenoxy)-4-chloropyrimidine (Intermediate 1, 1.3 g, 4.05 mmol) and $K_2CO_3$ (1.1 g, 8.1 mmol). The mixture was stirred at 85° C. for 24 h. The mixture was filtered and the filtrate was concentrated to purify by ISCO column chromatography on silica gel (from 100% DCM to 5% MeOH in DCM) to give 7-(5-(2-bromo-4-fluorophenoxy)pyrimidin-4-yl)-2,7-diazaspiro[4.4]nonan-3-one as colorless oil. Yield: 1.2 g (73%); LCMS Method C: $R_t$=0.659 min. $(M+H)^+$=407.0, 409.0 (bromo isotopes).

Step 3: 7-(5-(4-fluoro-2-(1-isopropyl-1H-pyrazol-5-yl)phenoxy)pyrimidin-4-yl)-2,7-diaza spiro[4.4]nonan-3-one

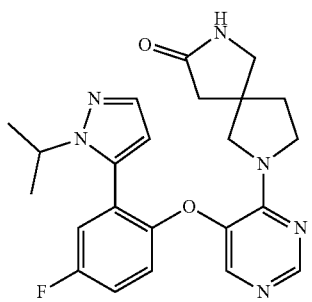 [SMILES: CC(C)n1nccc1-c1cc(F)ccc1Oc1cncnc1N1CCC2(CNC(=O)C2)C1]

To solution of 7-(5-(2-bromo-4-fluorophenoxy)pyrimidin-4-yl)-2,7-diazaspiro[4.4]nonan-3-one (850 mg, 2.09 mmmol) in dioxane:$H_2O$ (15 mL, 1:1) was added (1-isopropyl-1H-pyrazol-5-yl)boronic acid (385 mg, 2.51 mmol), Sphos Pallacycle-gen 2 (75 mg, 0.105 mmol) and $K_3PO_4$ (1.34 g, 6.27 mmol). The mixture was heated at 115° C. for 30 min in a microwave. The mixture was then concentrated and diluted with EtOAc (30 mL) and washed with brine (50 mL×2). The organic layers were concentrated and the residue was purified by ISCO column chromatography on silica gel (from 100% DCM to 10% MeOH in DCM) to afford a brown solid. This solid was purified by basic preparative RP-HPLC method D to afford 7-(5-(4-fluoro-2-(1-isopropyl-1H-pyrazol-5-yl)phenoxy)pyrimidin-4-yl)-2,7-diazaspiro[4.4]nonan-3-one as a white solid. Yield: 350 mg. LCMS Method C: $R_t$=0.629 min; $(M+H)^+$=437.2. $^1H$ NMR ($CDCl_3$): δ 8.40 (s, 1H), 7.82 (s, 1H), 7.57 (s, 1H), 7.05-7.15 (m, 2H), 6.81 (dd, J=9.2 4.4 Hz, 1H), 6.17 (d, J=2.0 Hz, 1H), 5.74 (s, 1H), 4.30-4.41 (m, 1H), 3.80-3.85 (m, 1H), 3.71 (d, J=11.2 Hz, 1H), 3.50-3.65 (m, 2H), 3.30-3.43 (m, 2H), 2.15-2.25 (m, 1H), 2.00-2.10 (m, 2H), 1.75-1.85 (m, 1H), 143 (d, J=6.8 Hz, 3H), 1.47 (d, J=6.8 Hz, 3H). $^{19}F$ NMR ($CDCl_3$): δ −119.08.

Step 4: 7-(5-(4-fluoro-2-(1-isopropyl-1H-pyrazol-5-yl) phenoxy)pyrimidin-4-yl)-2-(4-fluoro-3-nitrobenzyl)-2,7-diazaspiro[4.4]nonan-3-one

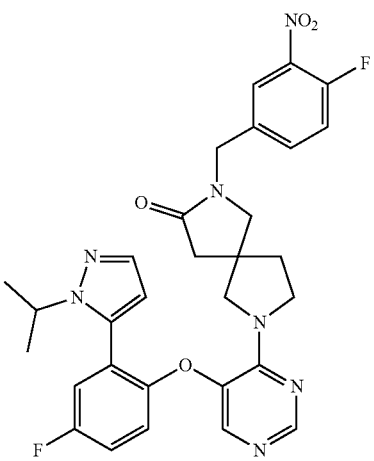 [SMILES: CC(C)n1nccc1-c1cc(F)ccc1Oc1cncnc1N1CCC2(CC(=O)N(Cc3ccc(F)c([N+](=O)[O-])c3)C2)C1]

To a solution of 7-(5-(4-fluoro-2-(1-isopropyl-1H-pyrazol-5-yl)phenoxy)pyrimidin-4-yl)-2,7-diazaspiro[4.4]nonan-3-one (50 mg, 0.11 mmmol) in anhydrous THF (3 mL) was added NaH (7 mg, 0.17 mmol) and n-$Bu_4I$ (4 mg, 0.01 mmol). Then 4-(bromomethyl)-1-fluoro-2-nitrobenzene (33 mg, 0.14 mmol, dissolved in 1 mL THF) was added dropwise into the mixture and the mixture was stirred at 0° C. for 30 min. Then the mixture was stirred at 16-25° C. for 2 h. The mixture was quenched with saturated $NH_4Cl$ (5 mL, aq.) and extracted with EtOAc (5 mL×2). The combined organic layers were dried over $Na_2SO_4$ and concentrated. The resulting residue was purified by acidic preparative RP-HPLC method A to give 7-(5-(4-fluoro-2-(1-isopropyl-1H-pyrazol-5-yl)phenoxy)pyrimidin-4-yl)-2-(4-fluoro-3-nitrobenzyl)-2,7-diazaspiro[4.4]nonan-3-one as the TFA salt as a white solid. Yield: 21 mg (32%); LCMS Method C: $R_t$=0.740 min; $(M+H)^+$=589.9. $^1H$ NMR (MeOD): δ 8.54 (s, 1H), 8.03 (d, J=6.8 Hz, 1H), 7.94 (s, 1H), 7.60-7.70 (m, 1H), 7.56 (s, 1H), 7.46 (t, J=9.2 Hz, 1H), 7.35-7.40 (m, 2H), 7.31 (d, J=8.8 Hz, 1H), 6.30 (s, 1H), 4.57 (s, 2H), 4.35-4.45 (m, 1H), 4.05-4.15 (m, 1H), 4.00-4.05 (m, 1H), 3.85-3.95 (m, 1H), 3.65-3.80 (m, 1H), 3.35-3.50 (m, 2H), 2.00-2.25 (m, 4H), 1.30-1.45 (m, 6H). $^{19}F$ NMR (MeOD): δ −77.21, −117.66, −122.07.

Step 5: 2-(4-amino-3-nitrobenzyl)-7-(5-(4-fluoro-2-(1-isopropyl-1H-pyrazol-5-yl)phenoxy)pyrimidin-4-yl)-2,7-diazaspiro[4.4]nonan-3-one

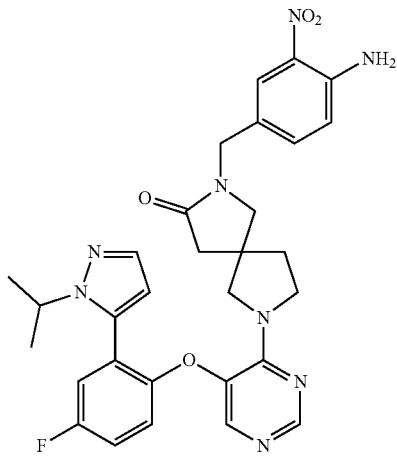 [SMILES: CC(C)n1nccc1-c1cc(F)ccc1Oc1cncnc1N1CCC2(CC(=O)N(Cc3ccc(N)c([N+](=O)[O-])c3)C2)C1]

To solution of 7-(5-(4-fluoro-2-(1-isopropyl-1H-pyrazol-5-yl)phenoxy)pyrimidin-4-yl)-2-(4-fluoro-3-nitrobenzyl)-2,7-diazaspiro[4.4]nonan-3-one (80 mg, 0.14 mmmol) in NH$_3$-MeOH (5 mL) was heated to 70° C. for 36 h in an autocalve. The mixture was then concentrated and purified by preparative TLC on silica gel (DCM:MeOH=10:1) to give 2-(4-amino-3-nitrobenzyl)-7-(5-(4-fluoro-2-(1-isopropyl-1H-pyrazol-5-yl)phenoxy)pyrimidin-4-yl)-2,7-diazaspiro[4.4]nonan-3-one as yellow solid. Yield: 65 mg (80%); LCMS method C: R$_t$=0.713 min; (M+H)$^+$=587.2. $^1$H NMR (MeOD): δ 8.29 (s, 1H), 7.96 (s, 1H), 7.83 (s, 1H), 7.51 (s, 1H), 7.22-7.30 (m, 2H), 7.19 (dd, J=8.0 2.8 Hz, 1H), 6.96-6.99 (m, 2H), 6.19 (s, 1H), 4.38-4.43 (m, 3H), 3.65-3.73 (m, 1H), 3.59-3.71 (m, 2H), 3.51 (d, J=12.0 Hz, 1H), 3.35 (s, 1H), 3.27-3.29 (m, 1H), 2.11-2.16 (m, 1H), 1.84-2.06 (m, 3H), 1.33-1.44 (m, 6H). $^{19}$F NMR (MeOD): δ −120.79.

Step 6: 2-(3,4-diaminobenzyl)-7-(5-(4-fluoro-2-(1-isopropyl-1H-pyrazol-5-yl)phenoxy)pyrimidin-4-yl)-2,7-diazaspiro[4.4]nonan-3-one

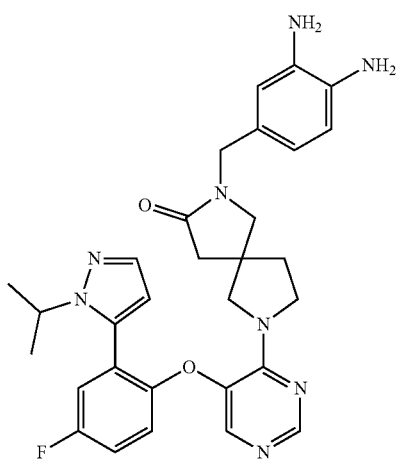 [SMILES: CC(C)n1nccc1-c1cc(F)ccc1Oc1cncnc1N1CCC2(CC(=O)N(Cc3ccc(N)c(N)c3)C2)C1]

To a solution of 2-(4-amino-3-nitrobenzyl)-7-(5-(4-fluoro-2-(1-isopropyl-1H-pyrazol-5-yl)phenoxy)pyrimidin-4-yl)-2,7-diazaspiro[4.4]nonan-3-one (50 mg, 0.85 mmol) in anhydrous EtOH (10 mL) was added Raney Ni (10 mg, wet) and stirred at 17-26° C. for 18 h under H$_2$ (15 psi). The mixture was filtered and the filtrate was concentrated. The residue was purified by preparative TLC on silica gel (DCM:MeOH=10:1) to give 2-(3,4-diaminobenzyl)-7-(5-(4-fluoro-2-(1-isopropyl-1H-pyrazol-5-yl)phenoxy)pyrimidin-4-yl)-2,7-diazaspiro[4.4]nonan-3-one as a white solid. Yield: 20 mg (42%); LCMS method C: R$_t$=0.624 min. (M+H)$^+$=557.3.

Step 7: 5-((7-(5-(4-fluoro-2-(1-isopropyl-1H-pyrazol-5-yl)phenoxy)pyrimidin-4-yl)-3-oxo-2,7-diazaspiro[4.4]nonan-2-yl)methyl)-1H-benzo[d]imidazol-2(3H)-one To solution of 2-(3,4-diaminobenzyl)-7-(5-(4-fluoro-2-(1-isopropyl-1H-pyrazol-5-yl)phenoxy)pyrimidin-4-yl)-2,7-diazaspiro[4.4]nonan-3-one (13 mg, 0.023 mmol) in anhydrous THF (5 mL) was added Et$_3$N (10 μL) and bis(trichlormethyl)carbonate (7 mg, 0.023 mmol) and the resulting mixture was stirred at 18-26° C. for 16 h. TLC (DCM:MeOH==10:1, R$_f$=0.7) showed a new spot and 2-(3,4-diaminobenzyl)-7-(5-(4-fluoro-2-(1-isopropyl-1H-pyrazol-5-yl)phenoxy)pyrimidin-4-yl)-2,7-diazaspiro[4.4]nonan-3-one was not consumed completely. The mixture was poured into water (5 mL) and extracted with EA (10 mL×2). The combined organic layers were washed with brine (30 mL×2), dried over Na$_2$SO$_4$ and concentrated to purify by basic preparative RP-HPLC method D to give 5-((7-(5-(4-fluoro-2-(1-isopropyl-1H-pyrazol-5-yl)phenoxy)pyrimidin-4-yl)-3-oxo-2,7-diazaspiro[4.4]nonan-2-yl)methyl)-1H-benzo[d]imidazol-2(3H)-one as a white solid. Yield: 2.9 mg (22%); LCMS method C: R$_t$=: 1.596 min, (M+H)$^+$=583.2. $^1$H NMR (MeOD): δ 8.30 (s, 1H), 7.83 (s, 1H), 7.48 (s, 1H), 7.25-7.35 (m, 1H), 7.21 (d, J=8.4 Hz, 1H), 7.00-7.05 (m, 1H), 6.95-7.00 (m, 3H), 6.16 (s, 1H), 4.35-4.55 (m, 3H), 3.80-3.90 (m, 1H), 3.55-3.70 (m, 2H), 3.45-3.55 (m, 1H), 3.20-3.30 (m, 2H), 1.85-2.20 (m, 4H), 1.35-1.45 (m, 6H). $^{19}$F NMR (MeOD): δ −120.78.

Examples 14A-14B

N-(4-fluoro-2-(5-isopropyl-3-methylisoxazol-4-yl)phenyl)-4-(6-((tetrahydro-2H-pyran-4-yl)methyl)-2,6-diazaspiro[3.3]heptan-2-yl)pyrimidin-5-amine (Example 14A) & 4-(5-fluoro-2-((4-(6-((tetrahydro-2H-pyran-4-yl)methyl)-2,6-diazaspiro[3.3]heptan-2-yl)pyrimidin-5-yl)oxy)phenyl)-5-isopropyl-3-methylisoxazole (Example 14B)

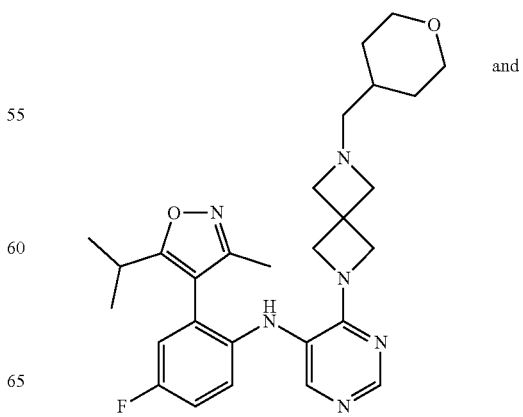

-continued

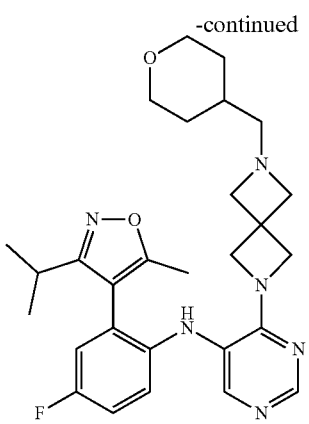

Step 1. 5-isopropyl-3-methylisoxazole and 3-isopropyl-5-methylisoxazole

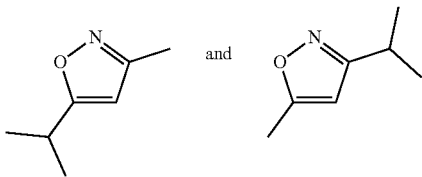

A suspension of 5-methylhexane-2,4-dione (300 mg, 2.34 mmol) and hydroxylamine HCl (194 mg, 2.82 mmol) in EtOH was heated for 3 min in a microwave at 130° C. The EtOH was evaporated and crude product was partitioned between Et$_2$O (5 mL) and water (3 mL). The Et$_2$O layer was dried using MgSO$_4$ and subsequently evaporated to give the crude product as a 4:1 mixture of isoxazole regioisomers. The major isomer was assigned as 5-isopropyl-3-methylisoxazole and the minor as 3-isopropyl-5-methylisoxazole. This crude mixture was used directly for the next step without further purification. LCMS method A: t$_R$=1.485; [M+H]$^+$=126.28.

Step 2. 4-bromo-5-isopropyl-3-methylisoxazole and 4-bromo-3-isopropyl-5-methylisoxazole

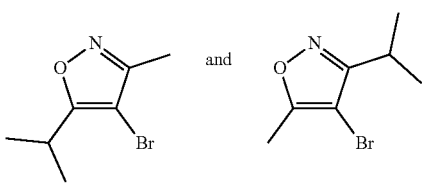

To a solution of crude 5-isopropyl-3-methylisoxazole (4:1 crude mixture from Step 1, 2.34 mmol) in DMF (3 mL) was added N-bromosuccinimide (625 mg, 3.51 mmol) at RT and the reaction mixture was stirred for 15 h at RT. EtOAc (10 mL) and H$_2$O (10 mL) were then added for the workup. The EtOAc layer was separated and washed with a saturated Na$_2$S$_2$O$_5$ aqueous solution followed by brine. The EtOAc layer was then dried using Na$_2$SO$_4$ and evaporated. The crude product was purified by ISCO flash column chromatography (eluting with 20% EtOAc in hexanes) to afford 200 mg (42% over 2 steps) of product as a 4:1 mixture of regioisomers. The major isomer was assigned as 4-bromo-5-isopropyl-3-methylisoxazole and the minor isomer as 4-bromo-3-isopropyl-5-methylisoxazole. LCMS method A: t$_R$=1.787; [M]$^+$=204.25 and 206.26. $^1$H NMR (CDCl$_3$): major isoxazole regioisomer (4-bromo-5-isopropyl-3-methylisoxazole) δ 3.21-3.14 (m, 1H), 2.26 (s, 3H), 1.32 (d, J=7.2 Hz, 6H).

Step 3. 5-isopropyl-3-methyl-4-(4,4,5,5-tetramethyl-1,3,2-dioxaborolan-2-yl)isoxazole and 3-isopropyl-5-methyl-4-(4,4,5,5-tetramethyl-1,3,2-dioxaborolan-2-yl)isoxazole

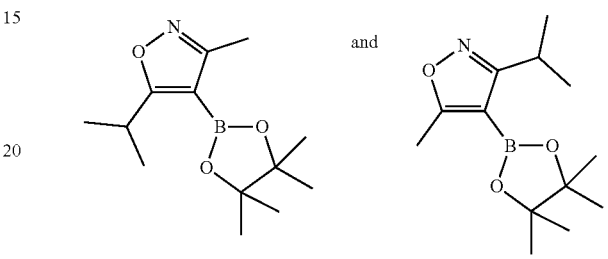

A mixture of 4-bromo-5-isopropyl-3-methylisoxazole (4:1 mixture of regioisomers from Step 2, 100 mg, 0.49 mmol), pinacol borane (0.11 mL, 0.78 mmol), PdCl$_2$(MeCN)$_2$ (3 mg, 2 mol %), SPhos ligand (10 mg, 5 mol %) and Et$_3$N (0.24 mL, 1.72 mmol) in dioxane (2 mL) was heated at 100° C. in a sealed vial under a blanket of N$_2$ for 1 h. The reaction mixture was cooled to RT, filtered through a plug of celite and evaporated. The crude residue was purified using ISCO flash column chromatography (eluting with 20% EtOAc in hexanes) to afford 100 mg of 5-isopropyl-3-methyl-4-(4,4,5,5-tetramethyl-1,3,2-dioxaborolan-2-yl)isoxazole and 3-isopropyl-5-methyl-4-(4,4,5,5-tetramethyl-1,3,2-dioxaborolan-2-yl)isoxazole as a 4:1 mixture of regioisomers and used in the next step without further purification.

Step 4. tert-butyl 6-(5-bromopyrimidin-4-yl)-2,6-diazaspiro[3.3]heptane-2-carboxylate

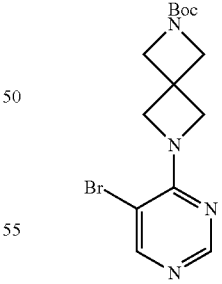

A suspension of 5-bromo-4-chloropyrimidine (1.67 g, 8.65 mmol), tert-butyl 2,6-diazaspiro[3.3]heptane-2-carboxylate hemioxalate salt (2 g, 4.12 mmol) and iPr$_2$NEt (1.80 mL, 10.3 mmol) in $^i$PrOH (10 mL) was heated at reflux for 15 h. Saturated NH$_4$Cl aqueous solution (10 mL) and EtOAc (20 mL) were added to the reaction for the workup. The EtOAc layer was separated and the aqueous layer was extracted again with EtOAc. The EtOAc layers were combined, washed with water, then brine, and dried using Na₂SO₄. Evaporation of the EtOAc gave tert-butyl 6-(5-bromopyrimidin-4-yl)-2,6-diazaspiro[3.3]heptane-2-carboxylate as an off-white foamy solid (2 grams, 70%) that was nearly pure by LCMS analysis and used directly for the next step without further purification. LCMS method A: $t_R$=1.330 min; [M+H]$^{30}$=355.41 and 357.

Step 5. tert-butyl 6-(5-((2-chloro-4-fluorophenyl)amino)pyrimidin-4-yl)-2,6-diazaspiro[3.3]heptane-2-carboxylate

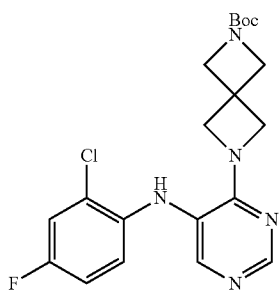 [SMILES: CC(C)(C)OC(=O)N1CC2(C1)CN(c1ncncc1Nc1ccc(F)cc1Cl)C2]

A mixture of tert-butyl 6-(5-bromopyrimidin-4-yl)-2,6-diazaspiro[3.3]heptane-2-carboxylate (100 mg, 0.28 mmol), 2-chloro-4-fluoroaniline (39 mg, 0.27 mmol), Pd₂(dba)₃ (5 mg, 0.005 mmol), Xphos (11 mg, 0.023 mmol) and NaOtBu (60 mg, 0.63 mmol) in toluene (2 mL) was heated in a CEM microwave at 160° C. for 30 min. Upon cooling, the reaction was diluted with 5 mL of EtOAc and filtered through a plug of celite. Evaporation of the solvents gave a crude solid which was triturated overnight using hexanes. Filtration of the solid material afforded 92 mg (79%) of tert-butyl 6-(5-((2-chloro-4-fluorophenyl)amino)pyrimidin-4-yl)-2,6-diazaspiro[3.3]heptane-2-carboxylate which was nearly pure by LCMS analysis and used directly in the next step without further purification. LCMS method A: $t_R$=1.411; [M+H]$^+$=420.54 and 422.55.

Step 6. tert-butyl 6-(5-((4-fluoro-2-(5-isopropyl-3-methylisoxazol-4-yl)phenyl)amino)pyrimidin-4-yl)-2,6-diazaspiro[3.3]heptane-2-carboxylate and tert-butyl 6-(5-((4-fluoro-2-(3-isopropyl-5-methylisoxazol-4-yl)phenyl)amino)pyrimidin-4-yl)-2,6-diazaspiro[3.3]heptane-2-carboxylate

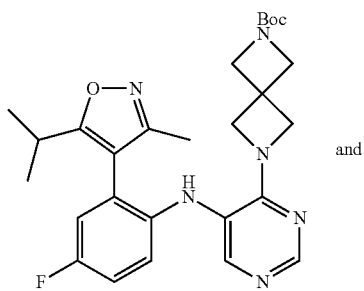 and

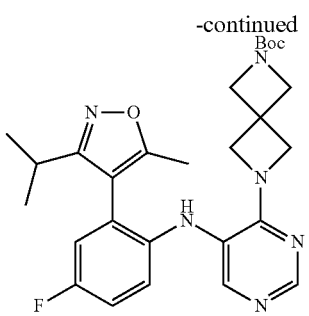

A mixture of tert-butyl 6-(5-((2-chloro-4-fluorophenyl)amino)pyrimidin-4-yl)-2,6-diazaspiro[3.3]heptane-2-carboxylate (35 mg, 0.083 mmol) and 5-isopropyl-3-methyl-4-(4,4,5,5-tetramethyl-1,3,2-dioxaborolan-2-yl)isoxazole and 3-isopropyl-5-methyl-4-(4,4,5,5-tetramethyl-1,3,2-dioxaborolan-2-yl)isoxazole as a 4:1 mixture of isomers (Step 3, 21 mg, 0.083 mmol), K₃PO₄ (53 mg, 0.25 mmol) and SPhos-palladacycle (CAS#:1375325-64-6, 3 mg, 0.004 mmol) in dioxane/H₂O (1 mL/0.40 mL) was heated to 120° C. for 15 min in a CEM microwave. Upon cooling, the reaction mixture was filtered through celite and evaporated. Purification by ISCO flash column chromatography (eluting with 100% EtOAc) gave tert-butyl 6-(5-((4-fluoro-2-(5-isopropyl-3-methylisoxazol-4-yl)phenyl)amino)pyrimidin-4-yl)-2,6-diazaspiro[3.3]heptane-2-carboxylate as the major isoxazole isomer (4:1 mixture) from the isomeric mixture of starting materials. This isomeric mixture of products was used directly for the next step without further purification. LCMS method A: $t_R$=1.367; [M+H]$^+$=509.70.

Step 7. N-(4-fluoro-2-(5-isopropyl-3-methylisoxazol-4-yl)phenyl)-4-(2,6-diazaspiro[3.3]heptan-2-yl)pyrimidin-5-amine and N-(4-fluoro-2-(3-isopropyl-5-methylisoxazol-4-yl)phenyl)-4-(2,6-diazaspiro[3.3]heptan-2-yl)pyrimidin-5-amine

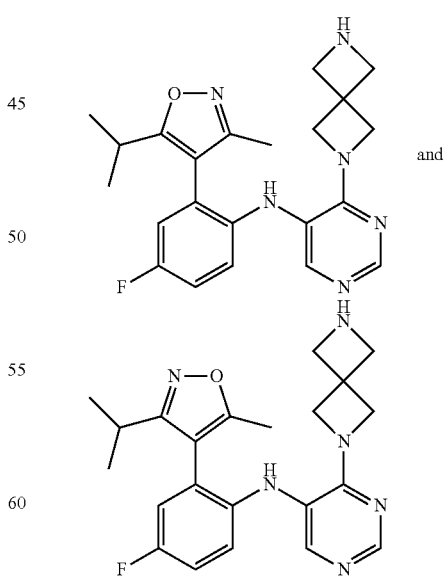

To a solution of tert-butyl 6-(5-((4-fluoro-2-(5-isopropyl-3-methylisoxazol-4-yl)phenyl)amino)pyrimidin-4-yl)-2,6-diazaspiro[3.3]heptane-2-carboxylate and tert-butyl 6-(5-

((4-fluoro-2-(3-isopropyl-5-methylisoxazol-4-yl)phenyl)amino)pyrimidin-4-yl)-2,6-diazaspiro[3.3]heptane-2-carboxylate (4:1 mixture of isoxazole regioisomers from Step 6, 40 mg, 0.079 mmol) in DCM (3 mL) was added TFA (1 mL) at RT. The reaction stirred for 1 h at RT and the solvents were then removed. DCM (2 mL) and Et₃N (0.05 mL) were added to form the free base amine from the TFA salt. Evaporation of the solvents and drying under high vacuum gave N-(4-fluoro-2-(5-isopropyl-3-methylisoxazol-4-yl)phenyl)-4-(2,6-diazaspiro[3.3]heptan-2-yl)pyrimidin-5-amine and N-(4-fluoro-2-(3-isopropyl-5-methylisoxazol-4-yl)phenyl)-4-(2,6-diazaspiro[3.3]heptan-2-yl)pyrimidin-5-amine as the free base (4:1 mixture of isoxazole regioisomers). This material was used directly for the next step without further purification.

Step 8. N-(4-fluoro-2-(5-isopropyl-3-methylisoxazol-4-yl)phenyl)-4-(6-((tetrahydro-2H-pyran-4-yl)methyl)-2,6-diazaspiro[3.3]heptan-2-yl)pyrimidin-5-amine and N-(4-fluoro-2-(3-isopropyl-5-methylisoxazol-4-yl)phenyl)-4-(6-((tetrahydro-2H-pyran-4-yl)methyl)-2,6-diazaspiro[3.3]heptan-2-yl)pyrimidin-5-amine To a solution of crude N-(4-fluoro-2-(5-isopropyl-3-methylisoxazol-4-yl)phenyl)-4-(2,6-diazaspiro[3.3]heptan-2-yl)pyrimidin-5-amine and N-(4-fluoro-2-(3-isopropyl-5-methylisoxazol-4-yl)phenyl)-4-(6-((tetrahydro-2H-pyran-4-yl)methyl)-2,6-diazaspiro[3.3]heptan-2-yl)pyrimidin-5-amine (4:1 mixture of isoxazole regioisomers from Step 7, 0.079 mmol) and tetrahydro-2H-pyran-4-carbaldehyde (27 mg, 0.24 mmol) in dichloroethane (2 mL, containing 1% AcOH) was added NaBH(OAc)₃ (50 mg, 0.24 mmol) at RT. The reaction mixture was stirred for 30 min and was complete by LCMS analysis. Evaporation of the solvent followed by purification using HPLC method A afforded N-(4-fluoro-2-(5-isopropyl-3-methylisoxazol-4-yl)phenyl)-4-(6-((tetrahydro-2H-pyran-4-yl)methyl)-2,6-diazaspiro[3.3]heptan-2-yl)pyrimidin-5-amine TFA salt and N-(4-fluoro-2-(3-isopropyl-5-methylisoxazol-4-yl)phenyl)-4-(6-((tetrahydro-2H-pyran-4-yl)methyl)-2,6-diazaspiro[3.3]heptan-2-yl)pyrimidin-5-amine TFA salt as a 4:1 mixture of isoxazole regioisomers (15 mg). LCMS method B: $t_R$=1.124; [M+H]⁺=507.70.

Example 14A: Major Isoxazole Regioisomer

LCMS method B: $t_R$=1.013; [M+H]⁺=507.70 ¹H NMR (CD₃OD). δ 8.55 (bs, 1H), 7.79 (bs, 1H), 7.17-7.12 (m, 1H), 7.00 (dd, J=3.2, 8.8 Hz, 1H), 6.83 (dd, J=5.2, 9.2 Hz, 1H), 4.60-4.35 (m, 8H), 3.93 (dd, J=4.0, 11.6 Hz, 2H), 3.40 (t, J=11.6 Hz, 2H), 3.11 (d, J=7.2 Hz, 2H), 3.07-3.00 (m, 1H), 2.17 (s, 3H), 1.93-1.87 (m, 1H), 1.60 (d, J=11.6 Hz, 2H), 1.37-1.20 (m, 1H), 1.27 (d, J=6.4 Hz, 3H), 1.26 (d, J=6.4 Hz, 3H), 1.21-1.16 (1H, m).

Example 14B: Minor Isoxazole Regioisomer

LCMS method B $t_R$=1.124; [M+H]⁺=507.70.

Example 15

N-(5-fluoro-2'-isopropyl-[1,1'-biphenyl]-2-yl)-4-(6-((tetrahydro-2H-pyran-4-yl)methyl)-2,6-diazaspiro[3.3]heptan-2-yl)pyrimidin-5-amine

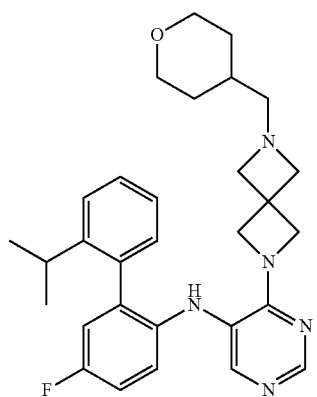 [SMILES: CC(C)c1ccccc1-c1cc(F)ccc1Nc1cncnc1N1CC2(CN(CC3CCOCC3)C2)C1]

The title product was synthesized by the method described in Examples 14A-14B. In Step 3, 2-isopropyl phenyl boronic acid was used. LCMS Method G: $R_t$=4.88 min; M+H⁺=502.85. ¹H NMR (d4-MeOH) 8.45 (s, 1H), 7.72, (s, 1H), 7.47 (d, 1H), 7.42 (m, 1H), 7.28 (m, 1H), 7.20 (d, 1H), 7.07 (m, 1H), 6.92 (m, 1H), 6.81 (m, 1H), 4.32-4.56 (m, 8H), 3.94 (m, 2H), 3.39 (m, 2H), 3.11 (d, 2H), 2.82 (m, 2H), 1.86 (m, 1H), 1.59 (d, 2H), 1.33 (m, 2H), 1.20 (d, 3H), 1.13 (d, 3H) ppm.

Example 16

5-fluoro-2-((4-(2-(2-hydroxy-2-methylpropyl)-2,7-diazaspiro[3.5]nonan-7-yl)pyrimidin-5-yl)amino)-N,N-diisopropylbenzamide

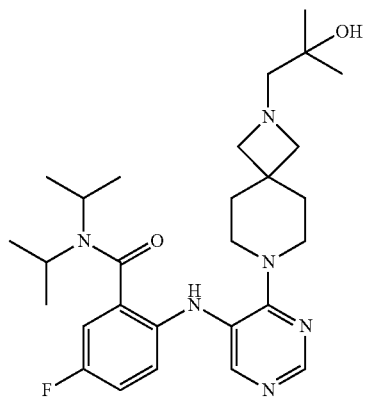 [SMILES: CC(C)N(C(=O)c1cc(F)ccc1Nc1cncnc1N1CCC2(CC1)CN(CC(C)(C)O)C2)C(C)C]

Step 1. 2-((4-(2-(tert-butoxycarbonyl)-2,7-diazaspiro[3.5]nonan-7-yl)pyrimidin-5-yl)amino)-5-fluorobenzoic Acid

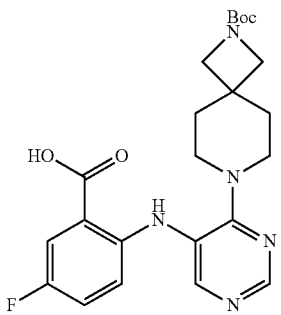 [SMILES: CC(C)(C)OC(=O)N1CC2(CCN(c3ncncc3Nc3ccc(F)cc3C(=O)O)CC2)C1]

To a round bottom flask was added tert-butyl 7-(5-iodopyrimidin-4-yl)-2,7-diazaspiro[3.5]nonane-2-carboxylate (Example 71, Step 1, 500 mg, 1 eq.), 2-amino-5-fluorobenzoic acid (216 mg, 1.2 eq), Pd$_2$(dba)$_3$ (21 mg, 0.02 eq.), Xantphos (54 mg, 0.08 eq.) and Cs$_2$CO$_3$ (1.33 g, 3.5 eq.). To this solid mixture was added dioxane (8 mL, 0.15 M with respect to tert-butyl 7-(5-iodopyrimidin-4-yl)-2,7-diazaspiro[3.5]nonane-2-carboxylate). The heterogenous solution was purged with a nitrogen stream for 1 min The flask was capped and the reaction was heated overnight at 100° C. The Cs$_2$CO$_3$ was then filtered off and the filtrate was diluted with EtOAc and 0.5 M HCl was added. The resulting while solid was filtered and dried over vacuum. Yield: 400 mg.

Step 2. tert-butyl 7-(5-((2-(diisopropylcarbamoyl)-4-fluorophenyl)amino)pyrimidin-4-yl)-2,7-diazaspiro[3.5]nonane-2-carboxylate

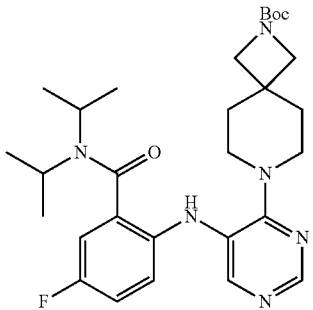 [SMILES: CC(C)N(C(=O)c1cc(F)ccc1Nc1cncnc1N1CCC2(CC1)CN(C(=O)OC(C)(C)C)C2)C(C)C]

To a round bottom flask were added 2-((4-(2-(tert-butoxycarbonyl)-2,7-diazaspiro[3.5]nonan-7-yl)pyrimidin-5-yl)amino)-5-fluorobenzoic acid (500 mg) and HOBt (184 mg). To this solid mixture was added DMF (3.65 mL), diisopropylamine (1 mL) and diisopropylethylamine (209 µL), followed by BOP reagent (532 mg, 1.1 eq.) and the mixture was stirred overnight. The mixture was then partitioned between EtOAc and water. The phases were separated and the aqueous phase was back-extracted with EtOAc twice. The combined organic phases were dried over magnesium sulfate and concentrated. The crude material was purified by flash chromatography (40 g SiO$_2$, MeOH/DCM as the eluents) yielding tert-butyl 7-(5-((2-(diisopropylcarbamoyl)-4-fluorophenyl)amino)pyrimidin-4-yl)-2,7-diazaspiro[3.5]nonane-2-carboxylate (300 mg).

Step 3. 5-fluoro-2-((4-(2-(2-hydroxy-2-methylpropyl)-2,7-diazaspiro[3.5]nonan-7-yl)pyrimidin-5-yl)amino)-N,N-diisopropylbenzamide To a round bottom flask was added tert-butyl 7-(5-((2-(diisopropylcarbamoyl)-4-fluorophenyl)amino)pyrimidin-4-yl)-2,7-diazaspiro[3.5]nonane-2-carboxylate (300 mg), DCM (5 mL), and TFA (5 mL) and the reaction mixture was stirred for 30 min at RT. The volatiles were then removed under vacuum. The crude residue was co-evaporated with DCM twice yielding 2-((4-(2,7-diazaspiro[3.5]nonan-7-yl)pyrimidin-5-yl)amino)-5-fluoro-N,N-diisopropylbenzamide bis-TFA salt. To a round bottom flask was added the bis-TFA salt (20 mg), 2,2-dimethyloxirane (11 mg), triethylamine (21 µL) and THF: ethanol (2 mL, 1:1 ratio). The flask was capped and the mixture was heated at 65° C. overnight. When the reaction was complete, the volatiles were removed under vacuum. The crude material was purified by RP-HPLC method A yielding 5-fluoro-2-((4-(2-(2-hydroxy-2-methylpropyl)-2,7-diazaspiro[3.5]nonan-7-yl)pyrimidin-5-yl)amino)-N,N-diisopropylbenzamide (3.7 mg). LCMS method G R$_t$=3.65 min; (M+H)$^+$=513.61. $^1$H NMR (d4-MeOH) 8.52 (s, 1H), 7.87 (s, 1H), 7.07-7.15 (m, 2H), 6.93 (m, 1H), 4.23 (d, 2H), 4.04 (d, 2H), 3.82-3.89 (m, 6H), 1.93-1.99 (m, 4H), 1.26-1.34 (m, 18H).

Example 17

5-((7-(5-(2-(dimethylphosphoryl)-4-fluorophenoxy)pyrimidin-4-yl)-2,7-diazaspiro[4.4]nonan-2-yl)methyl)-1H-benzo[d]imidazol-2(3H)-one

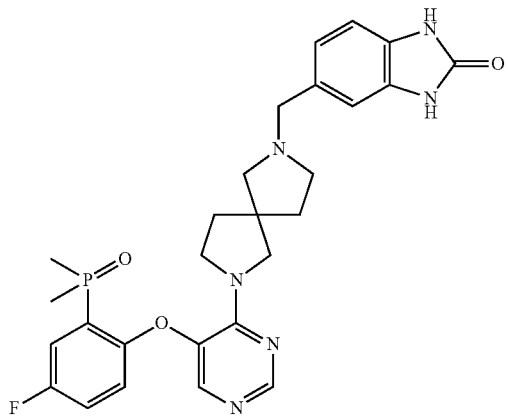 [SMILES: CP(C)(=O)c1cc(F)ccc1Oc1cncnc1N1CCC2(CCN(Cc3ccc4[nH]c(=O)[nH]c4c3)C2)C1]

Step 1. tert-Butyl 7-(5-(2-(dimethylphosphoryl)-4-fluorophenoxy)pyrimidin-4-yl)-2,7-diazaspiro[4.4]nonane-2-carboxylate

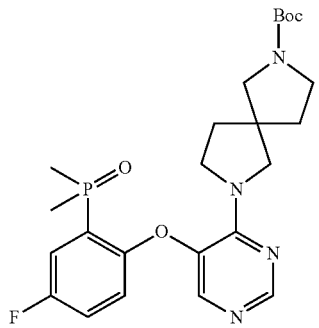 [SMILES: CC(C)(C)OC(=O)N1CCC2(CCN(c3ncncc3Oc3ccc(F)cc3P(C)(C)=O)C2)C1]

To a mixture of tert-butyl 7-(5-(2-bromo-4-fluorophenoxy)pyrimidin-4-yl)-2,7-diazaspiro[4.4]nonane-2-carboxylate (Intermediate 11, 200 mg, 0.41 mmol), (CH₃)₂PO (35 mg, 0.45 mmol), K₃PO₄ (104 mg, 0.49 mmol) in anhydrous DMF (3 mL) was added Pd(OAc)₂ (1.0 mg, 0.004 mmol) and Xantphos (4.0 mg, 0.006 mmol) and the reaction was stirred at 150° C. under a microwave for 30 min. The reaction was filtered through a Celite pad and concentrated under reduced pressure to afford the residue which was purified by column chromatography on silica gel (eluting with dichloromethane:methanol=1:0~10:1) to afford tert-butyl 7-(5-(2-(dimethylphosphoryl)-4-fluorophenoxy)pyrimidin-4-yl)-2,7-diazaspiro[4.4]nonane-2-carboxylate as light yellow oil. Yield: 120 mg. LCMS method E: $R_t$=0.836 min. (M+H)⁺=491.2.

Steps 2-3. 5-((7-(5-(2-(dimethylphosphoryl)-4-fluorophenoxy)pyrimidin-4-yl)-2,7-diazaspiro[4.4]nonan-2-yl)methyl)-1H-benzo[d]imidazol-2(3H)-one Steps 2-3 were performed according to the procedures of Steps 4-5 of Example 1. LCMS method E: $R_t$=1.344 min; (M+H)⁺=537.2. ¹H NMR (CD₃OD): δ 8.34 (s, 1H), 7.89 (s, 1H), 7.61 (m, 1H), 7.22-7.60 (m, 1H), 6.96-7.00 (m, 3H), 6.73-6.77 (m, 1H), 3.59 (s, 6H), 2.43-2.67 (m, 4H), 1.90 (d, J=14 Hz, 8H), 1.78 (t, J=6.4 Hz, 2H). ¹⁹F NMR (CD₃OD): δ −120.92.

Example 18

2-(5-(4-fluoro-2-(4-isopropylpyrimidin-5-yl)phenoxy)pyrimidin-4-yl)-N-(4-fluorobenzyl)-5-oxa-2-azaspiro[3.4]octan-7-amine

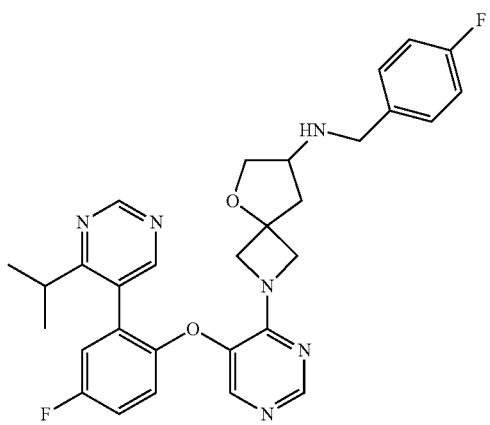 [SMILES: CC(C)c1ncncc1-c1cc(F)ccc1Oc1cncnc1N1CC2(CC(NCc3ccc(F)cc3)CO2)C1]

Step 1. 5-oxa-2-azaspiro[3.4]octan-7-one trifluoroacetate

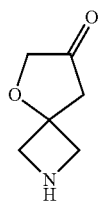

To a solution of tert-butyl 7-oxo-5-oxa-2-azaspiro[3.4]octane-2-carboxylate (300 mg, 1.32 mmol) in DCM (3 mL) was added TFA (1 mL) at RT and the reaction mixture was stirred for 1 h at RT. The solvents were removed to afford 5-oxa-2-azaspiro[3.4]octan-7-one TFA salt which was used directly for the next step without further purification. LCMS Method A: $t_R$=0.269 min; [M+H]⁺=128.28.

Step 2. 2-(5-(2-bromo-4-fluorophenoxy)pyrimidin-4-yl)-5-oxa-2-azaspiro[3.4]octan-7-one

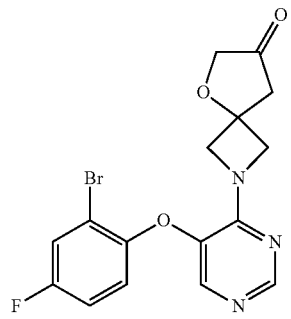 [SMILES: O=C1COC2(C1)CN(c1ncncc1Oc1ccc(F)cc1Br)C2]

A mixture of 5-oxa-2-azaspiro[3.4]octan-7-one TFA salt (168 mg, 1.32 mmol), 5-(2-bromo-4-fluorophenoxy)-4-chloropyrimidine (Intermediate 1, 481 mg, 1.58 mmol) and iPr₂NEt (0.92 mL, 5.28 mmol) in ⁱPrOH (3 mL) was heated at 100° C. for 12 h. Purification using ISCO flash column chromatography (eluting with 10% MeOH in DCM) gave 406 mg of 2-(5-(2-bromo-4-fluorophenoxy)pyrimidin-4-yl)-5-oxa-2-azaspiro[3.4]octan-7-one. LCMS Method A: $t_R$=0.961 min; [M+H]⁺=394.35 and 396.37.

Step 3. 2-(5-(4-fluoro-2-(4-isopropylpyrimidin-5-yl)phenoxy)pyrimidin-4-yl)-5-oxa-2-azaspiro[3.4]octan-7-one

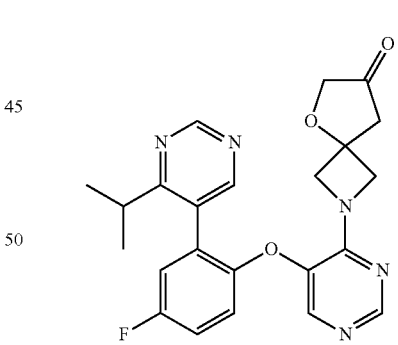

A mixture of 2-(5-(2-bromo-4-fluorophenoxy)pyrimidin-4-yl)-5-oxa-2-azaspiro[3.4]octan-7-one (147 mg, 0.37 mmol), (4-isopropylpyrimidin-5-yl)boronic acid (93 mg, 0.56 mmol), PdCl₂(PPh₃)₂ (26 mg, 0.037 mmol) and K₃PO₄ (237 mg, 1.12 mmol) in dioxane (2.5 mL) and water (0.25 mL) was heated at 120° C. in a CEM microwave for 2 h. The mixture was filtered through celite and evaporated. Purification using ISCO flash column chromatography (eluting with 10% MeOH in DCM) gave 151 mg of 2-(5-(4-fluoro-2-(4-isopropylpyrimidin-5-yl)phenoxy)pyrimidin-4-yl)-5-oxa-2-azaspiro[3.4]octan-7-one. LCMS Method A: $t_R$=0.926 min; [M+H]⁺=436.48.

Step 4. 2-(5-(4-fluoro-2-(4-isopropylpyrimidin-5-yl)phenoxy)pyrimidin-4-yl)-N-(4-fluorobenzyl)-5-oxa-2-azaspiro[3.4]octan-7-amine To a solution of 2-(5-(4-fluoro-2-(4-isopropylpyrimidin-5-yl)phenoxy)pyrimidin-4-yl)-5-oxa-2-azaspiro[3.4]octan-7-one (14 mg, 0.03 mmol) and (4-fluorophenyl)methanamine (0.006 mL, 0.047 mmol) in MeOH (2 mL) was added NaBH₃CN (8 mg, 0.12 mmol) and the reaction mixture was stirred at 50° C. for 6 h. Evaporation of the solvent and purification using a Gilson HPLC afforded 4.6 mg of 2-(5-(4-fluoro-2-(4-isopropylpyrimidin-5-yl)phenoxy)pyrimidin-4-yl)-N-(4-fluorobenzyl)-5-oxa-2-azaspiro[3.4]octan-7-amine TFA salt. LCMS Method A: $t_R$=0.572 min; [M+H]⁺=545.60. ¹H NMR (CD₃OD): δ 9.10 (s, 1H), 8.57 (s, 1H), 8.21 (s, 1H), 7.69 (s, 1H), 7.38-7.34 (m, 2H), 7.30-7.22 (m, 2H), 7.10-7.03 (m, 3H), 4.19 (bs, 1H), 4.14-4.03 (m, 3H), 3.91 (dd, J=6.0, 9.0 Hz, 1H), 3.75 (d, J=6.4 Hz, 2H), 3.71-3.66 (m, 1H), 3.46-3.41 (m, 1H), 3.08-3.01 (m, 1H), 2.35-2.30 (m, 1H), 2.08-2.02 (m, 1H), 1.19 (d, J=6.8 Hz, 6H).

Example 19

4-(((2-(5-((5-fluoro-2'-isopropyl-[1,1'-biphenyl]-2-yl)oxy)pyrimidin-4-yl)-5-oxa-2-azaspiro[3.4]octan-7-yl)amino)methyl)benzonitrile

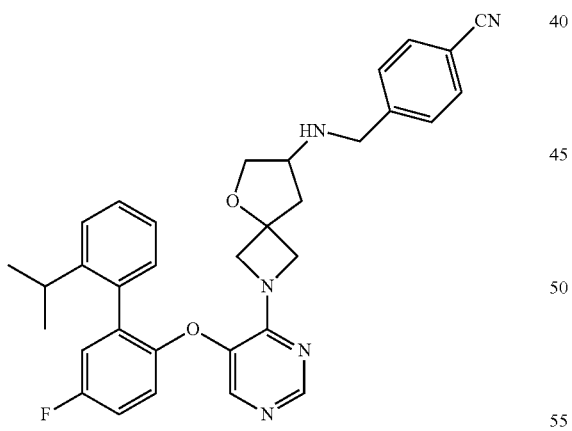

The title compound was synthesized according to the method described for Example 18. In Step 3, 2-isopropylphenyl boronic acid was used. In Step 4, 4-cyanobenzaldehyde was used. LCMS method A: $R_t$=1.125 min; (M+H)⁺=550.68. ¹H NMR (CD₃OD): δ 8.12 (s, 1H), 7.70 (d, J=7.6 Hz, 2H), 7.55 (d, J=7.6 Hz, 2H), 7.38-7.32 (m, 2H), 7.21-7.05 (m, 5H), 4.19-4.09 (m, 2H), 4.03-3.97 (m, 2H), 3.92-3.87 (m, 1H), 3.87-3.82 (m, 2H), 3.67 (dd, J=4.8, 9.0 Hz, 1H), 3.40 (bs, 1H), 2.84-2.78 (m, 1H), 2.29-2.22 (m, 1H), 2.05-2.01 (m, 2H), 1.11-1.08 (m, 6H).

Example 20

7-(5-(4-fluoro-2-(4-isopropylpyrimidin-5-yl)phenoxy)pyrimidin-4-yl)-N-(4-fluorobenzyl)-1-oxa-7-azaspiro[4.4]nonan-3-amine

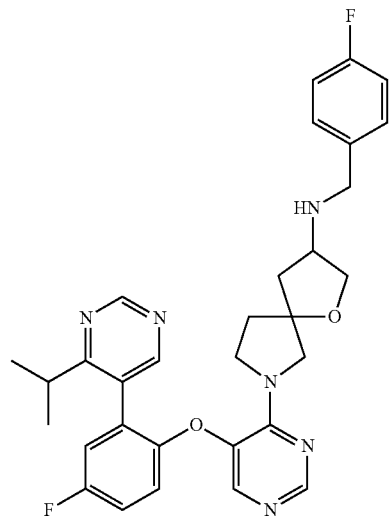 [SMILES: CC(C)c1ncncc1-c1cc(F)ccc1Oc1cncnc1N1CCC2(CC(NCc3ccc(F)cc3)CO2)C1]

The title compound was synthesized starting with tert-butyl 3-oxo-1-oxa-7-azaspiro[4.4]nonane-7-carboxylate according to the method described for Example 18. LCMS Method A: $t_R$=0.585; [M+H]⁺=559.61. ¹H NMR (CD₃OD): δ 9.10 (s, 1H), 8.57 (s, 1H), 8.21 (s, 1H), 7.78 (s, 1H), 7.41-7.35 (m, 2H), 7.28-7.20 (m, 2H), 7.09-6.95 (m, 3H), 4.42 (bs, 1H), 3.97-3.47 (m, 8H), 3.12-3.05 (m, 1H), 2.27-2.23 (m, 1H), 2.18-2.10 (m, 1H), 1.99-1.81 (m, 2H), 1.24-1.19 (m, 6H).

Example 21

5-fluoro-N-isopropyl-N-methyl-2-((4-(7-(((1r,4r)-4-(methylcarbamoyl)cyclohexyl)methyl)-2,7-diazaspiro[3.5]nonan-2-yl)pyrimidin-5-yl)oxy)benzamide

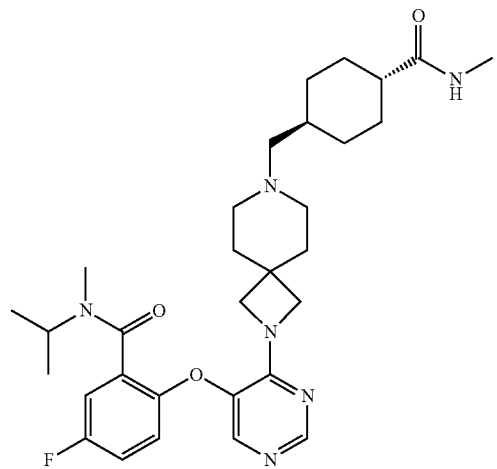 [SMILES: CNC(=O)[C@H]1CC[C@H](CN2CCC3(CC2)CN(c2ncncc2Oc2ccc(F)cc2C(=O)N(C)C(C)C)C3)CC1]

Step 1. methyl (1r,4r)-4-((2-(5-(4-fluoro-2-(isopropyl(methyl)carbamoyl)phenoxy)pyrimidin-4-yl)-2,7-diazaspiro[3.5]nonan-7-yl)methyl)cyclohexane-1-carboxylate

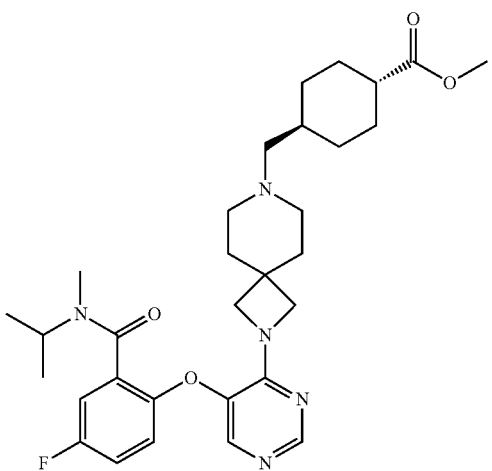 [SMILES: COC(=O)[C@H]1CC[C@H](CN2CCC3(CC2)CN(c2ncncc2Oc2ccc(F)cc2C(=O)N(C)C(C)C)C3)CC1]

The title compound was synthesized by reductive amination between 2-((4-(2,7-diazaspiro[3.5]nonan-2-yl)pyrimidin-5-yl)oxy)-5-fluoro-N-isopropyl-N-methylbenzamide (0.18 mmol) and methyl (1r,4r)-4-formylcyclohexane-1-carboxylate (100 μL) by the method described for Example 18, Step 4. LCMS method B: $R_t$=0.73 min, (M+H)$^+$=568.5.

Step 2. (1r,4r)-4-((2-(5-(4-fluoro-2-(isopropyl(methyl)carbamoyl)phenoxy)pyrimidin-4-yl)-2,7-diazaspiro[3.5]nonan-7-yl)methyl)cyclohexane-1-carboxylic acid

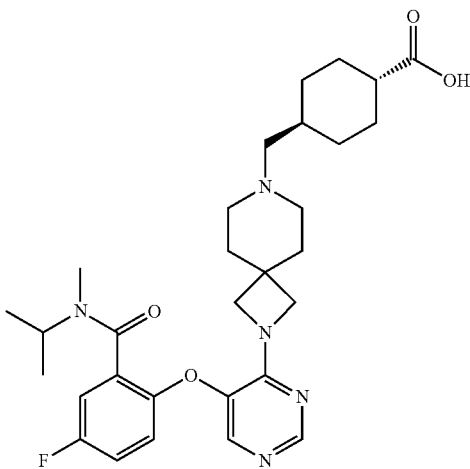 [SMILES: CC(C)N(C)C(=O)c1cc(F)ccc1Oc1cncnc1N1CC2(CCN(C[C@H]3CC[C@H](C(=O)O)CC3)CC2)C1]

To a solution of methyl (1r,4r)-4-((2-(5-(4-fluoro-2-(isopropyl(methyl)carbamoyl) phenoxy)pyrimidin-4-yl)-2,7-diazaspiro[3.5]nonan-7-yl)methyl)cyclohexane-1-carboxylate (30 mg, 0.053 mmol) in MeOH (1 mL), there was added 2 N LiOH solution (0.2 mL). The solution was stirred at RT overnight, the solvent was removed to dryness, and the residue was used for next step without purification; LCMS method B: $R_t$=0.63 min, (M+H)$^+$=554.6.

Step 3. 5-fluoro-N-isopropyl-N-methyl-2-((4-(7-(((1r,4r)-4-(methylcarbamoyl)cyclohexyl)methyl)-2,7-diazaspiro[3.5]nonan-2-yl)pyrimidin-5-yl)oxy)benzamide To a solution of the crude product from Step 2 in DMF (0.5 mL) was added MeNH$_2$HCl (15 mg) and Et$_3$N (200 μL), followed by HATU (20 mg) and the resulting solution was stirred at RT for 30 min. The product was purified by preparative RP-HPLC Method A to give 5-fluoro-N-isopropyl-N-methyl-2-((4-(7-(((1r,4r)-4-(methylcarbamoyl)cyclohexyl)methyl)-2,7-diazaspiro[3.5]nonan-2-yl)pyrimidin-5-yl)oxy)benzamide as a TFA salt (7 mg); LCMS method B: $R_t$=0.60 min, (M+H)$^+$=567.6; $^1$H NMR (MeOH-d4): δ 8.38, 8.37 (s, 1H), 7.73, 7.61 (br.s, 1H), 7.24-7.12 (m, 3H), 4.65 (m, 1H), 4.52-3.96 (m, 4H), 3.45 (m, 2H), 2.88 (m, 4H), 2.82, 2.68 (two s, 3H), 2.58 (s, 3H), 2.16 (m, 2H), 2.08-1.88 (m, 3H), 1.74 (m, 5H), 1.41 (m, 2H), 1.12-0.92 (m, 8H).

Examples 22A and 22B

2-((4-(7-amino-7-(4-cyanobenzyl)-2-azaspiro[4.4]nonan-2-yl)pyrimidin-5-yl)oxy)-5-fluoro-N,N-diisopropylbenzamide (Isomers 1-2)

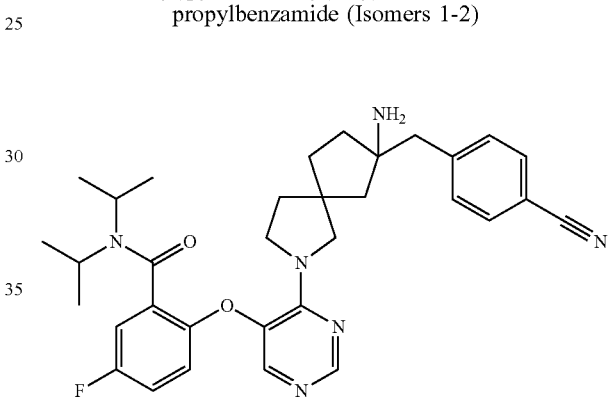

Step 1. tert-butyl 7-(4-bromobenzyl)-7-((tert-butylsulfinyl)amino)-2-azaspiro[4.4]nonane-2-carboxylate

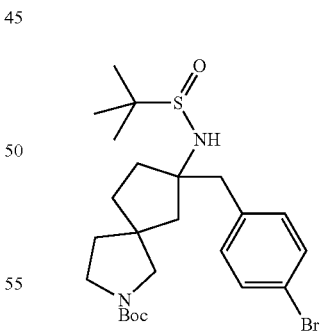

To a solution of tert-butyl-7-((tert-butylsulfinyl)imino)-2-azaspiro[4.4]nonane-2-carboxylate (Examples 250A-250B, Step 1, 0.73 g, 2.13 mmol) in THF (15 mL) at 0° C., 4-bromo-benzylmagnesium bromide (0.25M in Et$_2$O, 20 mL) was added, the solution was to warmed to RT. After 2 h, another 20 mL Grignard reagent was added and the mixture was stirred for another 2 h. The reaction was quenched reaction with sat. NH$_4$Cl and organic layer was separated. The aqueous layer was extracted with EtOAc (2×5 mL), the combined organic layers were dried over Na$_2$SO$_4$, and concentrated under vacuum. The residue was purified by silica gel column to give tert-butyl 7-(4-bromobenzyl)-7-((tert-butylsulfinyl)amino)-2-azaspiro[4.4]nonane-2-carboxylate (174.4 mg, 16%). LCMS method B: R$_t$=2.22 min; (M+H)$^+$=513.6.

Step 2. tert-butyl 7-((tert-butylsulfinyl)amino)-7-(4-cyanobenzyl)-2-azaspiro[4.4]nonane-2-carboxylate

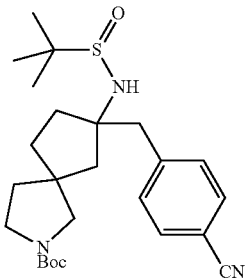 [SMILES: CC(C)(C)OC(=O)N1CCC2(CCC(Cc3ccc(C#N)cc3)(NS(=O)C(C)(C)C)C2)C1]

To a solution of tert-butyl 7-(4-bromobenzyl)-7-((tert-butylsulfinyl)amino)-2-azaspiro[4.4]nonane-2-carboxylate (88.4 mg, 0.17 mmol) in anhydrous DMF (0.5 mL), there was added Zn(CN)$_2$ (20 mg, 0.17 mmol) and Pd(PPh$_3$)$_4$ (20 mg, 0.02 mmol). The resulting solution was degassed, and heated at 110° C. under N$_2$ in an oil bath overnight. The reaction was cooled, diluted with EtOAc, washed with 1N HCl (5 mL), brine, and dried over Na$_2$SO$_4$. After removing the solvent, the residue was purified by silica gel column (0-9% MeOH/DCM) to give tert-butyl 7-((tert-butylsulfinyl)amino)-7-(4-cyanobenzyl)-2-azaspiro[4.4]nonane-2-carboxylate (56 mg, 72%). LCMS method B: R$_t$=1.67 min; (M+H)$^+$=460.6.

Step 3. 4-((7-amino-2-azaspiro[4.4]nonan-7-yl)methyl)benzonitrile

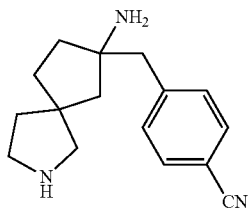 [SMILES: N#Cc1ccc(CC2(N)CCC3(CCNC3)C2)cc1]

To a solution of tert-butyl 7-((tert-butylsulfinyl)amino)-7-(4-cyanobenzyl)-2-azaspiro[4.4]nonane-2-carboxylate (56 mg, 0.12 mmol) in DCM (2 mL) was added TFA (50 μL), and the resulting solution was stirred at RT overnight to give 4-((7-amino-2-azaspiro[4.4]nonan-7-yl)methyl)benzonitrile. The solvent was removed and the resulting residue was used in the next step without purification. LCMS method B: R$_t$=0.32 min; (M+H)$^+$=256.6.

Step 4. 2-((4-(7-amino-7-(4-cyanobenzyl)-2-azaspiro[4.4]nonan-2-yl)pyrimidin-5-yl)oxy)-5-fluoro-N,N-diisopropylbenzamide (Isomers 1-2)

To a solution of the crude product from Step 3 in isopropanol (0.5 mL), was added 2-((4-chloropyrimidin-5-yl)oxy)-5-fluoro-N,N-diisopropylbenzamide (Intermediate 41, 30 mg) and Et$_3$N (200 μL), the resulting solution was heated in a CEM microwave reactor at 110° C. for 1 hr. The reaction was cooled down to RT, and purified by preparative RP-HPLC method A to give:

Isomer 1 as TFA salt (1.22 mg); LCMS method B: R$_t$=0.83 min; (M+H)$^+$=571.4. $^1$H NMR (MeOH-d4): δ 8.49 (s, 1H), 7.92 (s, 1H), 7.70 (m, 2H), 7.47 (d, J=6.8 Hz, 2H), 7.19 (m, 2H), 7.07 (br, 1H), 4.04-3.66 (m, 4H), 3.61 (m, 2H), 3.26 (m, 1H), 3.08 (s, 2H), 2.28-1.76 (m, 8H), 1.49 (m, 3H), 1.40 (m, 3H), 1.17 (d, J=7.6 Hz, 3H), 1.10 (m, 3H); and Isomer 2 as TFA salt (1.36 mg); LCMS method B: R$_t$=0.89 min; (M+H)$^+$=571.4. $^1$H NMR (MeOH-d4): δ 8.36 (s, 1H), 7.86 (br, 1H), 7.57 (d, J=8 Hz, 2H), 7.32 (d, J=7.6 Hz, 2H), 7.04 (d, J=7.6 Hz, 2H), 6.96 (br, 1H), 3.80-3.48 (m, 5H), 3.18 (m, 1H), 2.94 (s, 2H), 2.05 (m, 2H), 1.86-1.58 (m, 4H), 1.49 (m, 2H), 1.34 (d, J=6.8 Hz, 3H), 1.24 (d, J=6.4 Hz, 3H), 1.02 (d, J=6.8 Hz, 3H), 0.94 (d, J=6.8 Hz, 3H).

Examples 23A-23C 5-fluoro-2-((4-(7-hydroxy-8-((2-oxo-2,3-dihydro-1H-benzo[d]imidazol-5-yl)methyl)-2-azaspiro[4.4]nonan-2-yl)pyrimidin-5-yl)oxy)-N,N-diisopropylbenzamide (Isomers 1-3)

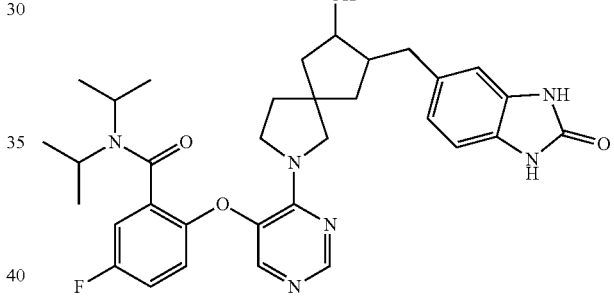

Step 1. tert-butyl-7-oxo-8-((2-oxo-2,3-dihydro-1H-benzo[d]imidazol-5-yl)methylene)-2-azaspiro[4.4]nonane-2-carboxylate

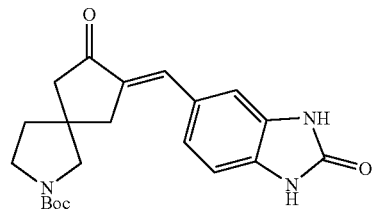 [SMILES: CC(C)(C)OC(=O)N1CCC2(CC(=O)/C(=C/c3ccc4[nH]c(=O)[nH]c4c3)C2)C1]

To a solution of tert-butyl 7-oxo-2-azaspiro[4.4]nonane-2-carboxylate (0.28 g, 1.17 mmol) and 2-oxo-2,3-dihydro-1H-benzo[d]imidazole-5-carbaldehyde (Intermediate 40, 0.23 g, 1.29 mmol) in DMSO (3 mL), there was added L-proline (40 mg), 3-ethyl-1-methyl-1H-imidazol-3-ium 2,2,2-trifluoroacetate ([EMIm][CF$_3$COO]) (79 mg, 0.35 mmol) and H$_2$O (0.32 g). The resulting mixture was heated at 80° C. for 4 days, cooled to RT, diluted with H$_2$O (5 mL), and extracted with EtOAc (4×5 mL). The combined organic layers were concentrated, and the residue was purified by silica gel column (0-4% MeOH/DCM) to give tert-butyl-7-oxo-8-((2-oxo-2,3-dihydro-1H-benzo[d]imidazol-5-yl)methylene)-2-azaspiro [4.4]nonane-2-carboxylate (~190 mg, ~42%, with the aldehyde starting material still present); LCMS method B: R$_t$=1.16 min; (M-55)$^+$=328.3; $^1$H NMR (MeOH-d4): δ 9.62 (br 1H), 9.46 (br, 1H), 7.40 (s, 1H), 7.18 (d, J=6.8 Hz, 1H), 7.03 (d, J=6.8 Hz, 1H), 5.24 (s, 1H), 3.40 (m, 2H), 3.28, 3.20 (two s, 2H), 2.88 (s, 2H), 2.40 (s, 2H), 1.80 (m, 2H), 1.4, 1.40 (two s, 9H).

Step 2. tert-butyl 7-hydroxy-8-((2-oxo-2,3-dihydro-1H-benzo[d]imidazol-5-yl)methyl)-2-azaspiro[4.4]nonane-2-carboxylate and tert-butyl 7-oxo-8-((2-oxo-2,3-dihydro-1H-benzo[d]imidazol-5-yl)methyl)-2-azaspiro[4.4]nonane-2-carboxylate

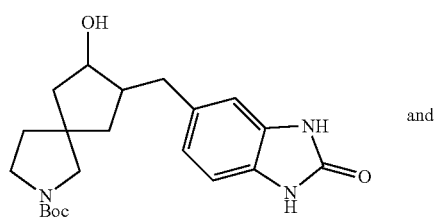

and

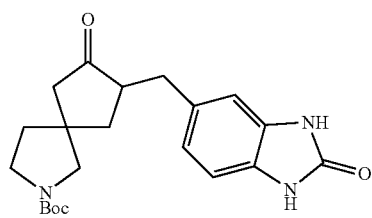

To a solution of tert-butyl-7-oxo-8-((2-oxo-2,3-dihydro-1H-benzo[d]imidazol-5-yl)methylene)-2-azaspiro [4.4]nonane-2-carboxylate (130 mg) in MeOH (10 mL), was added Pd—C (10 mg), and the solution was stirred at RT with a H$_2$ balloon overnight. LC-MS showed a mixture of tert-butyl 7-hydroxy-8-((2-oxo-2,3-dihydro-1H-benzo[d]imidazol-5-yl)methyl)-2-azaspiro[4.4]nonane-2-carboxylate and tert-butyl 7-oxo-8-((2-oxo-2,3-dihydro-1H-benzo[d]imidazol-5-yl)methyl)-2-azaspiro[4.4]nonane-2-carboxylate. The reaction mixture was filtered through a Celite pad, and solvent was removed under vacuum. The residue was purified by a silica gel column (3-7% MeOH/DCM) to give tert-butyl 7-oxo-8-((2-oxo-2,3-dihydro-1H-benzo[d]imidazol-5-yl)methyl)-2-azaspiro[4.4]nonane-2-carboxylate (~50 mg); LCMS method B: R$_t$=1.17 min; (M-55)$^+$=330.3; and tert-butyl 7-hydroxy-8-((2-oxo-2,3-dihydro-1H-benzo[d]imidazol-5-yl)methyl)-2-azaspiro[4.4]nonane-2-carboxylate (~80 mg); LCMS method B: R$_t$=1.17 min; (M-55)$^+$=332.3.

Step 3. 5-((8-hydroxy-2-azaspiro[4.4]nonan-7-yl)methyl)-1,3-dihydro-2H-benzo[d]imidazol-2-one

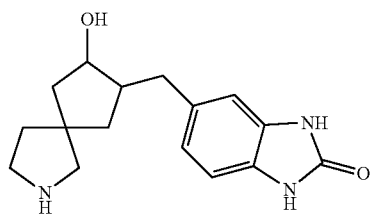 [SMILES: O=c1[nH]c2ccc(CC3CC4(CCNC4)CC3O)cc2[nH]1]

To a solution of tert-butyl 7-hydroxy-8-((2-oxo-2,3-dihydro-1H-benzo[d]imidazol-5-yl)methyl)-2-azaspiro[4.4]nonane-2-carboxylate (20 mg, 0.052 mmol) in DCM (0.5 mL), was added TFA (0.2 mL) and the solution was stirred at RT for half an h. The solvent was then removed to dryness to give a TFA salt of 5-((8-hydroxy-2-azaspiro[4.4]nonan-7-yl)methyl)-1,3-dihydro-2H-benzo[d]imidazol-2-one, which was used for the next step without purification; LCMS method B: R$_t$=0.47 min; (M+H)$^+$=288.3.

Step 4. 5-fluoro-2-((4-(7-hydroxy-8-((2-oxo-2,3-dihydro-1H-benzo[d]imidazol-5-yl)methyl)-2-azaspiro[4.4]nonan-2-yl)pyrimidin-5-yl)oxy)-N,N-diisopropylbenzamide (Isomers 1-3)

To a solution of the crude product from Step 3 in isopropanol (0.3 mL), there was added 2-((4-chloropyrimidin-5-yl)oxy)-5-fluoro-N,N-diisopropylbenzamide (Intermediate 41, 20 mg) and Et$_3$N (150 µL), and the resulting solution was heated in a CEM microwave reactor at 110° C. for 1 h. LC-MS showed three products at t$_R$=0.88, 0.90 and 0.95 min with a ratio of 1:1:5. The products were isolated by preparative RP-HPLC method A to give:

Isomer 1 as a TFA salt (1.4 mg), LCMS method B: R$_t$=0.88 min; (M+H)$^+$=603.5. $^1$H NMR (MeOH-d4): δ 8.37 (s, 1H), 7.68, 7.54 (two br, 1H), 7.10 (m, 3H), 6.84-6.72 (m, 3H), 4.08-3.94 (m, 2H), 3.94-3.50 (m, 5H), 3.00-2.74 (m, 1H), 2.52-2.26 (m, 1H), 2.14-1.78 (m, 5H), 1.68-1.30 (m, 6H), 1.24-1.02 (m, 6H), 1.02-0.82 (m, 2H);

Isomer 2 as a TFA salt (0.82 mg), LCMS method B: R$_t$=0.90 min; (M+H)$^+$=603.5. $^1$H NMR (MeOH-d4): δ 8.33 (s, 1H), 7.62, 7.50 (two br, 1H), 7.10 (m, 3H), 6.84-6.70 (m, 3H), 3.98-3.54 (m, 6H), 3.52-3.34 (m, 1H), 3.02-2.92 (m, 1H), 2.78, 2.48 (two br, 1H), 2.28 (m, 1H), 2.08-1.92 (m, 2H), 1.90-1.72 (m, 2H), 1.68-1.46 (m, 2H), 1.34 (m, 3H), 1.28-0.84 (m, 7H); and Isomer 3 as a TFA salt (5 mg), LCMS method B: R$_t$=0.95 min; (M+H)$^+$=603.5. $^1$H NMR (MeOH-d4): δ 8.35 (s, 1H), 7.68-7.50 (m, 1H), 7.22-7.04 (m, 3H), 6.77 (m, 3H), 4.08-3.90 (m, 2H), 3.90-3.56 (m, 4H), 3.56-3.32 (m, 1H), 2.76 (m, 1H), 2.45 (m, 1H), 2.11 (m, 1H), 1.88-1.58 (m, 4H), 1.55-1.24 (m, 6H), 1.22-0.98 (m, 6H), 0.92 (br, 1H), 0.84 (br, 1H).

Examples 24A-24B 2-((4-(7-amino-8-((2-oxo-2,3-dihydro-1H-benzo[d]imidazol-5-yl)methyl)-2-azaspiro[4.4]nonan-2-yl)pyrimidin-5-yl)oxy)-5-fluoro-N,N-diisopropylbenzamide (Isomers 1-2)

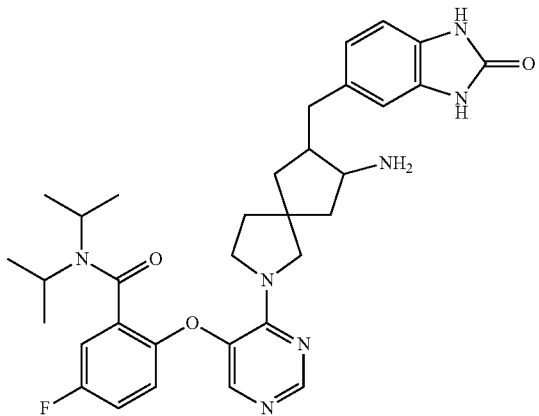 [SMILES: CC(C)N(C(=O)c1cc(F)ccc1Oc1cncnc1N1CCC2(CC(N)C(Cc3ccc4[nH]c(=O)[nH]c4c3)C2)C1)C(C)C]

Step 1. tert-butyl-7-((tert-butylsulfinyl)imino)-8-((2-oxo-2,3-dihydro-1H-benzo[d]imidazol-5-yl)methyl)-2-azaspiro[4.4]nonane-2-carboxylate

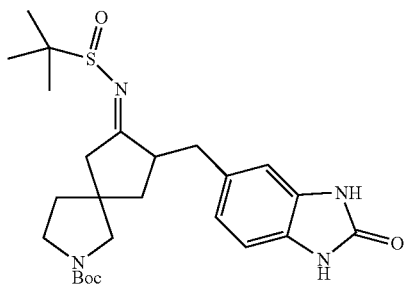 [SMILES: CC(C)(C)OC(=O)N1CCC2(C/C(=N\S(=O)C(C)(C)C)C(Cc3ccc4[nH]c(=O)[nH]c4c3)C2)C1]

The title product was synthesized as a mixture of multiple diasteoroisomers according the procedure described in Examples 23A-23C, Step 1, followed by Step 1 of Examples 250A-250B, starting with tert-butyl 7-oxo-8-((2-oxo-2,3-dihydro-1H-benzo[d]imidazol-5-yl)methyl)-2-azaspiro[4.4]nonane-2-carboxylate (see Examples 23A-23C, Step 2). The title product was used for the next step without purification. LCMS method B: $R_t$=1.29-1.32 min, multiple peaks; (M+H)$^+$=489.4.

Step 2. tert-butyl 7-((tert-butylsulfinyl)amino)-8-((2-oxo-2,3-dihydro-1H-benzo[d]imidazol-5-yl)methyl)-2-azaspiro[4.4]nonane-2-carboxylate

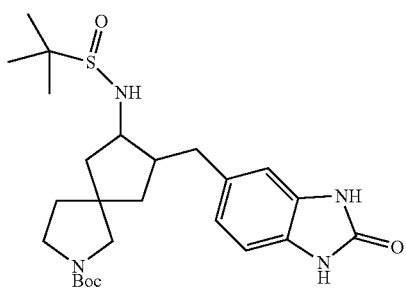 [SMILES: CC(C)(C)OC(=O)N1CCC2(CC(Cc3ccc4[nH]c(=O)[nH]c4c3)C(NS(=O)C(C)(C)C)C2)C1]

To a solution of the residue from Step 1 in THF (5 mL), was added NaBH$_4$ (10 mg, 0.26 mmol), and 1 drop of water. The resulting solution was stirred at RT for two h. The reaction was quenched with ice water and extracted with EtOAc. The combined organic layers was concentrated under vacuum and the residue was purified by preparative-RF HPLC method A to give two fractions of diasteoroiosmers: Fraction 1 (5.8 mg, TFA salt): LC-MS method B: $R_t$=1.26 min, (M+H)$^+$=491.4; Fraction 2 (18.8 mg, TFA salt): LC-MS method B: $R_t$=1.32 min, (M+H)$^+$=491.4.

Step 3. 2-methyl-N-(8-((2-oxo-2,3-dihydro-1H-benzo[d]imidazol-5-yl)methyl)-2-azaspiro[4.4]nonan-7-yl)propane-2-sulfinamide

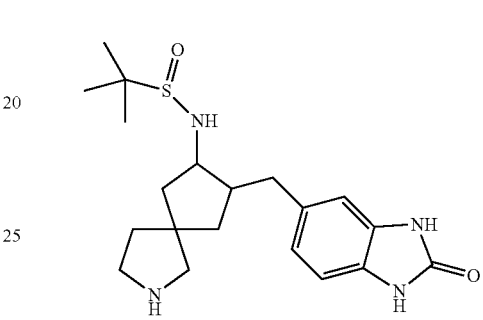

To a solution of tert-butyl 7-((tert-butylsulfinyl)amino)-8-((2-oxo-2,3-dihydro-1H-benzo[d]imidazol-5-yl)methyl)-2-azaspiro[4.4]nonane-2-carboxylate (18.8 mg, 0.038 mmol, Fraction 2, Step 2) in DCM (3 mL), was added TFA (50 µL) and the resulting solution was stirred at RT overnight. Et$_3$N was then added to the solution to neutralize the acid. Upon removing solvent, the residue was used for the next step without purification.

Step 4. 2-((4-(7-((tert-butylsulfinyl)amino)-8-((2-oxo-2,3-dihydro-1H-benzo[d]imidazol-5-yl)methyl)-2-azaspiro[4.4]nonan-2-yl)pyrimidin-5-yl)oxy)-5-fluoro-N,N-diisopropylbenzamide

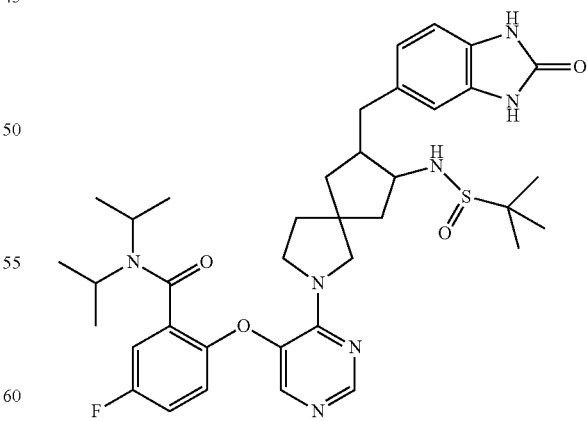

To a solution of the crude product from Step 3 in isopropanol (0.3 mL) was added 2-((4-chloropyrimidin-5-yl)oxy)-5-fluoro-N,N-diisopropylbenzamide (Intermediate 41, 20 mg) and Et$_3$N (100 µL), and the resulting solution was heated in a CEM microwave reactor at 110° C. for 1 h. The solvent was removed to give the crude product, which was used for the next step without purification; LCMS method B: $R_t$=1.06 min, (M+H)$^+$=706.6.

Step 5. 2-((4-(7-amino-8-((2-oxo-2,3-dihydro-1H-benzo[d]imidazol-5-yl)methyl)-2-azaspiro[4.4]nonan-2-yl)pyrimidin-5-yl)oxy)-5-fluoro-N,N-diisopropylbenzamide (Isomers 1-2)

To the crude product from Step 4 in MeOH (2 mL) was added 6N HCl (2 mL) and the resulting solution was stirred at RT overnight. LC-MS showed two product at $t_r$=0.65, 0.69 min with a ratio of 1:6; The products were isolated by preparative RP-HPLC method A to give two isomers.

Isomer 1 as a TFA salt (0.67 mg); LCMS method B: $R_t$=0.65 min, (M+H)$^+$=602.5; $^1$H NMR (MeOH-d4): δ 8.33, 8.31 (two s, 1H), 7.78, 7.71 (two br, 1H), 7.06 (m, 2H), 6.96 (m, 1H), 6.82 (m, 1H), 6.76 (m, 2H), 3.78-3.62 (m, 3H), 3.56-3.40 (m, 2H), 3.38-3.28 (m, 1H), 3.08-2.82 (m, 1H), 2.58-2.12 (m, 2H), 1.92-1.54 (m, 4H), 1.36 (m, 6H), 1.22 (m, 1H), 1.06 (m, 6H), 1.02-0.88 (m, 2H).

Isomer 2 as a TFA salt (4.24 mg); LCMS method B: $R_t$=0.69 min, (M+H)$^+$=602.5. $^1$H NMR (MeOH-d4): δ 8.34 (s, 1H), 7.80 (br, 1H), 7.09 (m, 2H), 6.99 (m, 1H), 6.82 (m, 1H), 6.76 (m, 2H), 3.84-3.62 (m, 3H), 3.58-3.42 (m, 2H), 3.36-3.26 (m, 1H), 3.08-2.98 (m, 1H), 2.45-2.12 (m, 2H), 1.88-1.54 (m, 4H), 1.37 (m, 6H), 1.22 (m, 1H), 1.05 (m, 6H), 0.95 (m, 2H).

Example 25

2-((4-(7-amino-8-((2-oxo-2,3-dihydro-1H-benzo[d]imidazol-5-yl)methyl)-2-azaspiro[4.4]nonan-2-yl)pyrimidin-5-yl)oxy)-5-fluoro-N,N-diisopropylbenzamide (Isomer 3)

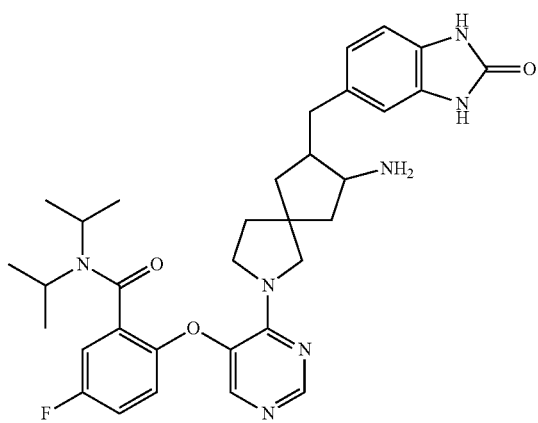 [SMILES: CC(C)N(C(=O)c1cc(F)ccc1Oc1cncnc1N1CCC2(CC(N)C(Cc3ccc4[nH]c(=O)[nH]c4c3)C2)C1)C(C)C]

The title compound was synthesized according to the procedure of Examples 24A-24B, using Fraction 1 (5.8 mg) prepared at Step 2 of Examples 24A-24B. LCMS method B: $R_t$=0.69 min, (M+H)$^+$=602.5.

Examples 26A-26B 5-fluoro-2-((4-(8-(4-fluorobenzyl)-7-(2-hydroxyethyl)-2,7-diazaspiro[4.4]nonan-2-yl)pyrimidin-5-yl)oxy)-N,N-diisopropylbenzamide (Isomers 1-2)

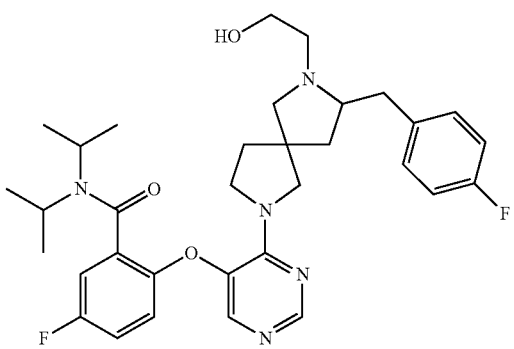 [SMILES: CC(C)N(C(=O)c1cc(F)ccc1Oc1cncnc1N1CCC2(CC(Cc3ccc(F)cc3)N(CCO)C2)C1)C(C)C]

Step 1. Tert-butyl 7-benzyl-3-oxo-2,7-diazaspiro[4.4]nonane-2-carboxylate

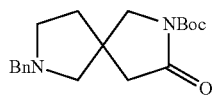

To a solution of 7-benzyl-2,7-diazaspiro[4.4]nonan-3-one (500 mg, 2.17 mmol) in DCM (15 mL) was added Boc$_2$O (1.04 g, 4.8 mmol) followed by portionwise addition of DMAP (662 mg, 5.4 mmol) at RT and the mixture was stirred at RT for 2 days. The reaction was quenched by addition of H$_2$O (20 mL) and the aqueous phase was extracted with EtOAc (30 mL). The organic layers were combined, dried over Na$_2$SO$_4$ and evaporated to afford crude product, which was purified by flash chromatography over silica gel eluting with 70% EtOAc/Hexanes to afford 400 mg tert-Butyl 7-benzyl-3-oxo-2,7-diazaspiro[4.4]nonane-2-carboxylate as a colorless oil (56% yield). LCMS Method A: $t_R$=0.73 min, [M+H]$^+$=331.4.

Step 2. Tert-butyl ((1-benzyl-3-(3-(4-fluorophenyl)-2-oxopropyl)pyrrolidin-3-yl)methyl)carbamate

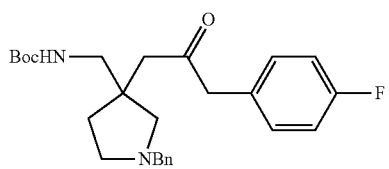 [SMILES: CC(C)(C)OC(=O)NCC1(CC(=O)Cc2ccc(F)cc2)CCN(Cc2ccccc2)C1]

At 0° C., to a solution of tert-butyl 7-benzyl-3-oxo-2,7-diazaspiro[4.4]nonane-2-carboxylate (280 mg, 0.85 mmol) in dry THF (2 mL) was added 0.25 M (4-fluorobenzyl)magnesium chloride in Et$_2$O (5.0 mL, 1.25 mmol) slowly under N$_2$. The mixture was stirred for 1 h at 0° C. then quenched by addition of H$_2$O (10 mL). The mixture was then extracted with EtOAc (2×30 mL). The organic layers were washed with brine, dried over Na₂SO₄ and evaporated to afford crude product, which was purified by flash chromatography over silica gel eluting with 30% EtOAc/Hexanes to afford 240 mg tert-Butyl ((1-benzyl-3-(3-(4-fluorophenyl)-2-oxopropyl)pyrrolidin-3-yl)methyl)carbamate as a colorless oil (65% yield). LCMS Method A: $t_R$=1.10 min, [M+H]⁺= 441.4.

Step 3. tert-butyl 7-benzyl-3-(4-fluorobenzyl)-2,7-diazaspiro[4.4]nonane-2-carboxylate

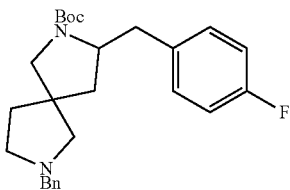 [SMILES: CC(C)(C)OC(=O)N1CC2(CCN(Cc3ccccc3)C2)CC1Cc1ccc(F)cc1]

To a solution of tert-butyl ((1-benzyl-3-(3-(4-fluorophenyl)-2-oxopropyl)pyrrolidin-3-yl)methyl) carbamate (240 mg, 0.55 mmol) in DCM (3 mL) was added TFA (0.5 mL) at RT and the reaction mixture was stirred for 1 h at RT and then concentrated under reduced pressure.

The resulting crude product was dissolved into DCM (3 mL) and neutralized with TEA, followed by addition of NaCNBH₃ (39 mg, 0.6 mmol) and the mixture was stirred at RT for 1 h. Boc₂O (135 mg, 0.65 mmol) was added to the reaction mixture and stirred at RT for 4 h. The mixture was diluted with H₂O (20 mL) and extracted with EtOAc (2×20 mL). The organic layers were combined, washed with brine, dried over Na₂SO₄, filtered and concentrated under reduced pressure. The crude product was purified by flash chromatography over silica gel eluting with 20% EtOAc/hexanes to afford 184 mg tert-butyl 7-benzyl-3-(4-fluorobenzyl)-2,7-diazaspiro[4.4]nonane-2-carboxylate as a colorless oil (80% yield). LCMS Method A: $t_R$=1.17 min, [M+H]⁺=425.5.

Step 4. Tert-butyl 3-(4-fluorobenzyl)-2,7-diazaspiro[4.4]nonane-2-carboxylate

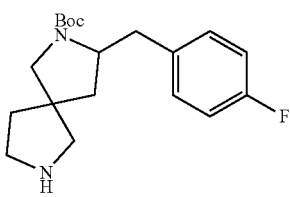 [SMILES: CC(C)(C)OC(=O)N1CC2(CCNC2)CC1Cc1ccc(F)cc1]

To a solution of tert-butyl 7-benzyl-3-(4-fluorobenzyl)-2,7-diazaspiro[4.4]nonane-2-carboxylate (184 mg, 0.43 mmol) in MeOH (5 mL) was added Pd(OH)₂ on Carbon (5% dry basis, 123 mg, 43 µmol). The mixture was stirred at RT under a hydrogen balloon for 40 h and filtered through a celite pad. The residue was concentrated under reduced pressure. The crude product was used directly for the next step reaction without further purification. LCMS Method A: $t_R$=1.01 min, [M+H]⁺=335.5.

Step 5. Tert-butyl 7-(5-(2-(diisopropylcarbamoyl)-4-fluorophenoxy)pyrimidin-4-yl)-3-(4-fluorobenzyl)-2,7-diazaspiro[4.4]nonane-2-carboxylate

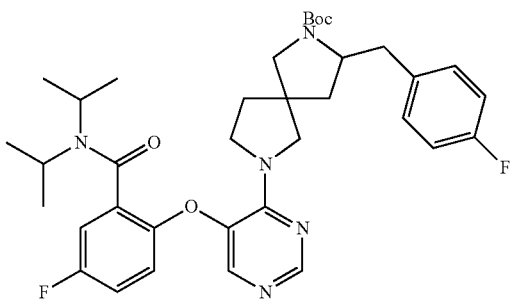 [SMILES: CC(C)N(C(=O)c1cc(F)ccc1Oc1cncnc1N1CCC2(CC(Cc3ccc(F)cc3)N(C(=O)OC(C)(C)C)C2)C1)C(C)C]

A solution of tert-butyl 3-(4-fluorobenzyl)-2,7-diazaspiro[4.4]nonane-2-carboxylate (94 mg, 0.28 mmol) and 2-((4-chloropyrimidin-5-yl)oxy)-5-fluoro-N,N-diisopropylbenzamide (Intermediate 41, 100 mg, 0.31 mmol) in ⁱPrOH (2 mL) was heated in a microwave reactor at 120° C. for 2 h. After cooling to RT, the mixture was diluted with H₂O (10 mL) and extracted with EtOAc (3×15 mL). The organic layer was washed with brine, dried over Na₂SO₄, and concentrated. The crude product was purified by flash chromatography over silica gel eluting with 70% EtOAc/Hexanes to afford 127 mg tert-butyl 7-(5-(2-(diisopropylcarbamoyl)-4-fluorophenoxy)pyrimidin-4-yl)-3-(4-fluorobenzyl)-2,7-diazaspiro[4.4]nonane-2-carboxylate as a colorless oil (70% yield). LCMS Method A: $t_R$=1.48 min, [M+H]⁺=650.4.

Step 6. 5-fluoro-2-((4-(8-(4-fluorobenzyl)-2,7-diazaspiro[4.4]nonan-2-yl)pyrimidin-5-yl)oxy)-N,N-diisopropylbenzamide

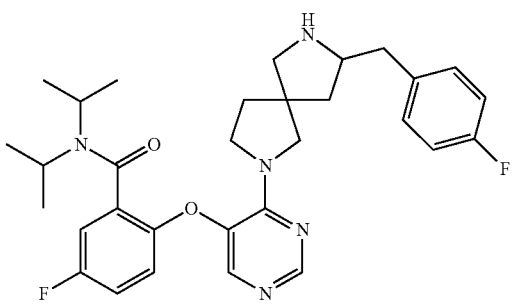 [SMILES: CC(C)N(C(=O)c1cc(F)ccc1Oc1cncnc1N1CCC2(CNC(Cc3ccc(F)cc3)C2)C1)C(C)C]

To a solution of tert-butyl 7-(5-(2-(diisopropylcarbamoyl)-4-fluorophenoxy)pyrimidin-4-yl)-3-(4-fluorobenzyl)-2,7-diazaspiro[4.4]nonane-2-carboxylate (100 mg, 0.15 mmol) in DCM (2 mL) was added TFA (0.4 mL) at RT. The reaction mixture was stirred for 1 h and neutralized with aqueous NaHCO₃ solution. The mixture was then extracted with DCM (4×15 mL). The organic layers were combined, dried over Na₂SO₄, filtered and concentrated under reduced pressure. The crude product was purified by flash chromatography over silica gel eluting with 10% MeOH/DCM to afford 65 mg 5-fluoro-2-((4-(8-(4-fluorobenzyl)-2,7-diazaspiro[4.4]nonan-2-yl)pyrimidin-5-yl)oxy)-N,N-diisopropylbenzamide as a colorless oil (80% yield). LCMS Method A: $t_R$=0.92 min, [M+H]⁺=550.5.

Step 6. 2-((4-(7-(2-(((tert-butyldimethylsilyl)oxy)ethyl)-8-(4-fluorobenzyl)-2,7-diazaspiro[4.4]nonan-2-yl)pyrimidin-5-yl)oxy)-5-fluoro-N,N-diisopropylbenzamide

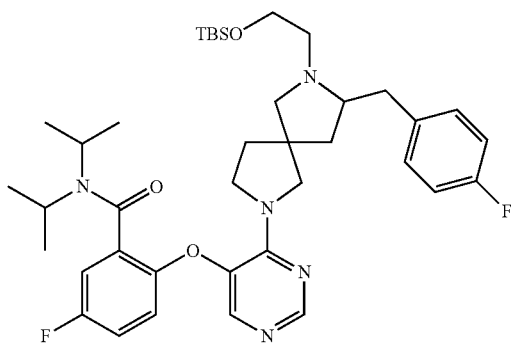 [SMILES: CC(C)N(C(=O)c1cc(F)ccc1Oc1cncnc1N1CCC2(CC(Cc3ccc(F)cc3)N(CCO[Si](C)(C)C(C)(C)C)C2)C1)C(C)C]

To a solution of 5-fluoro-2-((4-(8-(4-fluorobenzyl)-2,7-diazaspiro[4.4]nonan-2-yl)pyrimidin-5-yl)oxy)-N,N-diisopropylbenzamide (10 mg, 18 μmol) and (2-bromoethoxy)(tert-butyl) dimethylsilane (7 mg, 27 μmol) in DMF (0.5 mL) was added $K_2CO_3$ (7 mg, 45 μmol) at RT. The reaction mixture was stirred at 50° C. for 4 h and extracted with EtOAc (4×5 mL). The organic layers were combined, dried over $Na_2SO_4$, filtered and concentrated under reduced pressure. The crude product was used directly for the next step reaction without further purification. LCMS Method A: $t_R$=1.34 min, [M+H]$^+$=708.5.

Step 7. 5-fluoro-2-((4-(8-(4-fluorobenzyl)-7-(2-hydroxyethyl)-2,7-diazaspiro[4.4]nonan-2-yl)pyrimidin-5-yl)oxy)-N,N-diisopropylbenzamide (Isomers 1-2)

To a solution of crude 2-((4-(7-(2-((tert-butyldimethylsilyl)oxy)ethyl)-8-(4-fluorobenzyl)-2,7-diazaspiro[4.4]nonan-2-yl)pyrimidin-5-yl)oxy)-5-fluoro-N,N-diisopropylbenzamide in THF (0.5 mL) was added TBAF in THF solution (1 M, 0.1 mL, 0.1 μmol) at RT. The reaction mixture was stirred at RT for 2 h and concentrated under reduced pressure. The crude product was purified on a Gilson-HPLC to yield the title product as a mixture of two racemates.

Isomer 1:

LCMS Method A: $t_R$=0.93 min, [M+H]$^+$=594.3. $^1$H NMR (CD$_3$OD): δ 8.58 (s, 1H), 8.00 (s, 1H), 7.33-7.25 (m, 5H), 7.27-7.09 (m, 2H), 3.97-3.88 (m, 8H), 3.68-3.61 (m, 2H), 3.48-3.41 (m, 2H), 3.26-3.21 (m, 1H), 3.15-3.05 (m, 1H), 2.90-2.85 (m, 1H), 2.15-2.04 (m, 4H), 1.55-1.52 (m, 3H), 1.39-1.37 (m, 3H), 1.23-1.21 (m, 3H), 1.11-1.07 (m, 3H). $^{19}$F NMR (CD$_3$OD): δ −76.90, −77.38, −117.20.

Isomer 2:

LCMS Method A: $t_R$=0.92 min, [M+H]$^+$=594.3. $^1$H NMR (CD$_3$OD): δ 8.56 (s, 1H), 8.00 (s, 1H), 7.33-7.31 (m, 2H), 7.28-7.25 (m, 1H), 7.24-7.20 (m, 2H), 7.10-7.08 (m, 2H), 3.90-3.81 (m, 8H), 3.62-3.53 (m, 2H), 3.48-3.41 (m, 2H), 3.24-3.13 (m, 2H), 2.90-2.81 (m, 1H), 2.16-2.10 (m, 2H), 1.94-1.91 (m, 2H), 1.53-1.51 (m, 3H), 1.29-1.27 (m, 3H), 1.21-1.19 (m, 3H), 1.11-1.07 (m, 3H).

Example 27

6-((7-(5-(2-chloro-4-fluorophenoxy)pyrimidin-4-yl)-2-azaspiro[4.4]nonan-2-yl)methyl)-1-methyl-1H-benzo[d]imidazol-2(3H)-one

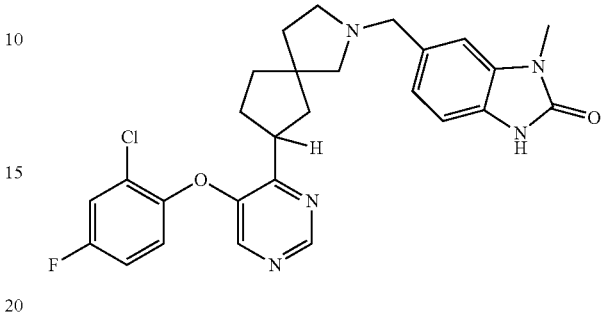

Step 1. tert-butyl 7-(((trifluoromethyl)sulfonyl)oxy)-2-azaspiro[4.4]non-7-ene-2-carboxylate

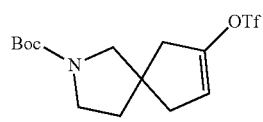

To a solution of LiHMDS (4 mL, 4 mmol, 1M in THF) in THF (10 mL, anhydrous) was added tert-butyl 7-oxo-2-azaspiro[4.4]nonane-2-carboxylate (500 mg, 2 mmol) in THF (4 mL, anhydrous) dropwise at −78° C. and the mixture was stirred at −78° C. for 1 h under N$_2$. PhNTf$_2$ (1.1 g, 3 mmol) in THF (6 mL, anhydrous) was added and the reaction was warmed to 12-21° C. and stirred for 16 h under N$_2$. The resulting mixture was quenched by sat. aq. NH$_4$Cl (30 mL) and extracted with EtOAc (3×30 mL). The organic layers were washed with brine (30 mL), dried over Na$_2$SO$_4$, filtered and concentrated to give the crude residue. The residue was purification by flash chromatography (SiO$_2$, 1%~50% EtOAc/Petroleum ether) to give tert-butyl 7-(((trifluoromethyl)sulfonyl)oxy)-2-azaspiro[4.4]non-7-ene-2-carboxylate (impure) as a colorless oil. Yield: 950 mg. $^1$H NMR (MeOD-d4): δ 5.69 (s, 1H), 3.38-3.50 (m, 2H), 3.20-3.30 (m, 2H), 2.65-2.80 (m, 2H), 1.90-2.10 (m, 3H), 1.77-1.85 (m, 1H), 1.46 (s, 9H).

Step 2. tert-butyl 7-(4,4,5,5-tetramethyl-1,3,2-dioxaborolan-2-yl)-2-azaspiro[4.4]non-7-ene-2-carboxylate

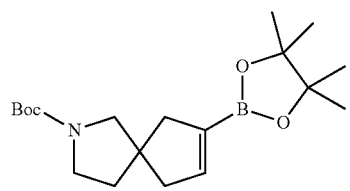 [SMILES: CC(C)(C)OC(=O)N1CCC2(CC=C(B3OC(C)(C)C(C)(C)O3)C2)C1]

To a solution of tert-butyl 7-(((trifluoromethyl)sulfonyl)oxy)-2-azaspiro[4.4]non-7-ene-2-carboxylate (950 mg, 2 mmol, 55% purity), and 4,4,4',4',5,5,5',5'-octamethyl-2,2'-bi(1,3,2-dioxaborolane) (760 mg, 3 mmol) in dioxane (10 mL, anhydrous) was added to Pd(dppf)Cl$_2$ (73 mg, 0.11 mmol) and KOAc (390 mg, 4 mmol) under N$_2$. The resulting mixture was stirred at 80° C. for 16 h under N$_2$. The resulting mixture was concentrated to give the crude residue. The residue was purified by flash chromatography (SiO$_2$, 1%~100% EtOAc in petroleum ether) to give tert-butyl 7-(4,4,5,5-tetramethyl-1,3,2-dioxaborolan-2-yl)-2-azaspiro[4.4]non-7-ene-2-carboxylate (impure crude) as a colorless oil. Yield: 800 mg. $^1$H NMR (MeOD-d4): δ 6.27 (s, 1H), 3.38-3.50 (m, 2H), 3.15-3.30 (m, 2H), 2.40-2.60 (m, 2H), 1.65-1.90 (m, 2H), 1.40-1.50 (m, 9H), 1.26 (s, 12H), 0.80-0.95 (m, 2H).

Step 3. tert-butyl 7-(5-(2-chloro-4-fluorophenoxy)pyrimidin-4-yl)-2-azaspiro[4.4]non-7-ene-2-carboxylate

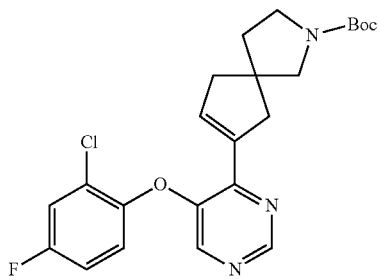 [SMILES: CC(C)(C)OC(=O)N1CCC2(CC=C(c3ncncc3Oc3ccc(F)cc3Cl)C2)C1]

To a solution of 4-chloro-5-(2-chloro-4-fluorophenoxy)pyrimidine (Intermediate 10A, 50 mg, 0.2 mmol), tert-butyl 7-(4,4,5,5-tetramethyl-1,3,2-dioxaborolan-2-yl)-2-azaspiro[4.4]non-7-ene-2-carboxylate (140 mg, 0.4 mmol, 50% purity) in dioxane (2.5 mL) and H$_2$O (0.5 mL) was added to Pd(dppf)Cl$_2$ (15 mg, 0.02 mmol) and Na$_2$CO$_3$ (42 mg, 0.4 mmol) under N$_2$. The resulting mixture was stirred at 80° C. for 16 h under N$_2$. The resulting mixture was diluted with water (10 mL) and extracted with EtOAc (3×20 mL). The organic layers were washed with brine (30 mL), dried over Na$_2$SO$_4$, filtered and concentrated to give the residue. The residue was purified by prep-TLC (EtOAc:petroleum ether=2:1) to give tert-butyl 7-(5-(2-chloro-4-fluorophenoxy)pyrimidin-4-yl)-2-azaspiro[4.4]non-7-ene-2-carboxylate as a yellow oil. Yield: 50 mg. LCMS method C: R$_t$=0.914 min; (M+H)$^+$=446.0, 448.0 (chlorine isotopes).

Step 4. tert-butyl 7-(5-(2-chloro-4-fluorophenoxy)pyrimidin-4-yl)-2-azaspiro[4.4]nonane-2-carboxylate

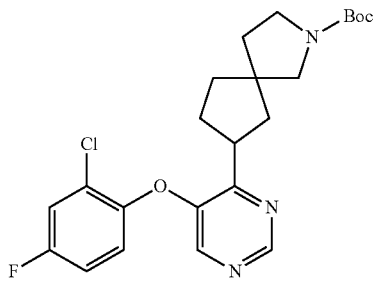 [SMILES: CC(C)(C)OC(=O)N1CCC2(CCC(c3ncncc3Oc3ccc(F)cc3Cl)C2)C1]

To a solution of tert-butyl 7-(5-(2-chloro-4-fluorophenoxy)pyrimidin-4-yl)-2-azaspiro[4.4]non-7-ene-2-carboxylate (50 mg, 0.11 mmol) in MeOH (5 mL, anhydrous) and THF (5 mL, anhydrous) was added PtO$_2$ (5 mg, 10%). The resulting mixture was stirred at 25° C. for about 16 h under H$_2$ (20 psi). The mixture was filtered and the filtrate was concentrated and purified by preparative TLC on silica gel (EtOAc:petroleum ether=1:5) to give tert-butyl 7-(5-(2-chloro-4-fluorophenoxy)pyrimidin-4-yl)-2-azaspiro[4.4]nonane-2-carboxylate as a yellow oil. Yield: 30 mg (61%). LCMS method C: R$_t$=0.923 min, (M+H)$^+$=448.0, 450.0 (chlorine isotopes).

Step 5. 7-(5-(2-chloro-4-fluorophenoxy)pyrimidin-4-yl)-2-azaspiro[4.4]nonane

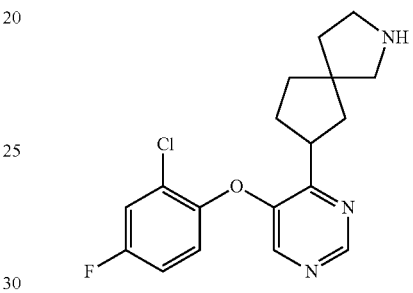

A solution of tert-butyl 7-(5-(2-chloro-4-fluorophenoxy)pyrimidin-4-yl)-2-azaspiro[4.4]nonane-2-carboxylate (30 mg, 0.07 mmol) in TFA-CH$_2$Cl$_2$ (3 mL, V:V=1:4) was stirred at 10-21° C. for about 3 h. The mixture was then concentrated. The resulting mixture was adjusted to pH 8 with sat. aq. NaHCO$_3$ and extracted with CH$_2$Cl$_2$ (2×20 mL). The combined organic layers were washed with brine (10 mL), dried over Na$_2$SO$_4$, filtered and concentrated to give 7-(5-(2-chloro-4-fluorophenoxy)pyrimidin-4-yl)-2-azaspiro[4.4]nonane as a yellow oil, which was used for next step directly without further purification. Yield: 30 mg. LCMS method C: R$_t$=0.642 min; (M+H)$^+$=348.0, 350.0 (chlorine isotopes).

Step 6. 6-((7-(5-(2-chloro-4-fluorophenoxy)pyrimidin-4-yl)-2-azaspiro[4.4]nonan-2-yl)methyl)-1-methyl-1H-benzo[d]imidazol-2(3H)-one To a solution of 7-(5-(2-chloro-4-fluorophenoxy)pyrimidin-4-yl)-2-azaspiro[4.4]nonane (30 mg, 0.07 mmol, crude) and 1-methyl-2-oxo-2,3-dihydro-1H-benzo[d]imidazole-5-carbaldehyde (12 mg, 0.07 mmol,) in MeOH (3 mL, anhydrous) was added NaBH$_3$CN (22 mg, 0.35 mmol). The resulting mixture was stirred at 10-21° C. for about 16 h. The mixture was concentrated and purified by acidic preparative RP-HPLC method A to give 6-((7-(5-(2-chloro-4-fluorophenoxy)pyrimidin-4-yl)-2-azaspiro[4.4]nonan-2-yl)methyl)-1-methyl-1H-benzo[d]imidazol-2(3H)-one (TFA salt) as a white solid. Yield: 15 mg. LCMS method E: R$_t$=0.902 min; (M+H)$^+$=508.3, 510.3 (chlorine isotopes). $^1$H NMR (MeOD-d4): δ 8.70-8.85 (m, 1H), 7.99 (d, J=5.2 Hz, 1H), 7.35-7.50 (m, 1H), 7.10-7.35 (m, 5H), 4.35-4.50 (m, 2H), 3.80-3.95 (m, 1H), 3.35-3.70 (m, 6H), 3.20-3.30 (m, 1H), 1.75-2.40 (m, 8H). $^{19}$F NMR (MeOD-d4): δ −77.02, −116.39.

Example 28

5-((7-(3-(4-fluoro-2-(4-isopropylpyrimidin-5-yl)phenoxy)pyridin-4-yl)-2,7-diazaspiro[4.4]nonan-2-yl)methyl)-1,3-dihydro-2H-benzo[d]imidazol-2-one

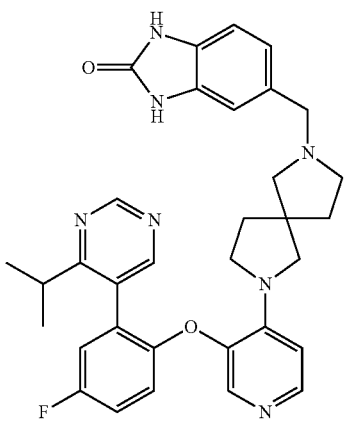

Step 1.
4-fluoro-2-(4-isopropylpyrimidin-5-yl)phenol

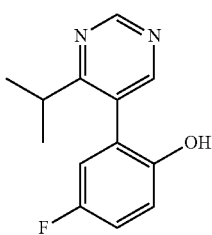 [SMILES: CC(C)c1ncncc1-c1cc(F)ccc1O]

To a solution of 2-bromo-4-fluorophenol (650 mg, 3.40 mmol) in dioxane (15 mL) and H$_2$O (3 mL) was added (4-isopropylpyrimidin-5-yl)boronic acid (622 mg, 3.74 mmol), Pd(dppf)Cl$_2$ (125 mg, 0.17 mmol) and Na$_2$CO$_3$ (720 mg, 6.55 mmol). The resulting mixture was degassed with N$_2$ and stirred at 90° C. in an oil bath under N$_2$ for about 20 h. The reaction mixture was concentrated under reduced pressure to remove dioxane and the resulting residue was diluted with EtOAc (20 mL). The suspension was filtered through a short pad of silica gel. The filtrate was diluted with EtOAc (20 mL) and water (20 mL). The organic layer was separated, washed with brine (2×30 mL) and concentrated under reduced pressure. The residue was purified by column chromatography on silica gel (petroleum ether:EtOAc=10:1 to 1:1) to give 4-fluoro-2-(4-isopropylpyrimidin-5-yl)phenol as a yellow solid. Yield: 300 mg. LCMS method C: R$_t$=0.705 min; (M+H)$^+$=233.1.

Step 2. tert-butyl 7-(3-(4-fluoro-2-(4-isopropylpyrimidin-5-yl)phenoxy)pyridin-4-yl)-2,7-diazaspiro[4.4]nonane-2-carboxylate

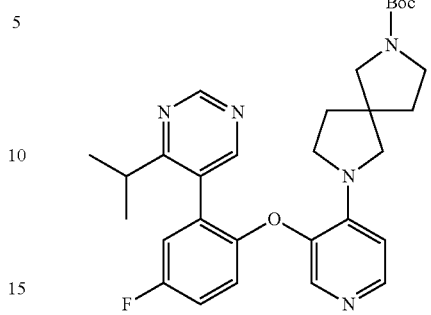

To a solution of 4-fluoro-2-(4-isopropylpyrimidin-5-yl)phenol (250 mg, 1.08 mmol) in DMSO (25 mL) was added tert-butyl 7-(3-bromopyridin-4-yl)-2,7-diazaspiro[4.4]nonane-2-carboxylate (412 mg, 1.08 mmol), CuI (206 mg, 1.08 mmol), 2-picolinic acid (266 mg, 2.16 mmol) and K$_3$PO$_4$ (916 mg, 4.32 mmol). The resulting mixture was purged with N$_2$ for 10 min and stirred at 110° C. in an oil bath under N$_2$ for about 24 h. The reaction mixture was diluted with water (30 mL) and extracted with EtOAc (2×30 mL). The organic layers were washed with brine (3×40 mL), dried over anhydrous Na$_2$SO$_4$, filtered and concentrated under reduced pressure. The residue was purified by preparative TLC (EtOAc) to give tert-butyl 7-(3-(4-fluoro-2-(4-isopropylpyrimidin-5-yl)phenoxy)pyridin-4-yl)-2,7-diazaspiro[4.4]nonane-2-carboxylate as a yellow solid. Yield: 25 mg. LCMS method C: R$_t$=0.747 min; (M+H)$^+$=534.1.

Steps 3-4. 5-((7-(3-(4-fluoro-2-(4-isopropylpyrimidin-5-yl)phenoxy) pyridin-4-yl)-2,7-diazaspiro[4.4]nonan-2-yl)methyl)-1H-benzo[d]imidazol-2(3H)-one Steps 3 and 4 were performed as described in Example 1, Steps 4-5. LCMS method C: R$_t$=1.190 min; (M+H)$^+$=580.3. $^1$H NMR (MeOD-d4): δ 9.12 (s, 1H), 8.67 (s, 1H), 7.91-8.10 (m, 2H), 7.10-7.38 (m, 6H), 6.89 (s, 1H), 4.40-4.48 (m, 2H), 3.37-3.87 (m, 8H), 3.00-3.14 (m, 1H), 1.99-2.25 (m, 4H), 1.11-1.29 (m, 6H). $^{19}$F NMR (MeOD-d4): δ −118.50, −76.93.

Example 29

5-((7-(5-(2-(3-cyclopropyl-1-methyl-6-oxo-1,6-dihydropyridin-2-yl)-4-fluorophenoxy)pyrimidin-4-yl)-2,7-diazaspiro[4.4]nonan-2-yl)methyl)-1,3-dihydro-2H-benzo[d]imidazol-2-one (Racemic Mixture)

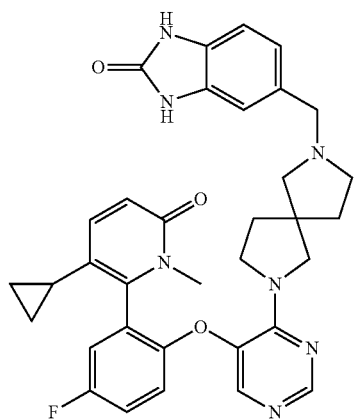 [SMILES: Cn1c(-c2cc(F)ccc2Oc2cncnc2N2CCC3(CCN(Cc4ccc5[nH]c(=O)[nH]c5c4)C3)C2)c(C2CC2)ccc1=O]

Step 1. 2-chloro-3-cyclopropyl-6-methoxypyridine

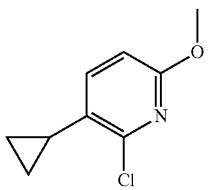

To a round bottom flask was added 3-bromo-2-chloro-6-methoxypyridine (10.57 g), cyclopropyl boronic acid (4.28 g), palladium acetate (533 mg), tricyclohexylphosphine (1.33 g) and potassium phosphate (35.2 g). To this solid mixture was added toluene:H$_2$O (158 mL; 9:1 ratio). The heterogeneous mixture was purged with a nitrogen stream for 1 min and then was heated at reflux overnight. The reaction mixture was diluted with EtOAc (100 mL) and water (100 mL). The phases were separated and the aqueous phase was back extracted twice with ethyl acetate (100 mL each). The combined organic phases were dried over magnesium sulfate and the crude residue was purified by flash chromatography (ethyl acetate/hexanes as the eluents) yielding 8.6 grams of 2-chloro-3-cyclopropyl-6-methoxypyridine as a colorless oil. LCMS method A: R$_t$=0.61 min; (M+H)$^+$= 222.2, 224.2. $^1$H NMR (CD$_3$OD): δ 8.45 (s, 1H), 8.33 (s, 1H), 3.90-4.00 (m, 2H), 3.70-3.80 (m, 2H), 3.20-3.55 (m, 4H), 1.80-2.0 (m, 4H), 1.27 (s, 9H).

Step 2. 6-chloro-5-cyclopropylpyridin-2(1H)-one

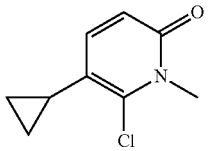

To a round bottom flask was added 2-chloro-3-cyclopropyl-6-methoxypyridine (15.6 g) and acetonitrile (170 mL). To this solution was added chlorotrimethylsilane (21.6 mL) followed by sodium iodide (25.6 g,). The heterogenous solution was heated at 50° C. for 3 h. Methanol (40 mL) was then added to quench the reaction and the volatiles were removed under vacuum. Dichloromethane was added (250 mL) and the solution was stirred for 30 min. The solids were precipitated, filtered out, and the filtrate was concentrated. The crude residue was purified by flash chromatography (120 g SiO$_2$, MeOH/CH$_2$Cl$_2$ as the eluents yielding a light brown oil (14 g). LCMS method A: R$_t$=0.0.54 min; (M+H)$^+$= 222.2, 224.2 $^1$H NMR (CDCl$_3$): δ 7.19 (d, J=8.4 Hz, 1H), 6.59 (d, J=8.0 Hz, 1H), 3.93 (s, 3H), 1.95-2.10 (m, 1H), 0.90-1.05 (m, 2H), 0.55-0.65 (m, 4H).

Step 3. 6-chloro-5-cyclopropyl-1-methylpyridin-2(1H)-one

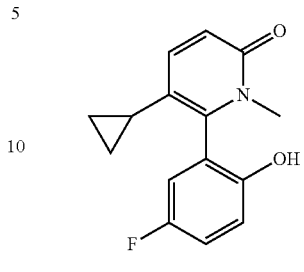

To a round bottom flask was added 6-chloro-5-cyclopropylpyridin-2(1H)-one (7.9 g), potassium carbonate (12.9 g), lithium bromide (8.12 g) and tetrabutyl ammonium bromide (1.5 g). To this solid mixture was added toluene:H$_2$O (156 mL, 100:1 ratio) followed by methyl iodide (14.6 mL) and the heterogenous mixture was heated at 50° C. The reaction mixture was diluted with EtOAc and washed with 1M HCl. The organic phase was dried over MgSO$_4$ and concentrated. The crude material was purified by flash chromatography (120 g SiO$_2$, MeOH/CH$_2$Cl$_2$ as the eluents) yielding 4.5 g of 6-chloro-5-cyclopropyl-1-methylpyridin-2(1H)-one as a light yellow oil. LCMS method A: R$_t$=0.0.63 min; (M+H)$^+$ =222.2, 224.2

Step 4. 5-cyclopropyl-6-(5-fluoro-2-hydroxyphenyl)-1-methylpyridin-2(1H)-one

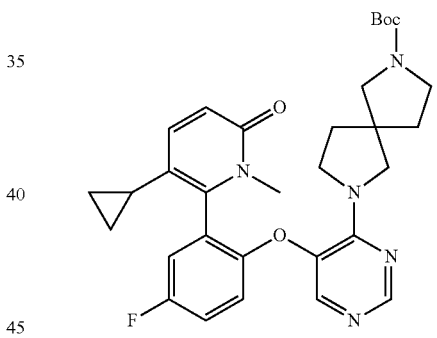

To a 100 mL round bottom flask was added (5-fluoro-2-hydroxyphenyl)boronic acid (852 mg), Sphos palladacyle Gen 2 (39 mg), potassium fluoride (951 mg), and 6-chloro-5-cyclopropyl-1-methylpyridin-2(1H)-one (500 mg). To this solid mixture was added dioxane (8 mL) and water (2 mL). The solution was purged with N$_2$ for 1 min and then heated at reflux for 2 h. Toluene:EtOAc (30 mL, 1:1 ratio) was added, followed by water (30 mL). The solid were filtered out and rinsed with 15 mL of toluene:EtOAc (1:1), Yielding 581 mg of the desired product. LC/MS (16 min method)— R$_t$=5.40 min.; M+H=260.56 1H NMR (d4-MeOH)—7.27 (d, 1H), 7.11 (dd, 1H), 6.99-6.3 (m, 2H), 6.55 (d, 1H), 3.32 (s, 3H), 1.40 (m, 1H), 0.71-0.66 (m, 1H), 0.49-0.60 (m, 3H) ppm.

Steps 5-7. 5-((7-(5-(2-(3-cyclopropyl-1-methyl-6-oxo-1,6-dihydropyridin-2-yl)-4-fluorophenoxy)pyrimidin-4-yl)-2,7-diazaspiro[4.4]nonan-2-yl)methyl)-1,3-dihydro-2H-benzo[d]imidazol-2-one The title product was prepared as described in Steps 2-4 of Example 28. LC/MS method G R$_t$=3.15 min.;

M+H=608.64. ¹H NMR (d4-MeOH) 8.21 (s, 1H), 7.75 (s, 1H), 7.30-7.34 (m, 2H), 7.15 (m, 1H), 6.97-7.06 (m, 4H), 6.54 (d, 1H), 3.57-3.69 (m, 4H), 3.42-3.52 (m, 2H), 3.31 (d, 3H), 2.72 (bm, 2H), 2.55 (bm, 2H), 1.89 (m, 2H), 1.79 (m, 2H), 1.28 (m, 1H), 0.75 (m, 1H), 0.66 (m, 1H), 0.55 (m, 1H), 0.48 (m, 1H) ppm.

Examples 29A-29B 5-((7-(5-(2-(3-cyclopropyl-1-methyl-6-oxo-1,6-dihydropyridin-2-yl)-4-fluorophenoxy)pyrimidin-4-yl)-2,7-diazaspiro[4.4]nonan-2-yl)methyl)-1,3-dihydro-2H-benzo[d]imidazol-2-one (Isomers 1-2)

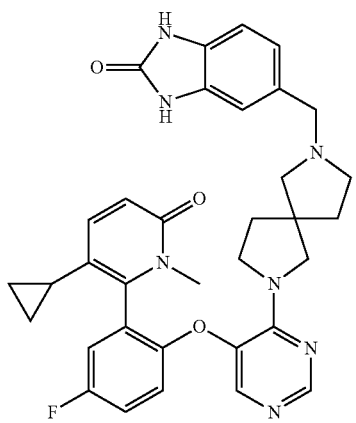 [SMILES: Cn1c(-c2cc(F)ccc2Oc2cncnc2N2CCC3(CCN(Cc4ccc5[nH]c(=O)[nH]c5c4)C3)C2)c(C2CC2)ccc1=O]

The compound of Example 29 was separated by SFC method A to afford two isomers.

Example 29A (Isomer 1)

¹H NMR (CD₃OD): δ 8.24 (d, J=5.2 Hz, 1H), 7.77 (s, 1H), 7.30-7.40 (m, 2H), 7.10-7.20 (m, 1H), 6.95-7.07 (m, 4H), 6.50-6.60 (m, 1H), 3.40-3.70 (m, 6H), 3.30-3.40 (m, 3H), 2.60-2.70 (m, 2H), 2.40-2.50 (m, 2H), 1.75-1.95 (m, 4H), 1.20-1.35 (m, 1H), 0.40-0.85 (m, 4H). ¹⁹F NMR: (CD₃OD 400 MHz): δ −119.20~−119.12. SFC: $t_R$=17.556 min, EE=98.93%. ROTATION: OR °Arc=0.389.

Example 29B (Isomer 2)

¹H NMR (CD₃OD): δ 8.24 (d, J=5.2 Hz, 1H), 7.77 (s, 1H), 7.30-7.40 (m, 2H), 7.10-7.20 (m, 1H), 7.00-7.07 (m, 4H), 6.50-6.60 (m, 1H), 3.50-3.70 (m, 6H), 3.30-3.40 (m, 3H), 2.60-2.75 (m, 2H), 2.40-2.50 (m, 2H), 1.75-1.95 (m, 4H), 1.20-1.35 (m, 1H), 0.45-0.85 (m, 4H). ¹⁹F NMR: (CD₃OD): δ −119.21~−119.13. SFC: $t_R$=14.363 min, EE=98.46%.

Example 30

N-(5-fluoro-2'-isopropyl-[1,1'-biphenyl]-2-yl)-4-(6-((tetrahydro-2H-pyran-4-yl)methyl)-2,6-diazaspiro[3.3]heptan-2-yl)pyridin-3-amine

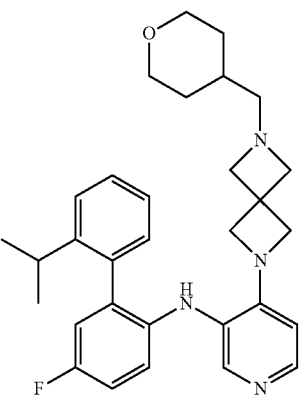 [SMILES: CC(C)c1ccccc1-c1cc(F)ccc1Nc1cnccc1N1CC2(CN(CC3CCOCC3)C2)C1]

The title product was synthesized by the method described for Example 28. In Step 1, 2-bromo-4-fluoroaniline and 2-isopropyl phenyl boronic acid were utilized. In Step 2, tert-butyl 2,6-diazaspiro[3.3]heptane-2-carboxylate was utilized. In Step 5, tetrahydro-2H-pyran-4-carbaldehyde was utilized. LCMS method A: $R_f$=0.96 min; (M+H)⁺=500. ¹H NMR (CD₃OD) δ: 8.00 (d, J=6.4 Hz, 1H), 7.77 (s, 1H), 7.49-7.43 (m, 2H), 7.31-7.23 (m, 2H), 7.02 (s, 1H), 6.88 (d, J=7.2 Hz, 1H), 6.64-6.57 (m, 2H).

Example 31

2-(5-((4',5-difluoro-2'-(2-fluoropropan-2-yl)-[1,1'-biphenyl]-2-yl)oxy)pyrimidin-4-yl)-6-((tetrahydro-2H-pyran-4-yl)methyl)-2,6-diazaspiro[3.3]heptane

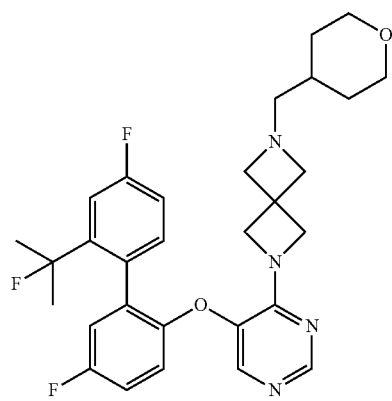 [SMILES: CC(C)(F)c1cc(F)ccc1-c1cc(F)ccc1Oc1cncnc1N1CC2(CN(CC3CCOCC3)C2)C1]

Step 1. methyl 2-bromo-5-fluorobenzoate

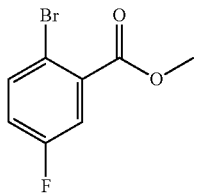

To a solution of 2-bromo-5-fluorobenzoic acid (4.00 g, 18.26 mmol) in MeOH (120 mL, anhydrous) was added SOCl$_2$ (3.26 g, 27.40 mmol) dropwise at 0° C. and the mixture was heated at 68° C. for 18 h. TLC (petroleum ether:EtOAc=5:1) confirmed the desired product. The mixture was concentrated and the residue was mixed with EtOAc (200 mL), washed by NaHCO$_3$ (150 mL), brine (150 mL), dried over anhydrous Na$_2$SO$_4$, filtered and concentrated to give methyl 2-bromo-5-fluorobenzoate as a colorless oil. Yield: 2.7 g LCMS method C: R$_t$=0.77 min.

Step 2: 2-(2-bromo-5-fluorophenyl)propan-2-ol

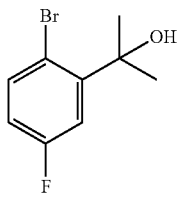

To a solution of 2-bromo-5-fluorobenzoate (2.70 g, 11.59 mmol) in THF (85 mL, anhydrous) at 0° C. under N$_2$ was added MeMgBr (9.66 mL, 28.97 mmol, 3.0 M in Et$_2$O) dropwise, and the mixture was stirred at 23-28° C. for 4 h. The mixture was quenched by aq. sat. NH$_4$Cl (80 mL) and extracted by EtOAc (60 mL). The organic layer was washed with brine (40 mL), dried over anhydrous Na$_2$SO$_4$, filtered and concentrated. The residue was purified by ISCO column chromatography on silica gel (13% EtOAc in petroleum ether) to give 2-(2-bromo-5-fluorophenyl)propan-2-ol as a colorless oil. Yield: 2.5 g (94%). $^1$H NMR (CDCl$_3$): δ 7.42-7.57 (m, 2H), 6.77-6.88 (m, 1H), 1.75 (s, 6H).

Step 3.
1-bromo-4-fluoro-2-(2-fluoropropan-2-yl)benzene

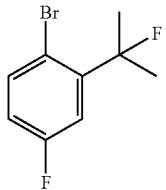

To a solution of 2-(2-bromo-5-fluorophenyl)propan-2-ol (2.54 g, 10.90 mmol) at −78° C. was added DAST (2.28 g, 14.17 mmol) dropwise. The resulting mixture was stirred at 21-27° C. for 18 h. The mixture was quenched by aq. sat. NH$_4$Cl (50 mL), extracted by EtOAc (50 mL), washed by brine (50 mL), dried over anhydrous Na$_2$SO$_4$, filtered and concentrated. The resulting residue was purified by ISCO column chromatography (5% EtOAc in petroleum ether) to give 1-bromo-4-fluoro-2-(2-fluoropropan-2-yl)benzene as a colorless oil. Yield: 2.2 g. $^1$H NMR (CDCl$_3$): δ 7.49-7.56 (m, 1H), 7.40 (dd, J=10.5, 3.0 Hz, 1H), 6.81-6.90 (m, 1H), 1.88 (s, 3H), 1.82 (s, 3H).

Step 4. 4',5-difluoro-2'-(2-fluoropropan-2-yl)-[1,1'-biphenyl]-2-ol

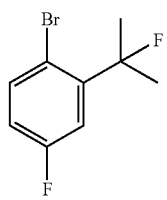

A solution of 1-bromo-4-fluoro-2-(2-fluoropropan-2-yl) benzene (400 mg, 1.70 mmol), (5-fluoro-2-hydroxyphenyl) boronic acid (316 mg, 2.04 mmol) and K$_3$PO$_4$ (720 mg, 3.40 mmol) in dioxane (9 mL) and H$_2$O (3 mL) was bubbled with N$_2$ for 1 min and SPhos Palladacycle (62 mg, 0.086 mmol) was then added. The resulting mixture was heated under a microwave at 115° C. for 0.5 h. The mixture was diluted by EtOAc (30 mL) and H$_2$O (30 mL). The organic layer was washed with brine (30 mL), dried over anhydrous Na$_2$SO$_4$, filtered and concentrated. The residue was purified by preparative TLC on silica gel (petroleum ether:EtOAc=5:1) to give 4',5-difluoro-2'-(2-fluoropropan-2-yl)-[1,1'-biphenyl]-2-ol as a light yellow gel. Yield: 380 mg. LCMS method A: R$_t$=1.070 min; (M+H)$^+$=247.1.

Step 5. tert-butyl 6-(5-((4',5-difluoro-2'-(2-fluoropropan-2-yl)-[1,1'-biphenyl]-2-yl)oxy) pyrimidin-4-yl)-2,6-diazaspiro[3.3]heptane-2-carboxylate

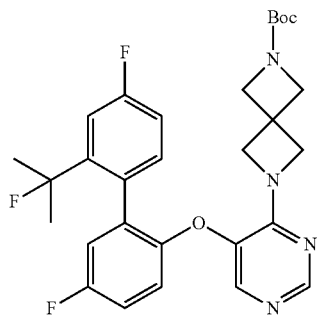 [SMILES: CC(C)(C)OC(=O)N1CC2(C1)CN(c1ncncc1Oc1ccc(F)cc1-c1ccc(F)cc1C(C)(C)F)C2]

To a solution of tert-butyl 6-(5-iodopyrimidin-4-yl)-2,6-diazaspiro[3.3]heptane-2-carboxylate (231 mg, 0.58 mmol) in DMSO (6 mL) was bubbled N$_2$ for 1 min and a solution of 4',5-difluoro-2'-(2-fluoropropan-2-yl)-[1,1'-biphenyl]-2-ol (183 mg, 0.69 mmol) in DMSO (2 mL) was then added. The resulting mixture was heated at 110° C. for 22 h. The mixture was then diluted by EtOAc (25 mL) and H$_2$O (25 mL). The organic layer was washed by brine (20 mL), dried over anhydrous Na$_2$SO$_4$, filtered and concentrated. The residue was purified by basic prep-HPLC to give tert-butyl 6-(5-((4',5-difluoro-2'-(2-fluoropropan-2-yl)-[1,1'-biphenyl]-2-yl)oxy) pyrimidin-4-yl)-2,6-diazaspiro[3.3]heptane-2-carboxylate as a colorless gel. Yield: 90 mg. LCMS method C: R$_f$=0.808 min; (M+H)$^+$=541.2.

Step 6. 2-(5-((4',5-difluoro-2'-(2-fluoropropan-2-yl)-[1,1'-biphenyl]-2-yl)oxy)pyrimidin-4-yl)-2,6-diazaspiro[3.3]heptane

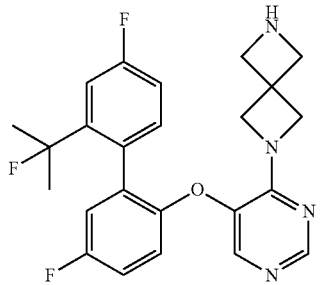 [SMILES: CC(C)(F)c1cc(F)ccc1-c1cc(F)ccc1Oc1cncnc1N1CC2(CNC2)C1]

To a solution of tert-butyl 6-(5-((4',5-difluoro-2'-(2-fluoropropan-2-yl)-[1,1'-biphenyl]-2-yl)oxy) pyrimidin-4-yl)-2,6-diazaspiro[3.3]heptane-2-carboxylate (40 mg, 0.09 mmol) in DCM (2 mL, anhydrous) cooled to 0° C. was added TFA (0.25 mmol). The mixture was stirred at 0° C. for 4 h. The mixture was quenched by aq. sat. NaHCO$_3$ (5 mL). Then DCM (20 mL) was added, the organic layer was separated, dried over anhydrous Na$_2$SO$_4$, filtered and concentrated to give the crude product of 2-(5-((4',5-difluoro-2'-(2-fluoropropan-2-yl)-[1,1'-biphenyl]-2-yl)oxy)pyrimidin-4-yl)-2,6-diazaspiro[3.3]heptane as a light yellow gel, which was directly used in the next step. Yield: 44 mg Step 7. 2-(5-((4',5-difluoro-2'-(2-fluoropropan-2-yl)-[1,1'-biphenyl]-2-yl)oxy) pyrimidin-4-yl)-6-((tetrahydro-2H-pyran-4-yl)methyl)-2,6-diazaspiro[3.3]heptanes To a solution of 2-(5-((4',5-difluoro-2'-(2-fluoropropan-2-yl)-[1,1'-biphenyl]-2-yl)oxy) pyrimidin-4-yl)-2,6-diazaspiro[3.3]heptane (44 mg, 0.10 mmol, crude) and tetrahydro-2H-pyran-4-carbaldehyde (15 mg, 0.13 mmol) in MeOH (2 mL, anhydrous) was added NaBH$_3$CN (12 mg, 0.20 mmol) and the mixture was stirred at 20-25° C. for 17 h. LCMS showed the desired product was produced in ~30% yield, and a byproduct was also produced in ~32% yield. The mixture was concentrated, and the residue was purified by basic RP-HPLC method D to give 2-(5-((4',5-difluoro-2'-(2-fluoropropan-2-yl)-[1,1'-biphenyl]-2-yl)oxy)pyrimidin-4-yl)-6-((tetrahydro-2H-pyran-4-yl)methyl)-2,6-diazaspiro[3.3]heptanes as a colorless gel. Yield: 6.7 mg. LCMS method C: R$_f$=0.88 min; (M+H)$^+$=539.2. $^1$H NMR (CD$_3$OD): δ 8.15 (s, 1H), 7.61 (s, 1H), 7.25 (dd, J=10.8, 2.4 Hz, 1H), 7.04-7.20 (m, 4H), 7.00 (dd, J=9.2, 4.8 Hz, 1H), 4.14-4.22 (m, 4H), 3.93 (dd, J=11.2, 4.0 Hz, 2H), 3.35-3.45 (m, 6H), 2.38 (d, J=6.4 Hz, 2H), 1.57-1.66 (m, 8H), 1.19-1.33 (m, 2H). $^{19}$F NMR (CD$_3$OD): δ −115.50, −121.33, −132.73.

Example 32

5-fluoro-N-isopropyl-2-((4-(6-((tetrahydro-2H-pyran-4-yl)methyl)-2,6-diazaspiro[3.3]heptan-2-yl)pyrimidin-5-yl)oxy)benzenesulfonamide

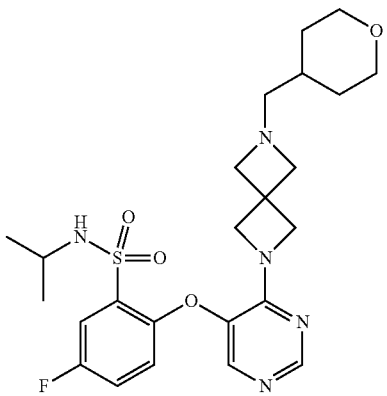 [SMILES: CC(C)NS(=O)(=O)c1cc(F)ccc1Oc1cncnc1N1CC2(CN(CC3CCOCC3)C2)C1]

Step 1. tert-butyl 6-(5-(2-(benzylthio)-4-fluorophenoxy)pyrimidin-4-yl)-2,6-diazaspiro[3.3]heptane-2-carboxylate

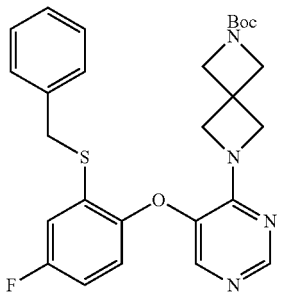 [SMILES: CC(C)(C)OC(=O)N1CC2(C1)CN(c1ncncc1Oc1ccc(F)cc1SCc1ccccc1)C2]

A mixture of tert-butyl 6-(5-(2-bromo-4-fluorophenoxy)pyrimidin-4-yl)-2,6-diazaspiro[3.3]heptane-2-carboxylate (Intermediate 20, 200 mg, 0.43 mmol), benzyl mercaptan (0.06 mL, 0.52 mmol), Pd$_2$(dba)$_3$ (39 mg, 10 mol %), Xantphos (50 mg, 20 mol %) and iPrNEt (0.15 mL, 0.86 mmol) in dioxane was heated to 110° C. in a CEM microwave for 2.5 h. The reaction mixture was then filtered through celite and the solvents evaporated. The crude residue was purified using ISCO flash column chromatography (eluting with 100% EtOAc) to afford 210 mg of tert-butyl 6-(5-(2-(benzylthio)-4-fluorophenoxy)pyrimidin-4-yl)-2,6-diazaspiro[3.3]heptane-2-carboxylate as a yellow solid (96%). LCMS method B: R$_f$=1.544 min; (M+H)$^+$=509.6.

Step 2. tert-butyl 6-(5-(2-(chlorosulfonyl)-4-fluorophenoxy)pyrimidin-4-yl)-2,6-diazaspiro[3.3]heptane-2-carboxylate

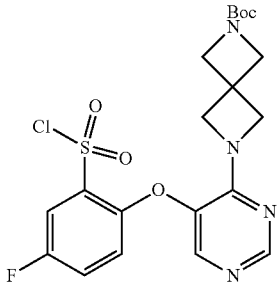 [SMILES: CC(C)(C)OC(=O)N1CC2(C1)CN(c1ncncc1Oc1ccc(F)cc1S(=O)(=O)Cl)C2]

To a solution of tert-butyl 6-(5-(2-(benzylthio)-4-fluorophenoxy)pyrimidin-4-yl)-2,6-diazaspiro[3.3]heptane-2-carboxylate (50 mg, 0.10 mmol) in MeCN (2 mL), H$_2$O (0.10 mL) and AcOH (0.10 mL) was added 1,3-dichloro-5,5-dimethylimidazolidine-2,4-dione (39 mg, 0.20 mmol) at 0° C. The reaction was warmed to RT and stirred for 2 h. EtOAc (5 mL) and H$_2$O (5 mL) were then added for the workup. The EtOAc layer was separated, dried using Na$_2$SO$_4$, and evaporated. The crude residue was purified using ISCO flash column chromatography (eluting with 10% MeOH in DCM) to afford 21 mg of tert-butyl 6-(5-(2-(chlorosulfonyl)-4-fluorophenoxy)pyrimidin-4-yl)-2,6-diazaspiro[3.3]heptane-2-carboxylate. LCMS method B: R$_t$=1.492 min; (M+H)$^+$=485.47 and 487.50

Step 3. tert-butyl 6-(5-(4-fluoro-2-(N-isopropylsulfamoyl)phenoxy)pyrimidin-4-yl)-2,6-diazaspiro[3.3]heptane-2-carboxylate

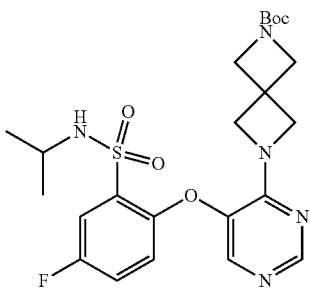 [SMILES: CC(C)NS(=O)(=O)c1cc(F)ccc1Oc1cncnc1N1CC2(CN(C(=O)OC(C)(C)C)C2)C1]

To a solution of tert-butyl 6-(5-(2-(chlorosulfonyl)-4-fluorophenoxy)pyrimidin-4-yl)-2,6-diazaspiro[3.3]heptane-2-carboxylate (21 mg, 0.04 mmol) in DCM (2 mL) was added propan-2-amine (0.20 mL) at RT. After 1 h, the solvents were removed and the crude product was triturated with 50% EtOAc in hexanes to afford 15 mg of tert-butyl 6-(5-(4-fluoro-2-(N-isopropylsulfamoyl)phenoxy)pyrimidin-4-yl)-2,6-diazaspiro[3.3]heptane-2-carboxylate (75%). LCMS method B: R$_t$=1.374 min; (M+H)$^+$=508.64

Step 4. 2-((4-(2,6-diazaspiro[3.3]heptan-2-yl)pyrimidin-5-yl)oxy)-5-fluoro-N-isopropylbenzenesulfonamide

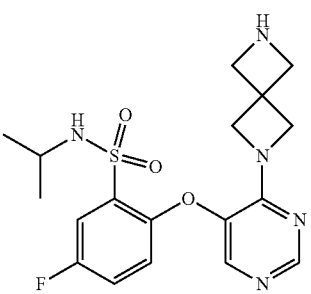 [SMILES: CC(C)NS(=O)(=O)c1cc(F)ccc1Oc1cncnc1N1CC2(CNC2)C1]

To a solution of tert-butyl 6-(5-(4-fluoro-2-(N-isopropylsulfamoyl)phenoxy)pyrimidin-4-yl)-2,6-diazaspiro[3.3]heptane-2-carboxylate (15 mg) in DCM (3 mL) was added TFA (1 mL) at RT. The reaction stirred for 30 min at RT and the solvents were then removed to afford 2-((4-(2,6-diazaspiro[3.3]heptan-2-yl)pyrimidin-5-yl)oxy)-5-fluoro-N-isopropylbenzenesulfonamide TFA salt. The material was mixed with DCM and Et$_3$N (0.10 mL) was added. Upon complete dissolution of the material, the solvents were removed to afford the product as the free base. This crude material was used directly for the next step without further purification.

Step 5. 5-fluoro-N-isopropyl-2-((4-(6-((tetrahydro-2H-pyran-4-yl)methyl)-2,6-diazaspiro[3.3]heptan-2-yl)pyrimidin-5-yl)oxy)benzenesulfonamide To solution of crude 2-((4-(2,6-diazaspiro[3.3]heptan-2-yl)pyrimidin-5-yl)oxy)-5-fluoro-N-isopropylbenzenesulfonamide and tetrahydro-2H-pyran-4-carbaldehyde (14 mg, 0.12 mmol) in dichloroethane (2 mL, containing 1% AcOH) was added NaBH(OAc)$_3$ (25 mg, 0.12 mmol) at RT. The reaction mixture was stirred for 30 min and the reaction was confirmed complete by LCMS analysis. Evaporation of the solvent followed by purification using a Gilson HPLC afforded 5-fluoro-N-isopropyl-2-((4-(6-((tetrahydro-2H-pyran-4-yl)methyl)-2,6-diazaspiro[3.3]heptan-2-yl)pyrimidin-5-yl)oxy)benzenesulfonamide TFA salt. LCMS method B: R$_t$=1.293 min; (M+H)$^+$=506.57. $^1$H NMR (CD$_3$OD): δ 8.55 (d, J=4.8 Hz, 1H), 7.77-7.75 (m, 2H), 7.53-7.49 (m, 1H), 7.40-7.37 (m, 1H), 4.60-4.40 (m, 8H), 3.96 (d, J=11.6 Hz, 2H), 3.57-3.54 (m, 1H), 3.44 (t, J=11.6 Hz, 2H), 3.17 (d, J=6.8 Hz, 2H), 2.00-1.84 (m, 1H), 1.63 (d, J=11.6 Hz, 2H), 1.40-1.32 (m, 2H), 1.17 (d, J=6.0 Hz, 6H).

Example 33

5-((7-(5-(4-fluoro-2-(2-methoxybutan-2-yl)phenoxy)pyrimidin-4-yl)-2,7-diazaspiro[4.4]nonan-2-yl)methyl)-1,3-dihydro-2H-benzo[d]imidazol-2-one

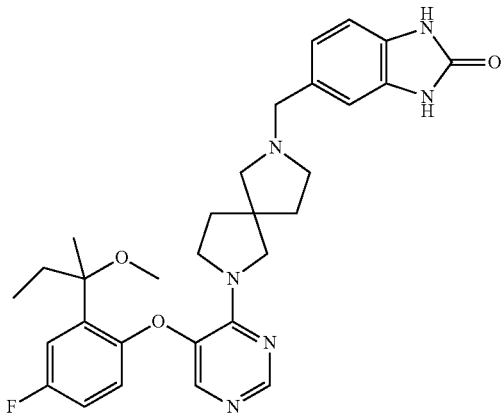 [SMILES: CCC(C)(OC)c1cc(F)ccc1Oc1cncnc1N1CCC2(CCN(Cc3ccc4[nH]c(=O)[nH]c4c3)C2)C1]

Step 1. tert-butyl 7-(5-(4-fluoro-2-(2-hydroxybutan-2-yl)phenoxy)pyrimidin-4-yl)-2,7-diazaspiro[4.4]nonane-2-carboxylate

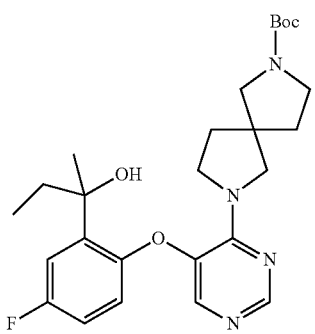 [SMILES: CCC(C)(O)c1cc(F)ccc1Oc1cncnc1N1CCC2(CCN(C(=O)OC(C)(C)C)C2)C1]

To a solution of tert-butyl 7-(5-(2-bromo-4-fluorophenoxy)pyrimidin-4-yl)-2,7-diazaspiro[4.4]nonane-2-carboxylate (Intermediate 11, 53 mg, 0.11 mmol) and butan-2-one (5 equiv.) in THF (2 mL) was added a 1.6 M solution of n-BuLi in hexanes (0.08 mL) at −78° C. The reaction mixture was warmed to RT over 1 h and upon reaching RT, a saturated NH$_4$Cl aqueous solution (1 mL) was added in addition to EtOAc (5 mL) for the workup. Purification of the crude residue using ISCO flash column chromatography (eluting with 5% MeOH in DCM) gave 20 mg of tert-butyl 7-(5-(4-fluoro-2-(2-hydroxybutan-2-yl)phenoxy)pyrimidin-4-yl)-2,7-diazaspiro[4.4]nonane-2-carboxylate (38%). LCMS method B: R$_t$=1.589 min; (M+H)$^+$=487.62. $^1$H NMR (CDCl$_3$): δ 8.42 (s, 1H), 7.76 (s, 1H), 7.36 (d, J=9.2 Hz, 1H), 6.90-6.86 (m, 1H), 6.58-6.50 (m, 1H), 3.80-3.25 (m, 8H), 2.53-2.42 (m, 1H), 2.15-2.05 (m, 1H), 1.95-1.82 (m, 5H), 1.65 (s, 3H), 1.45 (s, 9H), 0.84 (t, J=7.6 Hz, 3H).

Step 2. 2-(2-((4-(2,7-diazaspiro[4.4]nonan-2-yl)pyrimidin-5-yl)oxy)-5-fluorophenyl)butan-2-ol A 4 N solution of HCl in dioxane (2 mL) was added to tert-butyl-7-(5-(4-fluoro-2-(2-hydroxybutan-2-yl)phenoxy)pyrimidin-4-yl)-2,7-diazaspiro[4.4]nonane-2-carboxylate (10 mg) at RT and the reaction mixture was stirred for 2 h. The solvents were removed to afford the product as the HCl salt. DCM (2 mL) and Et$_3$N (0.10 mL) were added to the product and the solvents were removed to afford crude 2-(2-((4-(2,7-diazaspiro[4.4]nonan-2-yl)pyrimidin-5-yl)oxy)-5-fluorophenyl)butan-2-ol as the free base which was used for the next step without further purification.

Step 3. 5-((7-(5-(4-fluoro-2-(2-methoxybutan-2-yl)phenoxy)pyrimidin-4-yl)-2,7-diazaspiro[4.4]nonan-2-yl)methyl)-1,3-dihydro-2H-benzo[d]imidazol-2-one To a solution of crude 2-(2-((4-(2,7-diazaspiro[4.4]nonan-2-yl)pyrimidin-5-yl)oxy)-5-fluorophenyl)butan-2-ol and 2-oxo-2,3-dihydro-1H-benzo[d]imidazole-5-carbaldehyde (Intermediate 40, 7 mg, 0.04 mmol) in MeOH (3 mL) was added NaBH$_3$CN (8 mg, 0.13 mmol) at RT and the reaction mixture was stirred for 15 h. Evaporation of the solvent followed by purification by RP-HPLC method A afforded 5-((7-(5-(4-fluoro-2-(2-methoxybutan-2-yl)phenoxy)pyrimidin-4-yl)-2,7-diazaspiro[4.4]nonan-2-yl)methyl)-1,3-dihydro-2H-benzo[d]imidazol-2-one TFA salt. LCMS method G: R$_t$=4.01 min; (M+H)$^+$=547.62. $^1$H NMR (CD$_3$OD): δ 8.52 (bs, 1H), 7.65 (m, 1H), 7.34 (d, J=9.6 Hz, 1H), 7.21-7.18 (m, 2H), 7.13-7.10 (m, 3H), 4.43 (s, 2H), 4.20-3.95 (m, 4H), 3.70-3.50 (m, 2H), 3.47-3.36 (m, 2H), 3.15 (s, 3H), 2.34-2.05 (m, 4H), 1.96-1.87 (m, 2H), 1.58 (s, 3H), 0.76 (t, J=7.6 Hz, 3H).

Example 34

5-((7-(5-(4-fluoro-2-(3-hydroxypentan-3-yl)phenoxy)pyrimidin-4-yl)-2,7-diazaspiro[4.4]nonan-2-yl)methyl)-1,3-dihydro-2H-benzo[d]imidazol-2-one

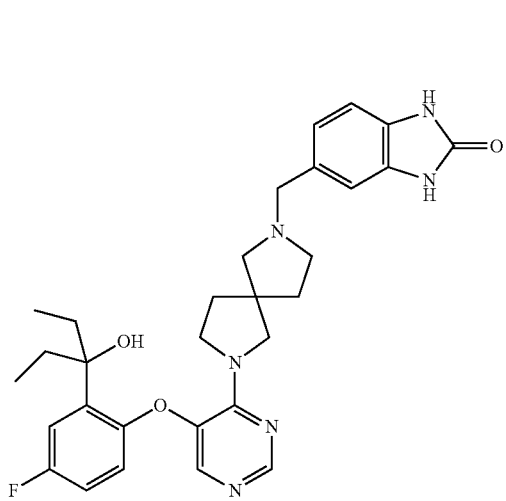 [SMILES: CCC(O)(CC)c1cc(F)ccc1Oc1cncnc1N1CCC2(CCN(Cc3ccc4[nH]c(=O)[nH]c4c3)C2)C1]

Step 1. tert-butyl 7-(5-(4-fluoro-2-(3-hydroxypentan-3-yl)phenoxy)pyrimidin-4-yl)-2,7-diazaspiro[4.4]nonane-2-carboxylate

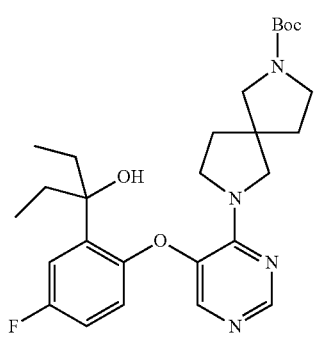 [SMILES: CCC(O)(CC)c1cc(F)ccc1Oc1cncnc1N1CCC2(CCN(C(=O)OC(C)(C)C)C2)C1]

To a solution of tert-butyl 7-(5-(2-bromo-4-fluorophenoxy)pyrimidin-4-yl)-2,7-diazaspiro[4.4]nonane-2-carboxylate (Intermediate 11, 106 mg, 0.22 mmol) and pentan-3-one (0.10 mL, 1.07 mmol) in THF (3 mL) was added a 1.6 M solution of n-BuLi in hexanes (0.66 mL) at −78° C. The reaction was warmed to RT over 1 h. Upon reaching RT, a saturated NH$_4$Cl aqueous solution (2 mL) was added in addition to EtOAc (8 mL) for the workup. Purification of the crude residue using flash column chromatography (eluting with 5% MeOH in DCM) gave 32 mg of tert-butyl-7-(5-(4-fluoro-2-(3-hydroxypentan-3-yl)phenoxy)pyrimidin-4-yl)-2,7-diazaspiro[4.4]nonane-2-carboxylate.

Step 2. 3-(2-((4-(2,7-diazaspiro[4.4]nonan-2-yl)pyrimidin-5-yl)oxy)-5-fluorophenyl)pentan-3-ol

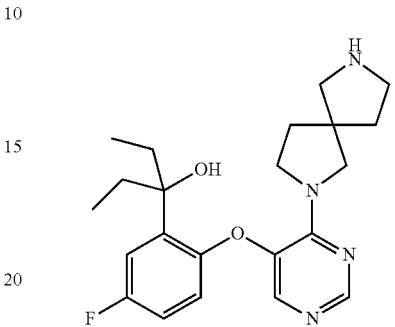

A 4 N solution of HCl in dioxane (2 mL) was added to tert-butyl 7-(5-(4-fluoro-2-(3-hydroxypentan-3-yl)phenoxy)pyrimidin-4-yl)-2,7-diazaspiro[4.4]nonane-2-carboxylate (32 mg) at RT and the reaction mixture was stirred for 2 h. The solvents were then removed to afford the product as the HCl salt. DCM (2 mL) and Et$_3$N (0.10 mL) were added to the product and the solvents were removed to afford crude 3-(2-((4-(2,7-diazaspiro[4.4]nonan-2-yl)pyrimidin-5-yl)oxy)-5-fluorophenyl)pentan-3-ol as the free base which was used for the next step without further purification.

Step 3. 5-((7-(5-(4-fluoro-2-(3-hydroxypentan-3-yl)phenoxy)pyrimidin-4-yl)-2,7-diazaspiro[4.4]nonan-2-yl)methyl)-1,3-dihydro-2H-benzo[d]imidazol-2-one To a solution of crude 3-(2-((4-(2,7-diazaspiro[4.4]nonan-2-yl)pyrimidin-5-yl)oxy)-5-fluorophenyl)pentan-3-ol from above and 2-oxo-2,3-dihydro-1H-benzo[d]imidazole-5-carbaldehyde (Intermediate 40, 20 mg, 0.12 mmol) in MeOH (3 mL) was added NaBH$_3$CN (10 mg, 0.16 mmol) at RT and the reaction mixture stirred for 4 h. Evaporation of the solvent followed by RP-HPLC method A afforded 5-((7-(5-(4-fluoro-2-(3-hydroxypentan-3-yl)phenoxy)pyrimidin-4-yl)-2,7-diazaspiro[4.4]nonan-2-yl)methyl)-1,3-dihydro-2H-benzo[d]imidazol-2-one. LCMS method G: R$_t$=3.197 min; (M+H)$^+$=547.61. $^1$H NMR (CD$_3$OD): δ 8.52 (bs, 1H), 7.60 (m, 1H), 7.45 (dd, J=2.8, 10.6 Hz, 1H), 7.21-7.18 (m, 2H), 7.11 (d, J=8.4 Hz, 2H), 7.05-6.96 (m, 1H), 4.43 (s, 2H), 4.20-3.90 (m, 4H), 3.70-3.50 (m, 2H), 3.48-3.33 (m, 2H), 2.34-1.90 (m, 6H), 1.89-1.80 (m, 2H), 0.78 (t, J=7.2 Hz, 6H).

Examples 35-36

2-(5-fluoro-2-((4-(7-((2-oxo-2,3-dihydro-1H-benzo[d]imidazol-5-yl)methyl)-2,7-diazaspiro[4.4]nonan-2-yl)pyrimidin-5-yl)oxy)phenyl)-N-methylcyclopropane carboxamide (Example 35) & 5-((7-(5-(4-fluoro-2-(3-hydroxy-3-methylbutyl)phenoxy)pyrimidin-4-yl)-2,7-diazaspiro[4.4]nonan-2-yl)methyl)-1H-benzo[d]imidazol-2(3H)-one (Example 36)

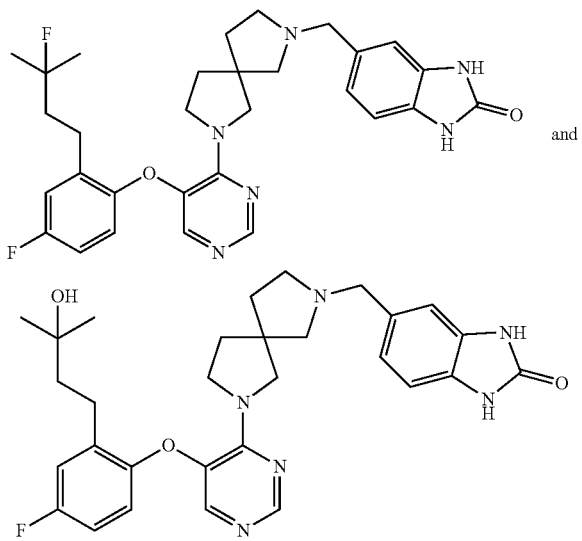

Step 1. tert-butyl 7-(5-(4-fluoro-2-(3-methoxy-3-oxopropyl)phenoxy)pyrimidin-4-yl)-2,7-diazaspiro[4.4]nonane-2-carboxylate

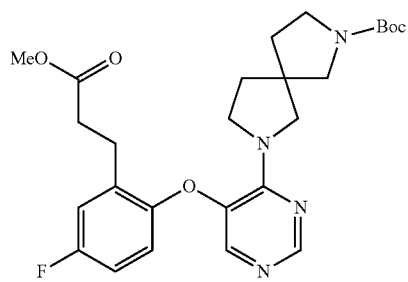 [SMILES: COC(=O)CCc1cc(F)ccc1Oc1cncnc1N1CCC2(CCN(C(=O)OC(C)(C)C)C2)C1]

To solution of (E)-tert-butyl 7-(5-(4-fluoro-2-(3-methoxy-3-oxoprop-1-en-1-yl)phenoxy)pyrimidin-4-yl)-2,7-diazaspiro[4.4]nonane-2-carboxylate (Example 37, Step 1, 450 mg, 0.9 mmmol) in anhydrous MeOH (25 mL) was added Pd/C (45 mg). The mixture was stirred under H$_2$ (30 psi) at 14-25° C. for 18 h. LCMS showed the reaction was complete. The mixture was filtered and concentrated to give tert-butyl 7-(5-(4-fluoro-2-(3-methoxy-3-oxopropyl)phenoxy)pyrimidin-4-yl)-2,7-diazaspiro[4.4]nonane-2-carboxylate as light yellow gel. Yield: 402 mg. LCMS method C: R$_t$=0.749 min; (M+H)$^+$=501.2.

Step 2. tert-butyl 7-(5-(4-fluoro-2-(3-hydroxy-3-methylbutyl)phenoxy)pyrimidin-4-yl)-2,7-diazaspiro[4.4]nonane-2-carboxylate

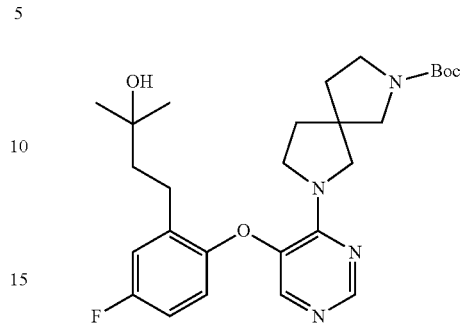

To solution of tert-butyl 7-(5-(4-fluoro-2-(3-methoxy-3-oxopropyl)phenoxy)pyrimidin-4-yl)-2,7-diazaspiro[4.4]nonane-2-carboxylate (200 mg, 0.4 mmol) in anhydrous THF (5 mL) was added dropwise methylmagnesium bromide (0.53 mL, 1.6 mmol) at 0° C. for 10 min. The mixture was quenched with saturation NH$_4$Cl (aq.) (10 mL) and extracted with ethyl acetate (20 mL×2). The combined organic layers were washed with brine (30 mL×3), dry over Na$_2$SO$_4$ and concentrated to purify by ISCO column on silica gel (100% DCM to 2% MeOH in DCM) to give tert-butyl 7-(5-(4-fluoro-2-(3-hydroxy-3-methylbutyl)phenoxy)pyrimidin-4-yl)-2,7-diazaspiro[4.4]nonane-2-carboxylate as colorless oil. Yield: 180 mg. LCMS method C: R$_t$=0.744 min; (M+H)$^+$=501.3.

Step 3. tert-butyl 7-(5-(4-fluoro-2-(3-fluoro-3-methylbutyl)phenoxy)pyrimidin-4-yl)-2,7-diazaspiro[4.4]nonane-2-carboxylate

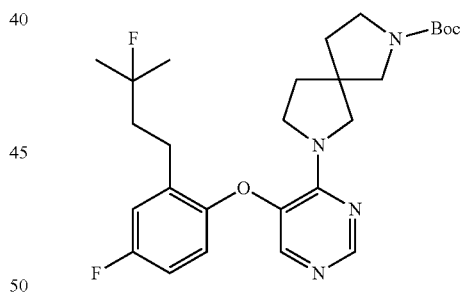

To solution of tert-butyl 7-(5-(4-fluoro-2-(3-hydroxy-3-methylbutyl)phenoxy)pyrimidin-4-yl)-2,7-diazaspiro[4.4]nonane-2-carboxylate (180 mg, 0.16 mmmol) in anhydrous CH$_2$Cl$_2$ (3 mL) was added DAST (70 mg, 0.43 mmol) at 0° C., dropwise over 5 min and the mixture was then stirred at 17-25° C. for 2 h. LCMS showed desired compound and that the tert-butyl 7-(5-(4-fluoro-2-(3-hydroxy-3-methylbutyl)phenoxy) pyrimidin-4-yl)-2,7-diazaspiro[4.4]nonane-2-carboxylate was consumed completely. The mixture was poured into saturated NH$_4$Cl (aq) (5 mL) and extracted with DCM (10 mL×3). The combined organic layers were dried over Na$_2$SO$_4$, concentrated, and purified by acidic preparative HPLC to give tert-butyl 7-(5-(4-fluoro-2-(3-fluoro-3-methylbutyl)phenoxy)pyrimidin-4-yl)-2,7-diazaspiro[4.4]nonane-2-carboxylate as colorless oil. Yield: 84 mg. LCMS method C: R$_t$=0.790 min; (M+H)$^+$=503.3.

Step 4. 2-(5-(4-fluoro-2-(3-fluoro-3-methylbutyl) phenoxy)pyrimidin-4-yl)-2,7-diazaspiro[4.4]nonane

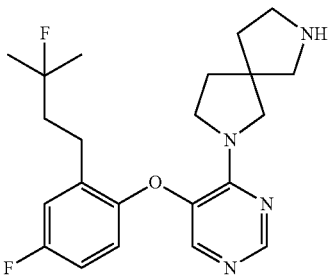 [SMILES: CC(C)(F)CCc1cc(F)ccc1Oc1cncnc1N1CCC2(CCNC2)C1]

To a solution of tert-butyl 7-(5-(4-fluoro-2-(3-fluoro-3-methylbutyl)phenoxy)pyrimidin-4-yl)-2,7-diazaspiro[4.4]nonane-2-carboxylate (80 mg, 0.16 mmmol) in anhydrous CH$_2$Cl$_2$ (4 mL) was added TFA (0.5 mL) and the resulting mixture was stirred at 16-25° C. for 2 h. The mixture was then poured into saturated NaHCO$_3$ (aq) (10 mL) and extracted with DCM (10 mL×2). The combined organic layers were dried over Na$_2$SO$_4$ and concentrated to give 2-(5-(4-fluoro-2-(3-fluoro-3-methylbutyl)phenoxy)pyrimidin-4-yl)-2,7-diazaspiro[4.4]nonane as a colorless oil, which was used in the next step without further purification. Yield: 50 mg.

Step 5: 5-((7-(5-(4-fluoro-2-(3-fluoro-3-methylbutyl)phenoxy)pyrimidin-4-yl)-2,7-diazaspiro[4.4]nonan-2-yl)methyl)-1H-benzo[d]200midazole-2(3H)-one and 5-((7-(5-(4-fluoro-2-(3-hydroxy-3-methylbutyl)phenoxy)pyrimidin-4-yl)-2,7-diazaspiro[4.4]nonan-2-yl)methyl)-1H-benzo[d]imidazol-2(3H)-one To a solution of 2-(5-(4-fluoro-2-(3-fluoro-3-methylbutyl)phenoxy)pyrimidin-4-yl)-2,7-diazaspiro[4.4]nonane (50 mg, 0.12 mmmol) in anhydrous MeOH (2 mL) was added 2-oxo-2,3-dihydro-1H-benzo[d]imidazole-5-carbaldehyde (Intermediate 40, 22 mg, 0.14 mmol) and NaBH$_3$CN (23 mg, 0.37 mmol) and the solution was stirred at 50° C. for 16 h. LCMS showed the desired compound and that the 2-(5-(4-fluoro-2-(3-fluoro-3-methylbutyl)phenoxy)pyrimidin-4-yl)-2,7-diazaspiro[4.4]nonane was consumed. The mixture was purified by basic preparative RP-HPLC method D to give 5-((7-(5-(4-fluoro-2-(3-fluoro-3-methylbutyl)phenoxy)pyrimidin-4-yl)-2,7-diazaspiro[4.4]nonan-2-yl)methyl)-1H-benzo[d]imidazol-2(3H)-one and 5-((7-(5-(4-fluoro-2-(3-hydroxy-3-methylbutyl)phenoxy) pyrimidin-4-yl)-2,7-diazaspiro[4.4]nonan-2-yl)methyl)-1H-benzo[d]imidazol-2(3H)-one, both products as a white solid.

Example 35

LCMS method E: R$_t$=0.618 min; (M+H)$^+$=610.3. $^1$H NMR (CD$_3$OD): δ 8.23 (d, J=5.6 Hz, 1H), 7.55 (s, 1H), 7.05-7.12 (m, 1H), 7.03 (s, 1H), 6.95-7.01 (m, 2H), 6.85-6.95 (m, 1H), 6.70-6.75 (m, 1H), 3.63-3.83 (m, 4H), 3.61 (s, 2H), 2.72-2.78 (m, 2H), 2.60-2.70 (m, 2H), 2.48-2.59 (m, 2H), 1.78-1.98 (m, 6H), 1.33 (d, J=21.6 Hz, 6H). $^{19}$F NMR (CD$_3$OD): δ −120.97, −140.72.

Example 36

LCMS method C: R$_t$=0.586 min; (M+H)$^+$=547.3. $^1$H NMR (CD$_3$OD): δ 8.23 (s, 1H), 7.56 (s, 1H), 7.09 (dd, J=9.2 2.8 Hz, 1H), 7.05 (s, 1H), 6.95-7.00 (m, 2H), 6.85-6.95 (m, 1H), 6.72 (dd, J=8.8 4.8 Hz, 1H), 3.69-3.83 (m, 4H), 3.65 (s, 2H), 2.49-2.75 (m, 6H), 1.90-2.00 (m, 2H), 1.84 (t, J=6.8 Hz, 2H), 1.67-1.76 (m, 2H), 1.20 (s, 6H). $^{19}$F NMR (MeOD): δ −121.18.

Example 37

Methyl 2-(5-fluoro-2-((4-(7-((2-oxo-2,3-dihydro-1H-benzo[d]imidazol-5-yl)methyl)-2,7-diazaspiro[4.4]nonan-2-yl)pyrimidin-5-yl)oxy)phenyl)cyclopropanecarboxylate

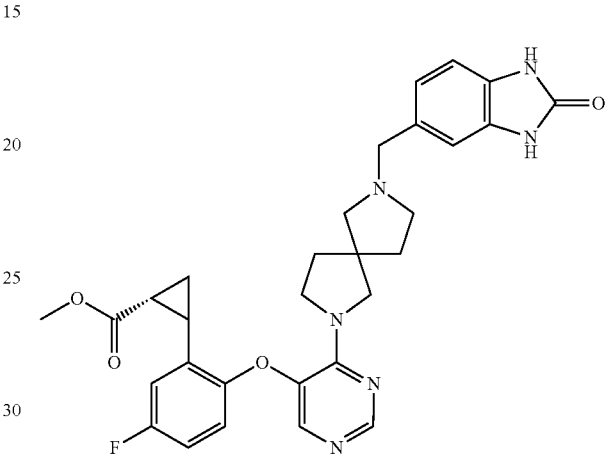

Step 1. (E)-tert-butyl 7-(5-(4-fluoro-2-(3-methoxy-3-oxoprop-1-en-1-yl)phenoxy)pyrimidin-4-yl)-2,7-diazaspiro[4.4]nonane-2-carboxylate

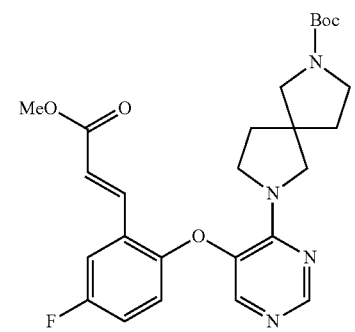 [SMILES: COC(=O)/C=C/c1cc(F)ccc1Oc1cncnc1N1CCC2(CCN(C(=O)OC(C)(C)C)C2)C1]

To a solution of tert-butyl 7-(5-(2-bromo-4-fluorophenoxy)pyrimidin-4-yl)-2,7-diazaspiro[4.4]nonane-2-carboxylate (Intermediate 11, 1.20 g, 2.44 mmol), methyl acrylate (838 mg, 9.74 mmol) and Et$_3$N (246 mg, 2.44 mmol) in THF (24 mL, anhydrous) was added P(o-Tol)$_3$ (292 mg, 0.96 mmol) followed by Pd$_2$(dba)$_3$ (448 mg, 0.48 mmol) under N$_2$. The mixture was heated in a sealed tube at 80° C. for 17 h. The mixture was then diluted by EtOAc (300 mL) and H$_2$O (30 mL). The organic layer was filtered and dried over anhydrous Na$_2$SO$_4$, filtered and concentrated. The residue was purified by RP-HPLC method D to give (E)-tert-butyl 7-(5-(4-fluoro-2-(3-methoxy-3-oxoprop-1-en-1-yl)phenoxy)pyrimidin-4-yl)-2,7-diazaspiro[4.4]nonane-2- carboxylate as a colorless gel. Yield: 482 mg. LCMS method E: $R_t$=1.005 min; (M+H)$^+$=499.3.

Step 2. tert-butyl 7-(5-(4-fluoro-2-(2-(methoxycarbonyl)cyclopropyl)phenoxy)pyrimidin-4-yl)-2,7-diazaspiro[4.4]nonane-2-carboxylate

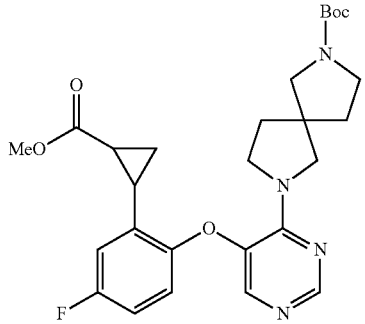 [SMILES: COC(=O)C1CC1c1cc(F)ccc1Oc1cncnc1N1CCC2(CCN(C(=O)OC(C)(C)C)C2)C1]

To a suspension of NaH (43 mg, 1.07 mmol, 60% in mineral oil) in DMSO (3 mL) was added Me$_3$SOI (383 mg, 1.74 mmol) under N$_2$. Then a solution of (E)-tert-butyl 7-(5-(4-fluoro-2-(3-methoxy-3-oxoprop-1-en-1-yl)phenoxy)pyrimidin-4-yl)-2,7-diazaspiro[4.4]nonane-2-carboxylate (383 mg, 1.74 mmol) in DMSO (3 mL) and THF (3 mL) was added and the mixture was stirred at 18-23° C. for 4 h. The mixture was then quenched by 1N HCl (20 mL) and extracted with EtOAc (20 mL). The organic layer was washed by H$_2$O, dried over anhydrous Na$_2$SO$_4$, filtered and concentrated. The residue was purified by ISCO column chromatography (EtOAc) to give tert-butyl 7-(5-(4-fluoro-2-(2-(methoxycarbonyl)cyclopropyl)phenoxy)pyrimidin-4-yl)-2,7-diazaspiro [4.4]nonane-2-carboxylate as a colorless gel. Yield: 300 mg. LCMS method E: $R_t$=1.014 min; (M+H)$^+$=513.3.

Step 3: methyl 2-(2-((4-(2,7-diazaspiro[4.4]nonan-2-yl) pyrimidin-5-yl)oxy)-5-fluorophenyl)cyclopropanecarboxylate

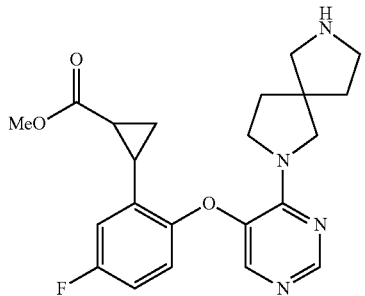 [SMILES: COC(=O)C1CC1c1cc(F)ccc1Oc1cncnc1N1CCC2(CCNC2)C1]

To a solution of tert-butyl 7-(5-(4-fluoro-2-(2-(methoxycarbonyl)cyclopropyl)phenoxy)pyrimidin-4-yl)-2,7-diazaspiro[4.4]nonane-2-carboxylate (300 mg, 0.58 mmol) in DCM (8 mL) was added HCl-dioxane (1.6 mL, 4 N). The mixture was stirred at 11-16° C. for 4 h, at which time TLC (DCM:Methanol=10:1) showed the reaction was complete. The mixture was concentrated, mixed with DCM (20 mL), washed by sat. aq. NaHCO$_3$ (20 mL), brine (20 mL), dried over anhydrous Na$_2$SO$_4$, filtered and concentrated to give methyl 2-(2-((4-(2,7-diazaspiro[4.4]nonan-2-yl)pyrimidin-5-yl)oxy)-5-fluorophenyl)cyclopropanecarboxylate as a colorless gel. Yield: 220 mg. LCMS method E: $R_t$=0.846 min; (M+H)$^+$=413.3.

Step 4. methyl 2-(5-fluoro-2-((4-(7-((2-oxo-2,3-dihydro-1H-benzo[d]imidazol-5-yl) methyl)-2,7-diazaspiro[4.4]nonan-2-yl)pyrimidin-5-yl)oxy)phenyl)cyclopropanecarboxylate To a solution of methyl 2-(2-((4-(2,7-diazaspiro[4.4]nonan-2-yl)pyrimidin-5-yl)oxy)-5-fluorophenyl)cyclopropanecarboxylate (110 mg, 0.27 mmol) and 2-oxo-2,3-dihydro-1H-benzo[d]imidazole-5-carbaldehyde (Intermediate 40, 53 mg, 0.33 mmol) in MeOH (2 mL) was added NaBH$_3$CN (34 mg, 0.54 mmol). The mixture was stirred at 11-16° C. for 16 h. The mixture was concentrated, and purified by silica chromatography (DCM:MeOH=10:1) to give methyl 2-(5-fluoro-2-((4-(7-((2-oxo-2,3-dihydro-1H-benzo[d]imidazol-5-yl)methyl)-2,7-diazaspiro[4.4]nonan-2-yl)pyrimidin-5-yl)oxy)phenyl)cyclopropanecarboxylate as a white solid. Yield: 80 mg. LCMS method E: $R_t$=0.898 min; (M+H)$^+$=599.3. $^1$H NMR (CDCl$_3$): δ 9.95-10.20 (s, 2H), 8.32-8.39 (m, 1H), 7.68 (d, J=8.8 Hz, 1H), 7.10 (d, J=6.0 Hz, 1H), 6.88-6.97 (m, 2H), 6.77-6.86 (m, 1H), 6.58-6.72 (m, 2H), 3.51-3.79 (m, 9H), 2.41-2.81 (m, 5H), 1.75-1.98 (m, 5H), 1.55-1.60 (m, 1H), 1.25-1.38 (m, 1H). $^{19}$F NMR (CDCl$_3$): δ −119.00.

Example 38

2-(5-fluoro-2-((4-(7-((2-oxo-2,3-dihydro-1H-benzo[d]imidazol-5-yl)methyl)-2,7-diazaspiro[4.4]nonan-2-yl)pyrimidin-5-yl)oxy)phenyl)-N-methylcyclopropane carboxamide

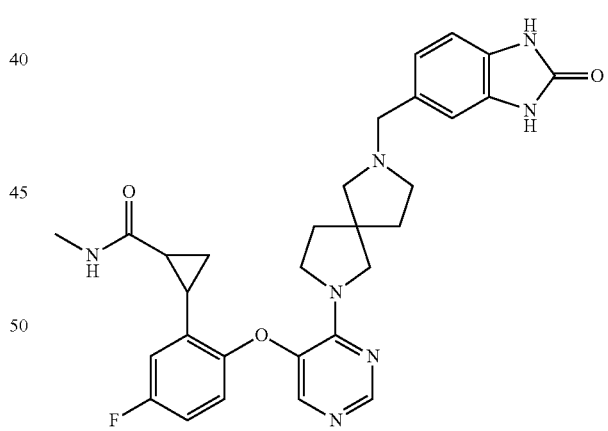

To a solution of methyl 2-(5-fluoro-2-((4-(7-((2-oxo-2,3-dihydro-1H-benzo[d]imidazol-5-yl)methyl)-2,7-diazaspiro [4.4]nonan-2-yl)pyrimidin-5-yl)oxy)phenyl)cyclopropanecarboxylate (Example 37, 36 mg, 0.064 mmol) in THF (0.5 mL) was added MeNH$_2$ (1 mL, water solution) and the mixture was stirred at 14-18° C. for 72 h. The mixture was then concentrated and the residue was purified by RP-HPLC method A to give 2-(5-fluoro-2-((4-(7-((2-oxo-2,3-dihydro-1H-benzo[d]imidazol-5-yl)methyl)-2,7-diazaspiro[4.4] nonan-2-yl)pyrimidin-5-yl)oxy)phenyl)-N-methylcyclopropanecarboxamide (TFA salt) as a white solid. Yield: 22 mg. LCMS method E: $R_t$=0.892 min; (M+H)$^+$=558.1. $^1$H NMR (CD₃OD): δ 8.49 (s, 1H), 7.46 (s, 1H), 7.17-7.28 (m, 3H), 7.05-7.15 (m, 2H), 6.98 (d, J=7.2 Hz, 1H), 4.46 (s, 2H), 4.05-4.20 (m, 4H), 3.35-3.78 (m, 4H), 2.66 (s, 3H), 2.45-2.50 (m, 1H), 2.02-2.40 (m, 4H), 1.65 (s, 1H), 1.27-1.47 (m, 2H). ¹⁹F NMR (CD₃OD): δ −77.03, −116.71.

Example 39

6-((2-(5-(2-chloro-4-fluorophenoxy)pyrimidin-4-yl)-2,6-diazaspiro[3.4]octan-6-yl)methyl)-3,3-dimethyl-indolin-2-one

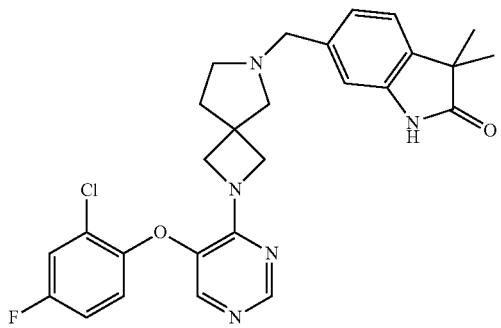 [SMILES: CC1(C)C(=O)Nc2cc(CN3CCC4(C3)CN(c3ncncc3Oc3ccc(F)cc3Cl)C4)ccc21]

A mixture of 2-(5-(2-chloro-4-fluorophenoxy)pyrimidin-4-yl)-2,6-diazaspiro[3.4]octane synthesized from Intermediate 24A by acid deprotection (80 mg, 0.19 mmol, 81% purity), Intermediate 45 (54 mg, 0.29 mmol) and NaBH₃CN (60 mg, 0.95 mmol) in MeOH (5 mL) was stirred at 70° C. (oil bath) for 18 h. The mixture was concentrated under reduced pressure and the residue was purified by basic preparative RP-HPLC method D to give 6-((2-(5-(2-chloro-4-fluorophenoxy)pyrimidin-4-yl)-2,6-diazaspiro[3.4] octan-6-yl)methyl)-3,3-dimethylindolin-2-one as a white solid. Yield: 17 mg. LCMS method E: R$_t$=0.584 min; (M+H)⁺= 508.0, 510.0 (chlorine isotopes). ¹H NMR (CD₃OD): δ 8.24 (s, 1H), 7.57 (s, 1H), 7.41-7.42 (m, 1H), 7.20 (m, J=7.6 Hz, 1H), 6.99-7.08 (m, 3H), 6.95 (s, 1H), 4.21-4.26 (m, 4H), 3.62 (s, 2H), 2.81 (s, 2H), 2.66 (t, J=6.8 Hz, 2H), 2.16 (t, J=7.2 Hz, 2H), 1.34 (s, 6H). ¹⁹F NMR (CD₃OD): δ −118.54~−117.89.

Example 40

2-(6-(5-(2-chloro-4-fluorophenoxy)pyrimidin-4-yl)-2,6-diazaspiro[3.3]heptane-2-carbonyl)-2,3-dihydro-1H-indene-5-sulfonamide

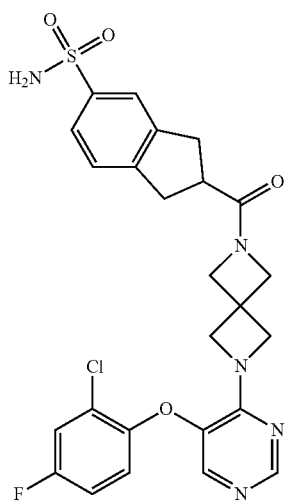 [SMILES: NS(=O)(=O)c1ccc2c(c1)CC(C(=O)N1CC3(C1)CN(c1ncncc1Oc1ccc(F)cc1Cl)C3)C2]

Step 1. methyl 2,3-dihydro-1H-indene-2-carboxylate

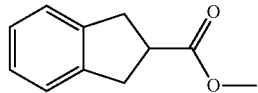

To a solution of 2,3-dihydro-1H-indene-2-carboxylic acid (8.40 g, 51.85 mmol) in MeOH (220 mL, anhydrous) was added H₂SO₄ (4.4 mL) at 0° C. and the mixture was heated at 70° C. for 17 h. The mixture was concentrated, diluted by EtOAc (80 mL), washed by H₂O (80 mL), dried over anhydrous Na₂SO₄, filtered and concentrated to give methyl 2,3-dihydro-1H-indene-2-carboxylate (8.70 g, 95%) as a light yellow oil. Yield: 8.7 g. LCMS method E: R$_t$=1.045 min; (M+H)⁺=177.2.

Step 2. methyl 5-(chlorosulfonyl)-2,3-dihydro-1H-indene-2-carboxylate

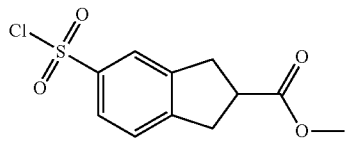 [SMILES: COC(=O)C1Cc2ccc(S(=O)(=O)Cl)cc2C1]

Methyl 2,3-dihydro-1H-indene-2-carboxylate (1.00 g, 5.68 mmol) was added over 20 min to a pre-cooled solution of ClSO₃H (5 mL) and the resulting mixture was stirred at 13-21° C. for 3 h, after which time, it was poured into ice-cooled water followed by EtOAc (30 mL). The organic layer was separated, and dried over anhydrous Na₂SO₄, filtered and concentrated to give methyl 5-(chlorosulfonyl)-2,3-dihydro-1H-indene-2-carboxylate as a colorless oil. Yield: 1.4 g. ¹H NMR (CDCl₃): δ 7.82-7.89 (m, 2H), 7.43 (d, J=8.4 Hz, 1H), 3.74-3.77 (m, 3H), 3.28-3.50 (m, 5H).

Step 3. methyl 5-sulfamoyl-2,3-dihydro-1H-indene-2-carboxylate

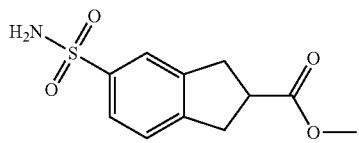 [SMILES: COC(=O)C1Cc2ccc(S(N)(=O)=O)cc2C1]

To a solution of methyl 5-(chlorosulfonyl)-2,3-dihydro-1H-indene-2-carboxylate (100 mg, 0.36 mmol) in THF (2 mL) was added NH₃.H₂O (100 μL) under 0° C. and the mixture was stirred at 0° C. for 1 h. The mixture was then concentrated, diluted by EtOAc (15 mL), washed by sat. aq. NH₄Cl (10 mL) and brine (10 mL), dried over anhydrous Na₂SO₄, filtered and concentrated to give methyl 5-sulfamoyl-2,3-dihydro-1H-indene-2-carboxylate as a colorless gel. Yield: 80 mg. ¹H NMR (CDCl₃): δ 7.65-7.75 (m, 2H), 7.34 (d, J=8.0 Hz, 1H), 3.70 (s, 3H), 3.37-3.46 (m, 1H), 3.21-3.27 (m, 4H).

Step 4.
5-sulfamoyl-2,3-dihydro-1H-indene-2-carboxylic Acid

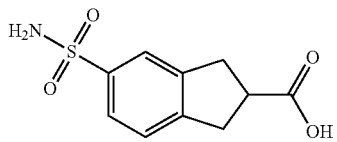 [SMILES: NS(=O)(=O)c1ccc2c(c1)CC(C(=O)O)C2]

To a solution of 5-sulfamoyl-2,3-dihydro-1H-indene-2-carboxylate (80 mg, 0.31 mmol), in MeOH (1 mL) was added H$_2$O (1 mL) followed by LiOH (96 mg, 4.0 mmol). The mixture was stirred at 18-23° C. for 4 h. The pH was adjusted to 2-3 with aq. HCl, and the mixture was concentrated to give crude 5-sulfamoyl-2,3-dihydro-1H-indene-2-carboxylic acid as a white solid. Yield: 131 mg.

Step 5. 2-(6-(5-(2-chloro-4-fluorophenoxy)pyrimidin-4-yl)-2,6-diazaspiro[3.3]heptanes-2-carbonyl)-2,3-dihydro-1H-indene-5-sulfonamide To a solution of 5-sulfamoyl-2,3-dihydro-1H-indene-2-carboxylic acid (131 mg, 0.31 mmol) and 2-(5-(2-chloro-4-fluorophenoxy)pyrimidin-4-yl)-2,6-diazaspiro[3.3]heptane synthesized from Intermediate 20A by acid deprotection (100 mg, 0.31 mmol) in DMF (4 mL, anhydrous) was added HATU (177 mg, 0.47 mmol) and DIEA (120 mg, 154 µL). The mixture was stirred at 13-20° C. for 17 h at which time LCMS showed the desired product was produced in about 17% yield. The mixture was diluted by EtOAc (20 mL), washed by H$_2$O (20 mL), brine (20 mL), dried over anhydrous Na$_2$SO$_4$, filtered and concentrated. The residue was purified by acidic preparative RP-HPLC method A to give 2-(6-(5-(2-chloro-4-fluorophenoxy)pyrimidin-4-yl)-2,6-diazaspiro[3.3]heptane-2-carbonyl)-2,3-dihydro-1H-indene-5-sulfonamide (TFA salt) as a white solid. Yield: 9 mg. LCMS method E: R$_t$=0.843 min; (M+H)$^+$=544.2. $^1$H NMR (CD$_3$OD): δ 8.48 (s, 1H), 7.67-7.76 (m, 2H), 7.59 (s, 1H), 7.50 (dd, J=8.4, 3.2 Hz, 1H), 7.33-7.43 (m, 2H), 7.21-7.29 (m, 1H), 4.71-4.86 (m, 4H), 4.57 (s, 2H), 4.27 (s, 2H), 3.36-3.45 (m, 1H), 3.17-3.24 (m, 4H). $^{19}$F NMR (CD$_3$OD): δ −77.02, −115.29.

Example 41

5-((7-(5-(((5-fluoro-2'-isopropyl-[1,1'-biphenyl]-2-yl)oxy) pyrimidin-4-yl)-2,7-diazaspiro[4.4]nonan-2-yl)methyl)-1H-benzo[d]imidazol-2(3H)-one

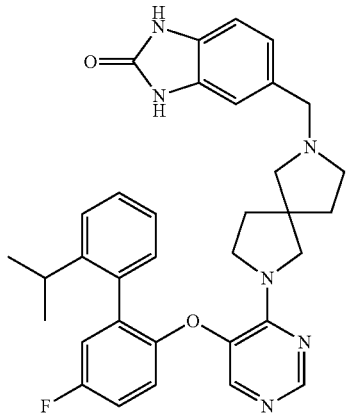 [SMILES: CC(C)c1ccccc1-c1cc(F)ccc1Oc1cncnc1N1CCC2(CCN(Cc3ccc4[nH]c(=O)[nH]c4c3)C2)C1]

Step 1. tert-butyl 7-(5-(2-bromo-4-fluorophenoxy) pyrimidin-4-yl)-2,7-diazaspiro[4.4]nonane-2-carboxylate

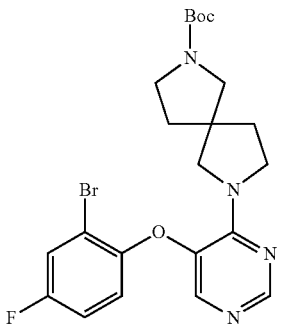 [SMILES: CC(C)(C)OC(=O)N1CCC2(CCN(c3ncncc3Oc3ccc(F)cc3Br)C2)C1]

A mixture of 5-(2-bromo-4-fluorophenoxy)-4-chloropyrimidine (Intermediate 1, 15 g, 49.4 mmol), tert-butyl 2,7-diazaspiro[4.4]nonane-2-carboxylate (14.7 g, 54.3 mmol) and Na$_2$CO$_3$ (20.9 g, 197.6 mmol) in CH$_3$CN (300 mL) was stirred at reflux for 3 h. The mixture was then filtered and the filtrate was concentrated under reduced pressure. The residue was purified by column chromatography on silica gel (eluting with ethyl acetate) to give tert-butyl 7-(5-(2-bromo-4-fluorophenoxy)pyrimidin-4-yl)-2,7-diazaspiro[4.4] nonane-2-carboxylate (i.e., Intermediate 11), as a yellow solid. Yield: 23 g. LCMS method A: R$_t$=0.759 min; (M+H)$^+$= 492.8, 494.9 (bromo isotopes). $^1$H NMR (CDCl$_3$): δ 8.35 (s, 1H), 7.71 (s, 1H), 7.31-7.33 (d, J=6.8 Hz, 1H), 6.90-6.95 (m, 1H), 6.68-6.70 (m, 1H), 3.50-3.85 (m, 4H), 3.10-3.45 (m, 4H), 1.80-1.95 (m, 4H), 1.39 (s, 9H).

Step 2. tert-butyl 7-(5-((5-fluoro-2'-isopropyl-[1,1'-biphenyl]-2-yl)oxy)pyrimidin-4-yl)-2,7-diazaspiro[4.4]nonane-2-carboxylate

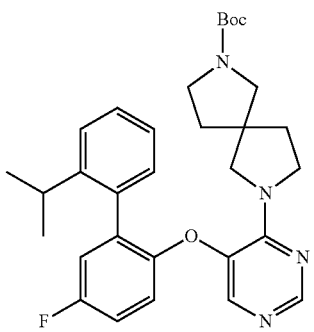 [SMILES: CC(C)c1ccccc1-c1cc(F)ccc1Oc1cncnc1N1CCC2(CCN(C(=O)OC(C)(C)C)C2)C1]

To a degassed mixture of Intermediate 11 (15 g, 30.4 mmol), (2-isopropylphenyl)boronic acid (7.8 g, 45.6 mmol) and K$_3$PO$_4$ (19.4 g, 91.2 mmol) in dioxane (360 mL) and H$_2$O (90 mL) was added Sphos Palladacycle (2.2 g, 3.04 mmol) under N$_2$ and the mixture was stirred at 90° C. for 18 h. The mixture was then filtered and the filtrate was concentrated under reduced pressure to remove dioxane. The resulting residue was extracted with ethyl acetate (3×100 mL). The combined organic layers were washed with H$_2$O (100 mL) and brine (100 mL), dried over anhydrous sodium sulfate, filtered and concentrated under reduced pressure. The residue was purified by column chromatograph on silica gel (eluting with petroleum ether:ethyl acetate=1:2 to 1:3) to give tert-butyl 7-(5-((5-fluoro-2'-isopropyl-[1,1'-biphenyl]-2-yl)oxy)pyrimidin-4-yl)-2,7-diazaspiro[4.4]nonane-2-carboxylate as a yellow solid. Yield: 8.6 g. LCMS method A: $R_t$=0.785 min; (M+H)$^+$=533.1. $^1$H NMR (CDCl$_3$): δ 8.33 (s, 1H), 7.76 (s, 1H), 7.3-7.38 (m, 2H), 7.10-7.20 (m, 1H), 6.90-7.05 (m, 3H), 6.70-6.80 (m, 1H), 3.30-3.70 (m, 6H), 3.10-3.30 (m, 2H), 2.80-2.90 (m, 1H), 1.70-1.85 (m, 4H), 1.46 (s, 9H), 1.11-1.16 (m, 6H).

Step 3. 2-(5-((5-fluoro-2'-isopropyl-[1,1'-biphenyl]-2-yl)oxy)pyrimidin-4-yl)-2,7-diazaspiro[4.4]nonane

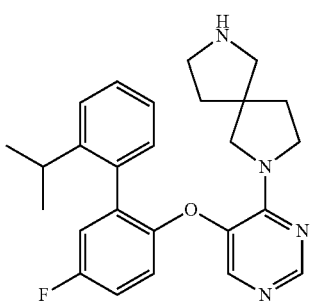 [SMILES: CC(C)c1ccccc1-c1cc(F)ccc1Oc1cncnc1N1CCC2(CCNC2)C1]

To a mixture of tert-butyl 7-(5-((5-fluoro-2'-isopropyl-[1,1'-biphenyl]-2-yl)oxy)pyrimidin-4-yl)-2,7-diazaspiro[4.4]nonane-2-carboxylate (8.6 g, 16.1 mmol) in CH$_2$Cl$_2$ (150 mL) was added HCl-dioxane (30 mL, 4 N) under ice-cold water and the mixture was stirred at 14-18° C. for 2 h. The mixture was then concentrated under reduced pressure and the residue was basified to pH 12-13 with 10% NaOH aqueous solution, extracted with EtOAc (3×100 mL). The combined organic layers were dried over anhydrous sodium sulfate, filtered and concentrated under reduced pressure to give 2-(5-((5-fluoro-2'-isopropyl-[1,1'-biphenyl]-2-yl)oxy)pyrimidin-4-yl)-2,7-diazaspiro[4.4]nonane as a yellow solid, which was used in the next step without further purification. Yield: 6.8 g. LCMS method C: $R_t$=0.649 min; (M+H)$^+$=433.1.

Step 4. 5-((7-(5-((5-fluoro-2'-isopropyl-[1,1'-biphenyl]-2-yl)oxy)pyrimidin-4-yl)-2,7-diazaspiro[4.4]nonan-2-yl)methyl)-1H-benzo[d]imidazol-2(3H)-one A mixture of 2-(5-((5-fluoro-2'-isopropyl-[1,1'-biphenyl]-2-yl)oxy)pyrimidin-4-yl)-2,7-diazaspiro[4.4]nonane (6.8 g, 15.7 mmol), 2-oxo-2,3-dihydro-1H-benzo[d]imidazole-5-carbaldehyde (Intermediate 40, 3.05 g, 18.8 mmol), NaBH$_3$CN (3.9 g, 62.8 mmol) and HOAc (3.4 mL) in MeOH (130 mL) was stirred at 70° C. for 18 h. The mixture was then concentrated under reduced pressure and the residue adjusted to pH=8 with saturated NaHCO$_3$ solution and extracted with ethyl acetate (3×150 mL). The combined organic layers were dried over anhydrous sodium sulfate, filtered and concentrated under reduced pressure. The residue was purified by basic preparative RP-HPLC method D to give 5-((7-(5-((5-fluoro-2'-isopropyl-[1,1'-biphenyl]-2-yl)oxy)pyrimidin-4-yl)-2,7-diazaspiro[4.4]nonan-2-yl)methyl)-1H-benzo[d]imidazol-2(3H)-one as a slight yellow solid. Yield: 7.2 g. LCMS method C: $R_t$=0.663 min; (M+H)$^+$= 579.1. $^1$H NMR (CD$_3$OD): δ 8.13 (s, 1H), 7.58 (d, J=6.8 Hz, 1H), 6.95-7.35 (m, 10H), 3.62 (s, 2H), 3.40-3.55 (m, 3H), 2.55-2.85 (m, 4H), 2.30-2.45 (m, 2H), 1.65-1.85 (m, 4H), 1.00-1.10 (m, 6H).

Examples 41A-41B 5-((7-(5-((5-fluoro-2'-isopropyl-[1,1'-biphenyl]-2-yl)oxy)pyrimidin-4-yl)-2,7-diazaspiro[4.4]nonan-2-yl)methyl)-1H-benzo[d]imidazol-2(3H)-one (Isomers 1-2)

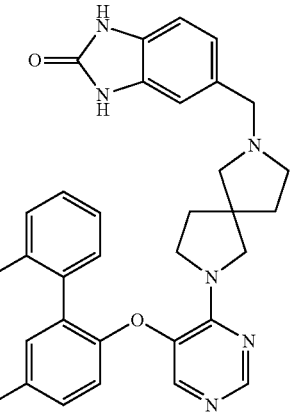

5-((7-(5-((5-fluoro-2'-isopropyl-[1,1'-biphenyl]-2-yl)oxy)pyrimidin-4-yl)-2,7-diazaspiro[4.4]nonan-2-yl)methyl)-1H-benzo[d]imidazol-2(3H)-one (Example 40, 1 g, 1.7 mmol) was purified by SFC separation method A to give two isomers as a white solids which were isolated as HCl salts.

Isomer 1:
LCMS method C: $R_t$=0.660 min; (M+H)$^+$=579.1. $^1$H NMR (CD$_3$OD): δ 8.28 (s, 1H), 7.66 (s, 1H), 7.10-7.37 (m, 10H), 4.45 (s, 2H), 3.71-3.34 (m, 8H), 2.77-2.85 (m, 1H), 2.03-2.11 (m, 4H), 1.06-1.14 (m, 6H). $^{19}$F NMR (CD$_3$OD): δ –119.18. SFC Anal. Method D: 8.122 min, ee=91.32%

Isomer 2:
LCMS method C: $R_t$=0.659 min; (M+H)$^+$=579.1.
$^1$H NMR (CD$_3$OD 400 MHz): δ 8.27 (s, 1H), 7.66 (s, 1H), 7.10-7.37 (m, 10H), 4.44 (s, 2H), 3.33-3.70 (m, 8H), 2.77-2.83 (m, 1H), 2.03-2.11 (m, 4H), 1.06-1.14 (m, 6H). $^{19}$F NMR (CD$_3$OD 400 MHz): δ –119.30. SFC Anal. Method D: 8.122 min, ee=93.84%

Example 42

2-cyclopropyl-5'-fluoro-2'-((4-(7-((2-oxo-2,3-dihydro-1H-benzo[d]imidazol-5-yl)methyl)-2,7-diazaspiro[4.4]nonan-2-yl)pyrimidin-5-yl)oxy)-[1,1'-biphenyl]-4-carbonitrile (Racemic Mixture)

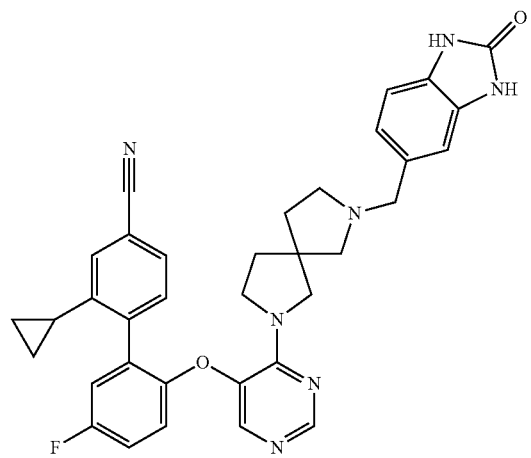 [SMILES: N#Cc1ccc(-c2cc(F)ccc2Oc2cncnc2N2CCC3(CCN(Cc4ccc5[nH]c(=O)[nH]c5c4)C3)C2)c(C2CC2)c1]

The title product was synthesized according to the method described for Example 41. In Step 2, 4-cyano-2-cyclopropyl phenyl boronic acid was used. LCMS method A: $R_t$=1.42 min, 602 (M+H)+. $^1$H NMR CD$_3$OD) δ: 8.15 (s, 1H), 7.64 (s, 1H), 7.42 (m, 1H), 7.29 (m, 1H), 7.23-7.14 (m, 3H), 7.07-7.01 (m, 4H), 3.65 (s, 2H), 3.58-3.41 (m, 4H), 2.68 (m, 2H), 2.47 (m, 2H), 1.85 (m, 2H), 1.72 (m, 3H), 0.87 (m, 2H), 0.65 (m, 2H).

Examples 42A-42B 2-cyclopropyl-5'-fluoro-2'-((4-(7-((2-oxo-2,3-di-hydro-1H-benzo[d]imidazol-5-yl)methyl)-2,7-diaz-aspiro[4.4]nonan-2-yl)pyrimidin-5-yl)oxy)-[1,1'-biphenyl]-4-carbonitrile (Isomers 1-2)

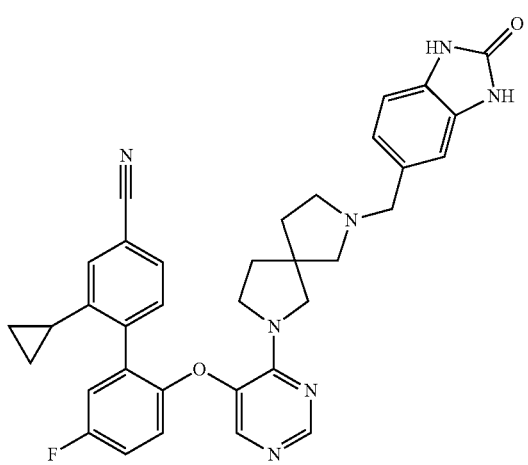 [SMILES: N#Cc1ccc(-c2cc(F)ccc2Oc2cncnc2N2CCC3(CCN(Cc4ccc5[nH]c(=O)[nH]c5c4)C3)C2)c(C2CC2)c1]

The compound of Example 42 was separated by SFC method A to afford two isomers.

Isomer 1:

LCMS method D: $R_t$ value: 1.435 min, M+H)+=602.2; $^1$H NMR (CD$_3$OD): δ 8.15 (s, 1H), 7.64 (s, 1H), 7.43 (d, J=9.6 Hz, 1H), 7.29 (d, J=5.6 Hz, 1H), 7.10-7.20 (m, 3H), 7.05-7.10 (m, 2H), 7.01 (s, 2H), 3.63 (s, 2H), 3.35-3.60 (m, 4H), 2.60-2.75 (m, 2H), 2.35-2.50 (m, 2H), 1.80-1.90 (m, 2H), 1.60-1.75 (m, 3H), 0.87 (s, 2H), 0.66 (s, 2H). $^{19}$F NMR (CD$_3$OD): δ −120.38. SFC Anal. Method D: $t_R$=5.306 min, ee=99.70%.

Isomer 2:

LCMS method D: $R_t$ value: 1.435 min, M+H)+=602.2; $^1$H NMR (CD$_3$OD 400 MHz): δ 8.15 (s, 1H), 7.64 (s, 1H), 7.42 (s, 1H), 7.29 (d, J=4.8 Hz, 1H), 7.10-7.25 (m, 3H), 6.95-7.10 (m, 4H), 3.60-3.70 (m, 2H), 3.35-3.60 (m, 4H), 2.55-2.75 (m, 2H), 2.35-2.50 (m, 2H), 1.80-1.90 (m, 2H), 1.60-1.75 (m, 3H), 0.87 (s, 2H), 0.65 (s, 2H). $^{19}$F NMR (CD$_3$OD 400 MHz): δ −120.383. SFC Anal. Method D: $t_R$=7.188 min, ee=99.32%.

Examples 43-44

2-cyclopropyl-5'-fluoro-2'-((4-(7-((2-oxo-2,3-di-hydro-1H-benzo[d]imidazol-5-yl)methyl)-2,7-diaz-aspiro[4.4]nonan-2-yl)pyrimidin-5-yl)oxy)-[1,1'-biphenyl]-4-carboxamide (Example 43) and
2-cyclopropyl-5'-fluoro-2'-((4-(7-((2-oxo-2,3-di-hydro-1H-benzo[d]imidazol-5-yl)methyl)-2,7-diaz-aspiro[4.4]nonan-2-yl)pyrimidin-5-yl)oxy)-[1,1'-biphenyl]-4-carboxylic Acid (Example 44)

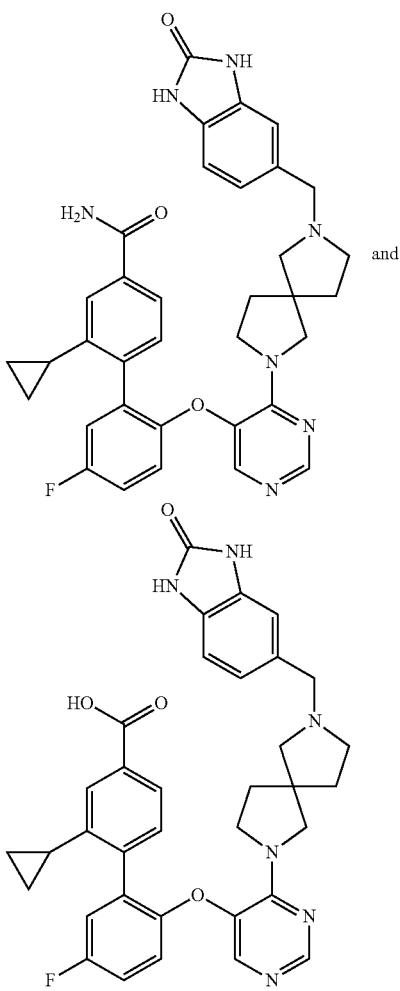

A mixture of 2-cyclopropyl-5'-fluoro-2'-((4-(7-((2-oxo-2,3-dihydro-1H-benzo[d]imidazol-5-yl)methyl)-2,7-diaz-aspiro[4.4]nonan-2-yl)pyrimidin-5-yl)oxy)-[1,1'-biphenyl]-4-carbonitrile bis-HCl salt (Example 42, 41 mg, 0.06 mmol), THF (3 mL) and 2 M LiOH (1 mL) was charged in a 10 mL CEM microwave test tube and heated to 120° C. for 4.5 h in a CEM microwave reactor. LC/MS showed two products in a ratio of about 1:1. The reaction mixture was neutralized with 1 M HCl solution, and evaporated to dryness and the resulting residue was purified by RP-HPLC method A to afford 2-cyclopropyl-5'-fluoro-2'-((4-(7-((2-oxo-2,3-di-hydro-1H-benzo[d]imidazol-5-yl)methyl)-2,7-diazaspiro[4.4]nonan-2-yl)pyrimidin-5-yl)oxy)-[1,1'-biphenyl]-4-carboxamide TFA salt and 2-cyclopropyl-5'-fluoro-2'-((4-(7-((2-oxo-2,3-dihydro-1H-benzo[d]imidazol-5-yl)methyl)-2,7-diazaspiro[4.4]nonan-2-yl)pyrimidin-5-yl)oxy)-[1,1'-biphenyl]-4-carboxylic acid as a TFA salt.

Example 43

LCMS method A: $R_f$=0.68 min, (M+H)$^+$=620.3. $^1$H NMR (CD$_3$OD) δ: 8.38 (s, 1H), 7.71 (s, 1H), 7.63 (m, 1H), 7.45 (dd, J=8.4, 4.4 Hz, 1H), 7.34-7.30 (m, 2H), 7.25-7.20 (m, 4H), 7.12 (d, J=8.0 Hz, 1H), 4.43 (s, 2H), 3.91-3.34 (m, 8H), 2.05 (m, 4H), 1.62 (s, 1H), 0.91-0.70 (m, 4H).

Example 44

LCMS method A: $R_f$=0.75 min, (M+H)$^+$=621.3. $^1$H NMR (CD$_3$OD) δ: 8.38 (s, 1H), 7.78 (d, J=7.2 Hz, 1H), 7.71 (s, 1H), 7.45-7.42 (m, 2H), 7.33 (td, J=8.4, 4.4 Hz, 1H), 7.28-7.23 (m, 3H), 7.20 (d, J=8.0 Hz, 1H), 7.12 (d, J=8.0 Hz, 1H), 4.42 (s, 2H), 3.82-3.46 (m, 8H), 2.07 (m, 4H), 1.63 (s, 1H), 0.92 (m, 2H), 0.65 (m, 2H).

Example 45

2-cyclopropyl-5'-fluoro-N,N-dimethyl-2'-((4-(7-((2-oxo-2,3-dihydro-1H-benzo[d]imidazol-5-yl)methyl)-2,7-diazaspiro[4.4]nonan-2-yl)pyrimidin-5-yl)oxy)-[1,1'-biphenyl]-4-carboxamide

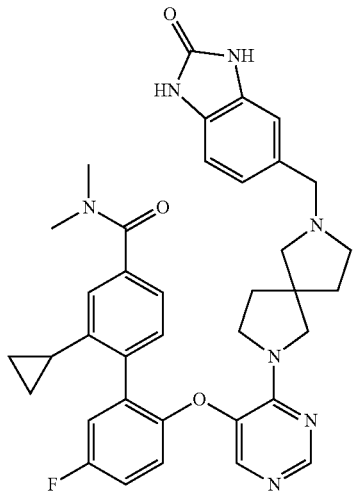 [SMILES: CN(C)C(=O)c1ccc(-c2cc(F)ccc2Oc2cncnc2N2CCC3(CCN(Cc4ccc5[nH]c(=O)[nH]c5c4)C3)C2)c(C2CC2)c1]

To a solution of 2-cyclopropyl-5'-fluoro-2'-((4-(7-((2-oxo-2,3-dihydro-1H-benzo[d]imidazol-5-yl)methyl)-2,7-diazaspiro[4.4]nonan-2-yl)pyrimidin-5-yl)oxy)-[1,1'-biphenyl]-4-carboxylic acid (Example 44, 10 mg, 0.012 mmol) in DCM (1 mL) was added TEA (0.05 mL), HATU (5 mg, 0.013 mmol) and 2.0 M Me$_2$NH in THF (0.2 mL). The resulting mixture was stirred overnight and then the solvents were removed under reduced pressure. The residue was then purified by RP-HPLC method A to afford 2-cyclopropyl-5'-fluoro-N,N-dimethyl-2'-((4-(7-((2-oxo-2,3-dihydro-1H-benzo[d]imidazol-5-yl)methyl)-2,7-diazaspiro[4.4]nonan-2-yl)pyrimidin-5-yl)oxy)-[1,1'-biphenyl]-4-carboxamide as a TFA salt. Yield: 8.5 mg. LCMS method A: $R_f$=0.74 min, (M+H)$^+$=648.3. $^1$H NMR (CD$_3$OD) δ: 8.40 (s, 1H), 7.34 (m, 1H), 7.45 (m, 1H), 7.33 (m, 1H), 7.26-7.22 (m, 5H), 7.12 (d, J=7.6 Hz, 1H), 6.84 (s, 1H), 4.45 (s, 2H), 3.85-3.42 (m, 8H), 3.06 (s, 3H), 2.95 (s, 3H), 2.09 (m, 4H), 1.62 (s, 1H), 0.91 (m, 2H), 0.62 (m, 2H).

Example 46

5-((7-(2-chloro-5-(4-fluoro-2-(1-isopropyl-1H-pyrazol-5-yl)phenoxy)pyrimidin-4-yl)-2,7-diazaspiro[4.4]nonan-2-yl)methyl)-1,3-dihydro-2H-benzo[d]imidazol-2-one

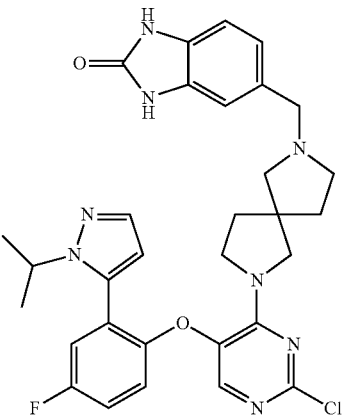 [SMILES: CC(C)n1nccc1-c1cc(F)ccc1Oc1cnc(Cl)nc1N1CCC2(CCN(Cc3ccc4[nH]c(=O)[nH]c4c3)C2)C1]

The title compound was synthesized as described in Example 41 starting from 2,4-dichloro-5-bromo pyrimidine. LCMS method B: $R_f$=1.45 min, (M+H)$^+$=603.6; $^1$H NMR (MeOH-d4): δ 7.90 (s, 1H), 7.45 (d, J=6.4 Hz, 1H), 7.30 (d, J=5.6 Hz, 2H), 7.21 (s, 1H), 7.18 (d, J=8 Hz, 1H), 7.16 (d, J=8 Hz, 1H), 7.12 (d, J=8 Hz, 1H), 6.14 (s, 1H), 4.41 (s, 2H), 4.37 (m, 1H), 3.90-3.65 (m, 3H), 3.64-3.34 (m, 4H), 3.26 (m, 1H), 2.18 (m, 1H), 2.32-1.92 (m, 3H), 1.36 (m, 6H).

Examples 47-52

Examples 47-52 were prepared according to the procedure provided in Example 41.

TABLE 7

Examples 47-52

| Example No. | Structure | Yield |
|---|---|---|
| 47. 5-((7-(5-((4,5-difluoro-2'-isopropyl-[1,1'-biphenyl]-2-yl)oxy)pyrimidin-4-yl)-2,7-diazaspiro[4.4]nonan-2-yl)methyl)-1H-benzo[d]imidazol-2(3H)-one | 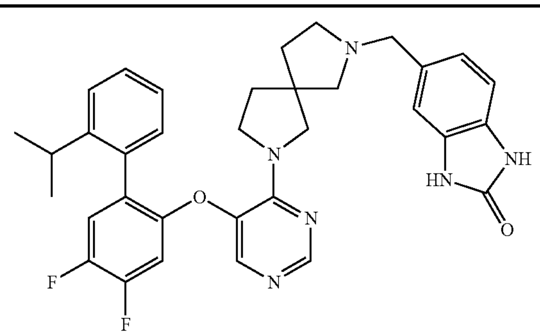 | 17% |

TABLE 7-continued

Examples 47-52

| Example No. | Structure | Yield |
|---|---|---|
| 48. 5'-fluoro-2-methyl-2'-((4-(7-((2-oxo-2,3-dihydro-1H-benzo[d]imidazol-5-yl)methyl)-2,7-diazaspiro[4.4]nonan-2-yl)pyrimidin-5-yl)oxy)-[1,1'-biphenyl]-4-carbonitrile | 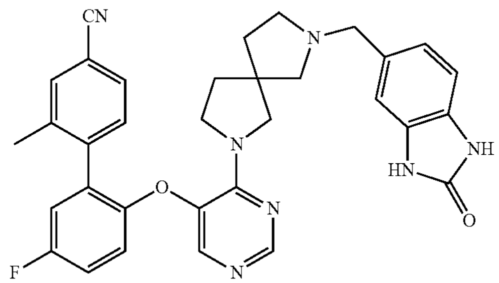 [SMILES: Cc1cc(C#N)ccc1-c1cc(F)ccc1Oc1cncnc1N1CCC2(CCN(Cc3ccc4[nH]c(=O)[nH]c4c3)C2)C1] | 22% |
| 49. 5-((7-(5-((2'-cyclopropyl-5-fluoro-[1,1'-biphenyl]-2-yl)oxy)pyrimidin-4-yl)-2,7-diazaspiro[4.4]nonan-2-yl)methyl)-1H-benzo[d]imidazol-2(3H)-one | 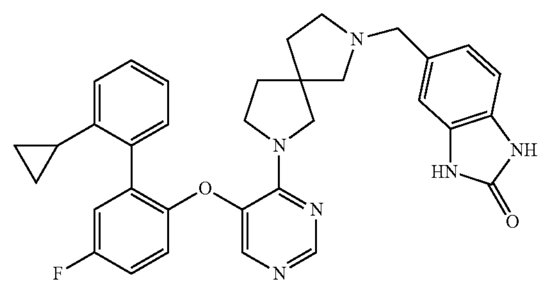 [SMILES: O=c1[nH]c2ccc(CN3CCC4(CCN(c5ncncc5Oc5ccc(F)cc5-c5ccccc5C5CC5)C4)C3)cc2[nH]1] | 46% |
| 50. 5-((7-(5-((5-fluoro-2'-(trifluoromethyl)-[1,1'-biphenyl]-2-yl)oxy)pyrimidin-4-yl)-2,7-diazaspiro[4.4]nonan-2-yl)methyl)-1H-benzo[d]imidazol-2(3H)-one (TFA salt) | 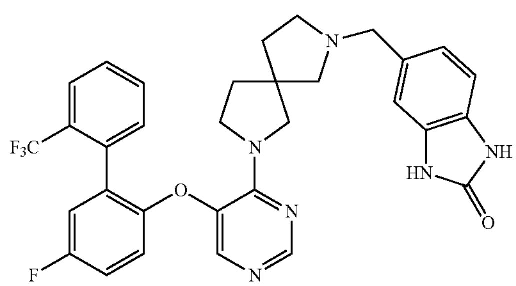 [SMILES: O=c1[nH]c2ccc(CN3CCC4(CCN(c5ncncc5Oc5ccc(F)cc5-c5ccccc5C(F)(F)F)C4)C3)cc2[nH]1] | 62% |
| 51. 5'-fluoro-2,6-dimethyl-2'-((4-(7-((2-oxo-2,3-dihydro-1H-benzo[d]imidazol-5-yl)methyl)-2,7-diazaspiro[4.4]nonan-2-yl)pyrimidin-5-yl)oxy)-[1,1'-biphenyl]-4-carbonitrile | 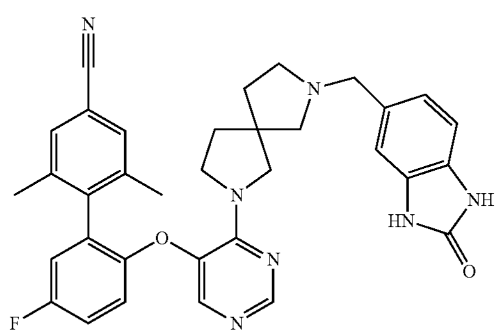 [SMILES: Cc1cc(C#N)cc(C)c1-c1cc(F)ccc1Oc1cncnc1N1CCC2(CCN(Cc3ccc4[nH]c(=O)[nH]c4c3)C2)C1] | 14% |
| 52. 2-cyclopropyl-3',5'-difluoro-2'-((4-(7-((2-oxo-2,3-dihydro-1H-benzo[d]imidazol-5-yl)methyl)-2,7-diazaspiro[4.4]nonan-2-yl)pyrimidin-5-yl)oxy)-[1,1'-biphenyl]-4-carbonitrile | 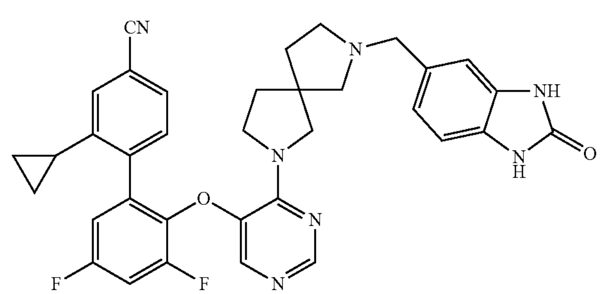 [SMILES: N#Cc1ccc(-c2cc(F)cc(F)c2Oc2cncnc2N2CCC3(CCN(Cc4ccc5[nH]c(=O)[nH]c5c4)C3)C2)c(C2CC2)c1] | 3% |

TABLE 8

Characterization Data for Examples 47-52.

| Example No. | NMR Data | Mass peak(s) (M + H)+ | $R_f$ or $R_t$ |
|---|---|---|---|
| 47. 5-((7-(5-((4,5-difluoro-2'-isopropyl-[1,1'-biphenyl]-2-yl)oxy)pyrimidin-4-yl)-2,7-diazaspiro[4.4]nonan-2-yl)methyl)-1H-benzo[d]imidazol-2(3H)-one | $^1$H NMR (CD$_3$OD) δ 8.45 (s, 1 H), 7.88 (s, 1 H), 7.00-7.45 (m, 9 H), 4.44 (s, 2 H), 3.33-3.83 (m, 8 H), 2.75-2.81 (m, 1 H), 1.96-2.09 (m, 4 H), 1.07-1.15 (m, 6 H). $^{19}$F NMR (CD$_3$OD): δ −137.27~−135.21, −142.54. | 597.3 | 1.620 min LCMS method E |
| 48. 5'-fluoro-2-methyl-2'-((4-(7-((2-oxo-2,3-dihydro-1H-benzo[d]imidazol-5-yl)methyl)-2,7-diazaspiro[4.4]nonan-2-yl)pyrimidin-5-yl)oxy)-[1,1'-biphenyl]-4-carbonitrile | $^1$H NMR (CD$_3$OD): δ 8.16 (s, 1H), 7.47-7.64 (m, 3H), 7.31-7.33 (m, 1H), 7.18-7.22 (m, 1H), 7.01-7.12 (m, 5H), 3.43-3.66 (m, 6H), 2.64-2.69 (m, 2H), 2.46 (s, 2H), 2.21 (s, 3H), 1.73-1.90 (m, 4H). $^{19}$F NMR (CD$_3$OD): δ −120.33. | 576.1 | 1.520 min in LCMS method E |
| 49. 5-((7-(5-((2'-cyclopropyl-5-fluoro-[1,1'-biphenyl]-2-yl)oxy)pyrimidin-4-yl)-2,7-diazaspiro[4.4]nonan-2-yl)methyl)-1H-benzo[d]imidazol-2(3H)-one | $^1$H NMR (CD$_3$OD): δ 8.35 (s, 1H), 7.66 (s, 1H), 7.35-7.45 (m, 1H), 7.25-7.35 (m, 2H), 7.10-7.25 (m, 3H), 7.10-7.15 (m, 1H), 6.95-7.10 (m, 2H), 6.65-6.80 (m, 1H), 4.45 (s, 2H), 3.75-3.90 (m, 4H), 3.35-3.75 (m, 4H), 2.00-2.30 (m, 4H), 1.50-1.65 (m, 1H), 0.70-1.00 (m, 2H), 0.50-0.70 (m, 2H). $^{19}$F NMR (CD$_3$OD): δ −76.96, −117.69$_o$ | 577.2 | 0.647 min in 1.520 min in LCMS method A |
| 50. 5-((7-(5-((5-fluoro-2'-(trifluoromethyl)-[1,1'-biphenyl]-2-yl)oxy)pyrimidin-4-yl)-2,7-diazaspiro[4.4]nonan-2-yl)methyl)-1H-benzo[d]imidazol-2(3H)-one (TFA salt) | $^1$H NMR (CD$_3$OD): δ 8.42 (s, 1H), 7.65-7.80 (m, 2H), 7.50-7.65 (m, 2H), 7.42 (d, J = 6.8 Hz, 1H), 7.29 (d, J = 6.4 Hz, 2H), 7.10-7.20 (m, 3H), 7.05-7.10 (m, 1H), 4.39 (s, 2H), 3.46-3.80 (m, 8H), 1.90-2.20 (m, 4H). $^{19}$F NMR (CD$_3$OD): δ −59.35, −118.69. | 605.1 | 0.645 min in LCMS method A |
| 51. 5'-fluoro-2,6-dimethyl-2'-((4-(7-((2-oxo-2,3-dihydro-1H-benzo[d]imidazol-5-yl)methyl)-2,7-diazaspiro[4.4]nonan-2-yl)pyrimidin-5-yl)oxy)-[1,1'-biphenyl]-4-carbonitrile | $^1$H NMR (CD$_3$OD): δ 8.17 (s, 1H), 7.66 (s, 1H), 7.46 (s, 1H), 7.39 (s, 1H), 7.20-7.25 (m, 1H), 7.10-7.15 (m, 1H), 7.00-7.10 (m, 4H), 3.67 (s, 2H), 3.37-3.57 (m, 4H), 2.65-2.70 (m, 2H), 2.40-2.50 (m, 2H), 2.08 (d, J = 1.2 Hz, 6H), 1.60-1.95 (m, 4H). $^{19}$F NMR (CD$_3$OD): δ −76.93, −119.73. | 592.0 | 0.644 min in LCMS method A |
| 52. 2-cyclopropyl-3',5'-difluoro-2'-((4-(7-((2-oxo-2,3-dihydro-1H-benzo[d]imidazol-5-yl)methyl)-2,7-diazaspiro[4.4]nonan-2-yl)pyrimidin-5-yl)oxy)-[1,1'-biphenyl]-4-carbonitrile | $^1$H NMR (CD$_3$OD): δ 8.05 (s, 1H), 7.36-7.47 (m, 2H), 7.30-7.33 (m, 1H), 7.25 (s, 1H), 7.13 (s, 1H), 6.95-7.10 (m, 4H), 3.35-3.75 (m, 6H), 2.64-2.77 (m, 2H), 2.40-2.54 (m, 2H), 1.70-1.96 (m, 4H), 1.52-1.66 (m, 1H), 0.65-0.95 (m, 2H), 0.50-0.60 (m, 2H). $^{19}$F NMR (CD$_3$OD): δ −113.73 (s, 2F). | 620.2 | 0.660 min in LCMS method A |

Example 53

5-((7-(5-(4-fluoro-2-(2-isopropyl-1H-imidazol-1-yl)
phenoxy)pyrimidin-4-yl)-2,7-diazaspiro[4.4]nonan-
2-yl)methyl)-1H-benzo[d]imidazol-2(3H)-one

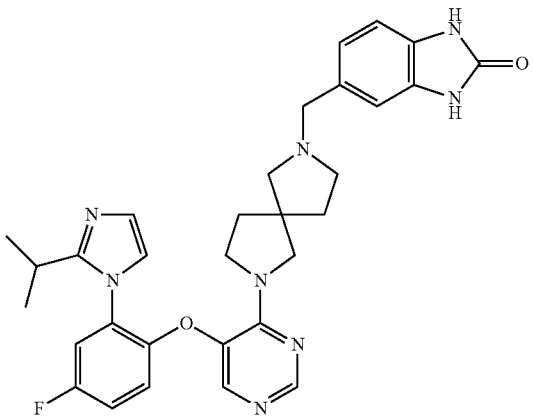 [SMILES: CC(C)c1nccn1-c1cc(F)ccc1Oc1cncnc1N1CCC2(CCN(Cc3ccc4[nH]c(=O)[nH]c4c3)C2)C1]

Step 1. 1-(5-fluoro-2-methoxyphenyl)-2-isopropyl-
1H-imidazole

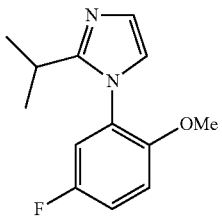 [SMILES: COc1ccc(F)cc1-n1ccnc1C(C)C]

To a solution of (5-fluoro-2-methoxyphenyl)boronic acid (12.0 g, 70.59 mmol), 2-isopropyl-1H-imidazole (7.0 g, 64.17 mmol) in anhydrous DCM (150 mL) was added Cu(OAc)$_2$ (1.73 g, 9.62 mmol) and pyridine (15 mL, 192.51 mmol) under O$_2$ (30 psi) and the resulting mixture was stirred at 20° C. for 16 h. The mixture was filtered and the filtrate was washed with water (2×100 mL), dried over anhydrous Na$_2$SO$_4$, filtered through celite, and concentrated under reduced pressure to give crude 1-(5-fluoro-2-methoxyphenyl)-2-isopropyl-1H-imidazole as a black oil, which was used for next step. Yield: 15.0 g. LCMS method E: R$_t$=0.948 min, (M+H)$^+$=253.3.

Step 2.
4-fluoro-2-(2-isopropyl-1H-imidazol-1-yl)phenol

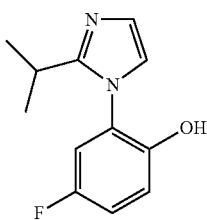 [SMILES: CC(C)c1nccn1-c1cc(F)ccc1O]

A solution of 1-(5-fluoro-2-methoxyphenyl)-2-isopropyl-1H-imidazole (15.0 g, 64.17 mmol) in HCl-Py (150 g) was stirred at 195° C. for 2 h under N$_2$. LCMS showed the starting material was consumed. The reaction was added water (500 mL), and adjusted to pH~10 by 1N NaOH solution. The mixture was extracted with EtOAc (3×200 mL), dried over anhydrous Na$_2$SO$_4$, filtered through a celite, concentrated under reduced pressure. The residue was purified by column chromatograph on silica gel (eluting with DCM/MeOH=10:1) to give 4-fluoro-2-(2-isopropyl-1H-imidazol-1-yl)phenol as a white solid. About 760 mg of 4-fluoro-2-(2-isopropyl-1H-imidazol-1-yl)phenol was further purified by column chromatograph on silica gel (eluting with dichloromethane:methanol=10:1) to give compound 4-fluoro-2-(2-isopropyl-1H-imidazol-1-yl)phenol (541.40 mg) as a white solid. Yield: 1.41 g. LCMS method E: R$_t$=0.980 min, (M+H)$^+$=221.2. $^1$H NMR (CD$_3$OD): δ 10.06 (s, 1H), 7.15-7.20 (m, 2H), 7.00-7.03 (m, 2H), 6.88 (s, 1H), 2.73-2.76 (m, 1H), 1.10 (d, J=6.8 Hz, 2H). $^{19}$F NMR (CD$_3$OD): δ −124.63.

Step 3. ethyl 2-(4-fluoro-2-(2-isopropyl-1H-imida-
zol-1-yl)phenoxy)acetate

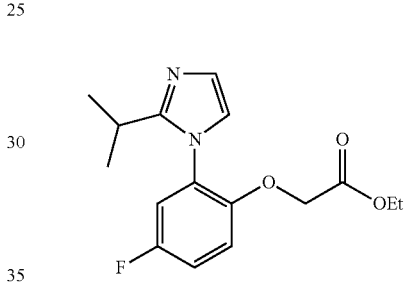

To a solution of 4-fluoro-2-(2-isopropyl-1H-imidazol-1-yl)phenol (0.65 g, 2.95 mmol) and ethyl 2-bromoacetate (492 mg, 2.95 mmol) in CH$_3$CN (15 mL) was added K$_2$CO$_3$ (610 mg, 4.42 mmol), then the reaction was stirred at 80° C. for 16 h under N$_2$. The reaction mixture was then filtered through Celite and the filtrate was concentrated under reduced pressure. The residue was purified by column chromatography on silica gel (eluting with petroleum ether: EtOAc=1:1~1:2) to afford ethyl 2-(4-fluoro-2-(2-isopropyl-1H-imidazol-1-yl)phenoxy)acetate as a yellow oil. Yield: 720 mg. LCMS method E: R$_t$=0.619 min, (M+H)$^+$=307.0

Step 4. 5-(4-fluoro-2-(2-isopropyl-1H-imidazol-1-
yl)phenoxy)-2-thioxo-2,3-dihydropyrimidin-4(1H)-
one

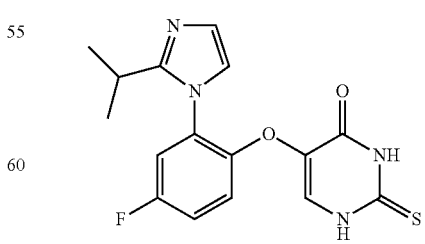

To a solution of ethyl 2-(4-fluoro-2-(2-isopropyl-1H-imidazol-1-yl)phenoxy)acetate (720 mg, 2.35 mmol) and ethyl formate (782 mg, 10.58 mmol) in anhydrous THF (15 mL)

was added NaH (141 mg, 3.52 mmol, 60% in mineral oil) under $N_2$ and the reaction mixture was stirred at 35° C. for 2 h. The solvent was removed under reduced pressure to afford ethyl (Z)-2-(4-fluoro-2-(2-isopropyl-1H-imidazol-1-yl)phenoxy)-3-hydroxyacrylate as light brown oil, which was used for the next step without further purification. The intermediate was dissolved in anhydrous EtOH (15 mL), and thiourea (179 mg, 2.35 mmol) was added under $N_2$. The reaction mixture was then stirred at 90° C. for about 16 h. The solvent was removed under reduced pressure to afford the residue which was purified by column chromatograph on silica gel (eluting with dichloromethane:methanol=20:1 to 10:1) to give 5-(4-fluoro-2-(2-isopropyl-1H-imidazol-1-yl)phenoxy)-2-thioxo-2,3-dihydropyrimidin-4(1H)-one as a yellow oil, and about 300 mg of ethyl 2-(4-fluoro-2-(2-isopropyl-1H-imidazol-1-yl)phenoxy)acetate was recycled. Yield: 280 mg. LCMS method E: $R_f$=0.945 min, $(M+H)^+$=347.1

Step 5. 5-(4-fluoro-2-(2-isopropyl-1H-imidazol-1-yl)phenoxy)pyrimidin-4-ol

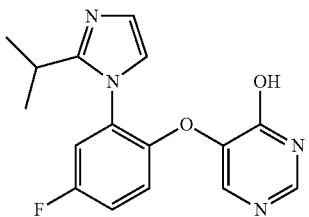 [SMILES: CC(C)c1nccn1-c1cc(F)ccc1Oc1cncnc1O]

To a solution of 5-(4-fluoro-2-(2-isopropyl-1H-imidazol-1-yl)phenoxy)-2-thioxo-2,3-dihydropyrimidin-4(1H)-one (280 mg, 0.813 mmol) in EtOH (10 mL) was added wet Raney nickel (1 g), and the reaction mixture was stirred at 90° C. for 16 h under $N_2$. The mixture was filtered and the filtrate was concentrated under reduced pressure to afford the 5-(4-fluoro-2-(2-isopropyl-1H-imidazol-1-yl)phenoxy)pyrimidin-4-ol (256 mg, 98% purity, crude 100%) as a yellow oil, which was used in the next step without further purification. Yield: 256 mg. LCMS method E: $R_f$=0.958 min, $(M+H)^+$=315.1

Step 6. 4-chloro-5-(4-fluoro-2-(2-isopropyl-1H-imidazol-1-yl)phenoxy)pyrimidine

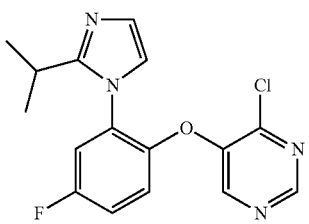 [SMILES: CC(C)c1nccn1-c1cc(F)ccc1Oc1cncnc1Cl]

To a solution of 5-(4-fluoro-2-(2-isopropyl-1H-imidazol-1-yl)phenoxy)pyrimidin-4-ol (256 mg, 0.813 mmol) in anhydrous $SOCl_2$ (5 mL) was added anhydrous DMF (0.5 mL) under $N_2$ and the reaction mixture was stirred at 80° C. for 2 h. The solvent was removed under reduced pressure to afford the residue which was mixed with $CH_2Cl_2$ (100 mL) and washed with sat. aq. $NaHCO_3$ (30 mL), brine (20 mL), dried over anhydrous $Na_2SO_4$, filtered and concentrated under reduced pressure to afford 4-chloro-5-(4-fluoro-2-(2-isopropyl-1H-imidazol-1-yl)phenoxy)pyrimidine as a yellow oil. Yield: 210 mg. LCMS method E: $R_f$=0.958 min, $(M+H)^+$=333.1.

Step 7. tert-butyl 7-(5-(4-fluoro-2-(2-isopropyl-1H-imidazol-1-yl)phenoxy)pyrimidin-4-yl)-2,7-diazaspiro[4.4]nonane-2-carboxylate

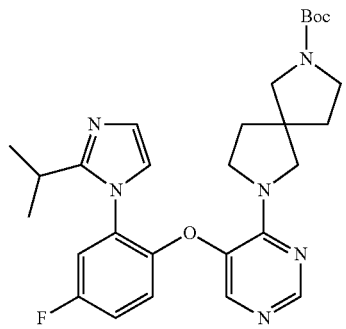 [SMILES: CC(C)c1nccn1-c1cc(F)ccc1Oc1cncnc1N1CCC2(CCN(C(=O)OC(C)(C)C)C2)C1]

A solution of 4-chloro-5-(4-fluoro-2-(2-isopropyl-1H-imidazol-1-yl)phenoxy)pyrimidine (100 mg, 0.301 mmol), tert-butyl 2,7-diazaspiro[4.4]nonane-2-carboxylate (82 mg, 0.301 mmol) and DIEA (116 mg, 0.903 mmol) in propan-2-ol (3 mL) was stirred at 90° C. for 2 h. The mixture was concentrated under reduced pressure to give crude tert-butyl 7-(5-(4-fluoro-2-(2-isopropyl-1H-imidazol-1-yl)phenoxy)pyrimidin-4-yl)-2,7-diazaspiro[4.4]nonane-2-carboxylate as a yellow oil, which was used in the next step. Yield: 157 mg. LCMS method E: $R_f$=0.675 min, $(M+H)^+$=523.1.

Step 8. 2-(5-(4-fluoro-2-(2-isopropyl-1H-imidazol-1-yl)phenoxy)pyrimidin-4-yl)-2,7-diazaspiro[4.4]nonane

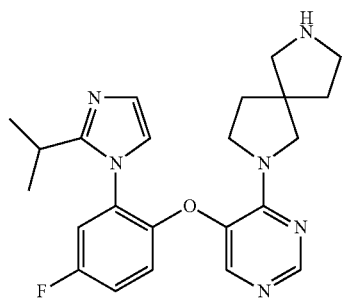 [SMILES: CC(C)c1nccn1-c1cc(F)ccc1Oc1cncnc1N1CCC2(CCNC2)C1]

To a solution of tert-butyl 7-(5-(4-fluoro-2-(2-isopropyl-1H-imidazol-1-yl)phenoxy)pyrimidin-4-yl)-2,7-diazaspiro[4.4]nonane-2-carboxylate (157 mg, 0.301 mmol) in anhydrous DCM (5 mL) was added TFA (1 mL) slowly at 0° C. under $N_2$ and the reaction mixture was stirred at 4-10° C. for 2 h. The reaction mixture was then concentrated under reduced pressure. The resulting residue was dissolved in water (30 mL) and adjusted to pH 10 with NaOH (10% in water) to pH 10. The aqueous layer was extracted with $CH_2Cl_2$/PrOH (10:1, 3×20 mL). The organic layer was dried over anhydrous $Na_2SO_4$, filtered and concentrated under reduced pressure to give 2-(5-(4-fluoro-2-(2-isopropyl-1H- imidazol-1-yl)phenoxy)pyrimidin-4-yl)-2,7-diazaspiro[4.4]
nonane as a yellow solid, which was used in the next step.

Step 9. 5-((7-(5-(4-fluoro-2-(2-isopropyl-1H-imidazol-1-yl)phenoxy)pyrimidin-4-yl)-2,7-diazaspiro[4.4]nonan-2-yl)methyl)-1H-benzo[d]imidazol-2(3H)-one To a solution of 2-(5-(4-fluoro-2-(2-isopropyl-1H-imidazol-1-yl)phenoxy)pyrimidin-4-yl)-2,7-diazaspiro[4.4]nonane (10 mg, 0.024 mmol) in anhydrous MeOH (2 mL) was added 2-oxo-2,3-dihydro-1H-benzo[d]imidazole-5-carbaldehyde (Intermediate 40, 6 mg, 0.036 mmol), and the mixture was stirred for 5 min under $N_2$. Then $NaBH_3CN$ (70 mg, 0.118 mmol) was added and the resulting mixture was stirred at 65° C. for 16 h. The reaction mixture was then concentrated under reduced pressure to afford the residue which was purified by preparative RP-HPLC method G to give 5-((7-(5-(4-fluoro-2-(2-isopropyl-1H-imidazol-1-yl)phenoxy)pyrimidin-4-yl)-2,7-diazaspiro[4.4]nonan-2-yl)methyl)-1H-benzo[d]imidazol-2(3H)-one as a white solid. Yield: 2.7 mg (20%) LCMS method D: $R_t$=1.675 min, $(M+H)^+$=569.1. $^1$H NMR (CD$_3$OD): δ 8.27 (s, 1H), 7.78 (s, 1H), 7.30-7.40 (m, 2H), 6.98-7.11 (m, 6H), 3.41-3.65 (m, 6H), 2.81-2.96 (m, 1H), 2.62-2.70 (m, 2H), 2.42-2.55 (m, 2H), 1.71-1.96 (m, 4H), 1.22 (d, J=5.2 Hz, 6H). $^{19}$F NMR (CD$_3$OD): δ −119.023.

Example 54

5-((7-(5-(2-(cyclopropylmethoxy)-4-fluorophenoxy)pyrimidin-4-yl)-2,7-diazaspiro[4.4]nonan-2-yl)methyl)-1,3-dihydro-2H-benzo[d]imidazol-2-one

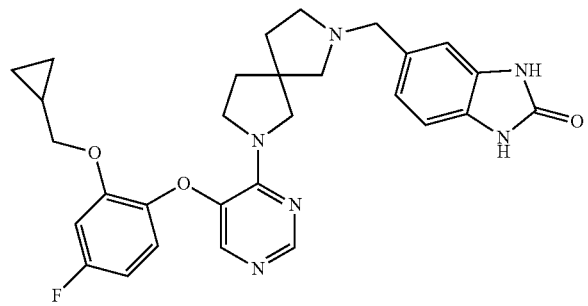 [SMILES: O=c1[nH]c2ccc(CN3CCC4(CCN(c5ncncc5Oc5ccc(F)cc5OCC5CC5)C4)C3)cc2[nH]1]

Step 1. tert-butyl 7-(5-(2-(cyclopropylmethoxy)-4-fluorophenoxy)pyrimidin-4-yl)-2,7-diazaspiro[4.4]nonane-2-carboxylate

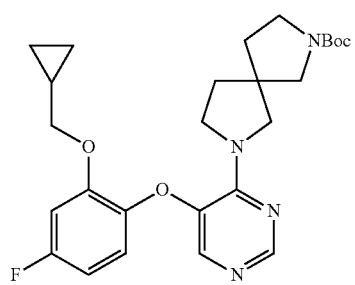 [SMILES: CC(C)(C)OC(=O)N1CCC2(CCN(c3ncncc3Oc3ccc(F)cc3OCC3CC3)C2)C1]

To a solution of Intermediate 43b (40 mg, 90 μmol) in DMF (0.5 mL) was added (bromomethyl)cyclopropane (11 μL, 110 μmol) followed by $K_2CO_3$ (20 mg, 135 μmol) and the resulting mixture was stirred at 50° C. for 15 h. After cooling to RT, the mixture was diluted with $H_2O$ (10 mL) and extracted with EtOAc (2×10 mL). The organic layer was washed with brine, dried over $Na_2SO_4$, and concentrated under vacuum. The crude product was purified by flash chromatography over silica gel eluting with 50% EtOAc/hexanes to afford 42 mg tert-butyl 7-(5-(2-(cyclopropylmethoxy)-4-fluorophenoxy)pyrimidin-4-yl)-2,7-diazaspiro[4.4]nonane-2-carboxylate as a yellow oil (90% yield). LCMS method B: $R_t$=1.69 min; $(M+H)^+$=485.6. $^1$H NMR (CD$_3$OD): δ 8.50 (s, 1H), 7.58 (s, 1H), 7.33-7.29 (m, 1H), 7.00-6.97 (m, 1H), 6.80-6.75 (m, 1H), 3.84-3.82 (m, 3H), 3.48-3.35 (m, 4H), 2.12-2.02 (m, 5H), 1.46 (s, 11H), 1.10-1.09 (m, 1H), 0.54-0.52 (m, 2H), 0.20-0.19 (m, 2H).

Step 2. 5-((7-(5-(2-(cyclopropylmethoxy)-4-fluorophenoxy)pyrimidin-4-yl)-2,7-diazaspiro[4.4]nonan-2-yl)methyl)-1,3-dihydro-2H-benzo[d]imidazol-2-one To a solution of tert-butyl 7-(5-(2-(cyclopropylmethoxy)-4-fluorophenoxy)pyrimidin-4-yl)-2,7-diazaspiro[4.4]nonane-2-carboxylate (42 mg, 87 mol) in DCM (2 mL) was added TFA (0.4 mL) at RT. The reaction mixture was stirred for 1 h and then neutralized with aqueous $NaHCO_3$ solution. The mixture was extracted with DCM (5×15 mL). The organic layers were combined, dried over $Na_2SO_4$, filtered and concentrated under reduced pressure. The crude product was used without further purification.

To a solution of the crude product, (12 mg, 30 μmol), 2-oxo-2,3-dihydro-1H-benzo[d]imidazole-5-carbaldehyde (Intermediate 40, 5 mg, 30 μmol) in MeOH (1 mL) was added $NaCNBH_3$ (10 mg, 45 μmol). The resulting mixture was stirred at RT for 15 h and purified by HPLC method A to afford 5-((7-(5-(2-(cyclopropylmethoxy)-4-fluorophenoxy)pyrimidin-4-yl)-2,7-diazaspiro[4.4]nonan-2-yl)methyl)-1,3-dihydro-2H-benzo[d]imidazol-2-one TFA salt as a colorless oil. LCMS method G: $R_t$=3.83 min; $(M+H)^+$=531.7. $^1$H NMR (CD$_3$OD): δ 8.51 (s, 1H), 7.59 (s, 1H), 7.30-7.28 (m, 1H), 7.22-7.18 (m, 2H), 7.12-7.10 (m, 1H), 6.98 (s, 1H), 6.77 (s, 1H), 4.43-4.41 (m, 2H), 4.12-4.09 (m, 2H), 3.80-3.78 (m, 2H), 2.30-2.15 (m, 5H), 1.29-1.20 (m, 5H), 0.90-0.88 (m, 1H), 0.51-0.48 (m, 2H), 0.15-0.13 (m, 2H).

Example 55

Ethyl 2-(7-(5-((4'-cyano-2'-cyclopropyl-5-fluoro-[1,1'-biphenyl]-2-yl)oxy)pyrimidin-4-yl)-2,7-diazaspiro[4.4]nonan-2-yl)thiazole-4-carboxylate

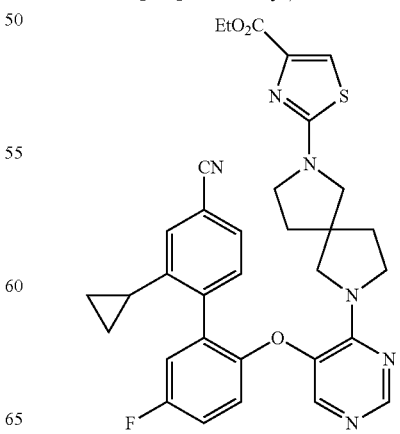

To a solution of 2'-((4-(2,7-diazaspiro[4.4]nonan-2-yl) pyrimidin-5-yl)oxy)-2-cyclopropyl-5'-fluoro-[1,1'-biphenyl]-4-carbonitrile (220 mg, 0.48 mmol) in DMF (5 mL) was added ethyl 2-chlorothiazole-4-carboxylate (111 mg, 0.58 mmol), CuI (9.2 mg, 0.048 mmol) and K₂CO₃ (132 mg, 0.96 mmol) and the reaction mixture was heated in a microwave at 100° C. for 16 h. The mixture was then filtered through celite and the filter cake was washed twice with EtOAc (30 mL). The filtrate was combined and diluted with H₂O (100 mL), extracted with EtOAc (50 mL×2). The combined organic layer was dried over Na₂SO₄, filtered and concentrated to give the crude product which was purified by preparative TLC (petroleum ether:ethyl acetate=1:2) to afford ethyl 2-(7-(5-((4'-cyano-2'-cyclopropyl-5-fluoro-[1,1'-biphenyl]-2-yl)oxy)pyrimidin-4-yl)-2,7-diazaspiro[4.4]nonan-2-yl)thiazole-4-carboxylate as a brown oil. Yield: 100 mg. LCMS method C: R$_f$=0.783 min, (M+H)⁺=610.9. ¹H NMR (CDCl₃): δ 8.35 (s, 1H), 7.77 (s, 1H), 7.35-7.50 (m, 2H), 7.15-7.25 (m, 2H), 6.95-7.10 (m, 2H), 6.83 (s, 1H), 4.30-4.45 (m, 2H), 3.60-3.75 (m, 2H), 3.40-3.60 (m, 6H), 1.85-2.05 (m, 4H), 1.55-1.80 (m, 1H), 1.20-1.50 (m, 3H), 0.85-0.95 (m, 2H), 0.60-0.75 (s, 2H). ¹⁹F NMR (CDCl): δ −118.94.

Example 56

2-(7-(5-((4'-cyano-2'-cyclopropyl-5-fluoro-[1,1'-biphenyl]-2-yl)oxy)pyrimidin-4-yl)-2,7-diazaspiro[4.4]nonan-2-yl)thiazole-4-carboxylic acid

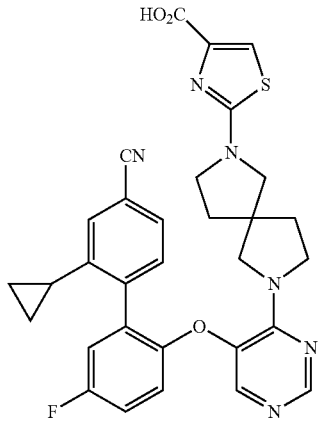 [SMILES: N#Cc1ccc(-c2cc(F)ccc2Oc2cncnc2N2CCC3(CCN(c4nc(C(=O)O)cs4)C3)C2)c(C2CC2)c1]

To a solution of ethyl 2-(7-(5-((4'-cyano-2'-cyclopropyl-5-fluoro-[1,1'-biphenyl]-2-yl)oxy)pyrimidin-4-yl)-2,7-diazaspiro[4.4]nonan-2-yl)thiazole-4-carboxylate (20 mg, 0.033 mmol) in THF (2 mL) was added aq. LiOH (1 mL, 4 N) and the reaction mixture was stirred at 18-26° C. for 16 h. The mixture was concentrated and purified by RP-HPLC method A to give 2-(7-(5-((4'-cyano-2'-cyclopropyl-5-fluoro-[1,1'-biphenyl]-2-yl)oxy)pyrimidin-4-yl)-2,7-diazaspiro[4.4]nonan-2-yl)thiazole-4-carboxylic acid as a solid. Yield: 6 mg. LCMS method C: R$_f$=0.726 min, (M+H)⁺=582.9. ¹H NMR (CD₃OD): δ 8.46 (s, 1H), 7.80 (s, 1H), 7.50-7.55 (m, 2H), 7.20-7.45 (m, 5H), 3.70-4.05 (m, 4H), 3.45-3.65 (m, 4H), 2.00-2.20 (m, 4H), 1.70-1.75 (m, 1H), 0.60-1.00 (m, 4H). ¹⁹F NMR (CD₃OD): δ −117.77.

Example 57

2-(7-(5-((4'-cyano-2'-cyclopropyl-5-fluoro-[1,1'-biphenyl]-2-yl)oxy)pyrimidin-4-yl)-2,7-diazaspiro[4.4]nonan-2-yl)-N-methylthiazole-4-carboxamide

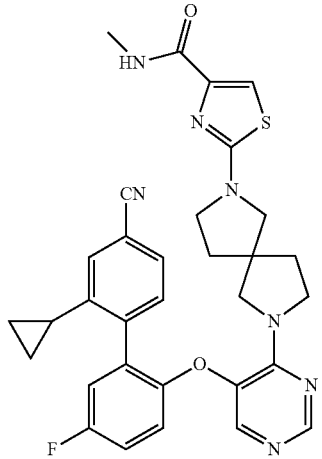 [SMILES: CNC(=O)c1csc(N2CCC3(CCN(c4ncncc4Oc4ccc(F)cc4-c4ccc(C#N)cc4C4CC4)C3)C2)n1]

To a solution of (2'-((4-(7-(4-amino-3-fluorobenzyl)-2,7-diazaspiro[4.4]nonan-2-yl)pyrimidin-5-yl)oxy)-2-cyclopropyl-5'-fluoro-[1,1'-biphenyl]-4-carbonitrile (25 mg, 0.03 mmol) in DMF (2 mL) were added DIEA (12 mg, 0.06 mmol), HATU (17 mg, 0.045 mmol) and methanamine solution of THF (30 μL, 0.06 mmol, 2 N). Then the reaction was stirred at 16-25° C. for 16 h. The mixture was purified by RP-HPLC method A to afford 2-(7-(5-((4'-cyano-2'-cyclopropyl-5-fluoro-[1,1'-biphenyl]-2-yl)oxy) pyrimidin-4-yl)-2,7-diazaspiro[4.4]nonan-2-yl)-N-methylthiazole-4-carboxamide (TFA salt) as a white solid. Yield: 2.7 mg. LCMS method C: R$_f$=0.744 min, (M+H)⁺=596.1. ¹H NMR (CD₃OD): δ 8.47 (s, 1H), 7.81 (s, 1H), 7.25-7.48 (m, 7H), 3.49-3.92 (m, 8H), 2.92 (s, 3H), 1.95-2.20 (m, 4H), 1.70 (s, 1H), 0.89-0.90 (m, 2H), 0.67 (s, 2H). ¹⁹F NMR: (CD₃OD 400 MHz): δ −117.725 (s 1F).

Example 58

2-(7-(5-((4'-cyano-2'-cyclopropyl-5-fluoro-[biphenyl]-2-yl)oxy)-[1,1'-biphenyl]-2-yl)oxy)pyrimidin-4-yl)-2,7-diazaspiro[4.4]nonan-2-yl)-N,N-dimethylthiazole-4-carboxamide

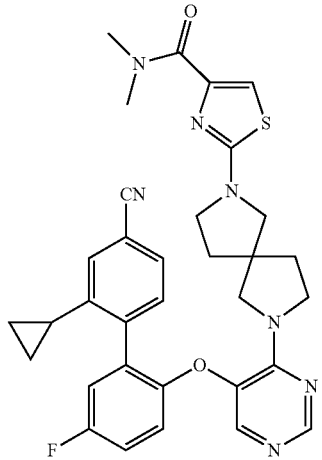 [SMILES: CN(C)C(=O)c1csc(N2CCC3(CCN(c4ncncc4Oc4ccc(F)cc4-c4ccc(C#N)cc4C4CC4)C3)C2)n1]

The title compound was synthesized according to the methods described for Example 57, substituting dimethyl amine for methyl amine. LCMS method D: $R_t$=1.191 min, (M+H)$^+$=610.3. $^1$H NMR (CD$_3$OD): δ 8.45 (s, 1H), 7.80 (s, 1H), 7.51 (s, 1H), 7.30-7.40 (m, 3H), 7.20-7.30 (m, 2H), 7.06 (s, 1H), 3.70-4.10 (m, 4H), 3.35-3.65 (m, 4H), 3.21 (s, 3H), 3.07 (s, 3H), 2.00-2.20 (m, 4H), 1.65-1.75 (m, 1H), 0.60-0.95 (m, 4H). $^{19}$F NMR (CD$_3$OD): δ −119.19.

Example 59

7-benzyl-2-(5-(4-fluoro-2-(4-isopropylpyrimidin-5-yl)phenoxy)pyrimidin-4-yl)-2-azaspiro[4.4]nonane

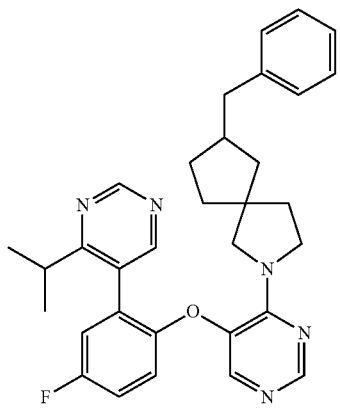 [SMILES: CC(C)c1ncncc1-c1cc(F)ccc1Oc1cncnc1N1CCC2(CCC(Cc3ccccc3)C2)C1]

Step 1. (E)-tert-butyl 7-benzylidene-2-azaspiro[4.4]nonane-2-carboxylate

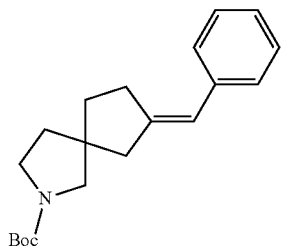

To a stirred suspension of NaH (160 mg, 4 mmol, 60% in mineral oil) in THF (8 mL, anhydrous) was added diethyl benzylphosphonate (920 mg, 4 mmol) in THF (6 mL, anhydrous) dropwise at 0° C. under N$_2$ and the mixture was stirred for 20 min at 0° C. A mixture of tert-butyl 7-oxo-2-azaspiro[4.4]nonane-2-carboxylate (200 mg, 0.8 mmol) and 15-crown-5 (880 mg, 4 mmol) in THF (6 mL, anhydrous) was added dropwise to the reaction mixture at 0° C. and the mixture was then warmed to 14-17° C. stirred for 16 h under N$_2$. The resulting mixture was quenched with sat. aq. NH$_4$Cl (20 mL) and extracted with EtOAc (3×30 mL). The organic layers were washed with brine (20 mL), dried over Na$_2$SO$_4$, filtered and concentrated to give a residue which was purified by flash chromatography (SiO$_2$, 10%~100% EtOAc/Petroleum ether) to give (E)-tert-butyl 7-benzylidene-2-azaspiro[4.4]nonane-2-carboxylate as a colorless oil. Yield: 230 mg. LCMS method C: $R_t$=0.911 min, (M+H)$^+$= 258.0.

Step 2. tert-butyl 7-benzyl-2-azaspiro[4.4]nonane-2-carboxylate

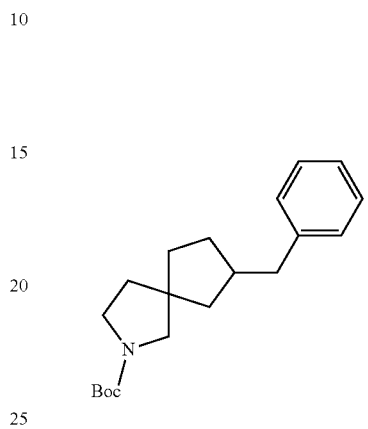

To a solution of (E)-tert-butyl 7-benzylidene-2-azaspiro[4.4]nonane-2-carboxylate (230 mg, 0.73 mmol) in MeOH (20 mL, anhydrous) was added Pd—C (100 mg, 10% on carbon, dry) and the resulting mixture was stirred at 30° C. for about 16 h under H$_2$ (40 psi). The suspension was filtered through fritted funnel and the filtrate was concentrated and purified by flash chromatography (EtOAc in petroleum ether from 10%~100%) to give tert-butyl 7-benzyl-2-azaspiro [4.4]nonane-2-carboxylate as a colorless oil. Yield: 120 mg. LCMS method C: $R_t$=0.965 min, (M+H)$^+$=338.0.

Step 3. 7-benzyl-2-azaspiro[4.4]nonane

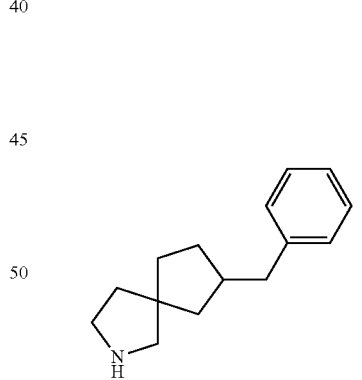

A solution of tert-butyl 7-benzyl-2-azaspiro[4.4]nonane-2-carboxylate (120 mg, 0.38 mmol) in TFA-CH$_2$Cl$_2$ (5 mL, v:v=1:4) was stirred at 12-18° C. for about 2 h at which time LCMS showed the reaction was complete. The resulting mixture was adjusted to pH=8 by sat. aq. NaHCO$_3$ and extracted with CH$_2$Cl$_2$ (3×10 mL). The combined organic layers were washed with brine (10 mL), dried over Na$_2$SO$_4$, filtered and concentrated to give crude 7-benzyl-2-azaspiro [4.4]nonane as a colorless oil, which was used for next step directly without further purification. Yield: 120 mg. LCMS method C: $R_t$=0.627 min, (M+H)$^+$=216.1.

Step 4. 7-benzyl-2-(5-(2-chloro-4-fluorophenoxy)pyrimidin-4-yl)-2-azaspiro[4.4]nonane

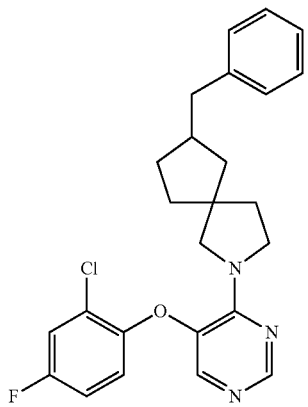 [SMILES: Fc1ccc(Oc2cncnc2N2CCC3(CCC(Cc4ccccc4)C3)C2)c(Cl)c1]

A solution of 7-benzyl-2-azaspiro[4.4]nonane (120 mg, 0.38 mmol, crude) and 4-chloro-5-(2-chloro-4-fluorophenoxy)pyrimidine (98 mg, 0.38 mmol) in MeCN (10 mL) was added $K_2CO_3$ (158 mg, 1.14 mmol). The resulting mixture was stirred at 90° C. for about 4 h. The mixture was filtered and filter cake washed with EtOAc (2×30 mL). The filtrate was concentrated and purified by RP-HPLC method A to give 7-benzyl-2-(5-(2-chloro-4-fluorophenoxy)pyrimidin-4-yl)-2-azaspiro[4.4]nonane (TFA salt) as a white solid. Yield: 80 mg. LCMS method D: $R_t$=1.144 min, $(M+H)^+$=483.8.

$^1H$ NMR ($CD_3OD$): δ 8.43-8.59 (m, 1H), 7.60-7.79 (m, 1H), 7.40-7.55 (m, 1H), 7.30-7.40 (m, 1H), 7.10-7.30 (m, 6H), 3.65-4.30 (m, 4H), 2.60-2.75 (m, 2H), 2.20-2.45 (m, 1H), 1.55-2.10 (m, 6H), 1.25-1.50 (m, 2H). $^{19}F$ NMR (MeOD): δ −77.26, −115.69.

Step 5. 7-benzyl-2-(5-(4-fluoro-2-(4-isopropylpyrimidin-5-yl)phenoxy)pyrimidin-4-yl)-2-azaspiro[4.4]nonane To a solution of 7-benzyl-2-(5-(2-chloro-4-fluorophenoxy)pyrimidin-4-yl)-2-azaspiro[4.4]nonane (70 mg, 0.16 mmol), (4-isopropylpyrimidin-5-yl)boronic acid (40 mg, 0.24 mmol) in dioxane (2 mL) and $H_2O$ (1 mL) was added to Sphos Pallodacyle (6 mg, 0.008 mmol) and $K_3PO_4$ (85 mg, 0.4 mmol) under $N_2$ and the resulting mixture was stirred at 115° C. for 45 min under microwave. The resulting mixture was diluted with water (20 mL) and extracted with EtOAc (3×20 mL). The organic layers were washed with brine (20 mL), dried over $Na_2SO_4$, filtered and concentrated to give a residue which was purified by RP-HPLC method A to give 7-benzyl-2-(5-(4-fluoro-2-(4-isopropylpyrimidin-5-yl)phenoxy)pyrimidin-4-yl)-2-azaspiro[4.4]nonane (TFA salt) as a white solid. Yield: 45 mg. LCMS method D: $R_t$=1.135 min, $(M+H)^+$=524.4. $^1H$ NMR (CD3OD): δ 9.03-9.20 (m, 1H), 8.55-8.67 (m, 1H), 8.48 (s, 1H), 7.93 (s, 1H), 7.21-7.40 (m, 5H), 7.10-7.20 (m, 3H), 3.35-3.93 (m, 4H), 2.95-3.12 (m, 1H), 2.55-2.70 (m, 2H), 2.20-2.40 (m, 1H), 1.49-1.96 (m, 6H), 1.10-1.30 (m, 8H) $^{19}F$ NMR (MeOD): δ −77.23, −117.91.

Example 60

5-((7-(5-((5-fluoro-2'-(1-hydroxyethyl)-[1,1'-biphenyl]-2-yl)oxy)pyrimidin-4-yl)-2,7-diazaspiro[4.4]nonan-2-yl)methyl)-1H-benzo[d]imidazol-2(3H)-one (Mixture)

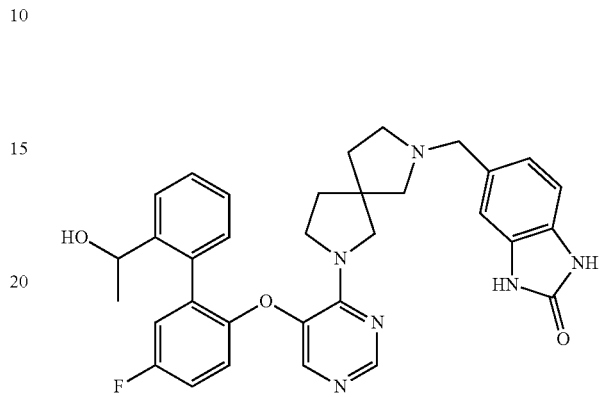

Step 1. tert-butyl 7-(5-((2'-acetyl-5-fluoro-[1,1'-biphenyl]-2-yl)oxy)pyrimidin-4-yl)-2,7-diazaspiro[4.4]nonane-2-carboxylate

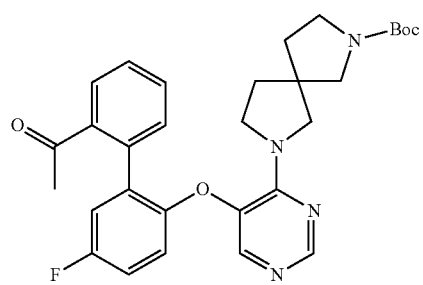 [SMILES: CC(=O)c1ccccc1-c1cc(F)ccc1Oc1cncnc1N1CCC2(CCN(C(=O)OC(C)(C)C)C2)C1]

To a solution of tert-butyl 7-(5-(2-bromo-4-fluorophenoxy)pyrimidin-4-yl)-2,7-diazaspiro[4.4]nonane-2-carboxylate (Intermediate 11, 600 mg, 1.2 mmol), (2-acetylphenyl)boronic acid (390 mg, 2.4 mmol) in dioxane (10 mL) and $H_2O$ (2 mL) was added to Pd(dppf)$Cl_2$ (87 mg, 0.12 mmol) and $Na_2CO_3$ (320 mg, 3 mmol) under $N_2$ and the resulting mixture was stirred at 80° C. for 16 h under $N_2$. The resulting mixture was diluted with water (50 mL) and extracted with EtOAc (3×30 mL). The organic layers were washed with brine (20 mL), dried over $Na_2SO_4$, filtered and concentrated in vacuo to give a residue Which was purified by flash chromatography ($SiO_2$, 10%~100% EtOAc/Petroleum ether) to give tert-butyl 7-(5-((2'-acetyl-5-fluoro-[1,1'-biphenyl]-2-yl)oxy)pyrimidin-4-yl)-2,7-diazaspiro[4.4]nonane-2-carboxylate as a yellow solid. Yield: 400 mg. LCMS method C: $R_t$=0.761 min, $(M+H)^+$=533.2.

Step 2. tert-butyl 7-(5-((5-fluoro-2'-(1-hydroxyethyl)-[1,1'-biphenyl]-2-yl)oxy)pyrimidin-4-yl)-2,7-diazaspiro[4.4]nonane-2-carboxylate

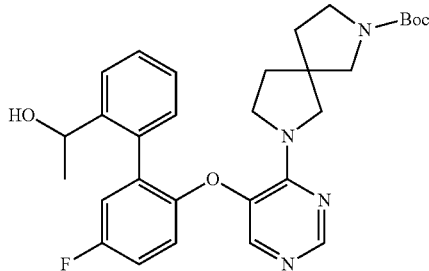 [SMILES: CC(O)c1ccccc1-c1cc(F)ccc1Oc1cncnc1N1CCC2(CCN(C(=O)OC(C)(C)C)C2)C1]

To a solution of tert-butyl 7-(5-((2'-acetyl-5-fluoro-[1,1'-biphenyl]-2-yl)oxy)pyrimidin-4-yl)-2,7-diazaspiro[4.4]nonane-2-carboxylate (350 mg, 0.66 mmol) in MeOH (20 mL, anhydrous) and THF (10 mL, anhydrous) was added NaBH$_4$ (98 mg, 2.65 mmol) and the resulting mixture was stirred at 50° C. for about 2 h under N$_2$. The resulting mixture was then quenched with sat. aq. NH$_4$Cl (20 mL) and extracted with EtOAc (3×20 mL). The organic layers were washed with brine (20 mL), dried over Na$_2$SO$_4$, filtered and concentrated to give tert-butyl 7-(5-((5-fluoro-2'-(1-hydroxyethyl)-[1,1'-biphenyl]-2-yl)oxy)pyrimidin-4-yl)-2,7-diazaspiro[4.4]nonane-2-carboxylate as a black solid, which was used for next step directly without further purification. Yield: 380 mg.

Step 3. 1-(2'-((4-(2,7-diazaspiro[4.4]nonan-2-yl)pyrimidin-5-yl)oxy)-5'-fluoro-[1,1'-biphenyl]-2-yl)ethanol

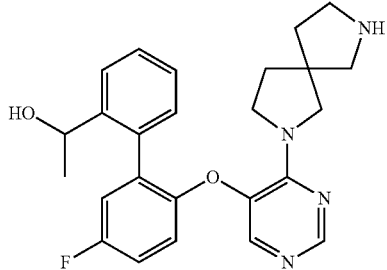 [SMILES: CC(O)c1ccccc1-c1cc(F)ccc1Oc1cncnc1N1CCC2(CCNC2)C1]

A solution of tert-butyl 7-(5-((5-fluoro-2'-(1-hydroxyethyl)-[1,1'-biphenyl]-2-yl)oxy)pyrimidin-4-yl)-2,7-diazaspiro[4.4]nonane-2-carboxylate (380 mg, 0.66 mmol, crude) in TFA-CH$_2$Cl$_2$ (9 mL, v:v=1:8) was stirred at 17-24° C. for about 2 h. The mixture was concentrated and adjusted to pH=8 with sat. aq. NaHCO$_3$ and extracted with EtOAc (3×20 mL). The combined organic layers were washed with brine (20 mL), dried over Na$_2$SO$_4$, filtered and concentrated to give 1-(2'-((4-(2,7-diazaspiro[4.4]nonan-2-yl)pyrimidin-5-yl)oxy)-5'-fluoro-[1,1'-biphenyl]-2-yl)ethanol as a yellow solid, which was used for next step directly without further purification. Yield: 330 mg. LCMS method C: R$_t$=0.581 min, (M+H)$^+$=435.2.

Step 4. 5-((7-(5-((5-fluoro-2'-(1-hydroxyethyl)-[1,1'-biphenyl]-2-yl)oxy)pyrimidin-4-yl)-2,7-diazaspiro[4.4]nonan-2-yl)methyl)-1H-benzo[d]imidazol-2(3H)-one To a solution of 1-(2'-((4-(2,7-diazaspiro[4.4]nonan-2-yl)pyrimidin-5-yl)oxy)-5'-fluoro-[1,1'-biphenyl]-2-yl)ethanol (330 mg, 0.66 mmol, crude) and 2-oxo-2,3-dihydro-1H-benzo[d]imidazole-5-carbaldehyde (Intermediate 40, 106 mg, 0.66 mmol,) in MeOH (10 mL, anhydrous) was added AcOH (0.2 mL). The mixture was stirred at 17-25° C. for about 30 min, then NaBH$_3$CN (82 mg, 1.32 mmol) was added and the resulting mixture was stirred at 17-25° C. for about 16 h. The mixture was quenched by sat. aq. NaHCO$_3$ (10 mL) and extracted with CH$_2$Cl$_2$ (3×20 mL). The combined organic layers were washed with brine (20 mL), dried over Na$_2$SO$_4$, filtered and concentrated to give a residue which was purified by RP-HPLC method A to give 5-((7-(5-((5-fluoro-2'-(1-hydroxyethyl)-[1,1'-biphenyl]-2-yl)oxy)pyrimidin-4-yl)-2,7-diazaspiro[4.4]nonan-2-yl)methyl)-1H-benzo[d]imidazol-2(3H)-one (TFA salt) as a white solid. Yield: 290 mg. LCMS method C: R$_t$=0.593 min, (M+H)$^+$=581.2 $^1$H NMR (CD$_3$OD): δ 8.00-8.15 (m, 1H), 7.50-7.70 (m, 2H), 6.90-7.40 (m, 9H), 4.67 (s, 1H), 4.43 (s, 2H), 3.35-3.95 (m, 8H), 1.90-2.25 (m, 4H), 1.20-1.35 (m, 3H). $^{19}$F NMR (CD$_3$OD): δ −76.92, −117.29∼−118.17.

Examples 60A-60D 5-((7-(5-((5-fluoro-2'-(1-hydroxyethyl)-[1,1'-biphenyl]-2-yl)oxy)pyrimidin-4-yl)-2,7-diazaspiro[4.4]nonan-2-yl)methyl)-1H-benzo[d]imidazol-2(3H)-one (Isomers 1-4)

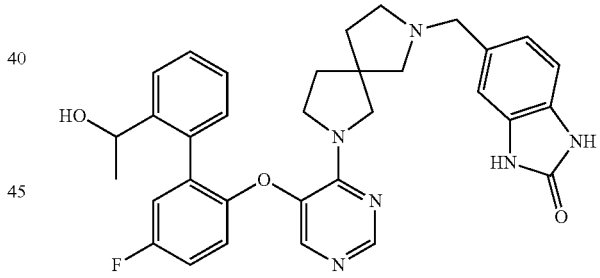

The title compound of Example 60 was separated as diastereomers by SFC method A and each diastereomer was further separated as enantiomers by SFC method 2.

Isomer 1:
LCMS method C: R$_t$=0.606 min, (M+H)$^+$=581.2. $^1$H NMR (CD$_3$OD): δ 8.30-8.45 (m, 1H), 7.52-7.79 (m, 2H), 7.10-7.40 (m, 8H), 6.95-7.10 (m, 1H), 4.66 (s, 1H), 4.35-4.50 (m, 2H), 3.55-3.95 (m, 5H), 3.35-3.50 (m, 3H), 1.82-2.26 (m, 4H), 1.20-1.35 (m, 3H). $^{19}$F NMR (CD$_3$OD): δ −76.99, −117.37∼−118.33. SFC: t$_R$=3.036 min (ee=100%).

Isomer 2:
LCMS method C: R$_t$=0.608 min, (M+H)$^+$=581.2. $^1$H NMR (CD$_3$OD): δ 8.30-8.45 (m, 1H), 7.50-7.75 (m, 2H), 7.25-7.40 (m, 3H), 7.10-7.25 (m, 5H), 6.95-7.10 (m, 1H), 4.66 (s, 1H), 4.35-4.45 (m, 2H), 3.55-4.00 (m, 8H), 1.95-2.30 (m, 4H), 1.20-1.35 (m, 3H). $^{19}$F NMR (CD$_3$OD): δ −76.98 8, −117.39∼−118.17. SFC: t$_R$=3.353 min (ee=100%).

Isomer 3:

LCMS method C: $R_t$=0.606 min, (M+H)⁺=581.2. ¹H NMR (CD₃OD): δ 8.15 (s, 1H), 7.57-7.66 (m, 2H), 7.31-7.40 (m, 1H), 7.10-7.25 (m, 3H), 6.83-7.10 (m, 5H), 4.72-4.82 (m, 1H), 3.63 (s, 2H), 3.35-3.60 (m, 4H), 2.55-2.75 (m, 2H), 2.35-2.50 (m, 2H), 1.65-1.90 (m, 4H), 1.20-1.30 (m, 3H). ¹⁹F NMR (CD₃OD): δ −120.89~−121.17. SFC: $t_R$=7.926 min (ee=100%).

Isomer 4:

LCMS method C: $R_t$=0.609 min, (M+H)⁺=581.2. ¹H NMR (CD₃OD): δ 8.15 (s, 1H), 7.55-7.68 (m, 2H), 7.30-7.40 (m, 1H), 6.81-7.27 (m, 8H), 4.71-4.82 (m, 1H), 3.40-3.72 (m, 6H), 2.60-2.70 (m, 2H), 2.40-2.50 (m, 2H), 1.65-1.90 (m, 4H), 1.28 (dd, J=13.6, 6.4 Hz, 3H). ¹⁹F NMR (CD₃OD): δ −120.79~−121.27 (m, 1F). SFC: $t_R$=9.407 min (ee=100%).

Example 61

5-fluoro-N-isopropyl-N-methyl-2-((4-(7-(3-(2-oxooxazolidin-3-yl)benzyl)-2,7-diazaspiro[4.4]nonan-2-yl)pyrimidin-5-yl)oxy)benzamide

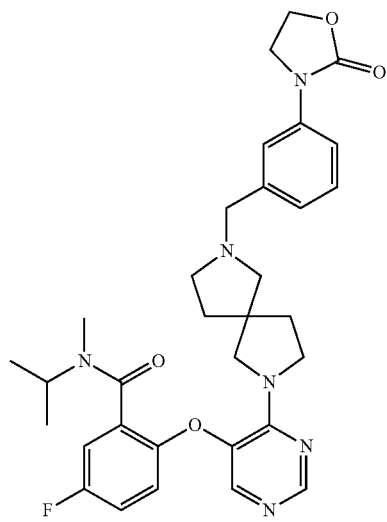 [SMILES: CC(C)N(C)C(=O)c1cc(F)ccc1Oc1cncnc1N1CCC2(CCN(Cc3cccc(N4CCOC4=O)c3)C2)C1]

Step 1. 3-(2-oxooxazolidin-3-yl)benzonitrile

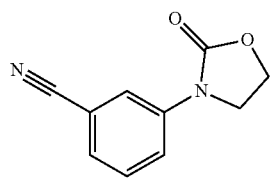 [SMILES: N#Cc1cccc(N2CCOC2=O)c1]

To a solution of oxazolidin-2-one (240 mg, 2.75 mmol), K₂CO₃ (760 mg, 5.5 mmol), CuI (16 mg, 0.083 mmol) and trans-cyclohexanediamine (32 mg, 0.275 mmol) in anhydrous dioxane (15 mL) was added 3-bromobenzonitrile (500 mg, 2.75 mmol) under a nitrogen atmosphere and the mixture was stirred at 110° C. for 16 h. Then the reaction mixture was added into EtOAc (30 mL) and filtered with diatomite. The filtrate was concentrated under a reduced pressure to give the crude product which was purified by column chromatography on silica gel (petroleum ether:ethyl acetate=1:1) to give 3-(2-oxooxazolidin-3-yl)benzonitrile as a white solid. Yield: 75 mg. ¹H NMR (CDCl₃): δ 7.80-7.90 (m, 2H), 7.45-7.55 (m, 1H), 7.35-7.45 (m, 1H), 4.45-4.55 (m, 2H), 4.00-4.10 (m, 2H).

Step 2. 3-(2-oxooxazolidin-3-yl)benzaldehyde

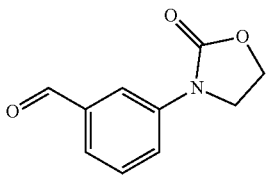 [SMILES: O=Cc1cccc(N2CCOC2=O)c1]

To a solution of 3-(2-oxooxazolidin-3-yl)benzonitrile (75 mg, 0.4 mmol) in HCO₂H (11 mL) and H₂O (4 mL) was added Ni—Al alloy (86 mg, 1 mmol) at 20-24° C., then the mixture was stirred at 90° C. for 16 h. The reaction mixture was stirred for an additional 6 h and was then filtered. The filtrate was concentrated under a reduced pressure and the resulting residue was added into water (50 mL) and extracted with CH₂Cl₂ (3×50 mL). The organic layers were dried over anhydrous Na₂SO₄, filtered and concentrated under a reduced pressure to give crude product 3-(2-oxooxazolidin-3-yl)benzaldehyde as a white solid. Yield: 60 mg. LCMS method D: $R_t$=0.911 min, (M+H)⁺=192.2.

Step 3. 5-fluoro-N-isopropyl-N-methyl-2-((4-(7-(3-(2-oxooxazolidin-3-yl)benzyl)-2,7-diazaspiro[4.4]nonan-2-yl)pyrimidin-5-yl)oxy)benzamide The title product was prepared according to the procedure described in Step 4 of Example 41. The crude product was purified by RP-HPLC method D to give 5-fluoro-N-isopropyl-N-methyl-2-((4-(7-(3-(2-oxooxazolidin-3-yl)benzyl)-2,7-diazaspiro [4.4]nonan-2-yl)pyrimidin-5-yl)oxy)benzamide as a white solid. LCMS method E: $R_t$=1.230 min, (M+H)⁺=589.2. ¹H NMR (CD₃OD): δ 8.20-8.30 (m, 1H), 7.70-7.85 (m, 1H), 7.56 (s, 1H), 7.40-7.50 (m, 1H), 7.25-7.35 (m, 1H), 7.05-7.20 (m, 3H), 6.75-6.95 (m, 1H), 4.40-4.55 (m, 2H), 4.00-4.15 (m, 2H), 3.55-3.80 (m, 6H), 2.94 (d, J=4.0 Hz, 2H), 2.77 (s, 2H), 2.60-2.75 (m, 2H), 2.40-2.60 (m, 2H), 1.85-2.00 (m, 2H), 1.70-1.85 (m, 2H), 1.05-1.25 (m, 6H). ¹⁹F NMR (MeOD): δ −120.09~−120.54.

Example 62

5-fluoro-N-isopropyl-N-methyl-2-((4-(7-(4-(2-oxooxazolidin-3-yl)benzyl)-2,7-diazaspiro[4.4]nonan-2-yl)pyrimidin-5-yl)oxy)benzamide

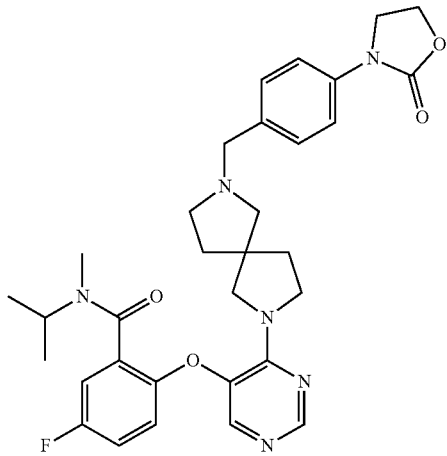 [SMILES: CC(C)N(C)C(=O)c1cc(F)ccc1Oc1cncnc1N1CCC2(CCN(Cc3ccc(N4CCOC4=O)cc3)C2)C1]

The title product was synthesized according to a method similar to the procedure described for Example 61 starting from 4-bromo cyanobenzene. LCMS method C: R$_t$=0.607 min, (M+H)$^+$=589.2. $^1$H NMR (CD$_3$OD): δ 8.29-8.33 (m, 1H), 7.80-7.88 (m, 1H), 7.60-7.62 (m, 2H), 7.43-7.45 (m, 2H), 7.18-7.20 (m, 2H), 6.83-6.97 (m, 1H), 4.50-4.52 (m, 2H), 4.11-4.15 (m, 2H), 3.93-3.96 (m, 3H), 3.55-3.76 (m, 4H), 2.95-3.05 (m, 2H), 2.75-2.90 (m, 3H), 1.93-2.05 (m, 5H), 1.18-1.35 (m, 7H). $^{19}$F NMR (CD$_3$OD): δ −120.17~−120.58

Example 63

5-((7-(5-((5-fluoro-2'-(2-hydroxypropan-2-yl)-[1,1'-biphenyl]-2-yl)oxy)pyrimidin-4-yl)-2,7-diazaspiro[4.4]nonan-2-yl)methyl)-1H-benzo[d]imidazol-2(3H)-one

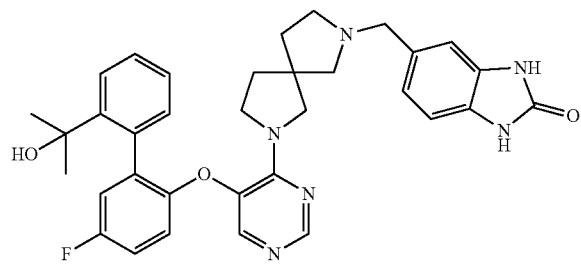 [SMILES: CC(C)(O)c1ccccc1-c1cc(F)ccc1Oc1cncnc1N1CCC2(CCN(Cc3ccc4[nH]c(=O)[nH]c4c3)C2)C1]

Step 1. 1-(2'-((4-(2,7-diazaspiro[4.4]nonan-2-yl)pyrimidin-5-yl)oxy)-5'-fluoro-[1,1'-biphenyl]-2-yl)ethanone

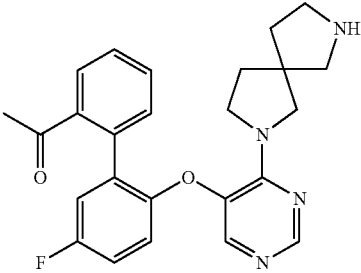 [SMILES: CC(=O)c1ccccc1-c1cc(F)ccc1Oc1cncnc1N1CCC2(CCNC2)C1]

A solution of tert-butyl 7-(5-((2'-acetyl-5-fluoro-[1,1'-biphenyl]-2-yl)oxy)pyrimidin-4-yl)-2,7-diazaspiro[4.4]nonane-2-carboxylate (200 mg, 0.37 mmol) in TFA-CH$_2$Cl$_2$ (5 mL, V:V=1:5) was stirred at 16-24° C. for about 2 h. The resulting mixture was concentrated and adjusted to pH=8 with sat. aq. Na$_2$CO$_3$. The mixture was then extracted with CH$_2$Cl$_2$ (3×20 mL) and the combined organic layers were washed with brine (10 mL), dried over Na$_2$SO$_4$, filtered and concentrated to give crude 1-(2'-((4-(2,7-diazaspiro[4.4]nonan-2-yl)pyrimidin-5-yl)oxy)-5'-fluoro-[1,1'-biphenyl]-2-yl)ethanone as a yellow oil, which was used for next step directly without further purification.

Step 2. 5-((7-(5-((2'-acetyl-5-fluoro-[1,1'-biphenyl]-2-yl)oxy) pyrimidin-4-yl)-2,7-diazaspiro[4. 4]nonan-2-yl) methyl)-1H-benzo[d]imidazol-2(3H)-one

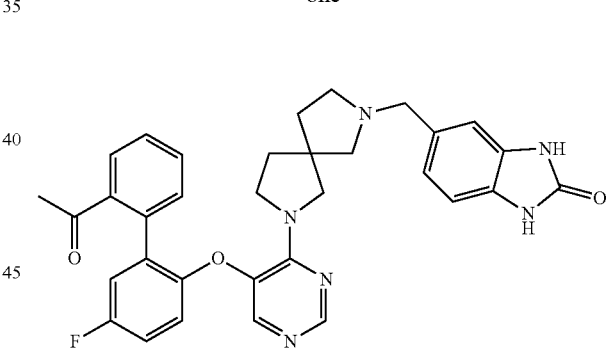

To a solution of 1-(2'-((4-(2,7-diazaspiro[4.4]nonan-2-yl)pyrimidin-5-yl)oxy)-5'-fluoro-[1,1'-biphenyl]-2-yl)ethanone (200 mg, 0.37 mmol, crude) and 2-oxo-2,3-dihydro-1H-benzo[d]imidazole-5-carbaldehyde (Intermediate 40, 60 mg, 0.37 mmol,) in MeOH (5 mL, anhydrous) was added AcOH (0.2 mL). The resulting mixture was stirred at 50° C. for about 2 h under N$_2$, then NaBH$_3$CN (156 mg, 0.74 mmol) was added and the resulting mixture was stirred at 50° C. for about 16 h. The mixture was quenched by sat. aq. NaHCO$_3$ (50 mL) and extracted with CH$_2$Cl$_2$ (5×20 mL). The combined organic layers were washed with brine (30 mL), dried over Na$_2$SO$_4$, filtered and concentrated to give a residue which was purified by flash chromatography on silica gel (MeOH in CH$_2$Cl$_2$ from 10%~100%) to give 5-((7-(5-((2'-acetyl-5-fluoro-[1,1'-biphenyl]-2-yl)oxy)pyrimidin-4-yl)-2,7-diazaspiro[4.4]nonan-2-yl)methyl)-1H-benzo[d]imidazol-2(3H)-one as a yellow solid. Yield: 100 mg. LCMS method C: R$_t$=0.606 min, (M+H)$^+$=579.2.

Step 3. 5-((7-(5-((5-fluoro-2'-(2-hydroxypropan-2-yl)-[1,1'-biphenyl]-2-yl)oxy)pyrimidin-4-yl)-2,7-diazaspiro[4.4]nonan-2-yl)methyl)-1H-benzo[d]imidazol-2(3H)-one To a solution of 5-((7-(5-((2'-acetyl-5-fluoro-[1,1'-biphenyl]-2-yl)oxy)pyrimidin-4-yl)-2,7-diazaspiro[4.4]nonan-2-yl)methyl)-1H-benzo[d]imidazol-2(3H)-one (100 mg, 0.17 mmol) in THF (5 mL, anhydrous) was added MeMgBr (0.6 mL, 1.7 mmol, 3 M in ether) dropwise at −78° C. under $N_2$ and the resulting mixture was stirred at −78° C. for about 4 h under $N_2$. The mixture was then quenched with sat. aq. $NH_4Cl$ (10 mL) and extracted with EtOAc (3×20 mL). The combined organic layers were washed with brine (20 mL), dried over $Na_2SO_4$, filtered and concentrated to give a residue which was purified by basic preparative RP-HPLC method D to give 5-((7-(5-((5-fluoro-2'-(2-hydroxypropan-2-yl)-[1,1'-biphenyl]-2-yl)oxy)pyrimidin-4-yl)-2,7-diazaspiro[4.4]nonan-2-yl) methyl)-1H-benzo[d]imidazol-2 (3H)-one as a white solid. Yield: 6 mg. LCMS method C: $R_t$=0.614 min, (M+H)$^+$=595.2. $^1$H NMR (CD$_3$OD): δ 8.10-8.31 (m, 1H), 7.58-7.86 (m, 2H), 7.24-7.40 (m, 1H), 6.81-7.22 (m, 8H), 4.04 (s, 2H), 3.45-3.63 (m, 4H), 2.69-3.20 (m, 4H), 1.80-2.03 (m, 4H), 1.23-1.55 (m, 6H). $^{19}$F NMR (CD$_3$OD): δ −76.92, −121.82.

Example 64

2-(1,4-dioxaspiro[4.5]decan-8-ylmethyl)-6-(5-(4-fluoro-2-(4-isopropyl pyrimidin-5-yl)phenoxy)pyrimidin-4-yl)-2,6-diazaspiro[3.3]heptane

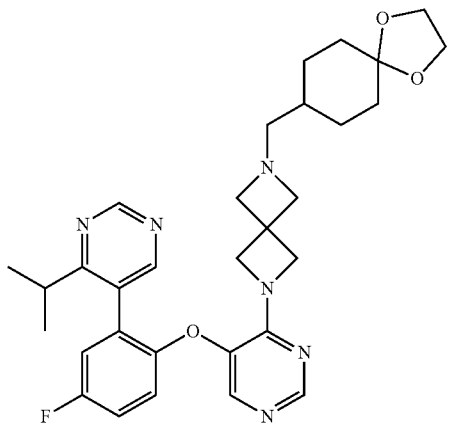 [SMILES: CC(C)c1ncncc1-c1cc(F)ccc1Oc1cncnc1N1CC2(CN(CC3CCC4(CC3)OCCO4)C2)C1]

The title compound was prepared from Intermediate 27 (200 mg, 0.49 mmol) and 1,4-dioxaspiro[4.5]decane-8-carbaldehyde (101 mg, 0.59 mmol), by reductive amination as described in Step 4 of Example 11. The product was purified by RP-HPLC method D to give 2-(1,4-dioxaspiro[4.5]decan-8-ylmethyl)-6-(5-(4-fluoro-2-(4-isopropylpyrimidin-5-yl)phenoxy)pyrimidin-4-yl)-2,6-diazaspiro[3.3]heptane as light-yellow oil. Yield: 50 mg. LCMS method D: $R_t$=0.803 min, (M+H)$^+$=561.4 $^1$H NMR (CD$_3$OD): δ 9.09 (s, 1H), 8.63 (s, 1H), 8.18 (s, 1H), 7.61-7.68 (m, 1H), 7.20-7.30 (m, 2H), 7.03-7.10 (m, 1H), 4.17 (s, 4H), 3.90 (s, 4H), 3.36 (s, 4H), 3.01-3.11 (m, 1H), 2.30-2.35 (m, 2H), 1.68-1.78 (m, 4H), 1.43-1.51 (m, 2H), 1.32-1.39 (m, 1H), 1.15-1.26 (m, 8H). $^{19}$F NMR (CD$_3$OD): δ −119.88.

Example 65

4-((6-(5-(4-fluoro-2-(4-isopropylpyrimidin-5-yl)phenoxy)pyrimidin-4-yl)-2,6-diazaspiro[3.3]heptan-2-yl) methyl)cyclohexanol

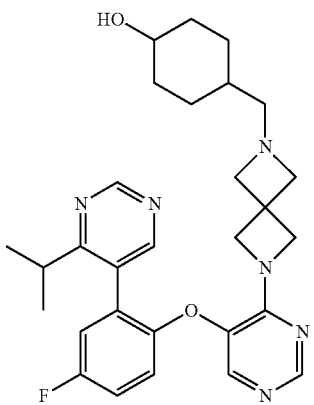 [SMILES: CC(C)c1ncncc1-c1cc(F)ccc1Oc1cncnc1N1CC2(CN(CC3CCC(O)CC3)C2)C1]

(2-(1,4-dioxaspiro[4.5]decan-8-ylmethyl)-6-(5-(4-fluoro-2-(4-isopropyl pyrimidin-5-yl)phenoxy)pyrimidin-4-yl)-2,6-diazaspiro[3.3]heptane (1.0 mmol) was treated with 4 N aq. HCl (10 ml) at RT for 6 h. The solvent was removed via rotary evaporation, the crude product was mixed with MeOH (5 mL), NaBH$_4$ (3.0 mmol) was added and the resulting mixture was stirred for 30 min. The solvent was removed via rotary evaporation and the resulting residue was purified by RP-HPLC method A to give 4-((6-(5-(4-fluoro-2-(4-isopropylpyrimidin-5-yl)phenoxy)pyrimidin-4-yl)-2,6-diazaspiro[3.3]heptan-2-yl) methyl)cyclohexanol (TFA salt) as a colorless oil. Yield: 6.3 mg. LCMS method C: $R_t$=0.854 min, (M+H)$^+$=519.4 $^1$H NMR (CD$_3$OD): δ 9.12 (s, 1H), 8.63 (s, 1H), 8.39 (s, 1H), 7.80 (s, 1H), 7.25-7.41 (m, 3H), 4.22-4.65 (m, 8H), 3.43-3.53 (m, 1H), 3.00-3.14 (m, 3H), 1.94-1.99 (m, 2H), 1.72-1.79 (m, 2H), 1.50-1.59 (m, 1H), 1.03-1.33 (m, 10H). $^{19}$F NMR (CD$_3$OD): δ −117.71, −77.02.

Example 66

2-cyclopropyl-5'-fluoro-2'-((4-(6-((4-hydroxycyclohexyl)methyl)-2,6-diazaspiro[3.3]heptan-2-yl) pyrimidin-5-yl)oxy)-[1,1'-biphenyl]-4-carbonitrile

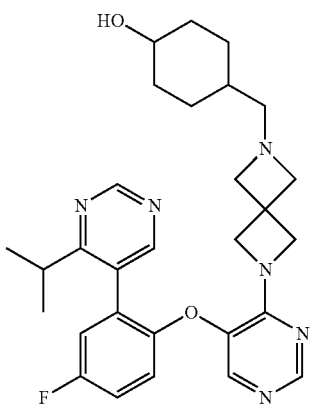 [SMILES: CC(C)c1ncncc1-c1cc(F)ccc1Oc1cncnc1N1CC2(CN(CC3CCC(O)CC3)C2)C1]

The title product was synthesized according to the method described for Example 65 starting from 2'-((4-(2,6-diazaspiro[3.3]heptan-2-yl)pyrimidin-5-yl)oxy)-2-cyclopropyl-5'-fluoro-[1,1'-biphenyl]-4-carbonitrile (Intermediate 32). LCMS method D: R$_t$=1.154 min, (M+H)$^+$=540.4.

Example 67

2-(5-((5-fluoro-2'-(1-methoxyethyl)-[1,1'-biphenyl]-2-yl)oxy)pyrimidin-4-yl)-6-((tetrahydro-2H-pyran-4-yl)methyl)-2,6-diazaspiro[3.3]heptane

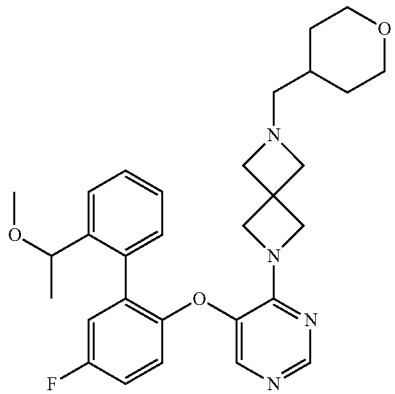 [SMILES: COC(C)c1ccccc1-c1cc(F)ccc1Oc1cncnc1N1CC2(CN(CC3CCOCC3)C2)C1]

Step 1. tert-butyl 6-(5-((2'-acetyl-5-fluoro-[1,1'-biphenyl]-2-yl)oxy)pyrimidin-4-yl)-2,6-diazaspiro[3.3]heptane-2-carboxylate

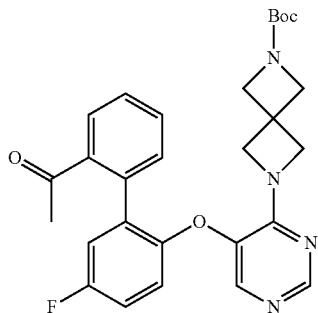 [SMILES: CC(=O)c1ccccc1-c1cc(F)ccc1Oc1cncnc1N1CC2(CN(C(=O)OC(C)(C)C)C2)C1]

To a solution of tert-butyl 6-(5-(2-bromo-4-fluorophenoxy)pyrimidin-4-yl)-2,6-diazaspiro[3.3]heptane-2-carboxylate (Intermediate 20, 150 mg, 0.322 mmol), (2-acetylphenyl)boronic acid (63 mg, 0.387 mmol) and K$_3$PO$_4$ (205 mg, 0.97 mmol) in dioxane/H$_2$O (2 mL/0.5 mL) was added Sphos palladcycle (23 mg, 0.032 mmol) under N$_2$. The reaction mixture was sealed and heated in a microwave at 115° C. for 0.5 h. The mixture was then diluted with H$_2$O (20 mL), filtered and extracted with ethyl acetate (20 mL×3). The combined organic layers were dried over anhydrous Na$_2$SO$_4$, filtered, and the filtrate was concentrated under reduced pressure. The crude residue were combined and purified by column chromatography on silica gel (eluting with petroleum ether:ethyl acetate=10:1 to 2:3) to afford tert-butyl 6-(5-((2'-acetyl-5-fluoro-[1,1'-biphenyl]-2-yl)oxy)pyrimidin-4-yl)-2,6-diazaspiro[3.3]heptane-2-carboxylate as a yellow oil. Yield: 180 mg. LCMS method C: R$_t$=0.755 min, (M+H)$^+$=505.2

Step 2. 6-(5-((5-fluoro-2'-(1-hydroxyethyl)-[1,1'-biphenyl]-2-yl)oxy)pyrimidin-4-yl)-2,6-diazaspiro[3.3]heptane-2-carboxylate

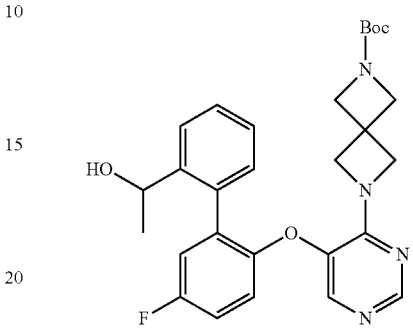

To a solution of tert-butyl 6-(5-((2'-acetyl-5-fluoro-[1,1'-biphenyl]-2-yl)oxy)pyrimidin-4-yl)-2,6-diazaspiro[3.3]heptane-2-carboxylate (180 mg, 0.36 mmol) in anhydrous THF (10 mL) was added NaBH$_4$ (40 mg, 1.07 mmol) at −30° C. under N$_2$ and the reaction mixture was stirred at RT for 2 h. The mixture was quenched with H$_2$O (20 mL) and concentrated under reduced pressure to remove THF and MeOH. The residue was extracted with EtOAc (20 mL×3) and the combined organic layers were dried over anhydrous Na$_2$SO$_4$, filtered and the filtrate was concentrated under reduced pressure to afford tert-butyl 6-(5-((5-fluoro-2'-(1-hydroxyethyl)-[1,1'-biphenyl]-2-yl)oxy)pyrimidin-4-yl)-2,6-diazaspiro[3.3]heptane-2-carboxylate as a yellow solid, which was used in the next step without further purification. Yield: 181 mg. LCMS method C: R$_t$=0.745 min, (M+H)$^+$= 507.2

Step 3. tert-butyl 6-(5-((5-fluoro-2'-(1-methoxyethyl)-[1,1'-biphenyl]-2-yl) oxy)pyrimidin-4-yl)-2,6-diazaspiro[3.3]heptane-2-carboxylate

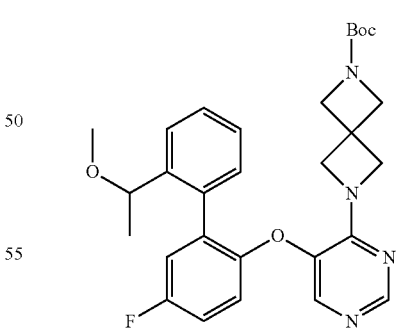

To a solution of tert-butyl 6-(5-((5-fluoro-2'-(1-hydroxyethyl)-[1,1'-biphenyl]-2-yl)oxy)pyrimidin-4-yl)-2,6-diazaspiro[3.3]heptane-2-carboxylate (100 mg, 0.20 mmol) in anhydrous THF (5 mL) was added NaH (40 mg, 1.00 mmol, 60% in mineral oil) at 0° C. under N$_2$ and the reaction mixture was stirred at 0° C. for 0.5 h. MeI (2.19 g, 15.43 mmol) was then added and the reaction mixture was stirred at RT for 18 h. The mixture was quenched with H$_2$O (0.1 mL) and concentrated under reduced pressure and purified by column chromatography on silica gel (eluting with petroleum ether:ethyl acetate=10:1 to 2:3) to afford tert-butyl 6-(5-((5-fluoro-2'-(1-methoxyethyl)-[1,1'-biphenyl]-2-yl)oxy)pyrimidin-4-yl)-2,6-diazaspiro[3.3]heptane-2-carboxylate as a yellow oil. Yield: 43 mg. LCMS method C: $R_t$=0.748 min, (M+H)$^+$=521.2

Step 4. 2-(5-((5-fluoro-2'-(1-methoxyethyl)-[1,1'-biphenyl]-2-yl)oxy)pyrimidin-4-yl)-2,6-diazaspiro[3.3]heptane

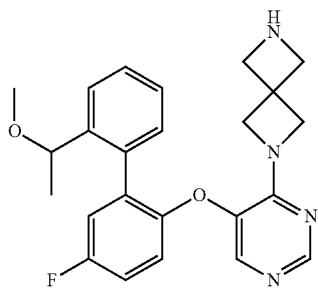 [SMILES: COC(C)c1ccccc1-c1cc(F)ccc1Oc1cncnc1N1CC2(CNC2)C1]

To a solution of tert-butyl 6-(5-((5-fluoro-2'-(1-methoxyethyl)-[1,1'-biphenyl]-2-yl)oxy)pyrimidin-4-yl)-2,6-diazaspiro[3.3]heptane-2-carboxylate (43 mg, 0.082 mmol) in anhydrous DCM (10 mL) was added TFA (2 mL) at 0° C. and the reaction mixture was stirred at 19-26° C. for 2 h. The mixture was diluted with 1N NaOH (20 mL) and extracted with ethyl acetate (20 mL×3). The combined organic layers were dried over anhydrous Na$_2$SO$_4$, filtered and the filtrate was concentrated under reduced pressure to afford 2-(5-((5-fluoro-2'-(1-methoxyethyl)-[1,1'-biphenyl]-2-yl)oxy)pyrimidin-4-yl)-2,6-diazaspiro[3.3]heptane as a yellow oil, which was used in the next step without further purification.

Step 5. 2-(5-((5-fluoro-2'-(1-methoxyethyl)-[1,1'-biphenyl]-2-yl)oxy)pyrimidin-4-yl)-6-((tetrahydro-2H-pyran-4-yl)methyl)-2,6-diazaspiro[3.3] heptane A solution of 2-(5-((5-fluoro-2'-(1-methoxyethyl)-[1,1'-biphenyl]-2-yl)oxy)pyrimidin-4-yl)-2,6-diazaspiro[3.3]heptane (35 mg, 0.083 mmol, crude), tetrahydro-2H-pyran-4-carbaldehyde (19 mg, 0.17 mmol), and HOAc (20 µL) in anhydrous MeOH (10 mL) was stirred at 19-25° C. for 0.5 h. NaBH$_3$CN (21 mg, 0.33 mmol) was then added and the reaction mixture was stirred at 60° C. for 4 h, at which time LCMS showed the desired product was produced. The mixture was then concentrated under reduced pressure and the resulting residue purified by HPLC method A to afford 2-(5-((5-fluoro-2'-(1-methoxyethyl)-[1,1'-biphenyl]-2-yl)oxy)pyrimidin-4-yl)-6-((tetrahydro-2H-pyran-4-yl)methyl)-2,6-diazaspiro[3.3]heptane (TFA salt) as a white solid. Yield: 22 mg. LCMS method C: $R_t$=0.735 min, (M+H)$^+$=519.2 $^1$H NMR (CD$_3$OD): δ 8.38 (d, J=1.6 Hz, 1H), 7.72 (s, 1H), 7.55-7.60 (m, 1H), 7.40-7.50 (m, 1H), 7.30-7.34 (m, 3H), 7.13-7.28 (m, 2H), 4.4.25-4.60 (m, 9H), 3.94 (d, J=11.6 Hz, 2H), 3.35-3.45 (m, 2H), 3.05-3.15 (m, 5H), 1.80-1.95 (m, 1H), 1.62 (d, J=12.4 Hz, 2H), 1.27-1.37 (m, 5H). $^{19}$F NMR (MeOD): δ −76.83, 117.75.

Example 68

5-(5-fluoro-2-((4-(6-((tetrahydro-2H-pyran-4-yl)methyl)-2,6-diazaspiro[3.3]heptan-2-yl)pyrimidin-5-yl)oxy)phenyl)-2,3-dihydro-1H-inden-2-amine

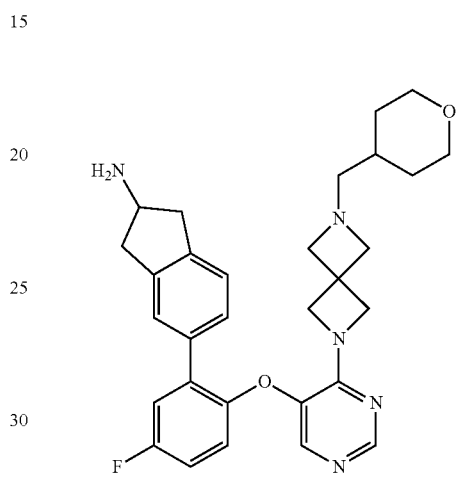

Step 1. 2-(5-(2-bromo-4-fluorophenoxy)pyrimidin-4-yl)-2,6-diazaspiro[3.3]heptane

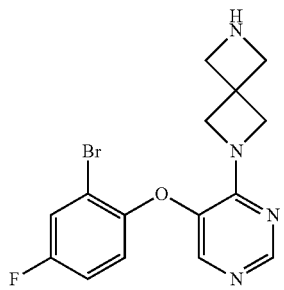 [SMILES: Fc1ccc(Oc2cncnc2N2CC3(CNC3)C2)c(Br)c1]

To a mixture of Intermediate 20 (120 mg, 0.3 mmol) in CH$_2$Cl$_2$ (3 mL) was added TFA (1 mL) under ice-cold water and the resulting mixture was stirred at RT for 2 h. The mixture was then concentrated under reduced pressure and the residue was adjusted to pH 10-12 with 10% NaOH solution and extracted with CH$_2$Cl$_2$ (3×30 mL). The combined organic layers were dried over anhydrous sodium sulfate, filtered and concentrated under reduced pressure to give 2-(5-(2-bromo-4-fluorophenoxy)pyrimidin-4-yl)-2,6-diazaspiro[3.3]heptane as a yellow solid, which was used in the next step without further purification.

Step 2. 2-(5-(2-bromo-4-fluorophenoxy)pyrimidin-4-yl)-6-((tetrahydro-2H-pyran-4-yl)methyl)-2,6-diazaspiro[3.3]heptane

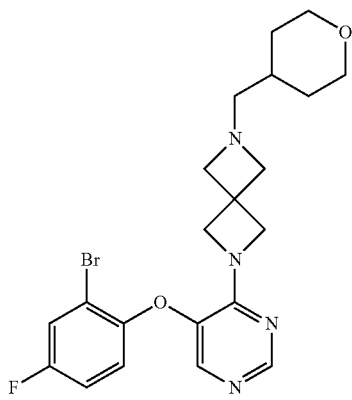 [SMILES: Fc1ccc(Oc2cncnc2N2CC3(CN(CC4CCOCC4)C3)C2)c(Br)c1]

A mixture of 2-(5-(2-bromo-4-fluorophenoxy)pyrimidin-4-yl)-2,6-diazaspiro[3.3]heptane (90 mg, 0.24 mmol), tetrahydro-2H-pyran-4-carbaldehyde (41 mg, 0.36 mmol), NaBH$_3$CN (60 mg, 0.96 mmol) and HOAc (0.05 mL) in MeOH (5 mL) was stirred at 70° C. for 5 h. Sat. solution of NaHCO$_3$ was then added to adjust the pH to 8. The mixture was concentrated under reduced pressure. Water (20 mL) was added to the residue and subsequently extracted with EtOAc (2×30 mL). The combined organic layers were dried over anhydrous sodium sulfate, filtered and concentrated under reduced pressure. The residue was purified by column chromatography on silica gel (eluting with dichloromethane:methanol=10:1) to give 2-(5-(2-bromo-4-fluorophenoxy)pyrimidin-4-yl)-6-((tetrahydro-2H-pyran-4-yl)methyl)-2,6-diazaspiro[3.3]heptane as a white solid. Yield: 90 mg. LCMS method C: R$_t$=0.539 min, (M+H)$^+$=463.0, 465.0 (bromine isotopes).

Step 3. tert-butyl (5-(5-fluoro-2-((4-(6-((tetrahydro-2H-pyran-4-yl)methyl)-2,6-diazaspiro[3.3]heptan-2-yl)pyrimidin-5-yl)oxy)phenyl)-2,3-dihydro-1H-inden-2-yl) carbamate

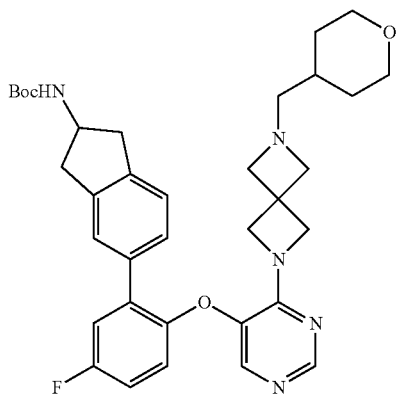 [SMILES: CC(C)(C)OC(=O)NC1Cc2ccc(-c3cc(F)ccc3Oc3cncnc3N3CC4(CN(CC5CCOCC5)C4)C3)cc2C1]

To a mixture of 2-(5-(2-bromo-4-fluorophenoxy)pyrimidin-4-yl)-6-((tetrahydro-2H-pyran-4-yl)methyl)-2,6-diazaspiro[3.3]heptane (50 mg, 0.13 mmol), tert-butyl (5-(4,4, 5,5-tetramethyl-1,3,2-dioxaborolan-2-yl)-2,3-dihydro-1H-inden-2-yl)carbamate (59 mg, 0.17 mmol) and K$_3$PO$_4$ (70 mg, 0.33 mmol) in dioxane (2 mL) and H$_2$O (0.5 mL) was added Sphos Palladacycle (8 mg, 0.011 mmol) under N$_2$ and the mixture was stirred at 115° C. for 30 min in a microwave. The mixture was then concentrated under reduced pressure. The resulting residue was added to H$_2$O (20 mL) and extracted with EtOAc (2×30 mL). The combined organic layers were dried over anhydrous sodium sulfate, filtered and concentrated under reduced pressure. The residue was purified by preparative TLC on silica gel (eluting with dichloromethane:methanol=10:1) to give tert-butyl (5-(5-fluoro-2-((4-(6-((tetrahydro-2H-pyran-4-yl)methyl)-2,6-diazaspiro[3.3]heptan-2-yl)pyrimidin-5-yl)oxy)phenyl)-2,3-dihydro-1H-inden-2-yl)carbamate as a yellow oil. Yield: 35 mg.

Step 4. 5-(5-fluoro-2-((4-(6-((tetrahydro-2H-pyran-4-yl)methyl)-2,6-diazaspiro[3.3]heptan-2-yl)pyrimidin-5-yl)oxy)phenyl)-2,3-dihydro-1H-inden-2-amine To a mixture of tert-butyl (5-(5-fluoro-2-((4-(6-((tetrahydro-2H-pyran-4-yl)methyl)-2,6-diazaspiro[3.3]heptan-2-yl)pyrimidin-5-yl)oxy)phenyl)-2,3-dihydro-1H-inden-2-yl)carbamate (35 mg, 0.06 mmol) in CH$_2$Cl$_2$ (3 mL) was added TFA (1 mL) under ice-cold water and the mixture was stirred at RT for 2 h. The mixture was concentrated under reduced pressure and the residue was purified by RP-HPLC method D to give 5-(5-fluoro-2-((4-(6-((tetrahydro-2H-pyran-4-yl)methyl)-2,6-diazaspiro[3.3]heptan-2-yl)pyrimidin-5-yl)oxy)phenyl)-2,3-dihydro-1H-inden-2-amine as a white solid. Yield: 1.2 mg. LCMS method C: R$_t$=0.516 min, (M+H)$^+$=516.2 $^1$H NMR (CD$_3$OD): δ 8.10 (s, 1H), 7.30-7.40 (m, 4H), 7.10-7.23 (m, 3H), 4.31 (s 4H), 3.90-4.05 (m, 3H), 3.35-3.40 (m, 8H), 2.85-2.95 (m, 2H), 2.37-2.39 (d, J=6.0 Hz, 2H), 1.62-1.64 (d, J=10.0 Hz, 3H), 1.20-1.35 (m, 2H). $^{19}$F NMR (CD$_3$OD): δ −76.93, −119.56.

Example 69

5-((7-(5-(((5-fluoro-2'-(1-hydroxypropan-2-yl)-[1,1'-biphenyl]-2-yl)oxy)pyrimidin-4-yl)-2,7-diazaspiro[4.4]nonan-2-yl)methyl)-1H-benzo[d]imidazol-2(3H)-one

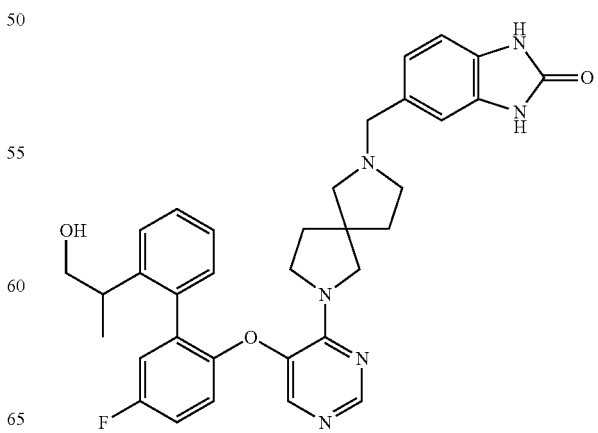

Step 1. tert-butyl 7-(5-((2'-bromo-5-fluoro-[1,1'-biphenyl]-2-yl)oxy) pyrimidin-4-yl)-2,7-diazaspiro[4.4] nonane-2-carboxylate

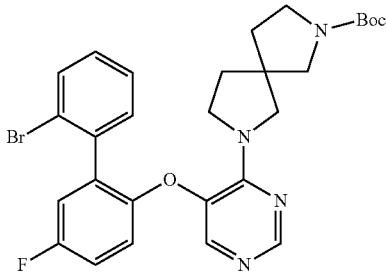 [SMILES: CC(C)(C)OC(=O)N1CCC2(CCN(c3ncncc3Oc3ccc(F)cc3-c3ccccc3Br)C2)C1]

A 100 mL round flask equipped with a nitrogen balloon and a condenser were charged with tert-butyl 7-(5-(2-bromo-4-fluorophenoxy)pyrimidin-4-yl)-2,7-diazaspiro[4.4]nonane-2-carboxylate (Intermediate 11, 1.0 g, 2.0 mmol), EtOH (20 mL), toluene (8 mL) and H$_2$O (8 mL) respectively. To the resulting mixture was added (2-bromophenyl)boronic acid (0.41 g, 2.0 mmol), Pd(OAc)$_2$ (9 mg, 0.04 mmol), PPh$_3$ (26 mg, 0.1 mmol) and Na$_2$CO$_3$ (636 mg, 6.0 mmol) respectively, under N$_2$ with stirring. After addition, the final mixture was degassed and purged with N$_2$ 3 times, then heated at 75-80° C. under N$_2$ for 16 h. The mixture was then concentrated under reduced pressure to remove organic solvents and H$_2$O (30 mL) and brine (30 mL) were added to the residue, then extracted with EtOAc (20 mL×3). The combined organic layers were washed with brine (20 mL×2), dried over Na$_2$SO$_4$, filtered and concentrated under reduced pressure, and the resulting residue was purified by RP-HPLC method D to give tert-butyl 7-(5-((2'-bromo-5-fluoro-[1,1'-biphenyl]-2-yl)oxy)pyrimidin-4-yl)-2,7-diazaspiro[4.4]nonane-2-carboxylate as a white solid. Yield: 0.26 g. LCMS method D: R$_t$=1.074 min, (M+H)$^+$=569.2.

Step 2. tert-butyl 7-(5-((5-fluoro-2'-(prop-1-en-2-yl)-[1,1'-biphenyl]-2-yl) oxy)pyrimidin-4-yl)-2,7-diazaspiro[4.4]nonane-2-carboxylate

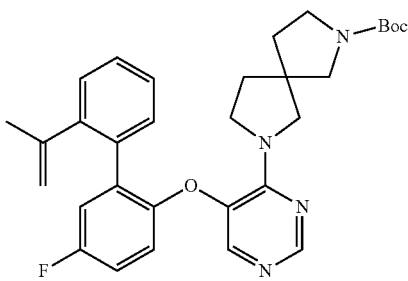 [SMILES: C=C(C)c1ccccc1-c1cc(F)ccc1Oc1cncnc1N1CCC2(CCN(C(=O)OC(C)(C)C)C2)C1]

To a suspension of tert-butyl 7-(5-((2'-bromo-5-fluoro-[1,1'-biphenyl]-2-yl)oxy)pyrimidin-4-yl)-2,7-diazaspiro[4.4]nonane-2-carboxylate (0.26 g, 0.37 mmol) in dioxane (15 mL) and H$_2$O (3 mL) was added 4,4,5,5-tetramethyl-2-(prop-1-en-2-yl)-1,3,2-dioxaborolane (0.12 g, 0.74 mmol) and K$_3$PO$_4$ (0.16 g, 0.74 mmol), Sphos palladacycle (13 mg, 0.019 mmol) under a nitrogen atmosphere. The resulting mixture was degassed and purged with N$_2$ 3 times, and subsequently heated at 70-75° C. under N$_2$ for 24 h. An additional batch of 4,4,5,5-tetramethyl-2-(prop-1-en-2-yl)-1,3,2-dioxaborolane (70 mg, 0.42 mmol) and Sphos palladacycle (7 mg, 0.0097 mmol) were added under N$_2$, and the resulting mixture was heated at 70-75° C. under N$_2$ for another 18 h, at which time LCMS showed the reaction was complete. After cooling, H$_2$O (30 mL) and brine (30 mL) were added to the mixture, which was then extracted with EtOAc (20 mL×3). The combined organic layers were washed with brine (20 mL×2), dried over Na$_2$SO$_4$, filtered and concentrated under reduced pressure, and the resulting residue was purified by column chromatography on silica gel (petroleum ether:EtOAc=1:1 to 1:2) to give tert-butyl 7-(5-((5-fluoro-2'-(prop-1-en-2-yl)-[1,1'-biphenyl]-2-yl)oxy) pyrimidin-4-yl)-2,7-diazaspiro[4.4]nonane-2-carboxylate as a white solid. Yield: 0.20 g. LCMS method D: R$_t$=1.108 min, (M+H)$^+$=531.2. $^1$H NMR (CDCl$_3$): δ 8.35 (s, 1H), 7.83 (s, 1H), 7.20-7.35 (m, 3H), 7.10-7.15 (m, 1H), 6.90-7.10 (m, 2H), 6.65-6.75 (m 1H), 5.03 (s, 1H), 4.80 (s, 1H), 3.50-3.65 (m 2H), 3.35-3.50 (m, 3H), 3.20-3.35 (m, 1H), 3.10-3.20 (m, 2H), 1.82 (s, 3H), 1.70-1.80 (m, 4H), 1.47 (s, 9H). $^{19}$F NMR (CDCl$_3$): δ −120.31.

Step 3. tert-butyl 7-(5-((5-fluoro-2'-(1-hydroxypropan-2-yl)-[1,1'-biphenyl]-2-yl)oxy)pyrimidin-4-yl)-2,7-diazaspiro[4.4]nonane-2-carboxylate

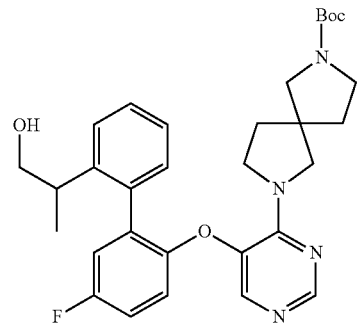 [SMILES: CC(CO)c1ccccc1-c1cc(F)ccc1Oc1cncnc1N1CCC2(CCN(C(=O)OC(C)(C)C)C2)C1]

A 500 mL round flask equipped with a nitrogen balloon charged with tert-butyl 7-(5-((5-fluoro-2'-(prop-1-en-2-yl)-[1,1'-biphenyl]-2-yl)oxy)pyrimidin-4-yl)-2,7-diazaspiro[4.4]nonane-2-carboxylate (140 mg, 0.23 mmol) and THF (5 mL, dry) under nitrogen atmosphere, and the resulting mixture was cooled to 0-3° C. under N$_2$. BH$_3$-THF (1 mL, 1.0 mmol, 1.0 M in THF) was then added dropwise at 0-3° C. under N$_2$ with stirring, and the reaction mixture was stirred at 0-3° C. under N$_2$ for 1 h, then warmed to RT overnight. H$_2$O (0.5 mL) and NaBO$_3$.4H$_2$O (50 mg, 0.32 mmol) were added sequentially and the resulting mixture was stirred at RT for 3 h. The reaction was quenched by addition of H$_2$O (30 mL). Brine (30 mL) was added to the residue and the mixture was extracted with EtOAc (15 mL×3). The combined organic layers were washed with brine (15 mL×2), dried over Na$_2$SO$_4$, filtered and concentrated under reduced pressure, and the resulting residue was purified using preparative TLC on silica gel (petroleum ether:EtOAc=1:4) to give tert-butyl 7-(5-((5-fluoro-2'-(1-hydroxypropan-2-yl)-[1,1'-biphenyl]-2-yl)oxy)pyrimidin-4-yl)-2,7-diazaspiro[4.4]nonane-2-carboxylate as a white solid. Yield: 71 mg. LCMS method D: R$_t$=1.019 min, (M+H)$^+$=549.2.

Step 4. 2-(2'-((4-(2,7-diazaspiro[4.4]nonan-2-yl)pyrimidin-5-yl) oxy)-5'-fluoro-[1,1'-biphenyl]-2-yl)propan-1-ol

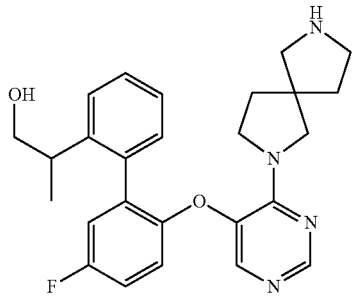 [SMILES: CC(CO)c1ccccc1-c1cc(F)ccc1Oc1cncnc1N1CCC2(CCNC2)C1]

To a solution of tert-butyl 7-(5-((5-fluoro-2'-(1-hydroxypropan-2-yl)-[1,1'-biphenyl]-2-yl)oxy)pyrimidin-4-yl)-2,7-diazaspiro[4.4]nonane-2-carboxylate (35 mg, 0.064 mmol) in CH$_2$Cl$_2$ (3 mL) was added HCl-MeOH (0.5 mL, 2 mmol, 4 M in MeOH) at 0-3° C. with stirring and the reaction mixture was stirred for 1 h. The reaction was quenched by addition of H$_2$O (5 mL), and adjusted to pH=12 with 10% aq. NaOH. Brine (10 mL) was added and the mixture was extracted with CH$_2$Cl$_2$ (10 mL×2). The combined organic layers were washed with brine (10 mL×2), dried over Na$_2$SO$_4$, filtered and concentrated under reduced pressure to give crude 2-(2'-((4-(2,7-diazaspiro[4.4]nonan-2-yl)pyrimidin-5-yl)oxy)-5'-fluoro-[1,1'-biphenyl]-2-yl)propan-1-ol as a yellow sticky solid.

Step 5. 5-((7-(5-((5-fluoro-2'-(1-hydroxypropan-2-yl)-[1,1'-biphenyl]-2-yl)oxy) pyrimidin-4-yl)-2,7-diazaspiro[4.4]nonan-2-yl)methyl)-1H-benzo[d]imidazol-2(3H)-one

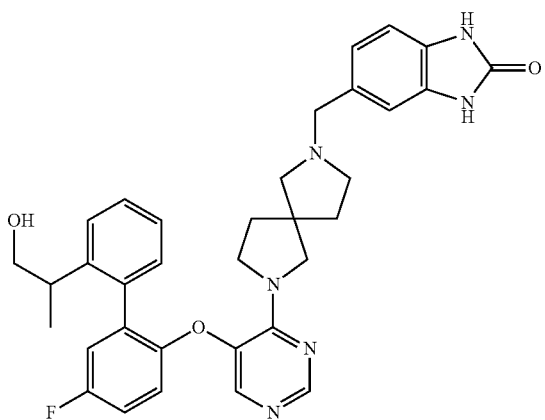 [SMILES: CC(CO)c1ccccc1-c1cc(F)ccc1Oc1cncnc1N1CCC2(CCN(Cc3ccc4[nH]c(=O)[nH]c4c3)C2)C1]

To a suspension of 2-(2'-((4-(2,7-diazaspiro[4.4]nonan-2-yl)pyrimidin-5-yl)oxy)-5'-fluoro-[1,1'-biphenyl]-2-yl)propan-1-ol (20 mg, 0.45 mmol) and 2-oxo-2,3-dihydro-1H-benzo[d]imidazole-5-carbaldehyde (Intermediate 40, 7.3 mg, 0.045 mmol) in anhydrous MeOH (3 mL) was added NaBH$_3$CN (5.8 mg, 0.09 mmol) under a nitrogen atmosphere and the mixture was stirred at 60-65° C. for 16 h. An additional batch of 2-oxo-2,3-dihydro-1H-benzo[d]imidazole-5-carbaldehyde (10 mg, 0.062 mmol) and NaBH$_3$CN (7 mg, 0.11 mmol) were added, the reaction mixture was stirred at 60-65° C. for an additional 18 h. The reaction mixture was concentrated under reduced pressure and purified by RP-HPLC-method A to give 5-((7-(5-((5-fluoro-2'-(1-hydroxypropan-2-yl)-[1,1'-biphenyl]-2-yl)oxy)pyrimidin-4-yl)-2,7-diazaspiro[4.4]nonan-2-yl)methyl)-1H-benzo[d]imidazol-2(3H)-one (TFA salt) as a white solid. Yield: 13 mg. LCMS method E: R$_t$=1.752 min, (M+H)$^+$=595.2 $^1$H NMR (CD$_3$OD): δ 8.45 (s, 1H), 7.74 (s, 1H), 7.07-7.44 (m, 10H), 4.35-4.50 (m, 2H), 3.40-3.95 (m, 9H), 3.10-3.25 (m, 1H), 2.75-2.85 (m, 1H), 1.95-2.20 (m, 4H), 1.00-1.25 (m, 3H). $^{19}$F NMR (C MeOD): δ −117.47, −76.69~−77.90.

Example 70

5-((7-(5-(4-fluoro-2-(morpholinomethyl)phenoxy)pyrimidin-4-yl)-2,7-diazaspiro[4.4]nonan-2-yl)methyl)-1H-benzo[d]imidazol-2(3H)-one

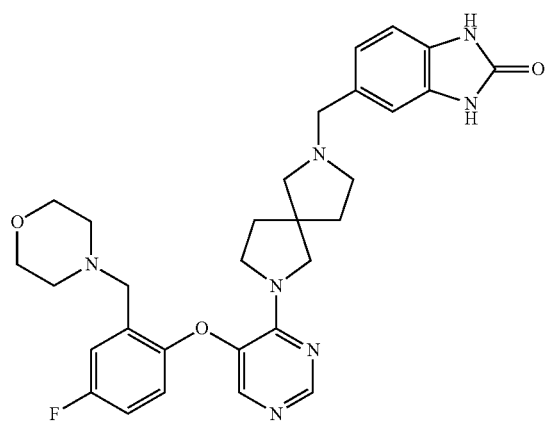 [SMILES: O=c1[nH]c2ccc(CN3CCC4(CCN(c5ncncc5Oc5ccc(F)cc5CN5CCOCC5)C4)C3)cc2[nH]1]

Step 1. tert-butyl 7-(5-(4-fluoro-2-(morpholine-4-carbonyl)phenoxy)pyrimidin-4-yl)-2,7-diazaspiro[4.4]nonane-2-carboxylate

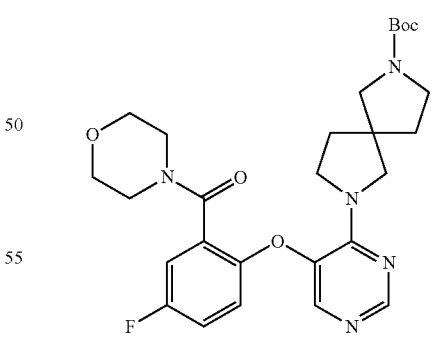

To a solution of 2-((4-(7-(tert-butoxycarbonyl)-2,7-diazaspiro[4.4]nonan-2-yl)pyrimidin-5-yl)oxy)-5-fluorobenzoic acid (Intermediate 33, Step 2, 60 mg, 0.13 mmol) in anhydrous CH$_2$Cl$_2$ (5 mL) was added HATU (61 mg, 0.16 mmol), DIEA (168 mg, 1.3 mmol) and morpholine (113 mg, 1.3 mmol) and the mixture was stirred at 7° C. for 16 h. The reaction mixture was concentrated under reduced pressure and purified by silica gel chromatography (CH$_2$Cl$_2$:

MeOH=20:1) to afford crude tert-butyl 7-(5-(4-fluoro-2-(morpholine-4-carbonyl)phenoxy)pyrimidin-4-yl)-2,7-diazaspiro[4.4]nonane-2-carboxylate as a brown oil. Yield: 60 mg. LCMS method C: $R_t$=0.700 min, (M+H)$^+$=528.2.

Step 2. tert-butyl 7-(5-(4-fluoro-2-(morpholinomethyl)phenoxy)pyrimidin-4-yl)-2,7-diazaspiro[4.4]nonane-2-carboxylate

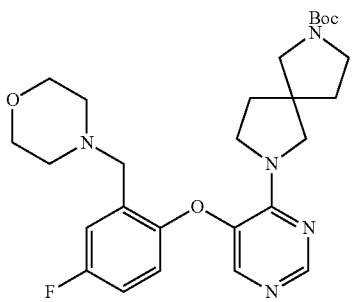 [SMILES: CC(C)(C)OC(=O)N1CCC2(CCN(c3ncncc3Oc3ccc(F)cc3CN3CCOCC3)C2)C1]

To a solution of tert-butyl 7-(5-(4-fluoro-2-(morpholine-4-carbonyl)phenoxy)pyrimidin-4-yl)-2,7-diazaspiro[4.4]nonane-2-carboxylate (50 mg, 0.09 mmol) in anhydrous THF (5 mL) was added BH$_3$-Me$_2$S (0.2 mL, 10.0 M in Me$_2$S) at 0° C. and the mixture was stirred at 60° C. for 4 h under N$_2$. The reaction mixture was quenched with MeOH (5 mL) at 0° C. and stirred at 60° C. for 0.5 h. The resulting mixture was concentrated under reduced pressure to afford a residue which was purified by silica gel chromatography (CH$_2$Cl$_2$:MeOH=20:1) to give tert-butyl 7-(5-(4-fluoro-2-(morpholinomethyl)phenoxy)pyrimidin-4-yl)-2,7-diazaspiro[4.4]nonane-2-carboxylate as a white solid. Yield: 35 mg. LCMS method C: $R_t$=0.642 min, (M+H)$^+$=514.2.

Step 3. 4-(2-((4-(2,7-diazaspiro[4.4]nonan-2-yl)pyrimidin-5-yl)oxy)-5-fluorobenzyl)morpholine

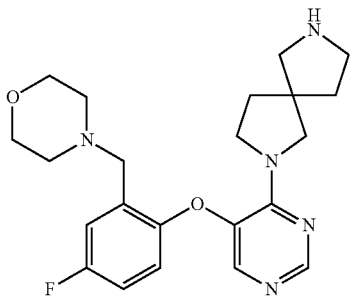 [SMILES: Fc1ccc(Oc2cncnc2N2CCC3(CCNC3)C2)c(CN2CCOCC2)c1]

To a solution of tert-butyl 7-(5-(4-fluoro-2-(morpholinomethyl)phenoxy)pyrimidin-4-yl)-2,7-diazaspiro[4.4]nonane-2-carboxylate (35 mg, 0.05 mmol) in anhydrous CH$_2$Cl$_2$ (3 mL) was added TFA (1 mL) and the mixture was stirred at 10° C. for 0.5 h under N$_2$. The reaction mixture was concentrated under reduced pressure to afford a residue which was adjusted to pH 9-10 with 10% NaOH solution and extracted with EtOAc (5 mL). The organic layer was dried over anhydrous Na$_2$SO$_4$, filtered and concentrated under reduced pressure to give 4-(2-((4-(2,7-diazaspiro[4.4]nonan-2-yl)pyrimidin-5-yl)oxy)-5-fluorobenzyl)morpholine as a brown oil which was used in the next step.

Step 4. 5-((7-(5-(4-fluoro-2-(morpholinomethyl)phenoxy)pyrimidin-4-yl)-2,7-diazaspiro[4.4]nonan-2-yl)methyl)-1H-benzo[d]imidazol-2(3H)-one To a solution of 4-(2-((4-(2,7-diazaspiro[4.4]nonan-2-yl)pyrimidin-5-yl)oxy)-5-fluorobenzyl)morpholine (20 mg, crude, 0.05 mmol) and 2-oxo-2,3-dihydro-1H-benzo[d]imidazole-5-carbaldehyde (Intermediate 40, 16 mg, 0.10 mmol) in anhydrous MeOH (3 mL) was added NaBH$_3$CN (17 mg, 0.25 mmol) under N$_2$ and the reaction mixture was stirred at 55° C. for 16 h. The reaction mixture was concentrated under reduced pressure to afford a residue which was purified by RP-HPLC method F to give the compound 5-((7-(5-(4-fluoro-2-(morpholinomethyl)phenoxy)pyrimidin-4-yl)-2,7-diazaspiro[4.4]nonan-2-yl)methyl)-1H-benzo[d]imidazol-2(3H)-one as a white solid. Yield: 7.10 mg. LCMS method E: $R_t$=1.635 min, (M+H)$^+$=560.2. $^1$H NMR (CD$_3$OD): δ 8.23 (s, 1H), 7.57 (s, 1H), 7.27 (dd, J=9.2, 3.2 Hz, 1H), 7.00-7.05 (dd, J=8.8, 4.4 Hz, 4H), 3.74-3.81 (m, 3H), 3.57-3.68 (m, 9H), 2.59-2.74 (m, 3H), 2.45-2.51 (m, 5H), 1.93-1.99 (s, 2H), 1.84 (t, J=6.8 Hz, 2H). $^{19}$F NMR (CD$_3$OD): δ −121.05.

Example 71

1-(7-(5-((2'-ethyl-5-fluoro-[1,1'-biphenyl]-2-yl)amino)pyrimidin-4-yl)-2,7-diazaspiro[3.5]nonan-2-yl)-2-methylpropan-2-ol

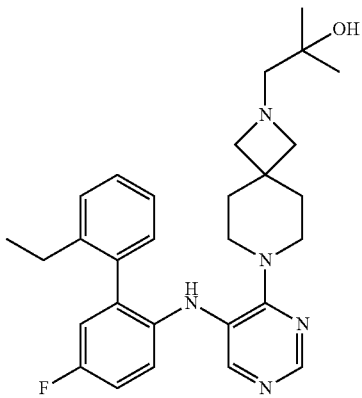 [SMILES: CCc1ccccc1-c1cc(F)ccc1Nc1cncnc1N1CCC2(CC1)CN(CC(C)(C)O)C2]

Step 1. tert-butyl 7-(5-iodopyrimidin-4-yl)-2,7-diazaspiro[3.5]nonane-2-carboxylate

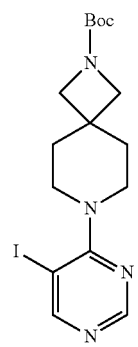 [SMILES: CC(C)(C)OC(=O)N1CC2(CCN(c3ncncc3I)CC2)C1]

To a solution of 4-chloro-5-iodopyrimidine (2 g, 8.3 mmol) in MeCN (30 mL) was added tert-butyl 2,7-diazaspiro[3.5]nonane-2-carboxylate (1.9 g, 8.3 mmol) and $K_2CO_3$ (2.3 g, 16.6 mmol) and the resulting suspension was stirred at 90° C. for 16 h. The mixture was filtered and the filtrate was concentrated and then purified by ISCO column on silica gel (petroleum ether:EtOAc=10:1 to 3:1) to afford tert-butyl 7-(5-iodopyrimidin-4-yl)-2,7-diazaspiro[3.5]nonane-2-carboxylate as a yellow solid. Yield: 3.4 g. LCMS method C: $R_t$=0.718 min, $(M+H)^+$=431.1.

Step 2. tert-butyl 7-(5-((2-bromo-4-fluorophenyl)amino)pyrimidin-4-yl)-2,7-diazaspiro[3.5]nonane-2-carboxylate

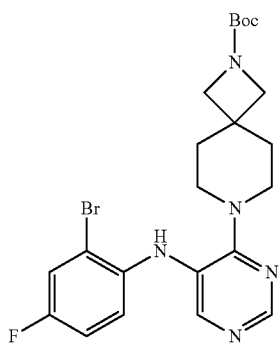 [SMILES: CC(C)(C)OC(=O)N1CC2(CCN(c3ncncc3Nc3ccc(F)cc3Br)CC2)C1]

To a solution of tert-butyl 7-(5-iodopyrimidin-4-yl)-2,7-diazaspiro[3.5]nonane-2-carboxylate (350 mg, 0.813 mmol) and 2-bromo-4-fluoroaniline (186 mg, 0.976 mmol) and NaO$^t$Bu (234 mg, 2.44 mmol) in anhydrous toluene (5 mL) was added Pd$_2$(dba)$_3$ (37 mg, 0.041 mmol) under $N_2$ and the reaction mixture was sealed and heated in a microwave at 120° C. for 1 h. The mixture was then diluted with $H_2O$ (20 mL), filtered and extracted with ethyl acetate (50 mL×3). The combined organic layers were dried over anhydrous $Na_2SO_4$, filtered, and the filtrate was concentrated under reduced pressure and purified by column chromatography on silica gel eluting with petroleum ether:EtOAc (100:0 to 1:1) to afford tert-butyl 7-(5-((2-bromo-4-fluorophenyl)amino)pyrimidin-4-yl)-2,7-diazaspiro[3.5]nonane-2-carboxylate as a brown solid. Yield: 485 mg. LCMS method E: $R_t$=2.229 min, $(M+H)^+$=492.1, 494.1 (bromine isotopes).

Step 3. tert-butyl 7-(5-((2'-ethyl-5-fluoro-[1,1'-biphenyl]-2-yl)amino)pyrimidin-4-yl)-2,7-diazaspiro[3.5]nonane-2-carboxylate

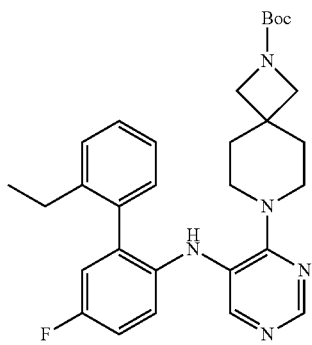 [SMILES: CCc1ccccc1-c1cc(F)ccc1Nc1cncnc1N1CCC2(CC1)CN(C(=O)OC(C)(C)C)C2]

To a mixture of tert-butyl 7-(5-((2-bromo-4-fluorophenyl)amino)pyrimidin-4-yl)-2,7-diazaspiro[3.5]nonane-2-carboxylate (350 mg, 0.711 mmol), (2-ethylphenyl) boronic acid (128 mg, 0.853 mmol) and $Na_2CO_3$ (226 mg, 2.133 mmol) in dioxane/$H_2O$ (20 mL/5 mL) was added Pd(dppf)Cl$_2$ (52 mg, 0.071 mmol) under $N_2$ and the reaction mixture was stirred at 100° C. for 18 h. The mixture was then diluted with $H_2O$ (20 mL), filtered and extracted with EtOAc (20 mL×3). The combined organic layers were dried over anhydrous $Na_2SO_4$, filtered, and the filtrate was concentrated under reduced pressure and purified by column chromatography on silica gel eluting with petroleum ether:EtOAc (10:1 to 3:2) to afford tert-butyl 7-(5-((2'-ethyl-5-fluoro-[1,1'-biphenyl]-2-yl)amino)pyrimidin-4-yl)-2,7-diazaspiro[3.5]nonane-2-carboxylate as a red oil. Yield: 300 mg. LCMS method C: $R_t$=0.803 min, $(M+H)^+$=518.3.

Step 4. N-(2'-ethyl-5-fluoro-[1,1'-biphenyl]-2-yl)-4-(2,7-diazaspiro[3.5]nonan-7-yl)pyrimidin-5-amine

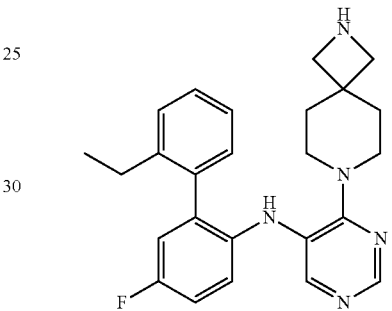

To a solution of tert-butyl 7-(5-((2'-ethyl-5-fluoro-[1,1'-biphenyl]-2-yl)amino)pyrimidin-4-yl)-2,7-diazaspiro[3.5]nonane-2-carboxylate (250 mg, 0.483 mmol) in anhydrous DCM (20 mL) was added HCl-dioxane (5 mL, 4 M in dioxane) at 0° C. and the mixture was stirred at 20-24° C. for 2 h. The resulting residue was concentrated under reduced pressure and high vacuum to afford N-(2'-ethyl-5-fluoro-[1,1'-biphenyl]-2-yl)-4-(2,7-diazaspiro[3.5]nonan-7-yl)pyrimidin-5-amine HCl salt as a grey oil, which was used in the next step without further purification.

Step 5. 1-(7-(5-((2'-ethyl-5-fluoro-[1,1'-biphenyl]-2-yl)amino)pyrimidin-4-yl)-2,7-diazaspiro[3.5]nonan-2-yl)-2-methylpropan-2-ol A solution of N-(2'-ethyl-5-fluoro-[1,1'-biphenyl]-2-yl)-4-(2-(3,3,3-trifluoropropyl)-2,7-diazaspiro[3.5]nonan-7-yl)pyrimidin-5-amine (20 mg, 0.05 mmol), 2,2-dimethyloxirane (5 mg, 0.07 mmol) and Et$_3$N (24 mg, 0.4 mL, 0.24 mmol) in anhydrous EtOH (3 mL) was stirred at 60° C. for 18 h. The mixture was concentrated under reduced pressure and purified by RP-HPLC method A to afford 1-(7-(5-((2'-ethyl-5-fluoro-[1,1'-biphenyl]-2-yl)amino)pyrimidin-4-yl)-2,7-diazaspiro[3.5]nonan-2-yl)-2-methylpropan-2-ol (TFA salt) as a colorless oil. Yield: 15.8 mg. LCMS method C: $R_t$=0.616 min, $(M+H)^+$=490.1. $^1$H NMR (CD$_3$OD): δ 8.39 (s, 1H), 7.68 (s, 1H), 7.30-7.40 (m, 2H), 7.15-7.25 (m, 1H), 7.05-7.15 (m, 2H), 6.98 (d, J=8.4 Hz, 1H), 6.85-6.95 (m, 1H), 4.15-4.25 (m, 2H), 3.95-4.05 (m, 2H), 3.65-3.85 (m, 4H), 3.25-3.35 (m, 2H), 2.40-2.55 (m, 2H), 1.70-2.00 (m, 4H), 1.27 (s, 1H), 1.08 (t, J=7.6 Hz, 3H). ¹⁹F NMR (CD₃OD): δ −76.88, −122.09.

Example 72

1-((6-(5-(4-fluoro-2-(1-isopropyl-3-(trifluoromethyl)-1H-pyrazol-5-yl)phenoxy)pyrimidin-4-yl)-2,6-diazaspiro[3.3]heptan-2-yl)methyl)cyclohexan-1-ol

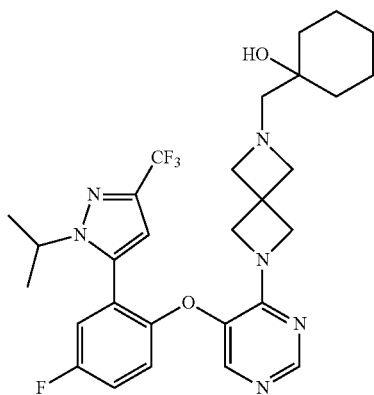 [SMILES: CC(C)n1nc(C(F)(F)F)cc1-c1cc(F)ccc1Oc1cncnc1N1CC2(CN(CC3(O)CCCCC3)C2)C1]

Step 1. tert-butyl 6-(5-(4-fluoro-2-(1-isopropyl-3-(trifluoromethyl)-1H-pyrazol-5-yl)phenoxy)pyrimidin-4-yl)-2,6-diazaspiro[3.3]heptane-2-carboxylate

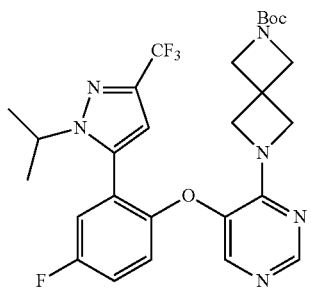 [SMILES: CC(C)n1nc(C(F)(F)F)cc1-c1cc(F)ccc1Oc1cncnc1N1CC2(CN(C(=O)OC(C)(C)C)C2)C1]

To a round bottom flask was added tert-butyl 6-(5-(2-bromo-4-fluorophenoxy)pyrimidin-4-yl)-2,6-diazaspiro[3.3]heptane-2-carboxylate (Intermediate 20, 1 g, 1 eq.), (1-isopropyl-3-(trifluoromethyl)-1H-pyrazol-5-yl)boronic acid (598 mg, 1.25 eq.), Sphos palladacycle 2ⁿᵈ generation (47 mg, 0.03 eq.; CAS #1375325-64-6) and potassium phosphate tribasic (1.37 g, 3 eq.). To this solid mixture was added dioxane (5.6 mL) and water (1.4 mL). The resulting solution was purged with a nitrogen stream for 1 min and heated at reflux overnight. The reaction mixture was then diluted with EtOAc and water. The phases were separated and the aqueous phase was back-extracted with EtOAc twice. The combined organic phases were dried over MgSO₄ and the filtrate was concentrated. The crude residue was purified by flash chromatography (80 g SiO₂, ethyl acetate/hexanes as the eluents) yielding tert-butyl 6-(5-(4-fluoro-2-(1-isopropyl-3-(trifluoromethyl)-1H-pyrazol-5-yl)phenoxy)pyrimidin-4-yl)-2,6-diazaspiro[3.3]heptane-2-carboxylate (1.0 g) as a white solid.

Step 2. 2-(5-(4-fluoro-2-(1-isopropyl-3-(trifluoromethyl)-1H-pyrazol-5-yl)phenoxy)pyrimidin-4-yl)-2,6-diazaspiro[3.3]heptane (Intermediate 101)

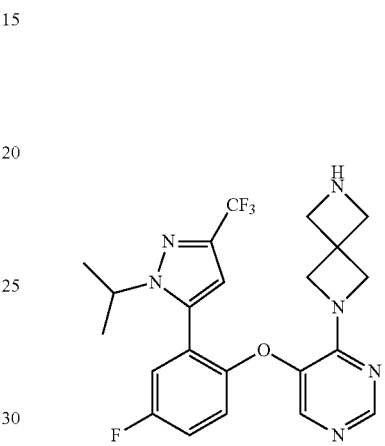

To a round bottom flask was added tert-butyl 6-(5-(4-fluoro-2-(1-isopropyl-3-(trifluoromethyl)-1H-pyrazol-5-yl)phenoxy)pyrimidin-4-yl)-2,6-diazaspiro[3.3]heptane-2-carboxylate (200 mg, 1 eq.), DCM (2 mL) and TFA (2 mL) and the reaction mixture was stirred for 30 min at RT. The volatiles were then removed under vacuum and the crude residue was co-evaporated with dichloromethane twice yielding 2-(5-(4-fluoro-2-(1-isopropyl-3-(trifluoromethyl)-1H-pyrazol-5-yl)phenoxy)pyrimidin-4-yl)-2,6-diazaspiro[3.3]heptane bis-TFA salt (i.e., Intermediate 101).

Step 3. 1-((6-(5-(4-fluoro-2-(1-isopropyl-3-(trifluoromethyl)-1H-pyrazol-5-yl)phenoxy)pyrimidin-4-yl)-2,6-diazaspiro[3.3]heptan-2-yl)methyl)cyclohexan-1-ol To a round bottom flask was added 2-(5-(4-fluoro-2-(1-isopropyl-3-(trifluoromethyl)-1H-pyrazol-5-yl)phenoxy)pyrimidin-4-yl)-2,6-diazaspiro[3.3]heptane bis-TFA salt (20 mg, 1 eq.), 1-oxaspiro[2.5]octane (16 mg, 5 eq.), triethylamine (21 μL, 5 eq.) and isopropanol (2 mL). The flask was capped and the mixture was heated at 70° C. overnight. The volatiles were then removed under vacuum and the resulting crude material was purified by RP-HPLC Method A yielding 1-((6-(5-(4-fluoro-2-(1-isopropyl-3-(trifluoromethyl)-1H-pyrazol-5-yl)phenoxy)pyrimidin-4-yl)-2,6-diazaspiro[3.3]heptan-2-yl)methyl)cyclohexan-1-ol (2.42 mg) as a colorless oil. LCMS Method G: R$_f$=5.58 min.; M+H=575.68. ¹H NMR (d4-MeOH) 8.41 (s, 1H), 7.84 (s, 1H), 7.25-7.38 (m, 3H), 6.67 (s, 1H), 4.58 (bs, 2H), 4.20-4.49 (m, 6H), 3.12-3.32 (m, 7H), 1.39 (m, 5H), 1.24-1.30 (m, 6H).

Example 73

N-(2-amino-2-oxoethyl)-N-(5-fluoro-2-((4-(7-((2-oxo-2,3-dihydro-1H-benzo[d]imidazol-5-yl)methyl)-2,7-diazaspiro[4.4]nonan-2-yl)pyrimidin-5-yl)oxy)phenyl)isobutyramide

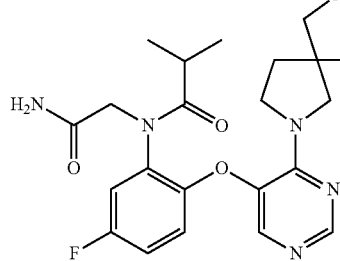

Step 1. tert-butyl 7-(5-(2-(N-(cyanomethyl)isobutyramido)-4-fluorophenoxy)pyrimidin-4-yl)-2,7-diazaspiro[4.4]nonane-2-carboxylate

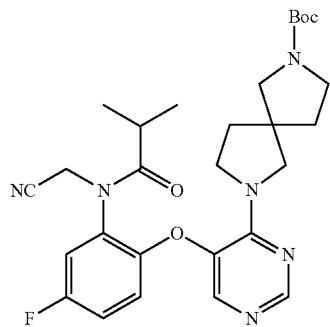 [SMILES: CC(C)C(=O)N(CC#N)c1cc(F)ccc1Oc1cncnc1N1CCC2(CCN(C(=O)OC(C)(C)C)C2)C1]

To a solution of tert-butyl 7-(5-(4-fluoro-2-isobutyramidophenoxy)pyrimidin-4-yl)-2,7-diazaspiro[4.4]nonane-2-carboxylate (100 mg, 0.2 mmol) in anhydrous THF (4 mL) was added NaH (24 mg, 1.0 mmol) under N$_2$, then the reaction mixture was stirred at RT for 30 min. 2-bromoacetonitrile (48 mg, 0.4 mmol) was added and the reaction mixture was stirred at RT for 12 h. The solvent was removed under reduced pressure and the residue was partitioned with EtOAc (10 mL) and H$_2$O (5 mL). The organic layer was washed with brine (20 mL), dried over anhydrous Na$_2$SO$_4$, filtered and concentrated under reduced pressure to afford tert-butyl 7-(5-(2-(N-(cyanomethyl)isobutyramido)-4-fluorophenoxy)pyrimidin-4-yl)-2,7-diazaspiro[4.4]nonane-2-carboxylate as a brown oil. Yield: 100 mg. LCMS method E: R$_t$=1.190 min, (M+H)$^+$=539.3.

Step 2. N-(2-((4-(2,7-diazaspiro[4.4]nonan-2-yl)pyrimidin-5-yl)oxy)-5-fluorophenyl)-N-(2-amino-2-oxoethyl)isobutyramide

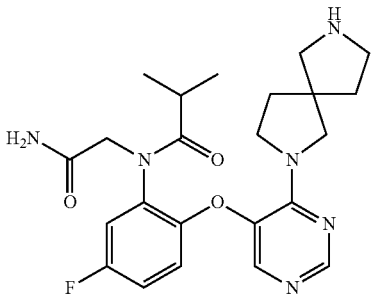 [SMILES: CC(C)C(=O)N(CC(N)=O)c1cc(F)ccc1Oc1cncnc1N1CCC2(CCNC2)C1]

To a solution of tert-butyl 7-(5-(2-(N-(cyanomethyl)isobutyramido)-4-fluorophenoxy)pyrimidin-4-yl)-2,7-diazaspiro[4.4]nonane-2-carboxylate (100 mg, 0.185 mmol) in anhydrous CH$_2$Cl$_2$ (10 mL) was added TFA (2 mL) under N$_2$ and the reaction mixture was stirred at RT for 2 h. The solvent was removed under reduced pressure to afford a residue and the pH was adjusted to 9-10 with 10% NaOH. Then the mixture was extracted with CH$_2$Cl$_2$ (10 mL×3). The organic layers were concentrated under reduced pressure to afford N-(2-((4-(2,7-diazaspiro[4.4]nonan-2-yl)pyrimidin-5-yl)oxy)-5-fluorophenyl)-N-(2-amino-2-oxoethyl)isobutyramide as a brown oil which was used for the next step without further purification. Yield: 80 mg. LCMS method E: R$_t$=1.714 min, (M+H)$^+$=457.2.

Step 3. N-(2-amino-2-oxoethyl)-N-(5-fluoro-2-((4-(7-((2-oxo-2,3-dihydro-1H-benzo[d]imidazol-5-yl)methyl)-2,7-diazaspiro[4.4]nonan-2-yl)pyrimidin-5-yl)oxy)phenyl)isobutyramide To a solution of N-(2-((4-(2,7-diazaspiro[4.4]nonan-2-yl)pyrimidin-5-yl)oxy)-5-fluorophenyl)-N-(2-amino-2-oxoethyl)isobutyramide (40 mg, crude) and 2-oxo-2,3-dihydro-1H-benzo[d]imidazole-5-carbaldehyde (Intermediate 40, 29 mg, 0.18 mmol) in anhydrous MeOH (4 mL) was added 4 Å-molecular sieves (50 mg), then the reaction was stirred at 50° C. for 2 h under N$_2$. After 2 h, NaBH$_3$CN (28 mg, 0.45 mmol) was added into the solution and the reaction mixture was stirred at 50° C. for 12 h. The reaction mixture was then filtered, concentrated under reduced pressure, and purified by RP-HPLC method G to afford N-(2-amino-2-oxoethyl)-N-(5-fluoro-2-((4-(7-((2-oxo-2,3-dihydro-1H-benzo[d]imidazol-5-yl)methyl)-2,7-diazaspiro[4.4]nonan-2-yl)pyrimidin-5-yl)oxy)phenyl)isobutyramide as a white solid. Yield: 7.00 mg. LCMS method E: R$_t$=1.498 min, (M+H)$^+$=603.3. $^1$H NMR (CD$_3$OD): δ 8.30 (s, 1H), 7.76 (d, J=2.4 Hz, 1H), 7.52 (d, J=8.8 Hz, 1H), 7.15 (t, J=8.0 Hz, 1H), 6.87-7.03 (m, 4H), 4.73 (dd, J=16.4, 3.6 Hz, 1H), 3.82 (dd, J=16.0, 4.8 Hz, 1H), 3.56-3.85 (m, 5H), 2.45-2.69 (m, 5H), 1.81-1.94 (m, 5H), 1.05 (dd, J=36.8, 6.8 Hz, 6H). $^{19}$F NMR (CD$_3$OD): δ -119.24.

Example 74

N-(5-fluoro-2-((4-(7-(((1r,4r)-4-(methylsulfonamido)cyclohexyl)methyl)-2,7-diazaspiro[3.5]nonan-2-yl)pyrimidin-5-yl)oxy)phenyl)propane-2-sulfonamide

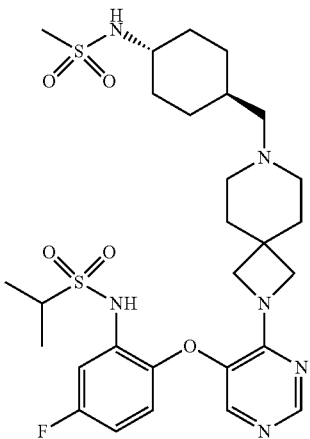 [SMILES: CC(C)S(=O)(=O)Nc1cc(F)ccc1Oc1cncnc1N1CC2(CCN(C[C@H]3CC[C@H](NS(C)(=O)=O)CC3)CC2)C1]

Step 1. tert-butyl 2-(5-(4-fluoro-2-(1-methylethyl-sulfonamido)phenoxy)pyrimidin-4-yl)-2,7-diazaspiro[3.5]nonane-7-carboxylate

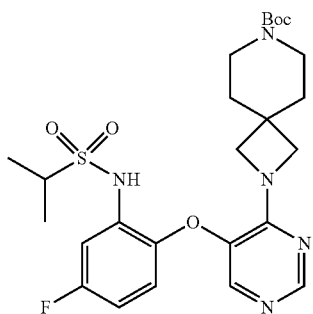 [SMILES: CC(C)S(=O)(=O)Nc1cc(F)ccc1Oc1cncnc1N1CC2(CCN(C(=O)OC(C)(C)C)CC2)C1]

A flask was charged with tert-butyl 7-(5-bromopyrimidin-4-yl)-2,7-diazaspiro[4.4]nonane-2-carboxylate (1.264 g, 3.3 mmol), N-(5-fluoro-2-hydroxyphenyl)propane-2-sulfonamide (0.727 g, 3.16 mmol), CuI (30 mg, 0.16 mmol), K$_3$PO$_4$ (1.34 g, 6.3 mmol) and picolinic acid (20 mg, 0.16 mmol) and was degassed and refilled with N$_2$ three times. Anhydrous DMSO (10 mL) was added and the mixture was degassed refilled with N$_2$, and the reaction mixture was heated at 80° C. for 16 h. The reaction mixture was diluted with EtOAc, washed with H$_2$O, brine, dried over anhydrous Na$_2$SO$_4$ and filtered. The filtrate was concentrated to dryness and the resulting residue was purified by flash chromatography using DCM/MeOH as an eluent to afford 1.33 g of tert-butyl 2-(5-(4-fluoro-2-(1-methylethyl sulfonamido)phenoxy)pyrimidin-4-yl)-2,7-diazaspiro[3.5]nonane-7-carboxylate. LCMS method B: R$_t$=1.35 min, (M+H)$^+$=536.3.

Step 2. N-(2-((4-(2,7-diazaspiro[3.5]nonan-2-yl)pyrimidin-5-yl)oxy)-5-fluorophenyl)propane-2-sulfonamide A mixture of tert-butyl 2-(5-(4-fluoro-2-(1-methylethyl-sulfonamido)phenoxy) pyrimidin-4-yl)-2,7-diazaspiro[3.5] nonane-7-carboxylate (526 mg, 0.98 mmol) in MeOH (10 mL) containing 4 M HCl/dioxane (4 mL) was stirred at RT for 30 min. The reaction mixture was concentrated under reduced pressure to yield N-(2-((4-(2,7-diazaspiro[3.5]nonan-2-yl)pyrimidin-5-yl)oxy)-5-fluorophenyl)propane-2-sulfonamide as the HCl salt. LCMS method B: R$_t$=0.56 min, (M+H)$^+$=436.1.

Steps 3-5. N-(5-fluoro-2-((4-(7-(((1r,4r)-4-(methylsulfonamido)cyclohexyl)methyl)-2,7-diazaspiro[3.5]nonan-2-yl)pyrimidin-5-yl)oxy)phenyl)propane-2-sulfonamide Steps 3-5 were performed as described for Steps 3-5 of Example 6A. LCMS method A: R$_t$=0.68 min, (M+H)$^+$=625.1. $^1$H NMR (CD$_3$OD) δ: 8.50 (s, 1H), 7.62 (brs, 1H), 7.35 (dd, J=8.8, 1.6 Hz, 1H), 7.24 (dd, J=8.8, 1.6 Hz, 1H), 7.03 (m, 1H), 4.64 (m, 2H), 4.22 (m, 2H), 3.58 (d, J=12.4 Hz, 2H), 3.47 (m, 1H), 3.17 (m, 1H), 3.03-2.94 (m, 7H), 2.28 (d, J=13.6 Hz, 2H), 2.13 (d, J=12.8 Hz, 2H), 2.06 (d, J=10.8 Hz, 2H), 1.87 (d, J=12.8 Hz, 2H), 1.81 (m, 1H), 1.41 (d, J=6.8 Hz, 6H), 1.36 (m, 2H), 1.17 (m, 2H).

Example 75 tert-butyl 7-(5-(4-fluoro-2-(N-methylisobutyramido)phenoxy)pyrimidin-4-yl)-2,7-diazaspiro[4.4]nonane-2-carboxylate

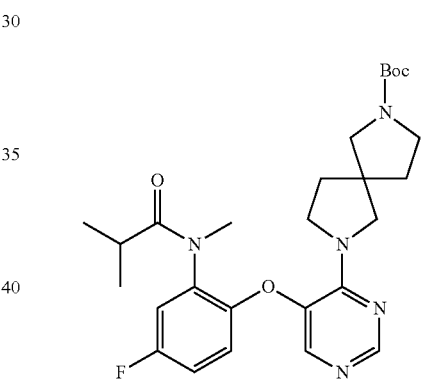

Step 1: tert-butyl 7-(5-(2-amino-4-fluorophenoxy)pyrimidin-4-yl)-2,7-diazaspiro[4.4]nonane-2-carboxylate (Intermediate 102)

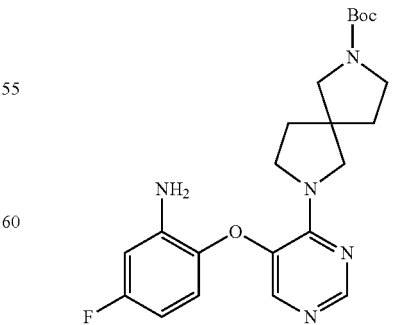

To a mixture of tert-butyl 7-(5-(2-bromo-4-fluorophenoxy)pyrimidin-4-yl)-2,7-diazaspiro[4.4]nonane-2-carboxylate (Intermediate 11, 2.0 g, 4.0 mmol) and NaN₃ (1.63 g, 25 mmol) in EtOH (20 mL) and H₂O (10 mL) was added CuI (1.0 g, 5.0 mmol) and -sodium ascorbate (0.5 g, 2.5 mmol) under N₂ and the reaction mixture was stirred at 100° C. for 24 h. The reaction mixture was filtered through Celite and concentrated under reduced pressure to afford a residue which was purified by column chromatography on silica gel (eluting with DCM:MeOH=1:0-10:1) to afford tert-butyl 7-(5-(2-amino-4-fluorophenoxy)pyrimidin-4-yl)-2,7-diazaspiro[4.4]nonane-2-carboxylate as a light brown solid. Yield: 1.4 g. LCMS method C: R$_t$=0.724 min, (M+H)⁺=430.1.

Step 2. tert-butyl 7-(5-(4-fluoro-2-isobutyramidophenoxy)pyrimidin-4-yl)-2,7-diazaspiro[4.4]nonane-2-carboxylate (Intermediate 103)

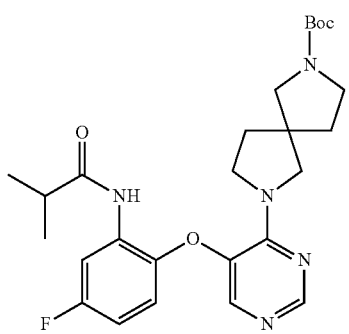 [SMILES: CC(C)C(=O)Nc1cc(F)ccc1Oc1cncnc1N1CCC2(CCN(C(=O)OC(C)(C)C)C2)C1]

To a mixture of tert-butyl 7-(5-(2-amino-4-fluorophenoxy)pyrimidin-4-yl)-2,7-diazaspiro[4.4]nonane-2-carboxylate (700 mg, 1.63 mmol) in pyridine (20 mL) was added isobutyryl chloride (1.73 g, 16.3 mmol) under N₂ and the reaction mixture was stirred at 19-21° C. for 12 h. The solvent was removed under reduced pressure to afford a residue which was extracted with EtOAc (20 mL) and H₂O (10 mL). The organic layer was washed with brine (20 mL), dried over anhydrous Na₂SO₄, filtered and concentrated under reduced pressure to afford tert-butyl 7-(5-(4-fluoro-2-isobutyramidophenoxy)pyrimidin-4-yl)-2,7-diazaspiro[4.4]nonane-2-carboxylate as brown oil. Yield: 700 mg. LCMS method C: R$_t$=0.732 min, (M+H)⁺=500.1.

Step 3. tert-butyl 7-(5-(4-fluoro-2-(N-methylisobutyramido)phenoxy)pyrimidin-4-yl)-2,7-diazaspiro[4.4]nonane-2-carboxylate To a mixture of tert-butyl 7-(5-(4-fluoro-2-isobutyramidophenoxy)pyrimidin-4-yl)-2,7-diazaspiro[4.4]nonane-2-carboxylate (400 mg, 0.80 mmol) and CH₃I (500 mg, 3.5 mmol) in anhydrous THF (10 mL) was added NaH (96 mg, 4.00 mmol) under N₂ and the reaction mixture was stirred at 12-21° C. for 2 h. The solvent was removed under reduced pressure to afford a residue which was extracted with EtOAc (10 mL) and H₂O (5 mL). The organic layer was washed with brine (20 mL), dried over anhydrous Na₂SO₄, filtered and concentrated under reduced pressure to afford a residue which was purified by column chromatography on silica gel (eluting with DCM:MeOH=1:0~10:1) to afford the tert-butyl 7-(5-(4-fluoro-2-(N-methylisobutyramido)phenoxy)pyrimidin-4-yl)-2,7-diazaspiro[4.4]nonane-2-carboxylate as a white solid. Yield: 201 mg. LCMS method D: R$_t$=0.995 min, (M+H)⁺=514.1. ¹H NMR (CD₃OD): δ 8.29-8.34 (m, 1H), 7.78 (s, 1H), 7.33 (d, J=8.0 Hz, 1H), 7.17-7.21 (m, 1H), 6.85-7.05 (m, 1H), 3.35-3.81 (m, 8H), 2.57-2.62 (m, 1H), 1.88-1.97 (m, 5H), 1.45 (s, 11H), 1.05 (dd, J=18.8, 6.8 Hz, 6H). ¹⁹F NMR (CD₃OD): δ −119.09.

Example 76

N-(5-fluoro-2-((4-(7-((2-oxo-2,3-dihydro-1H-benzo[d]imidazol-5-yl)methyl)-2,7-diazaspiro[4.4]nonan-2-yl)pyrimidin-5-yl)oxy)phenyl)-N-methylisobutyramide

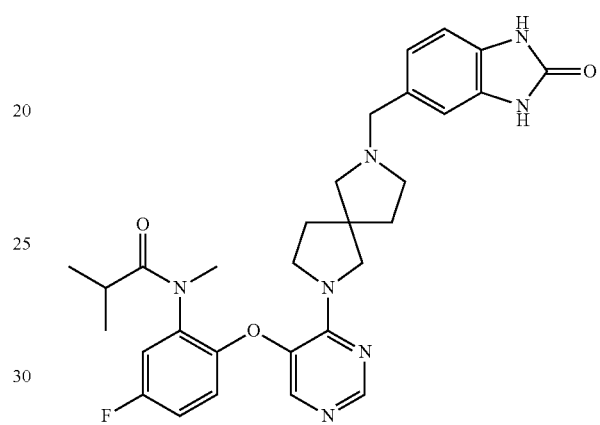

Step 1. N-(2-((4-(2,7-diazaspiro[4.4]nonan-2-yl)pyrimidin-5-yl)oxy)-5-fluorophenyl)-N-methylisobutyramide

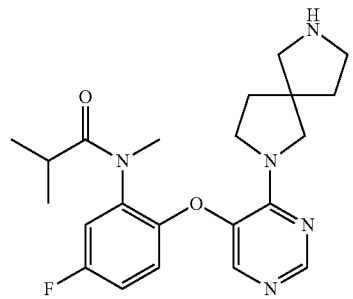 [SMILES: CC(C)C(=O)N(C)c1cc(F)ccc1Oc1cncnc1N1CCC2(CCNC2)C1]

To a solution of tert-butyl 7-(5-(4-fluoro-2-(N-methylisobutyramido)phenoxy)pyrimidin-4-yl)-2,7-diazaspiro[4.4]nonane-2-carboxylate (Example 75, 70 mg, 0.14 mmol) in anhydrous CH₂Cl₂ (10 mL) was added TFA (2 mL) under N₂ and the reaction mixture was stirred at 19-25° C. for 5 h. The solvent was removed under reduced pressure and the resulting residue was adjusted to pH 9-10 using 10% NaOH solution. The crude residue was then extracted with CH₂Cl₂ (3×15 mL). The organic layer was concentrated under reduced pressure to afford N-(2-((4-(2,7-diazaspiro[4.4]nonan-2-yl)pyrimidin-5-yl)oxy)-5-fluorophenyl)-N-methylisobutyramide as a brown oil which was used in the next step without further purification.

Step 2. N-(5-fluoro-2-((4-(7-((2-oxo-2,3-dihydro-1H-benzo[d]imidazol-5-yl)methyl)-2,7-diazaspiro[4.4]nonan-2-yl)pyrimidin-5-yl)oxy)phenyl)-N-methylisobutyramide To a mixture of N-(2-((4-(2,7-diazaspiro[4.4]nonan-2-yl)pyrimidin-5-yl)oxy)-5-fluorophenyl)-N-methylisobutyramide (55 mg, 0.15 mmol) and 2-oxo-2,3-dihydro-1H-benzo[d]imidazole-5-carbaldehyde (Intermediate 40, 45 mg, 0.28 mmol) in anhydrous MeOH (2 mL) and HOAc (0.1 mL) was added NaBH$_3$CN (43.4 mg, 0.7 mmol) under N$_2$ and the reaction mixture was stirred at 65° C. for 2 h, at which time LCMS showed that the starting material was consumed. The reaction mixture was filtered and concentrated under reduced pressure and the resulting residue was diluted with MeOH (5 mL) purified by preparative HPLC Method G to afford N-(5-fluoro-2-((4-(7-((2-oxo-2,3-dihydro-1H-benzo[d]imidazol-5-yl)methyl)-2,7-diazaspiro[4.4]nonan-2-yl)pyrimidin-5-yl)oxy)phenyl)-N-methylisobutyramide as a white solid. Yield: 7.8 mg. LCMS method E: R$_t$=0.936 min, (M+H)$^+$=560.1. $^1$H NMR (CD$_3$OD): δ 8.29 (s, 1H), 7.74 (s, 1H), 7.32 (d, J=8.4 Hz, 1H), 7.14 (brs, 1H), 6.87-6.91 (m, 4H), 3.60-3.73 (m, 2H), 3.61 (d, J=4.4 Hz, 2H), 3.21 (s, 3H), 2.45-2.67 (m, 6H), 1.79-1.95 (m, 5H), 1.06 (d, J=6.8 Hz, 6H). $^{19}$F NMR (CD$_3$OD): δ −119.16.

Example 77

5-((7-(5-(4-fluoro-2-isobutylphenoxy)pyrimidin-4-yl)-2,7-diazaspiro[4.4]nonan-2-yl)methyl)-1,3-dihydro-2H-benzo[d]imidazol-2-one

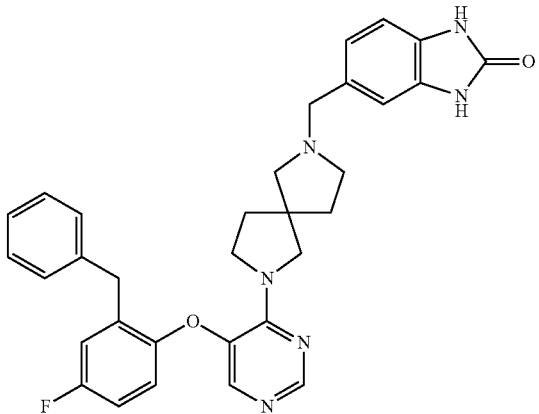 [SMILES: O=c1[nH]c2ccc(CN3CCC4(CCN(c5ncncc5Oc5ccc(F)cc5Cc5ccccc5)C4)C3)cc2[nH]1]

Step 1. tert-butyl 7-(5-(2-benzyl-4-fluorophenoxy)pyrimidin-4-yl)-2,7-diazaspiro[4.4]nonane-2-carboxylate

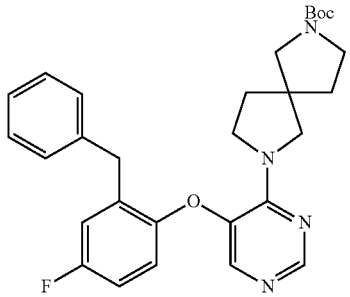 [SMILES: CC(C)(C)OC(=O)N1CCC2(CCN(c3ncncc3Oc3ccc(F)cc3Cc3ccccc3)C2)C1]

To a round bottom flask was added tert-butyl 7-(5-(2-bromo-4-fluorophenoxy)pyrimidin-4-yl)-2,7-diazaspiro[4.4]nonane-2-carboxylate (Intermediate 11, 50 mg, 1 eq.) and THF (1 mL) and the solution was purged with a nitrogen stream for 1 min. Benzylzinc bromide (610 μL, 0.5 M in THF, 3 eq.) was added and the solution was purged with a nitrogen stream. Pd(PtBu$_3$)$_2$ (3 mg, 0.05 eq.) was added and the solution was purged with a nitrogen stream for 1 min and the solution was heated to 60° C. The reaction mixture was then cooled to RT. Celite was added to the solution and concentrated under vacuum. The crude residue was purified by flash chromatography (12 g SiO$_2$, ethyl acetate/hexanes) using a dry loading technique. The corresponding fractions were combined and concentrated, yielding tert-butyl 7-(5-(2-benzyl-4-fluorophenoxy)pyrimidin-4-yl)-2,7-diazaspiro[4.4]nonane-2-carboxylate (70 mg).

Steps 2-4. 5-((7-(5-(2-benzyl-4-fluorophenoxy)pyrimidin-4-yl)-2,7-diazaspiro[4.4]nonan-2-yl)methyl)-1,3-dihydro-2H-benzo[d]imidazol-2-one The title product was synthesized from tert-butyl 7-(5-(2-benzyl-4-fluorophenoxy)pyrimidin-4-yl)-2,7-diazaspiro[4.4]nonane-2-carboxylate according to the methods described in Steps 3-4 of Example 41. LCMS method G: R$_t$=4.07 min.; M+H=551.59.

Example 78

2-(3-((2'-ethyl-5-fluoro-[1,1'-biphenyl]-2-yl)methyl)pyridin-4-yl)-6-((tetrahydro-2H-pyran-4-yl)methyl)-2,6-diazaspiro[3.3]heptane

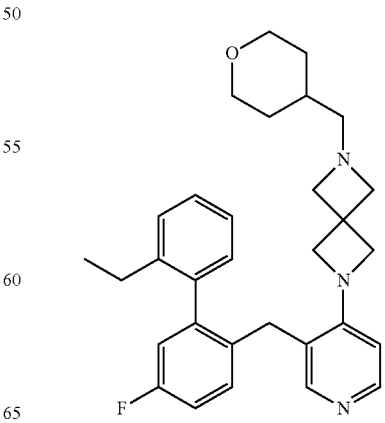

Step 1. tert-butyl 6-(3-(2-chloro-4-fluorobenzyl)pyridin-4-yl)-2,6-diazaspiro[3.3]heptane-2-carboxylate

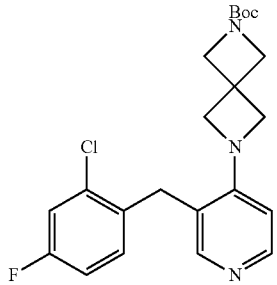 [SMILES: CC(C)(C)OC(=O)N1CC2(C1)CN(c1ccncc1Cc1ccc(F)cc1Cl)C2]

To a solution of tert-butyl 6-(3-bromopyridin-4-yl)-2,6-diazaspiro[3.3]heptane-2-carboxylate (63 mg, 0.178 mmol) in anhydrous THF (4 mL) under $N_2$ atmosphere was added (2-chloro-4-fluorophenyl)zinc(II) bromide solution in THF (0.7 mL, 0.35 mmol, 0.5 M), followed by $Pd(PBu_3)_2$ (6 mg, 7 mol %) and the mixture was heated at 70° C. for 1.5 h. The reaction mixture was diluted with EtOAc, washed with aqueous $NH_4Cl$, brine, dried over anhydrous $Na_2SO_4$, filtered and the filtrate was concentrated to dryness. The residue was purified by flash chromatography, followed by preparative HPLC method A to afford 29 mg of tert-butyl 6-(3-(2-chloro-4-fluorobenzyl)pyridin-4-yl)-2,6-diazaspiro[3.3]heptane-2-carboxylate as a TFA salt. LCMS method B: $R_f$=1.17 min.; M+H=418.1.

Step 2. tert-butyl 6-(3-((2'-ethyl-5-fluoro-[1,1'-biphenyl]-2-yl)methyl)pyridin-4-yl)-2,6-diazaspiro[3.3]heptane-2-carboxylate

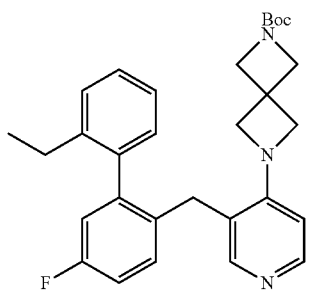 [SMILES: CCc1ccccc1-c1cc(F)ccc1Cc1cnccc1N1CC2(CN(C(=O)OC(C)(C)C)C2)C1]

tert-Butyl 6-(3-(2-chloro-4-fluorobenzyl)pyridin-4-yl)-2,6-diazaspiro[3.3]heptane-2-carboxylate TFA salt (29 mg, 0.055 mmol), (2-ethylphenyl)boronic acid (9.8 mg, 0.065 mmol), $K_3PO_4$ (80 mg, 0.38 mmol), SPhos-Pd-G2 (8 mg), and dioxane (2 mL) and $H_2O$ (1 mL) were mixed under $N_2$ atmosphere and heated at 110° C. for 15 min in a microwave. The reaction mixture was diluted with EtOAc, washed with $H_2O$, brine, dried over anhydrous $Na_2SO_4$, filtered, and the filtrate was concentrated to dryness. The residue was purified by flash chromatography to afford 16 mg of tert-butyl 6-(3-((2'-ethyl-5-fluoro-[1,1'-biphenyl]-2-yl)methyl)pyridin-4-yl)-2,6-diazaspiro[3.3]heptane-2-carboxylate. LCMS method B: $R_f$=1.34 min.; M+H=488.1.

Step 3: 2-(3-((2'-ethyl-5-fluoro-[1,1'-biphenyl]-2-yl)methyl)pyridin-4-yl)-2,6-diazaspiro[3.3]heptane

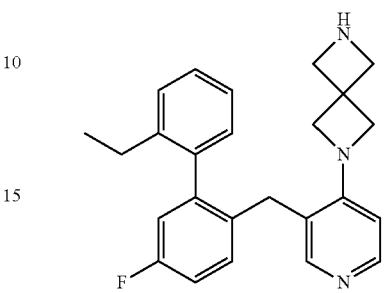

tert-Butyl 6-(3-((2'-ethyl-5-fluoro-[1,1'-biphenyl]-2-yl)methyl)pyridin-4-yl)-2,6-diazaspiro[3.3]heptane-2-carboxylate was dissolved in 20% TFA/DCM (1 mL) and stirred and RT for 30 min. The solvents were removed to give 2-(3-((2'-ethyl-5-fluoro-[1,1'-biphenyl]-2-yl)methyl)pyridin-4-yl)-2,6-diazaspiro[3.3]heptane as the TFA salt which was used for next step without further purification.

Step 4. 2-(3-((2'-ethyl-5-fluoro-[1,1'-biphenyl]-2-yl)methyl)pyridin-4-yl)-6-((tetrahydro-2H-pyran-4-yl)methyl)-2,6-diazaspiro[3.3]heptane 2-(3-((2'-Ethyl-5-fluoro-[1,1'-biphenyl]-2-yl)methyl)pyridin-4-yl)-2,6-diazaspiro[3.3]heptane was dissolved in MeOH (2 mL), $K_2CO_3$ (40 mg) was added and the resulting mixture was stirred for 10 min and filtered through an HPLC micro filter. The filtrate was concentrated to dryness to afford free amine. One third of the amine was dissolved in DCM (1 mL), and to this solution was added 1 drop of HOAc and tetrahydro-2H-pyran-4-carbaldehyde (1 drop), followed by $NaBH(OAc)_3$ (18 mg, 0.085 mmol). The mixture was stirred at RT for 30 min and concentrated to remove the solvent. The resulting residue was purified by preparative HPLC method A to give 1.93 mg of 2-(3-((2'-ethyl-5-fluoro-[1,1'-biphenyl]-2-yl)methyl)pyridin-4-yl)-6-((tetrahydro-2H-pyran-4-yl)methyl)-2,6-diazaspiro[3.3]heptane as a TFA salt. LCMS method B: $R_f$=0.89 min.; M+H=496.1. $^1$H NMR ($CD_3OD$) δ: 7.99 (d, J=7.2 Hz, 1H), 7.46 (s, 1H), 7.35 (s, 1H), 7.26 (m, 1H), 7.21-7.18 (m, 2H), 6.99 (m, 2H), 6.44 (d, J=7.2 Hz, 2H), 4.43 (m, 4H), 3.95 (m, 2H), 3.84 (d, J=16.4 Hz, 2H),), 3.71 (d, J=16.4 Hz, 2H), 3.41 (m, 2H), 3.12 (d, J=7.2 Hz, 2H), 2.31 (m, 2H), 1.90 (m, 1H), 1.61 (m, 2H), 1.34 (m, 2H), 1.06 (t, J=7.6 Hz, 3H).

Examples 79-240

Examples 79-240 were prepared according to the procedure described in Table 9 using the appropriate starting materials. Characterization data for Examples 79-240 is shown in Table 10.

TABLE 9

Examples 79-240

| Example | Name | Structure | Procedure |
|---|---|---|---|
| 79 | N-((1r,4r)-4-((2-(5-(2-(3-cyclopropyl-1-methyl-6-oxo-1,6-dihydropyridin-2-yl)-4-fluorophenoxy)pyrimidin-4-yl)-2,7-diazaspiro[3.5]nonan-7-yl)methyl)cyclohexyl)-2,2,2-trifluoroacetamide | 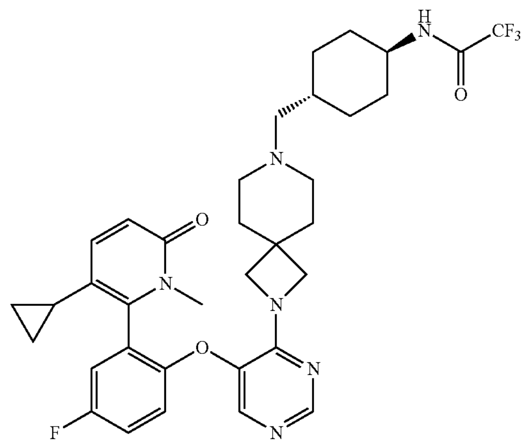 [SMILES: Cn1c(-c2cc(F)ccc2Oc2cncnc2N2CC3(CCN(C[C@H]4CC[C@H](NC(=O)C(F)(F)F)CC4)CC3)C2)c(C2CC2)ccc1=O] | Synthesized by a method similar to Example 74. In final step trifluoroaceticanhydride was used. |
| 80 | N-(4-((2-(5-(2-(3-cyclopropyl-1-methyl-6-oxo-1,6-dihydropyridin-2-yl)-4-fluorophenoxy)pyrimidin-4-yl)-2,7-diazaspiro[3.5]nonan-7-yl)methyl)cyclohexyl)methanesulfonamide | 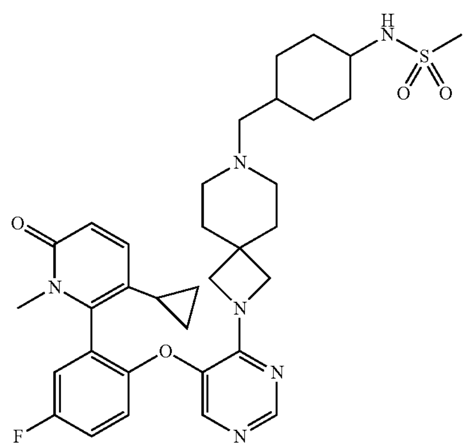 [SMILES: Cn1c(-c2cc(F)ccc2Oc2cncnc2N2CC3(CCN(CC4CCC(NS(C)(=O)=O)CC4)CC3)C2)c(C2CC2)ccc1=O] | Synthesized by a method similar to Example 74 starting from 5-cyclopropyl-6-(5-fluoro-2-hydroxyphenyl)-1-methylpyridin-2(1H)-one |
| 81A | Isomer 1: 5-((7-(5-(2-(3-cyclopropyl-1-methyl-6-oxo-1,6-dihydropyridin-2-yl)-4-fluorophenoxy)pyrimidin-4-yl)-2,7-diazaspiro[4.4]nonan-2-yl)methyl)-1-(2-hydroxyethyl)-1H-benzo[d]imidazol-2(3H)-one | 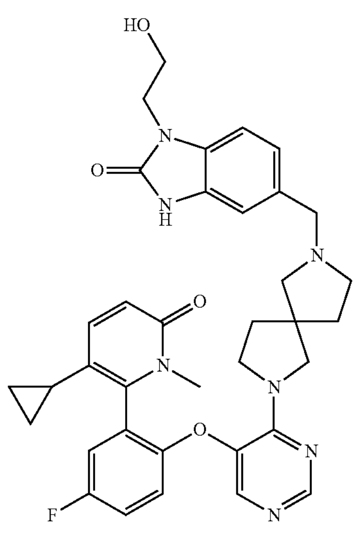 [SMILES: Cn1c(-c2cc(F)ccc2Oc2cncnc2N2CCC3(CCN(Cc4ccc5c(c4)[nH]c(=O)n5CCO)C3)C2)c(C2CC2)ccc1=O] | Synthesized by a method similar to Examples 29A-29B |

TABLE 9-continued

Examples 79-240

| Example | Name | Structure | Procedure |
|---|---|---|---|
| 81B | Isomer 2: 5-((7-(5-(2-(3-cyclopropyl-1-methyl-6-oxo-1,6-dihydropyridin-2-yl)-4-fluorophenoxy)pyrimidin-4-yl)-2,7-diazaspiro[4.4]nonan-2-yl)methyl)-1-(2-hydroxyethyl)-1H-benzo[d]imidazol-2(3H)-one | 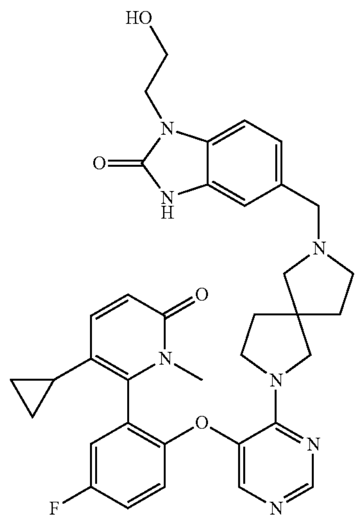 [SMILES: Cn1c(-c2cc(F)ccc2Oc2cncnc2N2CCC3(CCN(Cc4ccc5c(c4)[nH]c(=O)n5CCO)C3)C2)c(C2CC2)ccc1=O] | Synthesized by a method similar to Examples 29A-29B |
| 82 | (1r,4r)-4-(2-(6-(5-(2-(2-cyclopropylpyridin-3-yl)-4-fluorophenoxy)pyrimidin-4-yl)-2,6-diazaspiro[3.3]heptan-2-yl)ethyl)cyclohexan-1-amine | 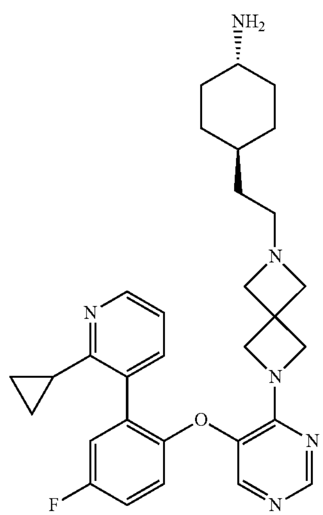 [SMILES: N[C@H]1CC[C@H](CCN2CC3(C2)CN(c2ncncc2Oc2ccc(F)cc2-c2cccnc2C2CC2)C3)CC1] | Synthesized from Example 88 by deprotection with TFA |
| 83 | tert-butyl ((1r,4r)-4-(((2-(5-(4-fluoro-2-(isopropyl(methyl)carbamoyl)phenoxy)pyrimidin-4-yl)-2-azaspiro[3.3]heptan-6-yl)amino)methyl)cyclohexyl)carbamate | 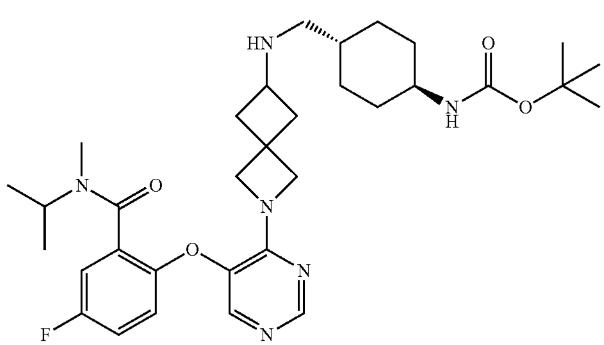 [SMILES: CC(C)N(C)C(=O)c1cc(F)ccc1Oc1cncnc1N1CC2(CC(NC[C@H]3CC[C@H](NC(=O)OC(C)(C)C)CC3)C2)C1] | Synthesized from Intermediate 38 and tert-butyl ((1r,4r)-4-formylcyclohexyl)carbamate by reductive amination as described in step 5 of Example 1 |

TABLE 9-continued

Examples 79-240

| Example | Name | Structure | Procedure |
|---|---|---|---|
| 84 | tert-butyl ((1r,4r)-4-((2-(5-(2-(N-ethylisobutyramido)-4-fluorophenoxy)pyrimidin-4-yl)-2,7-diazaspiro[3.5]nonan-7-yl)methyl)cyclohexyl)carbamate | 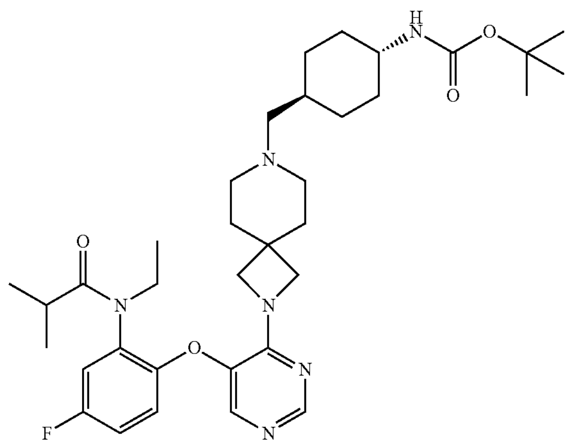 [SMILES: CCN(C(=O)C(C)C)c1cc(F)ccc1Oc1cncnc1N1CC2(CCN(C[C@H]3CC[C@H](NC(=O)OC(C)(C)C)CC3)CC2)C1] | Synthesized from Intermediate 23 by method descibed in synthesis of Example 75. In final step, it was condensed with tert-butyl ((1r,4r)-4-formylcyclohexyl)carbamate. |
| 85 | methyl ((1r,4r)-4-((2-(5-(2-(N-ethylisobutyramido)-4-fluorophenoxy)pyrimidin-4-yl)-2,7-diazaspiro[3.5]nonan-7-yl)methyl)cyclohexyl)carbamate | 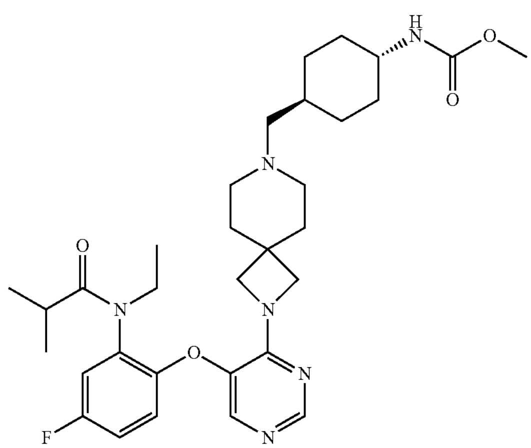 [SMILES: CCN(C(=O)C(C)C)c1cc(F)ccc1Oc1cncnc1N1CC2(CCN(C[C@H]3CC[C@H](NC(=O)OC)CC3)CC2)C1] | Synthesized from Example 84, by acid deprotection followed by reaction with methyl chloroformate |
| 86 | N-ethyl-N-(5-fluoro-2-((4-(7-(((1r,4r)-4-(methylsulfonamido)cyclohexyl)methyl)-2,7-diazaspiro[3.5]nonan-2-yl)pyrimidin-5-yl)oxy)phenyl)isobutyramide | 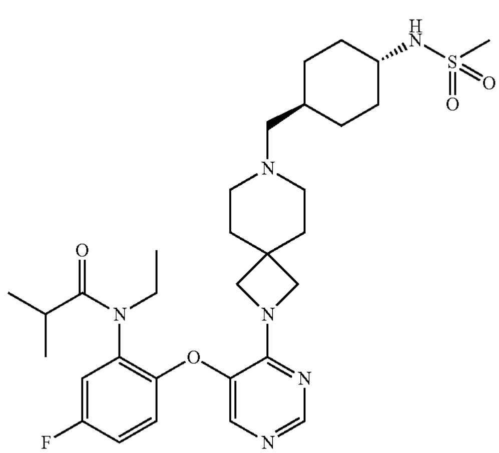 [SMILES: CCN(C(=O)C(C)C)c1cc(F)ccc1Oc1cncnc1N1CC2(CCN(C[C@H]3CC[C@H](NS(C)(=O)=O)CC3)CC2)C1] | Synthesized from Intermediate 23 by method described in synthesis of Example 75. In final step, it was condensed with N-((1r,4r)-4-formylcyclohexyl)methanesulfonamide. |

TABLE 9-continued

Examples 79-240

| Example | Name | Structure | Procedure |
|---|---|---|---|
| 87 | 2-((4-(6-(2-((1r,4r)-4-(3,3-dimethyl-butanamido)cyclo-hexyl)ethyl)-2,6-diazaspiro[3.3]heptan-2-yl)pyrimidin-5-yl)oxy)-5-fluoro-N,N-diisopropyl-benzamide | 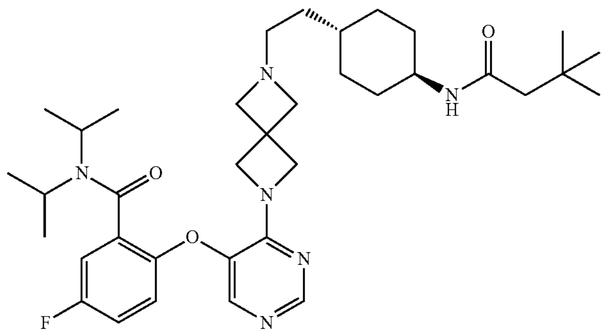 | Synthesized from Intermediate 41 by reductive amination with tert-butyl ((1r,4r)-4-(2-oxoethyl)cyclohexyl)carbamateas described in step 5 of Example 1. The BOC deprotection was followed by reaction with 3,3-dimethylbutanoyl chloride. |
| 88 | tert-butyl ((1r,4r)-4-(2-(6-(5-(2-(2-cyclopropylpyridin-3-yl)-4-fluorophenoxy)pyrimidin-4-yl)-2,6-diazaspiro[3.3]heptan-2-yl)ethyl)cyclohexyl)carbamate | 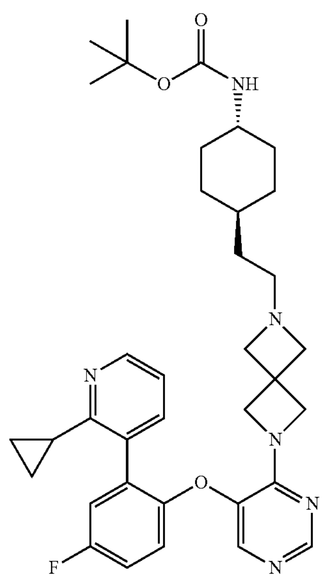 [SMILES: CC(C)(C)OC(=O)N[C@H]1CC[C@H](CCN2CC3(C2)CN(c2ncncc2Oc2ccc(F)cc2-c2cccnc2C2CC2)C3)CC1] | Synthesized from Intermediate 31C and tert-butyl ((1r,4r)-4-(2-oxoethyl)cyclohexyl)carbamate by method described in step 4 of Example 41 |
| 89 | 5-fluoro-2-((4-(7-(2-hydroxy-2-methylpropyl)-2,7-diazaspiro[3.5]nonan-2-yl)pyrimidin-5-yl)oxy)-N,N-diisopropylbenzamide | 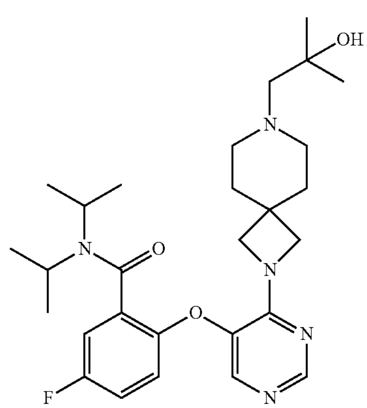 [SMILES: CC(C)N(C(=O)c1cc(F)ccc1Oc1cncnc1N1CC2(CCN(CC(C)(C)O)CC2)C1)C(C)C] | Synthesized from the intermediate prepared in step 2 of Example 6A and reacting with epoxide by method shown in step 5 of Example 71 |

TABLE 9-continued

Examples 79-240

| Example | Name | Structure | Procedure |
|---|---|---|---|
| 90 | 2-((4-(7-((3-cyano-3-methyl-2-oxoindolin-6-yl)methyl)-2,7-diazaspiro[4.4]nonan-2-yl)pyrimidin-5-yl)oxy)-5-fluoro-N,N-diisopropylbenzamide | 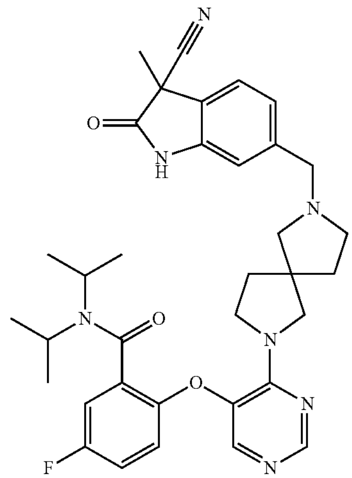 [SMILES: CC(C)N(C(=O)c1cc(F)ccc1Oc1cncnc1N1CCC2(CCN(Cc3ccc4c(c3)NC(=O)C4(C)C#N)C2)C1)C(C)C] | Synthesized from Example 99A and intermediate 46 by the method described in step 5 of Example 1 |
| 91 | methyl ethyl(5-fluoro-2-((4-(7-((2-oxo-2,3-dihydro-1H-benzo[d]imidazol-5-yl)methyl)-2,7-diazaspiro[4.4]nonan-2-yl)pyrimidin-5-yl)oxy)phenyl)carbamate | 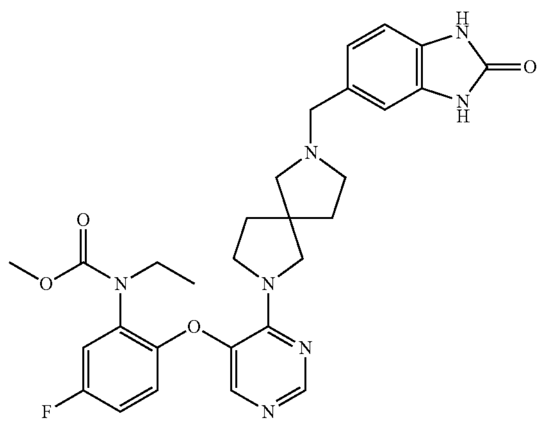 [SMILES: CCN(C(=O)OC)c1cc(F)ccc1Oc1cncnc1N1CCC2(CCN(Cc3ccc4[nH]c(=O)[nH]c4c3)C2)C1] | Synthesized by method similar to Example 75, starting from Intermediate 2, followed by acylation with methyl-chloroformate and alkylation with ethyl iodide |
| 91a | 5-fluoro-2-((4-(7-((1-(2-hydroxyethyl)-2-oxo-2,3-dihydro-1H-benzo[d]imidazol-5-yl)methyl)-2,7-diazaspiro[4.4]nonan-2-yl)pyrimidin-5-yl)oxy)-N-isopropyl-N-methylbenzamide | 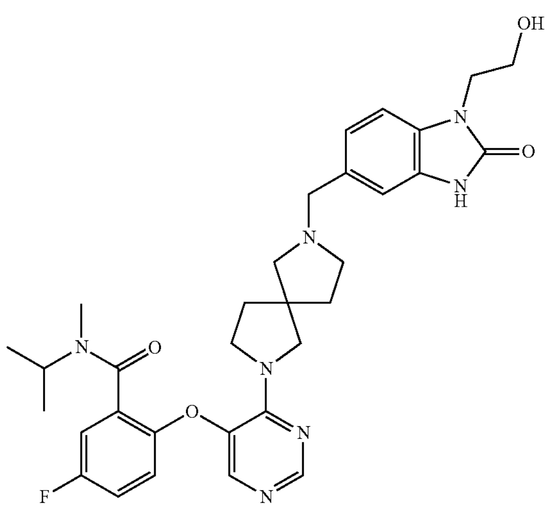 [SMILES: CC(C)N(C)C(=O)c1cc(F)ccc1Oc1cncnc1N1CCC2(CCN(Cc3ccc4c(c3)[nH]c(=O)n4CCO)C2)C1] | Synthesized by a method similar to Example 3 from intermediate 33 |

TABLE 9-continued

Examples 79-240

| Example | Name | Structure | Procedure |
|---|---|---|---|
| 92 | 5-fluoro-N-isopropyl-N-methyl-2-((4-(6-((tetrahydro-2H-pyran-4-yl)amino)-2-azaspiro[3.3]heptan-2-yl)pyrimidin-5-yl)oxy)benzamide | 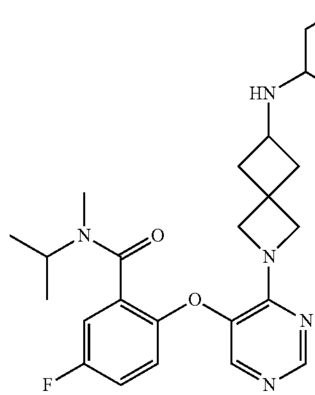 | Synthesized from Intermediate 38 and 4-pyran carboxyaldehyde by reductive amination as described in step 5 of Example 1 |
| 93 | 5-fluoro-N-isopropyl-N-methyl-2-((4-(7-(((1r,4r)-4-(methylsulfonamido)cyclohexyl)methyl)-2,7-diazaspiro[3.5]nonan-2-yl)pyrimidin-5-yl)oxy)benzamide | 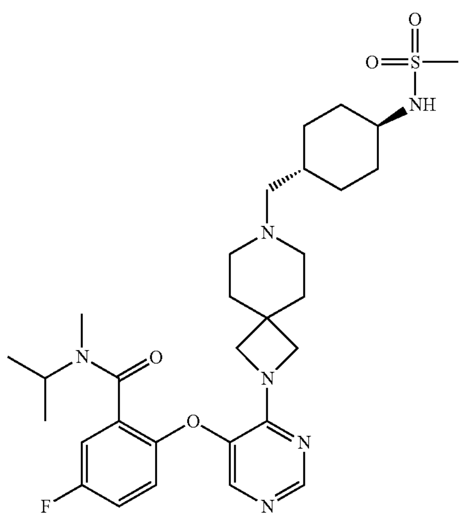 [SMILES: CC(C)N(C)C(=O)c1cc(F)ccc1Oc1cncnc1N1CC2(CCN(C[C@H]3CC[C@H](NS(C)(=O)=O)CC3)CC2)C1] | Synthesized from Intermediate 36 and N-((1r,4r)-4-formylcyclohexyl)methanesulfonamide by reductive amination as described in step 5 of Example 1. |
| 94 | tert-butyl ((1r,4r)-4-((2-(5-(4-fluoro-2-(isopropyl(methyl)carbamoyl)phenoxy)pyrimidin-4-yl)-2,7-diazaspiro[3.5]nonan-7-yl)methyl)cyclohexyl)carbamate | 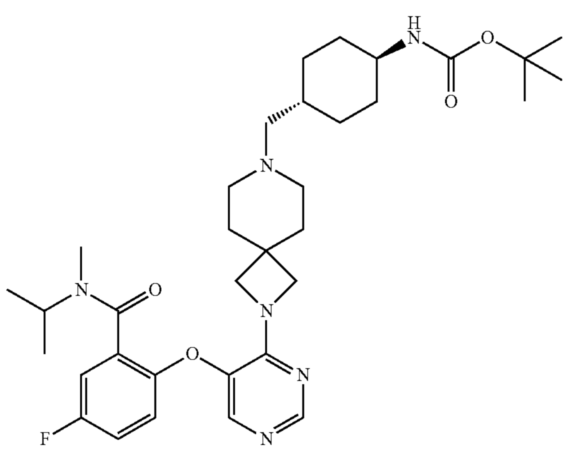 [SMILES: CC(C)N(C)C(=O)c1cc(F)ccc1Oc1cncnc1N1CC2(CCN(C[C@H]3CC[C@H](NC(=O)OC(C)(C)C)CC3)CC2)C1] | Synthesized from Intermediate 36 and tert-butyl ((1r,4r)-4-formylcyclohexyl)carbamate by reductive amination as described in step 5 of Example 1 |

TABLE 9-continued

Examples 79-240

| Example | Name | Structure | Procedure |
|---|---|---|---|
| 95 | methyl ((1r,4r)-4-(92-(5-(4-fluoro-2-(isopropyl(methyl)carbamoyl)phenoxy)pyrimdin-4-yl)-2,7-diazaspiro[3.5]nonan-7-yl)methyl)cyclohexyl)carbamate | 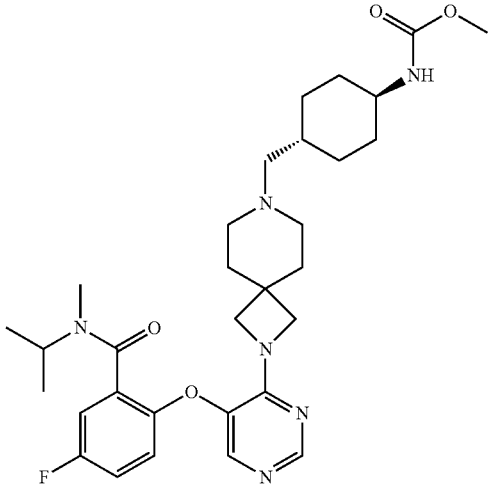 [SMILES: COC(=O)N[C@H]1CC[C@H](CN2CCC3(CC2)CN(c2ncncc2Oc2ccc(F)cc2C(=O)N(C)C(C)C)C3)CC1] | Synthesized from Intermediate 36 and methyl ((1r,4r)-4-formylcyclohexyl)carbamate by reductive amination as described in step 5 of Example 1 |
| 96 | N-(tert-butyl)-2-(5-(4-fluoro-2-(4-isopropylpyrimidin-5-yl)phenoxy)pyrimidin-4-yl)-2-azaspiro[3.4]octan-6-amine | 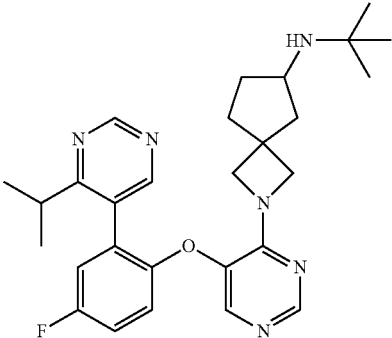 [SMILES: CC(C)c1ncncc1-c1cc(F)ccc1Oc1cncnc1N1CC2(CCC(NC(C)(C)C)C2)C1] | Synthesized by the method described in Example 18. In step 1, tert-butyl 6-oxo-2-azaspiro[3.4]octane-2-carboxylate was used. In step 3, tert-butyl amine was utilized. |
| 97 | 2-((4-(7-(((1r,4r)-4-(3,3-dimethylureido)cyclohexyl)methyl)-2,7-diazaspiro[3.5]nonan-2-yl)pyrimidin-5-yl)oxy)-5-fluoro-N,N-diisopropyl benzamide | 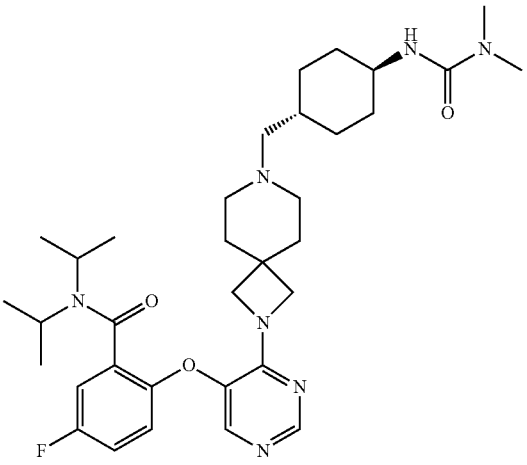 [SMILES: CC(C)N(C(=O)c1cc(F)ccc1Oc1cncnc1N1CC2(CCN(C[C@H]3CC[C@H](NC(=O)N(C)C)CC3)CC2)C1)C(C)C] | Synthesized from the intermediate prepared in step 4 of Example 6A by reaction with dimethylcarbamic chloride |

TABLE 9-continued

Examples 79-240

| Example | Name | Structure | Procedure |
|---|---|---|---|
| 98 | 5-fluoro-2-((4-(7-((4-hydroxycyclohexyl)methyl)-2,7-diazaspiro[3.5]nonan-2-yl)pyrimidin-5-yl)oxy)-N,N-diisopropylbenzamide | 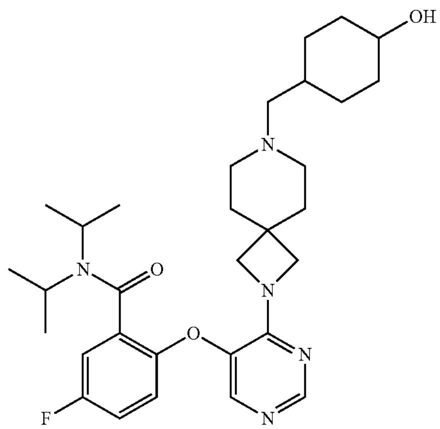 [SMILES: CC(C)N(C(=O)c1cc(F)ccc1Oc1cncnc1N1CC2(CCN(CC3CCC(O)CC3)CC2)C1)C(C)C] | Synthesized from Example 100 by treatment with acid followed by reduction with NaBH4 |
| 99 | 5-fluoro-2-((4-(6-((4-hydroxycyclohexyl)methyl)-2,6-diazaspiro[3.4]octan-2-yl)pyrimidin-5-yl)oxy)-N,N-diisopropylbenzamide | 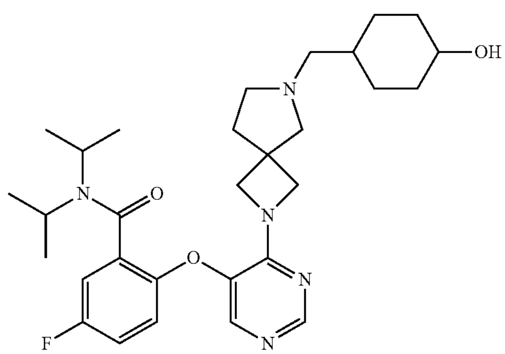 [SMILES: CC(C)N(C(=O)c1cc(F)ccc1Oc1cncnc1N1CC2(CCN(CC3CCC(O)CC3)C2)C1)C(C)C] | Synthesized by method similar to Example 98 starting from Intermediate 41b |
| 100 | 2-((4-(7-((1,4-dioxaspiro[4.5]decan-8-yl)methyl)-2,7-diazaspiro[3.5]nonan-2-yl)pyrimidin-5-yl)oxy)-5-fluoro-N,N-diisopropylbenzamide | 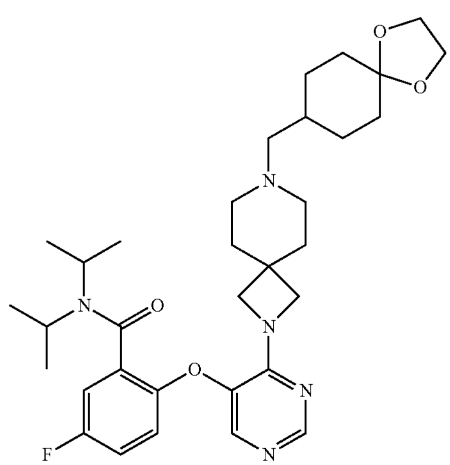 [SMILES: CC(C)N(C(=O)c1cc(F)ccc1Oc1cncnc1N1CC2(CCN(CC3CCC4(CC3)OCCO4)CC2)C1)C(C)C] | Synthesized from intermediate prepared in step 2 of Example 6A by reductive amination with 1,4-dioxaspiro[4.5]decane-8-carbaldehyde as described in step 5 of Example 1 |

TABLE 9-continued

Examples 79-240

| Example | Name | Structure | Procedure |
|---|---|---|---|
| 101 | 5-fluoro-N,N-diisopropyl-2-((4-(7-((tetrahydro-2H-pyran-4-yl)methyl)-2,7-diazaspiro[3.5]nonan-2-yl)pyrimidin-5-yl)oxy)benzamide | 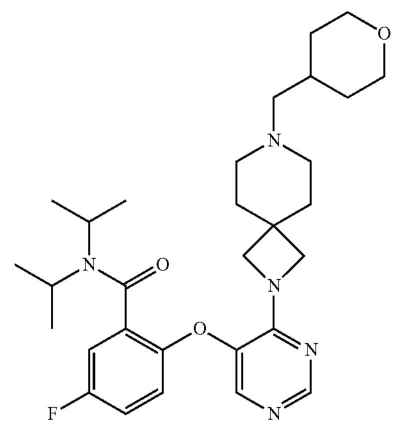 [SMILES: CC(C)N(C(=O)c1cc(F)ccc1Oc1cncnc1N1CC2(CCN(CC3CCOCC3)CC2)C1)C(C)C] | Synthesized from intermediate made in step 2 of Example 6A by reductive amination with tetrahydro-2H-pyran-4-carbaldehyde as described in step 5 of Example 1 |
| 102 | 5-fluoro-N,N-diisopropyl-2-((4-(6-neopentyl-2,6-diazaspiro[3.4]octan-2-yl)pyrimidin-5-yl)oxy)benzamide | 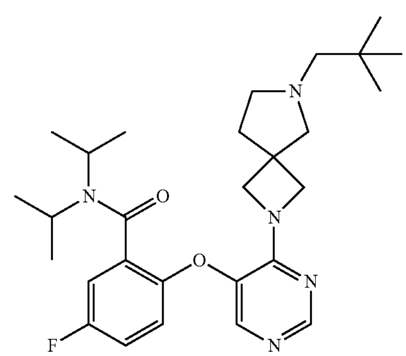 [SMILES: CC(C)N(C(=O)c1cc(F)ccc1Oc1cncnc1N1CC2(CCN(CC(C)(C)C)C2)C1)C(C)C] | Synthesized from Intermediate 41b by reductive amination with pivalaldehyde as described in step 5 of Example 1 |
| 103 | 2-((4-(6-(cyclopropylmethyl)-2,6-diazaspiro[3.4]octan-2-yl)pyrimidin-5-yl)oxy)-5-fluoro-N,N-diisopropylbenzamide | 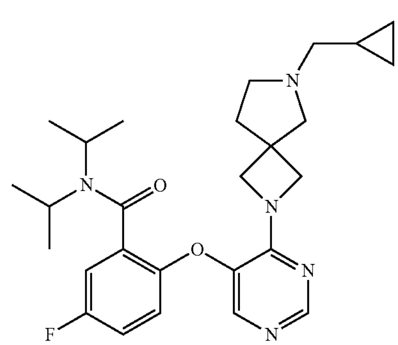 [SMILES: CC(C)N(C(=O)c1cc(F)ccc1Oc1cncnc1N1CC2(CCN(CC3CC3)C2)C1)C(C)C] | Synthesized from Intermediate 41b by reductive amination with cyclopropanecarbaldehyde as described in step 5 of Example 1 |

TABLE 9-continued

Examples 79-240

| Example | Name | Structure | Procedure |
|---|---|---|---|
| 104 | 2-((4-(6-(6-cyano-1,2,3,4-tetrahydro-naphthalen-2-yl)-2,6-diazaspiro[3.4]octan-2-yl)pyrimidin-5-yl)oxy)-5-fluoro-N,N-diisopropyl-benzamide | 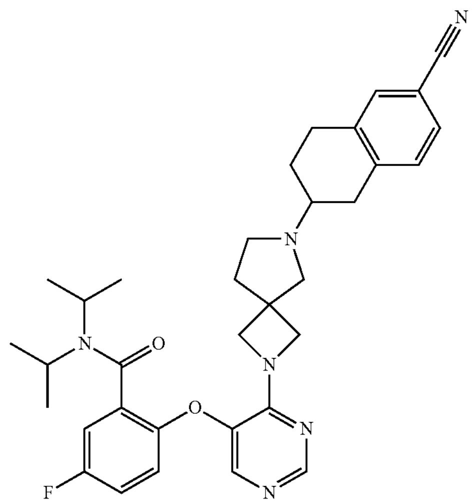 [SMILES: CC(C)N(C(=O)c1cc(F)ccc1Oc1cncnc1N1CC2(CCN(C3CCc4cc(C#N)ccc4C3)C2)C1)C(C)C] | Synthesized from Intermediate 41b by reductive amination with 6-oxo-5,6,7,8-tetrahydronaphthalene-2-carbonitrile as described in step 5 of Example 1 |
| 105 | 5-fluoro-N,N-diisopropyl-2-((4-(6-(2-((1r,4r)-4-pivalamidocyclohexyl)ethyl)-2,6-diazaspiro[3.3]heptan-2-yl)pyrimidin-5-yl)oxy)benzamide | 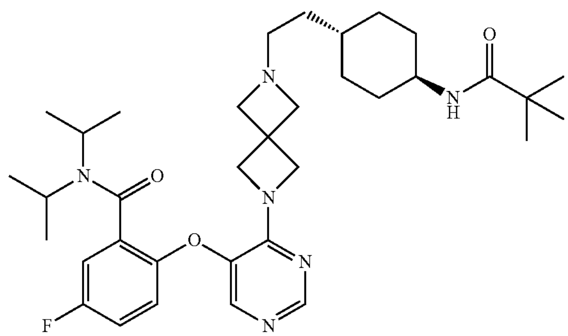 [SMILES: CC(C)N(C(=O)c1cc(F)ccc1Oc1cncnc1N1CC2(CN(CC[C@H]3CC[C@H](NC(=O)C(C)(C)C)CC3)C2)C1)C(C)C] | Synthesized from Intermediate 41 by reductive amination with N-((1r,4r)-4-(2-oxoethyl)cyclohexyl)pivalamide as described in step 5 of Example 1 |
| 106 | N-(2-((4-(6-(cyclohexylmethyl)-2,6-diaza-spiro[3.3]heptan-2-yl)pyrimidin-5-yl)oxy)-5-fluoro-phenyl)-N-ethylisobutyramide | 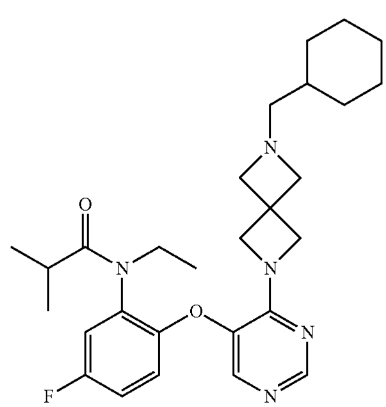 [SMILES: CCN(C(=O)C(C)C)c1cc(F)ccc1Oc1cncnc1N1CC2(CN(CC3CCCCC3)C2)C1] | Synthesized by a method similar to Example 75 starting from Intermediate 20 |

TABLE 9-continued

Examples 79-240

| Example | Name | Structure | Procedure |
|---|---|---|---|
| 107 | N-ethyl-5-fluoro-N-isopropyl-2-((4-(7-((1-methyl-2-oxo-2,3-dihydro-1H-benzo[d]imdazol-5-yl)methyl)-2,7-diazaspiro[4.4]nonan-2-yl)pyrimidin-5-yl)oxy)benzamide | 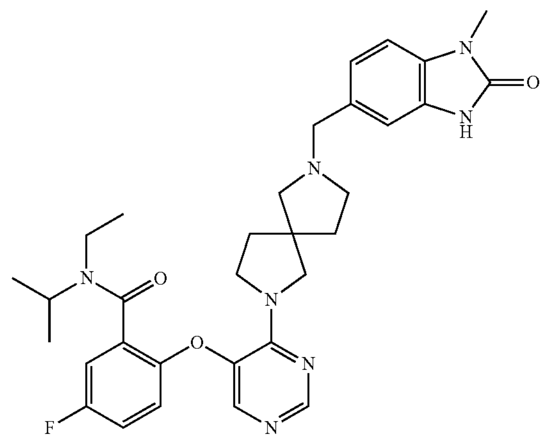 [SMILES: CCN(C(=O)c1cc(F)ccc1Oc1cncnc1N1CCC2(CCN(Cc3ccc4c(c3)[nH]c(=O)n4C)C2)C1)C(C)C] | Synthesized by a method similar to Example 1. In step 3, N-isoprpyl-N-ethyl amine was utilized. |
| 108 | 2-(5-(2-(cyclopentyloxy)-4-fluorophenoxy)pyrimidin-4-yl)-7-((tetrahydro-2H-pyran-4-yl)methyl)-2,7-diazaspiro[4.4]nonane | 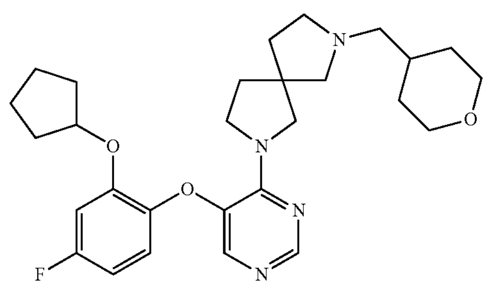 [SMILES: Fc1ccc(Oc2cncnc2N2CCC3(CCN(CC4CCOCC4)C3)C2)c(OC2CCCC2)c1] | Synthesized by the method described in Example 54 |
| 109 | 2-(5-(2-cyclopropoxy-4-fluoro-phenoxy)pyrimidin-4-yl)-7-((tetrahydro-2H-pyran-4-yl)methyl)-2,7-diazaspiro[4.4]nonane | 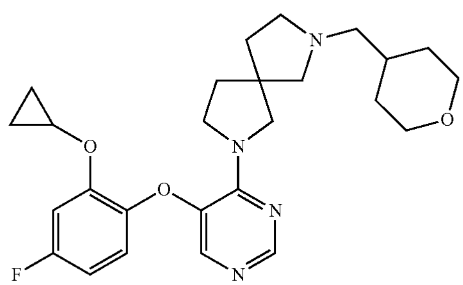 [SMILES: Fc1ccc(Oc2cncnc2N2CCC3(CCN(CC4CCOCC4)C3)C2)c(OC2CC2)c1] | Synthesized by the method described in Example 54 |
| 110 | N-ethyl-N-(5-fluoro-2-((4-(7-((tetrahydro-2H-pyran-4-yl)methyl)-2,7-diazaspiro[3.5]nonan-2-yl)pyrimidin-5-yl)oxy)phenyl)isobutyramide | 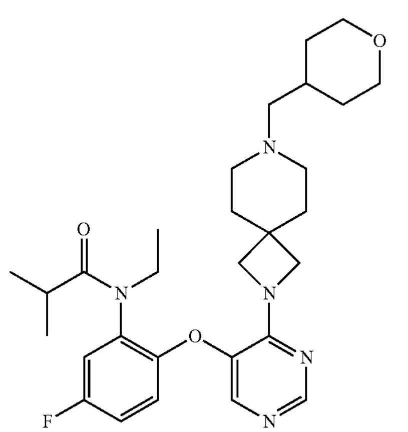 [SMILES: CCN(C(=O)C(C)C)c1cc(F)ccc1Oc1cncnc1N1CC2(CCN(CC3CCOCC3)CC2)C1] | Starting from Intermediate 23, it was synthesized by the method described in Example 75 |

TABLE 9-continued

Examples 79-240

| Example | Name | Structure | Procedure |
|---|---|---|---|
| 111 | 5-fluoro-N,N-diisopropyl-2-((4-(6-((tetrahydro-2H-pyran-4-yl)methyl)-2,6-diazaspiro[3.4]octan-2-yl)pyrimidin-5-yl)oxy)benzamide | 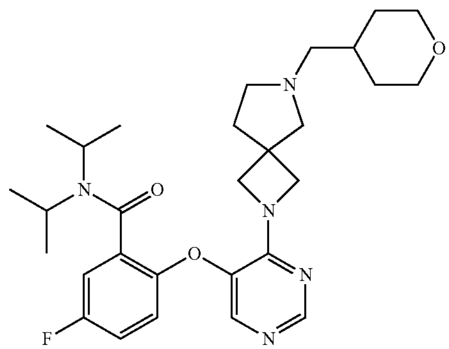 [SMILES: CC(C)N(C(=O)c1cc(F)ccc1Oc1cncnc1N1CC2(CCN(CC3CCOCC3)C2)C1)C(C)C] | Synthesized from Intermediate 41b by reductive amination with tetrahydro-2H-pyran-4-carbaldehyde, as described in step 5 of Example 1 |
| 112 | 5-fluoro-N,N-diisopropyl-2-((4-(6-((tetrahydro-2H-pyran-4-yl)methyl)-2,6-diazaspiro[3.3]heptan-2-yl)pyrimidin-5-yl)oxy)benzamide | 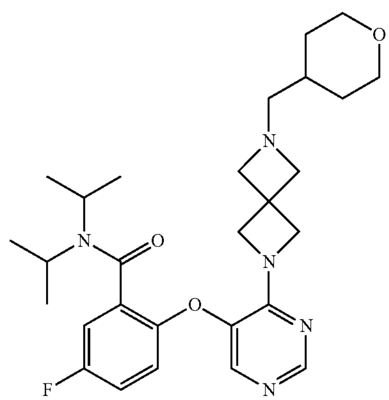 [SMILES: CC(C)N(C(=O)c1cc(F)ccc1Oc1cncnc1N1CC2(CN(CC3CCOCC3)C2)C1)C(C)C] | Synthesized from Intermediate 41a by reductive amination with tetrahydro-2H-pyran-4-carbaldehyde, as described in step 5 of Example 1 |
| 113 | 2-((4-((6-(2-(4-cyanophenyl)acetyl)-2,6-diazaspiro[3.4]octan-2-yl)pyrimidin-5-yl)oxy)-5-fluoro-N,N-diisopropylbenzamide | 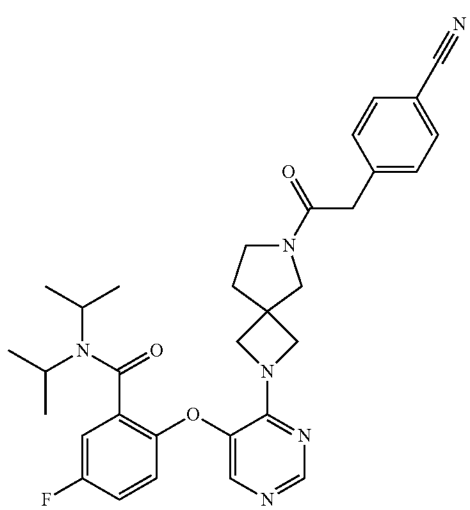 [SMILES: CC(C)N(C(=O)c1cc(F)ccc1Oc1cncnc1N1CC2(CCN(C(=O)Cc3ccc(C#N)cc3)C2)C1)C(C)C] | Synthesized from Intermediate 41b by amide formation with with 2-(4-cyanophenyl)acetic acid, as described in step 5 of Example 12 |

TABLE 9-continued

Examples 79-240

| Example | Name | Structure | Procedure |
|---|---|---|---|
| 114 | 5-fluoro-2-((4-(6-(6-fluoro-1,2,3,4-tetrahydronaphthalen-2-yl)-2,6-diazaspiro[3.4]octan-2-yl)pyrimidin-5-yl)oxy)-N,N-diisopropylbenzamide | 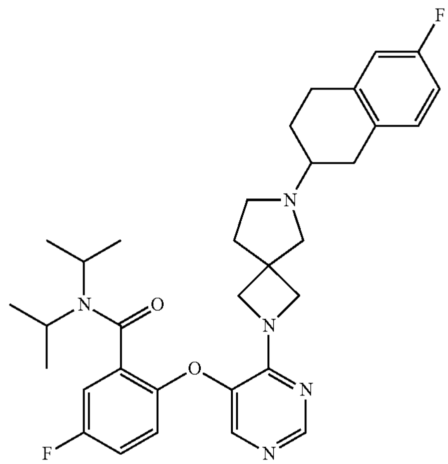 [SMILES: CC(C)N(C(=O)c1cc(F)ccc1Oc1cncnc1N1CC2(CCN(C3CCc4cc(F)ccc4C3)C2)C1)C(C)C] | Synthesized from Intermediate 41b by reductive amination with 2-fluoro 6-oxo-5,6,7,8-tetrahydronaphthalene, as described in step 5 of Example 1 |
| 115 | tert-butyl ((1r,4r)-4-(2-(6-(5-(2-(diisopropylcarbamoyl)-4-fluorophenoxy)pyrimidin-4-yl)-2,6-diazaspiro[3.3]heptan-2-yl)ethyl)cyclohexyl)carbamate | 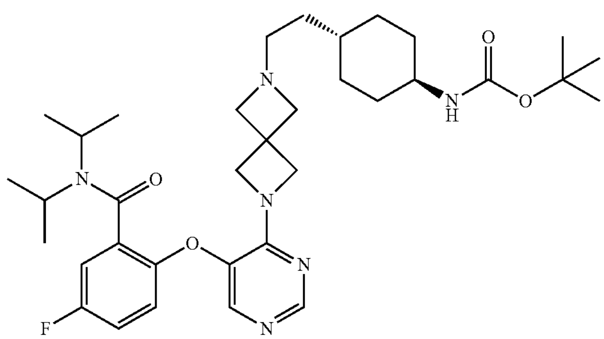 [SMILES: CC(C)N(C(=O)c1cc(F)ccc1Oc1cncnc1N1CC2(CN(CC[C@H]3CC[C@H](NC(=O)OC(C)(C)C)CC3)C2)C1)C(C)C] | Synthesized from Intermediate 41a by reductive amination with tert-butyl ((1r,4r)-4-(2-oxoethyl)cyclohexyl)carbamate, as described in step 5 of Example 1. |
| 116 | 2-((4-(6-(2-(4-cyanophenyl)acetyl)-2,6-diazaspiro[3.3]heptan-2-yl)pyrimidin-5-yl)oxy)-5-fluoro-N,N-diisopropylbenzamide | 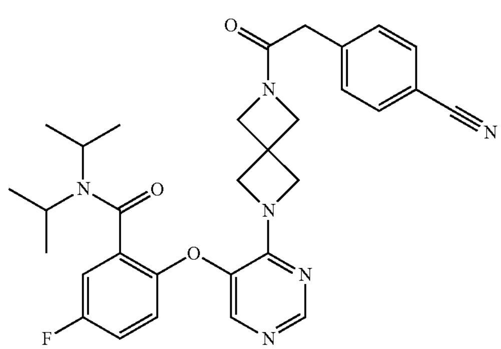 [SMILES: CC(C)N(C(=O)c1cc(F)ccc1Oc1cncnc1N1CC2(CN(C(=O)Cc3ccc(C#N)cc3)C2)C1)C(C)C] | Synthesized from Intermediate 41a by amide formation with with 2-(4-cyanophenyl)acetic acid, as described in step 5 of Example 12 |

TABLE 9-continued

Examples 79-240

| Example | Name | Structure | Procedure |
|---|---|---|---|
| 117 | N-ethyl-N-(5-fluoro-2-((4-(6-(5-(methylsulfonyl)-2,3-dihydro-1H-indene-2-carbonyl)-2,6diazaspiro[3.3]heptan-2-yl)pyrimidin-5-yl)oxy)phenyl)isobutyramide | 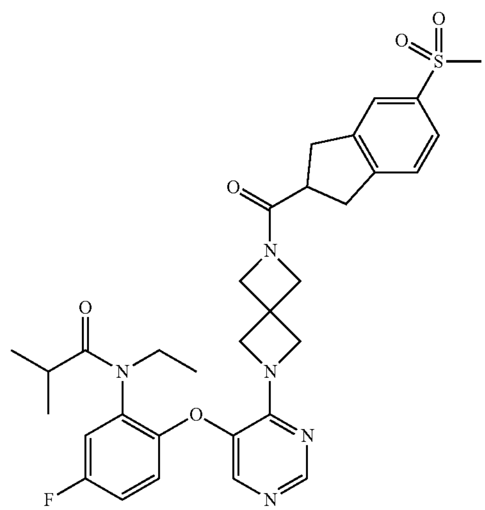 [SMILES: CCN(C(=O)C(C)C)c1cc(F)ccc1Oc1cncnc1N1CC2(CN(C(=O)C3Cc4ccc(S(C)(=O)=O)cc4C3)C2)C1] | Synthesized starting with Example 120 by conversion of bromo to methyl sulfone |
| 118 | 3-(((2-(5-(4-fluoro-2-(4-isopropylpyrimidin-5-yl)phenoxy)pyrimidin-4-yl)-2-azaspiro[3.3]heptan-6-yl)amino)methyl)bicyclo[1.1.1]pentane-1-carbonitrile | 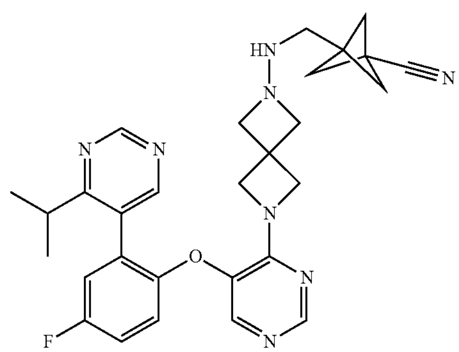 [SMILES: CC(C)c1ncncc1-c1cc(F)ccc1Oc1cncnc1N1CC2(CN(NCC34CC(C#N)(C3)C4)C2)C1] | Synthesized by method similar to the procedures described in Example 41. In first step, tert-butyl (2-azaspiro[3.3]heptan-6-yl)carbamate was used, in $2^{nd}$ step 4-isopropyl-4-pyrimidnyl boronic acid was used, and in $4^{th}$ step: 3-formylbicyclo[1.1.1]pentane-1-carbonitrile was used. |
| 119 | N-ethyl-N-(5-fluoro-2-((4-(6-(2-(4-(methylsulfonyl)phenyl)acetyl)-2,6-diazaspiro[3.3]heptan-2-yl)pyrimidin-5-yl)oxy)phenyl)isobutyramide | 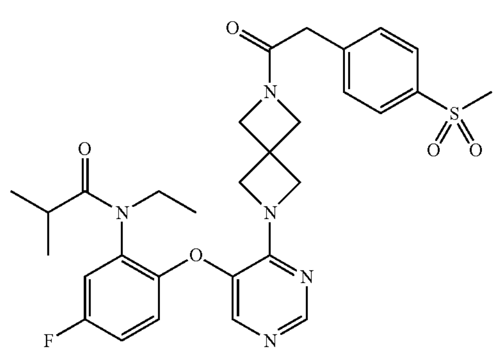 [SMILES: CCN(C(=O)C(C)C)c1cc(F)ccc1Oc1cncnc1N1CC2(CN(C(=O)Cc3ccc(S(C)(=O)=O)cc3)C2)C1] | Starting from Intermediate 22 and synthesized by the method described in Example 12. In final step, 2-(4-(methylsulfonyl)phenyl)acetic acid was utilized. |

TABLE 9-continued

Examples 79-240

| Example | Name | Structure | Procedure |
|---|---|---|---|
| 120 | N-(2-((4-(6-(5-bromo-2,3-dihydro-1H-indene-2-carbonyl)-2,6-diazaspiro[3.3]heptan-2-yl)pyrimidin-5-yl)oxy)-5-fluorophenyl)-N-ethylisobutyramide | 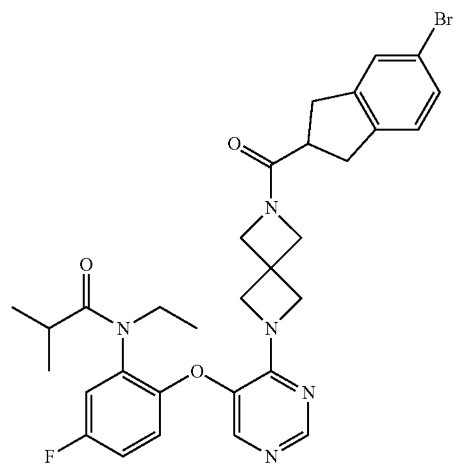 [SMILES: CCN(C(=O)C(C)C)c1cc(F)ccc1Oc1cncnc1N1CC2(CN(C(=O)C3Cc4ccc(Br)cc4C3)C2)C1] | Starting from Intermediate 22, and synthesized by method described in Example 12. In final step, 5-bromo-2,3-dihydro-1H-indene-2-carboxylic acid was utilized. |
| 121 | N-ethyl-N-(5-fluoro-2-((4-(6-((tetrahydro-2H-pyran-4-yl)methyl)-2,6-diazaspiro[3.3]heptan-2-yl)pyrimidin-5-yl)oxy)phenyl)isobutyramide | 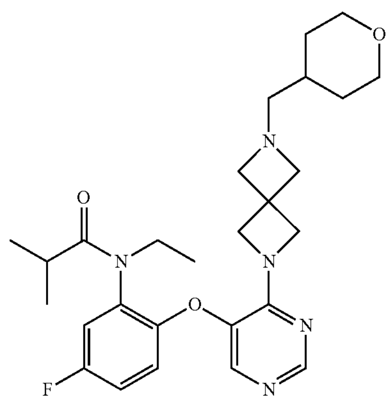 [SMILES: CCN(C(=O)C(C)C)c1cc(F)ccc1Oc1cncnc1N1CC2(CN(CC3CCOCC3)C2)C1] | Synthesized by a method similar to Example 75, starting from Intermediate 20, and in final step, it was condensed with tetrahydro-2H-pyran-4-carbaldehyde |
| 122 | N-cyclopropyl-5-fluoro-N-isopropyl-2-((4-(7-((2-oxo-2,3-dihydro-1H-benzo[d]imidazol-5-yl)methyl)-2,7-diazaspiro[4.4]nonan-2-yl)pyrimidin-5-yl)oxy)benzamide | 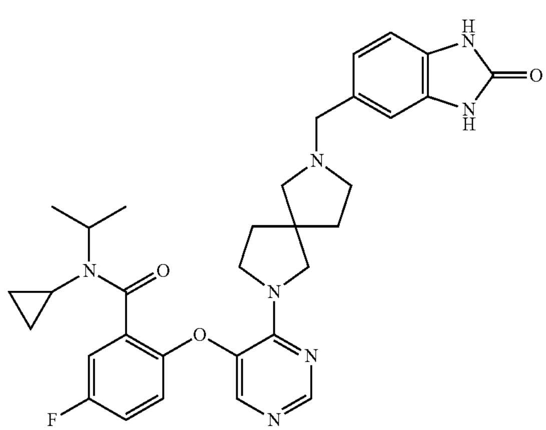 [SMILES: CC(C)N(C(=O)c1cc(F)ccc1Oc1cncnc1N1CCC2(CCN(Cc3ccc4[nH]c(=O)[nH]c4c3)C2)C1)C1CC1] | Synthesized by a method similar to Example 1. In step 4, N-isopropyl-N-cyclopropyl amine was utilized. |

TABLE 9-continued

Examples 79-240

| Example | Name | Structure | Procedure |
|---|---|---|---|
| 123 | 2-((4-(7-((1-(2-acetamidoethyl)-2-oxo-2,3-dihydro-1H-benzo[d]imidazol-5-yl)methyl)-2,7-diazaspiro[4.4]nonan-2-yl)pyrimidin-5-yl)oxy)-5-fluoro-N-isopropyl-N-methylbenzamide | 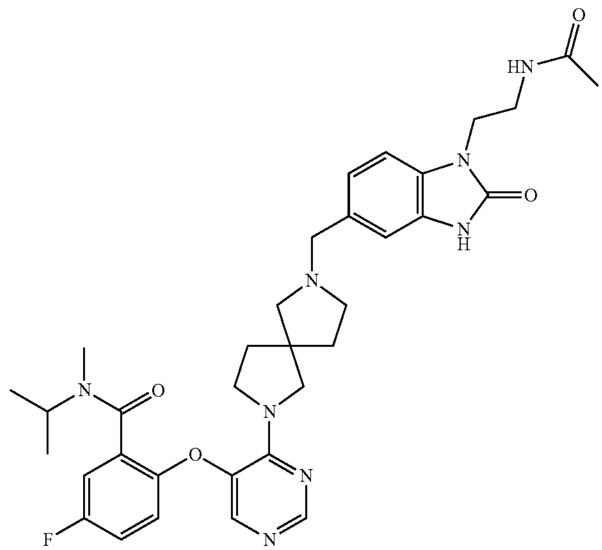 [SMILES: CC(=O)NCCn1c(=O)[nH]c2cc(CN3CCC4(CCN(c5ncncc5Oc5ccc(F)cc5C(=O)N(C)C(C)C)C4)C3)ccc21] | Synthesized by a method similar to Example 1, starting from Intermediate 33. In the final step, Intermediate 46 was utilized. |
| 124 | 2-((4-(7-((1-(2-(dimethylamino)ethyl)-2-oxo-2,3-dihydro-1H-benzo[d]imidazol-5-yl)methyl)-2,7-diazaspiro[4.4]nonan-2-yl)pyrimidin-5-yl)oxy)-5-fluoro-N-isopropyl-N-methylbenzamide | 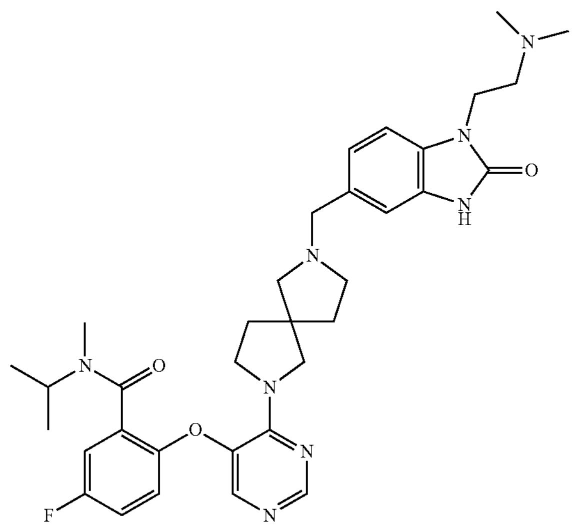 [SMILES: CC(C)N(C)C(=O)c1cc(F)ccc1Oc1cncnc1N1CCC2(CCN(Cc3ccc4c(c3)[nH]c(=O)n4CCN(C)C)C2)C1] | Synthesized by a method similar to Example 1, starting from Intermediate 33. In the final step, Intermediate 44a was utilized. |
| 125 | 2-((4-(7-((3-cyano-3-methyl-2-oxoindolin-6-yl)methyl)-2,7-diazaspiro[4.4]nonan-2-yl)pyrimidin-5-yl)oxy)-5-fluoro-N-isopropyl-N-methylbenzamide | 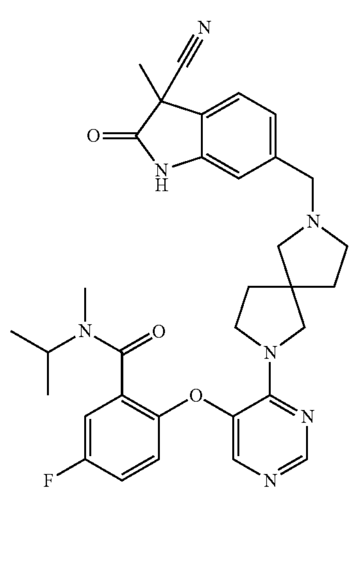 [SMILES: CC(C)N(C)C(=O)c1cc(F)ccc1Oc1cncnc1N1CCC2(CCN(Cc3ccc4c(c3)NC(=O)C4(C)C#N)C2)C1] | Synthesized by a method similar to Example 1, starting from Intermediate 33. In the final step, Intermediate 46 was utilized. |

TABLE 9-continued

Examples 79-240

| Example | Name | Structure | Procedure |
|---|---|---|---|
| 126 | 5-((7-(5-(4-fluoro-2-(1-isopropyl-1H-pyrazol-5-yl)phenoxy)-2-methylpyrimidin-4-yl)-2,7-diazaspiro[4.4]nonan-2-yl)methyl)-1,3-dihydro-2H-benzo[d]imidazol-2-one | 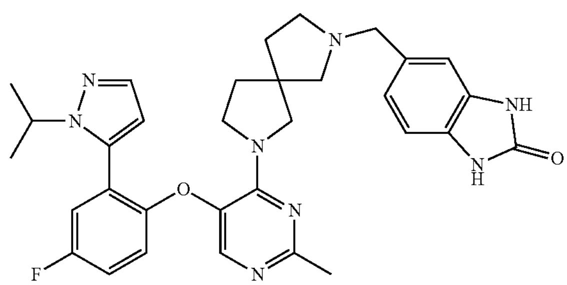 [SMILES: Cc1ncc(Oc2ccc(F)cc2-c2ccnn2C(C)C)c(N2CCC3(CCN(Cc4ccc5[nH]c(=O)[nH]c5c4)C3)C2)n1] | Synthesized by a method similar to Example 41, starting with 5-bromo-4-chloro-2-methyl pyrimidine. In $2^{nd}$ step, 2-isopropyl-3-pyrazole boronic acid was used. |
| 127 | 2-((4-(2-(2-(4-cyanophenyl)acetyl)-2,6-diazaspiro[3.4]octan-6-yl)pyrimidin-5-yl)oxy)-5-fluoro-N-isopropyl-N-methylbenzamide | 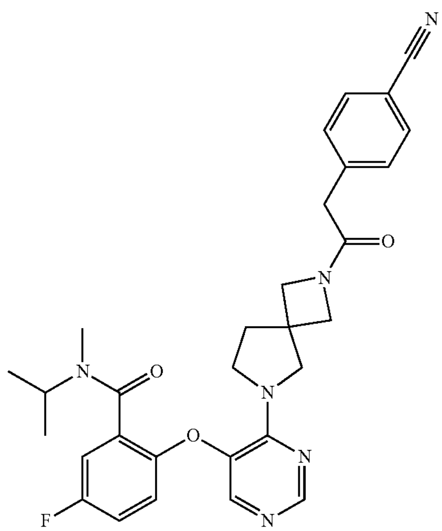 [SMILES: CC(C)N(C)C(=O)c1cc(F)ccc1Oc1cncnc1N1CCC2(CN(C(=O)Cc3ccc(C#N)cc3)C2)C1] | Synthesized from Intermediate 37 by coupling with (4-cyano-benzene)acetic acid, as described in Example 12 |
| 128 | 2-((4-(7-((1-ethyl-2-oxo-2,3-dihydro-1H-benzo[d]imidazol-5-yl)methyl)-2,7-diazaspiro[4.4]nonan-2-yl)pyrimidin-5-yl)oxy)-5-fluoro-N-isopropyl-N-methylbenzamide | 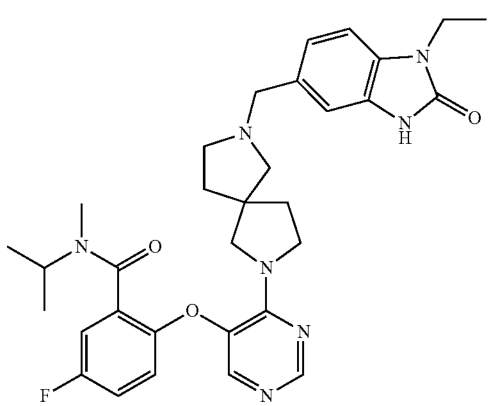 [SMILES: CCn1c(=O)[nH]c2cc(CN3CCC4(CCN(c5ncncc5Oc5ccc(F)cc5C(=O)N(C)C(C)C)C4)C3)ccc21] | Synthesized by a method similar to Example 1, starting from Intermediate 33. In the final step, 1-ethyl-2-oxo-2,3-dihydro-1H-benzo[d]imidazole-5-carbaldehyde was utilized. |

TABLE 9-continued

Examples 79-240

| Example | Name | Structure | Procedure |
|---|---|---|---|
| 129 | 5-fluoro-N-isopropyl-2-((4-(7-((1-(2-methoxyethyl)-2-oxo-2,3-dihydro-1H-benzo[d]imidazol-5-yl)methyl)-2,7-diazaspiro[4.4]nonan-2-yl)pyrimidin-5-yl)oxy)-N-methyl benzamide | 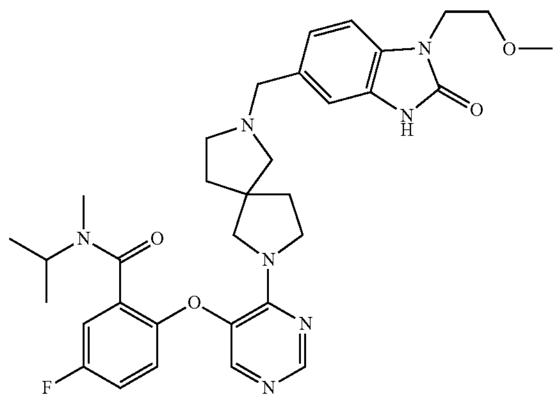 [SMILES: COCCn1c(=O)[nH]c2cc(CN3CCC4(CCN(c5ncncc5Oc5ccc(F)cc5C(=O)N(C)C(C)C)C4)C3)ccc21] | Synthesized by a method similar to Example 1, starting from Intermediate 33. In the final step, Intermediate 42A was utilized |
| 130 | 4-(2-(6-(5-(4-fluoro-2-(4-isopropylpyrimidin-5-yl)phenoxy)pyrimidin-4-yl)-2,6-diazaspiro[3.4]octan-2-yl)-2-oxoethyl)benzonitrile | 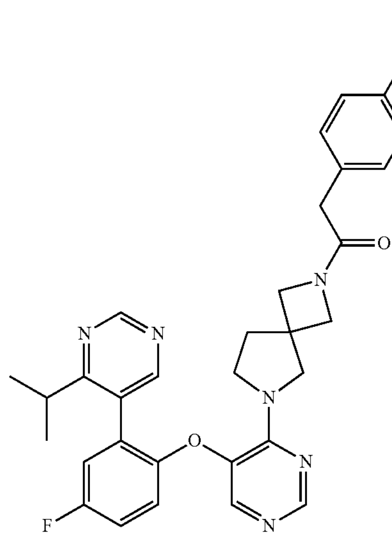 | Intermediate 28 was coupled with 4-cyanobenzene-acetyl chloride, as described in Example 12 |
| 131 | 5-((7-(5-(4-fluoro-2-(4-isopropylpyrimidin-5-yl)phenoxy)pyrimidin-4-yl)-2,7-diazaspiro[4.4]nonan-2-yl)methyl)-1-(2-methoxyethyl)-1,3-dihydro-2H-benzo[d]imidazol-2-one | 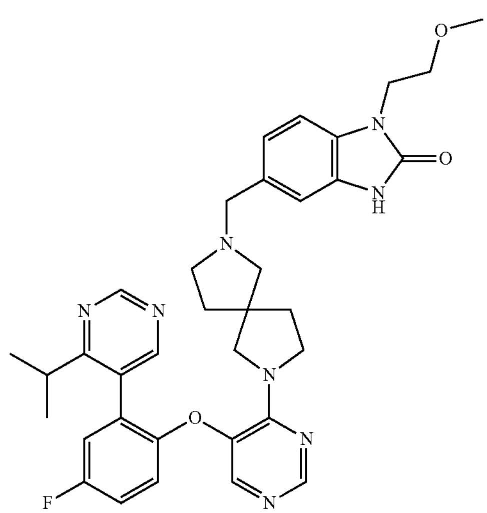 [SMILES: COCCn1c(=O)[nH]c2cc(CN3CCC4(CCN(c5ncncc5Oc5ccc(F)cc5-c5cncnc5C(C)C)C4)C3)ccc21] | Synthesized by a method similar to Example 41. In step 2, 4-isopropyl 5-pyrimidine-boronic acid was used and in step 4, Intermediate 42 was utilized. |

TABLE 9-continued

Examples 79-240

| Example | Name | Structure | Procedure |
|---|---|---|---|
| 132 | 1-(6-(5-(4-fluoro-2-(4-isopropylpyrimidin-5-yl)phenoxy)pyrimidin-4-yl)-2,6-diazaspiro[3.3]heptan-2-yl)-2-(6-methoxypyridin-3-yl)ethan-1-one | 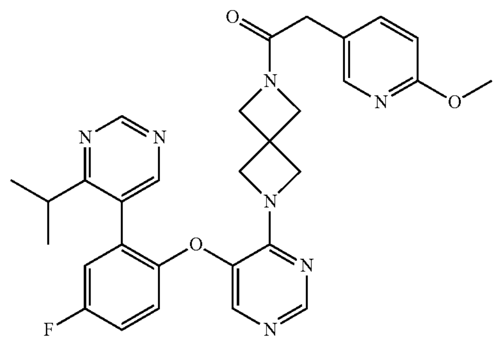 [SMILES: COc1ccc(CC(=O)N2CC3(C2)CN(c2ncncc2Oc2ccc(F)cc2-c2cncnc2C(C)C)C3)cn1] | Intermediate 27 was coupled with (2-methoxypyridyl)acetic acid, as described in step 5 of Example 12 |
| 133 | 6-(2-(6-(5-(4-fluoro-2-(4-isopropylpyrimidin-5-yl)phenoxy)pyrimidin-4-yl)-2,6-diazaspiro[3.3]heptan-2-yl)-2-oxoethyl)-3,3-dimethylindole-2-one | 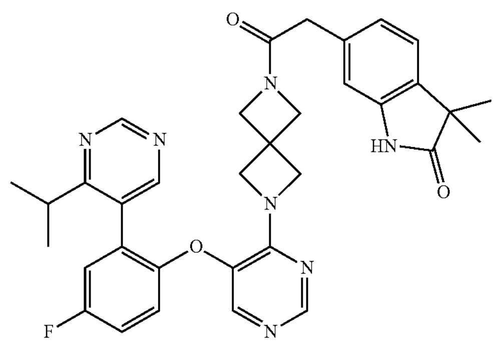 [SMILES: CC(C)c1ncncc1-c1cc(F)ccc1Oc1cncnc1N1CC2(CN(C(=O)Cc3ccc4c(c3)NC(=O)C4(C)C)C2)C1] | Intermediate 27 was coupled with 2-(3,3-dimethyl-2-oxoindolin-6-yl)acetic acid, as described in step 5 of Example 12 |
| 134 | tert-butyl ((1r,4r)-4-(2-(6-(5-(4-fluoro-2-(isopropyl(methyl)carbamoyl)phenoxy)pyrimidin-4-yl)-2,6-diazaspiro[3.3]heptan-2-yl)ethyl)cyclohexyl)carbamate | 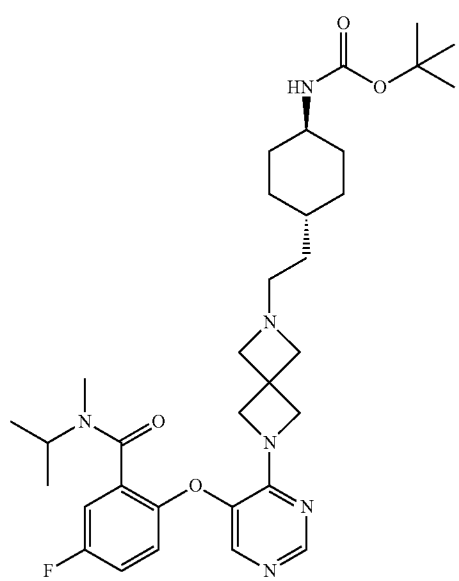 [SMILES: CC(C)N(C)C(=O)c1cc(F)ccc1Oc1cncnc1N1CC2(CN(CC[C@H]3CC[C@H](NC(=O)OC(C)(C)C)CC3)C2)C1] | Synthesized from Intermediate 39 by reductive amination with tert-butyl ((1r,4r)-4-(2-oxoethyl)cyclohexyl)carbamate, as described in the final step of Example 1 |

TABLE 9-continued

Examples 79-240

| Example | Name | Structure | Procedure |
|---|---|---|---|
| 135 | 5-((7-(5-(4-fluoro-2-((isopropyl(methyl)amino)methyl)phenoxy)pyrimidin-4-yl)-2,7-diazaspiro[4.4]nonan-2-yl)methyl)-1,3-dihydro-2H-benzo[d]imidazol-2-one | 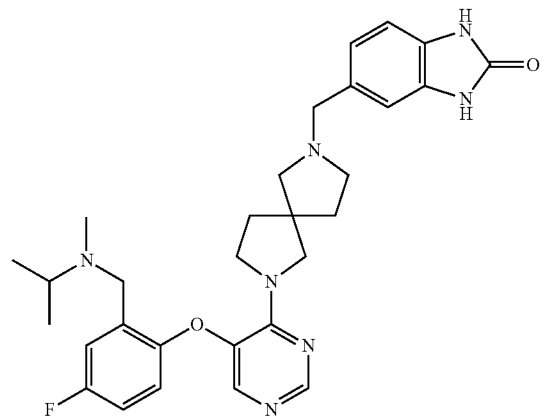 [SMILES: CC(C)N(C)Cc1cc(F)ccc1Oc1cncnc1N1CCC2(CCN(Cc3ccc4[nH]c(=O)[nH]c4c3)C2)C1] | Synthesized by a method similar to Example 70 |
| 136 | N-ethyl-N-(5-fluoro-2-((4-(6-isobutyl-2,6-diazaspiro[3.4]octan-2-yl)pyrimidin-5-yl)oxy)phenyl)isobutyramide | 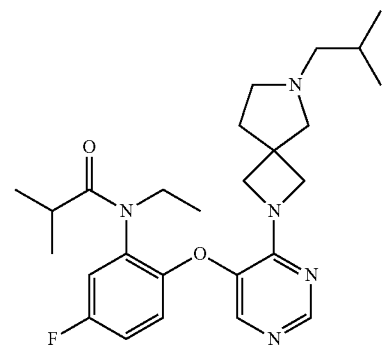 [SMILES: CCN(C(=O)C(C)C)c1cc(F)ccc1Oc1cncnc1N1CC2(CCN(CC(C)C)C2)C1] | Synthesized by a method similar to Example 75, starting from Intermediate 24 |
| 137 | N-(2-((4-(6-((4,4-difluorocyclohexyl)methyl)-2,6-diazaspiro[3.4]octan-2-yl)pyrimidin-5-yl)oxy)-5-fluorophenyl)-N-ethylisobutyramide | 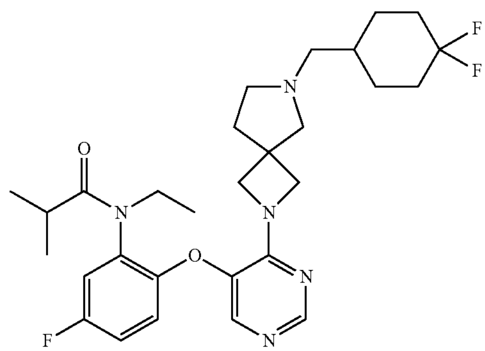 [SMILES: CCN(C(=O)C(C)C)c1cc(F)ccc1Oc1cncnc1N1CC2(CCN(CC3CCC(F)(F)CC3)C2)C1] | Synthesized by method similar to Example 75, starting from Intermediate 24, In final step 4, 4-difluorocyclohexane-1-carbaldehyde was used |
| 138 | tert-butyl ((1r,4r)-4-(2-(6-(5-(4-fluoro-2-(N-methyl-isobutyramido)phenoxy)pyrimidin-4-yl)-2,6-diazaspiro[3.3]heptan-2-yl)ethyl)cyclohexyl)carbamate | 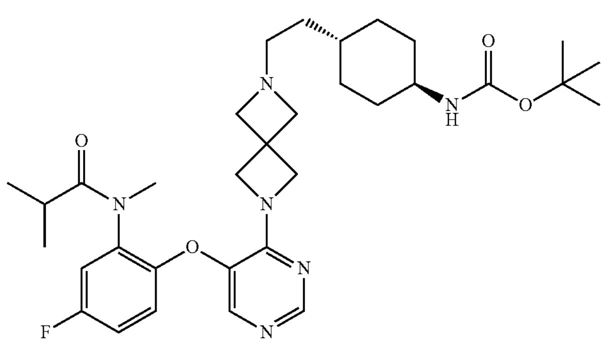 [SMILES: CC(C)C(=O)N(C)c1cc(F)ccc1Oc1cncnc1N1CC2(CN(CC[C@H]3CC[C@H](NC(=O)OC(C)(C)C)CC3)C2)C1] | Synthesized by method similar to Example 75, starting from Intermediate 24. In final step, tert-butyl ((1r,4r)-4-(2-oxoethyl)cyclohexyl)carbamate was used. |

TABLE 9-continued

Examples 79-240

| Example | Name | Structure | Procedure |
|---|---|---|---|
| 139 | 2-(5-(4-fluoro-2-(4-isopropylpyrimidin-5-yl)phenoxy)pyrimidin-4-yl)-7-(6-fluoro-3,4-dihydroisoquinolin-2(1H)-yl)-5-oxa-2-azaspiro[3.4]octane | 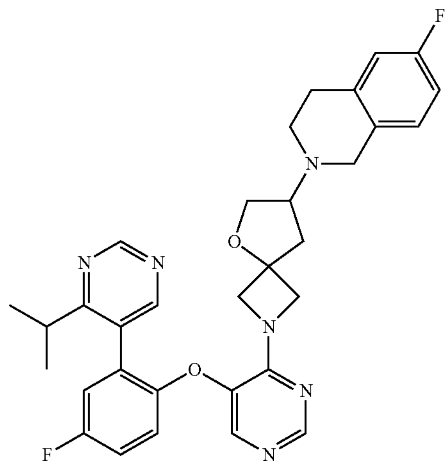 [SMILES: CC(C)c1ncncc1-c1cc(F)ccc1Oc1cncnc1N1CC2(CC(N3CCc4cc(F)ccc4C3)CO2)C1] | Synthesized by a method similar to Example 18. In step 4, 6-fluoro-1,2,3,4-tetrahydroisoquinoline was utilized. |
| 140 | 4-(((2-(5-(4-fluoro-2-(4-isopropylpyrimidin-5-yl)phenoxy)pyrimidin-4-yl)-2-azaspiro[3.3]heptan-6-yl)amino)methyl)-1-methylcyclohexane-1-carbonitrile | 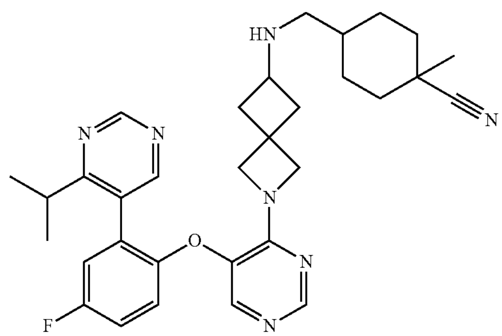 [SMILES: CC(C)c1ncncc1-c1cc(F)ccc1Oc1cncnc1N1CC2(CC(NCC3CCC(C)(C#N)CC3)C2)C1] | Intermediate 29 was condensed with 4-formyl-1-methylcyclohexane-1-carbonitrile, as described in step 4 of Example 41 |
| 141 | 4-(1-((2-(5-(4-fluoro-2-(4-isopropylpyrimidin-5-yl)phenoxy)pyrimidin-4-yl)-2-azaspiro[3.3]heptan-6-yl)amino)ethyl)benzonitrile | 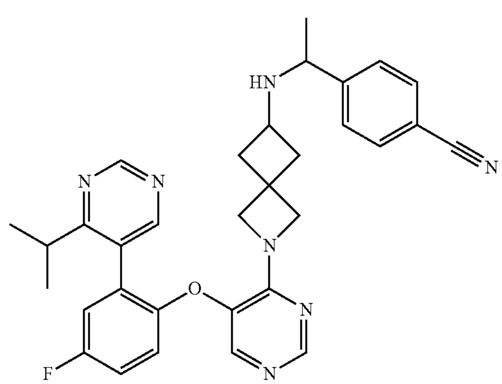 [SMILES: CC(C)c1ncncc1-c1cc(F)ccc1Oc1cncnc1N1CC2(CC(NC(C)c3ccc(C#N)cc3)C2)C1] | Intermediate 29 was condensed with 4-acetylbenzonitrile as described in step 4 of Example 41 |

TABLE 9-continued

Examples 79-240

| Example | Name | Structure | Procedure |
|---|---|---|---|
| 142 | 5-fluoro-N-isopropyl-N-methyl-2-((4-(7-(4-(2-oxooxazolidin-3-yl)benzyl)-2,7-diazaspiro[4.4]nonan-2-yl)pyrimidin-5-yl)oxy)benzamide | 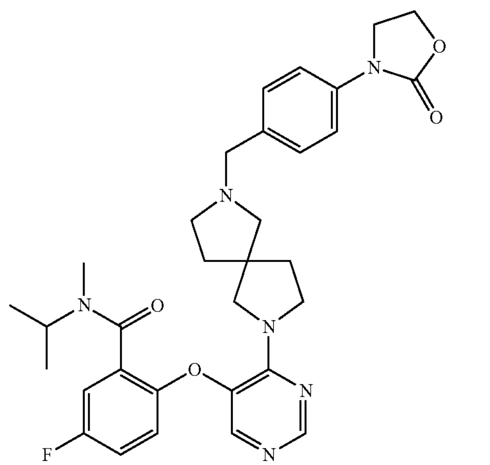 [SMILES: CC(C)N(C)C(=O)c1cc(F)ccc1Oc1cncnc1N1CCC2(CCN(Cc3ccc(N4CCOC4=O)cc3)C2)C1] | Synthesized from Intermediate 33 by reductive amination with 4-(2-oxooxazolidin-3-yl)benzaldehyde, as described in final step of Example 1 |
| 143 | N-((1r,4r)-4-(2-(6-(5-((4'-cyano-2'-cyclopropyl-5-fluoro-[1,1'-biphenyl]-2-yl)oxy)pyrimidin-4-yl)-2,6-diazaspiro[3.3]heptan-2-yl)ethyl)cyclohexyl)acetamide | 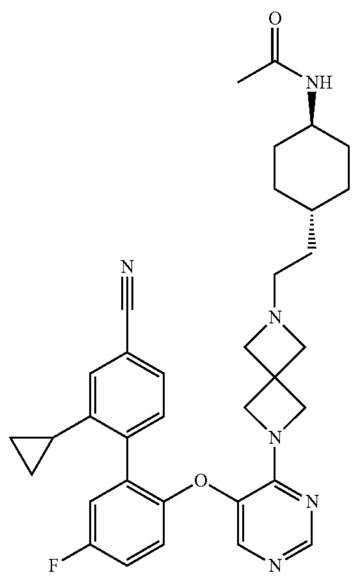 [SMILES: CC(=O)N[C@H]1CC[C@H](CCN2CC3(C2)CN(c2ncncc2Oc2ccc(F)cc2-c2ccc(C#N)cc2C2CC2)C3)CC1] | Synthesized from Intermediate 32 by reductive amination with N-((1r,4r)-4-(2-oxoethyl)cyclohexyl)acetamide, as described for step 4 of Example 41 |
| 144 | methyl (5-fluoro-2-((4-(7-((2-oxo-2,3-dihydro-1H-benzo[d]imidazol-5-yl)methyl)-2,7-diazaspiro[4.4]nonan-2-yl)pyrimidin-5-yl)oxy)phenyl)(isopropyl)carbamate | 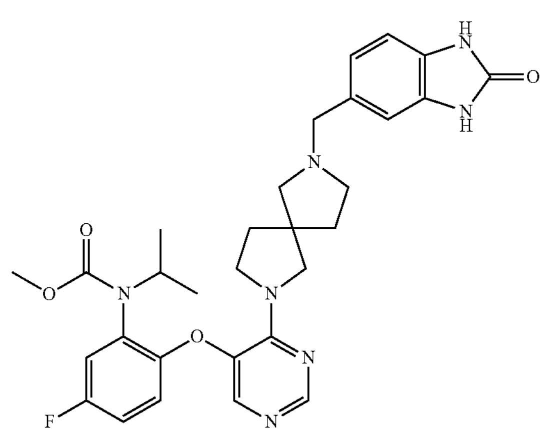 [SMILES: COC(=O)N(c1cc(F)ccc1Oc1cncnc1N1CCC2(CCN(Cc3ccc4[nH]c(=O)[nH]c4c3)C2)C1)C(C)C] | Synthesized by method similar to Example 75, starting from Intermediate 102 |

TABLE 9-continued

Examples 79-240

| Example | Name | Structure | Procedure |
|---|---|---|---|
| 145 | 2-((4-(7-((1H-indazol-6-yl)methyl)-2,7-diazaspiro[4.4]nonan-2-yl)pyrimidin-5-yl)oxy)-5-fluoro-N-isopropyl-N-methylbenzamide | 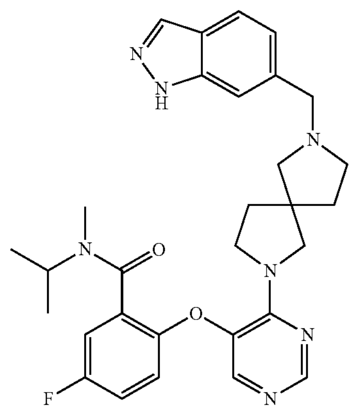 [SMILES: CC(C)N(C)C(=O)c1cc(F)ccc1Oc1cncnc1N1CCC2(CCN(Cc3ccc4cn[nH]c4c3)C2)C1] | Synthesized by a method similar to Example 1. In the last step, 1H-indazole-6-carbaldehyde was utilized. |
| 146 | 2-((4-(7-((3-cyano-1H-indazol-6-yl)methyl)-2,7-diazaspiro[4.4]nonan-2-yl)pyrimidin-5-yl)oxy)-5-fluoro-N-isopropyl-N-methylbenzamide | 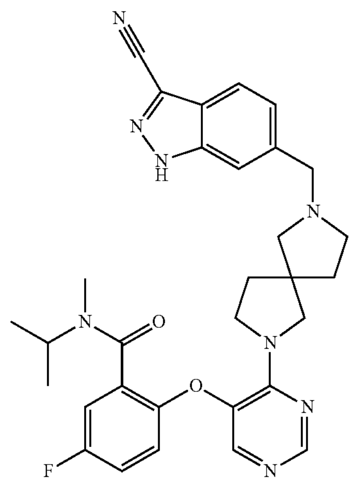 [SMILES: CC(C)N(C)C(=O)c1cc(F)ccc1Oc1cncnc1N1CCC2(CCN(Cc3ccc4c(C#N)n[nH]c4c3)C2)C1] | Synthesized from Intermediate 33 and 6-formyl-1H-indazole-3-carbonitrile, by method described in step 4 of Example 6A |
| 147 | tert-butyl ((1r,4r)-4-((7-(5-(2-(cyclopentyloxy)-4-fluorophenoxy)pyrimidin-4-yl)-2,7-diazaspiro[4.4]nonan-2-yl)methyl)cyclohexyl)carbamate | 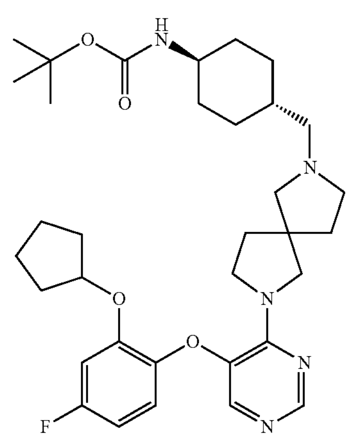 [SMILES: CC(C)(C)OC(=O)N[C@H]1CC[C@H](CN2CCC3(CCN(c4ncncc4Oc4ccc(F)cc4OC4CCCC4)C3)C2)CC1] | Synthesized by the method described in Example 54 |

TABLE 9-continued

Examples 79-240

| Example | Name | Structure | Procedure |
|---|---|---|---|
| 148A | Isomer 1: 4-((2-(5-(4-fluoro-2-(4-isopropylpyrimidin-5-yl)phenoxy)pyrimidin-4-yl)-2-azaspiro[3.3]heptan-6-yl)amino)-1-methylcyclohexane carbonitrile | 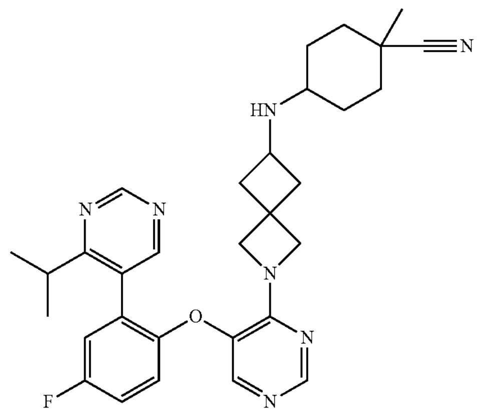 [SMILES: CC(C)c1ncncc1-c1cc(F)ccc1Oc1cncnc1N1CC2(CC(NC3CCC(C)(C#N)CC3)C2)C1] | Intermediate 29 was condensed with 1-methyl-4-oxocyclohexane-1-carbonitrile, as described in step 4 of Example 41 |
| 148B | Isomer 2: 4-((2-(5-(4-fluoro-2-(4-isopropylpyrimidin-5-yl)phenoxy)pyrimidin-4-yl)-2-azaspiro[3.3]heptan-6-yl)amino)-1-methylcyclohexane carbonitrile | 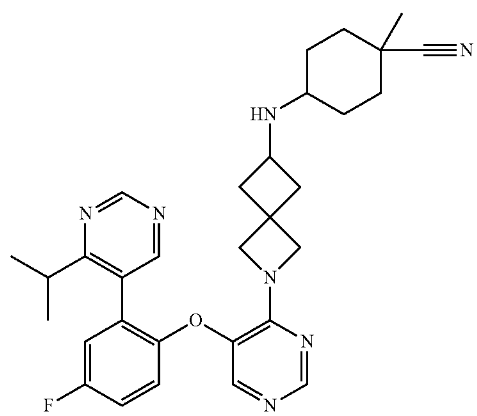 [SMILES: CC(C)c1ncncc1-c1cc(F)ccc1Oc1cncnc1N1CC2(CC(NC3CCC(C)(C#N)CC3)C2)C1] | Minor isomer separated from the synthesis of Example 148A by SFC method A |
| 149 | 4-(2-(2-(5-(4-fluoro-2-(4-isopropylpyrimidin-5-yl)phenoxy)pyrimidin-4-yl)-2,6-diazaspiro[3.4]octan-6-yl)-2-oxoethyl)benzonitrile | 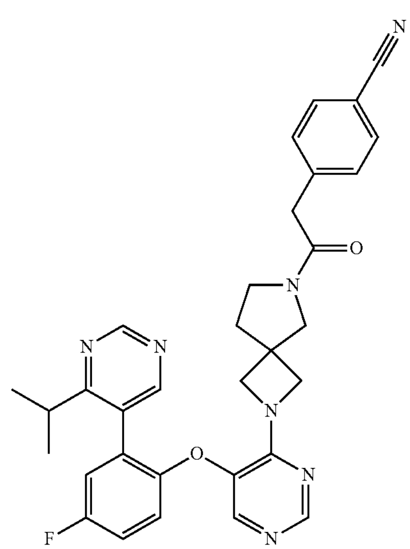 [SMILES: CC(C)c1ncncc1-c1cc(F)ccc1Oc1cncnc1N1CC2(CCN(C(=O)Cc3ccc(C#N)cc3)C2)C1] | Intermediate 28 was reacted with (4-cynophenyl)acetic acid, as described in Example 12 |

TABLE 9-continued

Examples 79-240

| Example | Name | Structure | Procedure |
|---|---|---|---|
| 150 | 5-((7-(5-(4-fluoro-2-(4-isopropylpyrimidin-5-yl)phenoxy)pyrimidin-4-yl)-2,7-diazaspiro[4.4]nonan-2-yl)methyl)-1-methyl-1,3-dihydro-2H-benzo[d]imidazol-2-one | 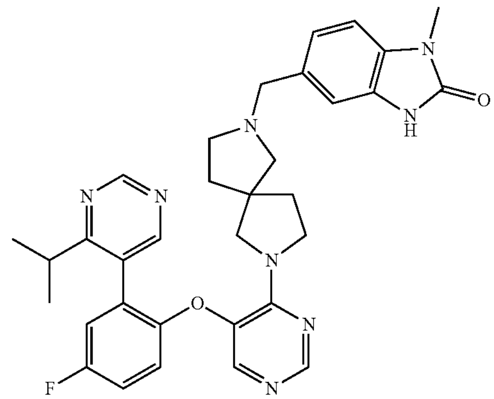 [SMILES: CC(C)c1ncncc1-c1cc(F)ccc1Oc1cncnc1N1CCC2(CCN(Cc3ccc4c(c3)[nH]c(=O)n4C)C2)C1] | Intermediate 26 was condensed with 1-methyl-2-oxo-2,3-dihydro-1H-benzo[d]imidazole-5-carbaldehyde, as described in step 4 of Example 41. |
| 151 | 2-cyclopropyl-5'-fluoro-2'-((4-(6-((4-hydroxycyclohexyl)methyl)-2,6-diazaspiro[3.3]heptan-2-yl)pyrimidin-5-yl)oxy)-[1,1'-biphenyl]-4-carbonitrile | 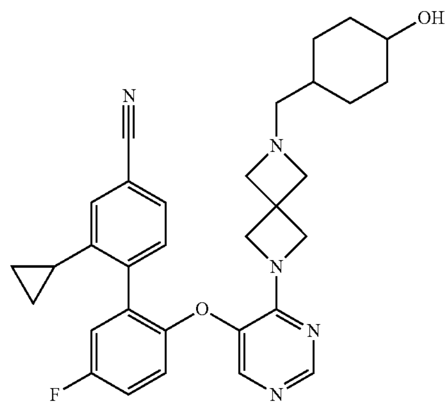 [SMILES: N#Cc1ccc(-c2cc(F)ccc2Oc2cncnc2N2CC3(CN(CC4CCC(O)CC4)C3)C2)c(C2CC2)c1] | Synthesized by a method similar to Example 65, starting with Intermediate 32. |
| 152 | 4-(((2-(5-(4-fluoro-2-(4-isopropylpyrimidin-5-yl)phenoxy)pyrimidin-4-yl)-2-azaspiro[3.3]heptan-6-yl)amino)methyl)benzonitrile | 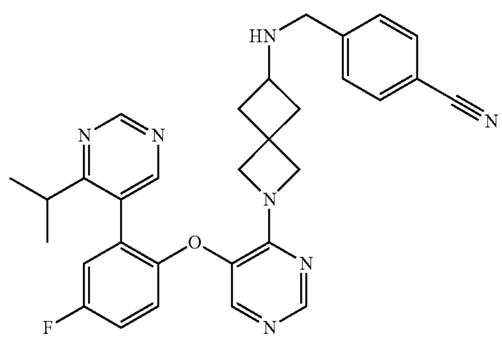 [SMILES: CC(C)c1ncncc1-c1cc(F)ccc1Oc1cncnc1N1CC2(CC(NCc3ccc(C#N)cc3)C2)C1] | Intermediate 29 was condensed with 4-cyanobenzaldehyde. |
| 153 | 5-((7-(5-(2-(2,5-dimethylpyrrolidine-1-carbonyl)-4-fluorophenoxy)pyrimidin-4-yl)-2,7-diazaspiro[4.4]nonan-2-yl)methyl)-1,3-dihydro-2H-benzo[d]imidazol-2-one | 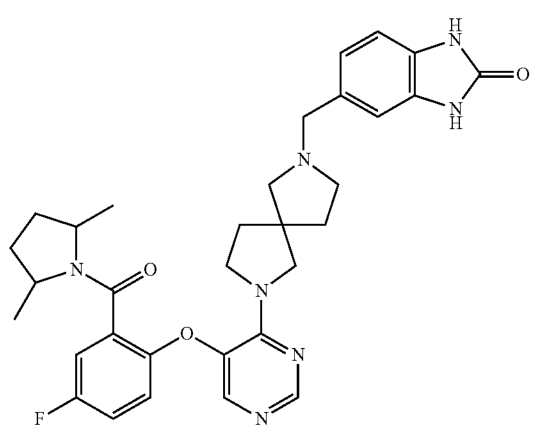 [SMILES: CC1CCC(C)N1C(=O)c1cc(F)ccc1Oc1cncnc1N1CCC2(CCN(Cc3ccc4[nH]c(=O)[nH]c4c3)C2)C1] | Synthesized by a method similar to Example 1. In step 4, 2,5-dimethypyrrolidine was utilized. |

TABLE 9-continued

Examples 79-240

| Example | Name | Structure | Procedure |
|---------|------|-----------|-----------|
| 154 | 5-((7-(5-(4-fluoro-2-(pyrrolidine-1-carbonyl)phenoxy)pyrimidin-4-yl)-2,7-diazaspiro[4.4]nonan-2-yl)methyl)-1,3-dihydro-2H-benzo[d]imidazol-2-one | 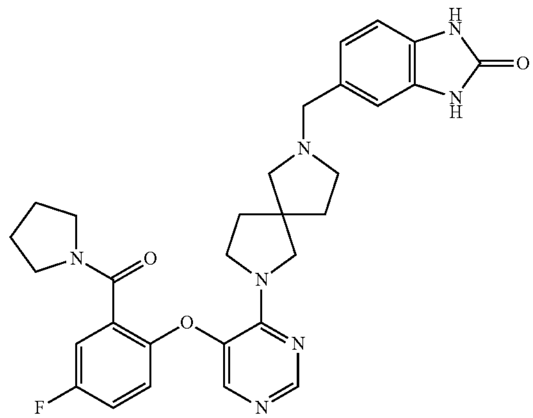 [SMILES: O=C(c1cc(F)ccc1Oc1cncnc1N1CCC2(CCN(Cc3ccc4[nH]c(=O)[nH]c4c3)C2)C1)N1CCCC1] | Synthesized by a method similar to Example 1. In step 4, pyrrolidine was utilized. |
| 155 | 5-((7-(5-(4-fluoro-2-(morpholine-4-carbonyl)phenoxy)pyrimidin-4-yl)-2,7-diazaspiro[4.4]nonan-2-yl)methyl)-1,3-dihydro-2H-benzo[d]imidazol-2-one | 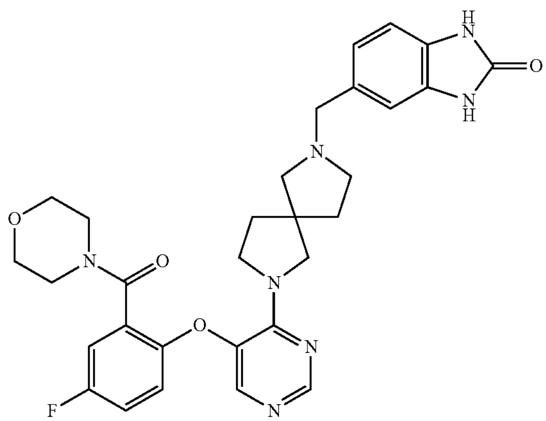 [SMILES: O=C(c1cc(F)ccc1Oc1cncnc1N1CCC2(CCN(Cc3ccc4[nH]c(=O)[nH]c4c3)C2)C1)N1CCOCC1] | Synthesized by a method similar to Example 1. In step 4, morpholine was utilized. |
| 156 | N-ethyl-N-(5-fluoro-2-((4-(6-((tetrahydro-2H-pyran-4-yl)methyl)-2,6-diazaspiro[3.4]octan-2-yl)pyrimidin-5-yl)oxy)phenyl)isobutyramide | 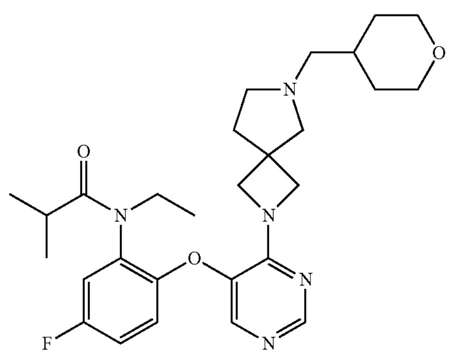 [SMILES: CCN(C(=O)C(C)C)c1cc(F)ccc1Oc1cncnc1N1CC2(CCN(CC3CCOCC3)C2)C1] | Synthesized by a method similar to Example 75, starting from Intermediate 24 |
| 157 | 7-(5-(4-fluoro-2-(4-isopropylpyrimidin-5-yl)phenoxy)pyrimidin-4-yl)-3-(6-fluoro-3,4-dihydroisoquinolin-2(1H)-yl)-1-oxa-7-azaspiro[4.4]nonane | 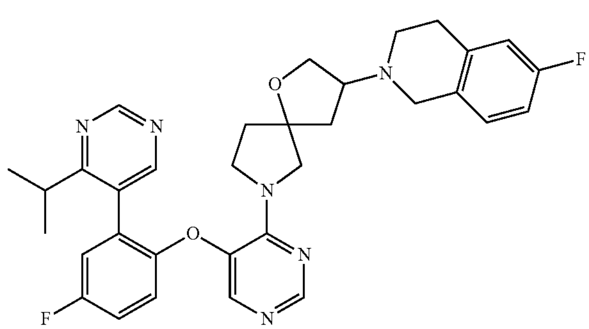 [SMILES: CC(C)c1ncncc1-c1cc(F)ccc1Oc1cncnc1N1CCC2(CC(N3CCc4cc(F)ccc4C3)CO2)C1] | Synthesized from 1-oxa-7-azaspiro[4.4]nonan-3-one, as described in synthesis of Example 18 |

TABLE 9-continued

Examples 79-240

| Example | Name | Structure | Procedure |
|---------|------|-----------|-----------|
| 158 | N-(2-((4-(6-(cyclohexylmethyl)-2,6-diazaspiro[3.4]octan-2-yl)pyrimidin-5-yl)oxy)-5-fluorophenyl)-N-ethylisobutyramide | 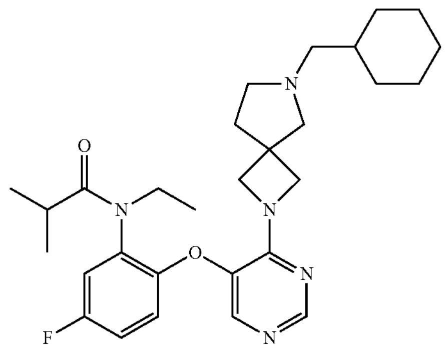 [SMILES: CCN(C(=O)C(C)C)c1cc(F)ccc1Oc1cncnc1N1CC2(CCN(CC3CCCCC3)C2)C1] | Starting from Intermediate 24 and synthesized by method similar to Example 75 |
| 159 | N-benzyl-2-(5-(4-fluoro-2-(4-isopropylpyrimidin-5-yl)phenoxy)pyrimidin-4-yl)-5-oxa-2-azaspiro[3.4]octan-7-amine | 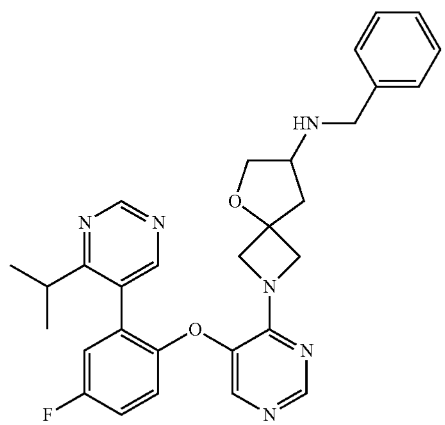 [SMILES: CC(C)c1ncncc1-c1cc(F)ccc1Oc1cncnc1N1CC2(CC(NCc3ccccc3)CO2)C1] | 2-(5-(4-fluoro-2-(4-isopropylpyrimidin-5-yl)phenoxy)pyrimidin-4-yl)-5-oxa-2-azaspiro[3.4]octan-7-one was condensed with benzaldehyde, as described in synthesis of Example 18 |
| 160 | 5-((7-(5-(4-fluoro-2-(4-isopropylpyrimidin-5-yl)phenoxy)pyrimidin-4-yl)-2,7-diazaspiro[4.4]nonan-2-yl)methyl)-1,3-dihydro-2H-benzo[d]imidazol-2-one | 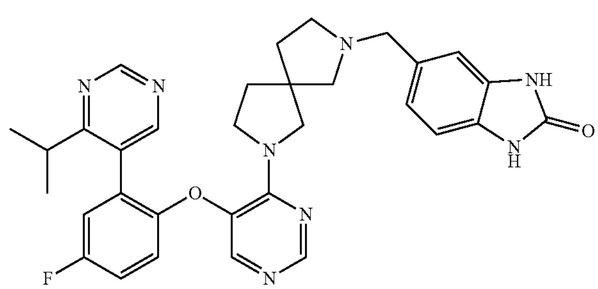 [SMILES: CC(C)c1ncncc1-c1cc(F)ccc1Oc1cncnc1N1CCC2(CCN(Cc3ccc4[nH]c(=O)[nH]c4c3)C2)C1] | Synthesized by a method similar to Example 41, starting from Intermediate 26. |
| 160A | Isomer 1: 5-((7-(5-(4-fluoro-2-(4-isopropylpyrimidin-5-yl)phenoxy)pyrimidin-4-yl)-2,7-diazaspiro[4.4]nonan-2-yl)methyl)-1,3-dihydro-2H-benzo[d]imidazol-2-one | 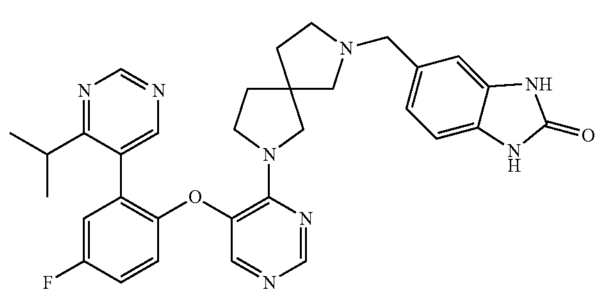 [SMILES: CC(C)c1ncncc1-c1cc(F)ccc1Oc1cncnc1N1CCC2(CCN(Cc3ccc4[nH]c(=O)[nH]c4c3)C2)C1] | Single isomer of Example 160, separated by SFC method A |

TABLE 9-continued

Examples 79-240

| Example | Name | Structure | Procedure |
|---|---|---|---|
| 160B | Isomer 2: 5-((7-(5-(4-fluoro-2-(4-isopropylpyrimidin-5-yl)phenoxy)pyrimidin-4-yl)-2,7-diazaspiro[4.4]nonan-2-yl)methyl)-1,3-dihydro-2H-benzo[d]imidazol-2-one | 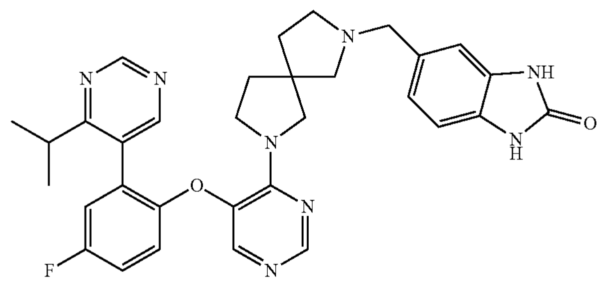 [SMILES: CC(C)c1ncncc1-c1cc(F)ccc1Oc1cncnc1N1CCC2(CCN(Cc3ccc4[nH]c(=O)[nH]c4c3)C2)C1] | Single isomer of Example 160, separated by SFC method A |
| 161 | 5-((7-(5-((5-fluoro-2'-(prop-1-en-2-yl)-[1,1'-biphenyl]-2-yl)oxy)pyrimidin-4-yl)-2,7-diazaspiro[4.4]nonan-2-yl)methyl)-1,3-dihydro-2H-benzo[d]imidazol-2-one | 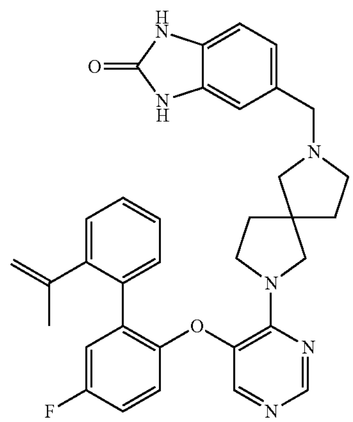 [SMILES: C=C(C)c1ccccc1-c1cc(F)ccc1Oc1cncnc1N1CCC2(CCN(Cc3ccc4[nH]c(=O)[nH]c4c3)C2)C1] | Synthesized by treating Example 63 with TFA |
| 162 | 2-(5-(4-fluoro-2-(2-isopropoxypyridin-3-yl)phenoxy)pyrimidin-4-yl)-6-((tetrahydro-2H-pyran-4-yl)methyl)-2,6-diazaspiro[3.3]heptane | 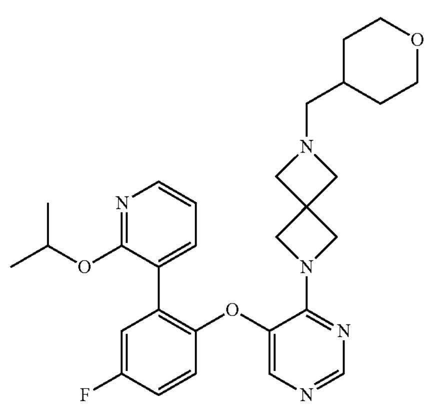 [SMILES: CC(C)Oc1ncccc1-c1cc(F)ccc1Oc1cncnc1N1CC2(CN(CC3CCOCC3)C2)C1] | Intermediate 20, was coupled with 2-isoprpoxy-3-pyridyl boronic acid. In step 4 of Example 41, tetrahydro-2H-pyran-4-carbaldehyde was utilized. |
| 163 | 5-fluoro-N-isopropyl-N-methyl-2-((4-(7-((1-methyl-2-oxo-2,3-dihydro-1H-benzo[d]imidazol-5-yl)methyl)-2,7-diazaspiro[4.4]nonan-2-yl)pyrimidin-5-yl)oxy)benzamide | 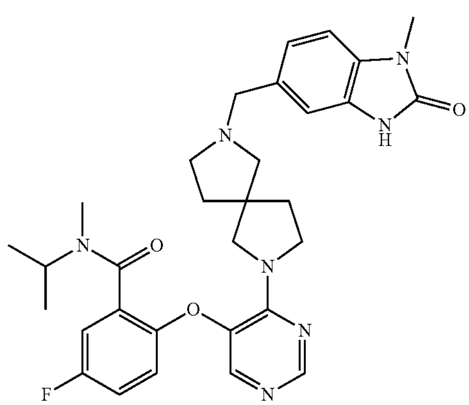 [SMILES: CC(C)N(C)C(=O)c1cc(F)ccc1Oc1cncnc1N1CCC2(CCN(Cc3ccc4c(c3)[nH]c(=O)n4C)C2)C1] | Synthesized by method similar to Example 1. In the last step, 1-methyl-2-oxo-2,3-dihydro-1H-benzo[d]imidazole-5-carbaldehyde was utilized. |

TABLE 9-continued

Examples 79-240

| Example | Name | Structure | Procedure |
|---|---|---|---|
| 164 | ethyl (5-fluoro-2-((4-(7-((2-oxo-2,3-dihydro-1H-benzo[d]imidazol-5-yl)methyl)-2,7-diazaspiro[4.4]nonan-2-yl)pyrimidin-5-yl)oxy)phenyl)(methyl)carbamate | 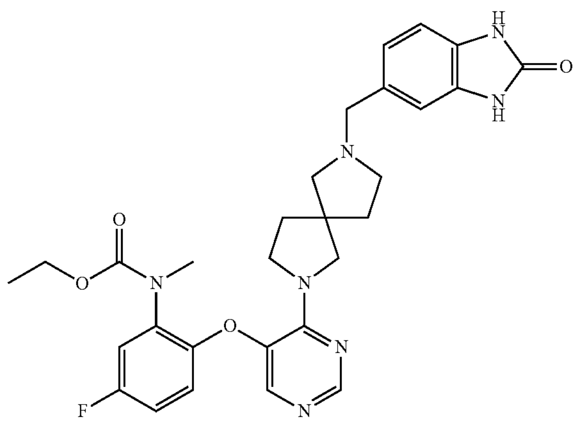 [SMILES: CCOC(=O)N(C)c1cc(F)ccc1Oc1cncnc1N1CCC2(CCN(Cc3ccc4[nH]c(=O)[nH]c4c3)C2)C1] | Starting from Intermediate 102, this compound was synthesized by a method similar to Example 75 |
| 165 | N-cyclopropyl-5-fluoro-N-methyl-2-((4-(7-((2-oxo-2,3-dihydro-1H-benzo[d]imidazol-5-yl)methyl)-2,7-diazaspiro[4.4]nonan-2-yl)pyrimidin-5-yl)oxy)benzamide | 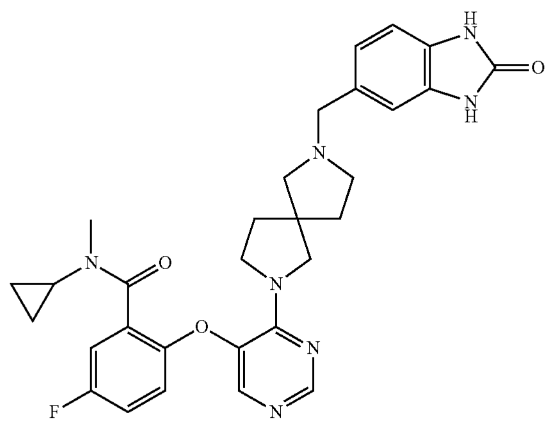 [SMILES: CN(C(=O)c1cc(F)ccc1Oc1cncnc1N1CCC2(CCN(Cc3ccc4[nH]c(=O)[nH]c4c3)C2)C1)C1CC1] | Synthesized by a method similar to Example 1. In step 4, N-methyl-cyclopropyl amine was utilized. |
| 166 | 5-fluoro-N-methyl-2-((4-(7-((2-oxo-2,3-dihydro-1H-benzo[d]imidazol-5-yl)methyl)-2,7-diazaspiro[4.4]nonan-2-yl)pyrimidin-5-yl)oxy)-N-phenylbenzamide | 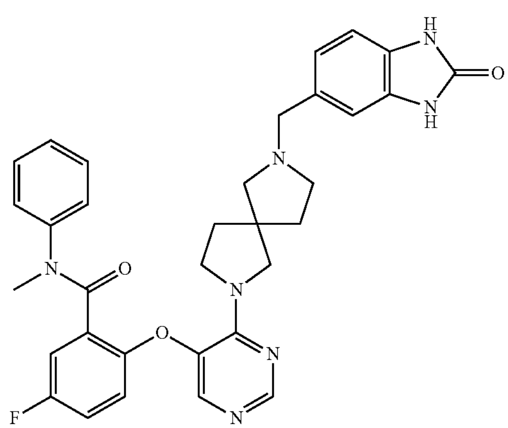 [SMILES: CN(C(=O)c1cc(F)ccc1Oc1cncnc1N1CCC2(CCN(Cc3ccc4[nH]c(=O)[nH]c4c3)C2)C1)c1ccccc1] | Synthesized by a method similar to Example 1. In step 4, N-methyl-aniline was utilized. |

TABLE 9-continued

Examples 79-240

| Example | Name | Structure | Procedure |
|---|---|---|---|
| 167 | 2-((4-(6-(cyclohexylmethyl)-2,6-diazaspiro[3.3]heptan-2-yl)pyrimidin-5-yl)oxy)-5-fluoro-N-isopropyl-N-methylbenzamide | 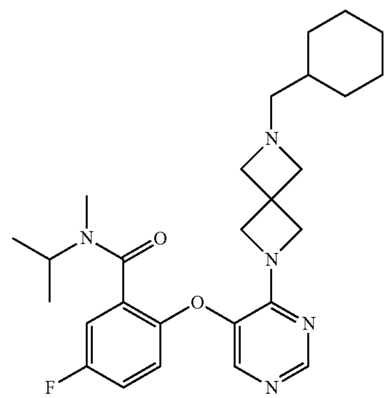 [SMILES: CC(C)N(C)C(=O)c1cc(F)ccc1Oc1cncnc1N1CC2(CN(CC3CCCCC3)C2)C1] | Synthesized from Intermediate 39 and cyclohexane carbaldehyde by reductive amination, as described in final step of Example 1 |
| 168 | 2-(5-(2-(cyclopentyloxy)-4-fluorophenoxy)pyrimidin-4-yl)-6-((tetrahydro-2H-pyran-4-yl)methyl)-2,6-diazaspiro[3.3]heptane | 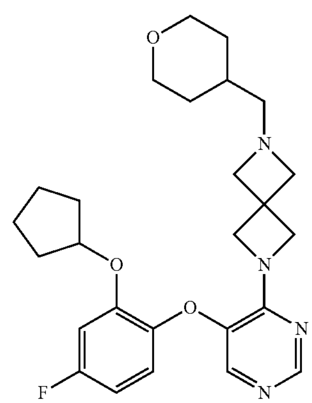 [SMILES: Fc1ccc(Oc2cncnc2N2CC3(CN(CC4CCOCC4)C3)C2)c(OC2CCCC2)c1] | Synthesized by method described in Example 54 from Intermediate 43a |
| 169 | 2-cyclopropyl-5'-fluoro-2'-((4-(7-((2-oxo-2,3-dihydrobenzo[d]oxazol-5-yl)methyl)-2,7-diazaspiro[4.4]nonan-2-yl)pyrimidin-5-yl)oxy)-[1,1'-biphenyl]-4-carbonitrile | 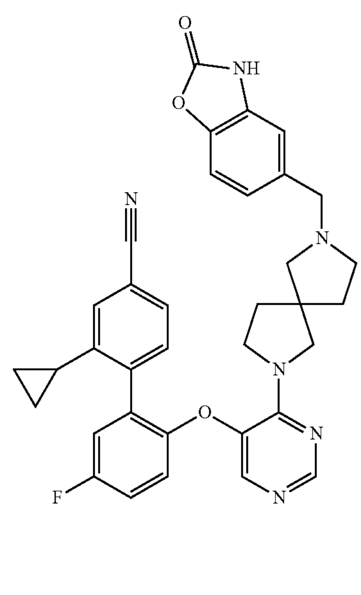 [SMILES: N#Cc1ccc(-c2cc(F)ccc2Oc2cncnc2N2CCC3(CCN(Cc4ccc5oc(=O)[nH]c5c4)C3)C2)c(C2CC2)c1] | Synthesized from Intermediate 31 by condenstation with 2-oxo-2,3-dihydrobenzo[d]oxazole-5-carbaldehyde, as described in step 4 of Example 41 |

TABLE 9-continued

Examples 79-240

| Example | Name | Structure | Procedure |
|---|---|---|---|
| 170 | methyl (3-((7-(5-((4'-cyano-2'-cyclopropyl-5-fluoro-[1,1'-biphenyl]-2-yl)oxy)pyrimidin-4-yl)-2,7-diazaspiro[4.4]nonan-2-yl)methyl)phenyl)carbamate | 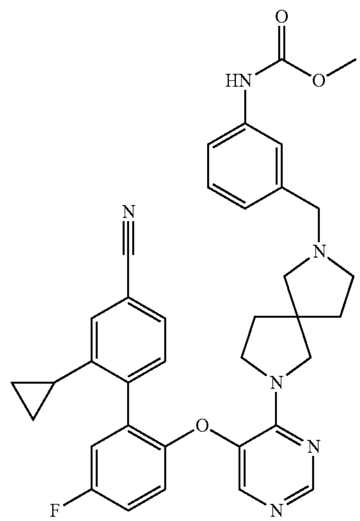 [SMILES: COC(=O)Nc1cccc(CN2CCC3(CCN(c4ncncc4Oc4ccc(F)cc4-c4ccc(C#N)cc4C4CC4)C3)C2)c1] | Synthesized from Intermediate 31 by condenstation with methyl (3-formylphenyl)carbamate, as described in step 4 of Example 41 |
| 171 | 2'-((4-(7-((1H-benzo[d][1,2,3]triazol-6-yl)methyl)-2,7-diazaspiro[4.4]nonan-2-yl)pyrimidin-5-yl)oxy)-2-cyclopropyl-5'-fluoro-[1,1'-biphenyl]-4-carbonitrile | 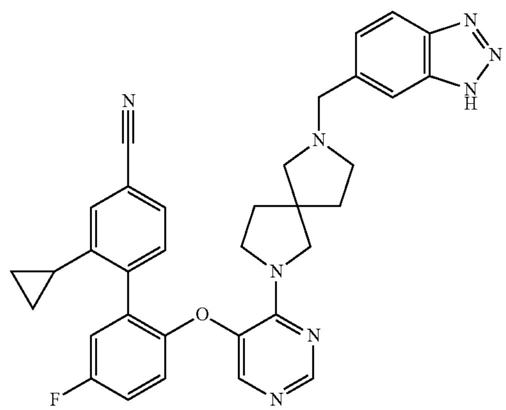 [SMILES: N#Cc1ccc(-c2cc(F)ccc2Oc2cncnc2N2CCC3(CCN(Cc4ccc5nn[nH]c5c4)C3)C2)c(C2CC2)c1] | Synthesized from Intermediate 31 by condenstation with 1H-benzo[d][1,2,3]triazole-6-carbaldehyde, as described in step 4 of Example 41 |
| 172 | N-(2-chloro-4-((7-(5-((4'-cyano-2'-cyclopropyl-5-fluoro-[1,1'-biphenyl]-2-yl)oxy)pyrimidin-4-yl)-2,7-diazaspiro[4.4]nonan-2-yl)methyl)phenyl)acetamide | 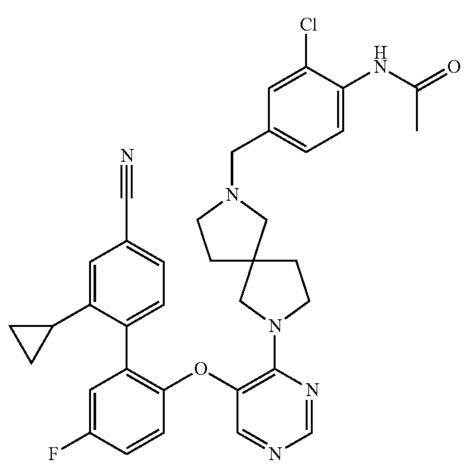 [SMILES: CC(=O)Nc1ccc(CN2CCC3(CCN(c4ncncc4Oc4ccc(F)cc4-c4ccc(C#N)cc4C4CC4)C3)C2)cc1Cl] | Synthesized from Intermediate 31 by condenstation with N-(2-chloro-4-formylphenyl)acetamide, as described in step 4 of Example 41 |

TABLE 9-continued

Examples 79-240

| Example | Name | Structure | Procedure |
|---|---|---|---|
| 173 | N,N-diethyl-5-fluoro-2-((4-(7-((2-oxo-2,3-dihydro-1H-benzo[d]imidazol-5-yl)methyl)-2,7-diazaspiro[4.4]nonan-2-yl)pyrimidin-yl)oxy)benzamide | 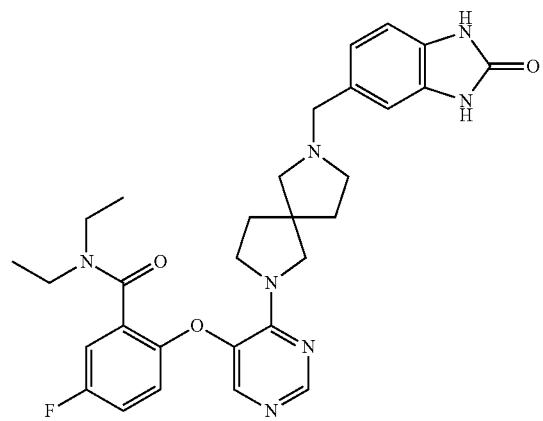 [SMILES: CCN(CC)C(=O)c1cc(F)ccc1Oc1cncnc1N1CCC2(CCN(Cc3ccc4[nH]c(=O)[nH]c4c3)C2)C1] | Synthesized by a method similar to Example 1. In step 4, N-N-diethylamine was utilized. |
| 174 | 5-fluoro-N-isopropyl-N-methyl-2-((4-(7-((2-oxo-2,3-dihydrobenzo[d]oxazol-5-yl)methyl)-2,7-diazaspiro[4.4]nonan-2-yl)pyrimidin-5-yl)oxy)benzamide | 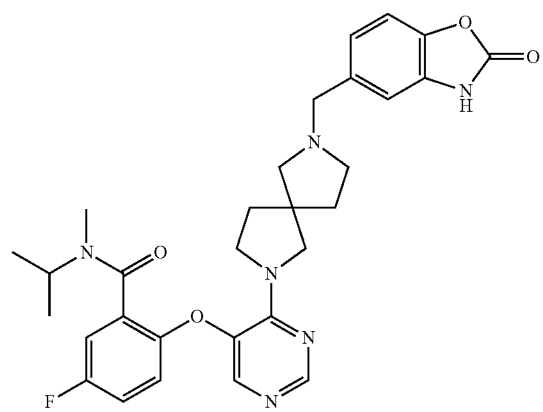 [SMILES: CC(C)N(C)C(=O)c1cc(F)ccc1Oc1cncnc1N1CCC2(CCN(Cc3ccc4oc(=O)[nH]c4c3)C2)C1] | Synthesized from intermediate 33 and 2-oxo-2,3-dihydrobenzo[d]oxazole-5-carbaldehyde by reductive amnination, as described in final step of Example 1 |
| 175 | N-(tert-butyl)-5-fluoro-N-methyl-2-((4-(7-((2-oxo-2,3-dihdyro-1H-benzo[d]imidazol-5-yl)methyl)-2,7-diazaspiro[4.4]nonan-2-yl)pyrimidin-5-yl)oxy)benzamide | 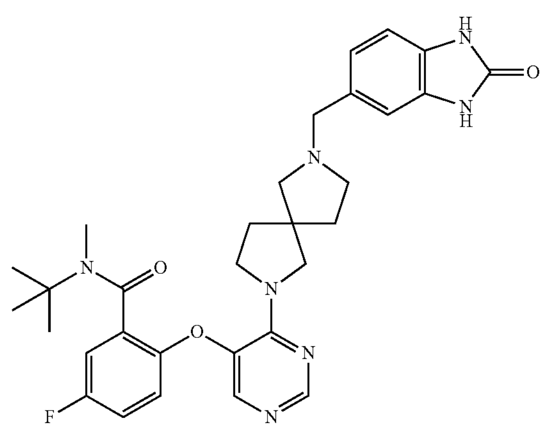 [SMILES: CN(C(=O)c1cc(F)ccc1Oc1cncnc1N1CCC2(CCN(Cc3ccc4[nH]c(=O)[nH]c4c3)C2)C1)C(C)(C)C] | Synthesized by a method similar to Example 1. In step 4, tert-butyl methyl amine was utilized. |

TABLE 9-continued

Examples 79-240

| Example | Name | Structure | Procedure |
|---|---|---|---|
| 176 | 1-(7-(5-(4-fluoro-2-(4-isopropylpyrimidin-5-yl)phenoxy)pyrimidin-4-yl)-2,7-diazaspiro[4.4]nonan-2-yl)-2-methylpropan-2-ol | 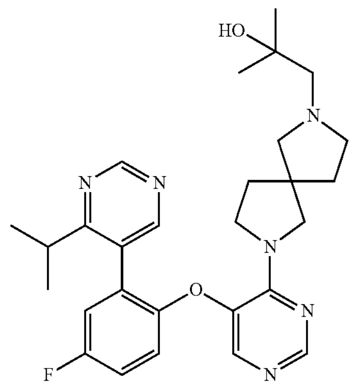 [SMILES: CC(C)c1ncncc1-c1cc(F)ccc1Oc1cncnc1N1CCC2(CCN(CC(C)(C)O)C2)C1] | Synthesized from Intermediate 26 and 2,2-dimethyloxirane, by method described in Example 72 |
| 177 | 2-(5-(2-(2-cyclopropylpyridin-3-yl)-4-fluorophenoxy)pyrimidin-4-yl)-6-((tetrahydro-2H-pyran-4-yl)methyl)-2,6-diazaspiro[3.3]heptane | 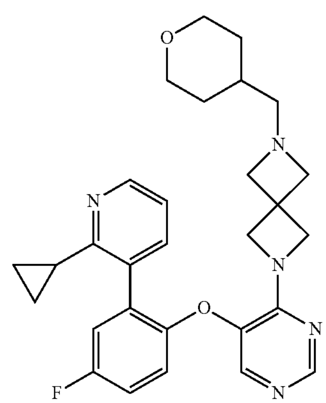 [SMILES: Fc1ccc(Oc2cncnc2N2CC3(CN(CC4CCOCC4)C3)C2)c(-c2cccnc2C2CC2)c1] | Synthesized from Intermediate 31c and tetrahydro-2H-pyran-4-carbaldehyde, by method described in step 4 of Example 41 |
| 178 | 6-((7-(5-(4-fluoro-2-(4-isopropylpyrimidin-5-yl)phenoxy)pyrimidin-4-yl)-2,7-diazaspiro[4.4]nonan-2-yl)methyl)-3,3-dimethylindolin-2-one | 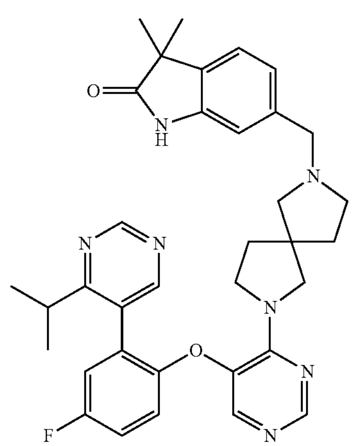 [SMILES: CC(C)c1ncncc1-c1cc(F)ccc1Oc1cncnc1N1CCC2(CCN(Cc3ccc4c(c3)NC(=O)C4(C)C)C2)C1] | Synthesized from Intermediate 26 by condenstation with Intermediate 45, as described in step 4 of Example 41 |

TABLE 9-continued

Examples 79-240

| Example | Name | Structure | Procedure |
|---|---|---|---|
| 179 | 6-((7-(5-(2-(2-cyclopropylpyridin-3-yl)-4-fluorophenoxy)pyrimidin-4-yl)-2,7-diazaspiro[4.4]nonan-2-yl)methyl)-3,3-dimethylindolin-2-one | 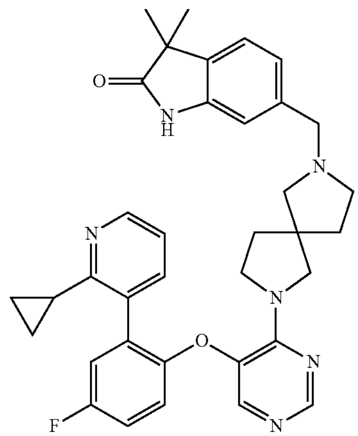 [SMILES: CC1(C)C(=O)Nc2cc(CN3CCC4(CCN(c5ncncc5Oc5ccc(F)cc5-c5cccnc5C5CC5)C4)C3)ccc21] | Synthesized from Intermediate 31b by condenstation with Intermediate 45, as described in step 4 of Example 41 |
| 180 | 5-((7-(5-(2-(2-cyclopropylpyridin-3-yl)-4-fluorophenoxy)pyrimidin-4-yl)-2,7-diazaspiro[4.4]nonan-2-yl)methyl)-1,3-dihydro-2H-benzo[d]imidazol-2-one | 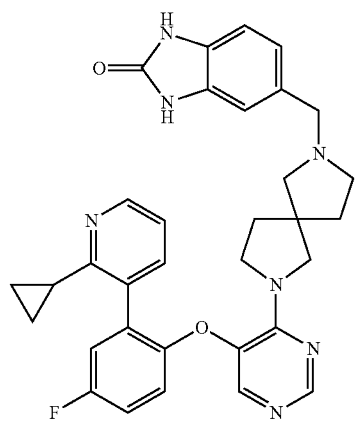 [SMILES: O=c1[nH]c2ccc(CN3CCC4(CCN(c5ncncc5Oc5ccc(F)cc5-c5cccnc5C5CC5)C4)C3)cc2[nH]1] | Synthesized by method similar to Example 41, starting from Intermediate 31b |
| 181 | 4-(((2-(5-(4-fluoro-2-(4-isopropylpyrimidin-5-yl)phenoxy)pyrimidin-4-yl)-5-oxa-2-azaspiro[3.4]octan-7-yl)(methyl)amino)methyl)benzonitrile | 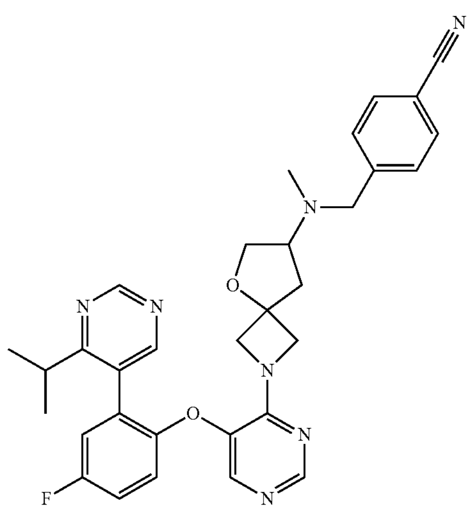 [SMILES: CC(C)c1ncncc1-c1cc(F)ccc1Oc1cncnc1N1CC2(CC(N(C)Cc3ccc(C#N)cc3)CO2)C1] | Synthesized by the method described for Example 157, starting from 5-oxa-2-azaspiro[3.4]octan-7-one |

TABLE 9-continued

Examples 79-240

| Example | Name | Structure | Procedure |
|---|---|---|---|
| 182 | 6-((7-(5-(4-fluoro-2-(2,2,2-trifluoroethoxy)phenoxy)pyrimidin-4-yl)-2,7-diazaspiro[4.4]nonan-2-yl)methyl)-3,3-dimethylindolin-2-one | 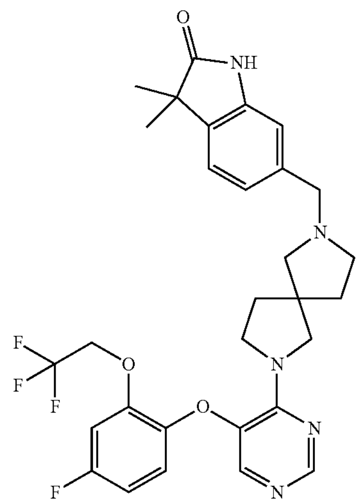 [SMILES: CC1(C)C(=O)Nc2cc(CN3CCC4(CCN(c5ncncc5Oc5ccc(F)cc5OCC(F)(F)F)C4)C3)ccc21] | Synthesized by the method described in Example 54 from Intermediate 43a |
| 183 | 5-fluoro-N-isopropyl-N-methyl-2-((4-(7-((2-oxo-2,3-dihydro-1H-benzo[d]imidazol-5-yl)methyl)-2,7-diazaspiro[4.4]nonan-2-yl)pyrimidin-5-yl)oxy)benzamide (mixture) | 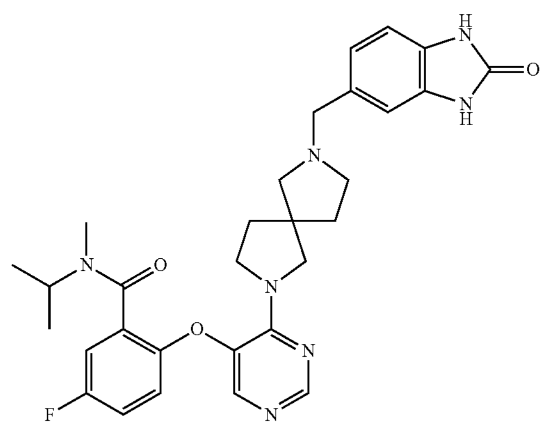 [SMILES: CC(C)N(C)C(=O)c1cc(F)ccc1Oc1cncnc1N1CCC2(CCN(Cc3ccc4[nH]c(=O)[nH]c4c3)C2)C1] | Synthesized from Intermediate 33 and 2-oxo-2,3-dihydro-1H-benzo[d]imidazole-5-carbaldehyde, as described in Example 1 |
| 183A | Isomer 1: 5-fluoro-N-isopropyl-N-methyl-2-((4-(7-((2-oxo-2,3-dihydro-1H-benzo[d]imidazol-5-yl)methyl)-2,7-diazaspiro[4.4]nonan-2-yl)pyrimidin-5-yl)oxy)benzamide | 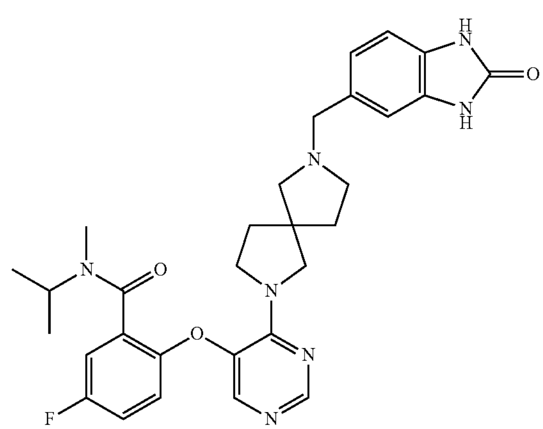 | Single enantiomer of Example 183 separrated by SFC method A |

TABLE 9-continued

Examples 79-240

| Example | Name | Structure | Procedure |
|---|---|---|---|
| 183B | Isomer 2: 5-fluoro-N-isopropyl-N-methyl-2-((4-(7-((2-oxo-2,3-dihydro-1H-benzo[d]imidazol-5-yl)methyl)-2,7-diazaspiro[4.4]nonan-2-yl)pyrimidin-5-yl)oxy)benzamide | 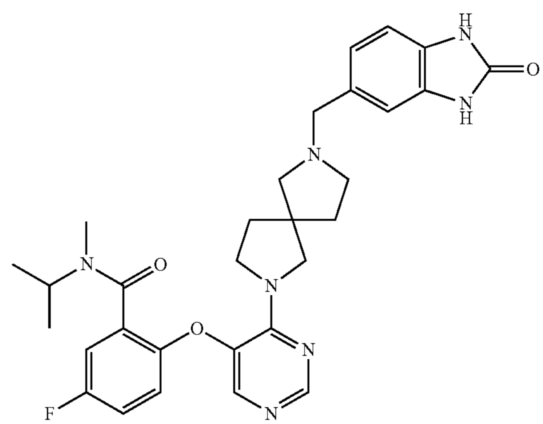 [SMILES: CC(C)N(C)C(=O)c1cc(F)ccc1Oc1cncnc1N1CCC2(CCN(Cc3ccc4[nH]c(=O)[nH]c4c3)C2)C1] | Single enantiomer of Example 183 separated by SFC method A |
| 184 | N-(cyclohexylmethyl)-2-(5-(4-fluoro-2-(4-isopropylpyrimidin-5-yl)phenoxy)pyrimidin-4-yl)-5-oxa-2-azaspiro[3.4]octan-7-amine | 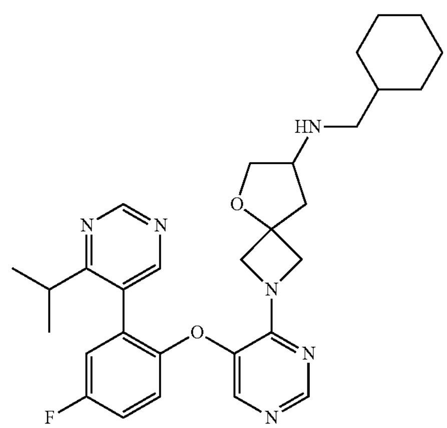 [SMILES: CC(C)c1ncncc1-c1cc(F)ccc1Oc1cncnc1N1CC2(CC(NCC3CCCCC3)CO2)C1] | Synthesized by a method similar to Example 19. In step 3,4-isoprpyl-5-pyrmidine boronic acid was used. In step 4, cyclohexylemthyl amine was utilized. |
| 185 | N-(5-fluoro-2-((4-(7-((2-oxo-2,3-dihydro-1H-benzo[d]imidazol-5-yl)methyl)-2,7-diazaspiro[4.4]nonan-2-yl)pyrimidin-5-yl)oxy)phenyl)-N-(2-hydroxyethyl)isobutyramide | 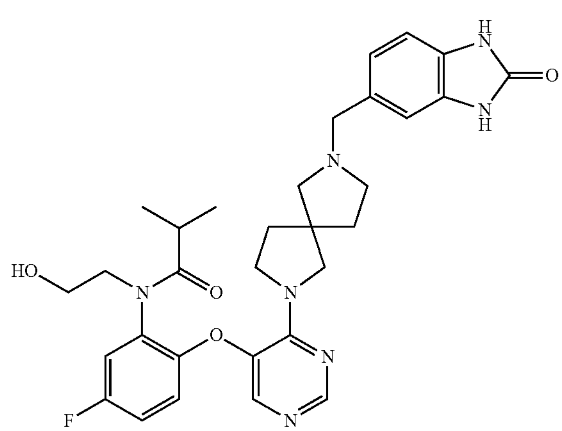 [SMILES: CC(C)C(=O)N(CCO)c1cc(F)ccc1Oc1cncnc1N1CCC2(CCN(Cc3ccc4[nH]c(=O)[nH]c4c3)C2)C1] | Synthesized by a method similar to Example 75, starting from Intermediate 103, and alkylated with (2-bromoethoxy)trimethylsilane |

TABLE 9-continued

Examples 79-240

| Example | Name | Structure | Procedure |
|---|---|---|---|
| 186 | N-ethyl-N-(5-fluoro-2-((4-(7-((2-oxo-2,3-dihydro-1H-benzo[d]imidazol-5-yl)methyl)-2,7-diazaspiro[4.4]nonan-2-yl)pyrimidin-5-yl)oxy)phenyl)isobutyramide | 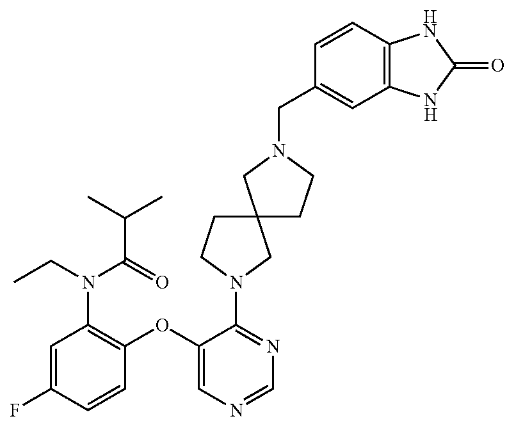 [SMILES: CCN(C(=O)C(C)C)c1cc(F)ccc1Oc1cncnc1N1CCC2(CCN(Cc3ccc4[nH]c(=O)[nH]c4c3)C2)C1] | Synthesized by a method similar to Example 75 |
| 187 | N-(5-fluoro-2-((4-(7-((2-oxo-2,3-dihydro-1H-benzo[d]imidazol-5-yl)methyl)-2,7-diazaspiro[4.4]nonan-2-yl)pyrimidin-5-yl)oxy)phenyl)-N-(2,2,2-trifluoroethyl)isobutyramide | 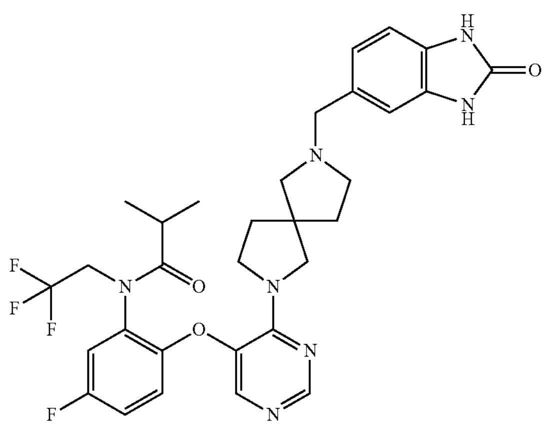 [SMILES: CC(C)C(=O)N(CC(F)(F)F)c1cc(F)ccc1Oc1cncnc1N1CCC2(CCN(Cc3ccc4[nH]c(=O)[nH]c4c3)C2)C1] | Synthesized by a method similar to Example 75, starting from Intermediate 103, and alkylated with 2,2,2-trifluoroethyl 4-methylbenzene-sulfonate |
| 188 | N-((1r,4r)-4-((7-(5-((4'-cyano-2'-cyclopropyl-5-fluoro-[1,1'-biphenyl]-2-yl)oxy)pyrimidin-4-yl)-2,7-diazaspiro[4.4]nonan-2-yl)methyl)cyclohexyl)acetamide | 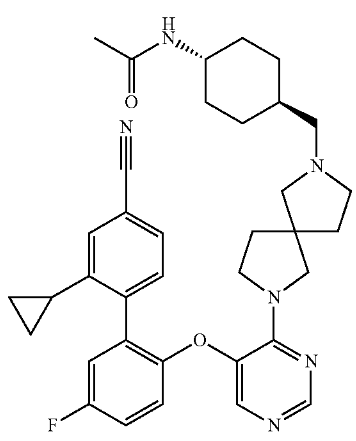 [SMILES: CC(=O)N[C@H]1CC[C@H](CN2CCC3(CCN(c4ncncc4Oc4ccc(F)cc4-c4ccc(C#N)cc4C4CC4)C3)C2)CC1] | Synthesized from Intermediate 31 and N-((1r,4r)-4-formylcyclohexyl)acetamide, as described in step 4 of Example 41 |

TABLE 9-continued

Examples 79-240

| Example | Name | Structure | Procedure |
|---|---|---|---|
| 189 | tert-butyl ((1r,4r)-4-(2-(6-(5-((4'-cyano-2'-cyclopropyl-5-fluoro-[1,1'-biphenyl]-2-yl)oxy)pyrimidin-4-yl)-2,6-diazaspiro[3.3]heptan-2-yl)ethyl)cyclohexyl)carbamate | 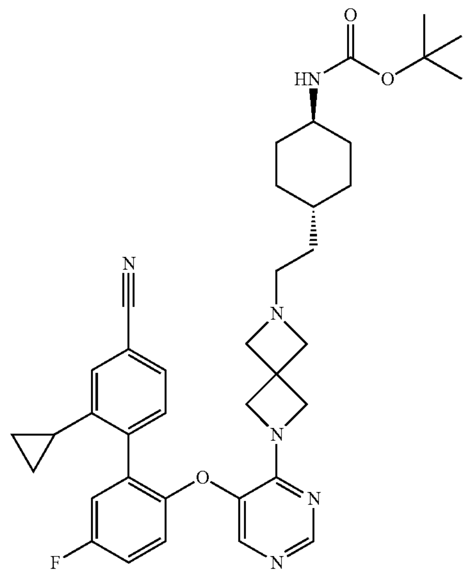 [SMILES: CC(C)(C)OC(=O)N[C@H]1CC[C@H](CCN2CC3(C2)CN(c2ncncc2Oc2ccc(F)cc2-c2ccc(C#N)cc2C2CC2)C3)CC1] | Synthesized from Intermediate 32 and tert-butyl ((1r,4r)-4-(2-oxoethyl)cyclohexyl)carbamate, by method described in step 4 of Example 41 |
| 190 | 5-((7-(5-(4-fluoro-2-(5-isopropylthiazol-4-yl)phenoxy)pyrimidin-4-yl)-2,7-diazaspiro[4.4]nonan-2-yl)methyl)-1,3-dihydro-2H-benzo[d]imidazol-2-one | 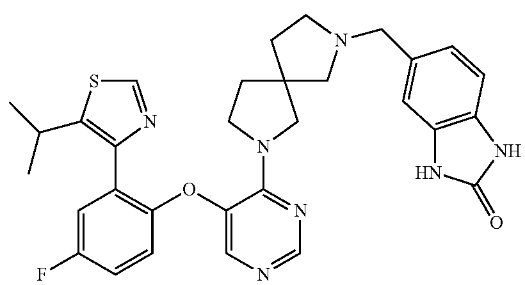 [SMILES: CC(C)c1scnc1-c1cc(F)ccc1Oc1cncnc1N1CCC2(CCN(Cc3ccc4[nH]c(=O)[nH]c4c3)C2)C1] | Synthesized by a method similar to Example 41. In step 1, 5-isopropyl-4-thiazole boronic acid was utilized. |
| 190A | N-((1s,4s)-4-((7-(5-((4'-cyano-2'-cyclopropyl-5-fluoro-[1,1'-biphenyl]-2-yl)oxy)pyrimidin-4-yl)-2,7-diazaspiro[4.4]nonan-2-yl)methyl)cyclohexyl)acetamide | 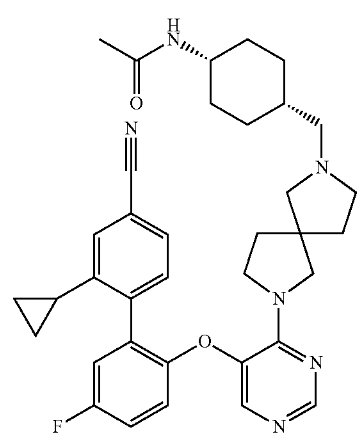 [SMILES: CC(=O)N[C@H]1CC[C@@H](CN2CCC3(CCN(c4ncncc4Oc4ccc(F)cc4-c4ccc(C#N)cc4C4CC4)C3)C2)CC1] | Minor isomer isolated from the synthesis of Example 188 using SFC method A |

TABLE 9-continued

Examples 79-240

| Example | Name | Structure | Procedure |
|---------|------|-----------|-----------|
| 191 | 2-cyclopropyl-2'-((4-(7-((1-ethyl-2-oxo-2,3-dihydro-1H-benzo[d]imidazol-5-yl)methyl)-2,7-diazaspiro[4.4]nonan-2-yl)pyrimidin-5-yl)oxy)-5'-fluoro-[1,1'-biphenyl]-4-carbonitrile | 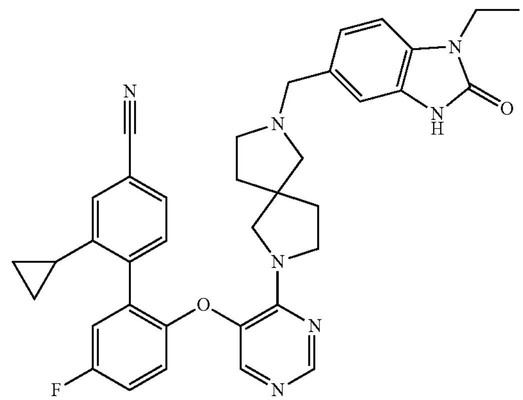 [SMILES: CCn1c(=O)[nH]c2cc(CN3CCC4(CCN(c5ncncc5Oc5ccc(F)cc5-c5ccc(C#N)cc5C5CC5)C4)C3)ccc21] | Synthesized from Intermediate 31 and Intermediate 42b, as described in step 4 of Example 41 |
| 192 | 3-((7-(5-(2-(cyclopentyloxy)-4-fluorophenoxy)pyrimidin-4-yl)-2,7-diazaspiro[4.4]nonan-2-yl)methyl)-1H-indole-6-carbonitrile | 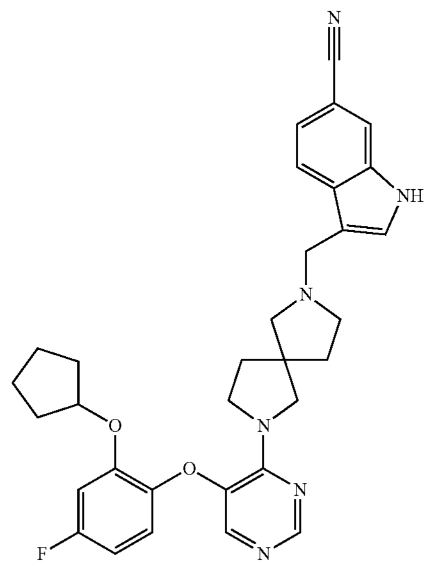 [SMILES: N#Cc1ccc2c(CN3CCC4(CCN(c5ncncc5Oc5ccc(F)cc5OC5CCCC5)C4)C3)c[nH]c2c1] | Synthesized by the method described in Example 54 from Intermediate 43a |
| 193 | 6-((7-(5-(2-(cyclopentyloxy)-4-fluorophenoxy)pyrimidin-4-yl)-2,7-diazaspiro[4.4]nonan-2-yl)methyl)-3,3-dimethylindolin-2-one | 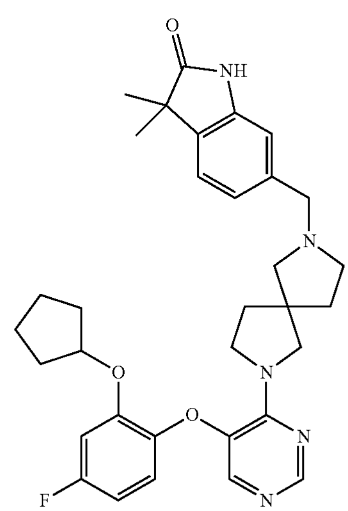 [SMILES: CC1(C)C(=O)Nc2cc(CN3CCC4(CCN(c5ncncc5Oc5ccc(F)cc5OC5CCCC5)C4)C3)ccc21] | Synthesized by the method described in Example 54 from Intermediate 43a |

TABLE 9-continued

Examples 79-240

| Example | Name | Structure | Procedure |
|---|---|---|---|
| 194 | 2-((4-(7-((6-cyano-1H-indol-3-yl)methyl)-2,7-diazaspiro[4.4]nonan-2-yl)pyrimidin-5-yl)oxy)-5-fluoro-N-isopropyl-N-methylbenzamide | 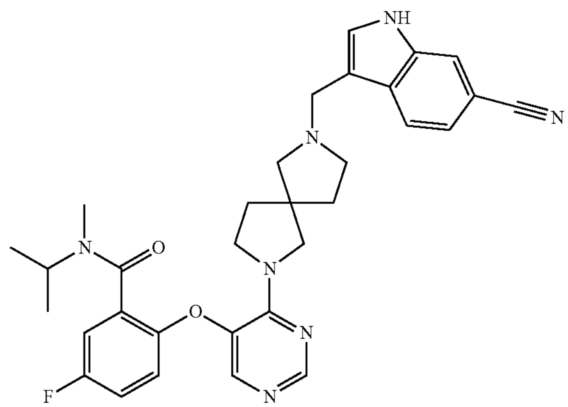 [SMILES: CC(C)N(C)C(=O)c1cc(F)ccc1Oc1cncnc1N1CCC2(CCN(Cc3c[nH]c4cc(C#N)ccc34)C2)C1] | Synthesized from Intermediate 33 and 3-formyl-1H-indole-6-carbonitrile, as described in last step of Example 1 |
| 195 | 2-cyclopropyl-5'-fluoro-2'-((4-(7-(4-(2-oxopyrrolidin-1-yl)benzyl)-2,7-diazaspiro[4.4]nonan-2-yl)pyrimidin-5-yl)oxy)-[1,1'-biphenyl]-4-carbonitrile | 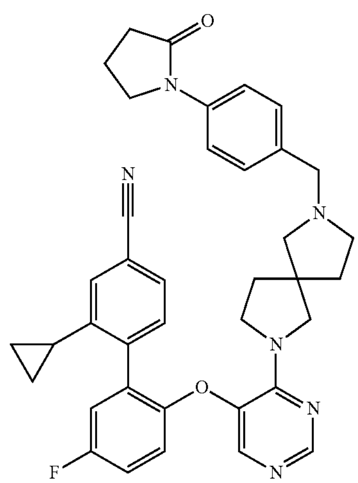 [SMILES: N#Cc1ccc(-c2cc(F)ccc2Oc2cncnc2N2CCC3(CCN(Cc4ccc(N5CCCC5=O)cc4)C3)C2)c(C2CC2)c1] | Synthesized from Intermediate 31 and 4-(2-oxopyrrolidin-1-yl)benzaldehyde, as described in step 4 of Example 41 |
| 196 | 2-cyclopropyl-5'-fluoro-2'-((4-(7-((2-oxoindolin-6-yl)methyl)-2,7-diazaspiro[4.4]nonan-2-yl)pyrimidin-5-yl)oxy)-[1,1'-biphenyl]-4-carbonitrile | 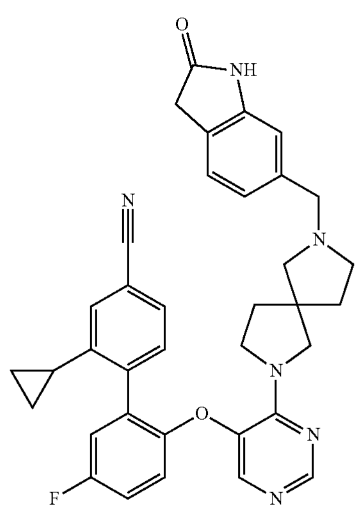 [SMILES: N#Cc1ccc(-c2cc(F)ccc2Oc2cncnc2N2CCC3(CCN(Cc4ccc5c(c4)NC(=O)C5)C3)C2)c(C2CC2)c1] | Synthesized from Intermediate 31 and 2-oxoindoline-6-carbaldehyde, as described in step 4 of Example 41 |

TABLE 9-continued

Examples 79-240

| Example | Name | Structure | Procedure |
|---|---|---|---|
| 197A | Isomer 1: 5-((7-(5-(4-fluoro-2-(1-isopropyl-1H-pyrazol-5-yl)phenoxy)pyrimidin-4-yl)-2,7-diazaspiro[4.4]nonan-2-yl)methyl)-1,3-dihydro-2H-benzo[d]imidazol-2-one | 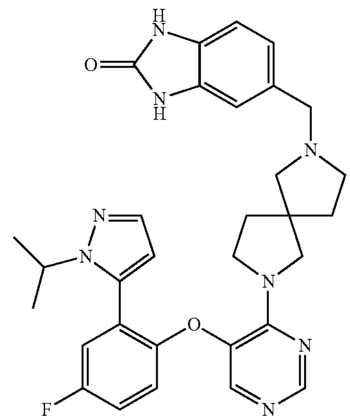 [SMILES: CC(C)n1nccc1-c1cc(F)ccc1Oc1cncnc1N1CCC2(CCN(Cc3ccc4[nH]c(=O)[nH]c4c3)C2)C1] | Single isomer of Example 237, separated by SFC method A |
| 197B | Isomer 2: 5-((7-(5-(4-fluoro-2-(1-isopropyl-1H-pyrazol-5-yl)phenoxy)pyrimidin-4-yl)-2,7-diazaspiro[4.4]nonan-2-yl)methyl)-1,3-dihydro-2H-benzo[d]imidazol-2-one | 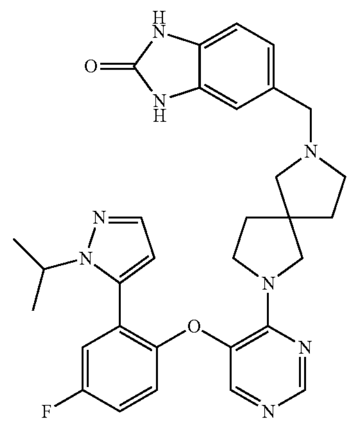 [SMILES: CC(C)n1nccc1-c1cc(F)ccc1Oc1cncnc1N1CCC2(CCN(Cc3ccc4[nH]c(=O)[nH]c4c3)C2)C1] | Single isomer of Example 237, separated by SFC method A |
| 198 | 6-((7-(5-(4-fluoro-2-(1-isopropyl-1H-pyrazol-5-yl)phenoxy)pyrimidin-4-yl)-2,7-diazaspiro[4.4]nonan-2-yl)methyl)-1H-benzo[d][1,2,3]triazole | 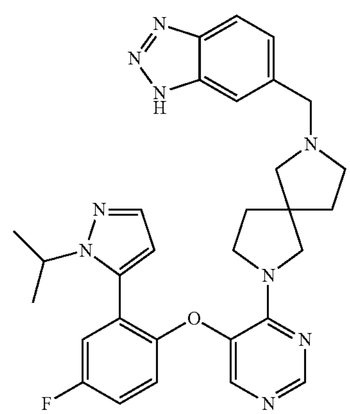 [SMILES: CC(C)n1nccc1-c1cc(F)ccc1Oc1cncnc1N1CCC2(CCN(Cc3ccc4nn[nH]c4c3)C2)C1] | Synthesized by a method similar to Example 41, starting from Intermediate 31a. 1H-benzo[d][1,2,3]triazole-6-carbaldehyde was used in step 4. |
| 199 | 2-cyclopropyl-3',5'-difluoro-2'-((4-(7-((2-oxo-2,3-dihydro-1H-benzo[d]imidazol-5-yl)methyl)-2,7-diazaspiro[4.4]nonan-2-yl)pyrimidin-5-yl)oxy)-[1,1'-biphenyl]-4-carbonitrile | 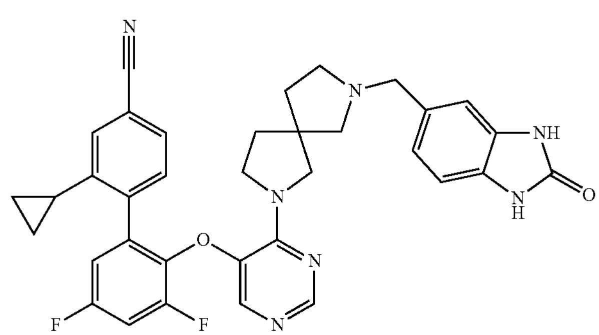 [SMILES: N#Cc1ccc(-c2cc(F)cc(F)c2Oc2cncnc2N2CCC3(CCN(Cc4ccc5[nH]c(=O)[nH]c5c4)C3)C2)c(C2CC2)c1] | Synthesized from Intermediate 17 by method described for Example 42 |

TABLE 9-continued

Examples 79-240

| Example | Name | Structure | Procedure |
|---|---|---|---|
| 200 | 3-((7-(5-(2-(cyclopropylmethoxy)-4-fluorophenoxy)pyrimidin-4-yl)-2,7-diazaspiro[4.4]nonan-2-yl)methyl)-1H-indole-6-carboxamide | 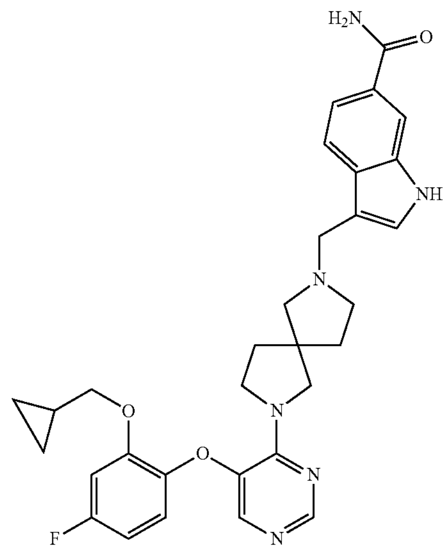 [SMILES: NC(=O)c1ccc2c(CN3CCC4(CCN(c5ncncc5Oc5ccc(F)cc5OCC5CC5)C4)C3)c[nH]c2c1] | Synthesized by the method described in Example 54 from Intermediate 43a |
| 201 | 3-((7-(5-(2-(cyclopropylmethoxy)-4-fluorophenoxy)pyrimidin-4-yl)-2,7-diazaspiro[4.4]nonan-2-yl)methyl)-1H-indole-6-carbonitrile | 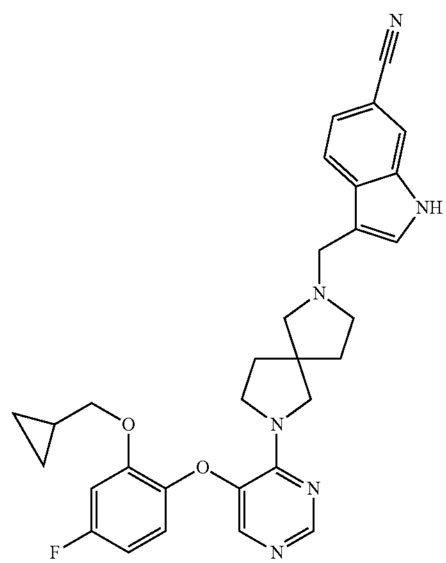 [SMILES: N#Cc1ccc2c(CN3CCC4(CCN(c5ncncc5Oc5ccc(F)cc5OCC5CC5)C4)C3)c[nH]c2c1] | Synthesized by the method described in Example 54 from Intermediate 43a |
| 202 | 2-((4-(7-((3,3-dimethyl-2-oxoindolin-6-yl)methyl)-2,7-diazaspiro[4.4]nonan-2-yl)pyrimidin-5-yl)oxy)-5-fluoro-N-isopropyl-N-methylbenzamide | 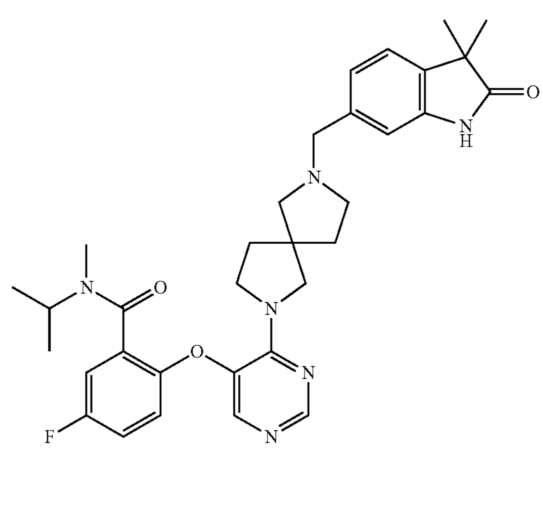 [SMILES: CC(C)N(C)C(=O)c1cc(F)ccc1Oc1cncnc1N1CCC2(CCN(Cc3ccc4c(c3)NC(=O)C4(C)C)C2)C1] | Synthesized from Intermediate 33 and 3,3-dimethyl-2-oxoindoline-6-carbaldehyde, as described in final step of Example 1 |

TABLE 9-continued

Examples 79-240

| Example | Name | Structure | Procedure |
|---|---|---|---|
| 203 | 2'-((4-(6-(4-cyanophenethyl)-2,6-diazaspiro[3.3]heptan-2-yl)pyrimidin-5-yl)oxy)-2-cyclopropyl-5'-fluoro-[1,1'-biphenyl]-4-carbonitrile | 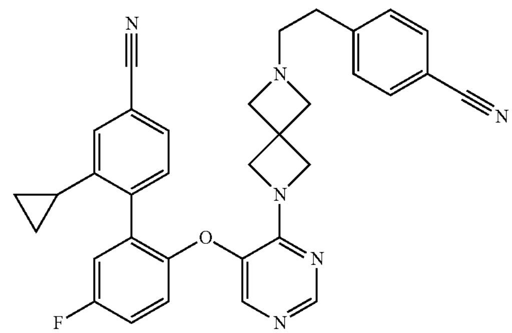 [SMILES: N#Cc1ccc(CCN2CC3(C2)CN(c2ncncc2Oc2ccc(F)cc2-c2ccc(C#N)cc2C2CC2)C3)cc1] | Synthesized from Intermediate 32 and 4-(2-oxoethyl)benzonitrile by the method described for Example 41 |
| 204 | 2-cyclopropyl-5'-fluoro-2'-((4-(7-((2-oxoindolin-5-yl)methyl)-2,7-diazaspiro[4.4]nonan-2-yl)pyrimidin-5-yl)oxy)-[1,1'-biphenyl]-4-carbonitrile | 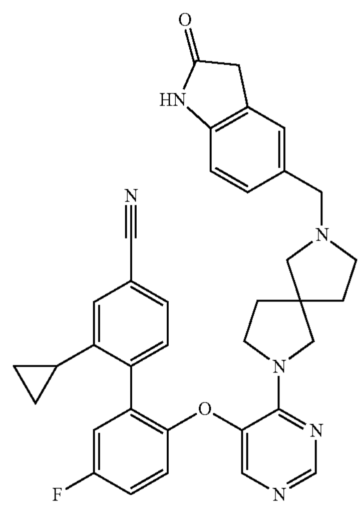 [SMILES: N#Cc1ccc(-c2cc(F)ccc2Oc2cncnc2N2CCC3(CCN(Cc4ccc5c(c4)CC(=O)N5)C3)C2)c(C2CC2)c1] | Synthesized from Intermediate 31 and 2-oxoindoline-5-carbaldehyde, as described in step 4 of Example 41 |
| 205 | 2-cyclopropyl-2'-((4-(7-((3,3-dimethyl-2-oxoindolin-6-yl)methyl)-2,7-diazaspiro[4.4]nonan-2-yl)pyrimidin-5-yl)oxy)-5'-fluoro-[1,1'-biphenyl]-4-carbonitrile | 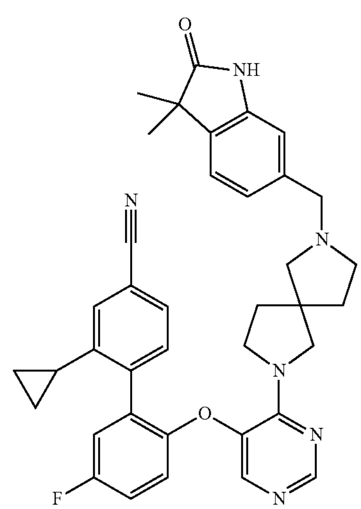 [SMILES: CC1(C)C(=O)Nc2cc(CN3CCC4(CCN(c5ncncc5Oc5ccc(F)cc5-c5ccc(C#N)cc5C5CC5)C4)C3)ccc21] | Synthesized from Intermediate 31 and Intermediate 42, as described in step 4 of Example 41 |

TABLE 9-continued

Examples 79-240

| Example | Name | Structure | Procedure |
|---|---|---|---|
| 206A | Isomer 1: 2-amino-2-cyclohexyl-1-(7-(5-(4-fluoro-2-(1-isopropyl-1H-pyrazol-5-yl)phenoxy)pyrimidin-4-yl)-2,7-diazaspiro[4.4]nonan-2-yl)ethanone | 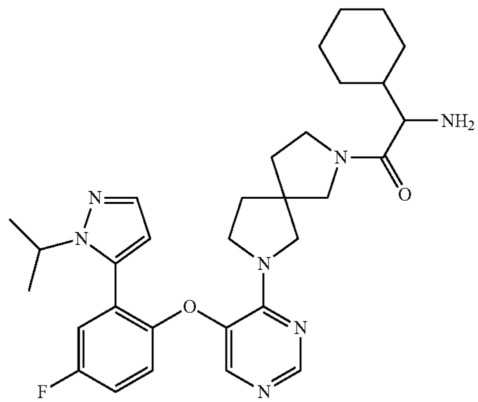 [SMILES: CC(C)n1nccc1-c1cc(F)ccc1Oc1cncnc1N1CCC2(CCN(C(=O)C(N)C3CCCCC3)C2)C1] | Synthesized from Intermediate 31a and (R)-2-((tert-butoxy-carbonyl)amino)-2-cyclohexylacetic acid, by the method described in Example 12, followed by deprotection of Boc group and separation of isomers by SFC method A |
| 206B | Isomer 2: 2-amino-2-cyclohexyl-1-(7-(5-(4-fluoro-2-(1-isopropyl-1H-pyrazol-5-yl)phenoxy)pyrimidin-4-yl)-2,7-diazaspiro[4.4]nonan-2-yl)ethanone | 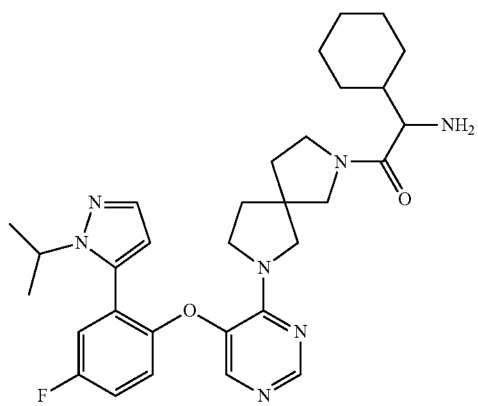 [SMILES: CC(C)n1nccc1-c1cc(F)ccc1Oc1cncnc1N1CCC2(CCN(C(=O)C(N)C3CCCCC3)C2)C1] | Synthesized from Intermediate 31a and (R)-2-((tert-butoxy-carbonyl)amino)-2-cyclohexylacetic acid, by the method described in Example 12, followed by deprotection of Boc group and separation of isomer by SFC method A |
| 206C | Isomer 3: 2-amino-2-cyclohexyl-1-(7-(5-(4-fluoro-2-(1-isopropyl-1H-pyrazol-5-yl)phenoxy)pyrimidin-4-yl)-2,7-diazaspiro[4.4]nonan-2-yl)ethanone | 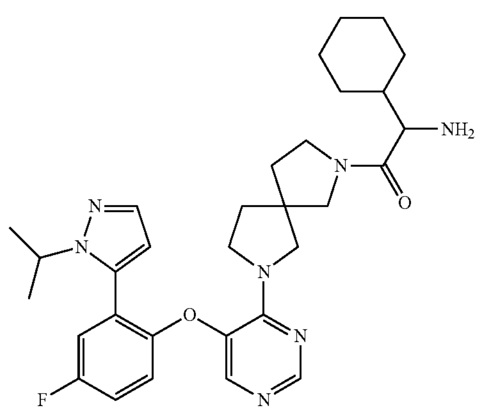 [SMILES: CC(C)n1nccc1-c1cc(F)ccc1Oc1cncnc1N1CCC2(CCN(C(=O)C(N)C3CCCCC3)C2)C1] | Synthesized from Intermediate 31a and (R)-2-((tert-butoxy-carbonyl)amino)-2-cyclohexylacetic acid, by method described in Example 12, followed by deprotection of Boc group and separation of isomers by SFC method A |

TABLE 9-continued

Examples 79-240

| Example | Name | Structure | Procedure |
| --- | --- | --- | --- |
| 207 | methyl (5-fluoro-2-((4-(7-((2-oxo-2,3-dihydro-1H-benzo[d]imidazol-5-yl)methyl)-2,7-diazaspiro[4.4]nonan-2-yl)pyrimidin-5-yl)oxy)phenyl)(methyl)carbamate | 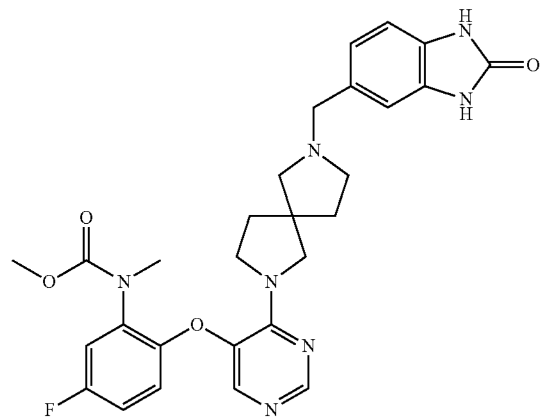 [SMILES: COC(=O)N(C)c1cc(F)ccc1Oc1cncnc1N1CCC2(CCN(Cc3ccc4[nH]c(=O)[nH]c4c3)C2)C1] | Synthesized by a method similar to Example 75. Intermediate 102 was reacted with methylchloroformate. |
| 208 | 5-((7-(5-(2-(benzyloxy)-4-fluorophenoxy)pyrimidin-4-yl)-2,7-diazaspiro[4.4]nonan-2-yl)methyl)-1,3-dihydro-2H-benzo[d]imidazol-2-one | 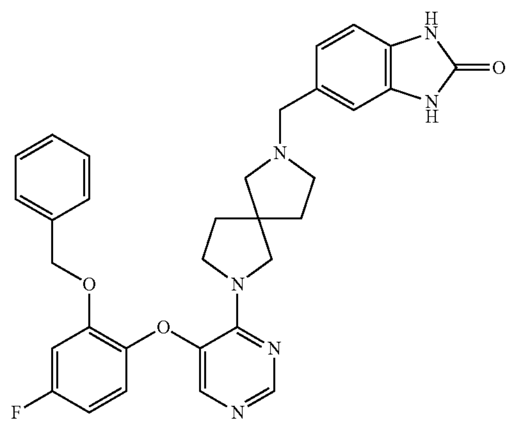 [SMILES: O=c1[nH]c2ccc(CN3CCC4(CCN(c5ncncc5Oc5ccc(F)cc5OCc5ccccc5)C4)C3)cc2[nH]1] | Synthesized by the method described in Example 54 from Intermediate 43a |
| 209 | 5-((7-(5-(4-fluoro-2-methoxyphenoxy)pyrimidin-4-yl)-2,7-diazaspiro[4.4]nonan-2-yl)methyl)-1,3-dihydro-2H-benzo[d]imidazol-2-one | 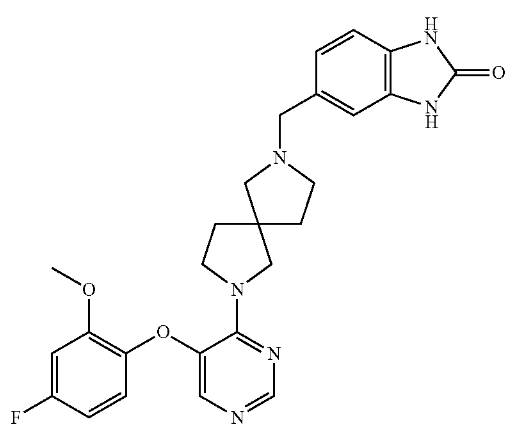 [SMILES: COc1cc(F)ccc1Oc1cncnc1N1CCC2(CCN(Cc3ccc4[nH]c(=O)[nH]c4c3)C2)C1] | Synthesized by the method described in Example 54 from Intermediate 43a |

US 10,683,302 B2

TABLE 9-continued

Examples 79-240

| Example | Name | Structure | Procedure |
|---|---|---|---|
| 210 | 5-fluoro-N-isopropyl-N-methyl-2-((4-(7-((3-oxo-3,4-dihydro-2H-benzo[b][1,4]oxazin-6-yl)methyl)-2,7-diazaspiro[4.4]nonan-2-yl)pyrimidin-5-yl)oxy)benzamide | 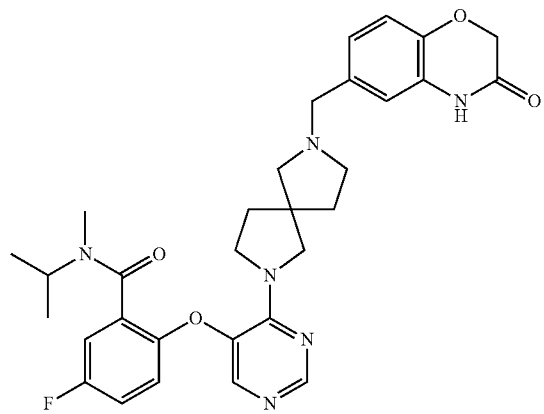 [SMILES: CC(C)N(C)C(=O)c1cc(F)ccc1Oc1cncnc1N1CCC2(CCN(Cc3ccc4c(c3)NC(=O)CO4)C2)C1] | Synthesized from Intermediate 33 and 3-oxo-3,4-dihydro-2H-benzo[b][1,4]oxazine-6-carbaldehyde, by method described in last step of Example 1 |
| 211 | 5-((7-(5-(4-fluoro-2-(2-methylpyrrolidine-1-carbonyl)phenoxy)pyrimidin-4-yl)-2,7-diazaspiro[4.4]nonan-2-yl)methyl)-1,3-dihydro-2H-benzo[d]imidazol-2-one | 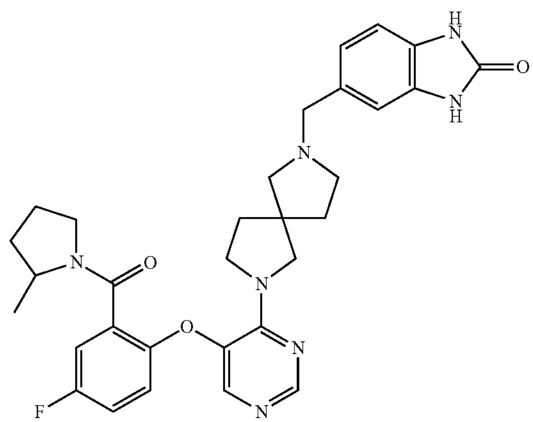 [SMILES: CC1CCCN1C(=O)c1cc(F)ccc1Oc1cncnc1N1CCC2(CCN(Cc3ccc4[nH]c(=O)[nH]c4c3)C2)C1] | Synthesized by the method described in Example 1. In step 4, 2-methyl pyrrolidine was utilized. |
| 212 | 5-((7-(5-(2-((1s,4s)-7-azabicyclo[2.2.1]heptane-7-carbonyl)-4-fluorophenoxy)pyrimidin-4-yl)-2,7-diazaspiro[4.4]nonan-2-yl)methyl)-1,3-dihydro-2H-benzo[d]imidazol-2-one | 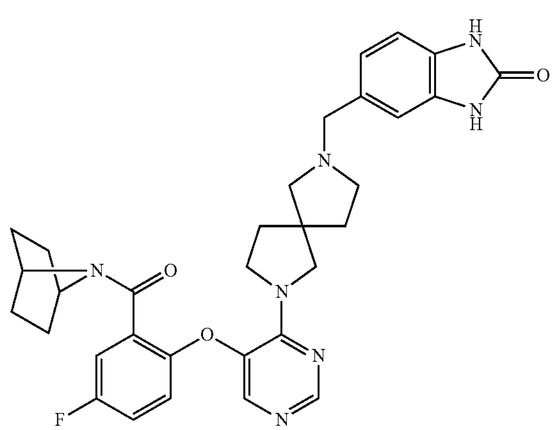 [SMILES: O=C(c1cc(F)ccc1Oc1cncnc1N1CCC2(CCN(Cc3ccc4[nH]c(=O)[nH]c4c3)C2)C1)N1C2CCC1CC2] | Synthesized by the method described in Example 1. In step 4, (1s,4s)-7-azabicyclo[2.2.1]heptane was utilized. |

TABLE 9-continued

Examples 79-240

| Example | Name | Structure | Procedure |
|---|---|---|---|
| 213 | 5-((7-(5-((2'-(1,1-difluoroethyl)-5-fluoro-[1,1'-biphenyl]-2-yl)oxy)pyrimidin-4-yl)-2,7-diazaspiro[4.4]nonan-2-yl)methyl)-1,3-dihydro-2H-benzo[d]imidazol-2-one | 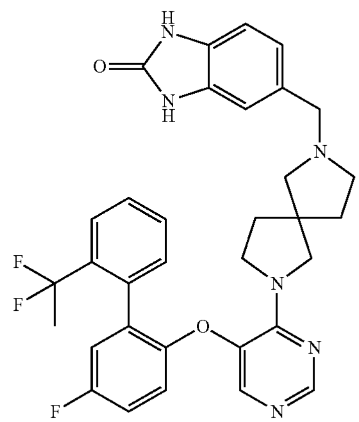 [SMILES: CC(F)(F)c1ccccc1-c1cc(F)ccc1Oc1cncnc1N1CCC2(CCN(Cc3ccc4[nH]c(=O)[nH]c4c3)C2)C1] | Synthesized by method similar to Example 41. In step 1, (2-(1,1-difluoroethyl)phenyl)boronic acid was utilized. |
| 214 | 2-cyclopropyl-5'-fluoro-2'-((4-(6-((4-hydroxytetrahydro-2H-pyran-4-yl)methyl)-2,6-diazaspiro[3.3]heptan-2-yl)pyrimidin-5-yl)oxy)-[1,1'-biphenyl]-4-carbonitrile | 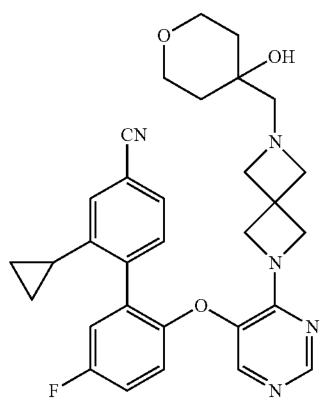 [SMILES: N#Cc1ccc(-c2cc(F)ccc2Oc2cncnc2N2CC3(CN(CC4(O)CCOCC4)C3)C2)c(C2CC2)c1] | Synthesized from Intermediate 32 and 4-(oxiran-2-yl)tetrahydro-2H-pyran, by method described in Example 72 |
| 215 | 2-cyclopropyl-5'-fluoro-2'-((4-(6-((tetrahydro-2H-pyran-4-yl)methyl)-2,6-diazaspiro[3.3]heptan-2-yl)pyrimidin-5-yl)oxy)-[1,1'-biphenyl]-4-carbonitrile | 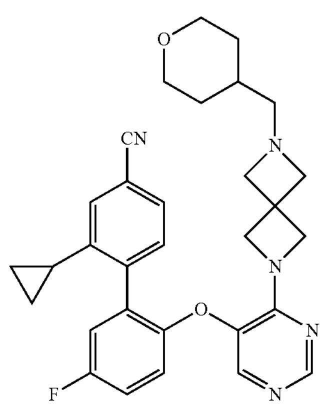 [SMILES: N#Cc1ccc(-c2cc(F)ccc2Oc2cncnc2N2CC3(CN(CC4CCOCC4)C3)C2)c(C2CC2)c1] | Synthesized from Intermediate 32 and tetrahydro-2H-pyran-4-carbaldehyde, by method described in step 4 of Example 41 |

TABLE 9-continued

Examples 79-240

| Example | Name | Structure | Procedure |
|---|---|---|---|
| 216 | 5-fluoro-N-isopropyl-N-methyl-2-((4-(7-((2-oxo-2,3-dihydro-1H-benzo[d]imidazol-5-yl)methyl)-2,7-diazaspiro[4.4]nonan-2-yl)pyrimidin-5-yl)oxy)benzamide | 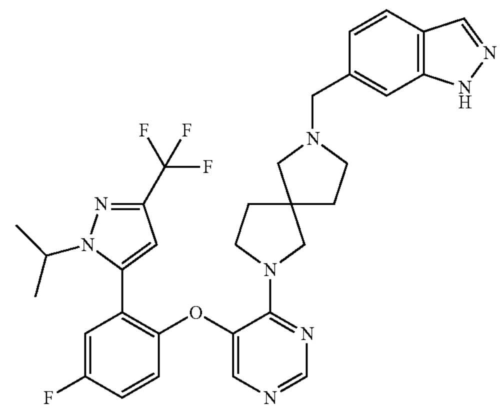 [SMILES: CC(C)n1nc(C(F)(F)F)cc1-c1cc(F)ccc1Oc1cncnc1N1CCC2(CCN(Cc3ccc4cn[nH]c4c3)C2)C1] | Synthesized by a method to similar to Example 41, starting with 1-isopropyl-5-(tributylstannyl)-3-(trifluoromethyl)-1H-pyrazole |
| 217 | 5-((7-(5-(4-fluoro-2-(1-isopropyl-3-(trifluoromethyl)-1H-pyrazol-5-yl)phenoxy)pyrimidin-4-yl)-2,7-diazaspiro[4.4]nonan-2-yl)methyl)-1,3-dihydro-2H-benzo[d]imidazol-2-one | 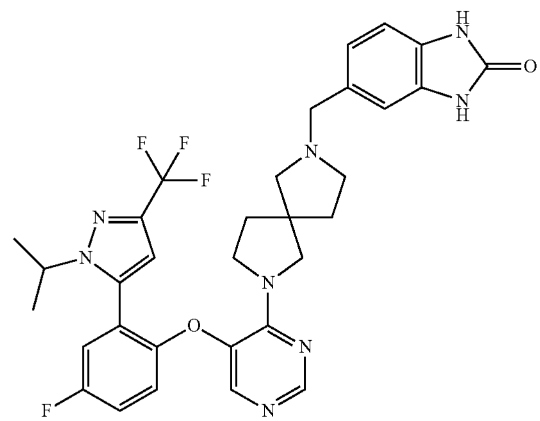 [SMILES: CC(C)n1nc(C(F)(F)F)cc1-c1cc(F)ccc1Oc1cncnc1N1CCC2(CCN(Cc3ccc4[nH]c(=O)[nH]c4c3)C2)C1] | Synthesized by a method similar to Example 41. In step 1, 1-isopropyl-5-(tributylstannyl)-3-(trifluoromethyl)-1H-pyrazole was utilized. |
| 218 | 5-((7-(5-(4-fluoro-2-(2-isopropyl-5-oxopyrrolidin-1-yl)phenoxy)pyrimidin-4-yl)-2,7-diazaspiro[4.4]nonan-2-yl)methyl)-1,3-dihydro-2H-benzo[d]imidazol-2-one | 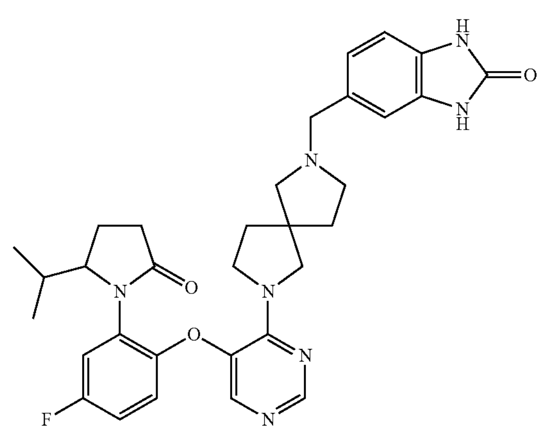 [SMILES: CC(C)C1CCC(=O)N1c1cc(F)ccc1Oc1cncnc1N1CCC2(CCN(Cc3ccc4[nH]c(=O)[nH]c4c3)C2)C1] | Synthesized from Intermediate 11 by copper coupling with 5-isopropylpyrrolidin-2-one, as described in steps 3 and 4 of Example 41 |

TABLE 9-continued

Examples 79-240

| Example | Name | Structure | Procedure |
|---|---|---|---|
| 219 | (1r,4r)-4-((7-(5-((5-fluoro-2'-isopropyl-[1,1'-biphenyl]-2-yl)oxy)pyrimidin-4-yl)-2,7-diazaspiro[4.4]nonan-2-yl)methyl)cyclohexan-1-amine | 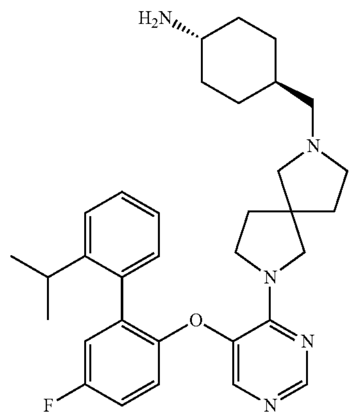 [SMILES: CC(C)c1ccccc1-c1cc(F)ccc1Oc1cncnc1N1CCC2(CCN(C[C@H]3CC[C@H](N)CC3)C2)C1] | Synthesized from Example 220 by acid deprotection |
| 220 | tert-butyl ((1r,4r)-4-((7-(5-((5-fluoro-2'-isopropyl-[1,1'-biphenyl]-2-yl)oxy)pyrimidin-4-yl)-2,7-diazaspiro[4.4]nonan-2-yl)methyl)cyclohexyl)carbamate | 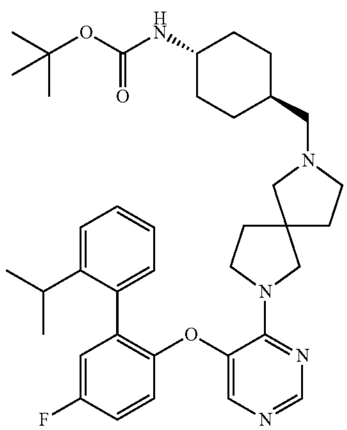 [SMILES: CC(C)c1ccccc1-c1cc(F)ccc1Oc1cncnc1N1CCC2(CCN(C[C@H]3CC[C@H](NC(=O)OC(C)(C)C)CC3)C2)C1] | Synthesized by the method described in Example 41. In step 4, tert-butyl ((1r,4r)-4-formylcyclohexyl)carbamate was utilized. |
| 221 | N-(4-((7-(5-((5-fluoro-2'-isopropyl-[1,1'-biphenyl]-2-yl)oxy)pyrimidin-4-yl)-2,7-diazaspiro[4.4]nonan-2-yl)methyl)phenyl)acetamide | 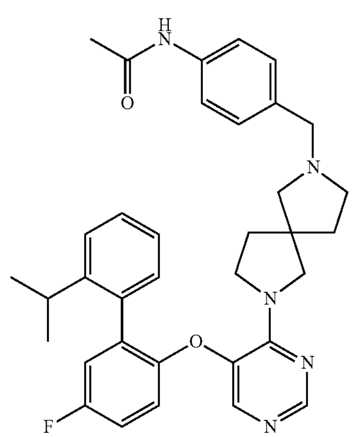 [SMILES: CC(=O)Nc1ccc(CN2CCC3(CCN(c4ncncc4Oc4ccc(F)cc4-c4ccccc4C(C)C)C3)C2)cc1] | Synthesized by a method similar to Example 41. In the final step, 4-acetamidobenzaldehyde was utilized. |

TABLE 9-continued

Examples 79-240

| Example | Name | Structure | Procedure |
|---|---|---|---|
| 222 | 5-fluoro-N-isopropyl-N-methyl-2-((4-(7-((2-oxo-2,3-dihydro-1H-benzo[d]imidazol-5-yl)methyl)-2,7-diazaspiro[4.4]nonan-2-yl)pyrimidin-5-yl)oxy)benzene-sulfonamide | 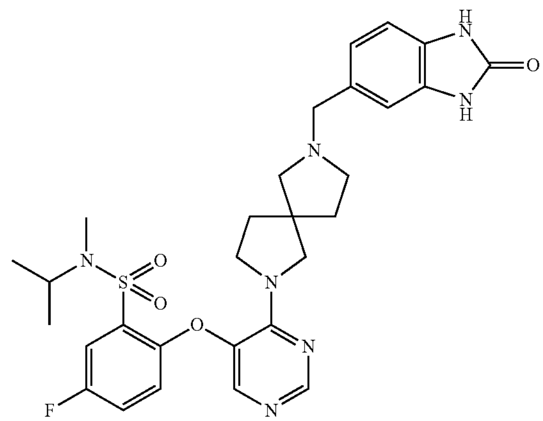 [SMILES: CC(C)N(C)S(=O)(=O)c1cc(F)ccc1Oc1cncnc1N1CCC2(CCN(Cc3ccc4[nH]c(=O)[nH]c4c3)C2)C1] | Synthesized by method similar to Example 74, starting from tert-butyl 7-(5-bromopyrimidin-4-yl)-2,7-diazaspiro[4.4]nonane-2-carboxylate |
| 223 | ethyl 5'-fluoro-2'-((4-(7-((2-oxo-2,3-dihydro-1H-benzo[d]imidazol-5-yl)methyl)-2,7-diazaspiro[4.4]nonan-2-yl)pyrimidin-5-yl)oxy)-[1,1'-biphenyl]-2-carboxylate | 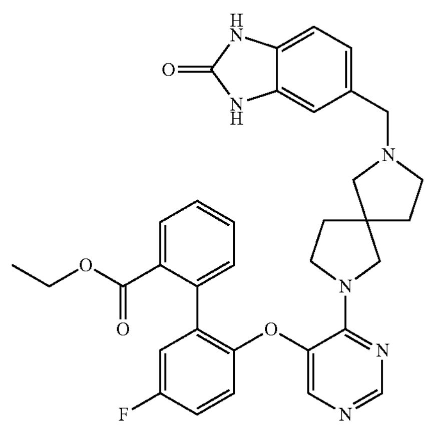 [SMILES: CCOC(=O)c1ccccc1-c1cc(F)ccc1Oc1cncnc1N1CCC2(CCN(Cc3ccc4[nH]c(=O)[nH]c4c3)C2)C1] | Synthesized by a method similar to Example 41, starting from 2-ethoxycarbonyl-phenyl boronic acid |
| 224 | 5-((7-(5-(4-fluoro-2-(4-isopropylthiazol-5-yl)phenoxy)pyrimidin-4-yl)-2,7-diazaspiro[4.4]nonan-2-yl)methyl)-1,3-dihydro-2H-benzo[d]imidazol-2-one | 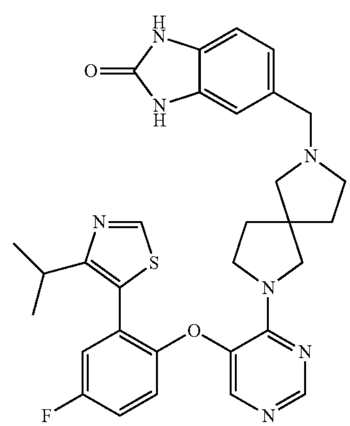 [SMILES: CC(C)c1ncsc1-c1cc(F)ccc1Oc1cncnc1N1CCC2(CCN(Cc3ccc4[nH]c(=O)[nH]c4c3)C2)C1] | Synthesized by a method similar to Example 41, starting from 4-isoprpyl-5-thiazole-boronic acid |

TABLE 9-continued

Examples 79-240

| Example | Name | Structure | Procedure |
|---|---|---|---|
| 225 | 5-fluoro-N-isopropyl-N-methyl-2-((4-(6-((tetrahydro-2H-pyran-4-yl)methyl)-2,6-diazaspiro[3.3]heptan-2-yl)pyrimidin-5-yl)oxy)benzamide | 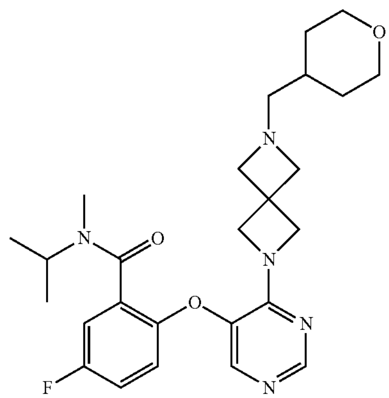 [SMILES: CC(C)N(C)C(=O)c1cc(F)ccc1Oc1cncnc1N1CC2(CN(CC3CCOCC3)C2)C1] | Synthesized from Intermediate 39 and 4-pyrancarbaldehyde, by the method described in Example 1 |
| 226 | 5'-fluoro-2-methyl-2'-((4-(7-((2-oxo-2,3-dihydro-1H-benzo[d]imidazol-5-yl)methyl)-2,7-diazaspiro[4.4]nonan-2-yl)pyrimidin-5-yl)oxy)-[1,1'-biphenyl]-4-carbonitrile | 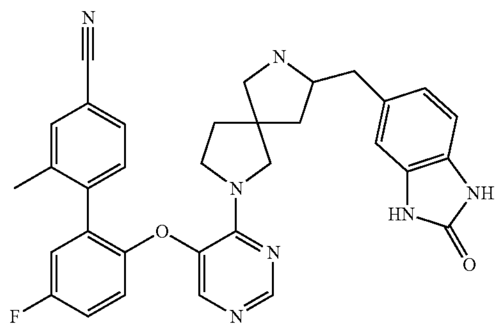 [SMILES: Cc1cc(C#N)ccc1-c1cc(F)ccc1Oc1cncnc1N1CCC2(CNC(Cc3ccc4[nH]c(=O)[nH]c4c3)C2)C1] | Synthesized from Example 41, starting from 4-cyano-2-methyl phenyl boronic acid |
| 227 | 4-(2-(6-(5-(4-fluoro-2-(4-isopropylpyrimidin-5-yl)phenoxy)pyrimidin-4-yl)-2,6-diazaspiro[3.3]heptan-2-yl)-2-oxoethyl)benzonitrile | 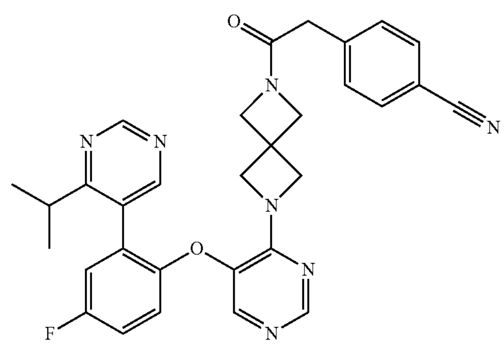 [SMILES: CC(C)c1ncncc1-c1cc(F)ccc1Oc1cncnc1N1CC2(CN(C(=O)Cc3ccc(C#N)cc3)C2)C1] | Synthesized from Intermediate 27 and and 4-cyanophenyl acetyl chloride, by method described in Example 12 |
| 228 | 4-(2-(6-(5-((5-fluoro-2'-isopropyl-[1,1'-biphenyl]-2-yl)oxy)pyrimidin-4-yl)-2,6-diazaspiro[3.3]heptan-2-yl)-2-oxoethyl)benzonitrile | 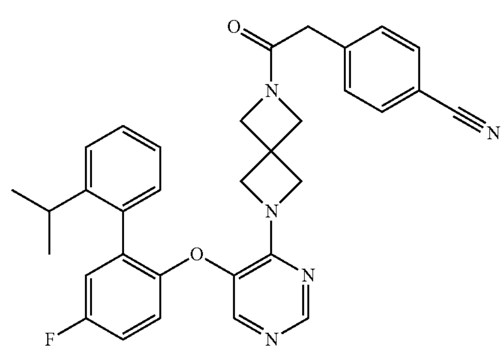 [SMILES: CC(C)c1ccccc1-c1cc(F)ccc1Oc1cncnc1N1CC2(CN(C(=O)Cc3ccc(C#N)cc3)C2)C1] | Synthesized from Intermediate 30 and 4-cyanophenyl acetyl chloride, by method described in Example 12 |

TABLE 9-continued

Examples 79-240

| Example | Name | Structure | Procedure |
|---|---|---|---|
| 229 | 1-(6-(5-((5-fluoro-2'-isopropyl-[1,1'-biphenyl]-2-yl)oxy)pyrimidin-4-yl)-2,6-diazaspiro[3.3]heptan-2-yl)-2-(4-(methylsulfonyl)phenyl)ethan-1-one | 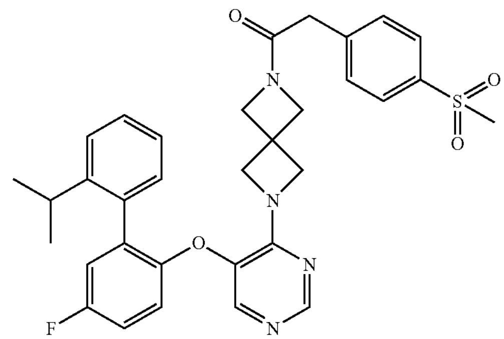 [SMILES: CC(C)c1ccccc1-c1cc(F)ccc1Oc1cncnc1N1CC2(CN(C(=O)Cc3ccc(S(C)(=O)=O)cc3)C2)C1] | Synthesized from Intermediate 30 and 2-(4-(methylsulfonyl)phenyl)acetyl chloride, by method described in Example 12 |
| 230 | 5'-fluoro-2-methyl-2'-((4-(7-((2-oxo-2,3-dihydro-1H-benzo[d]imidazol-5-yl)methyl)-2,7-diazaspiro[4.4]nonan-2-yl)pyrimidin-5-yl)oxy)-[1,1'-biphenyl]-3-carbonitrile | 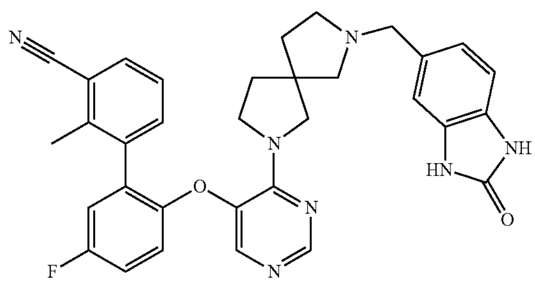 [SMILES: Cc1c(C#N)cccc1-c1cc(F)ccc1Oc1cncnc1N1CCC2(CCN(Cc3ccc4[nH]c(=O)[nH]c4c3)C2)C1] | Synthesized by a method similar to Example 41, starting from 3-cyano-2-methyl phenyl boronic acid |
| 231 | 2-((3,3-difluorocyclohexyl)methyl)-6-(5-(4-fluoro-2-(1-isopropyl-1H-pyrazol-5-yl)phenoxy)pyrimidin-4-yl)-2,6-diazaspiro[3.3]heptane | 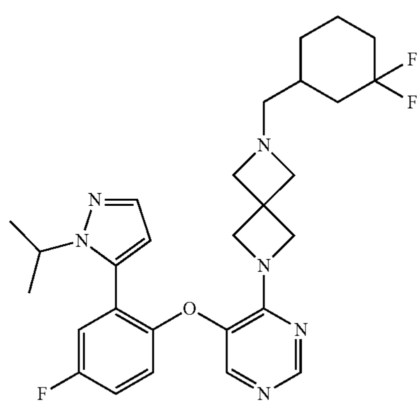 [SMILES: CC(C)n1nccc1-c1cc(F)ccc1Oc1cncnc1N1CC2(CN(CC3CCCC(F)(F)C3)C2)C1] | Synthesized from Intermediate 101 and 3,3-difluorocyclohexane-1-carbaldehyde by reductive amination, as described in step 4 of Example 41 |
| 232 | 2-((3,3-difluorocyclohexyl)methyl)-6-(5-(4-fluoro-2-(4-isopropylpyrimidin-5-yl)phenoxy)pyrimidin-4-yl)-2,6-diazaspiro[3.3]heptane | 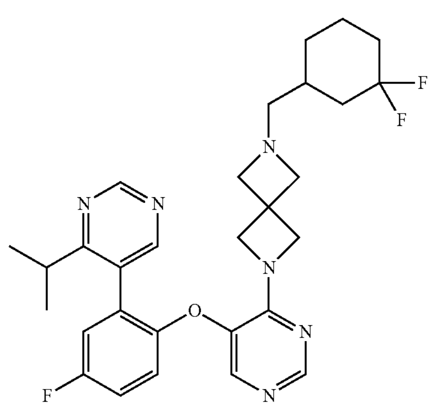 [SMILES: CC(C)c1ncncc1-c1cc(F)ccc1Oc1cncnc1N1CC2(CN(CC3CCCC(F)(F)C3)C2)C1] | Synthesized from Intermediate 27 and 3,3-difluorocyclohexane-1-carbaldehyde, by method described in step 4 of Example 41 |

TABLE 9-continued

Examples 79-240

| Example | Name | Structure | Procedure |
|---|---|---|---|
| 233 | 4-(((2-(5-(4-fluoro-2-(1-isopropyl-1H-pyrazol-5-yl)phenoxy)pyrimidin-4-yl)-5-oxa-2-azaspiro[3.4]octan-7-yl)amino)methyl)benzonitrile | 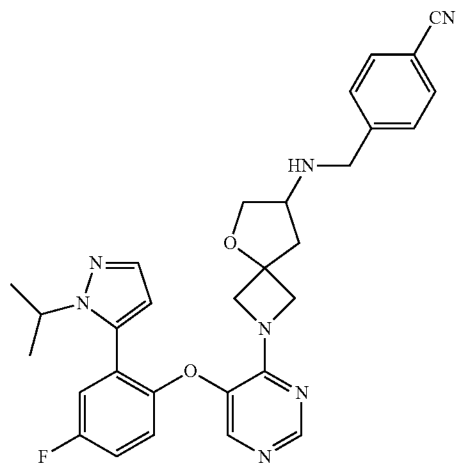 [SMILES: CC(C)n1nccc1-c1cc(F)ccc1Oc1cncnc1N1CC2(CC(NCc3ccc(C#N)cc3)CO2)C1] | Synthesized by method similar to Example 19. In step 3, 2-isoprpyl-3-pyrazole-boronic acid was utilized. |
| 234 | 5-((7-(5-(2-(2-ethylpyridin-3-yl)-4-fluorophenoxy)pyrimidin-4-yl)-2,7-diazaspiro[4.4]nonan-2-yl)methyl)-1,3-dihydro-2H-benzo[d]imidazol-2-one | 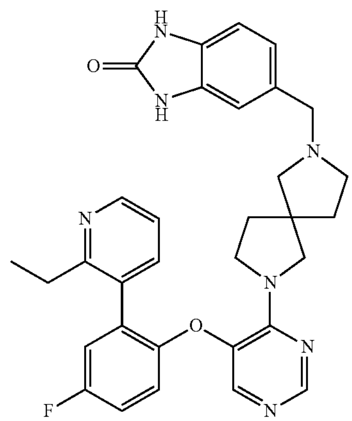 [SMILES: CCc1ncccc1-c1cc(F)ccc1Oc1cncnc1N1CCC2(CCN(Cc3ccc4[nH]c(=O)[nH]c4c3)C2)C1] | Synthesized by a method similar to Example 41, starting with 2-ethyl-3-pyridyl boronic acid |
| 235 | 5-((7-(5-(4-fluoro-2-isopentylphenoxy)pyrimidin-4-yl)-2,7-diazaspiro[4.4]nonan-2-yl)methyl)-1,3-dihydro-2H-benzo[d]imidazol-2-one | 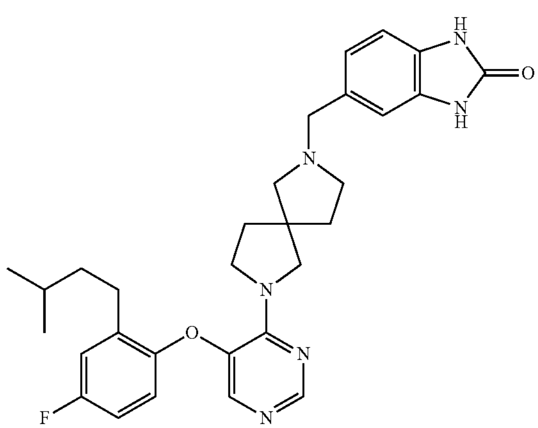 [SMILES: CC(C)CCc1cc(F)ccc1Oc1cncnc1N1CCC2(CCN(Cc3ccc4[nH]c(=O)[nH]c4c3)C2)C1] | By method described for Example 77, starting with isopentyl zinc chloride |

TABLE 9-continued

Examples 79-240

| Example | Name | Structure | Procedure |
|---|---|---|---|
| 236 | 5-((7-(5-(4-fluoro-2-isobutylphenoxy)pyrimidin-4-yl)-2,7-diazaspiro[4.4]nonan-2-yl)methyl)-1,3-dihydro-2H-benzo[d]imidazol-2-one | 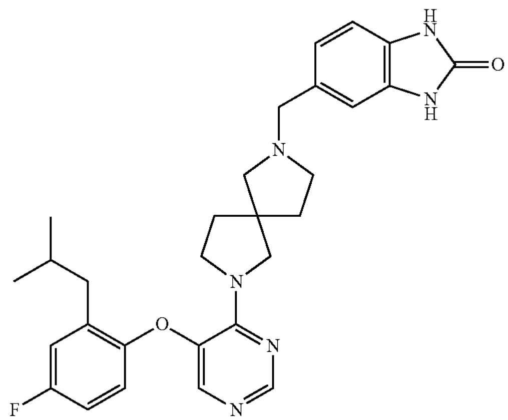 [SMILES: CC(C)Cc1cc(F)ccc1Oc1cncnc1N1CCC2(CCN(Cc3ccc4[nH]c(=O)[nH]c4c3)C2)C1] | By method described fro Example 77, starting with isobutyl zinc chloride |
| 237 | 5-((7-(5-(4-fluoro-2-(1-isopropyl-1H-pyrazol-5-yl)phenoxy)pyrimidin-4-yl)-2,7-diazaspiro[4.4]nonan-2-yl)methyl)-1,3-dihydro-2H-benzo[d]imidazol-2-one | 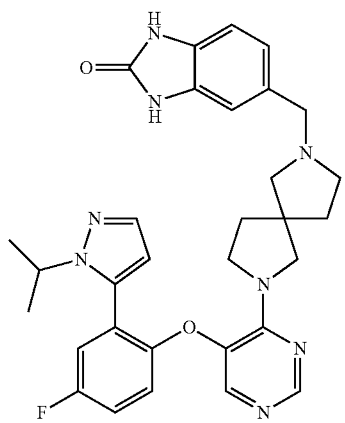 [SMILES: CC(C)n1nccc1-c1cc(F)ccc1Oc1cncnc1N1CCC2(CCN(Cc3ccc4[nH]c(=O)[nH]c4c3)C2)C1] | Synthesized from Intermediate 31a by the method described in Example 41 |
| 237A | 2-(5-((5-fluoro-2'-isopropyl-[1,1'-biphenyl]-2-yl)oxy)pyrimidin-4-yl)-6-((tetrahydro-2H-pyran-4-yl)methyl)-2,6-diazaspiro[3.3]heptane | 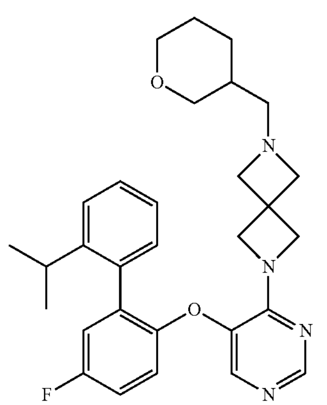 [SMILES: CC(C)c1ccccc1-c1cc(F)ccc1Oc1cncnc1N1CC2(CN(CC3CCCOC3)C2)C1] | Synthesized from Intermediate 30 by reductive amination with 4-pyran-carboxyladehyde |

TABLE 9-continued

Examples 79-240

| Example | Name | Structure | Procedure |
|---|---|---|---|
| 238 | N-ethyl-5-fluoro-N-isopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide | 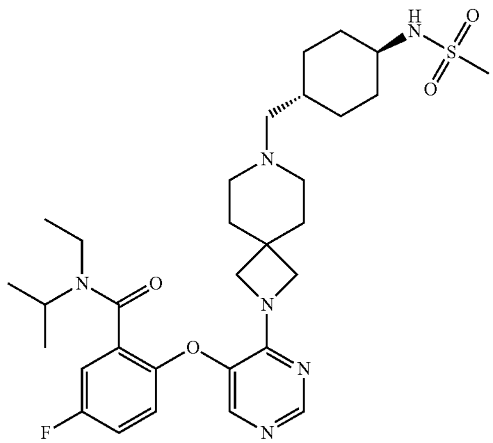 [SMILES: CCN(C(=O)c1cc(F)ccc1Oc1cncnc1N1CC2(CCN(C[C@H]3CC[C@H](NS(C)(=O)=O)CC3)CC2)C1)C(C)C] | Synthesized by method similar to Example 6A from Intermediate 41F |
| 239 | 5-fluoro-N,N-diisopropyl-2-((4-(6-((tetrahydro-2H-pyran-4-yl)amino)-2-azaspiro[3.3]heptan-2-yl)pyrimidin-5-yl)oxy)benzamide | 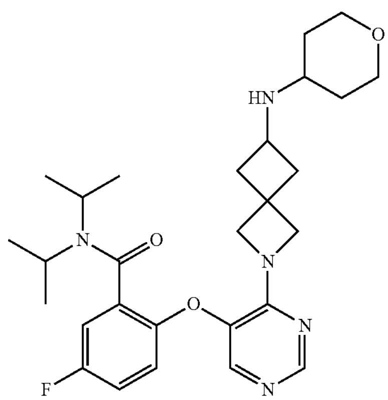 [SMILES: CC(C)N(C(=O)c1cc(F)ccc1Oc1cncnc1N1CC2(CC(NC3CCOCC3)C2)C1)C(C)C] | Synthesized from Intermediate 38 and 4-pyrancarbaldehyde, by method described in last step of Example 1 |
| 240 | 5-fluoro-N,N-diisopropyl-2-((4-(6-(methyl(tetrahydro-2H-pyran-4-yl)amino)-2-azaspiro[3.3]heptan-2-yl)pyrimidin-5-yl)oxy)benzamide | 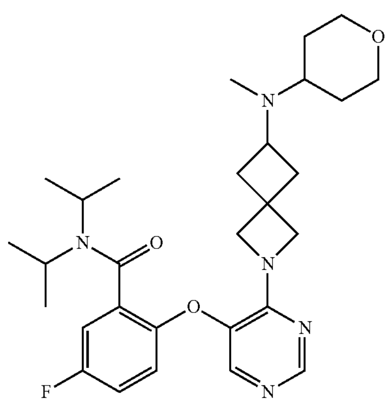 [SMILES: CC(C)N(C(=O)c1cc(F)ccc1Oc1cncnc1N1CC2(CC(N(C)C3CCOCC3)C2)C1)C(C)C] | Synthesized from Example 239 by reductive amination with formaldehyde. |

TABLE 10

Characterization Data for Examples 79-240.

| Example | 1H NMR | MS |
|---|---|---|
| 79 | 1H NMR (d4-MeOH) 8.44 (s, 1H), 7.83 (s, 1H), 7.57 (m, 1H), 7.46-7.51 (m, 2H), 7.06 (d, 1H), 6.60 (d, 1H), 3.93-4.40 (m, 4H), 3.72 (m, 1H), 3.55 (d, 2H), 3.32 (d, 3H), 2.94-3.04 (m, 4H), 2.20 (m, 2H), 1.90- | LCMS method G: $R_t$ = 4.25 min, $(M + H)^+$ = 669.6 |

TABLE 10-continued

Characterization Data for Examples 79-240.

| Example | 1H NMR | MS |
|---|---|---|
| | 2.06 (m, 7H), 1.45 (dd, 2H), 1.16-1.31 (m, 3H), 0.84 (m, 1H), 0.65 (m, 2H), 0.37 (m, 1H) ppm. | |
| 80 | 1H NMR (d4-MeOH)-8.42 (s, 1H), 7.82 (s, 1H), 7.47-7.55 (m, 3H), 7.04 (d, 1H), 6.61 (d, 1H), 3.71-4.40 (m, 4H), 3.54 (d, 2H), 3.31 (d, 3H), 3.19 (m, 1H), 3.00 (m, 4H), 2.94 (s, 3H), 1.75-2.20 (m, 9H), 1.20-1.36 (m, 5H), 0.82 (m, 2H), 0.63 (m, 2H), 0.36 (m, 1H) ppm. | LCMS method G: $R_t$ = 3.48 min, $(M + H)^+$ = 651.6 |
| 81A | $^1$H NMR (MeOD): δ 8.24 (s, 1H), 7.77 (s, 1H), 7.30-7.40 (m, 2H), 7.10-7.20 (m, 2H), 7.00-7.10 (m, 3H), 6.50-6.65 (m, 1H), 3.95-4.05 (m, 2H), 3.80-3.90 (m, 2H), 3.55-3.70 (m, 4H), 3.40-3.55 (m, 2H), 3.35-3.40 (m, 3H), 2.60-2.80 (m, 2H), 2.40-2.55 (m, 2H), 1.75-1.95 (m, 4H), 1.25-1.35 (m, 1H), 0.50-0.85 (m, 4H). $^{19}$F NMR (MeOD): δ −119.21~−119.14. | LCMS method D: $R_t$ = 2.045 min, $(M + H)^+$ = 652.3 |
| 81B | $^1$H NMR (MeOD): δ 8.24 (s, 1H), 7.77 (s, 1H), 7.30-7.40 (m, 2H), 7.10-7.20 (m, 2H), 7.00-7.10 (m, 3H), 6.56-6.59 (m, 1H), 3.95-4.05 (m, 2H), 3.80-3.87 (m, 2H), 3.55-3.70 (m, 4H), 3.40-3.55 (m, 2H), 3.35-3.40 (m, 3H), 2.40-2.80 (m, 4H), 1.75-1.96 (m, 4H), 1.20-1.35 (m, 1H), 0.40-0.85 (m, 4H). $^{19}$F NMR (MeOD): δ −119.15. | LCMS method D: $R_t$ = 2.048 min, $(M + H)^+$ = 652.3 |
| 82 | | LCMS method G: $R_t$ = 4.21 min, $(M + H)^+$ = 529.8 |
| 83 | $^1$H NMR (CD$_3$OD): δ 8.21-8.30 (m, 1H), 7.70-7.79 (m, 1H), 6.89-7.21 (m, 3H), 4.76-4.79 (m, 1H), 3.84-4.27 (m, 5H), 3.19-3.27 (m, 3H), 2.78-2.96 (m, 3H), 2.37-2.50 (m, 4H), 1.79-2.06 (m, 7H), 1.42 (s, 9H), 1.17-1.19 (m, 6H), 0.99-1.13 (m, 2H) $^{19}$F NMR (CD$_3$OD): δ −120.92~−118.61. | LCMS method G: $R_t$ = 0.936 min, $(M + H)^+$ = 611.4 |
| 84 | | LCMS method G: $R_t$ = 5.11 min, $(M + H)^+$ = 639.8 |
| 85 | | LCMS method G: $R_t$ = 3.21 min, $(M + H)^+$ = 597.2 |
| 86 | | LCMS method G: $R_t$ = 3.41 min, $(M + H)^+$ = 616.2 |
| 87 | | LCMS method G: $R_t$ = 5.21 min, $(M + H)^+$ = 637.8 |
| 88 | | LCMS method G: $R_t$ = 6.31 min, $(M + H)^+$ = 629.8 |
| 89 | | LCMS method G: $R_t$ = 2.21 min, $(M + H)^+$ = 514.6 |
| 90 | $^1$H NMR (CD$_3$OD) δ: 8.58 (s, 1H), 8.00 (m, 1H), 7.59 (d, J = 7.6 Hz, 1H), 7.29 (d, J = 8.4 Hz, 1H), 7.24 (m, 3H), 7.17 (s, 1H), 4.47 (m, 2H), 4.01-3.48 (m, 8H), 2.15 (m, 4H), 1.78 (s, 3H), 1.52 (s, 3H), 1.39 (s, 3H), 1.21 (d, J = 6.4 Hz, 3H). 1.21 (d, J = 6.4 Hz, 3H), 1.10 (d, J = 6.4 Hz, 3H). | LCMS method A: $R_t$ = 0.84 min, $(M + H)^+$ = 626 |

TABLE 10-continued

Characterization Data for Examples 79-240.

| Example | 1H NMR | MS |
|---|---|---|
| 91 | | LCMS method D: $R_t$ = 0.946 min, $(M + H)^+$ = 562.1 |
| 91A | $^1$H NMR(CD$_3$OD): δ 8.26 (d, J = 16.0 Hz, 1 H), 8.07 (d, J = 7.6 Hz, 1 H), 7.69-7.82 (m, 2 H), 7.33-7.38 (m, 1 H), 7.15 (d, J = 8.0 Hz, 2 H), 6.83-6.93 (m, 1 H), 3.93 (s, 1 H), 3.68 (brs, 6 H), 2.94 (s, 3 H), 2.77 (s, 3 H), 1.82-1.94 (m, 5 H), 1.18 (d, J = 6.8 Hz, 6 H).$^{19}$F NMR (CD$_3$OD): δ −120.66, −123.26. | LCMS method E: $R_t$ = 0.840 min, $(M + H)^+$ = 567.1 |
| 92 | | LCMS method D: $R_t$ = 0.826 min $(M + H)^+$ = 484.1 |
| 93 | $^1$H NMR (CD$_3$OD): δ 8.20-8.24 (m, 1H), 7.68-7.77 (m, 1H), 6.92-7.20 (m, 3H), 4.76-4.78 (m, 1H), 3.86-3.95 (m, 5H), 3.10-3.13 (m, 1H), 2.76-2.95 (m, 6H), 2.37-2.39 (m, 4H), 2.16-2.17 (m, 2H), 1.99-2.03 (m, 2H), 1.81-1.86 (m, 5H), 0.99-1.48 (m, 11H). $^{19}$F NMR (CD$_3$OD): δ −121.47~−118.42. | LCMS method E: $R_t$ = 1.740 min, $(M + H)^+$ = 603.3 |
| 94 | $^1$H NMR (CD$^3$OD): δ 8.20-8.24 (m, 1H), 7.67-7.76 (m, 1H), 7.15-7.20 (m, 2H), 6.93-7.04 (m, 1H), 4.76-4.78 (m, 1H), 3.85-3.95 (m, 5H), 3.23-3.24 (m, 4H), 2.76-2.94 (m, 3H), 2.12-2.35 (m, 6H), 1.80-1.90 (m, 7H), 1.41 (s, 9H), 1.14-1.17 (m, 6H), 0.92-1.01 (m, 2H). $^{19}$F NMR (CD$_3$OD): δ −120.43~−118.81. | LCMS method E: = 2.141 min; $(M + H)^+$ = 625.4 |
| 95 | $^1$H NMR (CD$_3$OD): δ 8.20-8.24 (m, 1H), 7.67-7.76 (m, 1H), 7.15-7.20 (m, 2H), 6.93-7.04 (m, 1H), 4.76-4.77 (m, 1H), 3.85-3.95 (m, 5H), 3.59 (s, 3H), 2.76-2.94 (m, 3H), 1.80-2.35 (m, 14H), 1.45-1.47 (m, 2H), 1.14-1.23 (m, 7H), 0.93-1.02 (m, 2H). $^{19}$F NMR (CD$_3$OD): δ −120.03~−119.55. | LCMS method D: $R_t$ = 1.829 min; $(M + H)^+$ = 583.3 |
| 96 | | LCMS method G: $R_t$ = 2.21 min; $(M + H)^+$ = 491.2 |
| 97 | | LCMS method G: $R_t$ = 4.21 min; $(M + H)^+$ = 624.69 |
| 98 | | LCMS method G: $R_t$ = 3.66 min; $(M + H)^+$ = 554.63 |
| 99 | | LCMS method G: $R_t$ = 3.68 min; $(M + H)^+$ = 540.63 |
| 100 | | LCMS method B: $R_t$ = 0.784 min; $(M + H)^+$ = 596.77 |
| 101 | | LCMS method G: $R_t$ = 3.79 min; $(M + H)^+$ = 540.7 |
| 102 | | LCMS method G: $R_t$ = 4.57 min; $(M + H)^+$ = 498.61 |
| 103 | | LCMS method G: $R_t$ = 4.12 min; $(M + H)^+$ = 482.54 |
| 104 | | LCMS method G: $R_t$ = 5.36 min; $(M + H)^+$ = 583.63 |
| 105 | | LCMS method G: $R_t$ = 5.40 min; $(M + H)^+$ = 623.70 |

TABLE 10-continued

Characterization Data for Examples 79-240.

| Example | 1H NMR | MS |
|---|---|---|
| 106 | | LCMS method D: $R_t$ = 0.897 min; $(M + H)^+$ = 496.2 |
| 107 | $^1$H NMR (CD$_3$OD): δ 8.56-8.65 (s, 1H), 7.81-8.15 (m, 1H), 7.27-7.39 (m, 5H), 7.20-7.22 (m, 1H), 4.32-4.51 (m, 3H), 3.90-4.06 (m, 3H), 3.41-3.58 (m, 9H), 3.32-3.33 (s, 1H), 2.11-2.28 (m, 4H), 1.11-1.37 (m, 9H). $^{19}$F NMR (CD$_3$OD): δ −117.18. | LCMS method D: $R_t$ = 1.73 min; $(M + H)^+$ = 588.3 |
| 108 | | LCMS method D: $R_t$ = 1.73 min; $(M + H)^+$ = 468.6 |
| 109 | | LCMS method D: $R_t$ = 1.65 min; $(M + H)^+$ = 497.6 |
| 110 | | LCMS method G: $R_t$ = 3.40 min; $(M + H)^+$ = 526.2 |
| 111 | | LCMS method G: $R_t$ = 3.88 min; $(M + H)^+$ = 526.69 |
| 112 | | LCMS method G: $R_t$ = 3.88 min; $(M + H)^+$ = 5120.63 |
| 113 | | LCMS method G: $R_t$ = 5.93 min; $(M + H)^+$ = 571.63 |
| 114 | | LCMS method G: $R_t$ = 5.93 min; $(M + H)^+$ = 576.69 |
| 115 | | LCMS method G: $R_t$ = 6.14 min; $(M + H)^+$ = 639.79 |
| 116 | | LCMS method G: $R_t$ = 5.84 min; $(M + H)^+$ = 557.62 |
| 117 | | LCMS method G: $R_t$ = 5.12 min; $(M + H)^+$ = 622.5 |
| 118 | | LCMS method G: $R_t$ = 3.99 min; $(M + H)^+$ = 526.62 |
| 119 | | LCMS method G: $R_t$ = 4.75 min; $(M + H)^+$ = 596.49 |
| 120 | | LCMS method G: $R_t$ = 7.22 min; $(M + H)^+$ = 622.49 & 624.44 |
| 121 | | LCMS method D: $R_t$ = 1.71 min; $(M + H)^+$ = 498.3 |
| 122 | | LCMS method E: $R_t$ 1.710 min; $(M + H)^+$ = 586.3 |
| 123 | $^1$H NMR (CD$_3$OD): δ 8.24-8.29 (m, 1 H), 7.74-7.83 (m, 1 H), 6.83-7.16 (m, 6 H), 3.92-3.99 (m, 3 H), 3.46-3.64 (m, 8 H), 2.94-2.95 (m, 2 H), 2.37-2.79 (m, 6 H), 1.92 (brs, 3 H), 1.80 (s, 3 H), 1.17-1.24 (m, 6H). $^{19}$F NMR (CD$_3$OD): δ −120.40 | LCMS method D: $R_t$ = 0.900 min; $(M + H)^+$ = 645.4 |
| 124 | | LCMS method E: $R_t$ + 1.711 min; $(M + H)^+$ = 631.3 |
| 125 | | LCMS method G: $R_t$ 3.710 min; $(M + H)^+$ = 598.3 |
| 126 | $^1$H NMR (MeOH-d4): δ 7.71 (s, 1 H), 7.40 (s, 1 H), 7.28-6.90 (m, 6 H), 6.17 (s, 1 H), 4.29 (s, 2 H), 4.24 (m, 1 H), 3.71 (m, 4 H), | LCMS method B: $R_t$ = 0.62 min, $(M + H)^+$ = 583.6 |

TABLE 10-continued

Characterization Data for Examples 79-240.

| Example | 1H NMR | MS |
|---|---|---|
|  | 3.58-3.32 (m, 4 H), 2.39 (s, 3 H), 1.97 (m, 4 H), 1.23 (m, 6 H). |  |
| 127 | $^1$H NMR (CD$_3$OD) δ 8.32 (d, J = 14.8 Hz, 1 H), 7.81-7.89 (m, 1 H), 7.70 (d, J = 8.4 Hz, 2 H), 7.47-7.50 (m, 2 H), 7.17-7.21 (m, 2 H), 6.88-7.00 (m, 1 H), 4.19-4.25 (m, 2 H), 3.63-3.98 (m, 9 H), 2.80-2.97 (m, 3 H), 2.05-2.15 (m, 2 H), 1.18-1.30 (m, 6 H). $^{19}$F NMR (CD$_3$OD): δ −120.11~−120.62. | LCMS method D: R$_t$ = 0.92; (M + H)$^+$ = 543.2 |
| 128 | $^1$H NMR (CD$_3$OD): δ 8.25-8.30 (m, 1 H), 7.76-7.83 (m, 1 H), 7.08-7.18 (m, 5 H), 6.84-6.95 (m, 1 H), 3.50-3.94 (m, 9 H), 2.77-2.98 (m, 3 H), 2.54-2.77 (m, 4 H), 1.83-1.95 (m, 4 H), 1.31 (t, J = 7.2 Hz, 3 H), 1.15-1.20 (m, 6 H). $^{19}$F NMR (CD$_3$OD): δ −120.12~−120.58. | LCMS method E: R$_t$ = 1.764 min; (M + H)$^+$ = 588.3 |
| 129 | $^1$H NMR (CD$_3$OD): δ 8.20-8.30 (m, 1 H), 7.70-7.85 (m, 1 H), 7.00-7.16 (m, 5 H), 6.80-6.93 (m, 1 H), 4.02 (t, J = 5.2 Hz, 2 H), 3.52-3.92 (m, 12 H), 2.75-2.93 (m, 3 H), 2.48-2.68 (m, 4 H), 1.81-1.93 (m, 4 H), 1.12-1.18 (m, 6 H). $^{19}$F NMR (CD$_3$OD): δ −120.12~−120.56. | LCMS method E: R$_t$ = 1.734 min; (M + H)$^+$ = 618.3 |
| 130 | $^1$H NMR (CD$_3$OD): δ 9.11 (s, 1 H), 8.63 (s, 1 H), 8.27 (s, 1 H), 7.79 (s, 1 H), 7.71 (d, J = 8.0 Hz, 2 H), 7.48 (d, J = 8.0 Hz, 2 H), 7.25-7.31 (m, 2 H), 7.04-7.06 (m, 1 H), 4.17 (s, 2 H), 3.90 (s, 2 H), 3.64-3.77 (m, 6 H), 3.06-3.13 (m, 1 H), 2.05-2.15 (m, 2 H), 1.22 (d, J = 5.6 Hz, 6H). $^{19}$F NMR (CD$_3$OD): δ −120.26~−120.34. | LCMS method E: R$_t$ = 0.835 min (M + H)$^+$ = 564.2 |
| 131 | $^1$H NMR (CD$_3$OD): δ 9.10 (s, 1 H), 8.61 (s, 1 H), 8.25 (s, 1 H), 7.76 (s, 1 H), 7.20-7.25 (m, 2 H), 6.90-7.15 (m, 4 H), 4.06 (t, J = 5.2 Hz, 2 H), 3.35-3.70 (m, 11 H), 3.05-3.11 (m, 1 H), 2.40-2.67 (m, 4 H), 1.70-1.95 (m, 4 H), 1.15-1.25 (m, 6 H). $^{19}$F NMR (CD$_3$OD): δ −120.63 (s, 1 F). | LCMS method E: R$_t$ = 1.834 min; (M + H)$^+$ = 693.3 |
| 132 | $^1$H NMR (CD$_3$OD): δ 9.09 (s, 1H), 8.62 (s, 1H), 8.20 (s, 1H), 7.98 (m, 1H), 7.67 (s, 1H), 7.50-7.60 (m, 1H), 7.20-7.30 (m, 2H), 7.05-7.10 (m, 1H), 6.75-6.77 (d, J = 8.8 Hz, 1H), 4.38 (s, 2H), 4.26 (s, 4H), 4.09 (s, 2H), 3.88 (s, 3H), 3.42 (s, 2H), 3.00-3.10 (m, 1H), 1.15-1.25 (m, 6H). $^{19}$F NMR (CD$_3$OD): δ −119.69~−119.72. | LCMS method E: R$_t$ = 31.370 min; M + H)$^+$ = 556.3 |
| 133 | $^1$H NMR (CD$_3$OD): δ 9.09 (s, 1H), 8.62 (s, 1H), 8.19 (s, 1H), 7.67 (s, 1H), 7.22-7.27 (m, 3H), 7.17-7.19 (m, 1H), 6.90-7.10 (m, 1H), 6.84 (s, 1H), 4.35 (s, 2H), 4.24 (s, 4H), 4.09 (s, 2H), 3.46 (s, 2H), 3.03-3.07 (m, 1H), 1.32 (s, 6H), 1.18-1.19 (m, 6H). $^{19}$F NMR (CD$_3$OD): δ −119.72~−119.69. | LCMS method D: R$_t$ = 0.910 min; (M + H)$^+$ = 608.4 |
| 134 |  | LCMS method D: R$_t$ = 0.910 min; (M + H)$^+$ = 611.6 |
| 135 |  | LCMS method E: R$_t$ = 1.894; (M + H) = 546.3 |
| 136 |  | LCMS method G: R$_t$ = 3.12 min; (M + H)$^+$ = 470.6 |

TABLE 10-continued

Characterization Data for Examples 79-240.

| Example | 1H NMR | MS |
|---|---|---|
| 137 | | LCMS method G: $R_t$ = 4.12 min; $(M + H)^+$ = 546.2 |
| 138 | | LCMS method G: $R_t$ = 5.32 min; $(M + H)^+$ = 611.7 |
| 139 | | LCMS method G: $R_t$ = 6.32 min; $(M + H)^+$ = 571.2 |
| 140 | $^1$H NMR (CD$_3$OD): δ 9.12 (s, 1H), 8.61 (s, 1H), 8.19 (s, 1H), 7.67 (s, 1H), 7.25-7.30 (m, 2H), 7.08-7.12 (m, 1H), 4.12 (s, 2H), 4.02 (s, 2H), 3.00-3.15 (m, 2H), 2.35-2.50 (m, 4H), 1.70-2.05 (m, 8H), 1.30-1.45 (m, 5H), 1.15-1.30 (m, 7H). $^{19}$F NMR (CD$_3$OD): δ −119.82. | LCMS method C: $R_t$ = 1.13 min; $(M + H)^+$ = 556.4 |
| 141 | $^1$H NMR (MeOD): δ 9.07 (s, 1H), 8.55 (s, 1H), 8.14 (s, 1H), 7.67-7.69 (m, 2H), 7.62 (s, 1H), 7.48-7.50 (m, 2H), 7.20-7.25 (m, 2H), 7.03-7.06 (m, 1H), 3.94-3.97 (m, 4H), 3.76-3.79 (m, 1H), 3.00-3.03 (m, 1H), 2.88-2.92 (m, 1H), 2.25-2.35 (m, 1H), 2.12-2.14 (m, 1H), 1.91-1.97 (m, 1H), 1.78-1.83 (m, 1H), 1.32 (d, J = 6.8 Hz, 3H), 1.18-1.18 (m, 6H). $^{19}$F NMR (CD$_3$OD): δ −119.85 | LCMS method C: $R_t$ = 0.639 min; $(M + H)^+$ = 550.1 |
| 142 | $^1$H NMR (CD$_3$OD 400 MHz): δ 8.29-8.33 (m, 1H), 7.80-7.88 (m, 1H), 7.60-7.62 (m, 2H), 7.43-7.45 (m, 2H), 7.18-7.20 (m, 2H), 6.83-6.97 (m, 1H), 4.50-4.52 (m, 2H), 4.11-4.15 (m, 2H), 3.93-3.96 (m, 3H), 3.55-3.76 (m, 4H), 2.95-3.05 (m, 2H), 2.75-2.90 (m, 3H), 1.93-2.05 (m, 5H), 1.18-1.35 (m, 7H). $^{19}$F NMR (CD$_3$OD): δ −120.17∼−120.58 | LCMS method C: $R_t$ = 0.607 min; $(M + H)^+$ = 589.0; |
| 143 | $^1$H NMR (CD$_3$OD): δ 8.15 (s, 1H), 7.55-7.57 (m, 3H), 7.37-7.39 (m, 1H), 7.15-7.27 (m, 3H), 4.26 (d, J = 8.4 Hz, 2H), 3.97-3.98 (m, 3H), 3.55-3.57 (m, 2H), 2.69-3.05 (m, 4H), 1.56-1.95 (m, 9H), 0.92-1.33 (m, 8H), 0.71-0.73 (m, 2H). $^{19}$F NMR (CD$_3$OD): δ −119.61∼−119.49. | LCMS method D: $R_t$ = 0.843 min; $(M + H)^+$ = 595.4 |
| 144 | | LCMS method E: $R_t$ = 0.780 min $(M + H)^+$ = 576.1 |
| 145 | | LCMS method E: $R_t$ = 0.68 min; $(M + H)^+$ = 544.1 |
| 146 | | LCMS method D: $R_t$ = 0.75 min; $(M + H)^+$ = 569.1 |
| 147 | | LCMS method B: $R_t$ = 1.34 min; $(M + H)^+$ = 610.2 |
| 148A | $^1$H NMR (CD$_3$OD): δ 9.10 (s, 1H), 8.59 (s, 1H), 8.17 (s, 1H), 7.64 (s, 1H), 7.22-7.28 (m, 2H), 7.06-7.10 (m, 1H), 4.10 (s, 2H), 3.98 (s, 2H), 3.16-3.20 (m, 1H), 3.05-3.08 (m, 1H), 2.65-2.75 (m, 1H), 2.44-2.46 (m, 2H), 1.92-1.97 (m, 2H), 1.70-1.80 (m, 6H), 1.45-1.60 (m, 2H), 1.35 (s, 3H), 1.20-1.21 (d, J = 6.8 Hz, 6H). $^{19}$F NMR (MeOD): δ −119.85∼−119.86. | LCMS method D: $R_t$ = 0.621 min; $(M + H)^+$ = 542.1 |
| 148B | $^1$H NMR (CD$_3$OD): δ 9.10 (s, 1H), 8.59 (s, 1H), 8.17 (s, 1H), | LCMS method C: $R_t$ = 0.713 min; |

TABLE 10-continued

Characterization Data for Examples 79-240.

| Example | 1H NMR | MS |
|---|---|---|
|  | 7.64 (s, 1H), 7.22-7.28 (m, 2H), 7.06-7.09 (m, 1H), 4.10 (s, 2H), 3.98 (s, 2H), 3.23-3.25 (m, 1H), 3.05-3.08 (m, 1H), 2.40-2.50 (m, 3H), 1.91-1.96 (m, 6H), 1.38-1.43 (m, 4H), 1.34 (s, 3H), 1.20-1.22 (d, J = 7.2 Hz, 6H). $^{19}$F NMR (CD$_3$OD): δ −119.85~−119.86. | (M + H)$^+$ = 542.1 |
| 149 |  | LCMS method D: R$_t$ = 0.816 min; (M + H)$^+$ = 573.2 |
| 150 | $^1$H NMR (CD$_3$OD): δ 9.09 (s, 1 H), 8.63 (s, 1 H), 8.45 (s, 1 H), 7.88 (s, 1 H), 7.18-7.37 (m, 6 H), 4.45 (s, 2 H), 3.75-3.90 (m, 4 H), 3.35-3.64 (m, 7 H), 2.95-3.15 (m, 1 H), 1.95-2.15 (s, 4 H), 1.05-1.25 (m, 6 H). | LCMS method D: R$_t$ = 0.616 min; (M + H)$^+$ = 595.0 |
| 151 |  | LCMS method C: R$_t$ = 0.421 min; (M + H)$^+$ = 540.2 |
| 152 | $^1$H NMR (CD$_3$OD): δ 9.12 (s, 1H), 8.60 (s, 1H), 8.19 (s, 1H), 7.67-7.70 (m, 2H), 7.67 (s, 1H), 7.50-7.55 (m, 2H), 7.25-7.30 (m, 2H), 7.05-7.10 (m, 1H), 4.09 (s, 2H), 4.02 (s, 2H), 3.75 (s, 2H), 3.14-3.18 (m, 1H), 3.06-3.09 (m, 1H), 2.39-2.42 (m, 2H), 1.95-2.00 (m, 2H), 1.21-1.22 (d, J = 6.0Hz, 6H). $^{19}$F NMR (CD$_3$OD): δ −119.81. | LCMS method D: R$_t$ = 0.626 min; (M + H)$^+$ = 536.1 |
| 153 |  | LCMS method D: R$_t$ = 0.959 min; (M + H)$^+$ = 586.1 |
| 154 |  | LCMS method C: R$_t$ = 0.541 min; (M + H)$^+$ = 558.0 |
| 155 |  | LCMS method D: R$_t$ = 0.875 min (M + H)+ = 574.1 |
| 156 |  | LCMS method G: R$_t$ = 3.12 min; (M + H)$^+$ = 512.2 |
| 157 |  | LCMS method G: R$_t$ = 5.813 min; (M + H)$^+$ = 585.7 |
| 158 |  | LCMS method G: R$_t$ = 7.22 min; (M + H)$^+$ = 510.2 |
| 159 |  | LCMS method G: R$_t$ = 6.38 min; (M + H)$^+$ = 527.2 |
| 160A | $^1$H NMR (CD$_3$OD): δ 9.10 (s, 1H), 8.61 (s, 1H), 8.25 (s, 1H), 7.76 (s, 1H), 7.20-7.30 (m, 2H), 6.80-7.15 (m, 4H), 3.80 (s, 2H), 3.40-3.65 (m, 4H), 3.00-3.15 (m, 1H), 2.50-3.00 (m, 4H), 1.75-2.00 (m, 4H), 1.22 (d, J = 6.4 Hz, 6H). $^{19}$F NMR (CD$_3$OD): δ −120.46. | LCMS method E: R$_t$ = 1.060: (M + H)$^+$ = 581.2 |
| 160B | $^1$H NMR (CD$_3$OD): δ 9.08 (s, 1H), 8.59 (s, 1H), 8.23 (s, 1H), 7.74 (s, 1H), 7.15-7.25 (m, 2H), 6.90-7.15 (m, 4H), 3.85-4.00 (m, 2H), 3.45-3.65 (m, 5H), 2.55-3.15 (m, 4H), 1.75-2.05 (m, 4H), 1.15-1.25 (m, 6H). $^{19}$F NMR (CD$_3$OD): δ −120.31. | LCMS method E: R$_t$ = 1.112 min; (M + H)$^+$ = 581.2 |
| 161 |  | LCMS method C: R$_t$ = 0.702 min; (M + H)$^+$ = 771 |
| 162 | $^1$H NMR (CD$_3$OD): δ 8.13-8.16 (m, 2H), 7.59-7.64 (m, 2H), 7.13-7.20 (m, 3H), 6.99-7.02 (m, 1H), | LCMS method C: R$_t$ = 0.612 min; (M + H)$^+$ = 520.1 |

TABLE 10-continued

Characterization Data for Examples 79-240.

| Example | 1H NMR | MS |
|---|---|---|
| | 5.23-5.31 (m, 1H), 4.19 (s, 4H), 3.91-3.94 (m, 2H), 3.32-3.37 (m, 6H), 2.34-2.36 (d, J = 6.4 Hz, 2H), 1.61-1.64 (m, 2H), 1.23-1.30 (m, 2H), 1.18-1.20 (d, J = 6.0 Hz, 6H). $^{19}$F NMR (CD$_3$OD): δ −120.36 | |
| 163 | $^1$H NMR (CD$_3$OD): δ 8.56 (d, J = 8.8 Hz, 1 H), 7.82-8.10 (m, 1 H), 7.05-7.40 (m, 6 H), 4.60-4.65 (m, 1 H), 4.47 (s, 2 H), 3.75-4.15 (m, 4 H), 3.33-3.72 (m, 7 H), 2.65-3.00 (m, 3 H), 1.91-2.36 (m, 4 H), 0.93-1.33 (m, 6 H). $^{19}$F NMR (CD$_3$OD): δ −76.96, −117.20~−117.40. | LCMS method C: R$_t$ = 0.598 min; (M + H)$^+$ = 574.0 |
| 164 | | LCMS method D: R$_t$ = 0.951 min; (M + H)$^+$ = 562.1 |
| 165 | | LCMS method E: R$_t$ = 0.911 min; (M + H)$^+$ = 558.1 |
| 166 | | LCMS method E: R$_t$ = 0.962 min; (M + H)+ = 594.1 |
| 167 | | LCMS method E: R$_t$ = 1.024 min; (M + H)$^+$ = 482.2 |
| 168 | | LCMS method G: R$_t$ = 3.12 min; (M + H)$^+$ = 469.2 |
| 169 | $^1$H NMR (MeOH-d4): δ 8.25 (s, 1 H), 7.59 (s, 1 H), 7.34 (d, J = 7.2 Hz, 1 H), 7.28-7.04 (m, 8 H), 4.29 (s, 2 H), 3.72 (m, 4 H), 3.32 (m, 4 H), 1.97 (m, 4 H), 1.52 (m, 1 H), 0.77 (m, 2 H), 0.56 (m, 2 H). | LCMS method B: R$_t$ = 1.63 min; (M + H)$^+$ = 603.7 |
| 170 | $^{19}$F NMR (MeOD): δ −76.962 (s, 7 F), −117.586 (s, 1 F). $^1$H NMR (MeOD): δ 8.40 (s, 1 H), 7.77 (d, J = 18.0 Hz, 2 H), 7.45-7.59 (m, 1 H), 7.29-7.44 (m, 5 H), 7.13-7.28 (m, 3 H), 4.40 (s, 2 H). 3.78-3.94 (m, 4 H), 3.75 (s, 3 H), 3.34-3.72 (m, 4 H) 1.98-2.37 (m, 4 H), 1.69 (s, 1 H), 0.93 (s, 2 H), 0.71 (s, 2 H) | LCMS method C: R$_t$ = 0.703 min; (M + H)$^+$ = 619.0 |
| 171 | $^1$H NMR (CD$_3$OD): δ 8.41 (s, 1H), 8.15 (s, 1H), 7.98 (d, J = 8.4 Hz, 1H), 7.75 (s, 1H), 7.65 (d, J = 8.8 Hz, 1H), 7.50 (d, J = 8.0 Hz, 1H), 7.30-7.45 (m, 3H), 7.10-7.30 (m, 2H), 4.64 (s, 2H), 3.86 (s, 4H), 3.48 (s, 4H), 2.13 (s, 4H), 1.68 (s, 1H), 0.92 (s, 2H), 0.71 (s, 2H). $^{19}$F NMR (CD$_3$OD): δ −77.106. | LCMS method C: R$_t$ = 0.845 min; (M + H)$^+$ = 587.3 |
| 172 | $^1$H NMR (CD$_3$OD): δ 8.16 (s, 1H), 7.68-7.73 (m, 1H), 7.67 (s, 1H), 7.48 (d, J = 8.0 Hz, 1H), 7.41 (s, 1H), 7.32 (d, J = 8.0 Hz, 1H), 7.13-7.26 (m, 4H), 7.03 (dd, J = 9.2 4.4 Hz, 1H), 3.44-3.64 (m, 5H), 3.30-3.40 (m, 1H), 2.54-2.72 (m, 2H), 2.34-2.46 (m, 2H), 2.18 (s, 3H), 1.65-1.95 (m, 5H), 0.85-0.95 (m, 2H), 0.60-0.75 (m, 2H). $^{19}$F NMR (CD$_3$OD): δ −120.48 (s, 1F). | LCMS method C: R$_t$ = 0.683 min; (M + H)$^+$ = 637.0 |
| 173 | | LCMS method C: R$_t$ = 0.56 min; (M + H)$^+$ = 560.0 |
| 174 | | LCMS method G: R$_t$ = 2.36 min; (M + H)$^+$ = 561.2 |

TABLE 10-continued

Characterization Data for Examples 79-240.

| Example | 1H NMR | MS |
|---|---|---|
| 175 | | LCMS method G: $R_t$ = 3.36 min; $(M + H)^+$ = 574.2 |
| 176 | | LCMS method A: $R_t$ = 0.66 min; $(M + H)^+$ = 507.1 |
| 177 | | LCMS method A: $R_t$ = 0.66 min; $(M + H)^+$ = 502.1 |
| 178 | | LCMS method B: $R_t$ = 1.51 min; $(M + H)^+$ = 608.1 |
| 179 | | LCMS method B: $R_t$ = 1.48 min; $(M + H)^+$ = 605.1 |
| 180 | $^1$H NMR (CD$_3$OD) δ: 8.48 (s, 1H), 8.03 (m, 1H), 7.88 (m, 1H), 7.49 (m, 1H), 7.39-7.36 (m, 3H), 7.23 (s, 1H), 7.19 (d, J = 8.4 Hz, 1H), 7.11 (d, J = 8.4 Hz, 1H), 4.43 (s, 1H), 3.91 (m, 4H), 3.64-3.42 (m, 3H), 2.22-2.03 (m, 5H), 1.11 (m, 4H). | LCMS method B: $R_t$ = 1.45 min; $(M + H)^+$ = 578.1 |
| 181 | | LCMS method B: $R_t$ = 1.45 min; $(M + H)^+$ = 566.2 |
| 182 | | LCMS method G: $R_t$ = 3.36 min; $(M + H)+$ = 586.2 |
| 183 | | LCMS method G: $R_t$ = 3.07 min; $(M + H)^+$ = 560.49 |
| 183A | $^1$H NMR (CD$_3$OD): δ 8.28 (s, 1H), 7.79 (s, 1H), 6.86-7.19 (m, 6H), 4.74-4.76 (m, 0.5 H), 3.55-3.96 (m, 6.5H), 2.95-2.96 (m, 2.0 H), 2.56-2.76 (m, 5 H), 1.84-1.96 (m, 4H), 1.14-1.20 (m, 6H). $^{19}$F NMR (CD$_3$OD): δ −120.340 SFC analytical method A: $t_R$ = 2.254 min, ee = 100%. | LCMS method E: $R_t$ = 1.595 min; $(M + H)^+$ = 560.3 |
| 183B | $^1$H NMR (CD$_3$OD): δ 8.28 (s, 1H), 7.79 (s, 1H), 6.86-7.19 (m, 6H), 4.74-4.76 (m, 0.5 H), 3.55-3.96 (m, 6.5H), 2.95-2.96 (m, 2.0 H), 2.56-2.76 (m, 5 H), 1.84-1.98 (m, 4H), 1.15-1.20 (m, 6H). $^{19}$F NMR (CD$_3$OD): δ −120.340 SFC analytical method A: $t_R$ = 0.879 min, ee = 100%. | LCMS method D: $R_t$ = 1.596 min; $(M + H)^+$ = 560.3 |
| 184 | | LCMS method B: $R_t$ = 1.36 min; $(M + H)^+$ = 533.2 |
| 185 | $^1$H NMR (CD$_3$OD): δ 8.44-8.53 (m, 1 H), 7.68-7.95 (m, 1 H), 7.02-7.37 (m, 6 H), 4.37-4.41 (m, 2 H), 3.88-4.11 (m, 5 H), 3.30-3.67 (m, 6 H), 2.07-2.45 (m, 6 H), 0.75-1.07 (m, 6 H). $^{19}$F NMR (CD$_3$OD): δ −116.59. | LCMS method D: $R_t$ = 0.898 min; $(M + H)^+$ = 590.2 |
| 186 | | LCMS method D: $R_t$ = 0.878 min; $(M + H)^+$ = 574.4 |
| 187 | $^1$H NMR (CD$_3$OD): δ 8.30 (s, 1 H), 7.78 (d, J = 1.2 Hz, 1 H), 7.32-7.35 (m, 1 H), 7.19-7.20 (m, 1 H), 6.90-7.02 (m, 4 H), 4.04-4.08 (m, 1 H), 3.56-3.68 (m, 7 H), 2.48-2.64 (m, 5 H), 1.78-1.93 (m, 4 H), 1.09 (d, J = 6.8 Hz, 3 H), 0.99-1.01 (m, 3 H). $^{19}$F NMR (CD$_3$OD): δ −70.50, −119.30. | LCMS method D: $R_t$ = 0.813 min; $(M + H)^+$ = 628.1 |
| 188 | $^1$H NMR (MeOH-d4): δ 8.42 (s, 1 H), 7.76 (s, 1 H), 7.44 (m, 1 H), 7.38 (m, 5 H), 7.22 (m, 2 H), 6.98 (d, J = 7.6 Hz, 1 H), 4.38 (s, | LCMS method B: $R_t$ = 1.49 min; $(M + H)^+$ = 601.5 |

TABLE 10-continued

Characterization Data for Examples 79-240.

| Example | 1H NMR | MS |
|---|---|---|
| | 2 H), 4.02-3.72 (m, 4 H), 3.62 (m, 2 H), 3.58 (s, 2 H), 3.40 (m, 2 H), 2.24-1.98 (m, 4 H), 1.64 (m, 1 H), 0.92 (m, 2 H), 0.70 (m, 2 H). | |
| 189 | $^1$H NMR (CD$_3$OD): δ 8.14 (s, 1H), 7.61 (s, 1H), 7.50-7.58 (m, 1H), 7.38 (d, J = 7.6 Hz, 1H), 7.10-7.30 (m, 4H), 4.17 (s, 4H), 3.35-3.40 (m, 5H), 2.45-2.50 (m, 2H), 1.85-1.95 (m, 2H), 1.65-1.75 (m, 3H), 1.44-1.74 (m, 10H), 1.15-1.35 (m, 5H), 0.90-1.10 (m, 4H), 0.70-0.80 (m, 1H). $^{19}$F NMR (MeOD): δ −119.75. | LCMS method C: $R_t$ = 0.750 min; $(M + H)^+$ = 653.1 |
| 190 | | LCMS method E: $R_t$ = 1.314 min; $(M + H)^+$ = 586.2 |
| 190A | | LCMS method E: $R_t$ = 1.724 min; $(M + H)^+$ = 608.2 |
| 191 | $^1$H NMR (CD3OD): δ 8.16 (s, 1H), 7.66 (s, 1H), 7.42 (s, 1H), 7.31 (s, 1H), 7.06-7.23 (m, 7H), 3.94 (q, J = 7.2 Hz, 2H), 3.75 (s, 2H), 3.41-3.63 (m, 4H), 2.78 (s, 2H), 2.56 (s, 2H), 1.69-1.92 (m, 5H), 1.31 (t, J = 7.2 Hz, 3H), 0.89 (s, 2H), 0.67 (s, 2H). $^{19}$F NMR (CD$_3$OD): δ −76.916 (s, 0.3F), −120.337 (s, 1F). | LCMS method E: $R_t$ = 1.614 min; $(M + H)^+$ = 630.3 |
| 192 | $^1$H NMR (CD$_3$OD): δ 11.77 (s, 1H), 8.51 (s, 1H), 7.92 (d, J = 8.4 Hz, 1H), 7.87-7.84 (m, 2H), 7.55 (s, 1H), 7.43 (d, J = 8.4 Hz, 1H), 7.28 (m, 1H), 7.00 (m, 1H), 6.76 (m, 1H), 4.80-4.70 (m, 1H), 4.68 (s, 2H), 4.45-4.30 (m, 2H), 4.05-3.95 (m, 2H), 3.80-3.60 (m, 2H), 3.50-3.30 (m, 2H), 2.35-2.10 (m, 5H), 1.85 (m, 2H), 1.57 (m, 4H), 1.30 (m, 2H). | LCMS method B: $R_t$ = 1.32 min; $(M + H)^+$ = 553.6 |
| 193 | $^1$H NMR (CD$_3$OD): δ 8.52 (s, 1H), 7.57 (s, 1H), 7.36 (d, J = 7.2 Hz, 1H), 7.32-7.30 (m, 1H), 7.19 (d, J = 7.2 Hz, 1H), 7.10 (s, 1H), 7.01-6.98 (m, 1H), 6.79-6.75 (m, 1H), 4.80-4.70 (m, 1H), 4.42 (s, 2H), 4.40-3.95 (m, 4H), 3.80-3.60 (m, 2H), 3.50-3.30 (m, 2H), 2.35-2.10 (m, 5H), 1.85 (m, 2H), 1.58 (m, 4H), 1.34 (s, 6H), 1.30 (m, 2H). | LCMS method B: $R_t$ = 1.43 min; $(M + H)^+$ = 532.7 |
| 194 | | LCMS method G: $R_t$ = 4.29 min; $(M + H)^+$ = 568.54 |
| 195 | $^1$H NMR (MeOH-d4): δ 8.27 (s, 1 H), 7.63 (m, 1 H), 7.60 (d, J = 8 Hz, 2 H), 7.42 (d, J = 8 Hz, 2 H), 7.39-7.14 (m, 4 H), 7.08 (m, 2 H), 4.27 (s, 2 H), 3.78 (t, J = 6.8 Hz, 2 H), 3.86-3.58 (m, 4 H), 3.58-3.22 (m, 4 H), 2.45 (t, J = 7.6 Hz, 2 H), 2.24-1.86 (m, 6 H), 1.54 (m, 1 H), 0.78 (m, 2 H), 0.56 (m, 2 H). | LCMS method B: $R_t$ = 1.43 min; $(M + H)^+$ = 629.8 |
| 196 | $^1$H NMR (MeOH-d4): δ 8.36 (s, 1 H), 7.74 (s, 1 H), 7.49 (d, J = 7.3 Hz, 1 H), 7.38-7.30 (m, 4 H), 7.24 (m, 2 H), 7.15 (d, J = 7.6 Hz, 1 H), 7.06 (s, 1 H), 4.29 (s, 2 H), 3.84-3.64 (m, 4 H), 3.60-3.48 (m, 1 H), 3.44 (m, 2 H), 3.40-3.26 (m, 2 H), 2.16-1.80 (m, 4 H), 1.57 (m, 1 H), 0.82 (m, 2 H), 0.60 (m, 2 H). | LCMS method B: $R_t$ = 1.37 min; $(M + H)^+$ = 601.5 |

TABLE 10-continued

Characterization Data for Examples 79-240.

| Example | 1H NMR | MS |
|---|---|---|
| 197A | | LCMS method E:<br>$R_t$ = 1.814 min;<br>$(M + H)^+$ = 568.6 |
| 197B | | LCMS method E:<br>$R_t$ = 1.834 min;<br>$(M + H)^+$ = 568.6 |
| 198 | $^1$H NMR (CD$_3$OD): δ 8.49 (s, 1H), 8.14 (s, 1H), 7.96 (d, J = 8.4 Hz, 1H), 7.84 (s, 1H), 7.65 (dd, J = 8.4, 1H), 7.45-7.6 (m, 1H), 7.37 (d, J = 5.2 Hz, 2H), 7.29 (d, J = 7.2 Hz, 1H), 6.30 (s, 1H), 4.64 (s, 2H), 4.38 (m, 1H), 3.90 (d, J = 2.8 Hz, 4H), 3.40-3.75 (m, 4H), 2.15 (brs, 4H), 1.36 (d, J = 6.4 Hz, 6H). $^{19}$F NMR (CD$_3$OD): δ −77.146, −117.398. | LCMS method D:<br>$R_t$ = 0.602 min;<br>$(M + H)+$ = 554.2 |
| 199 | $^1$H NMR (CD$_3$OD): δ 8.05 (s, 1H), 7.36-7.47 (m, 2H), 7.30-7.33 (m, 1H), 7.25 (s, 1H), 7.13 (s, 1H), 6.95-7.10 (m, 4H), 3.35-3.75 (m, 6H), 2.64-2.77 (m, 2H), 2.40-2.54 (m, 2H), 1.70-1.96 (m, 4H), 1.52-1.66 (m, 1H), 0.65-0.95 (m, 2H), 0.50-0.60 (m, 2H). $^{19}$F NMR(CD$_3$OD): δ −113.73 (s, 2F). | LCMS method D:<br>$R_t$ = 0.660 min;<br>$(M + H)^+$ = 620.2 |
| 200 | | LCMS method B:<br>$R_t$ = 1.48 min;<br>$(M + H)^+$ = 557.7 |
| 201 | $^1$H NMR (CD$_3$OD): δ 11.77 (s, 1H), 8.51 (s, 1H), 7.93-7.87 (m, 2H), 7.84 (s, 1H), 7.59 (s, 1H), 7.42 (d, J = 8.0 Hz, 1H), 7.30 (m, 1H), 6.96 (m, 1H), 6.77 (m, 1H), 4.68 (s, 2H), 4.40-4.35 (m, 2H), 4.05-3.95 (m, 2H), 3.80-3.60 (m, 4H), 3.50-3.30 (m, 2H), 2.28-2.11 (m, 5H), 1.01 (m, 1H), 0.47 (m, 2H), 0.15 (m, 2H). | LCMS method B:<br>$R_t$ = 1.48 min;<br>$(M + H)^+$ = 539.7 |
| 202 | | LCMS method B:<br>$R_t$ = 1.53 min;<br>$(M + H)^+$ = 587.6 |
| 203 | | LCMS methodG:<br>$R_t$ = 4.53 min;<br>$(M + H)^+$ = 557.3 |
| 204 | | LCMS methodG:<br>$R_t$ = 2.53 min;<br>$(M + H)^+$ = 601.7 |
| 205 | | LCMS method D:<br>$R_t$ = 1.48 min;<br>$(M + H)+$ = 629.1 |
| 206A | | LCMS method C:<br>$R_t$ = 1.38 min;<br>$(M + H)+$ = 562.7 |
| 206B | | LCMS method D:<br>$R_t$ = 0.723 min;<br>$(M + H)^+$ = 562.1 |
| 206C | | LCMS method D:<br>$R_t$ = 0.713 min;<br>$(M + H)^+$ = 562.1 |
| 207 | $^1$H NMR (CD$_3$OD): δ 8.25 (s, 1 H), 7.66 (brs, 1 H), 7.20 (dd, J = 8.8, 3.2 Hz, 1 H), 7.04 (s, 2 H), 6.98 (m, 2 H), 6.87-6.88 (m, 1 H), 3.58-3.69 (m, 9 H), 3.19 (s, 3 H), 2.64-2.67 (m, 4 H), 1.80-1.94 (m, 4 H). $^{19}$F NMR (CD$_3$OD): δ −119.65. | LCMS method D:<br>$R_t$ = 0.903 min;<br>$(M + H)^+$ = 548.1 |
| 208 | $^1$H NMR (CD$_3$OD): δ 8.48 (s, 1H), 7.64 (s, 1H), 7.35-7.33 (m, 4H), 7.20-7.10 (m, 6H), 6.85-6.81 (m, 1H), 5.01-4.95 (m, 2H), 4.40-4.35 (m, 2H), 4.30- | LCMS method B:<br>$R_t$ = 1.43 min;<br>$(M + H)^+$ = 567.6 |

TABLE 10-continued

Characterization Data for Examples 79-240.

| Example | 1H NMR | MS |
|---|---|---|
| | 4.05 (m, 2H), 3.80-3.53 (m, 2H), 3.48-3.30 (m, 3H), 2.06-1.90 (m, 5H). | |
| 209 | | LCMS method G: $R_t$ = 3.81 min; $(M + H)^+$ = 491.6 |
| 210 | | LCMS method G: $R_t$ = 3.59 min; $(M + H)^+$ = 575.54 |
| 211 | | LCMS method G: $R_t$ = 2.52 min; $(M + H)^+$ = 572.70 |
| 212 | | LCMS method G: $R_t$ = 2.99 min; $(M + H)^+$ = 584.72 |
| 213 | | LCMS method D: $R_t$ = 0.13 min; $(M + H)^+$ = 601.3 |
| 214 | | LCMS method A: $R_t$ = 1.40 min $(M + H)+$ = 542.1 |
| 215 | | LCMS method E: $R_t$ = 1.42 min; $(M + H)+$ = 526.1 |
| 216 | | LCMS method G: $R_t$ = 3.19 min; $(M + H)^+$ = 621.7 |
| 217 | | LCMS method D: $R_t$ = 0.39 min; $(M + H)^+$ = 637.3 |
| 218 | | LCMS method G: $R_t$ = 3.62 min; $(M + H)^+$ = 586.80 |
| 219 | | LCMS method A: $R_t$ = 0.1 min; $(M + H)^+$ = 544.1 |
| 220 | | LCMS method E: $R_t$ = 1.44 min; $(M + H)^+$ = 644.1 |
| 221 | | LCMS method E: $R_t$ = 3.83 min; $(M + H)^+$ = 596.76 |
| 222 | | LCMS method G: $R_t$ = 4.75 min; $(M + H)^+$ = 596.49 |
| 223 | | LCMS method D: $R_t$ = 0.13 min; $(M + H)^+$ = 609.1 |
| 224 | | LCMS method D: $R_t$ = 0.12 min; $(M + H)^+$ = 586.1 |
| 225 | | LCMS method C: $R_t$ = 0.539 min; $(M + H)^+$ = 484.2 |
| 226 | $^1$H NMR (CD$_3$OD): δ 8.16 (s, 1H), 7.47-7.64 (m, 3H), 7.31-7.33 (m, 1H), 7.18-7.22 (m, 1H), 7.01-7.12 (m, 5H), 3.43-3.66 (m, 6H), 2.64-2.69 (m, 2H), 2.46 (s, 2H), 2.21 (s, 3H), 1.73-1.90 (m, 4H). $^{19}$F NMR (CD$_3$OD): δ −120.33. | LCMS method C: $R_t$ = 0.361 min; $(M + H)^+$ = 576.1 |
| 227 | $^1$H NMR (CD$_3$OD): δ 9.12 (s, 1H), 8.65 (s, 1H), 8.22 (s, 1H), 7.67-7.71 (m, 3H), 7.46 (d, J = 8.8 Hz, 2H), 7.25-7.33 (m, 2H), 7.10-7.14 (m, 1H), 4.41 (s, 2H), 4.28 (s, 4H), 4.13 (s, 2H), 3.60 (s, 2H), 3.05-3.13 (m, 1H), 1.16-1.22 (m, 6H). $^{19}$F NMR (CD$_3$OD): δ −119.62. | LCMS method C: $R_t$ = 0.670 min; $(M + H)^+$ = 550.1 |
| 228 | $^1$H NMR (CD$_3$OD) δ 8.13 (s, 1H), 7.70 (d, J = 8.4 Hz, 2H), 7.56 (s, 1H), 7.47 (d, J = 8.4 Hz, 2H), 7.34-7.40 (m, 2H), 7.11-7.24 (m, 5H), 4.36 (s, 2H), 4.21 | LCMS method C: $R_t$ = 0.735 min; $(M + H)^+$ = 548.1 |

TABLE 10-continued

Characterization Data for Examples 79-240.

| Example | 1H NMR | MS |
|---|---|---|
| | (s, 4H), 4.09 (s, 2H), 3.61 (s, 2H), 2.78-2.89 (m, 1H), 1.13 (d, J = 6.8 Hz, 3H), 1.10 (d, J = 7.2 Hz, 3H). $^{19}$F NMR (CD$_3$OD): δ −119.81. | |
| 229 | $^1$H NMR(CD$_3$OD): δ 8.13 (s, 1H), 7.93 (d, J = 8.4 Hz, 2H), 7.53-7.57 (m, 3H), 7.35-7.40 (m, 2H), 7.10-7.22 (m, 5H), 4.38 (s, 2H), 4.22 (s, 4H), 4.10 (s, 2H), 3.64 (s, 2H), 3.13 (s, 3H), 2.79-2.88 (m, 1H), 1.13 (d, J = 6.8 Hz, 3H), 1.10 (d, J = 6.8 Hz, 3H). $^{19}$F NMR (CD$_3$OD): δ −119.81. | LCMS method C: R$_t$ = 0.712 min; (M + H)$^+$ = 601.1 |
| 230 | $^1$H NMR (CD$_3$OD): δ 8.15 (s, 1H), 7.62-7.66 (m, 2H), 7.41-7.47 (m, 1H), 7.18-7.32 (m, 2H), 7.13 (dd, J = 8.4, 2.8 Hz, 1H), 6.95-7.08 (m, 4H), 3.43-3.66 (m, 6H), 2.65-2.71 (m, 2H), 2.45-2.50 (m, 2H), 2.36 (s, 3H), 1.75-1.90 (m, 4H). $^{19}$F NMR (CD$_3$OD): δ −120.15∼−120.21. | LCMS method C: R$_t$ = 0.616 min; (M + H)$^+$ = 576.1 |
| 231 | | LCMS method D: R$_t$ = 0.682 min; (M + H)$^+$ = 526.6 |
| 232 | $^1$H NMR (CD$_3$OD): δ 9.14 (s, 1 H), 8.65 (s, 1 H), 8.40 (s, 1 H), 7.81 (s, 1H), 7.25-7.45 (m, 3 H), 4.30-4.50 (m, 8 H), 3.15-3.20 (m, 2 H), 3.05-3.15 (m, 1 H), 1.80-2.09 (m, 4 H), 1.70-1.79 (m, 2 H), 1.45-1.65 (m, 3 H), 1.10-1.25 (m, 6 H). $^{19}$F NMR (CD$_3$OD): δ −77.06, −117.77, −101.11∼−101.76, −90.19∼−90.83. | LCMS method C: R$_t$ = 0.652 min; (M + H)$^+$ = 539.2 |
| 233 | | LCMS method B: R$_t$ = 1.152 min; (M + H)$^+$ = 540.2 |
| 234 | $^1$H NMR (CD$_3$OD) δ: 8.68 (s, 1H), 8.47 (m, 1H), 8.18 (d, J = 7.2 Hz, 1H), 7.90 (m, 1H), 7.68 (m, 1H), 7.36-7.33 (m, 3H), 7.22 (s, 1H), 7.19 (d, J = 8.0 Hz, 1H), 7.11 (d, J = 8.0 Hz, 1H), 4.42 (s, 1H), 3.85 (m, 4H), 3.66-3.48 (m, 3H), 2.87 (q, J = 7.6 Hz, 2H), 2.11 (m, 4H), 2.87 (d, J = 7.6 Hz, 6H). | LCMS method D: R$_t$ = 0.812 min; (M + H)$^+$ = 566.1 |
| 235 | | LCMS method B: R$_t$ = 1.252 min; (M + H)$^+$ = 531.2 |
| 236 | | LCMS method B: R$_t$ = 1.112 min; (M + H)$^+$ = 517.2 |
| 237 | | LCMS method E: R$_t$ = 0.07 min; (M + H)$^+$ = 569.5 |
| 237A | $^1$H NMR (d4-MeOH) 8.38 (s, 1H), 7.62 (s, 1H), 7.16-7.42 (m, 5H), 7.14 (m, 2H), 4.25-4.62 (m, 8H), 3.94 (m, 2H), 3.41 (m, 2H), 3.12 (d, 2H), 2.81 (m, 1H), 1.88 (m, 1H), 1.61 (d, 2H), 1.33 (m, 2H), 1.14 (d, 3H), 1.10 (d, 3H) ppm. | LC/MS (16 min method) - Rt = 5.07 min; (M + H)$^+$ = 503.8 |
| 238 | $^1$H NMR (CD$_3$OD): δ 8.50-8.60 (m, 1H), 7.65-7.95 (m, 1H), 7.20-7.45 (m, 3H), 4.20-4.75 (m, 5H), 3.85-3.95 (m, 1H), 3.35-3.65 (m, 3H), 2.90-3.25 (m, 9H), 1.75-2.40 (m, 9H), 1.05-1.45 (m, 12H). $^{19}$F NMR (CD$_3$OD): δ −117.14∼−116.42, −83.63. | LCMS method D: R$_t$ = 0.709 min; (M + H)$^+$ = 617.3 |
| 239 | $^1$H NMR (MeOD): δ 8.52 (s, 1H), 7.84 (s, 1H), 7.20-7.35 (m, 3H), 4.30-4.60 (m, 4H), 3.85- | LCMS method D: R$_t$ = 1.055 min; (M + H)$^+$ = 512.3 |

TABLE 10-continued

Characterization Data for Examples 79-240.

| Example | 1H NMR | MS |
|---|---|---|
| | 4.05 (m, 3H), 3.75-3.85 (m, 1H), 3.60-3.70 (m, 1H), 3.40-3.50 (m, 2H), 3.25-3.30 (m, 1H), 2.65-2.80 (m, 2H), 2.45-2.60 (m, 2H), 1.90-2.05 (m, 2H), 1.55-1.70 (m, 2H), 1.40-1.55 (m, 6H), 1.05-1.25 (m, 6H). $^{19}$F NMR (MeOD): δ −116.90~117.18, −76.95. | |
| 240 | | LCMS method D: R$_t$ = 1.155 min; (M + H)$^+$ = 526.3 |

Examples 241-249

Examples 241-249 were prepared according to the procedure described in Table 11 using the appropriate starting materials. Characterization data for Examples 241-249 is shown in Table 12.

TABLE 11

Examples 241-249

| Example | Name | Structure | Synthetic method |
|---|---|---|---|
| 241 | tert-butyl ((1r,4r)-4-((7-(5-((2-(diisopropylcarbamoyl)-4-fluorophenyl)amino)pyrimidin-4-yl)-2,7-diazaspiro[3.5]nonan-2-yl)methyl)cyclohexyl)carbamate | 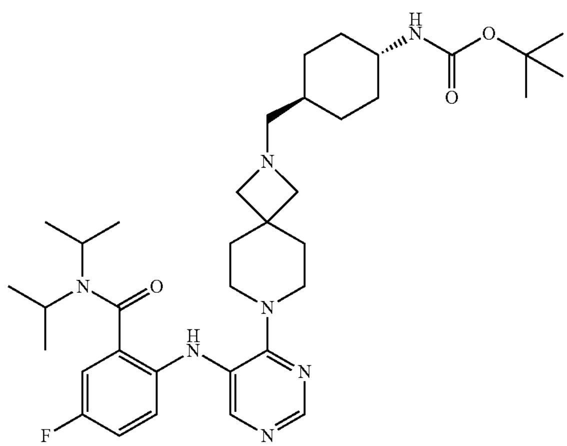 [SMILES: CC(C)N(C(=O)c1cc(F)ccc1Nc1cncnc1N1CCC2(CC1)CN(C[C@H]1CC[C@H](NC(=O)OC(C)(C)C)CC1)C2)C(C)C] | Synthesized by method described in Example 16. In final step, tert-butyl ((1r,4r)-4-formylcyclohexyl)carbamate was used under reductive amination conditions. |
| 242 | 1-((6-(5-((5-fluoro-2'-isopropyl-[1,1'-biphenyl]-2-yl)amino)pyrimidin-4-yl)-2,6-diazaspiro[3.3]heptan-2-yl)methyl)cyclohexan-1-ol | 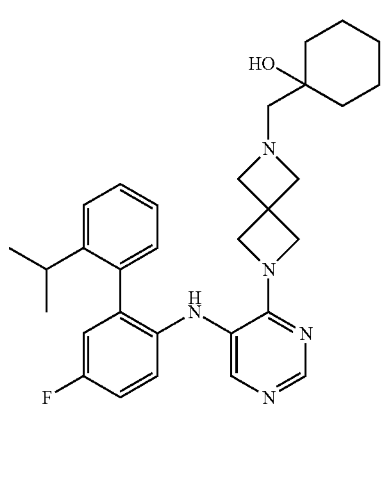 [SMILES: CC(C)c1ccccc1-c1cc(F)ccc1Nc1cncnc1N1CC2(CN(CC3(O)CCCCC3)C2)C1] | Synthesized by a method similar to Example 71 utilizing 1-oxaspiro[2.5]octane in final step |

TABLE 11-continued

Examples 241-249

| Example | Name | Structure | Synthetic method |
|---|---|---|---|
| 243 | 5-((7-(5-(((5-fluoro-2'-isopropyl-[1,1'-biphenyl]-2-yl)amino)pyrimidin-4-yl)-2,7-diazaspiro[4.4]nonan-2-yl)methyl)-1,3-dihydro-2H-benzo[d]imidazol-2-one | 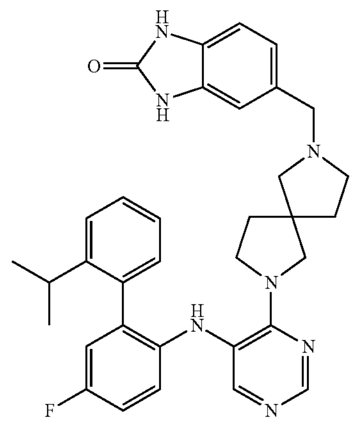 [SMILES: CC(C)c1ccccc1-c1cc(F)ccc1Nc1cncnc1N1CCC2(CCN(Cc3ccc4[nH]c(=O)[nH]c4c3)C2)C1] | Synthesized by a method similar to Example 71. In the final step, i 2-oxo-2,3-dihydro-1H-benzo[d]imidazole 5-carbaldehyde was used under reductive amination conditions. |
| 244 | N-(4-fluoro-2-(4-isopropylpyrimidin-5-yl)phenyl)-4-(6-((tetrahydro-2H-pyran-4-yl)methyl)-2,6-diazaspiro[3.3]heptan-2-yl)pyrimidin-5-amine | 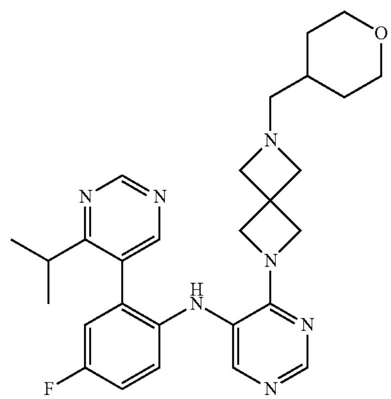 [SMILES: CC(C)c1ncncc1-c1cc(F)ccc1Nc1cncnc1N1CC2(CN(CC3CCOCC3)C2)C1] | Synthesized by method similar to Example 71. In the final step, tetrahydro-2H-pyran-4-carbaldehyde was used under reductive amination conditions. |
| 245 | N-(5-fluoro-2'-isopropoxy-[1,1'-biphenyl]-2-yl)-4-(2-isobutyl-2,7-diazaspiro[3.5]nonan-7-yl)pyrimidin-5-amine | 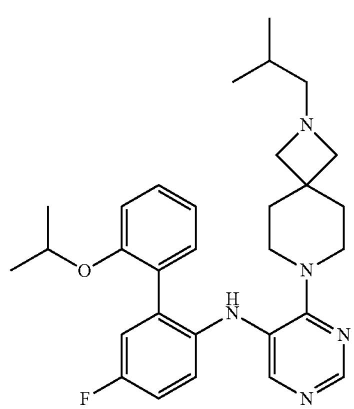 [SMILES: CC(C)CN1CC2(CCN(c3ncncc3Nc3ccc(F)cc3-c3ccccc3OC(C)C)CC2)C1] | Synthesized by a method similar to Example 71. In the final step, isobutyraldehyde was used under reductive amination conditions. |

TABLE 11-continued

Examples 241-249

| Example | Name | Structure | Synthetic method |
|---|---|---|---|
| 246 | N-(5-fluoro-2'-isopropyl-[1,1'-biphenyl]-2-yl)-4-(2-isobutyl-2,7-diazaspiro[3.5]nonan-7-yl)pyrimidin-5-amine | 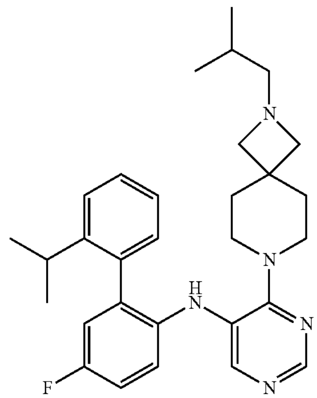 [SMILES: CC(C)CN1CC2(CCN(c3ncncc3Nc3ccc(F)cc3-c3ccccc3C(C)C)CC2)C1] | Synthesized by a method similar to Example 71. In the final step, isobutyraldehyde was used under reductive amination conditions. |
| 247 | N-(2'-ethyl-5-fluoro-[1,1'-biphenyl]-2-yl)-4-(2-isobutyl-2,7-diazaspiro[3.5]nonan-7-yl)pyrimidin-5-amine | 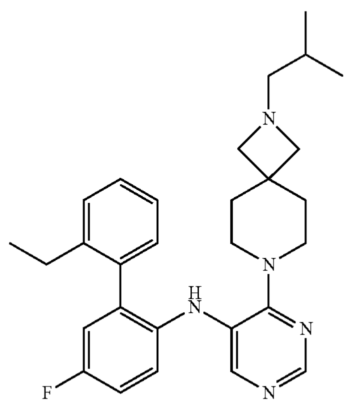 [SMILES: CCc1ccccc1-c1cc(F)ccc1Nc1cncnc1N1CCC2(CC1)CN(CC(C)C)C2] | Synthesized by a method similar to Example 71. In the final step, isobutyraldehyde was used under reductive amination conditions. |
| 248A | Isomer 1: 5-fluoro-N,N-diisopropyl-2-((4-(2-(4-(methylsulfonamido)cyclohexyl)-2,7-diazaspiro[3.5]nonan-7-yl)pyrimidin-5-yl)amino)benzamide | 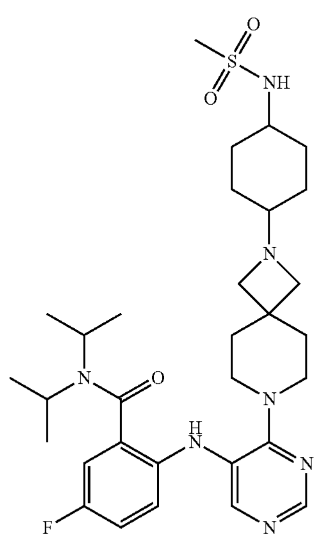 [SMILES: CC(C)N(C(=O)c1cc(F)ccc1Nc1cncnc1N1CCC2(CC1)CN(C1CCC(NS(C)(=O)=O)CC1)C2)C(C)C] | Synthesized by method described in Example 16. In final step, N-(4-oxocyclohexyl)methane sulfonamide was used under reductive amination conditions. |

TABLE 11-continued

Examples 241-249

| Example | Name | Structure | Synthetic method |
|---|---|---|---|
| 248B | Isomer 2: 5-fluoro-N,N-diisopropyl-2-((4-(2-(4-(methylsulfonamido)cyclohexyl)-2,7-diazaspiro[3.5]nonan-7-yl)pyrimidin-5-yl)amino)benzamide | 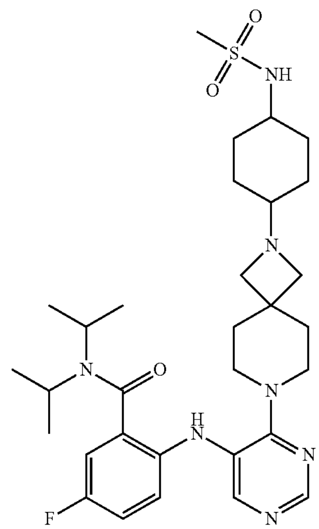 [SMILES: CC(C)N(C(=O)c1cc(F)ccc1Nc1cncnc1N1CCC2(CC1)CN(C1CCC(NS(C)(=O)=O)CC1)C2)C(C)C] | Minor isomer isolated from the preparation of Example 248A by SFC method A |
| 249 | 5-((7-(3-((5-fluoro-2'-isopropyl-[1,1'-biphenyl]-2-yl)oxy)pyridin-4-yl)-2,7-diazaspiro[4.4]nonan-2-yl)methyl)-1,3-dihydro-2H-benzo[d]imidazol-2-one | 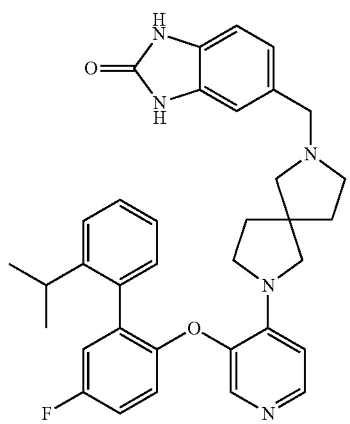 [SMILES: CC(C)c1ccccc1-c1cc(F)ccc1Oc1cnccc1N1CCC2(CCN(Cc3ccc4[nH]c(=O)[nH]c4c3)C2)C1] | Synthesized by a method similar to Example 41, starting with 3-bromo-4-chloro pyridine |

TABLE 12

Characterization Data for Examples 241-249

| Example | $^1$H NMR | MS |
|---|---|---|
| 241 | | LCMS method D: R$_t$ = 1.15 min; (M + H)$^+$ = 652.1 |
| 242 | | LCMS method D: R$_t$ = 1.055 min; (M + H)$^+$ = 516.1 |
| 243 | | LCMS method D: R$_t$ =: 0.8 min; (M + H)$^+$ = 578.1 |
| 244 | | LCMS method B: R$_t$ = 0.54 min; (M + H)$^+$ = 504.7 |
| 245 | $^1$H NMR (CD$_3$OD): δ 8.21 (s, 1H), 7.94 (s, 1H), 7.34 (t, J = 7.2 Hz, 1H), 7.22 (d, J = 7.6 Hz, 1H), 7.02-7.11 (m, 4H), 6.95-7.00 (m, 1H), 4.44-4.50 (m, 1H), 3.15-3.25 (m, 4H), 3.13 (s, 4H), 2.40 (d, J = 6.8 Hz, 2H), 1.60-1.70 (m, 1H), 1.50-1.60 (m, 4H), 1.11 (d, J = 5.6 Hz, 6H), 0.89 (d, J = 3.2 Hz, 6H). $^{19}$F NMR (MeOD): δ –123.08; | LCMS method D: R$_t$ = 0.890 min; (M + H)$^+$ = 504.3 |
| 246 | | LCMS method D: R$_t$ = 0.72 min; (M + H)$^+$ = 488.2 |
| 247 | | LCMS method B: R$_t$ = 0.68 min; (M + H)$^+$ = 474.7 |
| 248A | | LCMS method D: R$_t$ = 0.921 min; (M + H)$^+$ = 616.6. |
| 248B | | LCMS method D: R$_t$ = 0.932 min; (M + H)$^+$ = 616.6. |
| 249 | $^1$H NMR (CD$_3$OD): δ 7.95 (d, J = 8.0 Hz, 1H), 7.74 (s, 1H), 7.40-7.10 (m, 10 H), 6.77 (m, 1H), 4.41 (s, 2H), 3.63-3.26 (m, 8H), 2.78 (m, | LCMS method A: R$_t$ = 0.81 min; (M + H)$^+$ = 578.1 |

TABLE 12-continued

Characterization Data for Examples 241-249

| Example | ¹H NMR | MS |
|---|---|---|
| | 1H), 2.15 (m, 4H), 1.12 (d, J = 6.8 Hz, 3H), 1.03 (d, J = 6.8 Hz, 3H). | |

Examples 250A-250B

2'-((4-(7-amino-7-benzyl-2-azaspiro[4.4]nonan-2-yl)pyrimidin-5-yl)oxy)-2-cyclopropyl-5'-fluoro-[1,1'-biphenyl]-4-carbonitrile (Isomers 1-2)

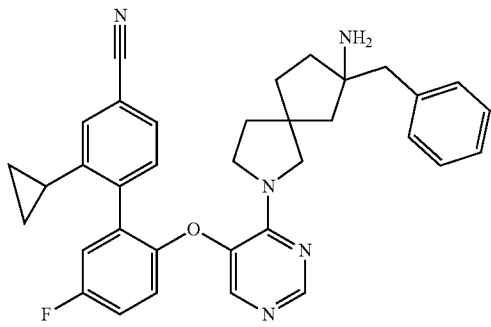 [SMILES: N#Cc1ccc(-c2cc(F)ccc2Oc2cncnc2N2CCC3(CCC(N)(Cc4ccccc4)C3)C2)c(C2CC2)c1]

Step 1. tert-butyl-7-((tert-butylsulfinyl)imino)-2-azaspiro[4.4]nonane-2-carboxylate

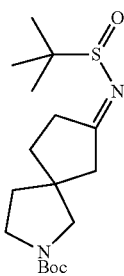 [SMILES: CC(C)(C)OC(=O)N1CCC2(CC/C(=N\S(=O)C(C)(C)C)C2)C1]

To a solution of tert-butyl 7-oxo-2-azaspiro[4.4]nonane-2-carboxylate (175 mg, 0.73 mmol) and 2-methylpropane-2-sulfinamide (106.2 mg, 1.2 eq) in THF (6 mL), was added tetraethoxytitanium (283 mg, 260 µL, 1.7 eq) and the resulting solution was heated at reflux under N₂ for 5 h. The reaction mixture was cooled to RT and brine (10 drops) was added to the solution, and stirred for 1 h at RT. The mixture was filtered through a pad of Celite and washed with EtOAc. The combined organic layers were removed to give tert-butyl-7-((tert-butylsulfinyl)imino)-2-azaspiro[4.4]nonane-2-carboxylate (0.16 g, 64%). LCMS method B: $R_t$=1.48 min; (M+H)⁺=343.1.

Step 2. tert-butyl 7-benzyl-7-((tert-butylsulfinyl)amino)-2-azaspiro[4.4]nonane-2-carboxylate

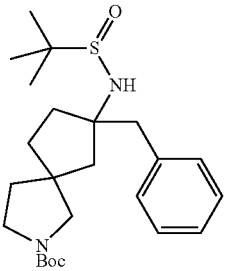 [SMILES: CC(C)(C)OC(=O)N1CCC2(CCC(Cc3ccccc3)(NS(=O)C(C)(C)C)C2)C1]

To the solution of tert-butyl-7-((tert-butylsulfinyl)imino)-2-azaspiro[4.4]nonane-2-carboxylate (0.16 g, 0.47 mmol) in THF (0.5 mL) at 0° C., was added benzylmagnesium bromide (1 N in THF, 1 mL). The resulting solution was warmed to RT stirred overnight, and then quenched with saturated NH₄Cl aqueous solution. Extraction with EtOAc gave tert-butyl 7-benzyl-7-((tert-butylsulfinyl)amino)-2-azaspiro[4.4]nonane-2-carboxylate (112 mg), which was used for the next step without purification.

Step 3. N-(7-benzyl-2-azaspiro[4.4]nonan-7-yl)-2-methylpropane-2-sulfinamide

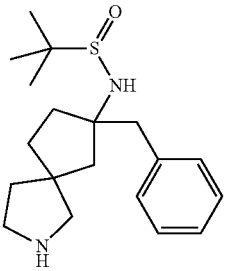 [SMILES: CC(C)(C)S(=O)NC1(Cc2ccccc2)CCC2(CCNC2)C1]

To a solution of tert-butyl 7-benzyl-7-((tert-butylsulfinyl)amino)-2-azaspiro[4.4]nonane-2-carboxylate (112 mg) in DCM (2 mL) was added TFA (200 µL), and the resulting solution was stirred at RT overnight. The solvent was removed under vacuum, and crude product was used for next step without purification. LCMS method B: $R_t$=1.27 min; (M+H)⁺=335.2.

Step 4. N-(7-benzyl-2-(5-(2-chloro-4-fluorophenoxy)pyrimidin-4-yl)-2-azaspiro[4.4]nonan-7-yl)-2-methylpropane-2-sulfinamide

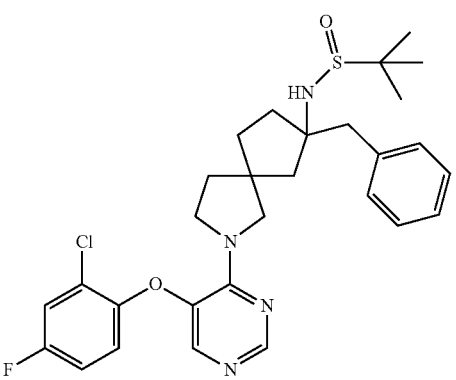 [SMILES: CC(C)(C)S(=O)NC1(Cc2ccccc2)CCC2(CCN(c3ncncc3Oc3ccc(F)cc3Cl)C2)C1]

To a TFA salt of N-(7-benzyl-2-azaspiro[4.4]nonan-7-yl)-2-methylpropane-2-sulfinamide (0.18 mmol) in ⁱPrOH (1 mL) was added trimethylamine (100 μL) and 4-chloro-5-(2-chloro-4-fluorophenoxy)pyrimidine (Intermediate 10a) (40 mg, 0.15 mmol). The resulting solution was heated in a CEM microwave at 110° C. for 1 hr. After cooling, the solution was diluted with EtOAc, filtered, and the filtrate was concentrated to dryness. The residue was purified with ISCO silica column with 100% EtOAc to give N-(7-benzyl-2-(5-(2-chloro-4-fluorophenoxy)pyrimidin-4-yl)-2-azaspiro[4.4]nonan-7-yl)-2-methylpropane-2-sulfinamide (31 mg, 31%). LCMS method B: $R_t$=1.72 min; $(M+H)^+$=558.1.

Step 5. N-(7-benzyl-2-(5-((4'-cyano-2'-cyclopropyl-5-fluoro-[1,1'-biphenyl]-2-yl)oxy)pyrimidin-4-yl)-2-azaspiro[4.4]nonan-7-yl)-2-methylpropane-2-sulfinamide

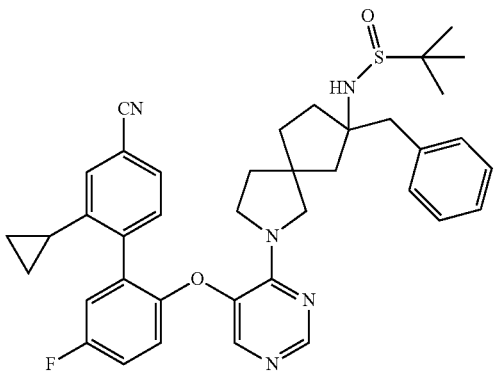 [SMILES: CC(C)(C)S(=O)NC1(Cc2ccccc2)CCC2(CCN(c3ncncc3Oc3ccc(F)cc3-c3ccc(C#N)cc3C3CC3)C2)C1]

To a solution of N-(7-benzyl-2-(5-(2-chloro-4-fluorophenoxy)pyrimidin-4-yl)-2-azaspiro[4.4]nonan-7-yl)-2-methylpropane-2-sulfinamide (31 mg, 0.056 mmol), 3-cyclopropyl-4-(4,4,5,5-tetramethyl-1,3,2-dioxaborolan-2-yl)benzonitrile (18 mg, 0.067 mmol), $K_3PO_4$ (24 mg, 0.112 mmol) in 1,4-dioxane (0.6 mL) and water (0.3 mL), was added chloro(2-dicyclohexylphosphino-2',6'-dimethoxy-1,1'-biphenyl)[2-(2'-amino-1,1'-biphenyl)]palladium(II) (2 mg, 5 mol %). The resulting solution was degassed, flushed with $N_2$, and heated in a CEM microwave reactor at 110° C. for 1 h. After cooling, the reaction mixture was extracted with EtOAc and washed with brine. The combined organic layers were dried over $Na_2SO_4$, concentrated to dryness to give crude product, which was used for next step. LCMS method B: $R_t$=1.79 min; $(M+H)^+$=664.7.

Step 5. 2'-((4-(7-amino-7-benzyl-2-azaspiro[4.4]nonan-2-yl)pyrimidin-5-yl)oxy)-2-cyclopropyl-5'-fluoro-[1,1'-biphenyl]-4-carbonitrile (Isomers 1-2)

To N-(7-benzyl-2-(5-((4'-cyano-2'-cyclopropyl-5-fluoro-[1,1'-biphenyl]-2-yl)oxy)pyrimidin-4-yl)-2-azaspiro[4.4]nonan-7-yl)-2-methylpropane-2-sulfinamide in MeOH (1 mL) was added 6 N HCl aq. solution (1 mL) and the resulting solution was stirred at room temperature until no starting material remained. The solvent was removed under vacuum and the residue was purified by preparative RP-HPLC method E to give the desired product as two isomers.

Isomer 1 as TFA salt (1.81 mg): LCMS method B: $R_t$=1.41 min; $(M+H)^+$=560.6. $^1$H NMR (MeOH-d4): δ 8.34 (s, 1H), 7.71 (s, 1H), 7.45-7.21 (m, 11H), 3.72 (m, 2H), 3.44 (m, 1H), 3.32 (m, 1H), 2.96 (s, 2H), 2.14 (m, 2H), 1.88 (m, 8H), 1.84 (m, 1H), 0.78 (m, 2H), 0.60 (m, 2H).

Isomer 2 as TFA salt (1.76 mg): LCMS method B: $R_t$=1.45 min; $(M+H)^+$=560.6. $^1$H NMR (MeOH-d4): δ 8.24 (s, 1H), 7.58 (s, 1H), 7.38 (d, J=8 Hz, 1H), 7.35-7.18 (m, 8H), 7.13 (m, 2H), 3.70-3.40 (m, 3H), 3.28 (m, 1H), 2.92 (s, 2H), 2.08 (m, 2H), 1.86-1.50 (m, 6H), 1.49 (m, 1H), 0.78 (m, 2H), 0.60 (m, 4H).

Example 251

2-((4-(3-(4-acetamidobenzyl)-2-amino-4-oxo-1,3,7-triazaspiro[4.4]non-1-en-7-yl)pyrimidin-5-yl)oxy)-5-fluoro-N-isopropyl-N-methylbenzamide

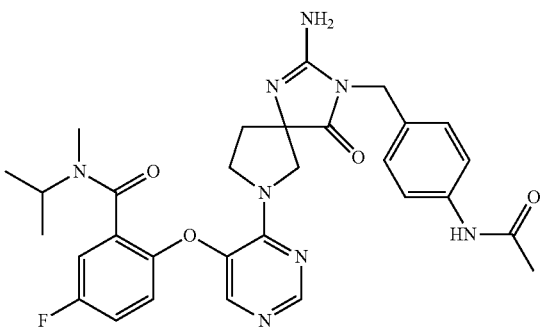 [SMILES: CC(=O)Nc1ccc(CN2C(=O)C3(CCN(c4ncncc4Oc4ccc(F)cc4C(=O)N(C)C(C)C)C3)N=C2N)cc1]

Step 1: tert-butyl 4-acetamidobenzylcarbamate

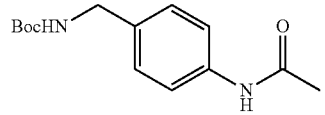 [SMILES: CC(=O)Nc1ccc(CNC(=O)OC(C)(C)C)cc1]

A cooled solution of tert-butyl 4-aminobenzylcarbamate (510 mg, 2.29 mmol) at 0° C. in pyridine (5 mL) was treated with the acetyl chloride (216 mg, 2.75 mmol) and stirred for 18 h at RT. The solvent was concentrated under reduced pressure and the residue was purified by flash column chromatography (ISCO) on silica gel (eluting with petroleum ether:EtOAc=10:1 to 1:1) to afford tert-butyl 4-acetamidobenzylcarbamate as a white solid. LCMS Method C: $R_t$=0.894 min; $(M+Na)^+$=287.2.

Step 2: N-(4-(aminomethyl)phenyl)acetamide

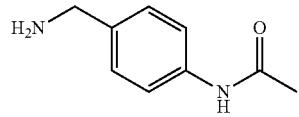

To a solution of tert-butyl 4-acetamidobenzylcarbamate (550 mg, 2.08 mmol) in anhydrous DCM (12 mL) was added TFA (3 mL) slowly at 0° C. under $N_2$ and the reaction mixture was stirred at 0° C. for 1.5 h. The mixture was concentrated under reduced pressure to afford N-(4-(aminomethyl)phenyl)acetamide, which was used for the next step

385 without further purification as a white solid as TFA salt. Yield: 342 mg (100% crude). LCMS Method D: $R_t$=0.1.338 min; $(2M+H)^+$=329.1.

Step 3: N-(4-((3-tert-butoxycarbonylthioureido)methyl)phenyl)acetamide

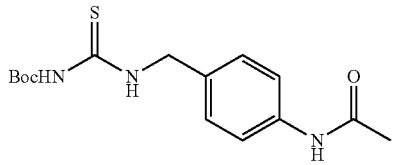 [SMILES: CC(=O)Nc1ccc(CNC(=S)NC(=O)OC(C)(C)C)cc1]

To a mixture of N,N'-bis-tert-butoxycarbonylthiourea (500 mg, 1.81 mmol) and anhydrous THF (20 mL) was added 60% NaH (87 mg, 2.17 mmol) at 0° C. The reaction mixture was stirred at 14-17° C. for 1 h, then TFAA (193 mg/0.129 mL, 1.99 mmol) was added and the stirring continued for an additional 1 h. Then, N-(4-(aminomethyl)phenyl)acetamide (249 mg, 1.99 mmol) and Et₃N (1 mL) in anhydrous THF (10 mL) was added and the resulting reaction was stirred at 14-17° C. for 18 h. H₂O (50 mL) was added to quench the reaction and the mixture was extracted with EtOAc (3×50 mL). The combined organic layers were washed with brine (2×40 mL), dried over with anhydrous Na₂SO₄, filtered, and the filtrate was concentrated under reduced pressure. The residue was purified by flash column chromatography (ISCO) on silica gel (eluting with petroleum ether:EtOAc=1:0 to 10:1) to afford N-(4-((3-tert-butoxycarbonyl thioureido)methyl)phenyl)acetamide as a white solid. LCMS Method C: $R_t$=0.998 min; $(M+Na)^+$=346.2.

Step 4: tert-butyl 3-(4-acetamidobenzyl)-2-((tert-butoxycarbonyl)amino)-4-oxo-1,3,7-triazaspiro[4.4]non-1-ene-7-carboxylate

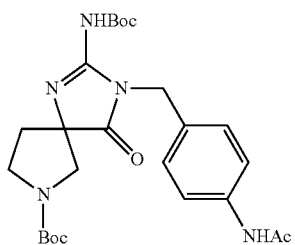 [SMILES: CC(=O)Nc1ccc(CN2C(=O)C3(CCN(C(=O)OC(C)(C)C)C3)N=C2NC(=O)OC(C)(C)C)cc1]

To a solution of 1-tert-butyl 3-methyl 3-aminopyrrolidine-1,3-dicarboxylate (100 mg, 0.409 mmol) in 5 mL of DMF was added N-(4-((3-tert-butoxycarbonylthioureido)methyl)phenyl)acetamide (159 mg, 0.491 mmol), EDCI (127 mg, 0.819 mmol) and DIEA (106 mg, 0.819 mmol). The mixture was stirred at RT for 48 h. The solvent was concentrated under reduced pressure. The residue was purified by flash column chromatography (ISCO) on silica gel (eluting with petroleum ether:EtOAc=10:1 to 1:1) to afford tert-butyl 3-(4-acetamidobenzyl)-2-((tert-butoxycarbonyl)amino)-4-oxo-1,3,7-triazaspiro[4.4]non-1-ene-7-carboxylate as a white solid. Yield: 114 mg (55% two steps). LCMS Method D: $R_t$=1.090 min; $(M+H)^+$=502.4.

386

Step 5: N-(4-((2-amino-4-oxo-1,3,7-triazaspiro[4.4]non-1-en-3-yl)methyl)phenyl)acetamide

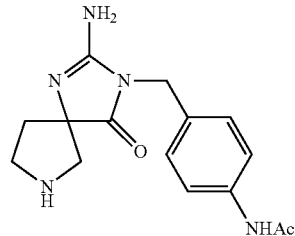 [SMILES: CC(=O)Nc1ccc(CN2C(=O)C3(CCNC3)N=C2N)cc1]

To a solution of tert-butyl 3-(4-acetamidobenzyl)-2-((tert-butoxycarbonyl)amino)-4-oxo-1,3,7-triazaspiro[4.4]non-1-ene-7-carboxylate (114 mg, 0.227 mmol) in anhydrous DCM (3 mL) was added TFA (1 mL) slowly at 0° C. under N₂ and the reaction mixture was stirred at RT for 30 min. The reaction mixture was concentrated under reduced pressure to afford crude N-(4-((2-amino-4-oxo-1,3,7-triazaspiro[4.4]non-1-en-3-yl)methyl)phenyl)acetamide which was used for the next step without further purification as a colorless oil. Yield: 68 mg (100% crude).

Step 6: 2-((4-(3-(4-acetamidobenzyl)-2-amino-4-oxo-1,3,7-triazaspiro[4.4]non-1-en-7-yl)pyrimidin-5-yl)oxy)-5-fluoro-N-isopropyl-N-methylbenzamide To a solution of N-(4-((2-amino-4-oxo-1,3,7-triazaspiro[4.4]non-1-en-3-yl)methyl)phenyl)acetamide (25 mg, 0.077 mmol) and Intermediate 43 (30 mg, 0.1 mmol) in i-PrOH (5 mL) was added DIEA (60 mg, 0.462 mmol) and the reaction mixture was heated to 110° C. at reflux for 18 h. The reaction mixture was concentrated under reduced pressure to afford the residue which was purified by prep HPLC method A to give the title product as a white solid. Yield: 10.20 mg (22%). LCMS Method D: $R_t$=0.995 min; $(M+H)^+$=589.1. ¹H NMR (CD₃OD): δ 8.55-8.79 (m, 1H), 7.99 (s, 1H), 7.61 (d, J=8.4 Hz, 2H), 7.25-7.46 (m, 5H), 4.16-4.88 (m, 6H), 3.91 (brs, 1H), 2.72-3.03 (m, 3H), 2.43-2.70 (m, 2H), 2.14 (s, 3H), 1.02-1.30 (m, 6H). ¹⁹F NMR (CD₃OD): δ −116.87, 117.22.

Example 252

N-Ethyl-2-((4-(7-(((1r,4r)-4-(ethylsulfonamido)cyclohexyl)methyl)-2,7-diazaspiro[3.5]nonan-2-yl)pyrimidin-5-yl)oxy)-5-fluoro-N-isopropylbenzamide

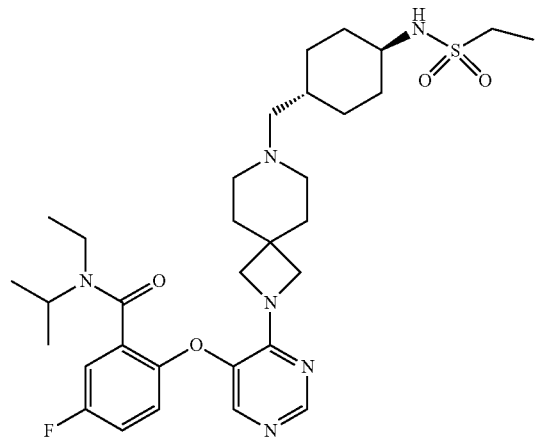 [SMILES: CCN(C(=O)c1cc(F)ccc1Oc1cncnc1N1CC2(CCN(C[C@H]3CC[C@H](NS(=O)(=O)CC)CC3)CC2)C1)C(C)C]

Step 1: tert-butyl 2-(5-(4-fluoro-2-(methoxycarbonyl)phenoxy)pyrimidin-4-yl)-2,7-diazaspiro[3.5]nonane-7-carboxylate

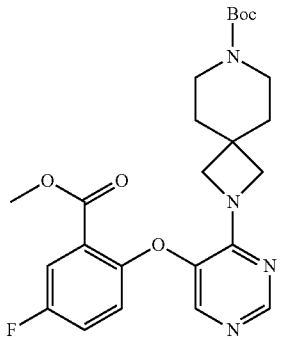 [SMILES: COC(=O)c1cc(F)ccc1Oc1cncnc1N1CC2(CCN(C(=O)OC(C)(C)C)CC2)C1]

A mixture of methyl 2-((4-chloropyrimidin-5-yl)oxy)-5-fluorobenzoate (Intermediate 48, 0.30 g, 0.11 mmol), tert-butyl 2,7-diazaspiro[3.5]nonane-7-carboxylate hydrochloride (CAS#: 1023301-84-9) (0.28 g, 1.06 mmol) and TEA (0.32 g, 3.18 mmol) in $^i$PrOH (3 mL) was heated with a CEM microwave reactor at 110° C. for 1 h. After cooling, the mixture was diluted with EtOAc (15 mL) and stirred until white solid formed, then filtered through a Celite™ pad, and subsequently washed with EtOAc (~10 mL). The combined filtrate was concentrated under vacuum to give the crude product tert-butyl 2-(5-(4-fluoro-2-(methoxycarbonyl)phenoxy)pyrimidin-4-yl)-2,7-diazaspiro[3.5]nonane-7-carboxylate as a dark solid (0.59 g, 100% conversion), which was used for the next step without purification; LCMS method B: $R_t$=1.13 min; (M+H)$^+$15=473.5.

Step 2: 2-((4-(7-(tert-butoxycarbonyl)-2,7-diazaspiro[3.5]nonan-2-yl)pyrimidin-5-yl)oxy)-5-fluorobenzoic acid

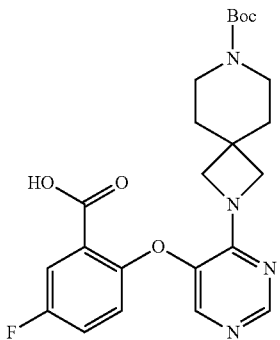 [SMILES: CC(C)(C)OC(=O)N1CCC2(CC1)CN(c1ncncc1Oc1ccc(F)cc1C(=O)O)C2]

To a solution of tert-butyl 2-(5-(4-fluoro-2-(methoxycarbonyl)-pyrimidin-4-yl)-2,7-diazaspiro[3.5]nonane-7-carboxylate (0.59 g, ~1.06 mmol) in MeOH (3 mL), was added 2N LiOH aqueous solution (1.1 mL, 2.2 mmol). The resulting solution was stirred at RT for 4 h, the solvent was removed, and the residue was washed with EtOAc (10 mL), acidified to pH=3, and dried to give 2-((4-(7-(tert-butoxycarbonyl)-2,7-diazaspiro[3.5]nonan-2-yl)pyrimidin-5-yl)oxy)-5-fluorobenzoic acid as a solid (0.47 g, 97%), which was used for the next step without purification; LCMS method B: $R_t$=1.02 min; (M+H)$^+$=458.6.

Step 3. tert-butyl 2-(5-(2-(ethyl(isopropyl)carbamoyl)-4-fluorophenoxy)pyrimidin-4-yl)-2,7-diazaspiro[3.5]nonane-7-carboxylate

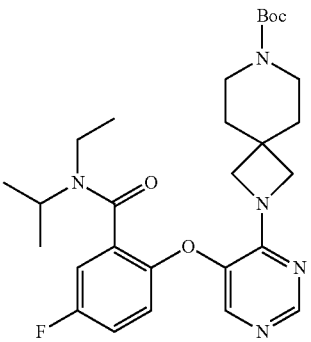 [SMILES: CCN(C(=O)c1cc(F)ccc1Oc1cncnc1N1CC2(CCN(C(=O)OC(C)(C)C)CC2)C1)C(C)C]

To a mixture of 2-((4-(7-(tert-butoxycarbonyl)-2,7-diazaspiro[3.5]nonan-2-yl)pyrimidin-5-yl)oxy)-5-fluorobenzoic acid (0.2 g, 0.44 mmol), N-ethylpropan-2-amine (114 mg, 1.32 mmol), and TEA (200 µL) in DMF (1 mL) at 0° C., was added BOP reagent (233 mg, 0.53 mmol). The resulting solution was warmed slowly to RT, and stirred for 4 h. Water was added, the mixture was extracted with DCM (4×, 5 mL), and the combined organic layers were washed with brine, concentrated to dryness, and purified by ISCO flash column (10% MeOH/DCM) to give tert-butyl 2-(5-(2-(ethyl(isopropyl)carbamoyl)-4-fluorophenoxy)pyrimidin-4-yl)-2,7-diazaspiro[3.5]nonane-7-carboxylate (160 mg, 70%) as a foam; LCMS method B: $R_t$=1.16 min; (M+H)$^+$=528.6.

Step 4: 2-((4-(2,7-diazaspiro[3.5]nonan-2-yl)pyrimidin-5-yl)oxy)-N-ethyl-5-fluoro-N-isopropylbenzamide

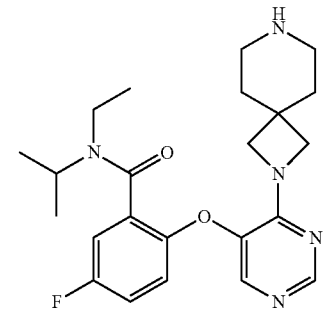 [SMILES: CCN(C(=O)c1cc(F)ccc1Oc1cncnc1N1CC2(CCNCC2)C1)C(C)C]

To a solution of tert-butyl 2-(5-(2-(ethyl(isopropyl)carbamoyl)-4-fluorophenoxy)-pyrimidin-4-yl)-2,7-diazaspiro[3.5]nonane-7-carboxylate (160 mg, 0.30 mmol) in anhydrous DCM (3 mL), was added TFA (0.6 mL). The resulting solution was stirred at RT for 30 min. The mixture was concentrated under reduced pressure to dryness and used for the next step as a crude TFA salt; LCMS method B: $R_t$=0.57 min, (M+H)$^+$=427.6.

Step 5: tert-butyl ((1r,4r)-4-((2-(5-(2-(ethyl(isopropyl)carbamoyl)-4-fluorophenoxy)pyrimidin-4-yl)-2,7-diazaspiro[3.5]nonan-7-yl)methyl)cyclohexyl)carbamate

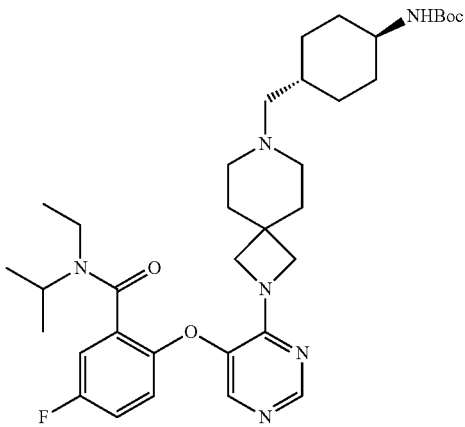 [SMILES: CCN(C(=O)c1cc(F)ccc1Oc1cncnc1N1CC2(CCN(C[C@H]3CC[C@H](NC(=O)OC(C)(C)C)CC3)CC2)C1)C(C)C]

To a solution of 2-((4-(2,7-diazaspiro[3.5]nonan-2-yl)pyrimidin-5-yl)oxy)-N-ethyl-5-fluoro-N-isopropylbenzamide (0.30 mmol) in anhydrous MeOH (5 mL) was added NaOAc (140 mg) to adjust the pH to 6-7. Then tert-butyl ((1r,4r)-4-formylcyclohexyl)carbamate (CAS#: 181308-57-6) (105 mg, 0.45 mmol) was added. After being stirred at RT for 10 min, NaBH$_3$CN (28 mg, 0.45 mmol) was added and the resulting mixture was stirred at RT overnight. The mixture was concentrated and the residue was purified on an ISCO flash column (8% MeOH/DCM) to give tert-butyl ((1r,4r)-4-((2-(5-(2-(ethyl(isopropyl)carbamoyl)-4-fluorophenoxy)pyrimidin-4-yl)-2,7-diazaspiro[3.5]nonan-7-yl)methyl)cyclohexyl)carbamate as a white solid (156.5 mg, 82% in two steps); LCMS method B: R$_t$=0.87 min; (M+H)$^+$=639.5.

Step 6: 2-((4-(7-(((1r,4r)-4-aminocyclohexyl)methyl)-2,7-diazaspiro[3.5]nonan-2-yl)pyrimidin-5-yl)oxy)-N-ethyl-5-fluoro-N-isopropylbenzamide

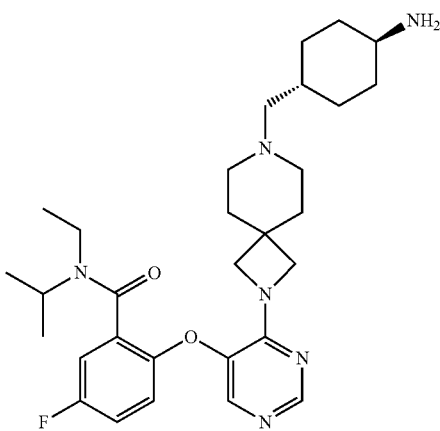 [SMILES: CCN(C(=O)c1cc(F)ccc1Oc1cncnc1N1CC2(CCN(C[C@H]3CC[C@H](N)CC3)CC2)C1)C(C)C]

A solution of tert-butyl ((1r,4r)-4-((2-(5-(2-(ethyl(isopropyl)carbamoyl)-4-fluorophenoxy)pyrimidin-4-yl)-2,7-diazaspiro[3.5]nonan-7-yl)methyl)cyclohexyl)carbamate (156.5 mg, 0.25 mmol) in 1.25 N HCl/MeOH (3 mL) was stirred at RT overnight. The solvent was then removed to give 2-((4-(7-(((1r,4r)-4-aminocyclohexyl)methyl)-2,7-diazaspiro[3.5]nonan-2-yl)pyrimidin-5-yl)oxy)-N-ethyl-5-fluoro-N-isopropylbenzamide as a HCl salt with 100% conversion, which was used for next step without further purification. LCMS method B: R$_t$=0.52 min; (M+H)$^+$=539.6.

Step 7: N-Ethyl-2-((4-(7-(((1r,4r)-4-(ethylsulfonamido)cyclohexyl)methyl)-2,7-diazaspiro[3.5]nonan-2-yl)pyrimidin-5-yl)oxy)-5-fluoro-N-isopropylbenzamide To a solution of 2-((4-(7-(((1r,4r)-4-aminocyclohexyl)methyl)-2,7-diazaspiro[3.5]nonan-2-yl)pyrimidin-5-yl)oxy)-N-ethyl-5-fluoro-N-isopropylbenzamide hydrochloride (0.25 mmol) and Et$_3$N (75 mg, 0.75 mmol) in anhydrous DCM (2 mL) at 0° C., was added ethanesulfonyl chloride (33 mg, 0.26 mmol) dropwise and the mixture was stirred at 0° C. for 2 h. The reaction mixture was quenched with H$_2$O (5 mL), extracted with DCM (3×5 mL), and the combined organic layers were washed with brine (5 mL), dried over anhydrous Na$_2$SO$_4$, filtered, and concentrated under reduced pressure. The residue was purified by ISCO flash column eluting with 8-10% MeOH/DCM to afford N-ethyl-2-((4-(7-(((1r,4r)-4-(ethylsulfonamido)-cyclohexyl)methyl)-2,7-diazaspiro[3.5]nonan-2-yl)pyrimidin-5-yl)oxy)-5-fluoro-N-isopropyl-benzamide as a white solid (41 mg, 26%); LCMS method B: R$_t$=0.73 min; (M+H)$^+$=631.6; $^1$H NMR (MeOD-d4): δ 8.23, 8.22 (two s, 1H), 7.74, 7.70 (two s, 1H), 7.22-7.15 (m, 2H), 7.03-6.96 (m, 1H), 4.45, 3.51 (two m, 1H), 4.08-3.82 (m, 4H), 3.36 (m, 1H), 3.24 (m, 1H), 3.12-2.94 (m, 3H), 2.32 (m, 4H), 2.10 (d, J=6.8 Hz, 2H), 1.96 (m, 2H), 1.88-1.76 (m, 6H), 1.48 (m, 1H), 1.20-1.04 (m, 14H), 1.02 (m, 2H); $^{19}$F NMR (MeOD-d4): δ −119.7.

Example 253

Scale-Up Synthesis of N-ethyl-2-((4-(7-(((1r,4r)-4-(ethylsulfonamido)cyclohexyl)methyl)-2,7-diazaspiro[3.5]nonan-2-yl)pyrimidin-5-yl)oxy)-5-fluoro-N-isopropylbenzamide

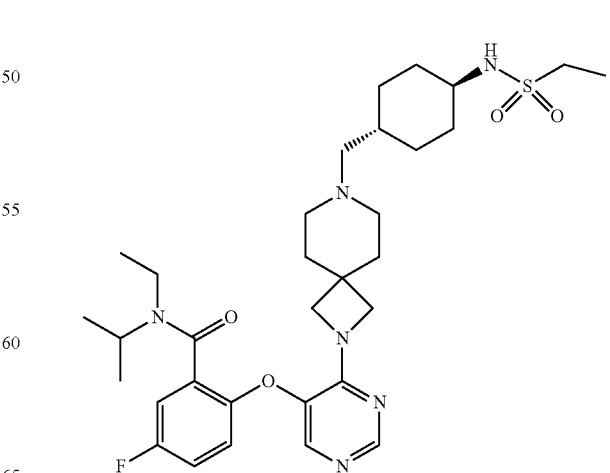

Step 1: N-ethyl-5-fluoro-N-isopropyl-2-(pyrimidin-5-yloxy)benzamide

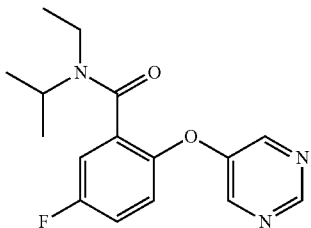 [SMILES: CCN(C(=O)c1cc(F)ccc1Oc1cncnc1)C(C)C]

To a solution of 5-fluoro-2-(pyrimidin-5-yloxy)benzoic acid (Intermediate 49, 5 g, 21.4 mmol) in anhydrous DCM (60 mL) at 0° C., was added oxalyl chloride (2.2 mL, 25.6 mmol) slowly. The mixture was stirred at 0° C. for 30 min and the solution turned cloudy. Triethylamine (3.6 mL, 25.6 mmol) was then added into the reactor portionwise every 30 min. After the addition was complete, the water bath was warmed to ambient temperature and the reaction mixture was stirred for about 3 h. Then a solution of isopropyl ethylamine (6.5 mL, 53.5 mmol) was added to the reaction mixture slowly and the mixture was stirred at RT for 10 h. The reactor contents were washed sequentially with 1 N HCl aqueous solution and 1 N sodium hydroxide. The organic layer was concentrated and dried under high vacuum to afford the crude product N-ethyl-5-fluoro-N-isopropyl-2-(pyrimidin-5-yloxy)benzamide as a brown oil (6.2 g); LCMS Method B: $t_R$=1.18 min; [M+H]$^+$=304.2

Step 2: 5-(2-(Ethyl(isopropyl)carbamoyl)-4-fluorophenoxy)pyrimidine 1-oxide

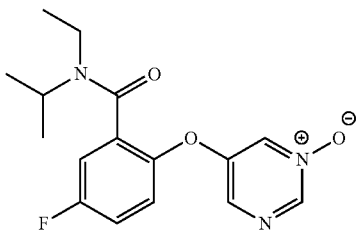 [SMILES: CCN(C(=O)c1cc(F)ccc1Oc1cnc[n+]([O-])c1)C(C)C]

At RT, a round bottom flask was charged with crude N-ethyl-5-fluoro-N-isopropyl-2-(pyrimidin-5-yloxy)benzamide from Step 1 and urea hydrogen peroxide powder (15-17% active oxygen basis, 14.1 g, 150 mmol) in THF (60 mL). Trifluoroacetic anhydride (6 mL, 42.8 mmol) was then added slowly into the reaction mixture. After the addition was complete, the mixture was stirred at RT for 45 min. The reaction was quenched by slow addition of saturated NaHCO$_3$ solution. The product was extracted with dichloromethane. The organic layer was treated with 1 M Na$_2$S$_2$O$_3$. The biphasic mixture was tested by KI-starch test paper and showed negative result. Then the phases were then separated, the organic layer was dried over Na$_2$SO$_4$ and concentrated under reduced pressure. The crude product 5-(2-(ethyl(isopropyl)carbamoyl)-4-fluorophenoxy)-pyrimidine 1-oxide was then dried in a high vacuum to furnish an orange oil (5.8 g); LC-MS Method B: $t_R$=1.03 min; [M+H]$^+$=320.3.

Step 3: 2-((4-Chloropyrimidin-5-yl)oxy)-N-ethyl-5-fluoro-N-isopropylbenzamide

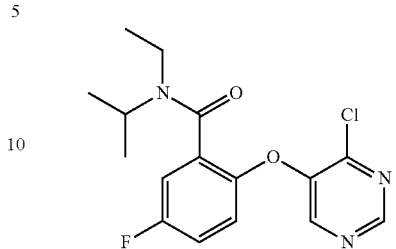

To a suspension of crude 5-(2-(ethyl(isopropyl)carbamoyl)-4-fluorophenoxy)pyrimidine 1-oxide from Step 2 (5.8 g, ~90% purity) and DIEA (16.2 mL, 90.9 mmol) in EtOAc (70 mL) was added POCl$_3$ (2.0 mL, 21.8 mmol) slowly at 0° C. After addition, the resulting reaction mixture was warmed to RT and stirred at RT for 1 h. The reaction mixture was cooled to 0° C. and quenched by slow addition of H$_2$O (30 mL). The organic layer was separated and the aqueous layer was extracted twice with EtOAc (2×50 mL). The combined organic layers were dried over brine, Na$_2$SO$_4$, filtered, and then concentrated under reduced pressure and dried under vacuum to afford the crude product 2-((4-chloropyrimidin-5-yl)oxy)-N-ethyl-5-fluoro-N-isopropylbenzamide as a dark solid, which was used directly for the next step without further purifications; LC-MS Method B: $t_R$=1.40 min; [M+H]$^+$=338.2

Step 4: tert-butyl 2-(5-(2-(ethyl(isopropyl)carbamoyl)-4-fluorophenoxy)pyrimidin-4-yl)-2,7-diazaspiro[3.5]nonane-7-carboxylate

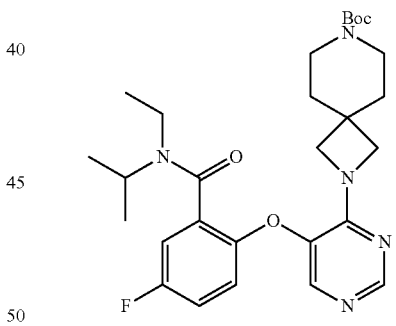

A mixture of crude 2-((4-chloropyrimidin-5-yl)oxy)-N-ethyl-5-fluoro-N-isopropylbenzamide from Step 3, tert-butyl 2,7-diazaspiro[3.5]nonane-7-carboxylate hydrochloride (CAS#: 1023301-84-9) (5.0 g, 19.1 mmol) and DIEA (9.8 mL, 54.6 mmol) in $^i$PrOH (35 mL) was stirred at 80° C. for 5 h. The reaction mixture was cooled to RT and diluted with EtOAc (60 mL). The mixture was then washed with H$_2$O (60 mL); the organic layer was separated and the aqueous layer was extracted with EtOAc (60 mL). The combined organic layers were dried over brine, Na$_2$SO$_4$, filtered, and then concentrated under reduced pressure and dried under vacuum. The crude product was purified by ISCO flash column (3% MeOH/DCM) to provide tert-butyl 2-(5-(2-(ethyl(isopropyl)-carbamoyl)-4-fluorophenoxy)pyrimidin-4-yl)-2,7-diazaspiro-[3.5]nonane-7-carboxylate as a brown solid (4.95 g, 44% over 4 steps); LC-MS Method B: $t_R$=1.17 min; [M+H]⁺=528.4; ¹H NMR (CD₃OD, 400 MHz): δ 8.24 (s, 1H), 7.76 (s, 1H), 7.21-7.15 (m, 2H), 7.00-6.96 (m, 1H), 4.05-3.95 (m, 2H), 3.95-3.90 (m, 3H), 3.31-3.27 (m, 2H), 1.75-1.70 (m, 5H), 1.45 (s, 9H), 1.31-1.10 (m, 12H).

Step 5: 2-((4-(2,7-diazaspiro[3.5]nonan-2-yl)pyrimidin-5-yl)oxy)-N-ethyl-5-fluoro-N-isopropylbenzamide

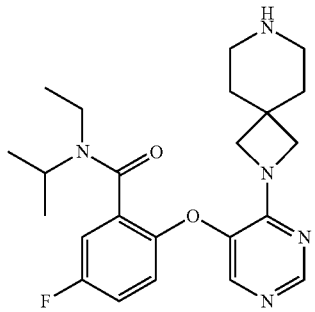

To a solution of tert-butyl 2-(5-(2-(ethyl(isopropyl)carbamoyl)-4-fluorophenoxy)-pyrimidin-4-yl)-2,7-diazaspiro[3.5]nonane-7-carboxylate from Step 4 (69 g, 130.9 mmol) in anhydrous DCM (300 mL) was added HCl-dioxane (110 mL, 4M in dioxane). The reaction mixture was stirred at 5-9° C. for 4 h. The mixture was diluted with water (500 mL) and extracted with DCM (3×400 m). The aqueous layer was adjusted to pH=12-14 with 10% NaOH solution and extracted with DCM (3×800 mL). The combined organic layers were dried over anhydrous Na₂SO₄, filtered, and concentrated under reduced pressure to give 2-((4-(2,7-diazaspiro[3.5]nonan-2-yl)pyrimidin-5-yl)oxy)-N-ethyl-5-fluoro-N-isopropyl-benzamide (46 g, 100%) as yellow solid, which was used for the next step directly without further purification; LC-MS Method C: R₁=0.416 min; [M+H]⁺=428.2.

Step 6: N-ethyl-2-((4-(7-(((1r,4r)-4-(ethylsulfonamido)cyclohexyl)methyl)-2,7-diazaspiro[3.5]nonan-2-yl)pyrimidin-5-yl)oxy)-5-fluoro-N-isopropylbenzamide To a mixture of 2-((4-(2,7-diazaspiro[3.5]nonan-2-yl)pyrimidin-5-yl)oxy)-N-ethyl-5-fluoro-N-isopropylbenzamide from Step 5 (39.0 g, 91.3 mmol) in N-methyl-2-pyrrolidone (400 mL) was added ((1r,4r)-4-(ethylsulfonamido)cyclohexyl)methyl 4-methylbenzenesulfonate (Intermediate 50, 41 g, 109.56 mmol), KI (16 g, 95.9 mmol) and K₂CO₃ (63 g, 456.5 mmol). The reaction mixture was then stirred at 70-75° C. for 6 h under N₂ atmosphere. The reaction was cooled to RT and additional ((1r,4r)-4-(ethylsulfonamido)cyclohexyl)methyl 4-methylbenzenesulfonate (Intermediate 50, 4.0 g, 10.9 mmol) was added and the reaction mixture was stirred at 70-75° C. for another 12 h under N₂ atmosphere. The mixture was cooled to RT, diluted with water (500 mL), and extracted with DCM (3×800 mL). The combined organic layers were washed with water (3×1.5 L), dried over anhydrous Na₂SO₄, filtered, and concentrated under reduced pressure. The residue was purified by neutral prep-HPLC Method A to afford N-ethyl-2-((4-(7-(((1r,4r)-4-(ethylsulfonamido)cyclohexyl)methyl)-2,7-diazaspiro[3.5]nonan-2-yl)pyrimidin-5-yl)oxy)-5-fluoro-N-isopropyl-benzamide (20.9 g, 36.8%) as white solid; LCMS Method A: R₁=1.82 min; [M+H]⁺=631.3; ¹H NMR (CDCl₃ 400 MHz): δ ppm 8.36-8.37 (m, 1H), 7.76 (s, 1H), 6.99-7.04 (m, 2H), 6.74-6.80 (m, 1H), 4.59-4.66 (m, 0.2H), 4.04-4.06 (m, 1H), 3.83-3.93 (m, 4H), 3.48-3.53 (m, 0.8H), 3.30-3.39 (m, 1H), 3.17-3.21 (m, 1H), 3.02-3.06 (m, 2H), 2.25 (s, 4H), 2.03-2.05 (m, 4H), 1.73-1.84 (m, 7H), 1.12-1.36 (m, 14H), 0.89-0.98 (m, 2H); ¹⁹F NMR (CDCl₃ 400 MHz): δ ppm –118.57; SFC Method A: t_R=1.357 min; HPLC Method A: t_R=6.84 min.

Example 254

N-Ethyl-2-((4-(7-(((1r,4r)-4-(ethylsulfonamido)cyclohexyl)methyl)-2,7-diazaspiro[3.5]nonan-2-yl) pyrimidin-5-yl)oxy)-5-fluoro-N-isopropylbenzamide Free Amine Crystallization Free amine of N-ethyl-2-((4-(7-(((1r,4r)-4-(ethylsulfonamido)cyclohexyl)methyl)-2,7-diazaspiro[3.5]nonan-2-yl) pyrimidin-5-yl)oxy)-5-fluoro-N-isopropylbenzamide (0.50 g) was dissolved in a mixture of EtOAc (6 mL) and hexane (9 mL) to give a clear solution, which was seeded with <1 mg of 5-fluoro-N,N-diisopropyl-2-((4-(7-(((1r,4r)-4-(methylsulfonamido)cyclohexyl)methyl)-2,7-diazaspiro[3.5] nonan-2-yl)pyrimidin-5-yl)oxy)benzamide free amine crystal (Example 6A). The resulting solution was stirred at 25° C. for 2 days, the white solid was collected by filtration, and dried over high vacuum overnight (0.39 g, 76%); ¹H NMR (MeOD-d4): δ 8.23, 8.22 (two s, 1H), 7.74, 7.70 (two s, 1H), 7.22-7.15 (m, 2H), 7.03-6.96 (m, 1H), 4.45, 3.51 (two m, 1H), 4.08-3.82 (m, 4H), 3.36 (m, 1H), 3.24 (m, 1H), 3.12-2.94 (m, 3H), 2.32 (m, 4H), 2.10 (d, J=6.8 Hz, 2H), 1.96 (m, 2H), 1.88-1.76 (m, 6H), 1.48 (m, 1H), 1.20-1.04 (m, 14H), 1.02 (m, 2H); ¹⁹F NMR (MeOD-d4): δ –119.7; melting point=156.6-157.6° C. Concentration in water to achieve pH=7: 7.6 mg/mL.

The X-ray powder diffraction (XRPD) pattern was determined for the free amine crystalline compound (XRPD Method A) and is shown in FIG. 1. A list of 2-theta peaks is provided in Table 13 below.

TABLE 13

| 2-theta (°) | Relative Height (%) |
|---|---|
| 5.5 | 3.38 |
| 7.4 | 4.45 |
| 8.7 | 4.46 |
| 9.7 | 10.26 |
| 10.7 | 1.11 |
| 11.6 | 12.68 |
| 12.6 | 15.77 |
| 14.8 | 2.8 |
| 15.3 | 7.52 |
| 15.6 | 6.68 |
| 15.8 | 8.92 |
| 16.6 | 100 |
| 17.5 | 12.82 |
| 17.9 | 5.84 |
| 18.8 | 32.29 |
| 19.2 | 28.69 |
| 19.8 | 22.32 |
| 21.0 | 18.85 |
| 21.4 | 7.86 |
| 22.0 | 3.31 |
| 22.8 | 6.98 |
| 23.4 | 3.78 |
| 24.6 | 2.77 |
| 25.3 | 7.45 |
| 26.1 | 2.04 |
| 26.6 | 4.55 |

Example 255

N-Ethyl-2-((4-(7-(((1r,4r)-4-(ethylsulfonamido)cyclohexyl)methyl)-2,7-diazaspiro[3.5]nonan-2-yl)pyrimidin-5-yl)oxy)-5-fluoro-N-isopropylbenzamide Sesquifumaric Acid Salt (Sesquifumarate) Crystallization N-Ethyl-2-((4-(7-(((1r,4r)-4-(ethylsulfonamido)cyclohexyl)methyl)-2,7-diazaspiro[3.5]nonan-2-yl)pyrimidin-5-yl)oxy)-5-fluoro-N-isopropylbenzamide free amine (497.2 mg, 0.79 mmol) and fumaric acid (137.2 mg, 1.5 eq) were dissolved in EtOH (5 mL) to give a clear solution; EtOH was removed under vacuum, and the salt was dried over high vacuum overnight.

The salt (0.54 g) was dissolved in EtOH/MeCN (21.8 mL, ~4% EtOH) and the resulting solution was stirred at 25° C. overnight, during which a white solid precipitated slowly. The white solid was collected by filtration and dried over high vacuum for 24 h (0.41 g, 76%). $^{1}$H-NMR (DMSO-d6, 25 s relax delay): δ 8.26, 8.25 (two s, 1H), 7.72, 7.66 (two s, 1H), 7.32-7.22 (m, 2H), 7.06 (m, 1H), 7.00 (d, J=7.6 Hz, 1H), 6.59 (s, 3H), 4.39, 3.72 (two m, 1H), 3.98-3.76 (m, 4H), 3.38 (m, 1H), 3.22 (m, 1H), 2.98 (m, 3H), 2.42 (m, 4H), 2.20 (d, J=6.4 Hz, 2H), 1.84 (m, 2H), 1.74 (m, 6H), 1.43 (m, 1H), 1.28-0.82 (m, 16H); $^{19}$F NMR (DMSO-d6): δ −118.43; melting point=176.1-177.8° C. Concentration in water to achieve pH=7: 224.7 mg/mL.

The X-ray powder diffraction (XRPD) pattern was determined for the sesquifumaric acid crystalline salt (XRPD Method B) and is shown in FIG. 2. A list of 2-theta peaks is provided in Table 14 below. Ratio of N-ethyl-2-((4-(7-(((1r,4r)-4-(ethylsulfonamido)cyclohexyl)methyl)-2,7-diazaspiro[3.5]nonan-2-yl)pyrimidin-5-yl)oxy)-5-fluoro-N-isopropylbenzamide:fumaric acid=1:1.5).

TABLE 14

| Peak No. | 2-theta (deg) | Rel. Int. I |
|---|---|---|
| 1 | 2.9 | 2.29 |
| 2 | 5.8 | 100 |
| 3 | 8.7 | 30.83 |
| 4 | 10.7 | 2 |
| 5 | 11.3 | 6.2 |
| 6 | 12.6 | 7.44 |
| 7 | 13.2 | 32.95 |
| 8 | 14.5 | 11.48 |
| 9 | 15.3 | 10.8 |
| 10 | 16.0 | 82.33 |
| 11 | 17.1 | 9.59 |
| 12 | 17.4 | 33.3 |
| 13 | 17.6 | 29.24 |
| 14 | 18.0 | 6.2 |
| 15 | 18.9 | 9.23 |
| 16 | 19.1 | 56.98 |
| 17 | 20.3 | 41.59 |
| 18 | 20.7 | 15.72 |
| 19 | 21.2 | 4.29 |
| 20 | 21.8 | 39.15 |
| 21 | 23.0 | 39.41 |
| 22 | 23.3 | 89.63 |
| 23 | 23.8 | 11.88 |
| 24 | 24.1 | 4.11 |
| 25 | 24.9 | 23.75 |
| 26 | 26.0 | 27.37 |
| 27 | 26.9 | 7.73 |
| 28 | 27.8 | 4.3 |
| 29 | 28.3 | 6.99 |
| 30 | 28.8 | 16.43 |
| 31 | 29.0 | 1.46 |
| 32 | 31.7 | 13.12 |
| 33 | 34.0 | 1.49 |
| 34 | 34.6 | 8.69 |
| 35 | 34.9 | 2.8 |
| 36 | 35.2 | 1 |
| 37 | 37.2 | 2.42 |
| 38 | 37.5 | 1.24 |
| 39 | 38.4 | 1.05 |
| 40 | 40.1 | 6.27 |
| 41 | 42.5 | 4.29 |
| 42 | 45.6 | 1.49 |

Example 256

N-Ethyl-2-((4-(7-(((1r,4r)-4-(ethylsulfonamido)cyclohexyl)methyl)-2,7-diazaspiro[3.5]nonan-2-yl)pyrimidin-5-yl)oxy)-5-fluoro-N-isopropylbenzamide Bis-Methanesulfonic Acid Salt (Bis-Mesylate) Crystallization To a clear solution of N-ethyl-2-((4-(7-(((1r,4r)-4-(ethylsulfonamido)cyclohexyl)methyl)-2,7-diazaspiro[3.5]nonan-2-yl)pyrimidin-5-yl)oxy)-5-fluoro-N-isopropylbenzamide free amine (419.7 mg) in $^{i}$PrOH (2.5 mL) and EtOAc (3 mL), was added MeSO$_3$H (>99.5%, Sigma-Aldrich) (0.13 g, 88.6 μL, 2.05 eq) dropwise. An additional 3 mL of EtOAc was added to the resultant solution, and the mixture was stirred at RT overnight. White solid was then collected by filtration, all solid was transferred with the mother liquor twice, and dried over high vacuum for 2 days (535.1 g, 97%); $^{1}$H-NMR (MeOD-d4): δ 8.53, 8.52 (two s, 1H), 7.92, 7.82, 7.71 (three s, 1H), 7.38-7.22 (m, 3H), 4.69-4.16 (br, m, 4H), 3.90 (m, 1H), 3.57 (m, 2H), 3.45 (m, 1H), 3.26 (m, 1H), 3.16 (m, 1H), 3.03 (q, J=7.6 Hz, 2H), 2.98 (m, 4H), 2.68 (s, 6H), 2.22-2.02 (m, 6H), 1.92-1.74 (m, 3H), 1.44-1.06 (m, 16H); $^{19}$F NMR (MeOD-d4): δ −116.53, −116.79, −117.27; melting point=207.6-209.7° C. Concentration in water to achieve pH=7: 261 mg/mL.

The X-ray powder diffraction (XRPD) pattern was determined for the bis-methanesulfonic acid crystalline salt (XRPD Method A) and is shown in FIG. 3. A list of 2-theta peaks is provided in Table 15 below. Ratio of N-ethyl-2-((4-(7-(((1r,4r)-4-(ethylsulfonamido)cyclohexyl)methyl)-2,7-diazaspiro[3.5]nonan-2-yl)pyrimidin-5-yl)oxy)-5-fluoro-N-isopropylbenzamide:methanesulfonic acid=1:2).

TABLE 15

| 2-theta (°) | Relative Height (%) |
|---|---|
| 5.6 | 58.6 |
| 11.0 | 4.48 |
| 13.3 | 6.67 |
| 16.7 | 100 |
| 17.5 | 2.81 |
| 18.1 | 2.75 |
| 20.1 | 13.43 |
| 20.6 | 7.78 |
| 20.9 | 15.37 |
| 22.1 | 4.08 |
| 23.6 | 4.44 |
| 24.4 | 0.88 |
| 24.9 | 4.33 |
| 25.8 | 2.33 |
| 27.0 | 3.5 |
| 28.0 | 1.91 |
| 29.6 | 6.5 |

TABLE 15-continued

| 2-theta (°) | Relative Height (%) |
|---|---|
| 30.4 | 0.82 |
| 31.8 | 1.61 |
| 33.7 | 1.18 |

Example 257

N-Ethyl-2-((4-(7-(((1r,4r)-4-(ethylsulfonamido)cyclohexyl)methyl)-2,7-diazaspiro[3.5]nonan-2-yl)pyrimidin-5-yl)oxy)-5-fluoro-N-isopropylbenzamide Bis-Hydrochloric Acid Salt (Bis-Hydrochloride) Crystallization To a clear solution of N-ethyl-2-((4-(7-(((1r,4r)-4-(ethylsulfonamido)cyclohexyl)methyl)-2,7-diazaspiro[3.5]nonan-2-yl)pyrimidin-5-yl)oxy)-5-fluoro-N-isopropylbenzamide free amine (0.71 g) in EtOH (3 mL) was added 1 N HCl aqueous solution (2.25 mL, 2 eq) dropwise. The resulting solution was mixed and evaporated to dryness under high vacuum.

The resultant salt (0.71 g) was dissolved in $^i$PrOH (4 mL) and EtOAc (7 mL) to give a clear solution. A seed crystal was generated by dissolving Example 252 (~5 mg) in EtOH (100 µL), followed by slow evaporation in a chamber containing iPrOH (~5 mL). The bis-hydrochloric acid salt solution was seeded with the seed crystal and the solution was stirred at 25° C. overnight. White solid was collected by filtration and dried over high vacuum for 2 days (0.54 g, 76%); $^1$H NMR (MeOD-d4): δ 8.54, 8.52 (two s, 1H), 7.92, 7.82, 7.71 (three s, 1H), 7.38-7.24 (m, 3H), 4.68-4.12 (br, m, 4H), 3.88 (m, 1H), 3.57 (m, 2H), 3.45 (m, 1H), 3.26 (m, 1H), 3.16 (m, 1H), 3.03 (q, J=7.6 Hz, 2H), 2.99 (m, 4H), 2.34-2.02 (m, 6H), 1.94-1.76 (m, 3H), 1.44-1.06 (m, 16H); $^{19}$F NMR (MeOD-d4): δ −116.48, −116.77, −117.26; melting point=219-220° C. Concentration in water to achieve pH=7: 317.6 mg/mL.

The X-ray powder diffraction (XRPD) pattern was determined for the bis-hydrochloric acid crystalline salt (XRPD Method A) and is shown in FIG. 4. A list of 2-theta peaks is provided in Table 16 below. Ratio of N-ethyl-2-((4-(7-(((1r,4r)-4-(ethylsulfonamido)cyclohexyl)methyl)-2,7-diazaspiro[3.5]nonan-2-yl)pyrimidin-5-yl)oxy)-5-fluoro-N-isopropylbenzamide:hydrochloric acid=1:2).

TABLE 16

| 2-theta (°) | Relative Height (%) |
|---|---|
| 4.7 | 87.32 |
| 9.3 | 8.17 |
| 10.7 | 15.59 |
| 11.4 | 11.99 |
| 11.9 | 9.62 |
| 13.4 | 16.46 |
| 14.0 | 6.76 |
| 15.1 | 7.1 |
| 15.9 | 33.04 |
| 17.0 | 100 |
| 18.6 | 14.63 |
| 19.5 | 39.53 |
| 20.1 | 16.47 |
| 21.4 | 12.15 |
| 23.8 | 34.71 |
| 24.4 | 8.37 |
| 25.1 | 4.31 |
| 25.8 | 22.42 |
| 26.6 | 4.53 |

TABLE 16-continued

| 2-theta (°) | Relative Height (%) |
|---|---|
| 28.1 | 16.14 |
| 28.7 | 8.75 |

Example 258

5-Fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide Free Amine Crystallization Free amine of 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide (Example 6A, 0.79 g) was dissolved in a mixture of EtOAc and hexane (28 mL, ~38% volume of EtOAc). Once all the material went into the solution, the clear solution gradually turned cloudy. The resulting solution was stirred at 25° C. overnight. The white solid was then collected by filtration and dried over high vacuum overnight (0.58 g, 73%); $^1$H-NMR showed pure compound with trace of EtOAc; melting point=177-178° C.

The X-ray powder diffraction (XRPD) pattern was determined for the free amine crystalline compound (XRPD Method B) and is shown in FIG. 5. A list of 2-theta peaks is provided in Table 17 below.

TABLE 17

| Peak No. | 2-theta (deg) | Rel. Int. I |
|---|---|---|
| 1 | 6.2 | 15.16 |
| 2 | 8.3 | 6.31 |
| 3 | 12.3 | 4.1 |
| 4 | 12.7 | 5.92 |
| 5 | 13.4 | 7.82 |
| 6 | 14.5 | 1.41 |
| 7 | 15.0 | 2.65 |
| 8 | 15.7 | 5.05 |
| 9 | 16.1 | 28.24 |
| 10 | 16.6 | 100 |
| 11 | 17.3 | 12.06 |
| 12 | 17.7 | 8.6 |
| 13 | 18.6 | 3.34 |
| 14 | 19.0 | 46.74 |
| 15 | 19.3 | 2.78 |
| 16 | 20.2 | 0.91 |
| 17 | 20.7 | 3.76 |
| 18 | 21.5 | 2.37 |
| 19 | 22.1 | 4.99 |
| 20 | 22.4 | 5.43 |
| 21 | 22.7 | 0.83 |
| 22 | 23.5 | 12.82 |
| 23 | 23.8 | 1.66 |
| 24 | 24.7 | 3.75 |
| 25 | 25.0 | 1.25 |
| 26 | 25.3 | 13.75 |
| 27 | 25.7 | 1.48 |
| 28 | 26.9 | 13.48 |
| 29 | 27.6 | 2.21 |
| 30 | 28.7 | 1.41 |
| 31 | 28.8 | 0.78 |
| 32 | 29.1 | 2.46 |
| 33 | 29.8 | 1.61 |
| 34 | 30.3 | 5.42 |
| 35 | 30.8 | 1.37 |
| 36 | 31.6 | 2.1 |
| 37 | 32.3 | 0.73 |
| 38 | 32.5 | 0.42 |
| 39 | 32.9 | 1.72 |

TABLE 17-continued

| Peak No. | 2-theta (deg) | Rel. Int. I |
|---|---|---|
| 40 | 33.5 | 5.09 |
| 41 | 34.0 | 0.91 |
| 42 | 34.6 | 0.93 |
| 43 | 35.7 | 0.65 |
| 44 | 36.1 | 0.99 |
| 45 | 36.9 | 0.46 |
| 46 | 37.6 | 0.53 |
| 47 | 37.9 | 1.78 |
| 48 | 38.8 | 0.44 |
| 49 | 39.2 | 0.24 |
| 50 | 39.5 | 0.32 |
| 51 | 39.8 | 0.48 |
| 52 | 41.2 | 1.47 |
| 53 | 41.9 | 0.49 |
| 54 | 42.1 | 1.43 |
| 55 | 42.6 | 1.06 |
| 56 | 42.9 | 0.74 |
| 57 | 44.0 | 0.55 |
| 58 | 44.3 | 1.39 |
| 59 | 45.0 | 0.15 |
| 60 | 45.8 | 2.16 |

Example 259

5-Fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide Bis-Methanesulfonic Acid Salt (Bis-Mesylate) Crystallization 5-Fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide (Example 6A) free amine (1.02 g) was dissolved in $^i$PrOH (25 mL) and MeSO$_3$H (>99.5%, Sigma-Aldrich) (0.31 g, 207.5 μL, 2.05 eq) was added to the solution slowly. The resulting solution was seeded with a single crystal of 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide bis-methanesulfonic acid salt (Example 264) and stirred at room temperature overnight. White solid was collected by filtration, and dried over high vacuum for 4 days (0.94 g, 73%); 1HNMR confirmed bis-mesylate without solvent peaks; melting point=217.6-219.6° C.

The X-ray powder diffraction (XRPD) pattern was determined for the bis-methanesulfonic acid crystalline salt (XRPD Method B), confirming it to be crystalline, and is shown in FIG. 6. A list of 2-theta peaks is provided in Table 18 below.

TABLE 18

| Peak No. | 2-theta (deg) | Rel. Int. I |
|---|---|---|
| 1 | 5.6 | 12.05 |
| 2 | 8.8 | 7.15 |
| 3 | 10.2 | 14.78 |
| 4 | 11.0 | 9.26 |
| 5 | 12.0 | 3.86 |
| 6 | 12.6 | 18.25 |
| 7 | 12.9 | 3.26 |
| 8 | 13.8 | 16.04 |
| 9 | 14.1 | 14.7 |
| 10 | 15.3 | 61.65 |
| 11 | 16.2 | 20.21 |
| 12 | 16.3 | 4.22 |
| 13 | 16.8 | 38.78 |

TABLE 18-continued

| Peak No. | 2-theta (deg) | Rel. Int. I |
|---|---|---|
| 14 | 17.6 | 100 |
| 15 | 18.6 | 33.5 |
| 16 | 20.3 | 57.51 |
| 17 | 20.7 | 12.84 |
| 18 | 20.9 | 19.21 |
| 19 | 21.2 | 18.21 |
| 20 | 21.5 | 15.41 |
| 21 | 21.8 | 9.06 |
| 22 | 22.1 | 2.08 |
| 23 | 22.4 | 14.23 |
| 24 | 22.7 | 17.02 |
| 25 | 23.6 | 3.46 |
| 26 | 24.6 | 17.45 |
| 27 | 24.9 | 4.88 |
| 28 | 25.3 | 11.87 |
| 29 | 25.7 | 5.37 |
| 30 | 26.0 | 9.41 |
| 31 | 26.3 | 10.65 |
| 32 | 26.7 | 7.5 |
| 33 | 27.2 | 11.08 |
| 34 | 27.8 | 1.58 |
| 35 | 28.6 | 4.7 |
| 36 | 29.5 | 3.58 |
| 37 | 30.0 | 1.54 |
| 38 | 30.4 | 12.64 |
| 39 | 31.7 | 4.4 |
| 40 | 32.7 | 5.31 |
| 41 | 36.2 | 1.99 |
| 42 | 37.9 | 1.86 |
| 43 | 39.6 | 2.29 |
| 44 | 40.2 | 2.82 |
| 45 | 42.1 | 3.32 |
| 46 | 42.7 | 1.03 |
| 47 | 45.4 | 2.2 |
| 48 | 46.0 | 0.99 |
| 49 | 47.0 | 0.71 |
| 50 | 49.3 | 1.14 |

Example 260

5-Fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide Sesquifumaric Acid Salt (Sesquifumarate) Crystallization 5-Fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide (Example 6A) free amine (0.34 g) was dissolved in MeCN (2 mL). Fumaric acid (82.3 mg, 1.3 eq) was dissolved in EtOH (1.5 mL, warmed until dissolved). The fumaric acid solution was then transferred to the amine solution, mixed well, then solvent was removed under vacuum to dryness. The resulting residue was redissolved in a mixture of MeCN (10 mL) and EtOH (0.2 mL) to give a clear solution. After seeding with a single crystal of the sesquifumaric acid salt (Example 265), the solution was stirred at 30° C. overnight. White solid was collected by filtration, and dried under high vacuum for 24 hr (0.35 g, 83%). Melting point=176-178° C.

The X-ray powder diffraction (XRPD) pattern was determined for the sesquifumaric acid crystalline salt (XRPD Method B) and is shown in FIG. 7. A list of 2-theta peaks is provided in Table 19 below.

TABLE 19

| Peak No. | 2-theta (deg) | Rel. Int. I |
|---|---|---|
| 1 | 2.9 | 56.27 |
| 2 | 5.8 | 73.54 |
| 3 | 7.6 | 1.21 |
| 4 | 8.7 | 33.16 |
| 5 | 10.7 | 2.9 |
| 6 | 11.3 | 5.23 |
| 7 | 12.6 | 5.55 |
| 8 | 13.2 | 35.83 |
| 9 | 14.3 | 6.7 |
| 10 | 14.5 | 6.96 |
| 11 | 15.1 | 8.22 |
| 12 | 15.3 | 4.32 |
| 13 | 16.0 | 100 |
| 14 | 17.1 | 11.22 |
| 15 | 17.4 | 22.99 |
| 16 | 17.6 | 46.84 |
| 17 | 18.1 | 10.97 |
| 18 | 18.9 | 12.77 |
| 19 | 19.1 | 70.8 |
| 20 | 20.3 | 21.58 |
| 21 | 20.4 | 21.2 |
| 22 | 20.8 | 18.63 |
| 23 | 21.2 | 3.5 |
| 24 | 21.8 | 45.24 |
| 25 | 22.2 | 2.33 |
| 26 | 22.9 | 12.63 |
| 27 | 23.0 | 46.11 |
| 28 | 23.3 | 83.24 |
| 29 | 23.8 | 13.36 |
| 30 | 24.2 | 4.36 |
| 31 | 24.9 | 29.15 |
| 32 | 25.9 | 8.57 |
| 33 | 26.0 | 25.8 |
| 34 | 26.9 | 10.93 |
| 35 | 27.6 | 2.42 |
| 36 | 27.8 | 2.71 |
| 37 | 28.3 | 5.33 |
| 38 | 28.5 | 3.73 |
| 39 | 28.8 | 7.98 |
| 40 | 29.0 | 6.07 |
| 41 | 29.4 | 8.58 |
| 42 | 30.1 | 0.81 |
| 43 | 30.4 | 1.3 |
| 44 | 30.9 | 2.63 |
| 45 | 31.2 | 0.88 |
| 46 | 31.7 | 13.42 |
| 47 | 32.1 | 1.94 |
| 48 | 32.3 | 1.12 |
| 49 | 32.8 | 1.86 |
| 50 | 34.0 | 1.79 |
| 51 | 34.4 | 3.03 |
| 52 | 34.6 | 7.16 |
| 53 | 34.9 | 4.56 |
| 54 | 35.2 | 1.64 |
| 55 | 36.0 | 2.93 |
| 56 | 37.2 | 2.95 |
| 57 | 37.5 | 1.55 |
| 58 | 38.4 | 1.44 |
| 59 | 39.1 | 1.82 |
| 60 | 39.7 | 2.22 |

Example 261

5-Fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide Bis-Hydrochloric Acid Salt (Bis-Hydrochloride)

To the crude free base of 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide (~86 grams, ~92% purity), was added EtOH (13 volumes) at RT. To this solution was added 3 equivalents of a 1-2 M solution of HCl in EtOH at RT. The solution was stirred for about 15 minutes and diisopropyl ether (iPr$_2$O, 7 volumes) was then slowly added to the stirring EtOH solution at RT. The mixture was stirred at RT and a white precipitate formed over about 1 day. The white precipitate was filtered and washed with a 1:1 mixture of EtOH and iPr$_2$O to afford 67 grams of the bis-HCl salt with a purity of ~96% by HPLC analysis. The resulting material appeared to be a mixture of amorphous and crystalline forms. Residual EtOH (~4.5 wt %) was removed by lyophilization with ~8 volumes of water. The material after lyophilization had a melting point of ~210-215° C. and appeared to decompose at these temperatures during melting point analysis.

The X-ray powder diffraction (XRPD) pattern was determined for the bis-hydrochloric acid salt (XRPD Method B) and is shown in FIG. 8. The powder pattern shown in FIG. 8 exhibited an essentially smooth and continuous profile characteristic of a non-crystalline material.

Example 262. Crystalline Response Analysis

Digital Filter Method

A percent crystalline response was determined for Examples 258-261. In X-ray powder diffraction data, the presence of crystalline material is indicated by the presence of sharp well defined diffraction peaks. The percent crystalline response is essentially the total diffraction signal contained in all the crystalline peaks expressed as a percentage with respect to the total diffraction signal from the sample. To determine the diffraction response from the sample, the measured data were first pre-processed by removing the instrumental background and then normalized to a common area. The pre-processed data were then passed through two digital filters, one to remove the Compton and thermal diffuse scattering and the other to remove the non-crystalline sample response from the pattern. The percentage of the total normalized intensity remaining after passing the data through the digital filters indicates the percentage of perfect crystalline material in the sample. The percent crystalline response values determined using the digital filter are summarized in Table 20. These numbers do not include defected crystalline material and, as a result, are not the absolute percent crystallinity value for the sample. The percent crystallinity values as provided in Table 20, allow for relative comparison of percent crystallinity between samples containing the same crystalline polymorph.

TABLE 20

| Example No. | Percent Crystalline (%) |
|---|---|
| 258 | 91.4 |
| 259 | 76.7 |
| 260 | 84.0 |
| 261 | 1.5 |

Bayesian Model

Taking the essentially non crystalline response observed for Example 261 as being a representative non-crystalline pattern for all samples, allows the definition of a Bayesian model which can be used to estimate the maximum non-crystalline component allowed by the observed data. The combined percent crystalline results using the Bayesian model are shown in Table 21. The Bayesian model provided a good approximation for the diffuse X-ray scattering observed for data set Example 259, which suggested that the percent crystalline values of between 71% to 75% are reasonable. The Bayesian model did not provide a good fit for Examples 258 and 260. Both data sets appear to be essentially crystalline in nature.

TABLE 21

| Example No. | Minimum Crystallinity (%) |
|---|---|
| 258 | 94 |
| 259 | 71 |
| 260 | 88 |

Example 263. Crystalline Form Screen of 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide Sesquifumaric Acid Salt Preparation of 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide Sesquifumaric Acid Salt The fumaric acid salt used in the solid form screen assays was prepared from 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide free amine base according to the following procedure:

The free amine base was purified by adding to water and stirring overnight. The resulting solids were then dried under nitrogen. Then 1.6 molar equivalents of fumaric acid was added to 4.4 g of the 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide free base in EtOH (35 mL) and the reaction mixture was stirred. An additional portion of EtOH (5 mL) was added and the reaction mixture was dried over $MgSO_4$. The mixture was then filtered and diethyl ether (150 mL) was added and the slurry was stirred overnight. A sample of the slurry solid was identified as Form B (see below). The resulting solids were then collected via vacuum filtration. A sample of the resulting wet cake was also identified as Form B. The wet cake was then dried under vacuum at 45° C. for 1 day and the resulting dry sample was identified as Form D (see below).

Identification of Solid Forms

Seven different solid forms of 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide sesquifumaric acid salt were observed and are described below. X-ray powder diffraction (XRPD) patterns (XRPD Method C) for the identified sesquifumaric acid salt forms are shown in FIG. 9.

Amorphous:
Formed from EtOH via fast evaporation.

Figure 11:
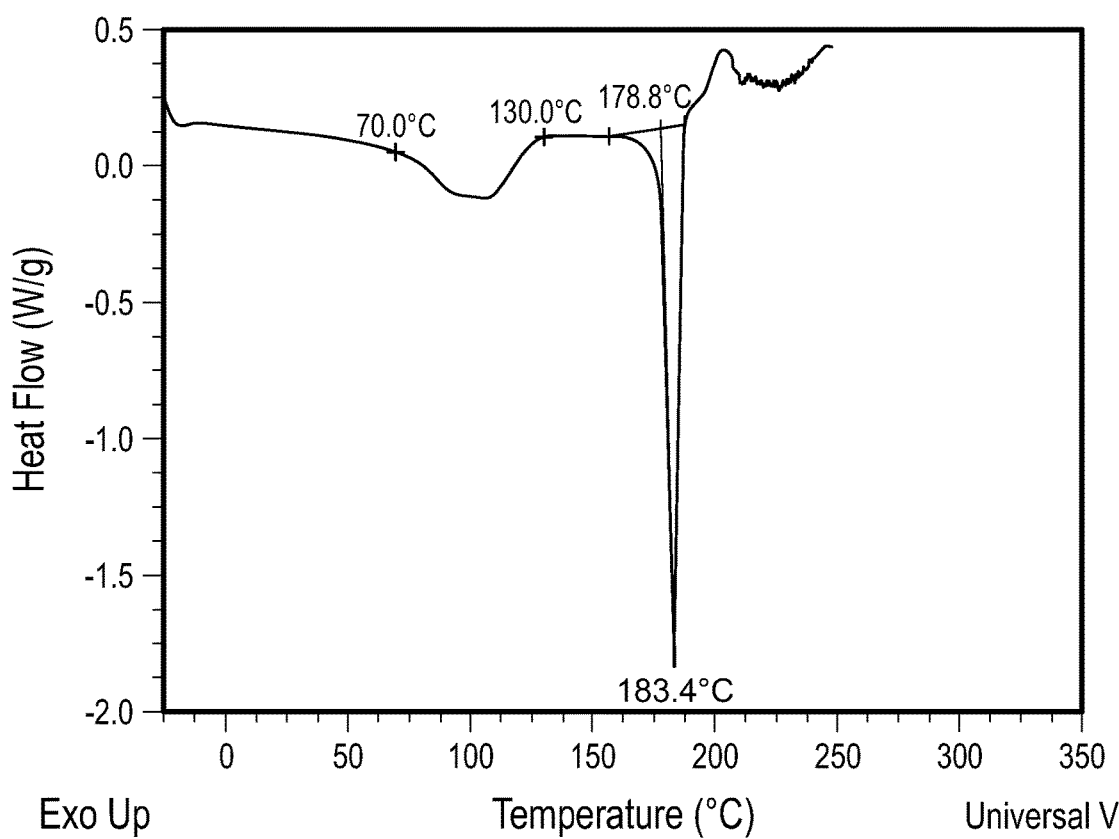
FIG. 11 shows a DSC thermogram characteristic of 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide sesquifumaric acid salt, crystalline Form A.
Figure 14:
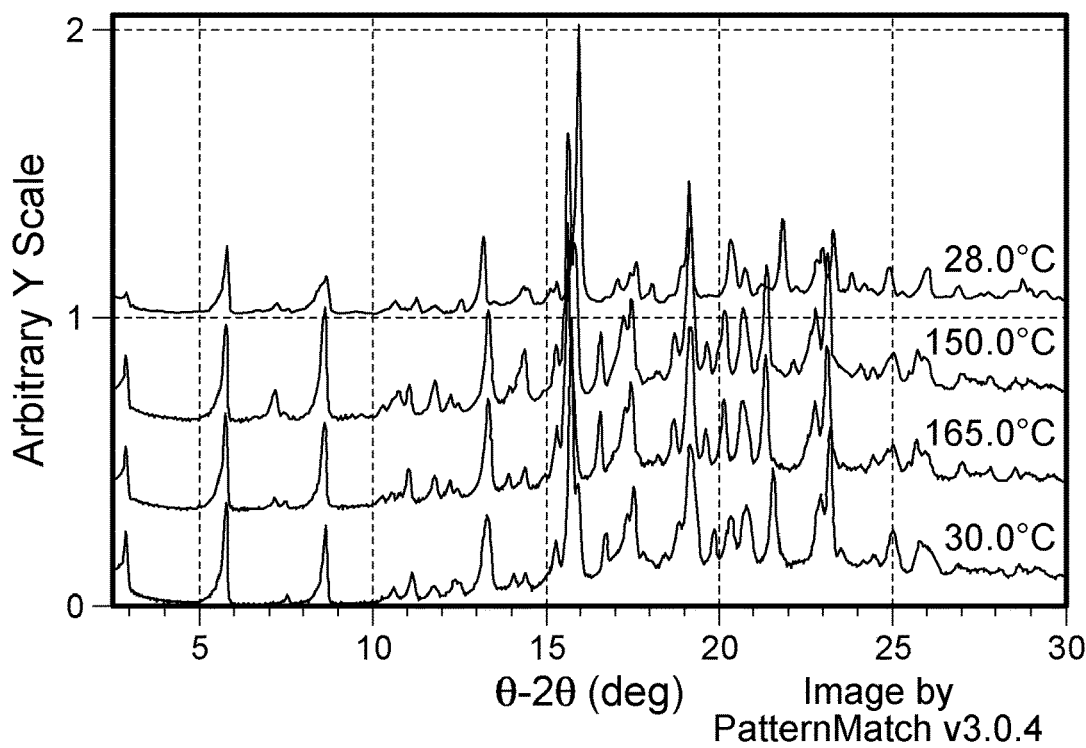
FIG. 14 shows variable temperature (VT)-XRPD patterns characteristic of 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide sesquifumaric acid salt, crystalline Form A.

Form A:
Sesquifumaric Acid Monohydrate; Ratio: 2:3:2 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide:fumaric acid:water.
XRPD: Consistent with sesquifumaric acid hydrate (XRPD Method C), as shown in FIG. 10. A list of 2-theta peaks is provided in Table 22 below.
DSC/TG: broad endotherm occurring concurrently with weight loss in the TG between 70 and 130° C. Final endothermic event with onset at 179° C., as shown in FIG. 11. A 1.7% weight loss observed up to 90° C. as shown in FIG. 12.
DVS: 0.92% weight gain from 5 to 95% RH. Weight lost upon desorption is shown FIG. 13.
Variable temperature (VT)-XRPD: No form change observed. Peak shifting consistent with thermal expansion upon heating, as shown in FIG. 14. XRPD pattern at 165° C. consistent with Form A.
No changes upon vacuum drying or heating.
Form B and Form D convert to Form A in water activity slurries at 0.22 $a_w$ and up.

TABLE 22

| Peak Number | 2-theta (deg) | Intensity (%) |
|---|---|---|
| 1 | 2.9 | 15 |
| 2 | 5.8 | 34 |
| 3 | 7.5 | 5 |
| 4 | 8.7 | 12 |
| 5 | 10.4 | 3 |
| 6 | 10.7 | 6 |
| 7 | 11.3 | 9 |
| 8 | 11.7 | 3 |
| 9 | 12.6 | 7 |
| 10 | 13.2 | 30 |
| 11 | 14.3 | 5 |
| 12 | 14.5 | 4 |
| 13 | 15.1 | 7 |
| 14 | 15.3 | 12 |
| 15 | 15.9 | 100 |
| 16 | 16.7 | 4 |
| 17 | 17.1 | 9 |
| 18 | 17.4 | 8 |
| 19 | 17.6 | 13 |
| 20 | 17.9 | 5 |
| 21 | 18.0 | 10 |
| 22 | 18.6 | 4 |
| 23 | 18.9 | 11 |
| 24 | 19.2 | 45 |
| 25 | 20.3 | 17 |
| 26 | 20.4 | 15 |
| 27 | 20.8 | 11 |
| 28 | 21.2 | 4 |
| 29 | 21.4 | 4 |
| 30 | 21.8 | 28 |
| 31 | 22.2 | 4 |
| 32 | 22.8 | 9 |
| 33 | 23.0 | 17 |
| 34 | 23.3 | 19 |
| 35 | 23.8 | 10 |
| 36 | 24.2 | 7 |
| 37 | 24.4 | 5 |
| 38 | 24.9 | 14 |
| 39 | 25.3 | 4 |
| 40 | 26.0 | 14 |
| 41 | 26.9 | 6 |

Figure 16:
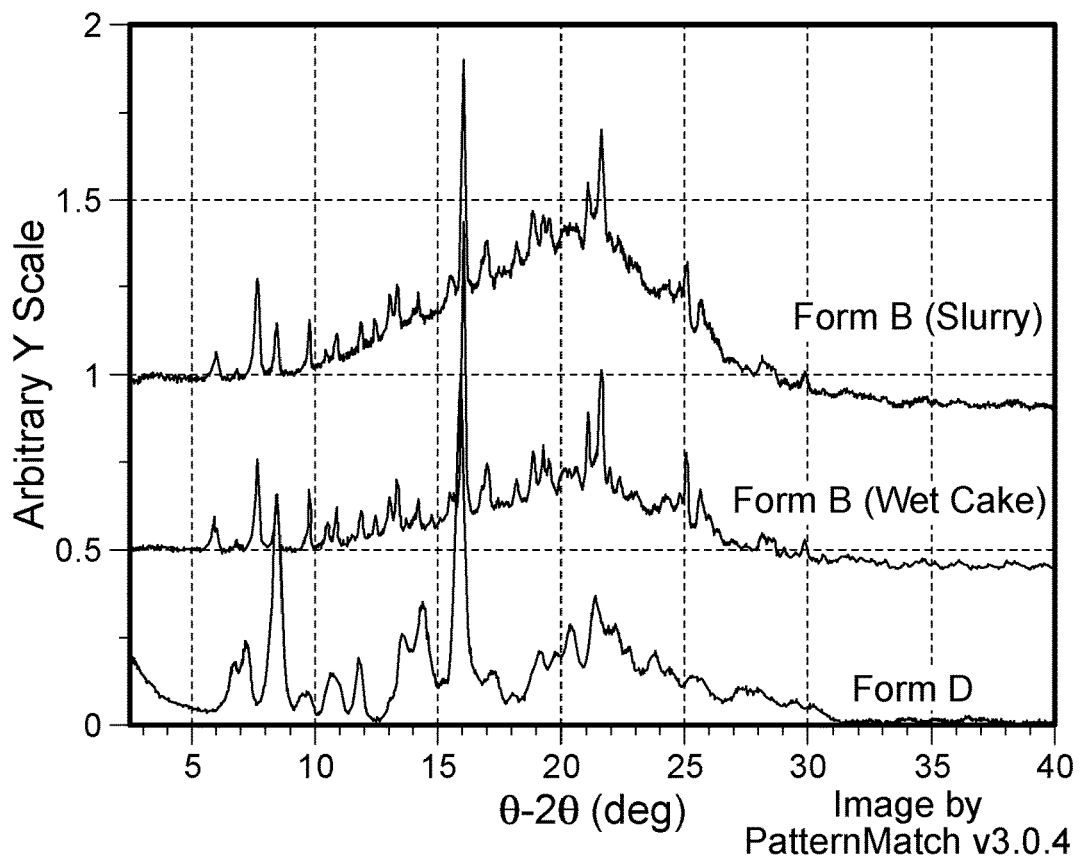
FIG. 16 shows XRPD patterns of 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide fumaric acid salt, crystalline Form B and Form D isolated from a scale-up preparation as a slurry (top trace; Form B), a wet cake after vacuum filtration (middle trace; Form B), and after drying the wet cake at 45° C. overnight (bottom trace; Form D).

Form B—
Isostructural solvate with MeOH or EtOH.
Form B observed from MeOH and EtOH experiments. XRPD pattern (XRPD Method C) indexed and consistent with solvate, as shown in FIG. 15. A list of 2-theta peaks is provided in Table 23 below.
$^1$H-NMR indicated limited amounts of MeOH in the sample analyzed.
During a scale-up experiment, two sub samples were isolated (slurry and wet cake) and observed to be Form B. Drying of the bulk material in a 45° C. vacuum oven converted to Form D, as shown in FIG. 16 (XRPD Method C).
Stability: Converted to Form A in water activity slurry, 0.22 $a_w$.

TABLE 23

| Peak Number | 2-theta (deg) | Intensity (%) |
|---|---|---|
| 1 | 6.2 | 24 |
| 2 | 6.9 | 7 |
| 3 | 7.8 | 57 |
| 4 | 8.5 | 29 |
| 5 | 9.6 | 8 |
| 6 | 9.8 | 13 |
| 7 | 10.4 | 8 |
| 8 | 10.9 | 24 |
| 9 | 11.4 | 12 |
| 10 | 11.9 | 17 |
| 11 | 12.4 | 6 |
| 12 | 12.6 | 20 |
| 13 | 13.0 | 9 |
| 14 | 13.2 | 21 |
| 15 | 13.5 | 33 |
| 16 | 13.7 | 6 |
| 17 | 14.0 | 13 |
| 18 | 14.2 | 14 |
| 19 | 15.4 | 9 |
| 20 | 15.7 | 10 |
| 21 | 16.1 | 100 |
| 22 | 16.9 | 15 |
| 23 | 17.0 | 8 |
| 24 | 17.2 | 12 |
| 25 | 18.6 | 16 |
| 26 | 19.0 | 24 |
| 27 | 19.3 | 23 |
| 28 | 19.7 | 12 |
| 29 | 19.9 | 9 |
| 30 | 20.2 | 9 |
| 31 | 20.4 | 12 |
| 32 | 20.6 | 15 |
| 33 | 20.8 | 12 |
| 34 | 21.0 | 11 |
| 35 | 21.2 | 28 |
| 36 | 21.4 | 27 |
| 37 | 21.6 | 36 |
| 38 | 22.0 | 10 |
| 39 | 22.4 | 7 |
| 40 | 22.4 | 8 |
| 41 | 22.7 | 6 |
| 42 | 22.9 | 13 |
| 43 | 23.2 | 7 |
| 44 | 24.0 | 8 |
| 45 | 24.1 | 8 |
| 46 | 24.4 | 8 |
| 47 | 24.7 | 8 |
| 48 | 25.0 | 9 |

Figure 17:
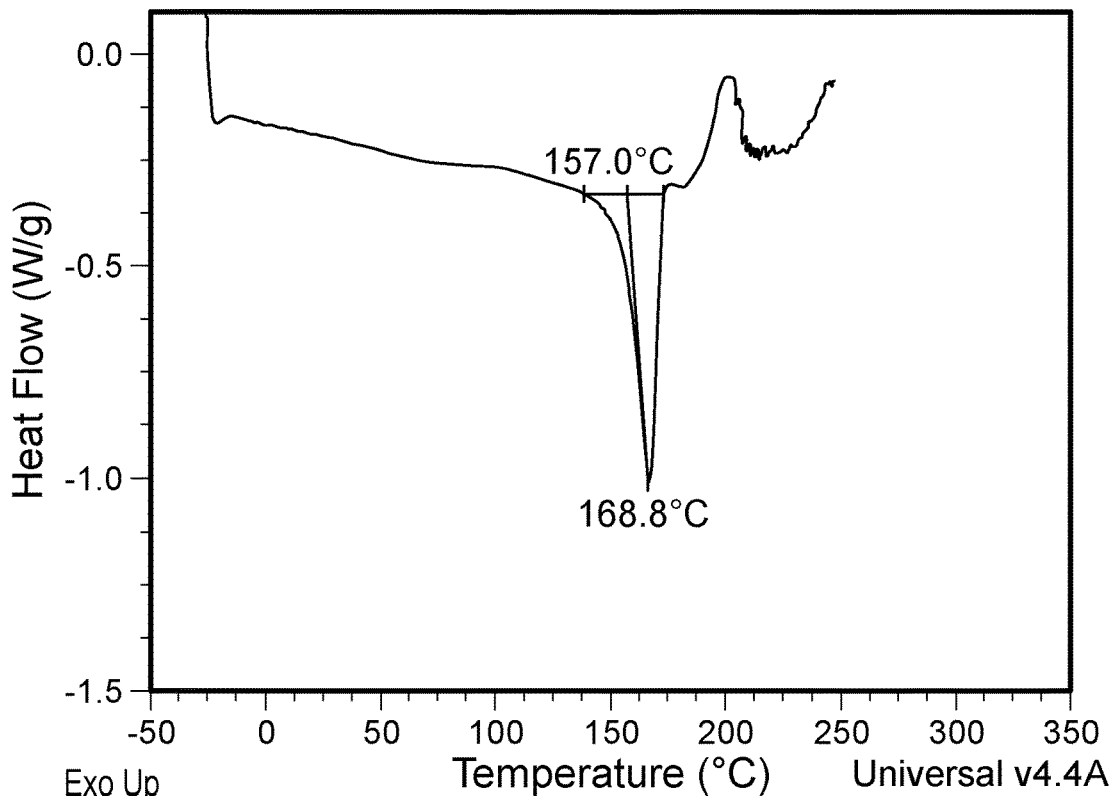
FIG. 17 shows a DSC thermogram characteristic of 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide sesquifumaric acid salt, crystalline Form D.

Form C:
  Observed as a mixture with Form A EtOH generated. Form C only observed from ethanol.
Form D:
  Formed from scale-up using "dry" conditions and from MeOH/heptane slow evaporation
  XRPD: lower crystallinity, as shown in FIGS. 16 and 23 (XRPD Method C). A list of 2-theta peaks is provided in Table 24 below.
  $^1$H NMR consistent with sesquifumarate salt, no organic solvent observed.
  DSC/TG: broad endothermic event with onset at 157° C. observed in the DSC (FIG. 17) and 0.4% weight loss upon heating up to 90° C., as shown in FIG. 18.
  Stability: Converted to Form A in water activity slurry, 0.22 $a_w$.

TABLE 24

| Peak Number | 2-theta (deg) | Intensity (%) |
|---|---|---|
| 1 | 0.6 | 14 |
| 2 | 7.2 | 35 |
| 3 | 8.5 | 60 |
| 4 | 9.5 | 20 |
| 5 | 10.6 | 24 |
| 6 | 10.9 | 16 |
| 7 | 11.8 | 28 |
| 8 | 13.5 | 19 |
| 9 | 14.1 | 29 |
| 10 | 14.5 | 35 |
| 11 | 15.0 | 13 |
| 12 | 16.0 | 100 |
| 13 | 17.4 | 28 |
| 14 | 18.1 | 12 |
| 15 | 19.3 | 26 |
| 16 | 19.7 | 27 |
| 17 | 20.4 | 26 |
| 18 | 21.8 | 35 |
| 19 | 22.7 | 23 |
| 20 | 23.8 | 20 |
| 21 | 24.4 | 22 |
| 22 | 25.7 | 18 |

Figure 19:
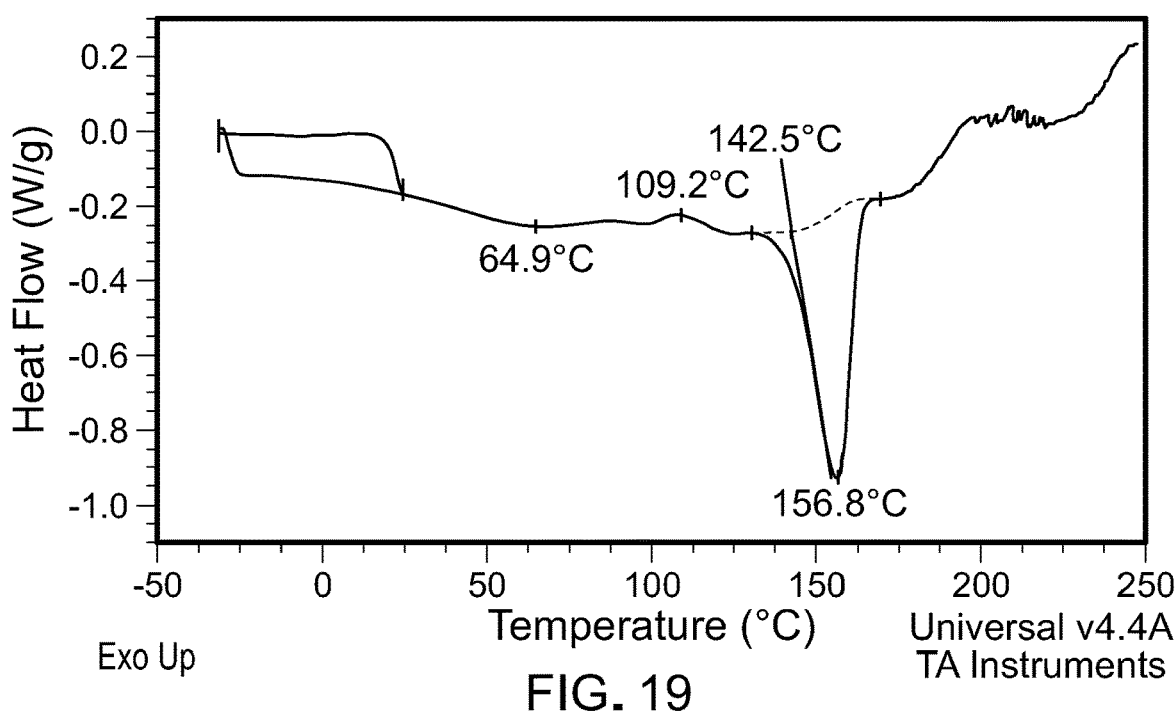
FIG. 19 shows a DSC thermogram characteristic of 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide sesquifumaric acid salt, crystalline Form F.

Form E: THF Solvate
  No changes observed in XRPD after 45° C. vacuum oven for 1 day (XRPD Method C).
  $^1$H-NMR indicates THF solvate. After vacuum drying, 0.6 moles of THF still evident.
Form F:
  DSC: Broad low temperature endotherm with maximum near 65° C. leading into an apparent exothermic event with maximum near 109° C. Final endotherm with an onset near 143° C., as shown in FIG. 19.
  Conversion to Form A was observed when slurried in ACN/water mixture.

Water Activity Analysis

Table 25 shows results of a water activity analysis of 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide sesquifumaric acid salt in various aqueous and organic solvent systems.

TABLE 25

| Solvent | Water Activity (vol % H$_2$O) | Condition | Observation | Result |
|---|---|---|---|---|
| H$_2$O/IPA | 0.96 (50%) | ambient, 7 days | white solids, yellow solution | Form A |
| H$_2$O/acetone | 0.91 (50%) | ambient, 7 days | white solids, yellow solution | Form A |
| H$_2$O/acetone | 0.80 (18%) | ambient, 7 days | white solids, yellow solution | Form A |
| H$_2$O/IPA | 0.70 (11%) | ambient, 7 days | yellow solids | Form A |
| H$_2$O/ACN | 0.60 (4%) | ambient, 7 days | white solids | Form A |
| H$_2$O/IPA | 0.50 (6%) | ambient, 7 days | yellow solids | Form A |
| H$_2$O/acetone | 0.44 (3%) | ambient, 7 days | white solids | Form A |
| H$_2$O/ACN | 0.38 (2%) | ambient, 7 days | white solids | Form A |
| H$_2$O/acetone | 0.22 (1%) | ambient, 7 days | white solids | Form A |

Physical Stability Analysis

Table 26 shows results of a physical stability analysis of 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide sesquifumaric acid salt.

TABLE 26

| Source | Method | Observation | Result |
|---|---|---|---|
| Form B + Form A | 75% RH, 2 days | white, free flowing | Form A |
| Form B + Form A | 75% RH, 3 days | — | Form A |
| Form D | 75% RH, 2 days | — | Form D |
| Form A | 105° C. 3 days | 20% LOD | Form A |
| Form A | 70° C. vacuum 3 days | no weight change | Form A + peaks |
| Form A | ambient vacuum 3 days | no weight change | Form A |
| Form A | 95° C., under $N_2$, 2 days | free-flowing white solids | Form A |
| Form A + B | 1. 45° C. vacuum, 4 days 2. ambient storage, 15 days | — | Form D + Form A |
| Form A + peaks | ambient vacuum, 2 days | — | Form A |
| Form E | 45° C. vacuum, 1 day | free flowing white solids | Form E |
| Form A + B | 45° C. vacuum, 4 days | white solids | Form A + Form B |

RH = relative humidity

Example 264. Preparation of Single Crystal 5-Fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide Bis-Methanesulfonic Acid Salt (Bis-Mesylate)

Figure 20:
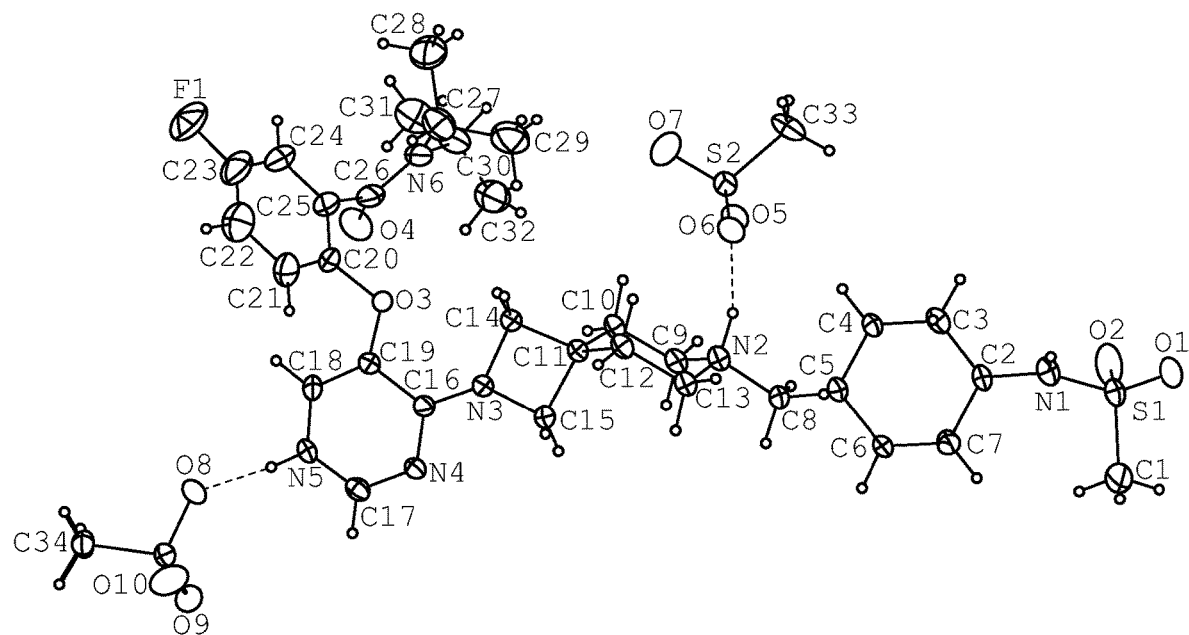
FIGS. 20-21 show ORTEP representations of 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide bis-methanesulfonic acid salt with 50% probability thermal ellipsoids.
Figure 21:
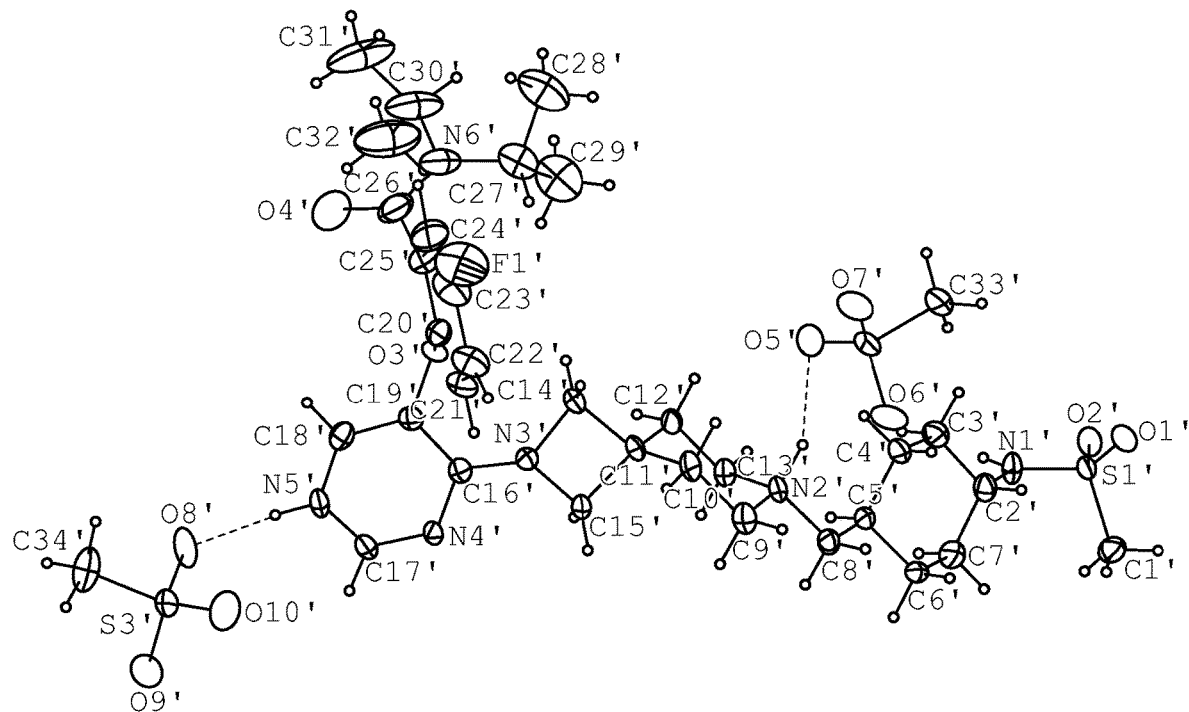

Single crystals of 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide bis-methanesulfonic acid salt were obtained by slow diffusion of EtOAc to an iPrOH solution and confirmed by X-ray structure analysis. A summary of the single crystal X-ray structure analysis is shown below in Table 27. ORTEP representations of the bis-methanesulfonic acid salt with 50% probability thermal ellipsoids displayed are shown in FIGS. 20-21.

TABLE 27

| Instrument | Bruker APEXII CCD area detector with graphite-monochromated Mo-Kα radiation (λ = 0.71073 Å) |
|---|---|
| Temperature/K | 100 |
| Crystal system | triclinic |
| Space group | P1 |
| a | 16.9767(4) Å |
| b | 17.1695(4) Å |
| c | 21.5658(5) Å |
| α | 72.8540(10)° |
| β | 81.8960(10)° |
| γ | 61.5280(10)° |
| Volume | 5280.2(2) Å$^3$ |
| Z | 4 |
| $d_{calc}$ | 1.166 g/cm$^3$ |
| μ | 0.200 mm$^{-1}$ |
| F(000) | 1984.0 |
| Crystal size, mm | 0.48 × 0.3 × 0.08 |
| 2θ range for data collection | 2.73-50.938° |
| Index ranges | −20 ≤ h ≤ 20, −20 ≤ k ≤ 18, −26 ≤ l ≤ 26 |
| Reflections collected | 159085 |
| Independent reflections | 19412[R(int) = 0.0273] |
| Data/restraints/parameters | 19412/162/1155 |
| Goodness-of-fit on F$^2$ | 1.115 |
| Final R indexes [I >= 2σ (I)] | R$_1$ = 0.0495, wR$_2$ = 0.1387 |
| Final R indexes [all data] | R$_1$ = 0.0609, wR$_2$ = 0.1497 |
| Largest diff peak/hole | 0.93/−0.75 eÅ$^{-3}$ |

Example 265. Preparation of Single Crystal 5-Fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide Sesquifumaric Acid Salt (Sesquifumarate)

Figure 22:
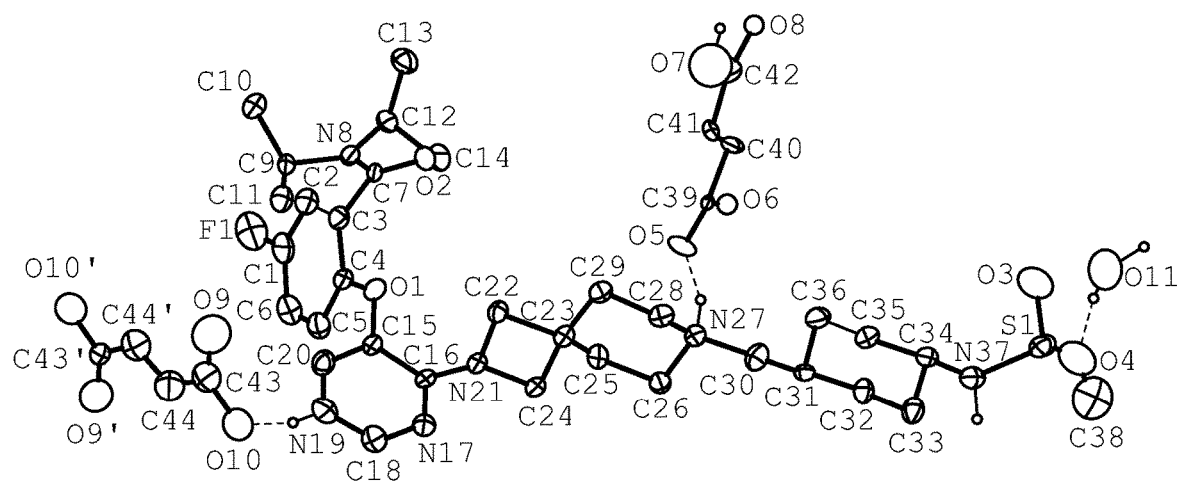
FIG. 22 shows an ORTEP representation of 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide sesquifumaric acid salt with 50% probability thermal ellipsoids.

Single crystals of the 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide sesquifumaric acid salt were obtained by slow evaporation in MeCN solution. X-ray analysis of the single crystal showed a ratio of 1:1.5 between 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide and fumaric acid. A summary of the single crystal X-ray structure analysis is shown below in Table 28. An ORTEP representation of the 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide sesquifumaric acid salt with 50% thermal ellipsoids is shown in FIG. 22.

TABLE 28

| Instrument | Bruker D8QUEST CMOS area detector with graphite-monochromated Mo-Kα radiation (λ = 0.71073 Å) |
|---|---|
| Temperature/K | 100 |
| Crystal system | monoclinic |
| Space group | C2/c |
| a | 60.682(3) Å |
| b | 11.7644(5) Å |
| c | 11.5570(6) Å |
| β | 93.854(2)° |
| Volume | 8231.8(7) Å$^3$ |
| Z | 8 |
| $d_{calc}$ | 1.328 g/cm$^3$ |
| μ | 0.149 mm$^{-1}$ |
| F(000) | 3504.0 |
| Crystal size, mm | 0.25 × 0.10 × 0.01 |
| 2θ range for data collection | 5.846-50.928° |
| Index ranges | −73 ≤ h ≤ 73, −13 ≤ k ≤ 14, −13 ≤ l ≤ 13 |
| Reflections collected | 164974 |
| Independent reflections | 7568[R(int) = 0.1031] |
| Data/restraints/parameters | 7568/451/583 |
| Goodness-of-fit on F$^2$ | 2.231 |
| Final R indexes [I >= 2σ(I)] | R$_1$ = 0.1568, wR$_2$ = 0.4560 |
| Final R indexes [all data] | R$_1$ = 0.1874, wR$_2$ = 0.4951 |
| Largest diff. peak/hole | 2.84/−3.16 eÅ$^{-3}$ |

Example 266. Preparation of Single Crystal 5-Fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide Bis-Hydrochloric Acid Salt A 5N HCl solution in $^i$PrOH (2 mL) was added to 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide free base (140 mg) at room temp. After being stirred at room temp for 30 min, the solvent was removed to afford the bis-hydrochloric acid salt of 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide. A portion of this white amorphous material (~25 mg) was taken and MeCN (0.5 mL) was added at room temp. The resulting suspension was gently heated for 2 minutes until complete dissolution of the material. The solution was then slowly cooled to RT overnight upon standing to afford crystalline 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide bis-hydrochloric acid salt. Melting point: ~210-215° C.

Example 267. Crystalline Salt Screen of 5-Fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide Pharmaceutically acceptable counterions were selected based on known pKa values and salt crystallization experiments were performed according to a general procedure of direct addition of approximately one or two molar equivalents of the counterion to 5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide free base (Example 6A) in solution or suspension. Solid materials were harvested when precipitation of sufficient quantity occurred. Additional steps such as cooling, anti-solvent addition, and/or slurrying were performed to induce crystallization or increase yields if needed. The products were qualitatively evaluated for crystallinity by polarized light microscopy (PLM) and/or XRPD. Vacuum drying was used to identify unsolvated crystal forms of the potential salts. Solution 1H-NMR spectroscopy was used to confirm composition and stoichiometry, that chemical degradation did not occur, and to evaluate the amount of solvent present. For hydrochloric acid salts, energy-dispersive X-ray (EDX) spectroscopy was used to confirm stoichiometry. Table 29 shows a list of pharmaceutically acceptable salts identified in the salt screening experiments. "n/a" refers to data not available (e.g., the salt was unable to be isolated in crystalline form; the salt deliquesced at 75% relative humidity; the salt converted to another form; or a disordered XRPD pattern was observed).

TABLE 29

| Salt Form | Stoichiometry (Example 6A:acid) |
|---|---|
| Acetate | n/a |
| Besylate Material A | 1:1 |
| Fumarate Material A | 2:1 |
| Fumarate Material B | n/a |
| Fumarate Material C | n/a |
| Fumarate Material D | n/a |
| Fumarate Material E | n/a |
| Sesquifumarate Form A | 2:3 |
| Sesquifumarate Material B | 2:3 |
| HCl Material A | n/a |
| HCl Material B | 1:2 |
| HCl Material C | 1:2 |
| Malate Material A | n/a |
| Malate Material B | 1:1 |
| Mesylate Material A | 1:1 |
| Mesylate Material B | n/a |
| Mesylate Material C | n/a |
| Napsylate (amorphous) | n/a |
| Napadisylate Material A | n/a |
| Napadisylate Material B | n/a |
| Phosphate (amorphous) | n/a |
| Succinate Material A | 2:1 |

TABLE 29-continued

| Salt Form | Stoichiometry (Example 6A:acid) |
|---|---|
| Succinate (amorphous) | n/a |
| Sulfate | n/a |
| Tartrate | n/a |
| Tosylate Material A | 1:1 |
| Tosylate Material B | 1:1 |
| Tosylate Material C | n/a |
| Tosylate Material D | 1:1 |

Biological Assays
Assay 1 (Binding Assay)

Potencies of inhibitor compounds against menin/MLL binding were assessed by AlphaLISA assay using biotinylated (1) wild-type menin or (2) mutated menin (described in Huang et al, 2012, *Nature*, 482, 542-546) and MLL-AF9 fusion protein bearing a FLAG epitope at its C-terminus. Menin proteins were expressed in *E. coli* and covalently modified with biotin using EZ-Link™ Sulfo-NHS-Biotin (ThermoFisher Cat. No. 21217) according to manufacturer's protocol. MLL1-1,396 fused to AF91-92 and the C-terminal FLAG peptide was expressed in HEK293 cells and used as a lysate cleared at 21,000×g for 10 min.

Compounds (2 µL of solutions in DMSO) were dispensed in white 96-well half-area plates (Corning Cat. No. 3693) and incubated for 30 min at RT with 5 nM biotinylated menin and appropriate amount of MLL-AF9-FLAG lysate in 40 µL of 50 mM Tris-HCl buffer pH 7.4 containing 5% (v/v) DMSO, 50 mM NaCl, 0.01% (w/v) bovine serum albumin (BSA) and 1 mM DTT. To this incubation mixture, 40 µL of AlphaLISA anti-FLAG acceptor (PerkinElmer Cat. No. AL112C) and streptavidin donor (PerkinElmer Cat. No. 6760002) beads (10 µg/mL each) was added and incubation continued at RT for 60 min. Alpha (amplified luminescent proximity homogeneous assay) signal was measured on an Envision multi-label plate reader at the end of the incubation. All steps were conducted under dim fluorescent light.

Percent inhibition values were calculated based on uninhibited (DMSO) and fully inhibited (10 µM MI-2-2, EMD Millipore Cat. No. 444825) controls. These percent inhibition values were regressed against compound concentrations in the assay using four parameter logit non-linear curve fitting (XLFit, IDBS). The $IC_{50}$ values were derived from the curve fitting as inflection points on the dose-response curves and are set out in Table 30 below.

Assay 2: (Cell Proliferation Assay)

Potencies of inhibitor compounds against cell proliferation was assessed against the human acute monocytic leukemia cell line MV-4-11 (ATCC® CRL-9591™) based on ATP quantitation. MV-4-11 cells or toxicity control HL-60 cells (ATCC® CCL-240™) were incubated in 96-well tissue culture plates ($1.67 \times 10^4$ cells in 200 µL culture media containing 10% FBS per well) with or without test compound for 72 h at 37° C., 5% $CO_2$. After incubation, each well was mixed by pipetting and 95 µL from each well was transferred to a well in 96-well black OptiPlate® plates (PerkinElmer). An equal volume of CellTiter-Glo® Luminescent Cell Viability Assay reagent (Promega) was added to each well, followed by mixing for 5 min on an orbital plate shaker. Luminescence was measured on a Wallac EnVision 2104 Multilabel Reader (PerkinElmer) to quantitate ATP. Percent inhibition of cell proliferation by test compounds was calculated based on uninhibited cell growth (DMSO) versus cells treated with a potent menin inhibitor at a concentration yielding at least $100 \times LD_{50}$. $EC_{50}$ values were calculated based on dose response curves of percent inhibition versus compound concentration and are set out in Table 30 below.

Data for Assays 1 and 2 are provided below in Table 27 ("n/a" refers to data not available; "+++" means <100 nM; "++" means ≥100 nM and <1000 nM; and "+" means ≥1000 nM).

TABLE 30

Biological Data

| Example | Assay 1 | Assay 2 |
| --- | --- | --- |
| 1 | +++ | +++ |
| 1A | +++ | +++ |
| 1B | +++ | +++ |
| 2 | +++ | +++ |
| 2A | +++ | +++ |
| 2B | +++ | +++ |
| 3A | +++ | +++ |
| 3B | +++ | +++ |
| 4 | +++ | +++ |
| 4A | +++ | +++ |
| 4B | +++ | +++ |
| 5 | +++ | +++ |
| 6A | +++ | +++ |
| 6B | +++ | +++ |
| 7 | +++ | ++ |
| 8 | +++ | +++ |
| 9 | +++ | + |
| 10 | +++ | + |
| 11 | +++ | +++ |
| 12 | +++ | ++ |
| 13 | +++ | n/a |
| 14A | +++ | n/a |
| 15 | +++ | ++ |
| 16 | +++ | ++ |
| 17 | ++ | n/a |
| 18 | +++ | ++ |
| 19 | +++ | ++ |
| 20 | ++ | n/a |
| 21 | ++ | n/a |
| 22A | +++ | + |
| 22B | +++ | n/a |
| 23A | +++ | ++ |
| 23B | ++ | n/a |
| 23C | +++ | + |
| 24A | +++ | + |
| 24B | +++ | + |
| 25 | +++ | + |
| 26A | +++ | ++ |
| 26B | +++ | + |
| 27 | +++ | + |
| 28 | +++ | +++ |
| 29 | +++ | +++ |
| 29A | +++ | +++ |
| 29B | +++ | ++ |
| 30 | +++ | n/a |
| 31 | +++ | n/a |
| 32 | +++ | n/a |
| 33 | +++ | ++ |
| 34 | +++ | + |
| 35 | +++ | ++ |
| 36 | +++ | ++ |
| 37 | +++ | ++ |
| 38 | +++ | + |
| 39 | ++ | n/a |
| 40 | ++ | + |
| 41 | +++ | +++ |
| 41A | +++ | +++ |
| 41B | +++ | +++ |
| 42 | +++ | +++ |
| 42A | +++ | +++ |
| 42B | +++ | +++ |
| 43 | +++ | +++ |
| 44 | +++ | ++ |
| 45 | +++ | +++ |
| 46 | ++ | n/a |
| 47 | +++ | ++ |

TABLE 30-continued

Biological Data

| Example | Assay 1 | Assay 2 |
| --- | --- | --- |
| 48 | +++ | ++ |
| 49 | +++ | n/a |
| 50 | +++ | n/a |
| 51 | +++ | +++ |
| 52 | +++ | +++ |
| 53 | +++ | +++ |
| 54 | +++ | ++ |
| 55 | + | n/a |
| 56 | + | n/a |
| 57 | +++ | n/a |
| 58 | ++ | n/a |
| 59 | + | n/a |
| 60 | +++ | ++ |
| 60A | +++ | +++ |
| 60B | +++ | +++ |
| 60C | +++ | +++ |
| 60D | +++ | +++ |
| 61 | ++ | n/a |
| 62 | +++ | ++ |
| 63 | +++ | +++ |
| 64 | +++ | ++ |
| 65 | +++ | ++ |
| 66 | +++ | + |
| 67 | +++ | ++ |
| 68 | +++ | + |
| 69 | +++ | +++ |
| 70 | +++ | +++ |
| 71 | +++ | n/a |
| 72 | +++ | ++ |
| 73 | +++ | ++ |
| 74 | +++ | n/a |
| 76 | +++ | +++ |
| 77 | +++ | + |
| 78 | ++ | n/a |
| 79 | +++ | +++ |
| 80 | +++ | +++ |
| 81A | +++ | ++ |
| 81B | +++ | +++ |
| 82 | +++ | ++ |
| 83 | +++ | ++ |
| 84 | +++ | +++ |
| 85 | +++ | ++ |
| 86 | +++ | +++ |
| 87 | +++ | ++ |
| 88 | +++ | +++ |
| 89 | +++ | ++ |
| 90 | +++ | +++ |
| 91 | +++ | +++ |
| 91A | +++ | +++ |
| 92 | +++ | ++ |
| 93 | +++ | ++ |
| 94 | +++ | ++ |
| 95 | +++ | ++ |
| 96 | +++ | ++ |
| 97 | +++ | ++ |
| 98 | +++ | ++ |
| 99 | +++ | ++ |
| 99A | +++ | +++ |
| 100 | +++ | ++ |
| 101 | +++ | ++ |
| 102 | +++ | +++ |
| 103 | +++ | ++ |
| 104 | +++ | +++ |
| 105 | +++ | +++ |
| 106 | +++ | +++ |
| 107 | +++ | +++ |
| 108 | +++ | + |
| 109 | +++ | + |
| 110 | +++ | ++ |
| 111 | +++ | +++ |
| 112 | +++ | +++ |
| 113 | +++ | +++ |
| 114 | +++ | ++ |
| 115 | +++ | +++ |
| 116 | +++ | ++ |
| 117 | +++ | ++ |

TABLE 30-continued

Biological Data

| Example | Assay 1 | Assay 2 |
|---|---|---|
| 118 | +++ | ++ |
| 119 | +++ | ++ |
| 120 | +++ | +++ |
| 121 | +++ | ++ |
| 122 | +++ | +++ |
| 123 | +++ | + |
| 124 | +++ | ++ |
| 125 | +++ | +++ |
| 126 | +++ | ++ |
| 127 | +++ | ++ |
| 128 | +++ | ++ |
| 129 | +++ | ++ |
| 130 | +++ | ++ |
| 131 | +++ | +++ |
| 132 | +++ | ++ |
| 133 | +++ | ++ |
| 134 | +++ | ++ |
| 135 | +++ | + |
| 136 | +++ | ++ |
| 137 | +++ | ++ |
| 138 | +++ | +++ |
| 139 | +++ | ++ |
| 140 | +++ | ++ |
| 141 | +++ | ++ |
| 142 | +++ | + |
| 143 | +++ | + |
| 144 | +++ | +++ |
| 145 | +++ | ++ |
| 146 | +++ | ++ |
| 147 | +++ | + |
| 148A | +++ | ++ |
| 148B | +++ | ++ |
| 149 | +++ | +++ |
| 150 | +++ | +++ |
| 151 | +++ | + |
| 152 | +++ | +++ |
| 153 | +++ | ++ |
| 154 | +++ | ++ |
| 155 | +++ | ++ |
| 156 | +++ | ++ |
| 157 | +++ | n/a |
| 158 | +++ | ++ |
| 159 | +++ | ++ |
| 160 | +++ | +++ |
| 160A | +++ | +++ |
| 160B | +++ | +++ |
| 161 | +++ | +++ |
| 162 | +++ | ++ |
| 163 | +++ | ++ |
| 164 | +++ | ++ |
| 165 | +++ | + |
| 166 | +++ | ++ |
| 167 | +++ | ++ |
| 168 | +++ | + |
| 169 | +++ | +++ |
| 170 | +++ | ++ |
| 171 | +++ | +++ |
| 172 | +++ | ++ |
| 173 | +++ | ++ |
| 174 | +++ | +++ |
| 175 | +++ | + |
| 176 | +++ | + |
| 177 | +++ | +++ |
| 178 | +++ | +++ |
| 179 | +++ | +++ |
| 180 | +++ | +++ |
| 181 | +++ | ++ |
| 182 | +++ | ++ |
| 183 | +++ | +++ |
| 183A | +++ | +++ |
| 183B | +++ | +++ |
| 184 | +++ | ++ |
| 185 | +++ | ++ |
| 186 | +++ | +++ |
| 187 | +++ | +++ |
| 188 | +++ | ++ |
| 189 | +++ | ++ |
| 190 | +++ | +++ |
| 190A | +++ | ++ |
| 191 | +++ | +++ |
| 192 | +++ | ++ |
| 193 | +++ | +++ |
| 194 | +++ | ++ |
| 195 | +++ | ++ |
| 196 | +++ | +++ |
| 197A | +++ | +++ |
| 197B | +++ | +++ |
| 198 | +++ | +++ |
| 199 | +++ | + |
| 200 | +++ | ++ |
| 201 | +++ | + |
| 202 | +++ | ++ |
| 203 | +++ | + |
| 204 | +++ | ++ |
| 205 | +++ | +++ |
| 206A | +++ | ++ |
| 206B | ++ | n/a |
| 206C | ++ | n/a |
| 207 | +++ | ++ |
| 208 | +++ | + |
| 209 | +++ | ++ |
| 210 | +++ | ++ |
| 211 | +++ | ++ |
| 212 | +++ | ++ |
| 213 | +++ | +++ |
| 214 | +++ | ++ |
| 215 | +++ | ++ |
| 216 | +++ | ++ |
| 217 | +++ | +++ |
| 218 | +++ | + |
| 219 | +++ | ++ |
| 220 | +++ | ++ |
| 221 | +++ | ++ |
| 222 | +++ | + |
| 223 | +++ | ++ |
| 224 | +++ | +++ |
| 225 | +++ | ++ |
| 226 | +++ | + |
| 227 | +++ | +++ |
| 228 | +++ | ++ |
| 229 | +++ | ++ |
| 230 | +++ | ++ |
| 231 | +++ | ++ |
| 232 | +++ | +++ |
| 233 | +++ | ++ |
| 234 | +++ | +++ |
| 235 | +++ | ++ |
| 236 | +++ | ++ |
| 237 | +++ | +++ |
| 237A | +++ | +++ |
| 238 | +++ | +++ |
| 239 | +++ | +++ |
| 240 | +++ | +++ |
| 241 | +++ | ++ |
| 242 | +++ | ++ |
| 243 | +++ | n/a |
| 244 | +++ | n/a |
| 245 | +++ | n/a |
| 246 | +++ | n/a |
| 247 | +++ | n/a |
| 248A | +++ | ++ |
| 248B | +++ | ++ |
| 249 | +++ | ++ |
| 250A | ++ | n/a |
| 250B | +++ | + |
| 251 | +++ | + |
| 252 | +++ | +++ |

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

The contents of all references (including literature references, issued patents, published patent applications, and co-pending patent applications) cited throughout this application are hereby expressly incorporated herein in their entireties by reference. Unless otherwise defined, all technical and scientific terms used herein are accorded the meaning commonly known to one with ordinary skill in the art.

What is claimed is:
1. A compound of Formula I:

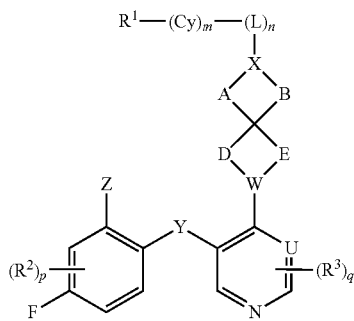

or a pharmaceutically acceptable salt thereof, wherein:
A, B, D, and E are each independently selected from —C($R^{A1}$)($R^{A2}$)—, —C($R^{A1}$)($R^{A2}$)—C($R^{A1}$)($R^{A2}$)—, —C($R^{A1}$)($R^{A2}$)—O—, —C($R^{A1}$)($R^{A2}$)—$NR^{A3}$—, —C(=O)—, —C($R^{A1}$)($R^{A2}$)—C(=O)—, and —N=C(NH$_2$)— wherein no more than one of A, B, D, and E is —C($R^{A1}$)($R^{A2}$)—O—, —C($R^{A1}$)($R^{A2}$)—$NR^{A3}$—, —C($R^{A1}$)($R^{A2}$)—C(=O)—, —C(=O)—, or —N=C(NH$_2$)—;

U is N or $CR^U$, wherein $R^U$ is H, halo, CN, OH, $C_{1-4}$ alkyl, $C_{1-4}$ alkoxy, amino, $C_{1-4}$ alkyl amino, or $C_{2-8}$ dialkylamino;

W is N or $CR^W$, wherein $R^W$ is H, halo, CN, OH, $C_{1-4}$ alkyl, $C_{1-4}$ alkoxy, amino, $C_{1-4}$ alkyl amino, or $C_{2-8}$ dialkylamino;

X is N or $CR^X$, wherein $R^X$ is H, halo, CN, OH, $C_{1-4}$ alkyl, $C_{1-4}$ alkoxy, amino, $C_{1-4}$ alkyl amino, or $C_{2-8}$ dialkylamino, wherein when X is N, the atom of L that is directly bonded with X is other than N, O, or S;

L is selected from —$C_{1-6}$ alkylene- and —($C_{1-4}$ alkylene)$_a$-Q-($C_{1-4}$ alkylene)$_b$-, wherein the $C_{1-6}$ alkylene group and any $C_{1-4}$ alkylene group of the —($C_{1-4}$ alkylene)$_a$-Q-($C_{1-4}$ alkylene)$_b$-group is optionally substituted with 1, 2, or 3 substituents independently selected from halo, CN, OH, $C_{1-3}$ alkyl, $C_{1-3}$ alkoxy, $C_{1-3}$ haloalkyl, $C_{1-3}$ haloalkoxy, amino, $C_{1-3}$ alkylamino, and di($C_{1-3}$ alkyl)amino;

Q is —O—, —S—, —S(=O)—, —S(=O)$_2$—, —C(=O)—, —C(=O)$NR^{q1}$—, —C(=O)O—, —OC(=O)$NR^{q1}$—, —$NR^{q1}$—, —$NR^{q1}$C(=O) O—, —$NR^{q1}$C(=O)$NR^{q1}$—, —S(=O)$_2$$NR^{q1}$—, —C(=$NR^{q2}$)—, or —C(=$NR^{q2}$)—$NR^{q1}$—, wherein each $R^{q1}$ is independently selected from H or $C_{1-6}$ alkyl, and wherein each $R^{q2}$ is independently selected from H, $C_{1-6}$ alkyl, and CN;

Cy is a linking $C_{6-14}$ aryl, $C_{3-18}$ cycloalkyl, 5-16 membered heteroaryl, or 4-18 membered heterocycle group, each of which is optionally substituted with 1, 2, 3, or 4 substituents independently selected from $R^{Cy}$, wherein the heteroaryl or heterocycle has 1-3 rings and 1-4 heteroatoms independently selected from nitrogen, sulfur, and oxygen;

each $R^{Cy}$ is independently selected from halo, $C_{1-6}$ alkyl, $C_{1-4}$ haloalkyl, $C_{1-4}$ cyanoalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycle, CN, NO$_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, and 4-10 membered heterocycle are each optionally substituted by 1, 2, 3, or 4 substituents independently selected from CN, NO$_2$, $OR^{a1}$, $SR^{a1}$, $C(O)R^{b1}$, $C(O)NR^{c1}R^{d1}$, $C(O)OR^{a1}$, $OC(O)R^{b1}$, $OC(O)NR^{c1}R^{d1}$, $C(=NR^{e1})NR^{c1}R^{d1}$, $NR^{c1}C(=NR^{e1})NR^{c1}R^{d1}$, $NR^{c1}R^{d1}$, $NR^{c1}C(O)R^{b1}$, $NR^{c1}C(O)OR^{a1}$, $NR^{c1}C(O)NR^{c1}R^{d1}$, $NR^{c1}S(O)R^{b1}$, $NR^{c1}S(O)_2R^{b1}$, $NR^{c1}S(O)_2NR^{c1}R^{d1}$, $S(O)R^{b1}$, $S(O)NR^{c1}R^{d1}$, $S(O)_2R^{b1}$, and $S(O)_2NR^{c1}R^{d1}$, wherein the heteroaryl or heterocycle has 1-3 rings and 1-4 heteroatoms independently selected from nitrogen, sulfur, and oxygen;

$R^1$ is H, $Cy^1$, halo, $C_{1-6}$ alkyl, $C_{1-4}$ haloalkyl, $C_{1-4}$ cyanoalkyl, $C_{2-6}$ alkenyl, $C_{2-6}$ alkynyl, CN, NO$_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$ and $S(O)_2NR^{c2}R^{d2}$, wherein said $C_{1-6}$ alkyl, $C_{2-6}$ alkenyl, and $C_{2-6}$ alkynyl are each optionally substituted by 1, 2, 3, or 4 substituents independently selected from halo, CN, NO$_2$, $OR^{a2}$, $SR^{a2}$, $C(O)R^{b2}$, $C(O)NR^{c2}R^{d2}$, $C(O)OR^{a2}$, $OC(O)R^{b2}$, $OC(O)NR^{c2}R^{d2}$, $C(=NR^{e2})NR^{c2}R^{d2}$, $NR^{c2}C(=NR^{e2})NR^{c2}R^{d2}$, $NR^{c2}R^{d2}$, $NR^{c2}C(O)R^{b2}$, $NR^{c2}C(O)OR^{a2}$, $NR^{c2}C(O)NR^{c2}R^{d2}$, $NR^{c2}S(O)R^{b2}$, $NR^{c2}S(O)_2R^{b2}$, $NR^{c2}S(O)_2NR^{c2}R^{d2}$, $S(O)R^{b2}$, $S(O)NR^{c2}R^{d2}$, $S(O)_2R^{b2}$, and $S(O)_2NR^{c2}R^{d2}$;

Y is O, S, $CR^{Y1}R^{Y2}$ or $NR^{Y3}$, wherein $R^{Y1}$, $R^{Y2}$, and $R^{Y3}$ are each independently selected from H and $C_{1-4}$ alkyl;

Z is $Cy^2$, halo, $C_{1-6}$ alkyl, $C_{1-4}$ haloalkyl, $C_{1-4}$ cyanoalkyl, $C_{2-6}$ alkenyl, $C_{2-6}$ alkynyl, CN, NO$_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, $S(O)_2NR^{c3}R^{d3}$, and $P(O)R^{c3}R^{d3}$ wherein said $C_{1-6}$ alkyl, $C_{2-6}$ alkenyl, and $C_{2-6}$ alkynyl are each optionally substituted by 1, 2, 3, or 4 substituents independently selected from $Cy^2$, halo, CN, NO$_2$, CN, NO$_2$, $OR^{a3}$, $SR^{a3}$, $C(O)R^{b3}$, $C(O)NR^{c3}R^{d3}$, $C(O)OR^{a3}$, $OC(O)R^{b3}$, $OC(O)NR^{c3}R^{d3}$, $C(=NR^{e3})NR^{c3}R^{d3}$, $NR^{c3}C(=NR^{e3})NR^{c3}R^{d3}$, $NR^{c3}R^{d3}$, $NR^{c3}C(O)R^{b3}$, $NR^{c3}C(O)OR^{a3}$, $NR^{c3}C(O)NR^{c3}R^{d3}$, $NR^{c3}S(O)R^{b3}$, $NR^{c3}S(O)_2R^{b3}$, $NR^{c3}S(O)_2NR^{c3}R^{d3}$, $S(O)R^{b3}$, $S(O)NR^{c3}R^{d3}$, $S(O)_2R^{b3}$, and $S(O)_2NR^{c3}R^{d3}$;

each $R^2$ and $R^3$ is independently selected from H, halo, $C_{1-6}$ alkyl, $C_{1-4}$ haloalkyl, $C_{1-4}$ cyanoalkyl, $C_{2-6}$ alkenyl, $C_{2-6}$ alkynyl, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $C(=NR^{e4})NR^{c4}R^{d4}$, $NR^{c4}C(=NR^{e4})NR^{c4}R^{d4}$, $NR^{c4}R^{d4}$, $NR^{c4}C(O)R^{b4}$, $NR^{c4}C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$, wherein said $C_{1-6}$ alkyl, $C_{2-6}$ alkenyl, and $C_{2-6}$ alkynyl are each optionally substituted by 1, 2, 3, or 4 substituents independently selected from halo, CN, $NO_2$, $OR^{a4}$, $SR^{a4}$, $C(O)R^{b4}$, $C(O)NR^{c4}R^{d4}$, $C(O)OR^{a4}$, $OC(O)R^{b4}$, $OC(O)NR^{c4}R^{d4}$, $C(=NR^{e4})NR^{c4}R^{d4}$, $NR^4C(=NR^{e4})NR^{c4}R^{d4}$, $NR^{c4}R^{d4}$, $NR^4C(O)R^{b4}$, $NR^4C(O)OR^{a4}$, $NR^{c4}C(O)NR^{c4}R^{d4}$, $NR^{c4}S(O)R^{b4}$, $NR^{c4}S(O)_2R^{b4}$, $NR^{c4}S(O)_2NR^{c4}R^{d4}$, $S(O)R^{b4}$, $S(O)NR^{c4}R^{d4}$, $S(O)_2R^{b4}$, and $S(O)_2NR^{c4}R^{d4}$;

each $R^{A1}$ is independently selected from H, halo, $C_{1-4}$ alkyl, $C_{1-4}$ alkoxy, $C_{1-4}$ haloalkyl, $C_{1-4}$ haloalkoxy, amino, $C_{1-4}$ alkylamino, $C_{2-8}$ dialkylamino, CN, $NO_2$, and OH;

each $R^{A2}$ is independently selected from H, halo, $C_{1-4}$ alkyl, $C_{1-4}$ alkoxy, $C_{1-4}$ haloalkyl, $C_{1-4}$ haloalkoxy, amino, $C_{1-4}$ alkylamino, $C_{2-8}$ dialkylamino, CN, $NO_2$, and OH;

each $R^{A3}$ is independently selected from H, $C_{1-4}$ alkyl, $C_{1-4}$ alkoxy, $C_{1-4}$ haloalkyl, $C(O)R^z$, and $C(O)OR^z$, wherein said $C_{1-4}$ alkyl is optionally substituted by phenyl, $C_{1-4}$ alkoxy, $C_{1-4}$ haloalkoxy, CN, $NO_2$, or OH;

$R^z$ is H, $C_{1-4}$ alkyl, or phenyl;

each $Cy^1$ is independently selected from $C_{6-14}$ aryl, $C_{3-18}$ cycloalkyl, 5-16 membered heteroaryl, and 4-18 membered heterocycle, each of which is optionally substituted with 1, 2, 3, or 4 substituents independently selected from $R^{Cy1}$, wherein the heteroaryl or heterocycle has 1-3 rings and 1-4 heteroatoms independently selected from nitrogen, sulfur, and oxygen;

each $Cy^2$ is independently selected from $C_{6-14}$ aryl, $C_{3-18}$ cycloalkyl, 5-16 membered heteroaryl, and 4-18 membered heterocycle, each of which is optionally substituted with 1, 2, 3, or 4 substituents independently selected from $R^{Cy2}$, wherein the heteroaryl or has 1-3 rings and 1-4 heteroatoms independently selected from nitrogen, sulfur, and oxygen;

each $R^{Cy1}$ and $R^{Cy2}$ is independently selected from halo, $C_{1-6}$ alkyl, $C_{1-4}$ haloalkyl, $C_{1-4}$ cyanoalkyl, $C_{2-6}$ alkenyl, $C_{2-6}$ alkynyl, phenyl, $C_{3-7}$ cycloalkyl, 5-6 membered heteroaryl, and 4-7 membered heterocycle, CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $C(=NR^{e5})NR^{c5}R^{d5}$, $NR^{c5}C(=NR^{e5})NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$, $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$, wherein said $C_{1-6}$ alkyl, $C_{2-6}$ alkenyl, $C_{2-6}$ alkynyl, phenyl, $C_{3-7}$ cycloalkyl, 5-6 membered heteroaryl, and 4-7 membered heterocycle are each optionally substituted by 1, 2, 3, or 4 substituents independently selected from CN, $NO_2$, $OR^{a5}$, $SR^{a5}$, $C(O)R^{b5}$, $C(O)NR^{c5}R^{d5}$, $C(O)OR^{a5}$, $OC(O)R^{b5}$, $OC(O)NR^{c5}R^{d5}$, $C(=NR^{e5})NR^{c5}R^{d5}$, $NR^{c5}C(=NR^{e5})NR^{c5}R^{d5}$, $NR^{c5}R^{d5}$, $NR^{c5}C(O)R^{b5}$, $NR^{c5}C(O)OR^{a5}$, $NR^{c5}C(O)NR^{c5}R^{d5}$ $NR^{c5}S(O)R^{b5}$, $NR^{c5}S(O)_2R^{b5}$, $NR^{c5}S(O)_2NR^{c5}R^{d5}$, $S(O)R^{b5}$, $S(O)NR^{c5}R^{d5}$, $S(O)_2R^{b5}$, and $S(O)_2NR^{c5}R^{d5}$, wherein the heteroaryl or heterocycle has 1-3 rings and 1-4 heteroatoms independently selected from nitrogen, sulfur, and oxygen;

each $R^{a1}$, $R^{b1}$, $R^{c1}$, $R^{d1}$, $R^{a2}$, $R^{b2}$, $R^{c2}$, $R^{d2}$, $R^{a3}$, $R^{b3}$, $R^{c3}$, $R^{d3}$, $R^{a4}$, $R^{b4}$, $R^{c4}$, $R^{d4}$, $R^{a5}$, $R^{b5}$, $R^{c5}$, and $R^{d5}$ is independently selected from H, $C_{1-6}$ alkyl, $C_{1-4}$ haloalkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycle, $C_{6-10}$ aryl-$C_{1-6}$ alkyl, $C_{3-10}$ cycloalkyl-$C_{1-6}$ alkyl, (5-10 membered heteroaryl)-$C_{1-6}$ alkyl, and (4-10 membered heterocycle)-$C_{1-6}$ alkyl, wherein said $C_{1-6}$ alkyl, $C_{2-6}$ alkenyl, $C_{2-6}$ alkynyl, $C_{6-10}$ aryl, $C_{3-10}$ cycloalkyl, 5-10 membered heteroaryl, 4-10 membered heterocycle, $C_{6-10}$ aryl-$C_{1-6}$ alkyl, $C_{3-10}$ cycloalky-$C_{1-6}$ alkyl, (5-10 membered heteroaryl)-$C_{1-6}$ alkyl, and (4-10 membered heterocycle)-$C_{1-6}$ alkyl are each optionally substituted with 1, 2, 3, 4, or 5 substituents independently selected from $R^g$, wherein the heteroaryl or heterocycle has 1-3 rings and 1-4 heteroatoms independently selected from nitrogen, sulfur, and oxygen;

each $R^{e1}$, $R^{e2}$, $R^{e3}$, $R^{e4}$, and $R^{e5}$ is independently selected from H, $C_{1-4}$ alkyl, and CN;

each $R^g$ is independently selected from the group consisting of OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thiol, $C_{1-6}$ alkylthio, $C_{1-6}$ alkylsulfinyl, $C_{1-6}$ alkylsulfonyl, carboxy, aminocarbonyl, $C_{1-6}$ alkylcarbonyl, and $C_{1-6}$ alkoxycarbonyl;

n is 0 or 1;

m is 0 or 1;

p is 0, 1, 2, or 3;

q is 0, 1, or 2;

a is 0 or 1; and b is 0 or 1, wherein any cycloalkyl or heterocycle group is optionally further substituted by 1 or 2 oxo groups.

2. The compound of claim 1, or a pharmaceutically acceptable salt thereof, wherein Y is O or $NR^{Y3}$.

3. The compound of claim 1, or a pharmaceutically acceptable salt thereof, wherein U is N or $CR^U$.

4. The compound of claim 1, or a pharmaceutically acceptable salt thereof, wherein W is N or $CR^W$.

5. The compound of claim 1, or a pharmaceutically acceptable salt thereof, wherein X is N or $CR^X$.

6. The compound of claim 1, or a pharmaceutically acceptable salt thereof, wherein A, B, D, and E are each independently selected from —$C(R^{A1})(R^{A2})$— or —$C(R^{A1})(R^{A2})$—$C(R^{A1})(R^{A2})$—.

7. The compound of claim 1, or a pharmaceutically acceptable salt thereof, wherein A, B, D, and E are each independently selected from —$CH_2$— or —$CH_2$—$CH_2$—.

8. The compound of claim 1, or a pharmaceutically acceptable salt thereof, wherein the spiro moiety represented by the below formula:

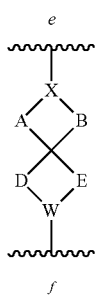
wherein e and f indicate points of attachment to the remainder of the molecule, is selected from:
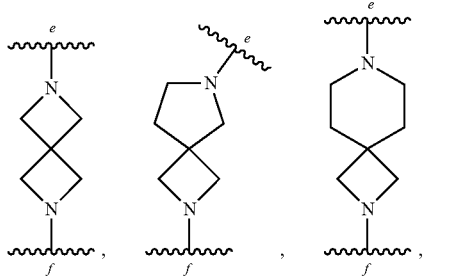
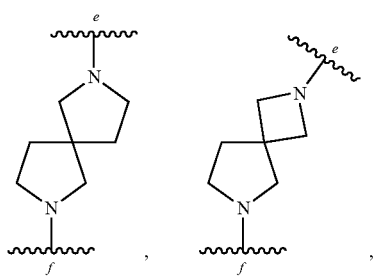
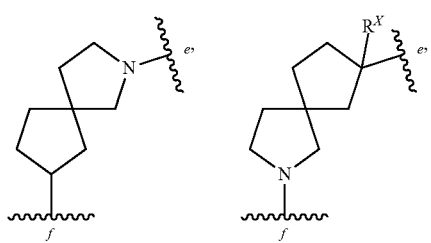
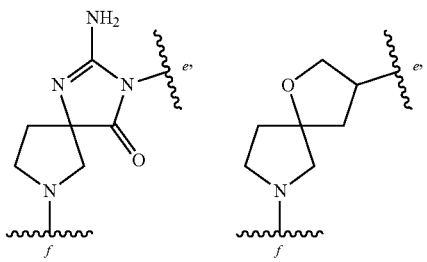
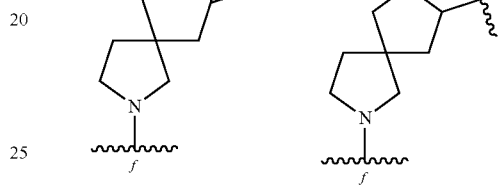
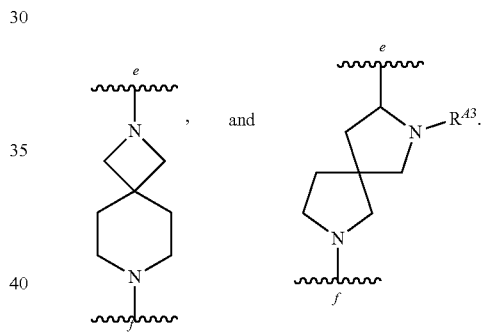
9. The compound of claim 1, or a pharmaceutically acceptable salt thereof, wherein the spiro moiety is represented by the below formula:
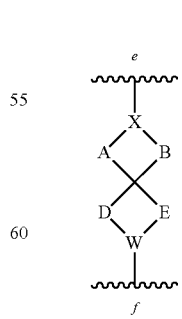
wherein e and f indicate points of attachment to the remainder of the molecule, is selected from:

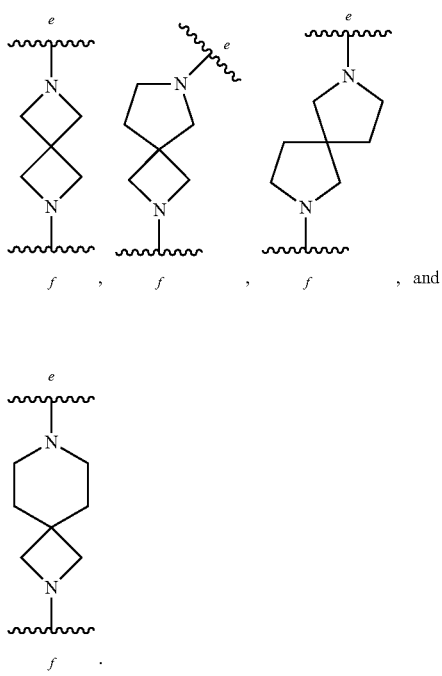

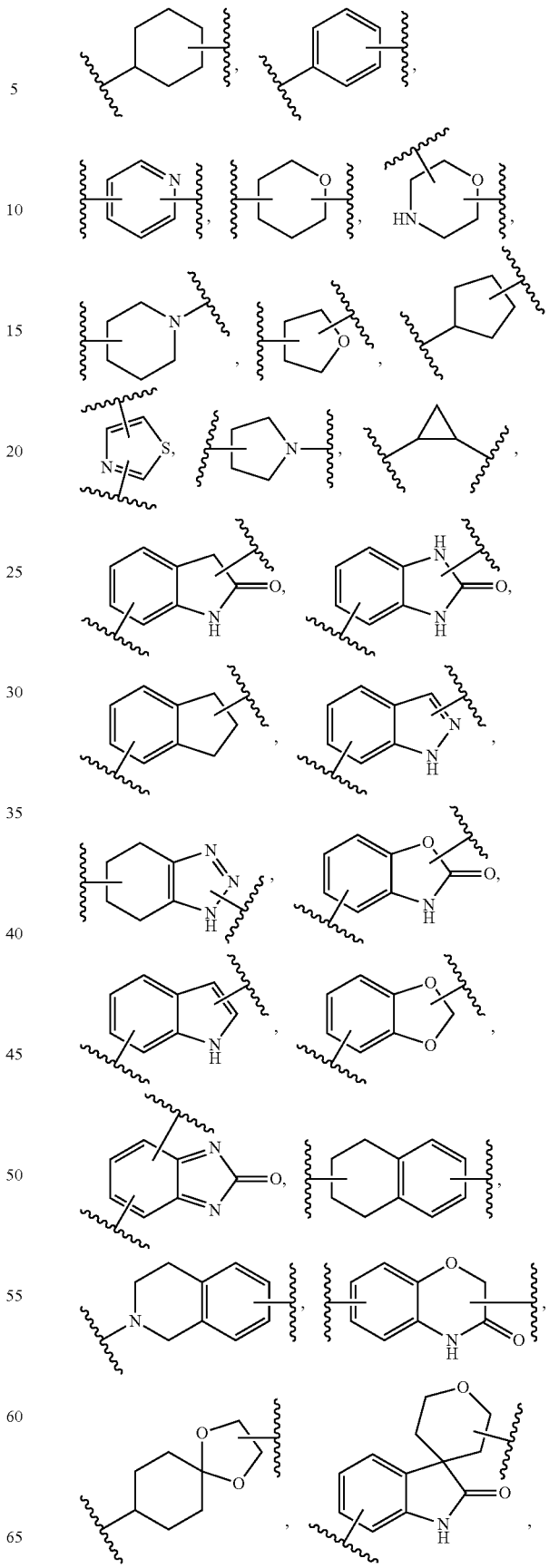

10. The compound of claim 1, or a pharmaceutically acceptable salt thereof, wherein L is selected from —$C_{1-6}$ alkylene- optionally substituted with 1, 2, or 3 substituents independently selected from halo, CN, OH, $C_{1-3}$ alkyl, $C_{1-3}$ alkoxy, $C_{1-3}$ haloalkyl, $C_{1-3}$ haloalkoxy, amino, $C_{1-3}$ alkylamino, and di($C_{1-3}$ alkyl)amino.

11. The compound of claim 1, or a pharmaceutically acceptable salt thereof, wherein L is selected from methylene, ethylene, and —$CH_2$—$CH(OH)$—.

12. The compound of claim 1, or a pharmaceutically acceptable salt thereof, wherein L is methylene.

13. The compound of claim 1, or a pharmaceutically acceptable salt thereof, wherein L is selected from —($C_{1-4}$ alkylene)$_a$-Q-($C_{1-4}$ alkylene)$_b$-, wherein any $C_{1-4}$ alkylene group of the —($C_{1-4}$ alkylene)$_a$-Q-($C_{1-4}$ alkylene)$_b$- group is optionally substituted with 1, 2, or 3 substituents independently selected from halo, CN, OH, $C_{1-3}$ alkyl, $C_{1-3}$ alkoxy, $C_{1-3}$ haloalkyl, $C_{1-3}$ haloalkoxy, amino, $C_{1-3}$ alkylamino, and di($C_{1-3}$ alkyl)amino.

14. The compound of claim 1, or a pharmaceutically acceptable salt thereof, wherein L is selected from —C(O)—$CH_2$—, —C(O)—$CH_2$—$CH_2$—, C(O), —NH—$CH_2$—, NH, —C(O)—$CH(NH_2)$—, —NH—$CH(CH_3)$—, —N(CH$_3$)—C(O)—, N(CH$_3$)—$CH_2$—, —$CH_2$—$CH_2$—O—, and —C(O)—NH—.

15. The compound of claim 1, or a pharmaceutically acceptable salt thereof, wherein Cy is a linking phenyl, $C_{3-18}$ cycloalkyl, 5-10 membered heteroaryl, or 4-9 membered heterocycle group, each of which is optionally substituted with 1, 2, 3, or 4 substituents independently selected from $R^{Cy}$, wherein the heteroaryl or heterocycle has 1 or 2 rings and 1-3 heteroatoms independently selected from nitrogen, sulfur, and oxygen.

16. The compound of claim 1, or a pharmaceutically acceptable salt thereof, wherein Cy is a linking group having the formula:

-continued

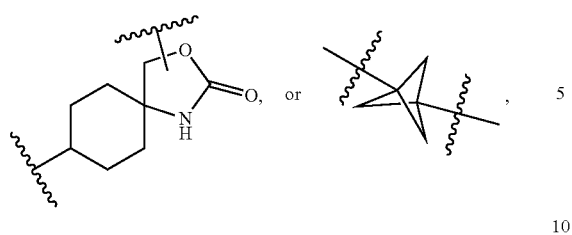

each of which is optionally substituted with 1, 2, 3, or 4 substituents independently selected from $R^{Cy}$.

17. The compound of claim 1, or a pharmaceutically acceptable salt thereof, wherein Cy is a linking group having the formula:

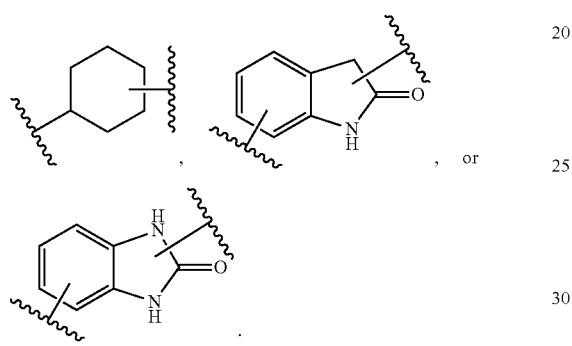

18. The compound of claim 1, or a pharmaceutically acceptable salt thereof, wherein Z is $Cy^2$ or $C(O)NR^{c3}R^{d3}$.

19. The compound of claim 1, or a pharmaceutically acceptable salt thereof, having Formula IIa, IIb, IIIa, or IIIb:

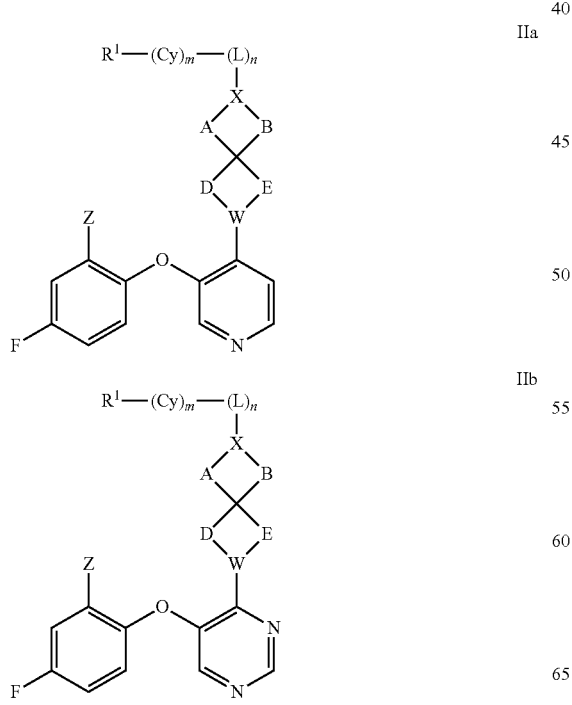

-continued

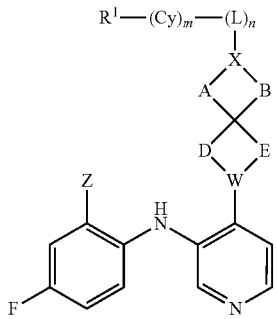
IIIa

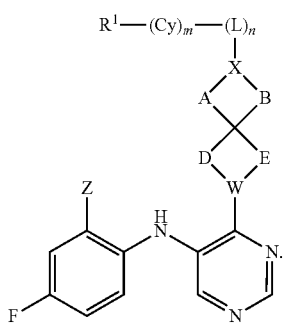
IIIb

20. The compound of claim 1, or a pharmaceutically acceptable salt thereof, having Formula IVa, IVb, IVc, IVd, IVe, or IVf:

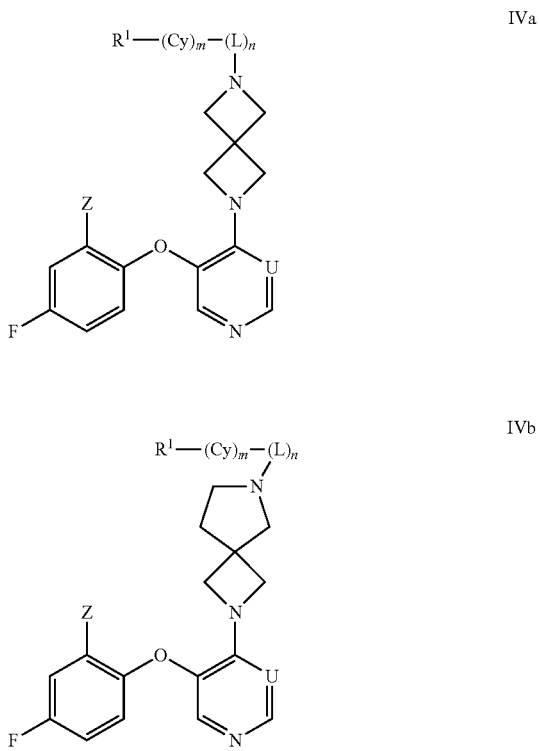

-continued

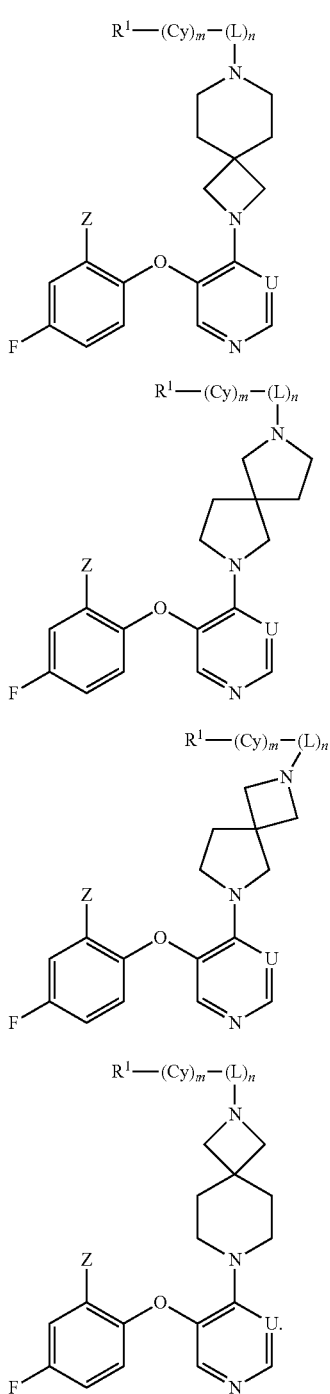

IVc

IVd

IVe

IVf

21. The compound of claim 1, wherein the compound is selected from:
5-fluoro-N,N-diisopropyl-2-((4-(7-((2-oxo-2,3-dihydro-1H-benzo[d]imidazol-5-yl)methyl)-2,7-diazaspiro[4.4]nonan-2-yl)pyrimidin-5-yl)oxy)benzamide;
N-ethyl-5-fluoro-N-isopropyl-2-((4-(7-((2-oxo-2,3-dihydro-1H-benzo[d]imidazol-5-yl)methyl)-2,7-diazaspiro[4.4]nonan-2-yl)pyrimidin-5-yl)oxy)benzamide;
5-fluoro-2-((4-(7-((1-(2-hydroxyethyl)-2-oxo-2,3-dihydro-1H-benzo[d]imidazol-5-yl)methyl)-2,7-diazaspiro[4.4]nonan-2-yl)pyrimidin-5-yl)oxy)-N,N-diisopropylbenzamide;
N-ethyl-5-fluoro-2-((4-(7-((1-(2-hydroxyethyl)-2-oxo-2,3-dihydro-1H-benzo[d]imidazol-5-yl)methyl)-2,7-diazaspiro[4.4]nonan-2-yl)pyrimidin-5-yl)oxy)-N-isopropylbenzamide;
5-fluoro-N-(2-hydroxyethyl)-N-isopropyl-2-((4-(7-((2-oxo-2,3-dihydro-1H-benzo[d]imidazol-5-yl)methyl)-2,7-diazaspiro[4.4]nonan-2-yl)pyrimidin-5-yl)oxy)benzamide;
5-fluoro-N,N-diisopropyl-2-((4-(7-(((1r,4r)-4-(methylsulfonamido)cyclohexyl)methyl)-2,7-diazaspiro[3.5]nonan-2-yl)pyrimidin-5-yl)oxy)benzamide;
5-fluoro-N,N-diisopropyl-2-((4-(7-(((1s,4s)-4-(methylsulfonamido)cyclohexyl)methyl)-2,7-diazaspiro[3.5]nonan-2-yl)pyrimidin-5-yl)oxy)benzamide;
5-((7-(5-(2-(amino(cyclopentyl)methyl)-4-fluorophenoxy)pyrimidin-4-yl)-2,7-diazaspiro[4.4]nonan-2-yl)methyl)-1,3-dihydro-2H-benzo[d]imidazol-2-one;
5-((7-(5-(2-(cyclopentyl(dimethylamino)methyl)-4-fluorophenoxy)pyrimidin-4-yl)-2,7-diazaspiro[4.4]nonan-2-yl)methyl)-1,3-dihydro-2H-benzo[d]imidazol-2-one;
N-(cyclopentyl(5-fluoro-2-((4-(7-((2-oxo-2,3-dihydro-1H-benzo[d]imidazol-5-yl)methyl)-2,7-diazaspiro[4.4]nonan-2-yl)pyrimidin-5-yl)oxy)phenyl)methyl)acetamide;
6-((7-(5-(4-fluoro-2-(1-hydroxy-2-methylpropyl)phenoxy)pyrimidin-4-yl)-2,7-diazaspiro[4.4]nonan-2-yl)methyl)-3,3-dimethylindolin-2-one;
6-((7-(5-(4-fluoro-2-isobutyrylphenoxy)pyrimidin-4-yl)-2,7-diazaspiro[4.4]nonan-2-yl)methyl)-3-methyl-2-oxoindoline-3-carbonitrile;
5-fluoro-2-((4-(6-(3-(4-fluorophenyl)propanoyl)-2,6-diazaspiro[3.4] octan-2-yl)pyrimidin-5-yl)oxy)-N,N-diisopropylbenzamide;
5-((7-(5-(4-fluoro-2-(1-isopropyl-1H-pyrazol-5-yl)phenoxy)pyrimidin-4-yl)-3-oxo-2,7-diazaspiro[4.4]nonan-2-yl)methyl)-1H-benzo[d]imidazol-2(3H)-one;
N-(4-fluoro-2-(5-isopropyl-3-methylisoxazol-4-yl)phenyl)-4-(6-((tetrahydro-2H-pyran-4-yl)methyl)-2,6-diazaspiro[3.3]heptan-2-yl)pyrimidin-5-amine;
4-(5-fluoro-2-((4-(6-((tetrahydro-2H-pyran-4-yl)methyl)-2,6-diazaspiro[3.3]heptan-2-yl)pyrimidin-5-yl)oxy)phenyl)-5-isopropyl-3-methylisoxazole;
N-(5-fluoro-2'-isopropyl-[1,1'-biphenyl]-2-yl)-4-(6-((tetrahydro-2H-pyran-4-yl)methyl)-2,6-diazaspiro[3.3]heptan-2-yl)pyrimidin-5-amine;
5-fluoro-2-((4-(2-(2-hydroxy-2-methylpropyl)-2,7-diazaspiro[3.5]nonan-7-yl)pyrimidin-5-yl)amino)-N,N-diisopropylbenzamide;
5-((7-(5-(2-(dimethylphosphoryl)-4-fluorophenoxy)pyrimidin-4-yl)-2,7-diazaspiro[4.4]nonan-2-yl)methyl)-1H-benzo[d]imidazol-2(3H)-one;
2-(5-(4-fluoro-2-(4-isopropylpyrimidin-5-yl)phenoxy)pyrimidin-4-yl)-N-(4-fluorobenzyl)-5-oxa-2-azaspiro[3.4]octan-7-amine;
4-(((2-(5-((5-fluoro-2'-isopropyl-[1,1'-biphenyl]-2-yl)oxy)pyrimidin-4-yl)-5-oxa-2-azaspiro[3.4]octan-7-yl)amino)methyl)benzonitrile;
7-(5-(4-fluoro-2-(4-isopropylpyrimidin-5-yl)phenoxy)pyrimidin-4-yl)-N-(4-fluorobenzyl)-1-oxa-7-azaspiro[4.4]nonan-3-amine;
5-fluoro-N-isopropyl-N-methyl-2-((4-(7-(((1r,4r)-4-(methylcarbamoyl)cyclohexyl)methyl)-2,7-diazaspiro[3.5]nonan-2-yl)pyrimidin-5-yl)oxy)benzamide;
2-((4-(7-amino-7-(4-cyanobenzyl)-2-azaspiro[4.4]nonan-2-yl)pyrimidin-5-yl)oxy)-5-fluoro-N,N-diisopropylbenzamide;

5-fluoro-2-((4-(7-hydroxy-8-((2-oxo-2,3-dihydro-1H-benzo[d]imidazol-5-yl)methyl)-2-azaspiro[4.4]nonan-2-yl)pyrimidin-5-yl)oxy)-N,N-diisopropylbenzamide;

2-((4-(7-amino-8-((2-oxo-2,3-dihydro-1H-benzo[d]imidazol-5-yl)methyl)-2-azaspiro[4.4]nonan-2-yl)pyrimidin-5-yl)oxy)-5-fluoro-N,N-diisopropylbenzamide;

5-fluoro-2-((4-(8-(4-fluorobenzyl)-7-(2-hydroxyethyl)-2,7-diazaspiro[4.4]nonan-2-yl)pyrimidin-5-yl)oxy)-N,N-diisopropylbenzamide;

6-((7-(5-(2-chloro-4-fluorophenoxy)pyrimidin-4-yl)-2-azaspiro[4.4]nonan-2-yl)methyl)-1-methyl-1H-benzo[d]imidazol-2(3H)-one;

5-((7-(3-(4-fluoro-2-(4-isopropylpyrimidin-5-yl)phenoxy)pyridin-4-yl)-2,7-diazaspiro[4.4]nonan-2-yl)methyl)-1,3-dihydro-2H-benzo[d]imidazol-2-one;

5-((7-(5-(2-(3-cyclopropyl-1-methyl-6-oxo-1,6-dihydropyridin-2-yl)-4-fluorophenoxy)pyrimidin-4-yl)-2,7-diazaspiro[4.4]nonan-2-yl)methyl)-1,3-dihydro-2H-benzo[d]imidazol-2-one;

N-(5-fluoro-2'-isopropyl-[1,1'-biphenyl]-2-yl)-4-(6-((tetrahydro-2H-pyran-4-yl)methyl)-2,6-diazaspiro[3.3]heptan-2-yl)pyridin-3-amine;

2-(5-((4',5-difluoro-2'-(2-fluoropropan-2-yl)-[1,1'-biphenyl]-2-yl)oxy)pyrimidin-4-yl)-6-((tetrahydro-2H-pyran-4-yl)methyl)-2,6-diazaspiro[3.3]heptane;

5-fluoro-N-isopropyl-2-((4-(6-((tetrahydro-2H-pyran-4-yl)methyl)-2,6-diazaspiro[3.3]heptan-2-yl)pyrimidin-5-yl)oxy)benzenesulfonamide;

5-((7-(5-(4-fluoro-2-(2-methoxybutan-2-yl)phenoxy)pyrimidin-4-yl)-2,7-diazaspiro[4.4]nonan-2-yl)methyl)-1,3-dihydro-2H-benzo[d]imidazol-2-one;

5-((7-(5-(4-fluoro-2-(3-hydroxypentan-3-yl)phenoxy)pyrimidin-4-yl)-2,7-diazaspiro[4.4]nonan-2-yl)methyl)-1,3-dihydro-2H-benzo[d]imidazol-2-one;

2-(5-fluoro-2-((4-(7-((2-oxo-2,3-dihydro-1H-benzo[d]imidazol-5-yl)methyl)-2,7-diazaspiro[4.4]nonan-2-yl)pyrimidin-5-yl)oxy)phenyl)-N-methylcyclopropanecarboxamide;

5-((7-(5-(4-fluoro-2-(3-hydroxy-3-methylbutyl)phenoxy)pyrimidin-4-yl)-2,7-diazaspiro[4.4]nonan-2-yl)methyl)-1H-benzo[d]imidazol-2(3H)-one;

methyl 2-(5-fluoro-2-((4-(7-((2-oxo-2,3-dihydro-1H-benzo[d]imidazol-5-yl)methyl)-2,7-diazaspiro[4.4]nonan-2-yl)pyrimidin-5-yl)oxy)phenyl)cyclopropanecarboxylate;

2-(5-fluoro-2-((4-(7-((2-oxo-2,3-dihydro-1H-benzo[d]imidazol-5-yl)methyl)-2,7-diazaspiro[4.4]nonan-2-yl)pyrimidin-5-yl)oxy)phenyl)-N-methylcyclopropanecarboxamide;

6-((2-(5-(2-chloro-4-fluorophenoxy)pyrimidin-4-yl)-2,6-diazaspiro[3.4]octan-6-yl)methyl)-3,3-dimethylindolin-2-one;

2-(6-(5-(2-chloro-4-fluorophenoxy)pyrimidin-4-yl)-2,6-diazaspiro[3.3]heptane-2-carbonyl)-2,3-dihydro-1H-indene-5-sulfonamide;

5-((7-(5-((5-fluoro-2'-isopropyl-[1,1'-biphenyl]-2-yl)oxy)pyrimidin-4-yl)-2,7-diazaspiro[4.4]nonan-2-yl)methyl)-1H-benzo[d]imidazol-2(3H)-one;

5-((7-(5-((5-fluoro-2'-isopropyl-[1,1'-biphenyl]-2-yl)oxy)pyrimidin-4-yl)-2,7-diazaspiro[4.4]nonan-2-yl)methyl)-1H-benzo[d]imidazol-2(3H)-one;

2-cyclopropyl-5'-fluoro-2'-((4-(7-((2-oxo-2,3-dihydro-1H-benzo[d]imidazol-5-yl)methyl)-2,7-diazaspiro[4.4]nonan-2-yl)pyrimidin-5-yl)oxy)-[1,1'-biphenyl]-4-carbonitrile;

2-cyclopropyl-5'-fluoro-2'-((4-(7-((2-oxo-2,3-dihydro-1H-benzo[d]imidazol-5-yl)methyl)-2,7-diazaspiro[4.4]nonan-2-yl)pyrimidin-5-yl)oxy)-[1,1'-biphenyl]-4-carboxamide;

2-cyclopropyl-5'-fluoro-2'-((4-(7-((2-oxo-2,3-dihydro-1H-benzo[d]imidazol-5-yl)methyl)-2,7-diazaspiro[4.4]nonan-2-yl)pyrimidin-5-yl)oxy)-[1,1'-biphenyl]-4-carboxylic acid;

2-cyclopropyl-5'-fluoro-N,N-dimethyl-2'-((4-(7-((2-oxo-2,3-dihydro-1H-benzo[d]imidazol-5-yl)methyl)-2,7-diazaspiro[4.4]nonan-2-yl)pyrimidin-5-yl)oxy)-[1,1'-biphenyl]-4-carboxamide;

5-((7-(2-chloro-5-(4-fluoro-2-(1-isopropyl-1H-pyrazol-5-yl)phenoxy)pyrimidin-4-yl)-2,7-diazaspiro[4.4]nonan-2-yl)methyl)-1,3-dihydro-2H-benzo[d]imidazol-2-one;

5-((7-(5-((4,5-difluoro-2'-isopropyl-[1,1'-biphenyl]-2-yl)oxy)pyrimidin-4-yl)-2,7-diazaspiro[4.4]nonan-2-yl)methyl)-1H-benzo[d]imidazol-2(3H)-one;

5'-fluoro-2-methyl-2'-((4-(7-((2-oxo-2,3-dihydro-1H-benzo[d]imidazol-5-yl)methyl)-2,7-diazaspiro[4.4]nonan-2-yl)pyrimidin-5-yl)oxy)-[1,1'-biphenyl]-4-carbonitrile;

5-((7-(5-((2'-cyclopropyl-5-fluoro-[1,1'-biphenyl]-2-yl)oxy)pyrimidin-4-yl)-2,7-diazaspiro[4.4]nonan-2-yl)methyl)-1H-benzo[d]imidazol-2(3H)-one;

5-((7-(5-((5-fluoro-2'-(trifluoromethyl)-[1,1'-biphenyl]-2-yl)oxy)pyrimidin-4-yl)-2,7-diazaspiro[4.4]nonan-2-yl)methyl)-1H-benzo[d]imidazol-2(3H)-one;

5'-fluoro-2,6-dimethyl-2'-((4-(7-((2-oxo-2,3-dihydro-1H-benzo[d]imidazol-5-yl)methyl)-2,7-diazaspiro[4.4]nonan-2-yl)pyrimidin-5-yl)oxy)-[1,1'-biphenyl]-4-carbonitrile;

2-cyclopropyl-3',5'-difluoro-2'-((4-(7-((2-oxo-2,3-dihydro-1H-benzo[d]imidazol-5-yl)methyl)-2,7-diazaspiro[4.4]nonan-2-yl)pyrimidin-5-yl)oxy)-[1,1'-biphenyl]-4-carbonitrile;

5-((7-(5-(4-fluoro-2-(2-isopropyl-1H-imidazol-1-yl)phenoxy)pyrimidin-4-yl)-2,7-diazaspiro[4.4]nonan-2-yl)methyl)-1H-benzo[d]imidazol-2(3H)-one;

5-((7-(5-(2-(cyclopropylmethoxy)-4-fluorophenoxy)pyrimidin-4-yl)-2,7-diazaspiro[4.4]nonan-2-yl)methyl)-1,3-dihydro-2H-benzo[d]imidazol-2-one;

ethyl 2-(7-(5-((4'-cyano-2'-cyclopropyl-5-fluoro-[1,1'-biphenyl]-2-yl)oxy)pyrimidin-4-yl)-2,7-diazaspiro[4.4]nonan-2-yl)thiazole-4-carboxylate;

2-(7-(5-((4'-cyano-2'-cyclopropyl-5-fluoro-[1,1'-biphenyl]-2-yl)oxy)pyrimidin-4-yl)-2,7-diazaspiro[4.4]nonan-2-yl)thiazole-4-carboxylic acid;

2-(7-(5-((4'-cyano-2'-cyclopropyl-5-fluoro-[1,1'-biphenyl]-2-yl)oxy)pyrimidin-4-yl)-2,7-diazaspiro[4.4]nonan-2-yl)-N-methylthiazole-4-carboxamide;

2-(7-(5-((4'-cyano-2'-cyclopropyl-5-fluoro-[1,1'-biphenyl]-2-yl)oxy)pyrimidin-4-yl)-2,7-diazaspiro[4.4]nonan-2-yl)-N,N-dimethylthiazole-4-carboxamide;

7-benzyl-2-(5-(4-fluoro-2-(4-isopropylpyrimidin-5-yl)phenoxy)pyrimidin-4-yl)-2-azaspiro[4.4]nonane;

5-((7-(5-((5-fluoro-2'-(1-hydroxyethyl)-[1,1'-biphenyl]-2-yl)oxy)pyrimidin-4-yl)-2,7-diazaspiro[4.4]nonan-2-yl)methyl)-1H-benzo[d]imidazol-2(3H)-one;

5-fluoro-N-isopropyl-N-methyl-2-((4-(7-(3-(2-oxooxazolidin-3-yl)benzyl)-2,7-diazaspiro[4.4]nonan-2-yl)pyrimidin-5-yl)oxy)benzamide;

5-fluoro-N-isopropyl-N-methyl-2-((4-(7-(4-(2-oxooxazolidin-3-yl)benzyl)-2,7-diazaspiro[4.4]nonan-2-yl)pyrimidin-5-yl)oxy)benzamide;

5-((7-(5-((5-fluoro-2'-(2-hydroxypropan-2-yl)-[1,1'-biphenyl]-2-yl)oxy)pyrimidin-4-yl)-2,7-diazaspiro[4.4]nonan-2-yl)methyl)-1H-benzo[d]imidazol-2(3H)-one;

2-(1,4-dioxaspiro[4 0.5]decan-8-ylmethyl)-6-(5-(4-fluoro-2-(4-isopropyl pyrimidin-5-yl)phenoxy)pyrimidin-4-yl)-2,6-diazaspiro[3.3]heptane;

4-((6-(5-(4-fluoro-2-(4-isopropylpyrimidin-5-yl)phenoxy)pyrimidin-4-yl)-2,6-diazaspiro [3.3]heptan-2-yl)methyl)cyclohexanol;

2-cyclopropyl-5'-fluoro-2'-((4-(6-((4-hydroxycyclohexyl)methyl)-2,6-diazaspiro[3.3]heptan-2-yl) pyrimidin-5-yl)oxy)-[1,1'-biphenyl]-4-carbonitrile;

2-(5-((5-fluoro-2'-(1-methoxyethyl)-[1,1'-biphenyl]-2-yl)oxy)pyrimidin-4-yl)-6-((tetrahydro-2H-pyran-4-yl)methyl)-2,6-diazaspiro[3.3]heptane;

5-(5-fluoro-2-((4-(6-((tetrahydro-2H-pyran-4-yl)methyl)-2,6-diazaspiro[3 0.3] heptan-2-yl)pyrimidin-5-yl)oxy)phenyl)-2,3-dihydro-1H-inden-2-amine;

5-((7-(5-((5-fluoro-2'-(1-hydroxypropan-2-yl)-[1,1'-biphenyl]-2-yl)oxy)pyrimidin-4-yl)-2,7-diazaspiro[4.4]nonan-2-yl)methyl)-1H-benzo[d]imidazol-2(3H)-one;

5-((7-(5-(4-fluoro-2-(morpholinomethyl)phenoxy)pyrimidin-4-yl)-2,7-diazaspiro[4.4]nonan-2-yl)methyl)-1H-benzo[d]imidazol-2(3H)-one;

1-(7-(5-((2'-ethyl-5-fluoro-[1,1'-biphenyl]-2-yl)amino)pyrimidin-4-yl)-2,7-diazaspiro[3 0.5]nonan-2-yl)-2-methylpropan-2-ol;

1-((6-(5-(4-fluoro-2-(1-isopropyl-3-(trifluoromethyl)-1H-pyrazol-5-yl)phenoxy)pyrimidin-4-yl)-2,6-diazaspiro[3.3]heptan-2-yl)methyl)cyclohexan-1-ol;

N-(2-amino-2-oxoethyl)-N-(5-fluoro-2-((4-(7-((2-oxo-2,3-dihydro-1H-benzo[d]imidazol-5-yl)methyl)-2,7-diazaspiro[4.4]nonan-2-yl)pyrimidin-5-yl)oxy)phenyl) isobutyramide;

N-(5-fluoro-2-((4-(7-(((1r,4r)-4-(methyl sulfonamido)cyclohexyl)methyl)-2,7-diazaspiro[3 0.5]nonan-2-yl)pyrimidin-5-yl)oxy)phenyl)propane-2-sulfonamide;

tert-butyl 7-(5-(4-fluoro-2-(N-methylisobutyramido)phenoxy)pyrimidin-4-yl)-2,7-diazaspiro[4.4]nonane-2-carboxylate;

N-(5-fluoro-2-((4-(7-((2-oxo-2,3-dihydro-1H-benzo[d]imidazol-5-yl)methyl)-2,7-diazaspiro[4.4]nonan-2-yl)pyrimidin-5-yl)oxy)phenyl)-N-methylisobutyramide;

5-((7-(5-(4-fluoro-2-isobutylphenoxy)pyrimidin-4-yl)-2,7-diazaspiro[4.4]nonan-2-yl)methyl)-1,3-dihydro-2H-benzo[d]imidazol-2-one;

2-(3-((2'-ethyl-5-fluoro-[1,1'-biphenyl]-2-yl)methyl)pyridin-4-yl)-6-((tetrahydro-2H-pyran-4-yl)methyl)-2,6-diazaspiro[3.3]heptane;

N-((1r,4r)-4-((2-(5-(2-(3-cyclopropyl-1-methyl-6-oxo-1,6-dihydropyridin-2-yl)-4-fluorophenoxy)pyrimidin-4-yl)-2,7-diazaspiro[3.5]nonan-7-yl)methyl)cyclohexyl)-2,2,2-trifluoroacetamide;

N-(4-((2-(5-(2-(3-cyclopropyl-1-methyl-6-oxo-1,6-dihydropyridin-2-yl)-4-fluorophenoxy)pyrimidin-4-yl)-2,7-diazaspiro[3.5]nonan-7-yl)methyl)cyclohexyl)methanesulfonamide;

5-((7-(5-(2-(3-cyclopropyl-1-methyl-6-oxo-1, 6-dihydropyridin-2-yl)-4-fluorophenoxy)pyrimidin-4-yl)-2,7-diazaspiro[4.4]nonan-2-yl)methyl)-1-(2-hydroxyethyl)-1H-benzo[d]imidazol-2(3H)-one;

(1r,4r)-4-(2-(6-(5-(2-(2-cyclopropylpyridin-3-yl)-4-fluorophenoxy) pyrimidin-4-yl)-2,6-diazaspiro[3.3]heptan-2-yl)ethyl)cyclohexan-1-amine;

tert-butyl ((1r,4r)-4-(((2-(5-(4-fluoro-2-(isopropyl(methyl)carbamoyl)phenoxy)pyrimidin-4-yl)-2-azaspiro[3.3]heptan-6-yl)amino)methyl)cyclohexyl) carbamate;

tert-butyl ((1r,4r)-4-((2-(5-(2-(N-ethylisobutyramido)-4-fluorophenoxy)pyrimidin-4-yl)-2,7-diazaspiro[3.5]nonan-7-yl)methyl)cyclohexyl) carbamate;

methyl ((1r,4r)-4-((2-(5-(2-(N-ethylisobutyramido)-4-fluorophenoxy)pyrimidin-4-yl)-2,7-diazaspiro[3.5]nonan-7-yl)methyl)cyclohexyl)carbamate;

N-ethyl-N-(5-fluoro-2-((4-(7-(((1r,4r)-4-(methylsulfonamido)cyclohexyl)methyl)-2,7-diazaspiro [3.5]nonan-2-yl)pyrimidin-5-yl)oxy)phenyl)isobutyramide;

2-((4-(6-(2-((1r,4r)-4-(3,3-dimethyl butanamido)cyclohexyl)ethyl)-2,6-diazaspiro[3.3]heptan-2-yl)pyrimidin-5-yl)oxy)-5-fluoro-N,N-diisopropyl benzamide;

tert-butyl ((1r,4r)-4-(2-(6-(5-(2-(2-cyclopropylpyridin-3-yl)-4-fluorophenoxy)pyrimidin-4-yl)-2,6-diazaspiro [3.3]heptan-2-yl)ethyl)cyclohexyl) carbamate;

5-fluoro-2-((4-(7-(2-hydroxy-2-methylpropyl)-2,7-diazaspiro[3.5]nonan-2-yl)pyrimidin-5-yl)oxy)-N,N-diisopropylbenzamide;

2-((4-(7-((3-cyano-3-methyl-2-oxoindolin-6-yl)methyl)-2,7-diazaspiro[4.4]nonan-2-yl)pyrimidin-5-yl)oxy)-5-fluoro-N,N-diisopropylbenzamide;

methyl ethyl(5-fluoro-2-((4-(7-((2-oxo-2,3-dihydro-1H-benzo[d]imidazol-5-yl)methyl)-2,7-diazaspiro [4.4]nonan-2-yl)pyrimidin-5-yl)oxy)phenyl)carbamate;

5-fluoro-2-((4-(7-((1-(2-hydroxyethyl)-2-oxo-2,3-dihydro-1H-benzo[d]imidazol-5-yl)methyl)-2,7-diazaspiro[4.4]nonan-2-yl)pyrimidin-5-yl)oxy)-N-isopropyl-N-methylbenzamide;

5-fluoro-N-isopropyl-N-methyl-2-((4-(6-((tetrahydro-2H-pyran-4-yl)amino)-2-azaspiro[3.3]heptan-2-yl)pyrimidin-5-yl)oxy)benzamide;

5-fluoro-N-isopropyl-N-methyl-2-((4-(7-(((1r,4r)-4-(methylsulfonamido)cyclohexyl) methyl)-2,7-diazaspiro [3.5]nonan-2-yl)pyrimidin-5-yl)oxy)benzamide;

tert-butyl ((1r,4r)-4-((2-(5-(4-fluoro-2-(isopropyl(methyl)carbamoyl)phenoxy)pyrimidin-4-yl)-2,7-diazaspiro [3.5]nonan-7-yl)methyl)cyclohexyl)carbamate;

methyl ((1r,4r)-4-((2-(5-(4-fluoro-2-(isopropyl(methyl)carbamoyl)phenoxy)pyrimidin-4-yl)-2,7-diazaspiro [3.5]nonan-7-yl)methyl)cyclohexyl)carbamate;

N-(tert-butyl)-2-(5-(4-fluoro-2-(4-isopropylpyrimidin-5-yl)phenoxy)pyrimidin-4-yl)-2-azaspiro[3.4]octan-6-amine;

2-((4-(7-(((1r,4r)-4-(3,3-dimethylureido)cyclohexyl) methyl)-2,7-diazaspiro [3.5]nonan-2-yl)pyrimidin-5-yl)oxy)-5-fluoro-N,N-diisopropyl benzamide;

5-fluoro-2-((4-(7-((4-hydroxycyclohexyl)methyl)-2,7-diazaspiro[3.5]nonan-2-yl)pyrimidin-5-yl)oxy)-N,N-diisopropylbenzamide;

5-fluoro-2-((4-(6-((4-hydroxycyclohexyl)methyl)-2,6-diazaspiro[3.4]octan-2-yl)pyrimidin-5-yl)oxy)-N,N-diisopropylbenzamide;

2-((4-(7-((1,4-dioxaspiro[4.5]decan-8-yl)methyl)-2,7-diazaspiro[3.5]nonan-2-yl)pyrimidin-5-yl)oxy)-5-fluoro-N,N-diisopropylbenzamide;

5-fluoro-N,N-diisopropyl-2-((4-(7-((tetrahydro-2H-pyran-4-yl)methyl)-2,7-diazaspiro[3.5]nonan-2-yl)pyrimidin-5-yl)oxy)benzamide;

5-fluoro-N,N-diisopropyl-2-((4-(6-neopentyl-2,6-diazaspiro[3.4]octan-2-yl)pyrimidin-5-yl)oxy)benzamide;

2-((4-(6-(cyclopropylmethyl)-2,6-diazaspiro [3.4]octan-2-yl)pyrimidin-5-yl)oxy)-5-fluoro-N,N-diisopropylbenzamide;

2-((4-(6-(6-cyano-1,2,3,4-tetrahydro naphthalen-2-yl)-2,6-diazaspiro[3.4]octan-2-yl)pyrimidin-5-yl)oxy)-5-fluoro-N,N-diisopropyl benzamide;

5-fluoro-N,N-diisopropyl-2-((4-(6-(2-((1r,4r)-4-pivalamidocyclohexyl)ethyl)-2,6-diazaspiro[3.3]heptan-2-yl)pyrimidin-5-yl)oxy)benzamide;

N-(2-((4-(6-(cyclohexylmethyl)-2,6-diazaspiro[3.3]heptan-2-yl) pyrimidin-5-yl)oxy)-5-fluoro phenyl)-N-ethylisobutyramide;

N-ethyl-5-fluoro-N-isopropyl-2-((4-(7-((1-methyl-2-oxo-2,3-dihydro-1H-benzo[d]imidazol-5-yl)methyl)-2,7-diazaspiro[4.4]nonan-2-yl)pyrimidin-5-yl)oxy)benzamide;

2-(5-(2-(cyclopentyloxy)-4-fluorophenoxy)pyrimidin-4-yl)-7-((tetrahydro-2H-pyran-4-yl) methyl)-2,7-diazaspiro[4.4]nonane;

2-(5-(2-cyclopropoxy-4-fluoro phenoxy)pyrimidin-4-yl)-7-((tetrahydro-2H-pyran-4-yl) methyl)-2,7-diazaspiro[4.4]nonane;

N-ethyl-N-(5-fluoro-2-((4-(7-((tetrahydro-2H-pyran-4-yl)methyl)-2,7-diazaspiro[3.5]nonan-2-yl)pyrimidin-5-yl)oxy)phenyl)isobutyramide;

5-fluoro-N,N-diisopropyl-2-((4-(6-((tetrahydro-2H-pyran-4-yl)methyl)-2,6-diazaspiro[3.4]octan-2-yl)pyrimidin-5-yl)oxy)benzamide;

5-fluoro-N,N-diisopropyl-2-((4-(6-((tetrahydro-2H-pyran-4-yl)methyl)-2,6-diazaspiro[3.3]heptan-2-yl)pyrimidin-5-yl)oxy)benzamide;

2-((4-(6-(2-(4-cyanophenyl)acetyl)-2,6-diazaspiro[3.4]octan-2-yl)pyrimidin-5-yl)oxy)-5-fluoro-N,N-diisopropylbenzamide;

5-fluoro-2-((4-(6-(6-fluoro-1,2,3,4-tetrahydronaphthalen-2-yl)-2,6-diazaspiro[3.4]octan-2-yl)pyrimidin-5-yl)oxy)-N,N-diisopropylbenzamide;

tert-butyl ((1r,4r)-4-(2-(6-(5-(2-(diisopropylcarbamoyl)-4-fluorophenoxy)pyrimidin-4-yl)-2,6-diazaspiro[3.3]heptan-2-yl)ethyl)cyclohexyl)carbamate;

2-((4-(6-(2-(4-cyanophenyl)acetyl)-2,6-diazaspiro[3.3]heptan-2-yl)pyrimidin-5-yl)oxy)-5-fluoro-N,N-diisopropylbenzamide;

N-ethyl-N-(5-fluoro-2-((4-(6-(5-(methylsulfonyl)-2,3-dihydro-1H-indene-2-carbonyl)-2,6diazaspiro[3.3]heptan-2-yl)pyrimidin-5-yl)oxy)phenyl)isobutyramide;

3-(((2-(5-(4-fluoro-2-(4-isopropylpyrimidin-5-yl)phenoxy)pyrimidin-4-yl)-2-azaspiro[3.3]heptan-6-yl) amino)methyl)bicyclo[1.1.1]pentane-1-carbonitrile;

N-ethyl-N-(5-fluoro-2-((4-(6-(2-(4-(methylsulfonyl)phenyl)acetyl)-2,6-diazaspiro[3.3]heptan-2-yl) pyrimidin-5-yl)oxy) phenyl)isobutyramide;

N-(2-((4-(6-(5-bromo-2,3-dihydro-1H-indene-2-carbonyl)-2,6-diazaspiro [3.3]heptan-2-yl)pyrimidin-5-yl)oxy)-5-fluorophenyl)-N-ethylisobutyramide;

N-ethyl-N-(5-fluoro-2-((4-(6-((tetrahydro-2H-pyran-4-yl)methyl)-2,6-diazaspiro[3.3]heptan-2-yl)pyrimidin-5-yl)oxy) phenyl)isobutyramide;

N-cyclopropyl-5-fluoro-N-isopropyl-2-((4-(7-((2-oxo-2,3-dihydro-1H-benzo[d]imidazol-5-yl)methyl)-2,7-diazaspiro[4.4]nonan-2-yl)pyrimidin-5-yl)oxy)benzamide;

2-((4-(7-((1-(2-acetamidoethyl)-2-oxo-2,3-dihydro-1H-benzo[d]imidazol-5-yl)methyl)-2,7-diazaspiro[4.4]nonan-2-yl)pyrimidin-5-yl)oxy)-5-fluoro-N-isopropyl-N-methylbenzamide;

2-((4-(7-((1-(2-(dimethylamino)ethyl)-2-oxo-2,3-dihydro-1H-benzo[d]imidazol-5-yl)methyl)-2,7-diazaspiro[4.4]nonan-2-yl)pyrimidin-5-yl)oxy)-5-fluoro-N-isopropyl-N-methylbenzamide;

2-((4-(7-((3-cyano-3-methyl-2-oxoindolin-6-yl)methyl)-2,7-diazaspiro [4.4]nonan-2-yl)pyrimidin-5-yl)oxy)-5-fluoro-N-isopropyl-N-methylbenzamide;

5-((7-(5-(4-fluoro-2-(1-isopropyl-1H-pyrazol-5-yl)phenoxy)-2-methylpyrimidin-4-yl)-2,7-diazaspiro[4.4]nonan-2-yl)methyl)-1,3-dihydro-2H-benzo[d]imidazol-2-one;

2-((4-(2-(2-(4-cyanophenyl)acetyl)-2,6-diazaspiro[3.4]octan-6-yl)pyrimidin-5-yl)oxy)-5-fluoro-N-isopropyl-N-methylbenzamide;

2-((4-(7-((1-ethyl-2-oxo-2,3-dihydro-1H-benzo[d]imidazol-5-yl)methyl)-2,7-diazaspiro[4.4]nonan-2-yl)pyrimidin-5-yl)oxy)-5-fluoro-N-isopropyl-N-methylbenzamide;

5-fluoro-N-isopropyl-2-((4-(7-((1-(2-methoxyethyl)-2-oxo-2,3-dihydro-1H-benzo[d]imidazol-5-yl)methyl)-2,7-diazaspiro[4.4]nonan-2-yl)pyrimidin-5-yl)oxy)-N-methyl benzamide;

4-(2-(6-(5-(4-fluoro-2-(4-isopropylpyrimidin-5-yl)phenoxy)pyrimidin-4-yl)-2,6-diazaspiro[3.4]octan-2-yl)-2-oxoethyl)benzonitrile;

5-((7-(5-(4-fluoro-2-(4-isopropylpyrimidin-5-yl)phenoxy)pyrimidin-4-yl)-2,7-diazaspiro[4.4]nonan-2-yl)methyl)-1-(2-methoxyethyl)-1,3-dihydro-2H-benzo[d]imidazol-2-one;

1-(6-(5-(4-fluoro-2-(4-isopropylpyrimidin-4-yl)-2,6-diazaspiro[3.3]heptan-2-yl)-2-(6-methoxypyridin-3-yl)ethan-1-one;

6-(2-(6-(5-(4-fluoro-2-(4-isopropylpyrimidin-5-yl)phenoxy)pyrimidin-4-yl)-2,6-diazaspiro[3.3]heptan-2-yl)-2-oxoethyl)-3,3-dimethylindolin-2-one;

tert-butyl ((1r,4r)-4-(2-(6-(5-(4-fluoro-2-(isopropyl(methyl)carbamoyl)phenoxy)pyrimidin-4-yl)-2,6-diazaspiro[3.3]heptan-2-yl)ethyl)cyclohexyl)carbamate;

5-((7-(5-(4-fluoro-2-((isopropyl(methyl) amino)methyl) phenoxy)pyrimidin-4-yl)-2,7-diazaspiro[4.4]nonan-2-yl)methyl)-1,3-dihydro-2H-benzo[d]imidazol-2-one;

N-ethyl-N-(5-fluoro-2-((4-(6-isobutyl-2,6-diazaspiro[3.4]octan-2-yl)pyrimidin-5-yl)oxy)phenyl)isobutyramide;

N-(2-((4-(6-((4,4-difluorocyclohexyl)methyl)-2,6-diazaspiro[3.4]octan-2-yl)pyrimidin-5-yl)oxy)-5-fluorophenyl)-N-ethylisobutyramide;

tert-butyl ((1r,4r)-4-(2-(6-(5-(4-fluoro-2-(N-methyl isobutyramido)phenoxy)pyrimidin-4-yl)-2,6-diazaspiro [3.3]heptan-2-yl)ethyl) cyclohexyl)carbamate;

2-(5-(4-fluoro-2-(4-isopropylpyrimidin-5-yl)phenoxy)pyrimidin-4-yl)-7-(6-fluoro-3,4-dihydroisoquinolin-2 (1H)-yl)-5-oxa-2-azaspiro[3.4]octane;

4-(((2-(5-(4-fluoro-2-(4-isopropylpyrimidin-5-yl)phenoxy)pyrimidin-4-yl)-2-azaspiro[3.3]heptan-6-yl) amino)methyl)-1-methylcyclohexane-1-carbonitrile;

4-(1-((2-(5-(4-fluoro-2-(4-isopropylpyrimidin-5-yl)phenoxy)pyrimidin-4-yl)-2-azaspiro[3.3]heptan-6-yl) amino)ethyl)benzonitrile;

5-fluoro-N-isopropyl-N-methyl-2-((4-(7-(4-(2-oxooxazolidin-3-yl)benzyl)-2,7-diazaspiro[4.4]nonan-2-yl)pyrimidin-5-yl)oxy)benzamide;

N-((1r,4r)-4-(2-(6-(5-((4'-cyano-2'-cyclopropyl-5-fluoro-[1,1'-biphenyl]-2-yl)oxy)pyrimidin-4-yl)-2,6-diazaspiro[3.3]heptan-2-yl)ethyl)cyclohexyl)acetamide;

methyl (5-fluoro-2-((4-(7-((2-oxo-2,3-dihydro-1H-benzo[d]imidazol-5-yl)methyl)-2,7-diazaspiro[4.4]nonan-2-yl)pyrimidin-5-yl)oxy)phenyl)(isopropyl)carbamate;

2-((4-(7-((1H-indazol-6-yl)methyl)-2,7-diazaspiro[4.4]nonan-2-yl)pyrimidin-5-yl)oxy)-5-fluoro-N-isopropyl-N-methylbenzamide;

2-((4-(7-((3-cyano-1H-indazol-6-yl)methyl)-2,7-diazaspiro[4.4]nonan-2-yl)pyrimidin-5-yl)oxy)-5-fluoro-N-isopropyl-N-methylbenzamide;

tert-butyl ((1r,4r)-4-((7-(5-(2-(cyclopentyloxy)-4-fluorophenoxy)pyrimidin-4-yl)-2,7-diazaspiro[4.4]nonan-2-yl)methyl)cyclohexyl)carbamate;

4-((2-(5-(4-fluoro-2-(4-isopropylpyrimidin-5-yl)phenoxy)pyrimidin-4-yl)-2-azaspiro[3.3]heptan-6-yl)amino)-1-methylcyclohexanecarbonitrile;

4-(2-(2-(5-(4-fluoro-2-(4-isopropylpyrimidin-5-yl)phenoxy)pyrimidin-4-yl)-2,6-diazaspiro[3.4]octan-6-yl)-2-oxoethyl)benzonitrile;

5-((7-(5-(4-fluoro-2-(4-isopropylpyrimidin-5-yl)phenoxy)pyrimidin-4-yl)-2,7-diazaspiro[4.4]nonan-2-yl)methyl)-1-methyl-1,3-dihydro-2H-benzo[d]imidazol-2-one;

2-cyclopropyl-5'-fluoro-2'-((4-(6-((4-hydroxycyclohexyl)methyl)-2,6-diazaspiro[3.3]heptan-2-yl) pyrimidin-5-yl)oxy)-[1,1'-biphenyl]-4-carbonitrile;

4-(((2-(5-(4-fluoro-2-(4-isopropylpyrimidin-5-yl)phenoxy)pyrimidin-4-yl)-2-azaspiro[3.3]heptan-6-yl)amino)methyl)benzonitrile;

5-((7-(5-(2-(2,5-dimethylpyrrolidine-1-carbonyl)-4-fluorophenoxy)pyrimidin-4-yl)-2,7-diazaspiro[4.4]nonan-2-yl)methyl)-1,3-dihydro-2H-benzo[d]imidazol-2-one;

5-((7-(5-(4-fluoro-2-(pyrrolidine-1-carbonyl)phenoxy)pyrimidin-4-yl)-2,7-diazaspiro [4.4]nonan-2-yl)methyl)-1,3-dihydro-2H-benzo[d]imidazol-2-one;

5-((7-(5-(4-fluoro-2-(morpholine-4-carbonyl) phenoxy)pyrimidin-4-yl)-2,7-diaza spiro[4.4]nonan-2-yl)methyl)-1,3-dihydro-2H-benzo[d]imidazol-2-one;

N-ethyl-N-(5-fluoro-2-((4-(6-((tetrahydro-2H-pyran-4-yl)methyl)-2,6-diazaspiro[3.4]octan-2-yl)pyrimidin-5-yl)oxy)phenyl)isobutyramide;

7-(5-(4-fluoro-2-(4-isopropylpyrimidin-5-yl)phenoxy)pyrimidin-4-yl)-N-(4-fluorobenzyl)-1-oxa-7-azaspiro[4.4]nonan-3-amine;

N-(2-((4-(6-(cyclohexylmethyl)-2,6-diazaspiro[3.4]octan-2-yl)pyrimidin-5-yl)oxy)-5-fluorophenyl)-N-ethylisobutyramide;

N-benzyl-2-(5-(4-fluoro-2-(4-isopropylpyrimidin-5-yl)phenoxy)pyrimidin-4-yl)-5-oxa-2-azaspiro[3.4]octan-7-amine;

5-((7-(5-(4-fluoro-2-(4-isopropylpyrimidin-5-yl)phenoxy)pyrimidin-4-yl)-2,7-diazaspiro[4.4]nonan-2-yl)methyl)-1,3-dihydro-2H-benzo[d]imidazol-2-one;

5-((7-(5-((5-fluoro-2'-(prop-1-en-2-yl)-[1,1'-biphenyl]-2-yl)oxy)pyrimidin-4-yl)-2,7-diazaspiro[4.4]nonan-2-yl)methyl)-1,3-dihydro-2H-benzo[d]imidazol-2-one;

2-(5-(4-fluoro-2-(2-isopropoxypyridin-3-yl)phenoxy)pyrimidin-4-yl)-6-((tetrahydro-2H-pyran-4-yl)methyl)-2,6-diazaspiro[3.3]heptane;

5-fluoro-N-isopropyl-N-methyl-2-((4-(7-((1-methyl-2-oxo-2,3-dihydro-1H-benzo[d]imidazol-5-yl)methyl)-2,7-diazaspiro[4.4]nonan-2-yl)pyrimidin-5-yl)oxy)benzamide;

ethyl (5-fluoro-2-((4-(7-((2-oxo-2,3-dihydro-1H-benzo[d]imidazol-5-yl)methyl)-2,7-diazaspiro[4.4]nonan-2-yl)pyrimidin-5-yl)oxy)phenyl)(methyl)carbamate;

N-cyclopropyl-5-fluoro-N-methyl-2-((4-(7-((2-oxo-2,3-dihydro-1H-benzo[d]imidazol-5-yl)methyl)-2,7-diazaspiro[4.4]nonan-2-yl)pyrimidin-5-yl)oxy)benzamide;

5-fluoro-N-methyl-2-((4-(7-((2-oxo-2,3-dihydro-1H-benzo[d]imidazol-5-yl)methyl)-2,7-diazaspiro[4.4]nonan-2-yl)pyrimidin-5-yl)oxy)-N-phenylbenzamide;

2-((4-(6-(cyclohexylmethyl)-2,6-diazaspiro[3.3]heptan-2-yl)pyrimidin-5-yl)oxy)-5-fluoro-N-isopropyl-N-methylbenzamide;

2-(5-(2-(cyclopentyloxy)-4-fluorophenoxy) pyrimidin-4-yl)-6-((tetrahydro-2H-pyran-4-yl)methyl)-2,6-diazaspiro[3.3]heptane;

2-cyclopropyl-5'-fluoro-2'-((4-(7-((2-oxo-2,3-dihydrobenzo[d]oxazol-5-yl)methyl)-2,7-diazaspiro[4.4]nonan-2-yl)pyrimidin-5-yl)oxy)-[1,1'-biphenyl]-4-carbonitrile;

methyl (3-((7-(5-((4'-cyano-2'-cyclopropyl-5-fluoro-[1,1'-biphenyl]-2-yl)oxy)pyrimidin-4-yl)-2,7-diazaspiro[4.4]nonan-2-yl)methyl)phenyl)carbamate;

2'-((4-(7-((1H-benzo[d][1,2,3]triazol-6-yl)methyl)-2,7-diazaspiro[4.4]nonan-2-yl)pyrimidin-5-yl)oxy)-2-cyclopropyl-5'-fluoro-[1,1'-biphenyl]-4-carbonitrile;

N-(2-chloro-4-((7-(5-((4'-cyano-2'-cyclopropyl-5-fluoro-[1, 1'-biphenyl]-2-yl)oxy)pyrimidin-4-yl)-2,7-diazaspiro[4.4]nonan-2-yl)methyl)phenyl)acetamide;

N,N-di ethyl-5-fluoro-2-((4-(7-((2-oxo-2,3-dihydro-1H-benzo[d]imidazol-5-yl)methyl)-2,7-diazaspiro[4.4]nonan-2-yl)pyrimidin-5-yl)oxy)benzamide;

5-fluoro-N-isopropyl-N-methyl-2-((4-(7-((2-oxo-2,3-dihydrobenzo[d]oxazol-5-yl)methyl)-2,7-diazaspiro[4.4]nonan-2-yl)pyrimidin-5-yl)oxy)benzamide;

N-(tert-butyl)-5-fluoro-N-methyl-2-((4-(7-((2-oxo-2,3-dihydro-1H-benzo[d]imidazol-5-yl)methyl)-2,7-diazaspiro[4.4]nonan-2-yl)pyrimidin-5-yl)oxy)benzamide;

1-(7-(5-(4-fluoro-2-(4-isopropylpyrimidin-5-yl)phenoxy) pyrimidin-4-yl)-2,7-diazaspiro[4.4]nonan-2-yl)-2-methylpropan-2-ol;

2-(5-(2-(2-cyclopropylpyridin-3-yl)-4-fluorophenoxy)pyrimidin-4-yl)-6-((tetrahydro-2H-pyran-4-yl)methyl)-2,6-diazaspiro[3.3]heptane;

6-((7-(5-(4-fluoro-2-(4-isopropylpyrimidin-5-yl)phenoxy)pyrimidin-4-yl)-2,7-diazaspiro[4.4]nonan-2-yl)methyl)-3,3-dimethylindolin-2-one;

6-((7-(5-(2-(2-cyclopropylpyridin-3-yl)-4-fluorophenoxy)pyrimidin-4-yl)-2,7-diazaspiro[4.4]nonan-2-yl)methyl)-3,3-dimethylindolin-2-one;

5-((7-(5-(2-(2-cyclopropylpyridin-3-yl)-4-fluorophenoxy)pyrimidin-4-yl)-2,7-diazaspiro[4.4]nonan-2-yl)methyl)-1,3-dihydro-2H-benzo[d]imidazol-2-one;

4-(((2-(5-(4-fluoro-2-(4-isopropylpyrimidin-5-yl)phenoxy)pyrimidin-4-yl)-5-oxa-2-azaspiro[3 0.4] octan-7-yl)(methyl)amino)methyl)benzonitrile;

6-((7-(5-(4-fluoro-2-(2,2,2-trifluoroethoxy) phenoxy)pyrimidin-4-yl)-2,7-diazaspiro[4.4]nonan-2-yl)methyl)-3,3-dimethylindolin-2-one;

5-fluoro-N-isopropyl-N-methyl-2-((4-(7-((2-oxo-2,3-dihydro-1H-benzo[d]imidazol-5-yl)methyl)-2,7-diazaspiro[4.4]nonan-2-yl)pyrimidin-5-yl)oxy)benzamide;

N-(cyclohexylmethyl)-2-(5-(4-fluoro-2-(4-isopropylpyrimidin-5-yl)phenoxy)pyrimidin-4-yl)-5-oxa-2-azaspiro[3.4]octan-7-amine;

N-(5-fluoro-2-((4-(7-((2-oxo-2,3-dihydro-1H-benzo[d]imidazol-5-yl)methyl)-2,7-diazaspiro[4.4]nonan-2-yl) pyrimidin-5-yl)oxy)phenyl)-N-(2-hydroxyethyl)isobutyramide;

N-ethyl-N-(5-fluoro-2-((4-(7-((2-oxo-2,3-dihydro-1H-benzo[d]imidazol-5-yl)methyl)-2,7-diazaspiro[4.4]nonan-2-yl)pyrimidin-5-yl)oxy)phenyl)isobutyramide;

N-(5-fluoro-2-((4-(7-((2-oxo-2,3-dihydro-1H-benzo[d]imidazol-5-yl)methyl)-2,7-diazaspiro[4.4]nonan-2-yl) pyrimidin-5-yl)oxy)phenyl)-N-(2,2,2-trifluoroethyl)isobutyramide;

N-((1r,4r)-4-((7-(5-((4'-cyano-2'-cyclopropyl-5-fluoro-[1,1'-biphenyl]-2-yl)oxy)pyrimidin-4-yl)-2,7-diazaspiro[4.4]nonan-2-yl)methyl)cyclohexyl)acetamide;

tert-butyl ((1r,4r)-4-(2-(6-(5-((4'-cyano-2'-cyclopropyl-5-fluoro-[1,1'-biphenyl]-2-yl)oxy)pyrimidin-4-yl)-2,6-diazaspiro[3.3]heptan-2-yl)ethyl)cyclohexyl)carbamate;

5-((7-(5-(4-fluoro-2-(5-isopropylthiazol-4-yl)phenoxy)pyrimidin-4-yl)-2,7-diazaspiro[4.4]nonan-2-yl)methyl)-1,3-dihydro-2H-benzo[d]imidazol-2-one;

N-((1s,4s)-4-((7-(5-((4'-cyano-2'-cyclopropyl-5-fluoro-[1,1'-biphenyl]-2-yl)oxy)pyrimidin-4-yl)-2,7-diazaspiro[4.4]nonan-2-yl)methyl)cyclohexyl)acetamide;

2-cyclopropyl-2'-((4-(7-((1-ethyl-2-oxo-2,3-dihydro-1H-benzo[d]imidazol-5-yl)methyl)-2,7-diazaspiro[4.4]nonan-2-yl)pyrimidin-5-yl)oxy)-5'-fluoro-[1,1'-biphenyl]-4-carbonitrile;

3-((7-(5-(2-(cyclopentyloxy)-4-fluorophenoxy)pyrimidin-4-yl)-2,7-diazaspiro[4.4]nonan-2-yl)methyl)-1H-indole-6-carbonitrile;

6-((7-(5-(2-(cyclopentyloxy)-4-fluorophenoxy)pyrimidin-4-yl)-2,7-diazaspiro[4.4]nonan-2-yl)methyl)-3,3-dimethylindolin-2-one;

2-((4-(7-((6-cyano-1H-indol-3-yl)methyl)-2,7-diazaspiro[4.4]nonan-2-yl)pyrimidin-5-yl)oxy)-5-fluoro-N-isopropyl-N-methylbenzamide;

2-cyclopropyl-5'-fluoro-2'-((4-(7-(4-(2-oxopyrrolidin-1-yl)benzyl)-2,7-diazaspiro [4.4]nonan-2-yl)pyrimidin-5-yl)oxy)-[1,1'-biphenyl]-4-carbonitrile;

2-cyclopropyl-5'-fluoro-2'-((4-(7-((2-oxoindolin-6-yl)methyl)-2,7-diazaspiro[4.4]nonan-2-yl)pyrimidin-5-yl)oxy)-[1,1'-biphenyl]-4-carbonitrile;

6-((7-(5-(4-fluoro-2-(1-isopropyl-1H-pyrazol-5-yl)phenoxy)pyrimidin-4-yl)-2,7-diazaspiro[4.4]nonan-2-yl)methyl)-1H-benzo[d][1,2,3]triazole;

2-cyclopropyl-3',5'-difluoro-2'-((4-(7-((2-oxo-2,3-dihydro-1H-benzo[d]imidazol-5-yl)methyl)-2,7-diazaspiro[4.4]nonan-2-yl)pyrimidin-5-yl)oxy)-[1,1'-biphenyl]-4-carbonitrile;

3-((7-(5-(2-(cyclopropylmethoxy)-4-fluorophenoxy)pyrimidin-4-yl)-2,7-diazaspiro[4.4]nonan-2-yl)methyl)-1H-indole-6-carboxamide;

3-((7-(5-(2-(cyclopropylmethoxy)-4-fluorophenoxy)pyrimidin-4-yl)-2,7-diazaspiro[4.4]nonan-2-yl)methyl)-1H-indole-6-carbonitrile;

2-((4-(7-((3,3-dimethyl-2-oxoindolin-6-yl)methyl)-2,7-diazaspiro[4.4]nonan-2-yl)pyrimidin-5-yl)oxy)-5-fluoro-N-isopropyl-N-methylbenzamide;

2'-((4-(6-(4-cyanophenethyl)-2,6-diazaspiro[3.3]heptan-2-yl)pyrimidin-5-yl)oxy)-2-cyclopropyl-5'-fluoro-[1,1'-biphenyl]-4-carbonitrile;

2-cyclopropyl-5'-fluoro-2'-((4-(7-((2-oxoindolin-5-yl)methyl)-2,7-diazaspiro[4.4]nonan-2-yl)pyrimidin-5-yl)oxy)-[1,1'-biphenyl]-4-carbonitrile;

2-cyclopropyl-2'-((4-(7-((3,3-dimethyl-2-oxoindolin-6-yl)methyl)-2,7-diazaspiro[4.4]nonan-2-yl)pyrimidin-5-yl)oxy)-5'-fluoro-[1,1'-biphenyl]-4-carbonitrile;

2-amino-2-cyclohexyl-1-(7-(5-(4-fluoro-2-(1-isopropyl-1H-pyrazol-5-yl)phenoxy)pyrimidin-4-yl)-2,7-diazaspiro[4.4]nonan-2-yl)ethanone;

methyl (5-fluoro-2-((4-(7-((2-oxo-2,3-dihydro-1H-benzo[d]imidazol-5-yl)methyl)-2,7-diazaspiro[4.4]nonan-2-yl)pyrimidin-5-yl)oxy)phenyl)(methyl)carbamate;

5-((7-(5-(2-(benzyloxy)-4-fluorophenoxy) pyrimidin-4-yl)-2,7-diazaspiro [4.4]nonan-2-yl)methyl)-1,3-dihydro-2H-benzo[d]imidazol-2-one;

5-((7-(5-(4-fluoro-2-methoxyphenoxy)pyrimidin-4-yl)-2,7-diazaspiro[4.4]nonan-2-yl)methyl)-1,3-dihydro-2H-benzo[d]imidazol-2-one;

5-fluoro-N-isopropyl-N-methyl-2-((4-(7-((3-oxo-3,4-dihydro-2H-benzo[b][1,4]oxazin-6-yl)methyl)-2,7-diazaspiro[4.4]nonan-2-yl)pyrimidin-5-yl)oxy)benzamide;

5-((7-(5-(4-fluoro-2-(2-methylpyrrolidine-1-carbonyl)phenoxy)pyrimidin-4-yl)-2,7-diazaspiro[4.4]nonan-2-yl)methyl)-1,3-dihydro-2H-benzo [d]imidazol-2-one;

5-((7-(5-(2-((1s,4s)-7-azabicyclo[2.2.1]heptane-7-carbonyl)-4-fluorophenoxy) pyrimidin-4-yl)-2,7-diazaspiro[4.4]nonan-2-yl)methyl)-1,3-dihydro-2H-benzo[d]imidazol-2-one;

5-((7-(5-((2'-(1,1-difluoroethyl)-5-fluoro-[1,1'-biphenyl]-2-yl)oxy)pyrimidin-4-yl)-2,7-diazaspiro[4.4]nonan-2-yl)methyl)-1,3-dihydro-2H-benzo[d]imidazol-2-one;

2-cyclopropyl-5'-fluoro-2'-((4-(6-((4-hydroxytetrahydro-2H-pyran-4-yl)methyl)-2,6-diazaspiro[3.3]heptan-2-yl)pyrimidin-5-yl)oxy)-[1,1'-biphenyl]-4-carbonitrile;

2-cyclopropyl-5'-fluoro-2'-((4-(6-((tetrahydro-2H-pyran-4-yl)methyl)-2,6-diazaspiro [3.3]heptan-2-yl)pyrimidin-5-yl)oxy)-[1,1'-biphenyl]-4-carbonitrile;

5-fluoro-N-isopropyl-N-methyl-2-((4-(7-((2-oxo-2,3-dihydro-1H-benzo[d]imidazol-5-yl)methyl)-2,7-diazaspiro[4.4]nonan-2-yl)pyrimidin-5-yl)oxy)benzamide;

5-((7-(5-(4-fluoro-2-(1-isopropyl-3-(trifluoromethyl)-1H-pyrazol-5-yl)phenoxy)pyrimidin-4-yl)-2,7-diazaspiro[4.4]nonan-2-yl)methyl)-1,3-dihydro-2H-benzo [d]imidazol-2-one;

5-((7-(5-(4-fluoro-2-(2-isopropyl-5-oxopyrrolidin-1-yl)phenoxy)pyrimidin-4-yl)-2,7-diazaspiro[4.4]nonan-2-yl)methyl)-1,3-dihydro-2H-benzo[d]imidazol-2-one;

(1r,4r)-4-((7-(5-((5-fluoro-2'-isopropyl-[1,1'-biphenyl]-2-yl)oxy)pyrimidin-4-yl)-2,7-diazaspiro[4.4]nonan-2-yl)methyl)cyclohexan-1-amine;

tert-butyl ((1r,4r)-4-((7-(5-((5-fluoro-2'-isopropyl-[1,1'-biphenyl]-2-yl)oxy)pyrimidin-4-yl)-2,7-diazaspiro[4.4]nonan-2-yl)methyl)cyclohexyl)carbamate;

N-(4-((7-(5-((5-fluoro-2'-isopropyl-[1,1'-biphenyl]-2-yl)oxy)pyrimidin-4-yl)-2,7-diazaspiro[4.4]nonan-2-yl)methyl)phenyl)acetamide;

5-fluoro-N-isopropyl-N-methyl-2-((4-(7-((2-oxo-2,3-dihydro-1H-benzo[d]imidazol-5-yl)methyl)-2,7-diazaspiro[4.4]nonan-2-yl)pyrimidin-5-yl)oxy)benzenesulfonamide;

ethyl 5'-fluoro-2'-((4-(7-((2-oxo-2,3-dihydro-1H-benzo[d]imidazol-5-yl)methyl)-2,7-diazaspiro[4.4]nonan-2-yl)pyrimidin-5-yl)oxy)-[1,1'-biphenyl]-2-carboxylate;

5-((7-(5-(4-fluoro-2-(4-isopropylthiazol-5-yl)phenoxy) pyrimidin-4-yl)-2,7-diazaspiro[4.4]nonan-2-yl)methyl)-1,3-dihydro-2H-benzo[d]imidazol-2-one;

5-fluoro-N-isopropyl-N-methyl-2-((4-(6-((tetrahydro-2H-pyran-4-yl)methyl)-2,6-diazaspiro[3.3]heptan-2-yl)pyrimidin-5-yl)oxy)benzamide;

5'-fluoro-2-methyl-2'-((4-(7-((2-oxo-2,3-dihydro-1H-benzo[d]imidazol-5-yl)methyl)-2,7-diazaspiro[4.4]nonan-2-yl)pyrimidin-5-yl)oxy)-[1,1'-biphenyl]-4-carbonitrile;

4-(2-(6-(5-(4-fluoro-2-(4-isopropylpyrimidin-5-yl)phenoxy)pyrimidin-4-yl)-2,6-diazaspiro[3.3]heptan-2-yl)-2-oxoethyl)benzonitrile;

4-(2-(6-(5-((5-fluoro-2'-isopropyl-[1,1'-biphenyl]-2-yl)oxy)pyrimidin-4-yl)-2,6-diazaspiro[3.3]heptan-2-yl)-2-oxoethyl)benzonitrile;

1-(6-(5-((5-fluoro-2'-isopropyl-[1,1'-biphenyl]-2-yl)oxy)pyrimidin-4-yl)-2,6-diazaspiro[3.3]heptan-2-yl)-2-(4-(methylsulfonyl)phenyl)ethan-1-one;

5'-fluoro-2-methyl-2'-((4-(7-((2-oxo-2,3-dihydro-1H-benzo[d]imidazol-5-yl)methyl)-2,7-diazaspiro[4.4] nonan-2-yl)pyrimidin-5-yl)oxy)-[1,1'-biphenyl]-3-carbonitrile;

2-((3,3-difluorocyclohexyl)methyl)-6-(5-(4-fluoro-2-(1-isopropyl-1H-pyrazol-5-yl)phenoxy)pyrimidin-4-yl)-2,6-diazaspiro[3.3]heptane;

2-((3,3-difluorocyclohexyl)methyl)-6-(5-(4-fluoro-2-(4-isopropylpyrimidin-5-yl)phenoxy)pyrimidin-4-yl)-2,6-diazaspiro[3.3]heptane;

4-(((2-(5-(4-fluoro-2-(1-isopropyl-1H-pyrazol-5-yl)phenoxy)pyrimidin-4-yl)-5-oxa-2-azaspiro[3.4]octan-7-yl)amino)methyl)benzonitrile;

5-((7-(5-(2-(2-ethylpyridin-3-yl)-4-fluorophenoxy)pyrimidin-4-yl)-2,7-diazaspiro[4.4]nonan-2-yl)methyl)-1,3-dihydro-2H-benzo[d]imidazol-2-one;

5-((7-(5-(4-fluoro-2-isopentylphenoxy)pyrimidin-4-yl)-2,7-diazaspiro[4.4]nonan-2-yl)methyl)-1,3-dihydro-2H-benzo[d]imidazol-2-one;

5-((7-(5-(4-fluoro-2-isobutylphenoxy)pyrimidin-4-yl)-2,7-diazaspiro[4.4]nonan-2-yl)methyl)-1,3-dihydro-2H-benzo[d]imidazol-2-one;

5-((7-(5-(4-fluoro-2-(1-isopropyl-1H-pyrazol-5-yl)phenoxy)pyrimidin-4-yl)-2,7-diazaspiro[4.4]nonan-2-yl)methyl)-1,3-dihydro-2H-benzo[d]imidazol-2-one;

2-(5-((5-fluoro-2'-isopropyl-[1,1'-biphenyl]-2-yl)oxy)pyrimidin-4-yl)-6-((tetrahydro-2H-pyran-4-yl)methyl)-2,6-diazaspiro[3.3]heptane;

N-ethyl-5-fluoro-N-isopropyl-2-((4-(7-(((1r,4r)-4-(methylsulfonamido)cyclohexyl)methyl)-2,7-diazaspiro[3.5] nonan-2-yl)pyrimidin-5-yl)oxy)benzamide;

5-fluoro-N,N-diisopropyl-2-((4-(6-((tetrahydro-2H-pyran-4-yl)amino)-2-azaspiro[3.3]heptan-2-yl)pyrimidin-5-yl)oxy)benzamide;

5-fluoro-N,N-diisopropyl-2-((4-(6-(methyl(tetrahydro-2H-pyran-4-yl)amino)-2-azaspiro[3.3]heptan-2-yl)pyrimidin-5-yl)oxy)benzamide;

tert-butyl ((1r,4r)-4-((7-(5-((2-(diisopropylcarbamoyl)-4-fluorophenyl)amino)pyrimidin-4-yl)-2,7-diazaspiro [3.5]nonan-2-yl)methyl) cyclohexyl) carbamate;

1-((6-(5-((5-fluoro-2'-isopropyl-[1,1'-biphenyl]-2-yl) amino) pyrimidin-4-yl)-2,6-diaza spiro[3.3]heptan-2-yl)methyl)cyclohexan-1-ol;

5-((7-(5-((5-fluoro-2'-isopropyl-[1,1'-biphenyl]-2-yl) amino) pyrimidin-4-yl)-2,7-diazaspiro [4.4]nonan-2-yl)methyl)-1,3-dihydro-2H-benzo[d]imidazol-2-one;

N-(4-fluoro-2-(4-isopropylpyrimidin-5-yl)phenyl)-4-(6-((tetrahydro-2H-pyran-4-yl)methyl)-2,6-diazaspiro [3.3]heptan-2-yl)pyrimidin-5-amine;

N-(5-fluoro-2'-isopropoxy-[1,1'-biphenyl]-2-yl)-4-(2-isobutyl-2,7-diazaspiro[3.5]nonan-7-yl)pyrimidin-5-amine;

N-(5-fluoro-2'-isopropyl-[1,1'-biphenyl]-2-yl)-4-(2-isobutyl-2,7-diazaspiro[3.5]nonan-7-yl)pyrimidin-5-amine;

N-(2'-ethyl-5-fluoro-[1,1'-biphenyl]-2-yl)-4-(2-isobutyl-2,7-diazaspiro[3.5]nonan-7-yl)pyrimidin-5-amine;

5-fluoro-N,N-diisopropyl-2-((4-(2-(4-(methylsulfonamido)cyclohexyl)-2,7-diazaspiro[3.5]nonan-7-yl)pyrimidin-5-yl)amino)benzamide;

5-((7-(3-((5-fluoro-2'-isopropyl-[1,1'-biphenyl]-2-yl)oxy) pyridin-4-yl)-2,7-diazaspiro[4.4]nonan-2-yl)methyl)-1,3-dihydro-2H-benzo[d]imidazol-2-one;

2'-((4-(7-amino-7-benzyl-2-azaspiro[4.4]nonan-2-yl)pyrimidin-5-yl)oxy)-2-cyclopropyl-5'-fluoro-[1, 1'-biphenyl]-4-carbonitrile;

tert-butyl ((1r,4r)-4-((2-(5-(2-(diisopropylcarbamoyl)-4-fluorophenoxy)pyrimidin-4-yl)-2,7-diazaspiro[3.5] nonan-7-yl)methyl)cyclohexyl)carbamate;

2-((4-(3-(4-acetamidobenzyl)-2-amino-4-oxo-1,3,7-triazaspiro[4.4]non-1-en-7-yl)pyrimidin-5-yl)oxy)-5-fluoro-N-isopropyl-N-methylbenzamide; and N-ethyl-2-((4-(7-(((1r,4r)-4-(ethylsulfonamido)cyclohexyl)methyl)-2,7-diazaspiro[3.5]nonan-2-yl)pyrimidin-5-yl)oxy)-5-fluoro-N-isopropylbenzamide;

or a pharmaceutically acceptable salt thereof.

22. The compound of claim 1, which is 5-fluoro-N,N-diisopropyl-2-((4-(7-(((r,4r)-4-(methylsulfonamido)cyclohexyl)methyl)-2,7-diazaspiro[3.5]nonan-2-yl)pyrimidin-5-yl)oxy)benzamide or N-ethyl-2-((4-(7-(((1r,4r)-4-(ethylsulfonamido)cyclohexyl)methyl)-2,7-diazaspiro[3.5] nonan-2-yl)pyrimidin-5-yl)oxy)-5-fluoro-N-isopropylbenzamide, or a pharmaceutically acceptable salt thereof.

23. A pharmaceutically acceptable salt of the compound of claim 22, wherein the salt is a bis-methanesulfonic acid salt, a bis-hydrochloric acid salt, or a sesquifumaric acid salt.

24. A crystalline form of the salt of claim 23.

25. The crystalline form of claim 24, which is substantially anhydrous.

26. The crystalline form of claim 24, which is hydrated or solvated.

27. The crystalline form of claim 24, which is a monohydrate.

28. A pharmaceutical composition comprising a compound of claim 1, or a pharmaceutically acceptable salt thereof, and at least one pharmaceutically acceptable carrier.

* * * * *